United States Patent
Cohen et al.

(10) Patent No.: US 9,868,720 B2
(45) Date of Patent: Jan. 16, 2018

(54) C-LINKED HETEROCYCLOAKLYL SUBSTITUTED PYRIMIDINES AND THEIR USES

(71) Applicant: Genentech, Inc., South San Francisco, CA (US)

(72) Inventors: Frederick Cohen, San Francisco, CA (US); Snahel Patel, Foster City, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 14/928,034

(22) Filed: Oct. 30, 2015

(65) Prior Publication Data

US 2016/0046608 A1 Feb. 18, 2016

Related U.S. Application Data

(63) Continuation of application No. PCT/EP2014/058635, filed on Apr. 29, 2014.

(60) Provisional application No. 61/818,046, filed on May 1, 2013.

(51) Int. Cl.

| | | |
|---|---|---|
| *A61K 31/506* | (2006.01) |
| *C07D 401/14* | (2006.01) |
| *C07D 405/14* | (2006.01) |
| *C07D 403/14* | (2006.01) |
| *C07D 471/04* | (2006.01) |
| *C07D 493/08* | (2006.01) |
| *A61K 31/5377* | (2006.01) |
| *A61K 31/5386* | (2006.01) |
| *A61K 31/553* | (2006.01) |
| *A61K 35/30* | (2015.01) |
| *C07D 409/14* | (2006.01) |
| *C07D 413/14* | (2006.01) |
| *C07D 487/04* | (2006.01) |
| *C07D 491/08* | (2006.01) |
| *C07D 491/107* | (2006.01) |
| *C07D 498/08* | (2006.01) |

(52) U.S. Cl.
CPC .......... *C07D 401/14* (2013.01); *A61K 31/506* (2013.01); *A61K 31/5377* (2013.01); *A61K 31/5386* (2013.01); *A61K 31/553* (2013.01); *A61K 35/30* (2013.01); *C07D 403/14* (2013.01); *C07D 405/14* (2013.01); *C07D 409/14* (2013.01); *C07D 413/14* (2013.01); *C07D 471/04* (2013.01); *C07D 487/04* (2013.01); *C07D 491/08* (2013.01); *C07D 491/107* (2013.01); *C07D 493/08* (2013.01); *C07D 498/08* (2013.01)

(58) Field of Classification Search
CPC .......................... C07D 401/14; A61K 31/506
See application file for complete search history.

(56) References Cited

U.S. PATENT DOCUMENTS

| | | | | |
|---|---|---|---|---|
| 9,266,862 B2* | 2/2016 | Estrada | ............... | C07D 403/14 |
| 2005/0197342 A1* | 9/2005 | Hollingworth | ....... | C07D 401/04 |
| | | | | 514/252.04 |
| 2005/0267089 A1* | 12/2005 | Wang | .................. | C07D 401/14 |
| | | | | 514/184 |
| 2010/0249126 A1* | 9/2010 | Burger | ................. | C07D 401/04 |
| | | | | 514/232.2 |
| 2010/0317643 A1 | 12/2010 | Goodacre et al. | | |
| 2011/0065726 A1 | 3/2011 | Chen et al. | | |
| 2012/0190666 A1* | 7/2012 | Bode | .................... | C07D 401/14 |
| | | | | 514/210.21 |
| 2013/0090309 A1 | 4/2013 | Romeo et al. | | |
| 2013/0225548 A1 | 8/2013 | Fujihara et al. | | |

(Continued)

FOREIGN PATENT DOCUMENTS

| | | |
|---|---|---|
| EP | 1854793 | 11/2007 |
| WO | 2002072571 | 9/2002 |

(Continued)

OTHER PUBLICATIONS

CAS Registry Nos. (2012).*
Probst et al., "Highly selective c-Jun N-terminal kinase (JNK) 2 and 3 inhibitors with in vitro CNS-like pharmacokinetic properties prevent neurodegeneration" Bioorganic & Medicinal Chemistry Letters 21:315-319 (2011).
International Search Report issued in International Application No. PCT/EP2013/060351, dated Jan. 7, 2013.
Chemical Abstracts STN Registry database record RN724721-57-7, entered Aug. 10, 2004.

*Primary Examiner* — Alexander R Pagano
(74) *Attorney, Agent, or Firm* — Jonathan Duffield

(57) ABSTRACT

The present invention provides for pyrimidine compounds of Formula I-I and embodiments thereof

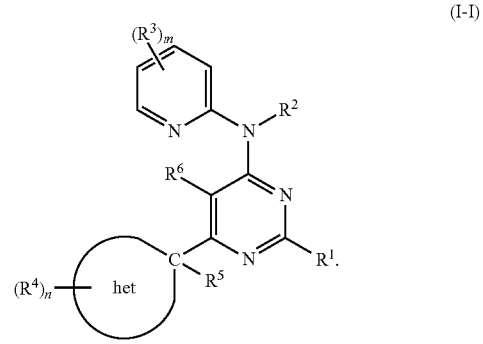

(I-I)

In Formula I-I in which $R^1$, $R^2$, $R^3$, $R^4$, $R^5$, $R^6$, m, n and the "het" ring are as described herein. Also provided are pharmaceutical compositions comprising compounds of Formula I and methods of using such compounds and compositions.

20 Claims, No Drawings

(56) References Cited

U.S. PATENT DOCUMENTS

| | | | | |
|---|---|---|---|---|
| 2013/0281443 | A1* | 10/2013 | Liang | C07D 213/74 514/227.8 |
| 2014/0328805 | A1* | 11/2014 | Estrada | C07D 401/14 424/93.7 |
| 2015/0080367 | A1* | 3/2015 | Cohen | C07D 401/14 514/210.18 |
| 2015/0175619 | A1 | 6/2015 | Siu et al. | |
| 2016/0002228 | A1 | 1/2016 | Estrada et al. | |
| 2016/0046608 | A1 | 2/2016 | Cohen et al. | |
| 2016/0052940 | A1* | 2/2016 | Estrada | C07D 519/00 514/210.18 |

FOREIGN PATENT DOCUMENTS

| | | |
|---|---|---|
| WO | 2010068806 | 6/2010 |
| WO | 2011014515 | 2/2011 |
| WO | 2011044181 | 4/2011 |
| WO | 2011050192 | 4/2011 |
| WO | 2012041476 | 4/2012 |
| WO | 2012057262 | 5/2012 |
| WO | 2012154518 | 11/2012 |
| WO | 2012154520 | 11/2012 |
| WO | 2013034238 | 3/2013 |
| WO | 2013174780 | 11/2013 |

* cited by examiner

C-LINKED HETEROCYCLOAKLYL SUBSTITUTED PYRIMIDINES AND THEIR USES

CROSS-REFERENCE TO RELATED APPLICATIONS

This application is a continuation application of International Application No. PCT/EP2014/058635, filed on Apr. 29, 2014, which claims priority to U.S. Provisional Application No. 61/818,046, filed on May 1, 2013, the entire contents of which are incorporated herein by reference.

FIELD OF THE INVENTION

The present invention relates to organic compounds useful for therapy and/or prophylaxis in a mammal, and in particular to inhibitors of DLK (useful for treating neurodegeneration diseases and disorders.

BACKGROUND OF THE INVENTION

Neuron or axon degeneration plays a central role in the proper development of the nervous system and is a hall mark of many neurodegenerative diseases including for example, amyotrophic lateral sclerosis (ALS), glaucoma, Alzheimer's disease, and Parkinson's disease, as well a traumatic injury to the brain and spinal cord. Recent patent publication WO2011/050192, incorporated herein by reference, describes the role of the Dual Leucine Zipper Kinase (DLK), also referred to as MAP3K12, to cause neuronal cell death. Neurodegenerative diseases and injuries are devastating to patients and caregivers, and also result in great financial burdens, with annual costs currently exceeding several hundred billion dollars in the United States alone. Most current treatments for these diseases and conditions are inadequate. Adding to the urgency of the problems created by these diseases is the fact that many such diseases are age related, and thus their incidence is increasing rapidly as population demographics change. There is a great need for the development of effective approaches to treating neurodegenerative diseases and nervous system injuries, including for example, through the inhibitors of DLK in neurons.

SUMMARY OF THE INVENTION

In one aspect the invention provides for compounds of Formula I and Formula I-I and embodiments thereof. In compounds of Formula I-I

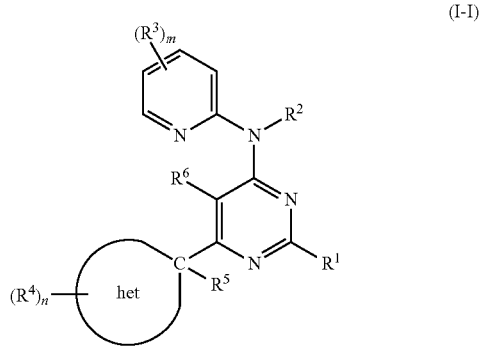

(I-I)

R1 is selected from the group consisting of C1-6 alkyl, C1-6 haloalkyl, C1-6 heteroalkyl, C1-6 alkoxy, 3-10 membered cycloalkyl, 3-10 membered heterocycloalkyl, 6-10 membered aryl, 5-10 membered heteroaryl, —OR1a, —SR1a, —N(H)(R1a), and —N(R1a)(R1b) wherein R1a and R1b are each independently selected from the group consisting of C1-6 alkyl, C1-6 haloalkyl, C1-6 heteroalkyl, 3-10 membered cycloalkyl and 3-10 membered heterocycloalkyl, and wherein the aliphatic and aromatic portions of R1 are independently further substituted with 0 to 5 RA1 substituents selected from the group consisting of —F, —Cl, —Br, —I, —CN, —NO2, —SF5, —OH, —NH2, —CF3, =O, C1-4 alkyl, C1-4 haloalkyl, C1-4 heteroalkyl, C1-4 alkoxy, C1-4 alkylthio, C1-4 alkylamino, C1-4 dialkylamino, R1c-C(=O)—, R1c-C(=O)N(H)—, R1c-C(=O)N(R1d)-, R1c-C(=O)O—, R1c-S(O)1-2-, R1c-S(O)1-2N(R1d)-, R1c-S(O)1-2N(H)—, 3-6 membered cycloalkyl, phenyl, 5-6 membered heteroaryl and 3-7 membered heterocycloalkyl, wherein R1c is selected from the group consisting of C1-6 alkyl, C1-6 haloalkyl, C5-6 heteroaryl, 3-7 membered heterocycloalkyl, phenyl and 3-6 membered cycloalkyl, R1d is selected from the group consisting of hydrogen, C1-3 alkyl and C1-3 haloalkyl, and wherein said 5-6 membered heteroaryl, phenyl, 3-6 membered cycloalkyl and 3-7 membered heterocycloalkyl of a RA1 substituent are substituted with from 0-4 substituents selected from —F, —Cl, —Br, I, —CN, —NO2, —SF5, —OH, —NH2, —CF3, C1-4 alkyl, C1-4 haloalkyl, C1-4 alkoxy, C1-4 alkylthio, C1-4 alkylamino and C1-4 dialkylamino; R2 is selected from the group consisting of hydrogen, C1-6 alkyl and C1-6 haloalkyl; R3 is selected from the group consisting of —F, —Cl, —Br, —I, —(X3)0-1-CN, —(X3)0-1-NO2, —(X3)0-1-SF5, —(X3)0-1-OH, —(X3)0-1-NH2, —(X3)0-1-N(H)(R3a), —(X3)0-1-N(R3b)(R3a), —(X3)0-1-CF3, C1-6 alkyl, C1-6 haloalkyl, C1-6 heteroalkyl, C1-6 alkoxy, C1-6 alkylthio, —(X3)0-1-3-7 membered cycloalkyl, —(X3)0-1-3-7 membered heterocycloalkyl, —(X3)0-1-5-6 membered heteroaryl, —(X3)0-1-C6 aryl, —(X3)0-1-C(=Y3)N(H)(R3a), —(X3)0-1-C(=Y3)NH2, —(X3)0-1-C(=Y3)N(R3a)(R3b), —(X3)0-1-C(=Y3)OR3a, —(X3)0-1-C(=Y3)OH, —(X3)0-1-N(H)C(=Y3)(R3a), —(X3)0-1-N(R3b)C(=Y3)(R3a), —(X3)0-1-N(H)C(=Y3)OR3a, —(X3)0-1-N(R3b)C(=Y3)OR3a, —(X3)0-1-S(O)1-2R3a, —(X3)0-1-N(H)S(O)1-2R3a, —(X3)0-1-N(R3b)S(O)1-2R3a, —(X3)0-1-S(O)0-1N(H)(R3a), —(X3)0-1-S(O)0-1N(R3b)(R3a), —(X3)0-1-S(O)0-1NH2, —(X4)0-1-S(=O)(=NR3b)R3a, —(X3)0-1-C(=Y3)R3a, —(X3)0-1-C(=Y3)H, —(X3)0-1-C(=NOH)R3a, —(X3)0-1-C(=NOR3b)R3a, —(X3)0-1-NHC(=Y3)N(H)(R3a), —(X3)0-1-NHC(=Y3)NH2, —(X3)0-1-NHC(=Y3)N(R3b)(R3a), —(X3)0-1-N(R3a)C(=Y3)N(H)(R3a), —(X3)0-1-N(R3a)C(=Y3)NH2, —(X3)0-1-OC(=Y3)R3a, —(X3)0-1-OC(=Y3)H, —(X3)0-1-OC(=Y3)OR3a, —(X3)0-1-OP(=Y3)(OR3a)(OR3b), —(X3)-SC(=Y3)OR3a and —(X3)-SC(=Y3)N(R3a)(R3b) wherein X3 is selected from the group consisting of C1-4 alkylene, C1-4 haloalkylene, C1-4 heteroalkylene, C2-4 alkenylene, and C2-4 alkynylene, R3a and R3b are each independently selected from the group consisting of C1-6 alkyl, C1-6 haloalkyl, C1-6 heteroalkyl, 3-7 membered cycloalkyl, 3-7 membered cycloalkyl-C1-4 alkyl, 3-7 membered heterocycloalkyl, 3-7 membered heterocycloalkyl-C1-4 alkyl, 5-6 membered heteroaryl, 5-6 membered heteroaryl-C1-4 alkyl, C6 aryl, C6 aryl-C1-4 alkyl and benzyl; Y3 is O, NR3d or S wherein R3d is hydrogen or C1-6 alkyl; wherein aliphatic or aromatic portion of R3 is independently further substituted with from 0 to 4 RA3 substituents selected from the group consisting of —F, —Cl, —Br, —I, —CN, —NO2, —SF5, —OH, —NH2, —CF3, =O, C1-6 alkyl, C1-6 haloalkyl, C1-6 heteroalkyl, C1-6 alkoxy, C1-6 alkylthio, 3-6 membered cycloalkyl, 3-6 membered heterocycloalkyl, —C(=O)N(H)(C1-6 alkyl), —C(=O)N(C1-6 alkyl)2, —C(=O)NH2, —C(=O)OC1-6 alkyl, —C(=O)OH, —N(H)C(=O)(C1-6 alkyl), —N(C1-6 alkyl)C(=O)(C1-6 alkyl), —N(H)C(=O)OC1-6 alkyl, —N(C1-6 alkyl)C(=O)OC1-6 alkyl, —S(O)1-2C1-6 alkyl, —N(H)S(O)1-2C1-6 alkyl, —N(C1-6 alkyl)S(O)1-2C1-6 alkyl, —S(O)0-1N(H)(C1-6 alkyl), —S(O)0-1N(C1-6 alkyl)2, —S(O)0-1NH2, —C(=O)C1-6 alkyl, —C(=NOH)C1-6 alkyl, —C(=NOC1-6 alkyl)C1-6 alkyl, —NHC(=O)N(H)(C1-6 alkyl), —NHC(=O)N(C1-6 alkyl)2, —NHC(=O)NH2, —N(C1-6 alkyl)C(=O)N(H)(C1-6 alkyl), —N(C1-6 alkyl)C(=O)NH2, —OC(=O)C1-6 alkyl, —OC(=O)OC1-6 alkyl, —OP(=O)(OC1-6 alkyl)2, —SC(=O)OC1-6 alkyl and —SC(=O)N(C1-6 alkyl)2; alternatively any two R3 substituents located on adjacent atoms are optionally combined to form a 5-6 membered heteroaryl ring comprising 1-2 heteroatoms selected from N, O and S and further comprising 0 to 4 R3a substituents; m is an integer from 0 to 4; the ring represented by the structure

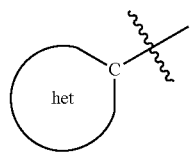 [SMILES: *C(C)C]

is a 4 to 10 membered heterocyclic ring comprising 1 to 2 heteroatoms selected from N, O and S, wherein said 4 to 7 membered heterocyclic ring is optionally substituted with 1 to 3 R4 groups; R4 is selected from the group consisting of —F, —Cl, —Br, —I, —(X4)0-1-CN, —(X4)0-1-NO2, —(X4)0-1-SF5, —(X4)0-1-OH, —(X4)0-1-NH2, —(X4)0-1-N(H)(R4a), —(X4)0-1-N(R4b)(R4a), —(X4)0-1-CF3, C1-6 alkyl, C1-6 haloalkyl, C1-6 heteroalkyl, C1-6 alkoxy, C1-6 alkylthio, —(X4)0-1-(3-10 membered heterocycloalkyl), —(X4)0-1-(5-10 membered heteroaryl), —(X4)0-1-(3-7 membered cycloalkyl), —(X4)0-1-C(=Y4)N(H)(R4a), —(X4)0-1-C(=Y4)NH2, —(X4)0-1-C(=Y4)N(R4a)(R4b), —(X4)0-1-C(=Y4)OR4a, —(X4)0-1-C(=Y4)OH, —(X4)0-1-N(H)C(=Y4)(R4a), —(X4)0-1-N(R4b)C(=Y4)(R4a), —(X4)0-1-N(H)C(=Y4)OR4a, —(X4)0-1-N(R4b)C(=Y4)OR4, —(X4)0-1-S(O)1-2R4a, —(X4)0-1-N(H)S(O)1-2R4a, —(X4)0-1-N(R4b)S(O)1-2R4a, —(X4)0-1-S(O)0-1N(H)(R4a), —(X4)0-1-S(O)0-1N(R4b)(R4a), —(X4)0-1-S(O)0-1NH2, —(X4)0-1-S(=O)(=NR4b)R4a, —(X4)0-1-C(=Y4)R4a, —(X4)0-1-C(=Y4)H, —(X4)0-1-C(=NOH)R4a, —(X4)0-1-C(=NOR4b)R4a, —(X4)0-1-NHC(=Y4)N(H)(R4a), —(X4)0-1-NHC(=Y4)NH2, —(X4)0-1-NHC(=Y4)N(R4b)(R4a), —(X4)0-1-NR4aC(=Y4)N(H)(R4a), —(X4)0-1-N(R4a)C(=Y4)NH2, —(X4)0-1-OC(=Y4)R4a, —(X4)0-1-OC(=Y4)H, —(X4)0-1-OC(=Y4)OR4a, —(X4)0-1-OP(=Y4)(OR4a)(OR4b), —SC(=Y4)OR4a and —SC(=Y4)N(R4a)(R4b) wherein R4a and R4b at each occurrence are each independently selected from the group consisting of C1-6 alkyl, C1-6 haloalkyl, C1-6 heteroalkyl, 6-10 membered aryl, 3-7 membered cycloalkyl, 5-10 membered heteroaryl, 3-7 membered heterocycloalkyl, 6-10 membered aryl-C1-4 alkyl, 3-7 membered cycloalkyl-C1-4 alkyl, 5-10 membered heteroaryl-C1-4 alkyl and 3-7 membered heterocycloalkyl-C1-4 alkyl, and X4 is selected from the group consisting of C1-4 alkylene, C1-4 haloalkylene, C1-4 heteroalkylene, C2-4 alkenylene and C2-4 alkynylene; Y4 is O, NR4c or S wherein R4c is hydrogen or C1-6 alkyl; wherein the aromatic and aliphatic portions of R4 is independently further substituted with 0 to 4 RA4 substituents selected from the group consisting of —F, —Cl, —Br, I, —CN, —NO2, —SF5, —OH, —NH2, —CF3, =O, C1-6 alkyl, C1-6 haloalkyl, C1-6 heteroalkyl, C1-6 alkoxy, C1-6 alkylthio, 3-6 membered cycloalkyl, 3-6 membered heterocycloalkyl, —C(=O)N(H)(C1-6 alkyl), —C(=O)N(C1-6 alkyl)2, —C(=O)NH2, —C(=O)OC1-6 alkyl, —C(=O)OH, —N(H)C(=O)(C1-6 alkyl), —N(C1-6 alkyl)C(=O)(C1-6 alkyl), —N(H)C(=O)OC1-6 alkyl, —N(C1-6 alkyl)C(=O)OC1-6 alkyl, —S(O)1-2C1-6 alkyl, —N(H)S(O)1-2C1-6 alkyl, —N(C1-6 alkyl)S(O)1-2C1-6 alkyl, —S(O)0-1N(H)(C1-6 alkyl), —S(O)0-1N(C1-6 alkyl)2, —S(O)0-1NH2, —C(=O)C1-6 alkyl, —C(=NOH)C1-6 alkyl, —C(=NOC1-6 alkyl)C1-6 alkyl, —NHC(=O)N(H)(C1-6 alkyl), —NHC(=O)N(C1-6 alkyl)2, —NHC(=O)NH2, —N(C1-6 alkyl)C(=O)N(H)(C1-6 alkyl), —N(C1-6 alkyl)C(=O)NH2, —OC(=O)C1-6 alkyl, —OC(=O)OC1-6 alkyl, —OP(=O)(OC1-6 alkyl)2, —SC(=O)OC1-6 alkyl and —SC(=O)N(C1-6 alkyl)2;

n is an integer from 0 to 5; R5 is absent or is selected from the group consisting of hydrogen, C1-6 alkyl, C1-6 haloalkyl, —OH, OR5a, —CN and halogen, wherein R5a is selected from the group consisting of C1-6 alkyl, C1-6 haloalkyl and C1-6 heteroalkyl; or optionally R4 and R5 are optionally combined to form a 5-7 membered cycloalkyl or heterocycloalkyl and is independently further substituted with 0-4 RA4 substituents; R6 is hydrogen, —F, —Cl, —Br, —I, C1-3 alkyl or C1-3 haloalkyl. In compounds of Formula I:

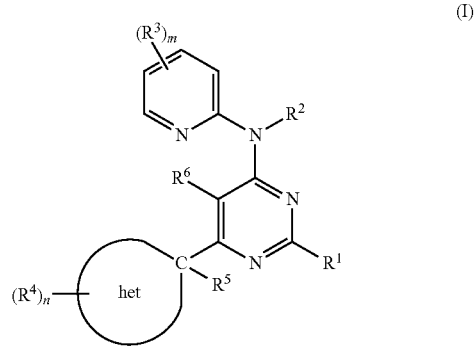

(I)

The R1, R2, R3, R4, R5, R6, m, n, and the ring represented by the structure

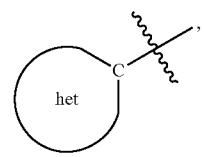 [SMILES: *C(C)C]

are all the same as described for compounds of Formula I-I with the proviso that a compound of formula I is not: 1-(3-(2-methyl-6-((4-methylpyridin-2-yl)amino)pyrimidin-4-yl)piperidin-1-yl)-2-phenylethanone.

In another aspect, the invention provides for pharmaceutical compositions comprising compounds of Formula I and Formula I-I.

In another aspect, the invention provides for methods of using compounds of Formula I and Formula I-I in an in vivo and ex vivo setting.

DETAILED DESCRIPTION OF THE INVENTION

A. Definitions

As used herein, the term "alkyl", by itself or as part of another substituent, means, unless otherwise stated, a straight or branched chain hydrocarbon radical, having the number of carbon atoms designated (i.e., C1-8 means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon ring system having 3 to 10 overall number of ring atoms (i.e., 3-10 membered cycloalkyl) and being fully saturated or having no more than one double bond between ring vertices for a 3-5 membered cycloalkyl and being saturated or having no more than two double bonds between ring vertices for 6 or larger membered cycloalkyl. As used herein, "cycloalkyl," "carbocyclic," or "carbocycle" is also meant to refer to bicyclic, polycyclic and spirocyclic hydrocarbon ring system such as, for example, bicyclo[2.2.1]heptane, pinane, bicyclo[2.2.2]octane, adamantane, norborene, spirocyclic C5-12 alkane, etc. As used herein, the terms, "alkenyl," "alkynyl," "cycloalkyl, ", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —CH2-CH2-O—CH3, —CH2-CH2-O—CF3, —CH2-CH2-NH—CH3, —CH2-CH2-N(CH3)-CH3, —CH2-S—CH2-CH3, —S(O)—CH3, —CH2-CH2-S(O)2-CH3, —CH=CH—O—CH3, —Si(CH3)3, —CH2-CH=N—OCH3, and —CH=CH=N(CH3)-CH3. Up to two heteroatoms can be consecutive, such as, for example, —CH2-NH—OCH3 and —CH2-O—Si(CH3)3.

The term "heterocycloalkyl," "heterocyclic," or "heterocycle" refers to a saturated or partially unsaturated ring system radical having from 3 to 10 overall number of ring atoms and containing from one to five heteroatoms selected from N, O, and S, wherein the nitrogen and sulfur atoms are optionally oxidized, nitrogen atom(s) are optionally quaternized, as ring atoms. Unless otherwise stated, a "heterocloalkyl," "heterocyclic," or "heterocycle" ring system can be a monocyclic, a bicyclic, spirocyclic or a polycyclic ring system. A "heterocycloalkyl," "heterocyclic," or "heterocycle" group can be attached to the remainder of the molecule through one or more ring carbons or heteroatoms. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and the like. A "heterocycloalkyl," "heterocyclic," or "heterocycle" can include mono- and poly-halogenated variants thereof.

The term "alkylene" by itself or as part of another substituent means a divalent radical derived from an alkane, as exemplified by —CH2CH2CH2CH2-. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —CH2-CH2-S—CH2CH2- and —CH2-S—CH2-CH2-NH—CH2-, —O—CH2-CH=CH—, —CH2-CH=C(H)CH2-O—CH2- and —S—CH2-C≡C—. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C1-4 haloalkyl" is mean to include trifluoromethyl, 2,2,2-trifluoroethyl, 4-chlorobutyl, 3-bromopropyl, difluoromethyl, and the like.

The term "aryl" means, unless otherwise stated, a polyunsaturated, typically aromatic, hydrocarbon ring, which can be a single ring or multiple rings (up to three rings) which are fused together. The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl and cycloalkyl) can be a variety of groups including, but not limited to, -halogen, —OR', —NR'R", —SR', —SiR'R"R'", —OC(O)R', —C(O)R', —CO2R', —CONR'R", —OC(O)NR'R", —NR"C(O)R', —NR'"C(O)NR'R", —NR"C(O)2R', —NHC(NH2)=NH, —NR'C(NH2)=NH, —NHC(NH2)=NR', —NR'"C(NR'R")=N—CN, —NR'"C(NR'R")=NOR', —NHC(NH2)=NR', —S(O)R', —S(O)2R', —S(O)2NR'R", —NR'S(O)2R", —NR'"S(O)2NR'R", —CN, —NO2, —(CH2)1-4-OR', —(CH2)1-4-NR'R", —(CH2)1-4-SR', —(CH2)1-4-SiR'R"R'", —(CH2)1-4-OC(O)R', —(CH2)1-4-C(O)R', —(CH2)1-4-CO2R', —(CH2)1-4CONR'R", in a number ranging from zero to (2m'+1), where m' is the total number of carbon atoms in such radical. R', R" and R'" each independently refer groups including, for example, hydrogen, unsubstituted C1-6 alkyl, unsubstituted heteroalkyl, unsubstituted aryl, aryl substituted with 1-3 halogens, unsubstituted C1-6 alkyl, C1-6 alkoxy or C1-6 thioalkoxy groups, or unsubstituted aryl-C1-4 alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substitutents for alkyl radicals, including heteroalkyl, alkylene, include for example, =O, =NR, =N—OR', =N—CN, =NH, wherein R' include substituents as described above. When a substituent for the alkyl radicals (including those groups often referred to as alkylene, alkenyl, alkynyl, heteroalkyl and cycloalkyl) contains an alkylene, alkenylene, alkynylene linker (e.g., —(CH2)1-4-NR'R" for alkylene), the alkylene linker includes halo variants as well. For example, the linker "—(CH2)1-4-" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R", —SR', —R', —CN, —NO2, —CO2R', —CONR'R", —C(O)R', —OC(O)NR'R", —NR"C(O)R', —NR"C(O)2R', —NR'C(O)NR"R'", —NHC(NH2)=NH, —NR'C(NH2)=NH, —NHC(NH2)=NR', —S(O)R', —S(O)2R', —S(O)2NR'R", —NR'S(O)2R", —N3, perfluoro-C1-4 alkoxy, and perfluoro-C1-4 alkyl, —(CH2)1-4-OR', —(CH2)1-4-NR'R", —(CH2)1-4-SR', —(CH2)1-4-SiR'R"R'", —(CH2)1-4-OC(O)R', —(CH2)1-4-C(O)R', —(CH2)1-4-CO2R', —(CH2)1-4CONR'R", in a number ranging from zero to the total number of open valences on the aromatic ring system; and where R', R" and R'" are independently selected from hydrogen, C1-6 alkyl, C3-6 cycloalkyl, C2-6 alkenyl, C2-6 alkynyl, unsubstituted aryl and heteroaryl, (unsubstituted aryl)-C1-4 alkyl, and unsubstituted aryloxy-C1-4 alkyl. Other suitable substituents include each of the above aryl substituents attached to a ring atom by an alkylene tether of from 1-4 carbon atoms. When a substituent for the aryl or heteroaryl group contains an alkylene, alkenylene, alkynylene linker (e.g., —(CH2)1-4-NR'R" for alkylene), the alkylene linker includes halo variants as well. For example, the linker "—(CH2)1-4-" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line " $\sim\!\!\sim\!\!\sim$ " that intersects a bond in a chemical structure indicate the point of attachment of the atom to which the wavy bond is connected in the chemical structure to the remainder of a molecule, or to the remainder of a fragment of a molecule.

As used herein, the representation of a group (e.g., Xd) in parenthesis followed by a subscript integer range (e.g., (Xd)0-2) means that the group can have the number of occurrences as designated by the integer range. For example, (Xd)0-1 means the group Xd can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4th edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as (C1-6)alkanoyloxymethyl, 1-((C1-6)alkanoyloxy)ethyl, 1-methyl-1-((C1-6)alkanoyloxy)ethyl, (C1-6)alkoxycarbonyloxymethyl, N—(C1-6)alkoxycarbonylaminomethyl, succinoyl, (C1-6)alkanoyl, alpha-amino (C1-4)alkanoyl, arylacyl and alpha-aminoacyl, or alpha-aminoacyl-alpha-aminoacyl, where each alpha-aminoacyl group is independently selected from the naturally occurring L-amino acids, P(O)(OH)2, —P(O)(O(C1-6)alkyl)2 or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., 14C or 3H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as 2H ("D"), 3H, 11C, 13C, 14C, 13N, 15N, 15O, 17O, 18O, 32P, 33P, 35S, 18F, 36Cl, 123I and 125I. Certain isotopically labeled compounds of the present invention (e.g., those labeled with 3H or 14C) are useful in compound and/or substrate tissue distribution assays. Tritiated (3H) and carbon-14 (14C) isotopes are useful for their ease of preparation and detectability. Further substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Positron emitting isotopes such as 15O, 13N, 11C, and 18F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some embodiments, a therapeutically effective amount is an amount of a chemical entity described herein sufficient to significantly decrease or delay neuronal cell death.

The term "administering" as used herein refers to contacting a neuron or portion thereof with a compound described herein. This includes administration of the compound to a subject in which the neuron or portion thereof is present, as well as introducing the inhibitor into a medium in which a neuro or portion thereof is cultured.

The term "patient" as used herein refers to any mammal, including humans, higher non-human primates, rodents domestic and farm animals such as cow, horses, dogs and cats. In one embodiment, the patient is a human patient.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The phrases "preventing axon degeneration," "preventing neuron degeneration," "preventing CNS neuron degeneration," "inhibiting axon degeneration," "inhibiting neuron degeneration" "inhibiting CNS neuron degeneration" as used herein include (i) the ability to inhibit or presenve axon or neuron degeneration in patients diagnosed as having a neurodegenerative disease or risk of developing a neurodegenerative disease and (ii) the ability to inhibit or prevent further axon or neuron degeneration in patients who are already suffering from, or have symptoms of a neurodegenerative disease. Preventing axon or neuron degeneration includes decreasing or inhibiting axon or neuron degeneration, which may be characterized by complete or partial inhibition or neuron or axon degeneration. This can be assessed, for example, by analysis of neurological function. The above-listed terms also include in vitro and ex vivo methods. Further, the phrases "preventing neuron degeneration" and "inhibiting neuron degeneration" in clued such inhibition with respect to the entire neuron or a portion thereof, such as the neuron ell body, axons and dendrites. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90% or even 100% decrease in one or more symptoms of a disorder of the nervous system, a condition of the nervous system that is secondary to a disease, condition, or therapy having a primary effect outside of the nervous system; an injury to the nervous system caused by physical, mechanical or chemical trauma, pain; an docular related neurodegeneration; memory loss; or a psychiatric disorder (e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity) in a subject or population compared to a control subject or population that does not receive the one or more agent described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a disorder of the nervous system; a condition of the nervous system that is secondary to a disease, condition, or therapy having a primary effect outside of the nervous system; an injury to the nervous system caused by physical, mechanical, or chemical trauma, pain; an ocular-related neurodegeneration; memory loss; or a psychiatric disorder in a subject or a subject population compared to a control subject or population not treated with the one or more compounds described herein.

The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the invention include cerebellar granule neurons, dorsal root ganglion neurons, and cortical neurons.

B. Compounds

In one aspect the invention provides compounds of Formula (I)

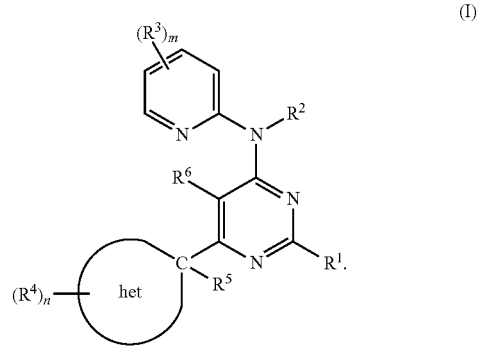

In Formula I, R1 is selected from the group consisting of C1-6 alkyl, C1-6 haloalkyl, C1-6 heteroalkyl, C1-6 alkoxy, 3-10 membered cycloalkyl, 3-10 membered heterocycloalkyl, 6-10 membered aryl, 5-10 membered heteroaryl, —OR1a, —SR1a, —N(H)(R1a), and —N(R1a)(R1b) wherein R1a and R1b are each independently selected from the group consisting of C1-6 alkyl, C1-6 haloalkyl, C1-6 heteroalkyl, 3-10 membered cycloalkyl and 3-10 membered heterocycloalkyl, and wherein the aliphatic and aromatic portions of R1 are independently further substituted with 0 to 5 RA1 substituents selected from the group consisting of —F, —Cl, —Br, —I, —CN, —NO2, —SF5, —OH, —NH2, —CF3, =O, C1-4 alkyl, C1-4 haloalkyl, C1-4 heteroalkyl, C1-4 alkoxy, C1-4 alkylthio, C1-4 alkylamino, C1-4 dialkylamino, R1c-C(=O)—, R1c-C(=O)N(H)—, R1c-C(=O)N(R1d)-, R1c-C(=O)O—, R1c-S(O)1-2-, R1c-S(O)1-2N(R1d)-, R1c-S(O)1-2N(H)—, 3-6 membered cycloalkyl, phenyl, 5-6 membered heteroaryl and 3-7 membered heterocycloalkyl, wherein R1c is selected from the group consisting of C1-6 alkyl, C1-6 haloalkyl, C5-6 heteroaryl, 3-7 membered heterocycloalkyl, phenyl and 3-6 membered cycloalkyl, R1d is selected from the group consisting of hydrogen, C1-3 alkyl and C1-3 haloalkyl, and wherein said 5-6 membered heteroaryl, phenyl, 3-6 membered cycloalkyl and 3-7 membered heterocycloalkyl of a RA1 substituent are substituted with from 0-4 substituents selected from —F, —Cl, —Br, I, —CN, —NO2, —SF5, —OH, —NH2, —CF3, C1-4 alkyl, C1-4 haloalkyl, C1-4 alkoxy, C1-4 alkylthio, C1-4 alkylamino and C1-4 dialkylamino. In Formula I, R2 is selected from the group consisting of hydrogen, C1-6 alkyl and C1-6 haloalkyl. R3 is selected from the group consisting of —F, —Cl, —Br, —I, —(X3)0-1-CN, —(X3)0-1-NO2, —(X3)0-1-SF5, —(X3)0-1-OH, —(X3)0-1-NH2, —(X3)0-1-N(H)(R3a), —(X3)0-1-N(R3b)(R3a), —(X3)0-1-CF3, C1-6 alkyl, C1-6 haloalkyl, C1-6 heteroalkyl, C1-6 alkoxy, C1-6 alkylthio, —(X3)0-1-3-7 membered cycloalkyl, —(X3)0-1-3-7 membered heterocycloalkyl, —(X3)0-1-5-6 membered heteroaryl, —(X3)0-1-C6 aryl, —(X3)0-1-C(=Y3)N(H)(R3a), —(X3)0-1-C(=Y3)NH2, —(X3)0-1-C(=Y3)N(R3a)(R3b), —(X3)0-1-C(=Y3)OR3a, —(X3)0-1-C(=Y3)OH, —(X3)0-1-N(H)C(=Y3)(R3a), —(X3)0-1-N(R3b)C(=Y3)(R3a), —(X3)0-1-N(H)C(=Y3)OR3a, —(X3)0-1-N(R3b)C(=Y3)OR3a, —(X3)0-1-S(O)1-2R3a, —(X3)0-1-N(H)S(O)1-2R3a, —(X3)0-1-N(R3b)S(O)1-2R3a, —(X3)0-1-S(O)0-1N(H)(R3a), —(X3)0-1-S(O)0-1N(R3b)(R3a), —(X3)0-1-S(O)0-1NH2, —(X4)0-1-S(=O)(=NR3b)R3a, —(X3)0-1-C(=Y3)R3a, —(X3)0-1-C(=Y3)H, —(X3)0-1-C(=NOH)R3a, —(X3)0-1-C(=NOR3b)R3a, —(X3)0-1-NHC(=Y3)N(H)(R3a), —(X3)0-1-NHC(=Y3)NH2, —(X3)0-1-NHC(=Y3)N(R3b)(R3a), —(X3)0-1-N(R3a)C(=Y3)N(H)(R3a), —(X3)0-1-N(R3a)C(=Y3)NH2, —(X3)0-1-OC(=Y3)R3a, —(X3)0-1-OC(=Y3)H, —(X3)0-1-OC(=Y3)OR3a, —(X3)0-1-OP(=Y3)(OR3a)(OR3b), —(X3)-SC(=Y3)OR3a and —(X3)-SC(=Y3)N(R3a)(R3b) wherein X3 is selected from the group consisting of C1-4 alkylene, C1-4 haloalkylene, C1-4 heteroalkylene, C2-4 alkenylene, and C2-4 alkynylene, R3a and R3b are each independently selected from the group consisting of C1-6 alkyl, C1-6 haloalkyl, C1-6 heteroalkyl, 3-7 membered cycloalkyl, 3-7 membered cycloalkyl-C1-4 alkyl, 3-7 membered heterocycloalkyl, 3-7 membered heterocycloalkyl-C1-4 alkyl, 5-6 membered heteroaryl, 5-6 membered heteroaryl-C1-4 alkyl, C6 aryl, C6 aryl-C1-4 alkyl and benzyl; Y3 is O, NR3d or S wherein R3d is hydrogen or C1-6 alkyl; wherein aliphatic or aromatic portion of R3 is independently further substituted with from 0 to 4 RA3 substituents selected from the group consisting of —F, —Cl, —Br, —I, —CN, —NO2, —SF5, —OH, —NH2, —CF3, =O, C1-6 alkyl, C1-6 haloalkyl, C1-6 heteroalkyl, C1-6 alkoxy, C1-6 alkylthio, 3-6 membered cycloalkyl, 3-6 membered heterocycloalkyl, —C(=O)N(H)(C1-6 alkyl), —C(=O)N(C1-6 alkyl)2, —C(=O)NH2, —C(=O)OC1-6 alkyl, —C(=O)OH, —N(H)C(=O)(C1-6 alkyl), —N(C1-6 alkyl)C(=O)(C1-6 alkyl), —N(H)C(=O)OC1-6 alkyl, —N(C1-6 alkyl)C(=O)OC1-6 alkyl, —S(O)1-2C1-6 alkyl, —N(H)S(O)1-2C1-6 alkyl, —N(C1-6 alkyl)S(O)1-2C1-6 alkyl, —S(O)0-1N(H)(C1-6 alkyl), —S(O)0-1N(C1-6 alkyl)2, —S(O)0-1NH2, —C(=O)C1-6 alkyl, —C(=NOH)C1-6 alkyl, —C(=NOC1-6 alkyl)C1-6 alkyl, —NHC(=O)N(H)(C1-6 alkyl), —NHC(=O)N(C1-6 alkyl)2, —NHC(=O)NH2, —N(C1-6 alkyl)C(=O)N(H)(C1-6 alkyl), —N(C1-6 alkyl)C(=O)NH2, —OC(=O)C1-6 alkyl, —OC(=O)OC1-6 alkyl, —OP(=O)(OC1-6 alkyl)2, —SC(=O)OC1-6 alkyl and —SC(=O)N(C1-6 alkyl)2; alternatively any two R3 substituents located on adjacent atoms are optionally combined to form a 5-6 membered heteroaryl ring comprising 1-2 heteroatoms selected from N, O and S and further comprising 0 to 4 R3a substituents;

m is an integer from 0 to 4.

In Formula I, the ring represented by the structure

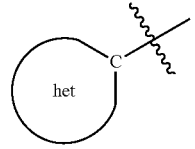

is a 4 to 10 membered heterocyclic ring comprising 1 to 2 heteroatoms selected from N, O and S, wherein said 4 to 7 membered heterocyclic ring is optionally substituted with 1 to 3 R4 groups;

R4 is selected from the group consisting of —F, —Cl, —Br, —I, —(X4)0-1-CN, —(X4)0-1-NO2, —(X4)0-1-SF5, —(X4)0-1-OH, —(X4)0-1-NH2, —(X4)0-1-N(H)(R4a), —(X4)0-1-N(R4b)(R4a), —(X4)0-1-CF3, C1-6 alkyl, C1-6 haloalkyl, C1-6 heteroalkyl, C1-6 alkoxy, C1-6 alkylthio, —(X4)0-1-(3-10 membered heterocycloalkyl), —(X4)0-1-(5-10 membered heteroaryl), —(X4)0-1-(3-7 membered cycloalkyl), —(X4)0-1-C(=Y4)N(H)(R4a), —(X4)0-1-C(=Y4)NH2, —(X4)0-1-C(=Y4)N(R4a)(R4b), —(X4)0-1-C(=Y4)OR4a, —(X4)0-1-C(=Y4)OH, —(X4)0-1-N(H)C(=Y4)(R4a), —(X4)0-1-N(R4b)C(=Y4)(R4a), —(X4)0-1-N(H)C(=Y4)OR4a, —(X4)0-1-N(R4b)C(=Y4)OR4, —(X4)0-1-S(O)1-2R4a, —(X4)0-1-N(H)S(O)1-2R4a, —(X4)0-1-N(R4b)S(O)1-2R4a, —(X4)0-1-S(O)0-1N(H)(R4a), —(X4)0-1-S(O)0-1N(R4b)(R4a), —(X4)0-1-S(O)0-1NH2, —(X4)0-1-S(=O)(=NR4b)R4a, —(X4)0-1-C(=Y4)R4a, —(X4)0-1-C(=Y4)H, —(X4)0-1-C(=NOH)R4a, —(X4)0-1-C(=NOR4b)R4a, —(X4)0-1-NHC(=Y4)N(H)(R4a), —(X4)0-1-NHC(=Y4)NH2, —(X4)0-1-NHC(=Y4)N(R4b)(R4a), —(X4)0-1-NR4aC(=Y4)N(H)(R4a), —(X4)0-1-N(R4a)C(=Y4)NH2, —(X4)0-1-OC(=Y4)R4a, —(X4)0-1-OC(=Y4)H, —(X4)0-1-OC(=Y4)OR4a, —(X4)0-1-OP(=Y4)(OR4a)(OR4b), —SC(=Y4)OR4a and —SC(=Y4)N(R4a)(R4b) wherein R4a and R4b at each occurrence are each independently selected from the group consisting of C1-6 alkyl, C1-6 haloalkyl, C1-6 heteroalkyl, 6-10 membered aryl, 3-7 membered cycloalkyl, 5-10 membered heteroaryl, 3-7 membered heterocycloalkyl, 6-10 membered aryl-C1-4 alkyl, 3-7 membered cycloalkyl-C1-4 alkyl, 5-10 membered heteroaryl-C1-4 alkyl and 3-7 membered heterocycloalkyl-C1-4 alkyl, and X4 is selected from the group consisting of C1-4 alkylene, C1-4 haloalkylene, C1-4 heteroalkylene, C2-4 alkenylene and C2-4 alkynylene; Y4 is O, NR4c or S wherein R4c is hydrogen or C1-6 alkyl; wherein the aromatic and aliphatic portions of R4 is independently further substituted with 0 to 4 RA4 substituents selected from the group consisting of —F, —Cl, —Br, I, —CN, —NO2, —SF5, —OH, —NH2, —CF3, =O, C1-6 alkyl, C1-6 haloalkyl, C1-6 heteroalkyl, C1-6 alkoxy, C1-6 alkylthio, 3-6 membered cycloalkyl, 3-6 membered heterocycloalkyl, —C(=O)N(H)(C1-6 alkyl), —C(=O)N(C1-6 alkyl)2, —C(=O)NH2, —C(=O)OC1-6 alkyl, —C(=O)OH, —N(H)C(=O)(C1-6 alkyl), —N(C1-6 alkyl)C(=O)(C1-6 alkyl), —N(H)C(=O)OC1-6 alkyl, —N(C1-6 alkyl)C(=O)OC1-6 alkyl, —S(O)1-2C1-6 alkyl, —N(H)S(O)1-2C1-6 alkyl, —N(C1-6 alkyl)S(O)1-2C1-6 alkyl, —S(O)0-1N(H)(C1-6 alkyl), —S(O)0-1N(C1-6 alkyl)2, —S(O)0-1NH2, —C(=O)C1-6 alkyl, —C(=NOH)C1-6 alkyl, —C(=NOC1-6 alkyl)C1-6 alkyl, —NHC(=O)N(H)(C1-6 alkyl), —NHC(=O)N(C1-6 alkyl)2, —NHC(=O)NH2, —N(C1-6 alkyl)C(=O)N(H)(C1-6 alkyl), —N(C1-6 alkyl)C(=O)NH2, —OC(=O)C1-6 alkyl, —OC(=O)OC1-6 alkyl, —OP(=O)(OC1-6 alkyl)2, —SC(=O)OC1-6 alkyl and —SC(=O)N(C1-6 alkyl)2. In Formula I, n is an integer from 0 to 5. In Formula I, R5 is absent or is selected from the group consisting of hydrogen, C1-6 alkyl, C1-6 haloalkyl, —OH, OR5a, —CN and halogen, wherein R5a is selected from the group consisting of C1-6 alkyl, C1-6 haloalkyl and C1-6 heteroalkyl; or optionally R4 and R5 are optionally combined to form a 5-7 membered cycloalkyl or heterocycloalkyl and is independently further substituted with 0-4 RA4 substituents. R6 is hydrogen, —F, —Cl, —Br, —I, C1-3 alkyl or C1-3 haloalkyl; and with the proviso that a compound of formula I is not:

1-(3-(2-methyl-6-((4-methylpyridin-2-yl)amino)pyrimidin-4-yl)piperidin-1-yl)-2-phenylethanone.

In another aspect, the invention provides compounds of Formula (I-I)

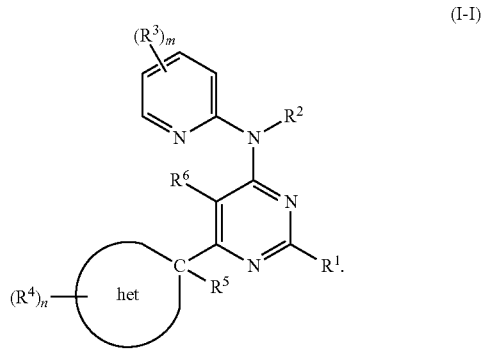

(I-I)

In Formula I-I, R1 is selected from the group consisting of C1-6 alkyl, C1-6 haloalkyl, C1-6 heteroalkyl, C1-6 alkoxy 3-10 membered cycloalkyl, 3-10 membered heterocycloalkyl, 6-10 membered aryl, 5-10 membered heteroaryl, —OR1a, —SR1a, —N(H)(R1a), and —N(R1a)(R1b) wherein R1a and R1b are each independently selected from the group consisting of C1-6 alkyl, C1-6 haloalkyl, C1-6 heteroalkyl, 3-10 membered cycloalkyl and 3-10 membered heterocycloalkyl, and wherein the aliphatic and aromatic portions of R1 are independently further substituted with 0 to 5 RA1 substituents selected from the group consisting of —F, —Cl, —Br, —I, —CN, —NO2, —SF5, —OH, —NH2, —CF3, =O, C1-4 alkyl, C1-4 haloalkyl, C1-4 heteroalkyl, C1-4 alkoxy, C1-4 alkylthio, C1-4 alkylamino, C1-4 dialkylamino, R1c-C(=O)—, R1c-C(=O)N(H)—, R1c-C(=O)N(R1d)-, R1c-C(=O)O—, R1c-S(O)1-2-, R1c-S(O)1-2N(R1d)-, R1c-S(O)1-2N(H)—, 3-6 membered cycloalkyl, phenyl, 5-6 membered heteroaryl and 3-7 membered heterocycloalkyl, wherein R1c is selected from the group consisting of C1-6 alkyl, C1-6 haloalkyl, C5-6 heteroaryl, 3-7 membered heterocycloalkyl, phenyl and 3-6 membered cycloalkyl, R1d is selected from the group consisting of hydrogen, C1-3 alkyl and C1-3 haloalkyl, and wherein said 5-6 membered heteroaryl, phenyl, 3-6 membered cycloalkyl and 3-7 membered heterocycloalkyl of a RA1 substituent are substituted with from 0-4 substituents selected from —F, —Cl, —Br, I, —CN, —NO2, —SF5, —OH, —NH2, —CF3, C1-4 alkyl, C1-4 haloalkyl, C1-4 alkoxy, C1-4 alkylthio, C1-4 alkylamino and C1-4 dialkylamino. In Formula I, R2 is selected from the group consisting of hydrogen, C1-6 alkyl and C1-6 haloalkyl. R3 is selected from the group consisting of —F, —Cl, —Br, —I, —(X3)0-1-CN, —(X3)0-1-NO2, —(X3)0-1-SF5, —(X3)0-1-OH, —(X3)0-1-NH2, —(X3)0-1-N(H)(R3a), —(X3)0-1-N(R3b)(R3a), —(X3)0-1-CF3, C1-6 alkyl, C1-6 haloalkyl, C1-6 heteroalkyl, C1-6 alkoxy, C1-6 alkylthio, —(X3)0-1-3-7 membered cycloalkyl, —(X3)0-1-3-7 membered heterocycloalkyl, —(X3)0-1-5-6 membered heteroaryl, —(X3)0-1-C6 aryl, —(X3)0-1-C(=Y3)N(H)(R3a), —(X3)0-1-C(=Y3)NH2, —(X3)0-1-C(=Y3)N(R3a)(R3b), —(X3)0-1-C(=Y3)OR3a, —(X3)0-1-C(=Y3)OH, —(X3)0-1-N(H)C(=Y3)(R3a), —(X3)0-1-N(R3b)C(=Y3)(R3a), —(X3)0-1-N(H)C(=Y3)OR3a, —(X3)0-1-N(R3b)C(=Y3)OR3a, —(X3)0-1-S(O)1-2R3a, —(X3)0-1-N(H)S(O)1-2R3a, —(X3)0-1-N(R3b)S(O)1-2R3a, —(X3)0-1-S(O)0-1N(H)(R3a), —(X3)0-1-S(O)0-1N(R3b)(R3a), —(X3)0-1-S(O)0-1NH2, —(X4)0-1-S(=O)(=NR3b)R3a, —(X3)0-1-C(=Y3)R3a, —(X3)0-1-C(=Y3)H, —(X3)0-1-C(=NOH)R3a, —(X3)0-1-C(=NOR3b)R3a, —(X3)0-1-NHC(=Y3)N(H)(R3a), —(X3)0-1-NHC(=Y3)NH2, —(X3)0-1-NHC(=Y3)N(R3b)(R3a), —(X3)0-1-N(R3a)C(=Y3)N(H)(R3a), —(X3)0-1-N(R3a)C(=Y3)NH2, —(X3)0-1-OC(=Y3)R3a, —(X3)0-1-OC(=Y3)H, —(X3)0-1-OC(=Y3)OR3a, —(X3)0-1-OP(=Y3)(OR3a)(OR3b), —(X3)-SC(=Y3)OR3a and —(X3)-SC(=Y3)N(R3a)(R3b) wherein X3 is selected from the group consisting of C1-4 alkylene, C1-4 haloalkylene, C1-4 heteroalkylene, C2-4 alkenylene, and C2-4 alkynylene, R3a and R3b are each independently selected from the group consisting of C1-6 alkyl, C1-6 haloalkyl, C1-6 heteroalkyl, 3-7 membered cycloalkyl, 3-7 membered cycloalkyl-C1-4 alkyl, 3-7 membered heterocycloalkyl, 3-7 membered heterocycloalkyl-C1-4 alkyl, 5-6 membered heteroaryl, 5-6 membered heteroaryl-C1-4 alkyl, C6 aryl, C6 aryl-C1-4 alkyl and benzyl; Y3 is O, NR3d or S wherein R3d is hydrogen or C1-6 alkyl; wherein aliphatic or aromatic portion of R3 is independently further substituted with from 0 to 4 RA3 substituents selected from the group consisting of —F, —Cl, —Br, —I, —CN, —NO2, —SF5, —OH, —NH2, —CF3, =O, C1-6 alkyl, C1-6 haloalkyl, C1-6 heteroalkyl, C1-6 alkoxy, C1-6 alkylthio, 3-6 membered cycloalkyl, 3-6 membered heterocycloalkyl, —C(=O)N(H)(C1-6 alkyl), —C(=O)N(C1-6 alkyl)2, —C(=O)NH2, —C(=O)OC1-6 alkyl, —C(=O)OH, —N(H)C(=O)(C1-6 alkyl), —N(C1-6 alkyl)C(=O)(C1-6 alkyl), —N(H)C(=O)OC1-6 alkyl, —N(C1-6 alkyl)C(=O)OC1-6 alkyl, —S(O)1-2C1-6 alkyl, —N(H)S(O)1-2C1-6 alkyl, —N(C1-6 alkyl)S(O)1-2C1-6 alkyl, —S(O)0-1N(H)(C1-6 alkyl), —S(O)0-1N(C1-6 alkyl)2, —S(O)0-1NH2, —C(=O)C1-6 alkyl, —C(=NOH)C1-6 alkyl, —C(=NOC1-6 alkyl)C1-6 alkyl, —NHC(=O)N(H)(C1-6 alkyl), —NHC(=O)N(C1-6 alkyl)2, —NHC(=O)NH2, —N(C1-6 alkyl)C(=O)N(H)(C1-6 alkyl), —N(C1-6 alkyl)C(=O)NH2, —OC(=O)C1-6 alkyl, —OC(=O)OC1-6 alkyl, —OP(=O)(OC1-6 alkyl)2, —SC(=O)OC1-6 alkyl and —SC(=O)N(C1-6 alkyl)2; alternatively any two R3 substituents located on adjacent atoms are optionally combined to form a 5-6 membered heteroaryl ring comprising 1-2 heteroatoms selected from N, O and S and further comprising 0 to 4 R3a substituents;

m is an integer from 0 to 4. In Formula I, the ring represented by the structure

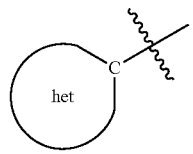 [SMILES: *C(C)C]

is a 4 to 10 membered heterocyclic ring comprising 1 to 2 heteroatoms selected from N, O and S, wherein said 4 to 7 membered heterocyclic ring is optionally substituted with 1 to 3 R4 groups;

R4 is selected from the group consisting of —F, —Cl, —Br, —I, —(X4)0-1-CN, —(X4)0-1-NO2, —(X4)0-1-SF5, —(X4)0-1-OH, —(X4)0-1-NH2, —(X4)0-1-N(H)(R4a), —(X4)0-1-N(R4b)(R4a), —(X4)0-1-CF3, C1-6 alkyl, C1-6 haloalkyl, C1-6 heteroalkyl, C1-6 alkoxy, C1-6 alkylthio, —(X4)0-1-(3-10 membered heterocycloalkyl), —(X4)0-1-(5-10 membered heteroaryl), —(X4)0-1-(3-7 membered cycloalkyl), —(X4)0-1-C(=Y4)N(H)(R4a), —(X4)0-1-C(=Y4)NH2, —(X4)0-1-C(=Y4)N(R4a)(R4b), —(X4)0-1-C(=Y4)OR4a, —(X4)0-1-C(=Y4)OH, —(X4)0-1-N(H)C(=Y4)(R4a), —(X4)0-1-N(R4b)C(=Y4)(R4a), —(X4)0-1-N(H)C(=Y4)OR4a, —(X4)0-1-N(R4b)C(=Y4)OR4, —(X4)0-1-S(O)1-2R4a, —(X4)0-1-N(H)S(O)1-2R4a, —(X4)0-1-N(R4b)S(O)1-2R4a, —(X4)0-1-S(O)0-1N(H)(R4a), —(X4)0-1-S(O)0-1N(R4b)(R4a), —(X4)0-1-S(O)0-1NH2, —(X4)0-1-S(=O)(=NR4b)R4a, —(X4)0-1-C(=Y4)R4a, —(X4)0-1-C(=Y4)H, —(X4)0-1-C(=NOH)R4a, —(X4)0-1-C(=NOR4b)R4a, —(X4)0-1-NHC(=Y4)N(H)(R4a), —(X4)0-1-NHC(=Y4)NH2, —(X4)0-1-NHC(=Y4)N(R4b)(R4a), —(X4)0-1-NR4aC(=Y4)N(H)(R4a), —(X4)0-1-N(R4a)C(=Y4)NH2, —(X4)0-1-OC(=Y4)R4a, —(X4)0-1-OC(=Y4)H, —(X4)0-1-OC(=Y4)OR4a, —(X4)0-1-OP(=Y4)(OR4a)(OR4b), —SC(=Y4)OR4a and —SC(=Y4)N(R4a)(R4b) wherein R4a and R4b at each occurrence are each independently selected from the group consisting of C1-6 alkyl, C1-6 haloalkyl, C1-6 heteroalkyl, 6-10 membered aryl, 3-7 membered cycloalkyl, 5-10 membered heteroaryl, 3-7 membered heterocycloalkyl, 6-10 membered aryl-C1-4 alkyl, 3-7 membered cycloalkyl-C1-4 alkyl, 5-10 membered heteroaryl-C1-4 alkyl and 3-7 membered heterocycloalkyl-C1-4 alkyl, and X4 is selected from the group consisting of C1-4 alkylene, C1-4 haloalkylene, C1-4 heteroalkylene, C2-4 alkenylene and C2-4 alkynylene; Y4 is O, NR4c or S wherein R4c is hydrogen or C1-6 alkyl; wherein the aromatic and aliphatic portions of R4 is independently further substituted with 0 to 4 RA4 substituents selected from the group consisting of —F, —Cl, —Br, I, —CN, —NO2, —SF5, —OH, —NH2, —CF3, =O, C1-6 alkyl, C1-6 haloalkyl, C1-6 heteroalkyl, C1-6 alkoxy, C1-6 alkylthio, 3-6 membered cycloalkyl, 3-6 membered heterocycloalkyl, —C(=O)N(H)(C1-6 alkyl), —C(=O)N(C1-6 alkyl)2, —C(=O)NH2, —C(=O)OC1-6 alkyl, —C(=O)OH, —N(H)C(=O)(C1-6 alkyl), —N(C1-6 alkyl)C(=O)(C1-6 alkyl), —N(H)C(=O)OC1-6 alkyl, —N(C1-6 alkyl)C(=O)OC1-6 alkyl, —S(O)1-2C1-6 alkyl, —N(H)S(O)1-2C1-6 alkyl, —N(C1-6 alkyl)S(O)1-2C1-6 alkyl, —S(O)0-1N(H)(C1-6 alkyl), —S(O)0-1N(C1-6 alkyl)2, —S(O)0-1NH2, —C(=O)C1-6 alkyl, —C(=NOH)C1-6 alkyl, —C(=NOC1-6 alkyl)C1-6 alkyl, —NHC(=O)N(H)(C1-6 alkyl), —NHC(=O)N(C1-6 alkyl)2, —NHC(=O)NH2, —N(C1-6 alkyl)C(=O)N(H)(C1-6 alkyl), —N(C1-6 alkyl)C(=O)NH2, —OC(=O)C1-6 alkyl, —OC(=O)OC1-6 alkyl, —OP(=O)(OC1-6 alkyl)2, —SC(=O)OC1-6 alkyl and —SC(=O)N(C1-6 alkyl)2. In Formula I, n is an integer from 0 to 5. In Formula I, R5 is absent or is selected from the group consisting of hydrogen, C1-6 alkyl, C1-6 haloalkyl, —OH, OR5a, —CN and halogen, wherein R5a is selected from the group consisting of C1-6 alkyl, C1-6 haloalkyl and C1-6 heteroalkyl; or optionally R4 and R5 are optionally combined to form a 5-7 membered cycloalkyl or heterocycloalkyl and is independently further substituted with 0-4 RA4 substituents. R6 is hydrogen, —F, —Cl, —Br, —I, C1-3 alkyl or C1-3 haloalkyl.

In one embodiment, in compounds of Formula I or Formula I-I, the 4 to 10 membered heterocyclic ring represented by the structure

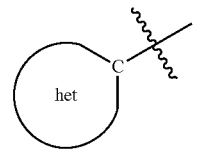 [SMILES: *C(C)C]

comprises an optionally substituted ring selected from the group consisting of morpholine, morpholinone, piperazine, piperazinone, thiomorpholine, thiomorpholinone, homopiperidine, homopiperidinone, piperidine, valerolactam, pyrrolidine, butyrolactam, azetidine, azetidinone, thiazepane-1,1-dioxide, thiazinane-1,1-dioxide, isothiazolidine-1,1-dioxide, pyridinone, tetrahydropyran, oxetane and tetrahydrofuran attached to the remainder of the compound represented by formula I.

In another embodiment, in compounds of Formula I or Formula I-I, the 4 to 10 membered heterocyclic ring represented by the structure

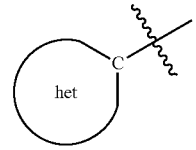 [SMILES: *C(C)C]

is selected from the group consisting of:

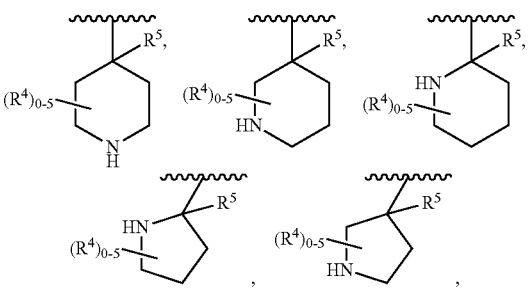

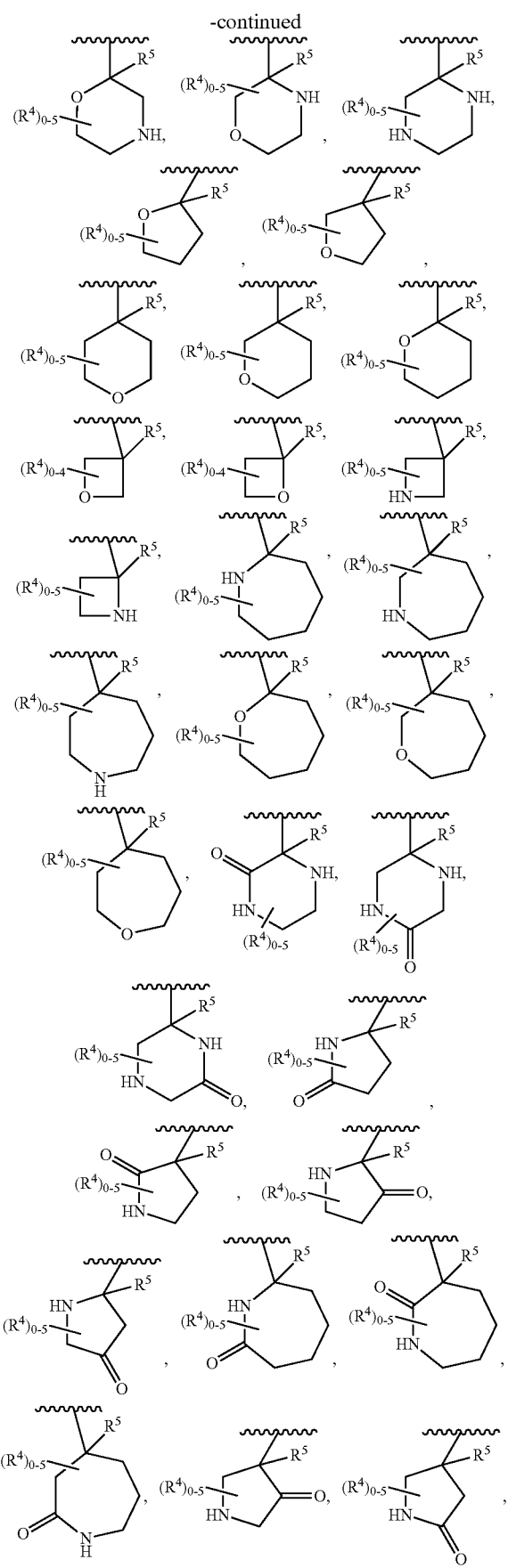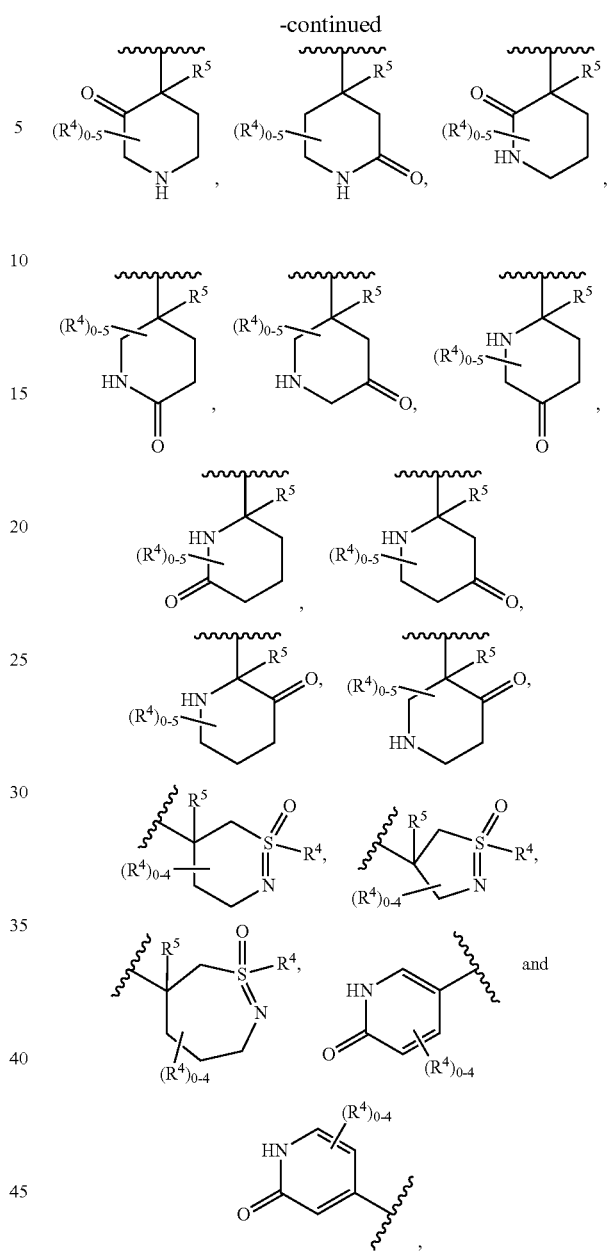
wherein the R4 substituent, if present replaces a hydrogen atom that is attached to a carbon ring atom or a hydrogen atom attached to a nitrogen ring atom of said 4-10 membered heterocyclic ring.
In another embodiment, in compounds of Formula I or Formula I-I, the 4 to 10 membered heterocyclic ring represented by the structure
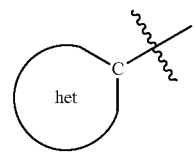 [SMILES: *C(C)C]
is selected from the group consisting of:

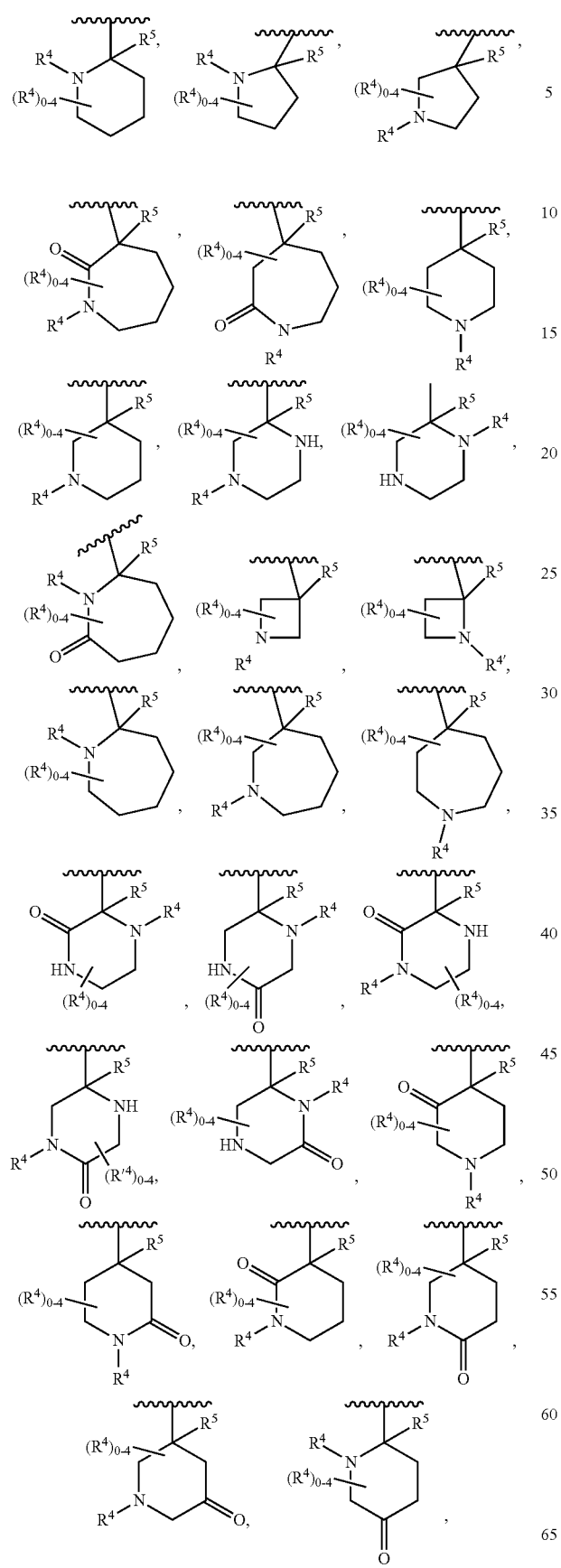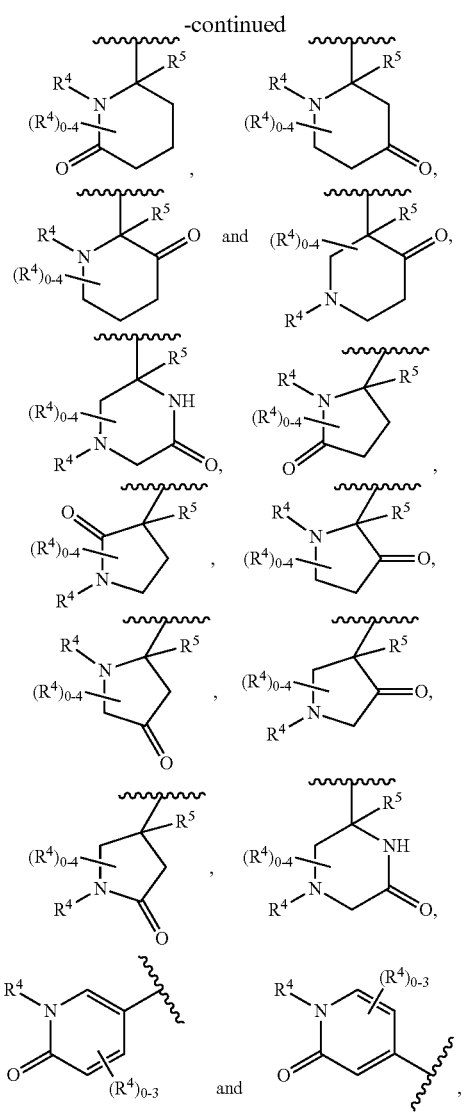

wherein R4 attached to the nitrogen atom of said 4 to 10 membered heterocyclic ring is selected from the group consisting of —(X4)0-1-CN, —(X4)0-1-NO2, —(X4)0-1-SF5, —(X4)0-1-OH, —(X4)0-1-NH2, —(X4)0-1-N(H)(R4a), —(X4)0-1-N(R4b)(R4a), —(X4)0-1-CF3, C1-6 alkyl, C1-6 haloalkyl, C1-6 heteroalkyl, C1-6 alkoxy, C1-6 alkylthio, —(X4)0-1-(3-10 membered heterocycloalkyl), —(X4)0-1-(5-10 membered heteroaryl), —(X4)0-1-(3-7 membered cycloalkyl), —(X4)0-1-C(=Y4)N(H)(R4a), —(X4)0-1-C(=Y4)NH2, —(X4)0-1-C(=Y4)N(R4a)(R4b), —(X4)0-1-C(=Y4)OR4a, —(X4)0-1-C(=Y4)OH, —(X4)0-1-N(H)C(=Y4)(R4a), —(X4)0-1-N(R4b)C(=Y4)(R4a), —(X4)0-1-N(H)C(=Y4)OR4a, —(X4)0-1-N(R4b)C(=Y4)OR4, —(X4)0-1-S(O)1-2R4a, —(X4)0-1-N(H)S(O)1-2R4a, —(X4)0-1-N(R4b)S(O)1-2R4a, —(X4)0-1-S(O)0-1N(H)(R4a), —(X4)0-1-S(O)0-1N(R4b)(R4a), —(X4)0-1-S(O)0-1NH2, —(X4)0-1-S(=O)(=NR4b)R4a, —(X4)0-1-C(=Y4)R4a, —(X4)0-1-C(=Y4)H, —(X4)0-1-C(=NOH)R4a, —(X4)0-1-C(=NOR4b)R4a, —(X4)0-1-NHC(=Y4)N(H)(R4a), —(X4)0-1-NHC(=Y4)NH2, —(X4)0-1-NHC(=Y4)N(R4b)(R4a), —(X4)0-1-NR4aC(=Y4)N(H)(R4a), —(X4)0-1-N(R4a)C(=Y4)NH2, —(X4)0-1-OC(=Y4)R4a, —(X4)0-1-OC(=Y4)H, —(X4)

0-1-OC(=Y4)OR4a, —(X4)0-1-OP(=Y4)(OR4a)(OR4b), —SC(=Y4)OR4a and —SC(=Y4)N(R4a)(R4b) wherein R4a and R4b at each occurrence are each independently selected from the group consisting of C1-6 alkyl, C1-6 haloalkyl, C1-6 heteroalkyl, 6-10 membered aryl, 3-7 membered cycloalkyl, 5-10 membered heteroaryl, 3-7 membered heterocycloalkyl, 6-10 membered aryl-C1-4 alkyl, 3-7 membered cycloalkyl-C1-4 alkyl, 5-10 membered heteroaryl-C1-4 alkyl and 3-7 membered heterocycloalkyl-C1-4 alkyl, and X4 is selected from the group consisting of C1-4 alkylene, C1-4 haloalkylene, C1-4 heteroalkylene, C2-4 alkenylene and C2-4 alkynylene; Y4 is O, NR4c or S wherein R4c is hydrogen or C1-6 alkyl; wherein the aromatic and aliphatic portions of R4 is independently further substituted with 0 to 4 RA4 substituents selected from the group consisting of —F, —Cl, —Br, I, —CN, —NO2, —SF5, —OH, —NH2, —CF3, =O, C1-6 alkyl, C1-6 haloalkyl, C1-6 heteroalkyl, C1-6 alkoxy, C1-6 alkylthio, 3-6 membered cycloalkyl, 3-6 membered heterocycloalkyl, —C(=O)N(H)(C1-6 alkyl), —C(=O)N(C1-6 alkyl)2, —C(=O)NH2, —C(=O)OC1-6 alkyl, —C(=O)OH, —N(H)C(=O)(C1-6 alkyl), —N(C1-6 alkyl)C(=O)(C1-6 alkyl), —N(H)C(=O)OC1-6 alkyl, —N(C1-6 alkyl)C(=O) OC1-6 alkyl, —S(O)1-2C1-6 alkyl, —N(H)S(O)1-2C1-6 alkyl, —N(C1-6 alkyl)S(O)1-2C1-6 alkyl, —S(O)0-1N(H) (C1-6 alkyl), —S(O)0-1N(C1-6 alkyl)2, —S(O)0-1NH2, —C(=O)C1-6 alkyl, —C(=NOH)C1-6 alkyl, —C(=NOC1-6 alkyl)C1-6 alkyl, —NHC(=O)N(H)(C1-6 alkyl), —NHC(=O)N(C1-6 alkyl)2, —NHC(=O)NH2, —N(C1-6 alkyl)C(=O)N(H)(C1-6 alkyl), —N(C1-6 alkyl) C(=O)NH2, —OC(=O)C1-6 alkyl, —OC(=O)OC1-6 alkyl, —OP(=O)(OC1-6 alkyl)2, —SC(=O)OC1-6 alkyl and —SC(=O)N(C1-6 alkyl)2; and the remainder R4, if present on said 4-10 membered heterocyclic ring, is each independently selected from the group consisting of: —F, —Cl, —Br, I, —(X4)0-1-CN, —(X4)0-1-NO2, —(X4)0-1-SF5, —(X4)0-1-OH, —(X4)0-1-NH2, —(X4)0-1-N(H) (R4a), —(X4)0-1-N(R4b)(R4a), —(X4)0-1-CF3, C1-6 alkyl, C1-6 haloalkyl, C1-6 heteroalkyl, C1-6 alkoxy and C1-6 alkylthio wherein X4 is selected from the group consisting of C1-4 alkylene, C1-4 haloalkylene, C1-4 heteroalkylene, C2-4 alkenylene and C2-4 alkynylene and R4a and R4b is each independently selected from the group consisting of: C1-6 alkyl, C1-6 haloalkyl and C1-6 heteroalkyl.

In another embodiment, in compounds of Formula I or Formula I-I, R4 is attached to a nitrogen atom (if present) in said 4-10 membered heterocyclic ring or is attached to a carbon atom of said 4-10 membered heterocyclic ring, wherein R4 is selected from the group consisting of C1-6 alkyl, C1-6 haloalkyl, C1-6 heteroalkyl, C1-6 alkoxy, C1-6 alkylthio, —(X4)0-1-(3-10 membered heterocycloalkyl), —(X4)0-1-(5-10 membered heteroaryl), —(X4)0-1-(3-7 membered cycloalkyl), —(X4)0-1-S(O)1-2R4a and —(X4) 0-1-C(=Y4)R4a, wherein Y4 is O.

In another embodiment, in compounds of Formula I or Formula I-I, the 4 to 10 membered heterocyclic ring represented by the structure

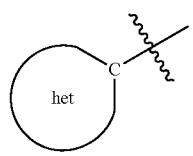 [SMILES: *C(C)C]

is selected from the group consisting of:

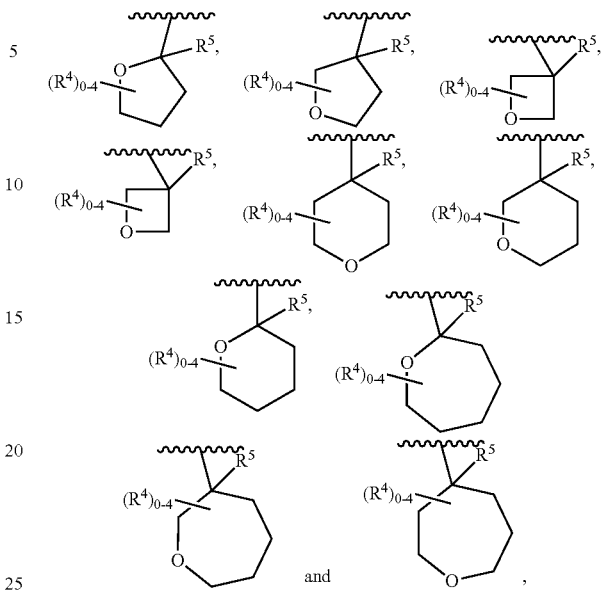

wherein R4 is selected from the group consisting of: —F, —Cl, —Br, —I, —(X4)0-1-CN, —(X4)0-1-NO2, —(X4)0-1-SF5, —(X4)0-1-OH, —(X4)0-1-NH2, —(X4)0-1-N(H) (R4a), —(X4)0-1-N(R4b)(R4a), —(X4)0-1-CF3, C1-6 alkyl, C1-6 haloalkyl, C1-6 heteroalkyl, C1-6 alkoxy and C1-6 alkylthio wherein X4 is selected from the group consisting of C1-4 alkylene, C1-4 haloalkylene, C1-4 heteroalkylene, C2-4 alkenylene and C2-4 alkynylene and R4a and R4b is each independently selected from the group consisting of: C1-6 alkyl, C1-6 haloalkyl and C1-6 heteroalkyl.

In another embodiment, in compounds of Formula I or Formula I-I, R5 is selected from the group consisting of hydrogen, C1-4 alkyl, C1-4 haloalkyl, hydroxy, OR5a, —CN, —F, —Cl, —Br and —I.

In another embodiment, in compounds of Formula I or Formula I-I, wherein R1 is selected from the group consisting of C1-6 alkyl, C1-6 haloalkyl, C1-6 heteroalkyl, —OR1a, —SR1a, —N(H)(R1a), and —N(R1a)(R1b), methyl, ethyl, propyl, isopropyl, butyl, sec-butyl, tert-butyl, cyclopropane, cyclobutane, cyclopentane, cyclohexane, cycloheptane, morpholine, homomorpholine, piperidine, homopiperidine, piperazine, homopiperazine, azetidine, pyrrolidine, benzene, pyrrole, pyrazole, imidazole, triazole, tetrazole, pyridine, pyrimidine, pyrazine, pyridazine, oxetane, tetrahydrofuran, tetrahydropyran, -oxa-5-azabicyclo [2.2.1]heptane, 2-oxa-6-azaspiro[3.3]heptane, 8-oxa-3-azabicyclo[3.2.1]octane, 3-oxa-8-azabicyclo[3.2.1]octane, 7-oxabicyclo[2.2.1]heptane, 7-azabicyclo[2.2.1]heptane, nonbornane, bicyclo[2.2.2]octane, 2-azabicyclo[2.2.2]octane, 2-oxabicyclo[2.2.2]octane, 2-oxa-5-azabicyclo[2.2.2] octane and 2,5-diazabicyclo[2.2.2]octane, 5,6,7,8-tetrahydroimidazo[1,2-a]pyrazine, 4,5,6,7-tetrahydro-3H-imidazo [4,5-c]pyridine, wherein R1a and R1b are each independently selected from the group consisting of C1-6 alkyl, C1-6 haloalkyl, C1-6 heteroalkyl, 3-10 membered cycloalkyl and 3-10 membered heterocycloalkyl, and wherein the aliphatic and aromatic portions of R1 are independently further substituted with 0 to 5 RA1 substituents selected from the group consisting of —F, —Cl, —Br, I, —CN, —NO2, —SF5, —OH, —NH2, —CF3, =O, C1-4 alkyl, C1-4 haloalkyl, C1-4 heteroalkyl, C1-4 alkoxy, C1-4 alkylthio, C1-4 alkylamino, C1-4 dialkylamino, R1c-C (=O)—, —R1c-C(=O)N(H)—, R1c-C(=O)N(R1d)-, R1c-C(=O)O—, R1c-S(O)1-2-, R1c-S(O)1-2N(R1d)-, R1c-S(O)1-2N(H)—, 3-6 membered cycloalkyl, phenyl, 5-6 membered heteroaryl and 3-7 membered heterocycloalkyl, wherein R1c is selected from the group consisting of C1-6 alkyl, C1-6 haloalkyl, C5-6 heteraryl, 3-7 membered heterocycloalkyl, phenyl and 3-6 membered cycloalkyl, R1d is selected from the group consisting of hydrogen, C1-3 alkyl and C1-3 haloalkyl, and wherein said 5-6 membered heteraryl, phenyl, 3-6 membered heteroaryl, 3-6 membered cycloalkyl and 3-7 membered heterocycloalkyl of the RA1 substituent are substituted with from 0-4 substituents selected from —F, —Cl, —Br, I, —CN, —NO2, —SF5, —OH, —NH2, —CF3, C1-4 alkyl, C1-4 haloalkyl, C1-4 alkoxy, C1-4 alkylthio, C1-4 alkylamino and C1-4 dialkylamino.

In another embodiment, in compounds of Formula I or Formula I-I, wherein R1 is selected from the group consisting of pyrrolidin-1-yl, phenyl, piperidin-1-yl, pyrrol-1-yl, azetidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 2-oxa-6-azaspiro[3.3]hept-6-yl, -8-oxa-3-azabicyclo [3.2.1]octane, methyl, isopropyl, isobutyl, cyclopropyl, pyrazol-1-yl, 4,5,6,7-tetrahydro-1H-imidazo[4,5-c]pyridin-5-yl, 3,5,6,7,8,8a-hexahydroimidazo[1,2-a]pyrazin-7-yl, —N(H)R1a), and —N(R1a)(R1b), wherein R1a and R1b are each independently selected from the group consisting of methyl, ethyl, propyl, butyl, methoxyethyl, ethoxyethyl, hydroxyethyl, methoxypropyl, ethyoxypropyl and hydroxypropyl, wherein the aliphatic and/or aromatic portions or R1 is substituted with 0 to 4 substituents selected from the group consisting of methyl, ethyl, propyl, isopropyl, butyl, isobutyl, fluoro, chloro, bromo, iodo, cyano, methoxymethyl, methoxyethyl, methoxypropyl, trifluoromethyl, monofluoromethyl, difluromethyl, 2-methylpyrimidin-4-yl, 4-methyltriazol-3-yl, 1,2,4-triazol-3-yl, morphlinocarbonyl, morpholino, 2-methyl-pyrimidin-6-yl, 6-methyl-pyrimidin-2-yl, 4-methyl-1,2,4-triazol-3-yl, methylaminomethylcarbonyl and hydroxy.

In another embodiment, in compounds of Formula I, R3 is selected from the group consisting of —F, —Cl, —Br, I, —(X3)0-1-CN, —(X3)0-1-NO2, —(X3)0-1-SF5, —(X3)0-1-OH, —(X3)0-1-NH2, —(X3)0-1-N(H)(R3a), —(X3)0-1-N(R3b)(R3a), —(X3)0-1-CF3, C1-6 alkyl, C1-6 haloalkyl, C1-6 heteroalkyl, C1-6 alkoxy, C1-6 alkylthio, —(X3)0-1-3-7 membered cycloalkyl, —(X3)0-1-3-7 membered heterocycloalkyl, —(X3)0-1-5-6 membered heteroaryl, —(X3)0-1-C6 aryl, —(X3)0-1-C(=Y3)N(H)(R3a), —(X3)0-1-C(=Y3)NH2, —(X3)0-1-C(=Y3)N(R3a)(R3b), —(X3)0-1-C(=Y3)OR3a, —(X3)0-1-C(=Y3)OH, —(X3)0-1-N(H)C(=Y3)(R3a), —(X3)0-1-N(R3b)C(=Y3)(R3a), —(X3)0-1-N(H)C(=Y3)OR3a, —(X3)0-1-N(R3b)C(=Y3)OR3a, —(X3)0-1-S(O)1-2R3a, —(X3)0-1-N(H)S(O)1-2R3a, —(X3)0-1-N(R3b)S(O)1-2R3a, —(X3)0-1-S(O)0-1N(H) (R3a), —(X3)0-1-S(O)0-1N(R3b)(R3a), —(X3)0-1-S(O)0-1NH2, —(X3)0-1-C(=Y3)R3a, —(X3)0-1-C(=Y3)H, —(X3)0-1-NHC(=Y3)N(H)(R3a), —(X3)0-1-NHC(=Y3) NH2, —(X3)0-1-NHC(=Y3)N(R3b)(R3a), —(X3)0-1-N (R3a)C(=Y3)N(H)(R3a), —(X3)0-1-N(R3a)C(=Y3)NH2, wherein Y is O, or alternatively, any two R3 substituents located on adjacent atoms are optionally combined to form a 5-6 membered heteroaryl ring comprising 1-2 heteroatoms selected from N, O and S and further comprising 0 to 4 R3a substituents, and m is an integer from 1 to 4.

In another embodiment, in compounds of Formula I or Formula I-I, R3 is selected from the group consisting of —F, —Cl, —Br, I, C1-6 alkyl, C1-6 haloalkyl, C1-6 heteroalkyl, C1-6 alkoxy, —(X3)0-1-N(H)C(=Y3)(R3a), —(X3)0-1-N (R3b)C(=Y3)(R3a), —(X3)0-1-C(=Y3)N(H)(R3a), —(X3)0-1-C(=Y3)NH2, —(X3)0-1-C(=Y3)N(R3a) (R3b), thiophene, wherein if R3 is thiophene, or R3a and R3b is independently 3-7 membered cycloalkyl, 3-7 membered cycloalkyl-C1-4 alkyl, 3-7 membered heterocycloalkyl, 3-7 membered heterocycloalkyl-C1-4 alkyl, 5-6 membered heteroaryl, 5-6 membered heteroaryl-C1-4 alkyl, C6 aryl, C6 aryl-C1-4 alkyl or benzyl then said thiophene, 3-7 membered cycloalkyl, 3-7 membered cycloalkyl-C1-4 alkyl, 3-7 membered heterocycloalkyl, 3-7 membered heterocycloalkyl-C1-4 alkyl, 5-6 membered heteroaryl, 5-6 membered heteroaryl-C1-4 alkyl, C6 aryl, C6 aryl-C1-4 alkyl or benzyl is substituted from 0 to 4 RA3 substituents, or alternatively, any two R3 substituents located on adjacent atoms are optionally combined to form a thiazole ring further comprising 0 to 4 R3a substituents, and m is an integer from 1 to 4.

In another embodiment, in compound of Formula I or Formula I-I, R3 is selected from the group consisting of trifluoromethyl, methyl, ethyl, propyl, butyl, isopropyl, sec-butyl, tert-butyl, methoxy, ethoxy, cyclopropyl, cyclobutyl, thienyl and —C(=O)NH2.

In another embodiment, in compounds of Formula I or Formula I-I, the compound has the subformula selected from the group consisting of:

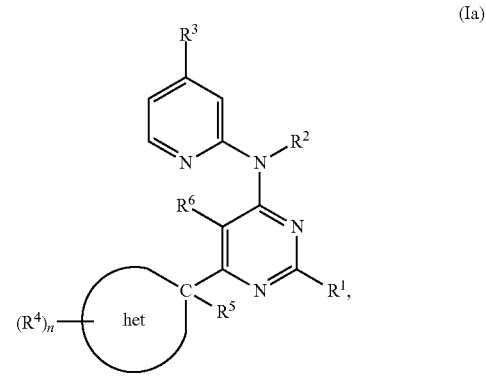

(Ia)

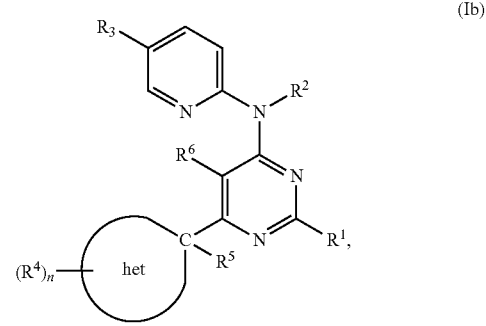

(Ib)

-continued
(Ic)
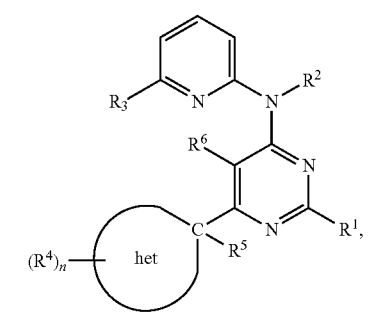
(Id)
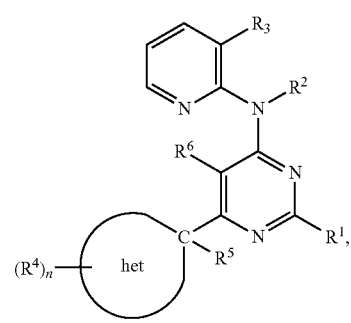
(Ie)
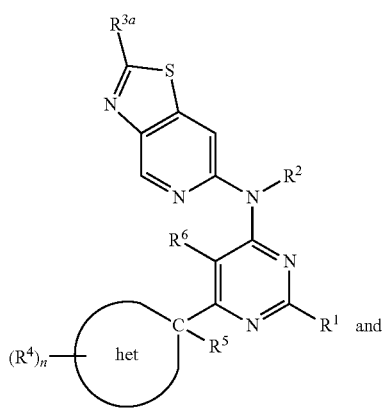
(If)
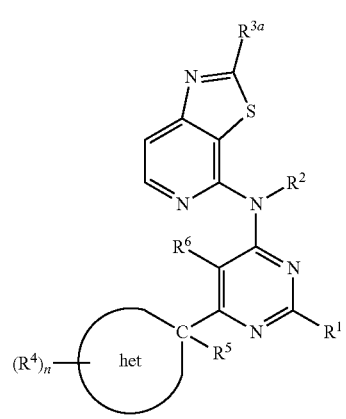
In another embodiment, in compounds of Formula I or Formula I-I, the compound has a subformula selected from the group consisting of:
(IIa)
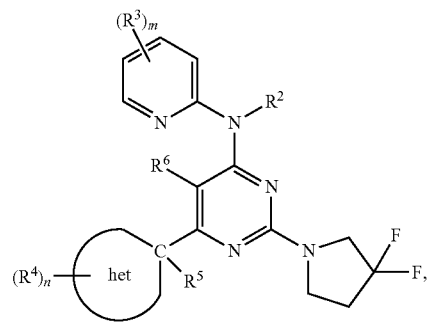
(IIb)
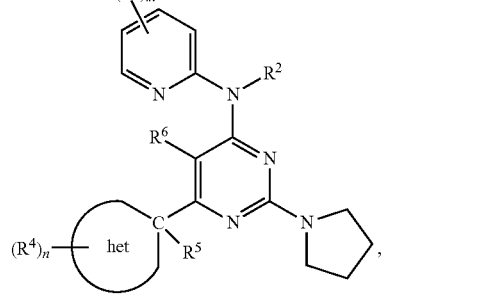
(IIc)
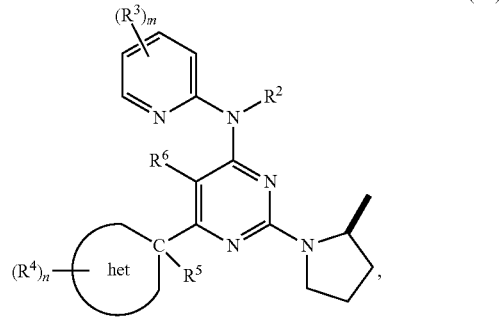
(IId)
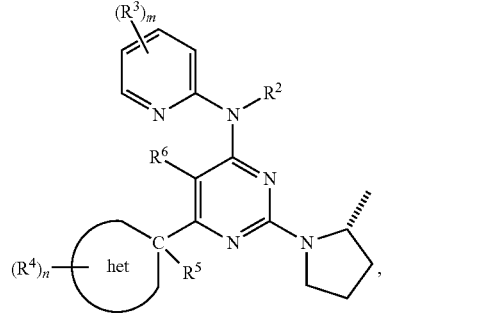
(IIe)
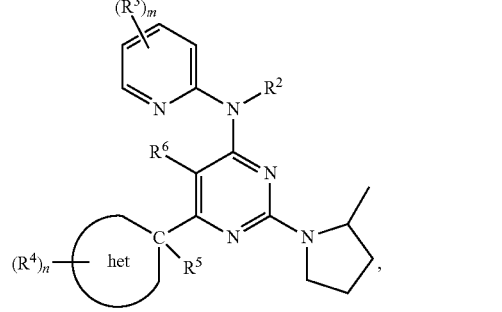

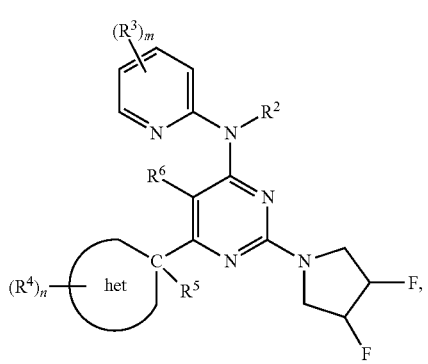
(IIf)
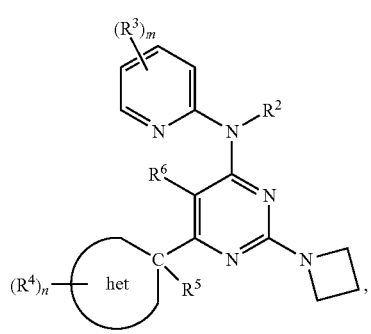
(IIg)
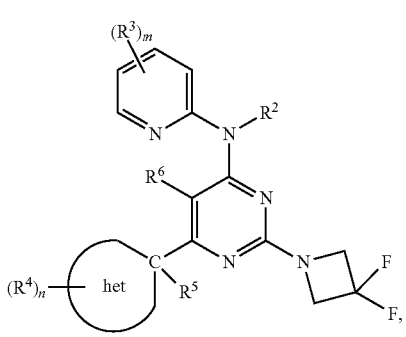
(IIh)
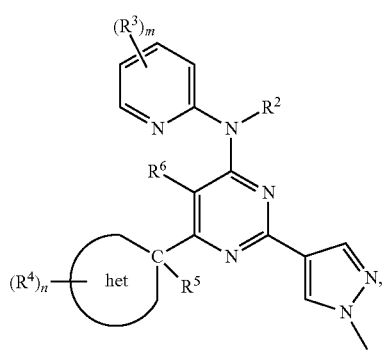
(IIi)
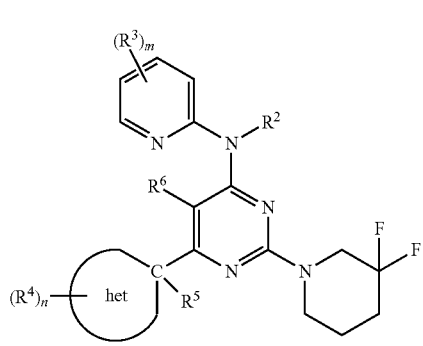
(IIj)
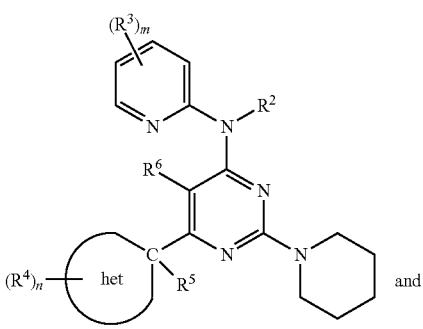
(IIk)
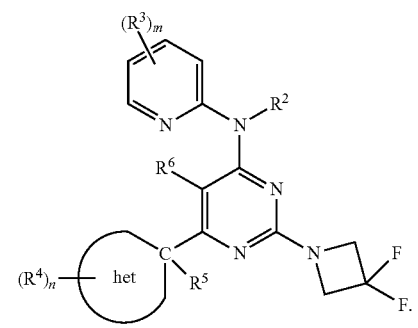
and
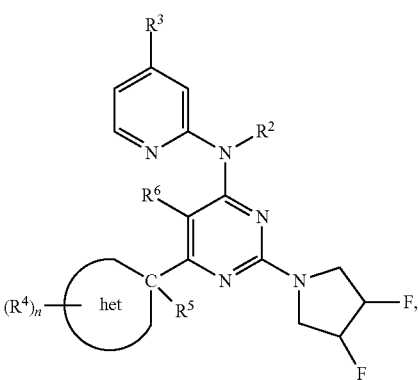
(III)
In another embodiment, in compounds of Formula I or Formula I-I, a compound has the subformula selected from the group consisting of:
(IIIa)

33
-continued
(IIIb)
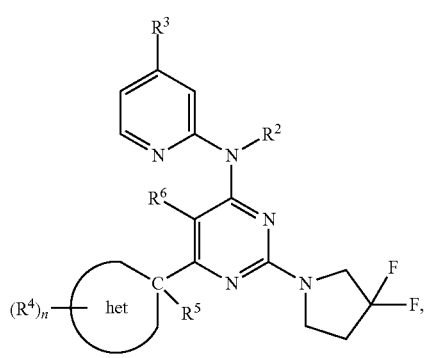
(IIIc)
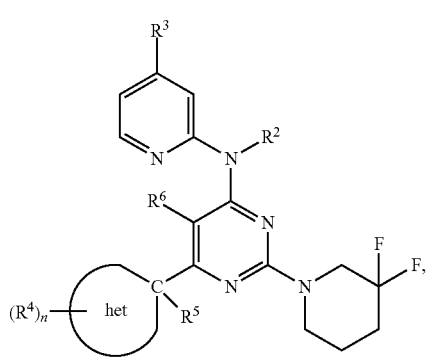
(IIId)
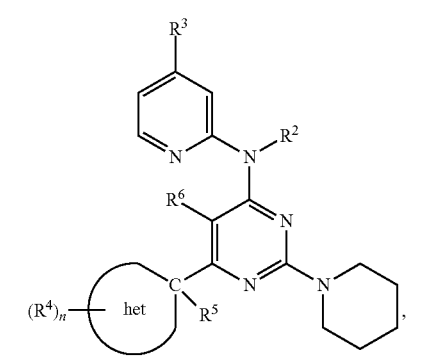
(IIIe)
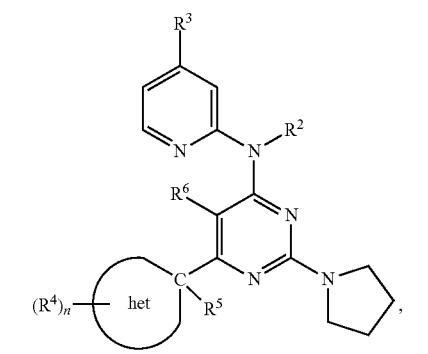
34
-continued
(IIIf)
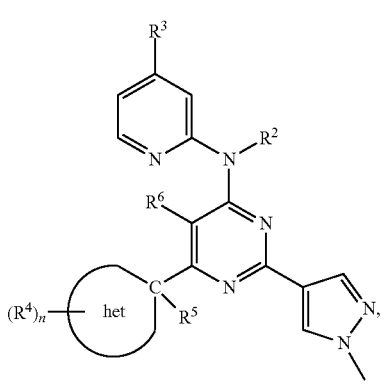
(IIIg)
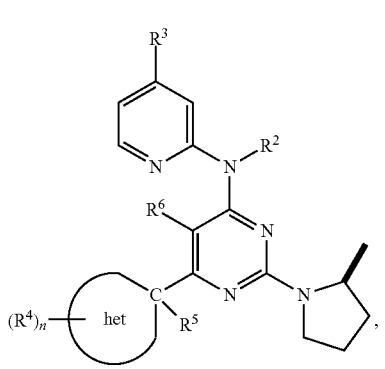
(IIIh)
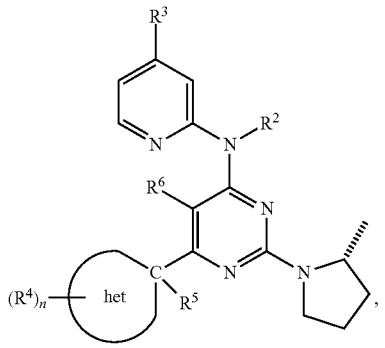

(IIIi)

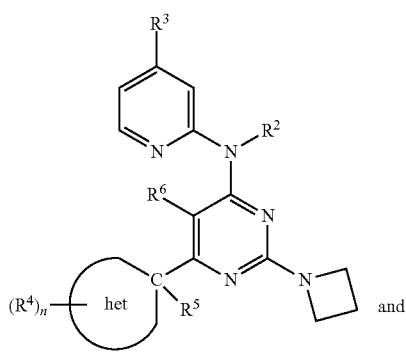

and (IIIj)

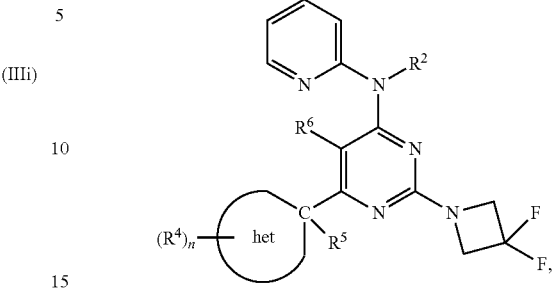

wherein R3 is selected from the group consisting of methyl, monofluoromethyl, difluoromethyl, trifluoromethyl, isopropyl, cyclopropyl, cyclobutyl and methoxy.

In another embodiment, the compounds of Formula I or Formula I-I are selected from the group of compounds in Table A.

TABLE A

| No. | Structure | Name |
| --- | --- | --- |
| 1 | 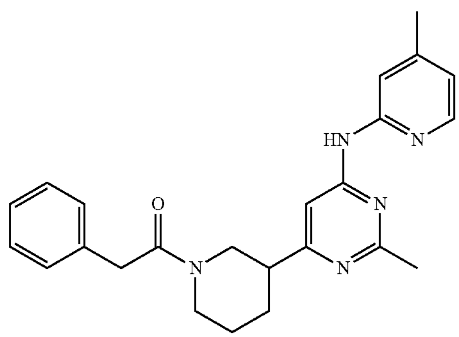 [SMILES: Cc1ccnc(Nc2cc(C3CCCN(C(=O)Cc4ccccc4)C3)nc(C)n2)c1] | 1-{3-2-Methyl-6-(4-methyl-pyridin-2-ylamino)-pyrimidin-4-yl]-piperidin-1-yl}-2-phenyl-ethanone |
| 2 | 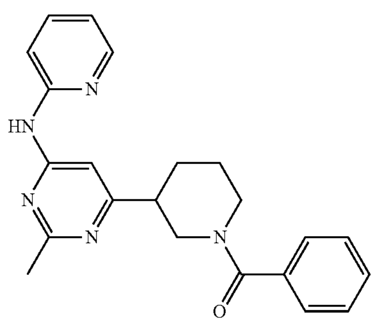 [SMILES: Cc1nc(Nc2ccccn2)cc(C2CCCN(C(=O)c3ccccc3)C2)n1] | {3-[2-Methyl-6-(pyridin-2-ylamino)-pyrimidin-4-yl]-piperidin-1-yl}-phenyl-methanone |
| 3 | 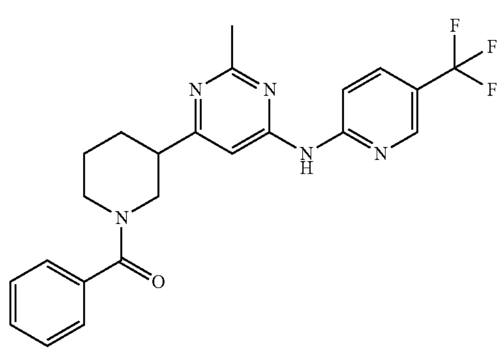 [SMILES: Cc1nc(Nc2ccc(C(F)(F)F)cn2)cc(C2CCCN(C(=O)c3ccccc3)C2)n1] | {3-[2-Methyl-6-(5-tri-fluoromethyl-pyridin-2-ylamino)-pyrimidin-4-yl]-piperidin-1-yl}-phenyl-methanone |

TABLE A-continued

| No. | Structure | Name |
|---|---|---|
| 4 | 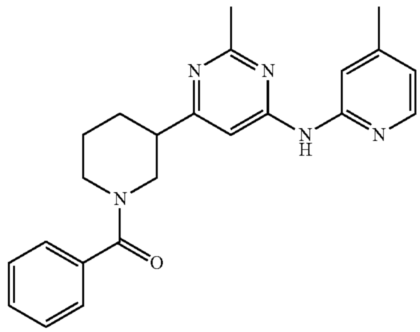 [SMILES: Cc1ccnc(Nc2cc(C3CCCN(C(=O)c4ccccc4)C3)nc(C)n2)c1] | {3-[2-Methyl-6-(4-methyl-pyridin-2-ylamino)-pyrimidin-4-yl]-piperidin-1-yl}-phenyl-methanone |
| 5 | 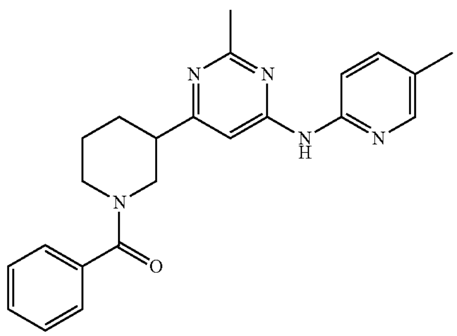 [SMILES: Cc1ccc(Nc2cc(C3CCCN(C(=O)c4ccccc4)C3)nc(C)n2)nc1] | {3-[2-Methyl-6-(5-methyl-pyridin-2-ylamino)-pyrimidin-4-yl]-piperidin-1-yl}-phenyl-methanone |
| 6 | 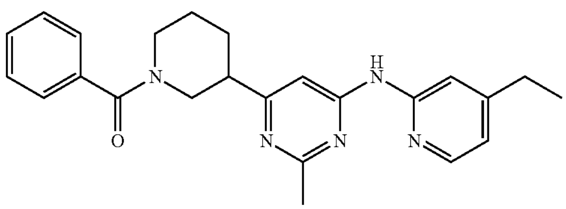 [SMILES: CCc1ccnc(Nc2cc(C3CCCN(C(=O)c4ccccc4)C3)nc(C)n2)c1] | {3-[6-(4-Ethyl-pyridin-2-ylamino)-2-methyl-pyrimidin-4-yl]-piperidin-1-yl}-phenyl-methanone |
| 7 | 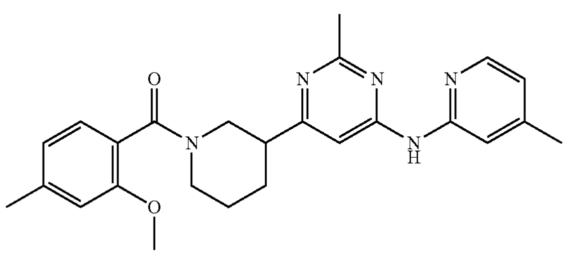 | (2-Methoxy-4-methyl-phenyl)-{3-[2-methyl-6-(4-methyl-pyridin-2-ylamino)-pyrimidin-4-yl]-piperidin-1-yl}-methanone |
| 8 | 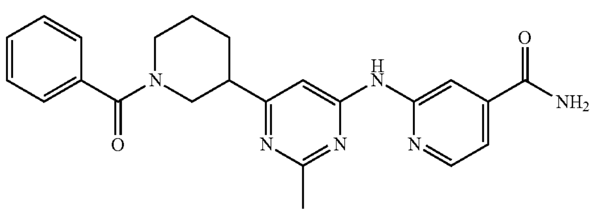 [SMILES: Cc1nc(Nc2cc(C(N)=O)ccn2)cc(C2CCCN(C(=O)c3ccccc3)C2)n1] | 2-[6-(1-Benzoyl-piperidin-3-yl)-2-methyl-pyrimidin-4-ylamino]-isonicotinamide |
| 9 | 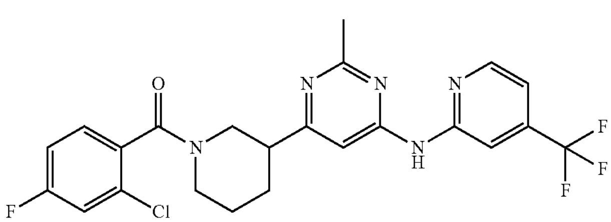 [SMILES: Cc1nc(Nc2cc(C(F)(F)F)ccn2)cc(C2CCCN(C(=O)c3ccc(F)cc3Cl)C2)n1] | (2-Chloro-4-fluoro-phenyl)-{3-[2-methyl-6-(4-trifluoromethyl-pyridin-2-ylamino)-pyrimidin-4-yl]-piperidin-1-yl}-methanone |

TABLE A-continued

| No. | Structure | Name |
|---|---|---|
| 10 | 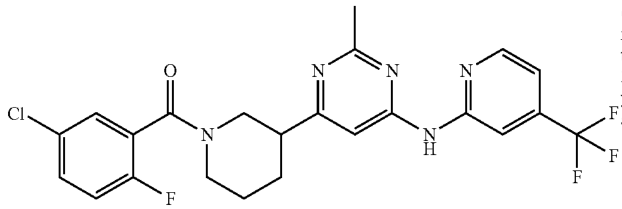 | (5-Chloro-2-fluoro-phenyl)-{3-[2-methyl-6-(4-trifluoromethyl-pyridin-2-ylamino)-pyrimidin-4-yl]-piperidin-1-yl}-methanone |
| 11 | 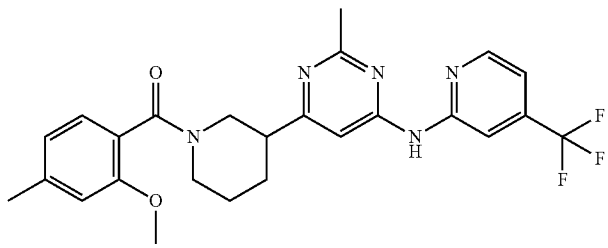 [SMILES: COc1cc(C)ccc1C(=O)N1CCCC(c2cc(Nc3cc(C(F)(F)F)ccn3)nc(C)n2)C1] | (2-Methoxy-4-methyl-phenyl)-{3-[2-methyl-6-(4-trifluoromethyl-pyridin-2-ylamino)-pyrimidin-4-yl]-piperidin-1-yl}-methanone |
| 12 | 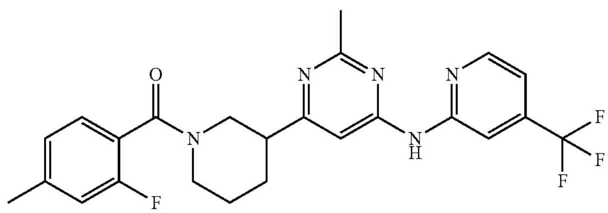 [SMILES: Cc1ccc(C(=O)N2CCCC(c3cc(Nc4cc(C(F)(F)F)ccn4)nc(C)n3)C2)c(F)c1] | (2-Fluoro-4-methyl-phenyl)-{3-[2-methyl-6-(4-trifluoromethyl-pyridin-2-ylamino)-pyrimidin-4-yl]-piperidin-1-yl}-methanone |
| 13 | 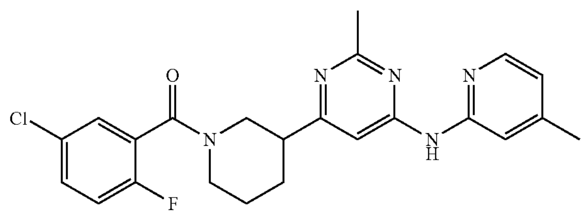 [SMILES: Cc1ccnc(Nc2cc(C3CCCN(C(=O)c4cc(Cl)ccc4F)C3)nc(C)n2)c1] | (5-Chloro-2-fluoro-phenyl)-{3-[2-methyl-6-(4-methyl-pyridin-2-ylamino)-pyrimidin-4-yl]-piperidin-1-yl}-methanone |
| 14 | 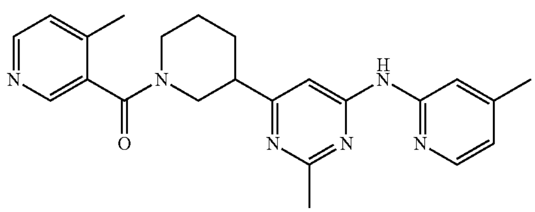 [SMILES: Cc1ccnc(Nc2cc(C3CCCN(C(=O)c4cnccc4C)C3)nc(C)n2)c1] | {3-[2-Methyl-6-(4-methyl-pyridin-2-ylamino)-pyrimidin-4-yl]-piperidin-1-yl}-(4-methyl-pyridin-3-yl)-methanone |
| 15 | 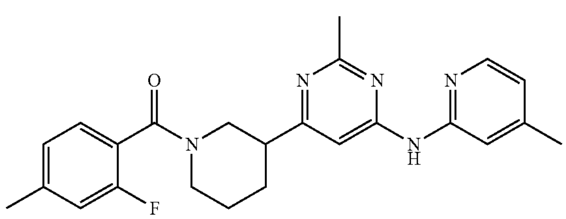 | (2-Fluoro-4-methyl-phenyl)-{3-[2-methyl-6-(4-methyl-pyridin-2-ylamino)-pyrimidin-4-yl]-piperidin-1-yl}-methanone |
| 16 | 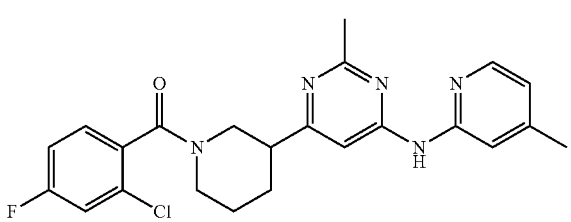 [SMILES: Cc1ccnc(Nc2cc(C3CCCN(C(=O)c4ccc(F)cc4Cl)C3)nc(C)n2)c1] | (2-Chloro-4-fluoro-phenyl)-{3-[2-methyl-6-(4-methyl-pyridin-2-ylamino)-pyrimidin-4-yl]-piperidin-1-yl}-methanone |

TABLE A-continued

| No. | Structure | Name |
|---|---|---|
| 17 | 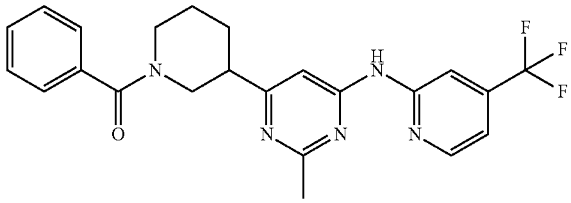 [SMILES: Cc1nc(Nc2cc(C(F)(F)F)ccn2)cc(C2CCCN(C(=O)c3ccccc3)C2)n1] | {3-[2-Methyl-6-(4-trifluoromethyl-pyridin-2-yl-amino)-pyrimidin-4-yl]-piperidin-1-yl}-phenyl-methanone |
| 18 | 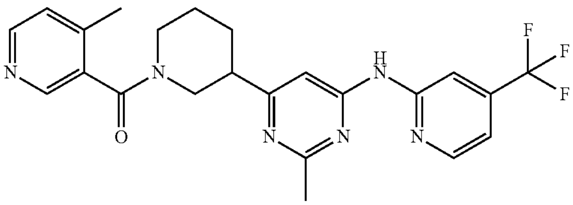 [SMILES: Cc1nc(Nc2cc(C(F)(F)F)ccn2)cc(C2CCCN(C(=O)c3cnccc3C)C2)n1] | (4-Methyl-pyridin-3-yl)-{3-[2-methyl-6-(4-trifluoromethyl-pyridin-2-ylamino)-pyrimidin-4-yl]-piperidin-1-yl}-methanone |
| 19 | 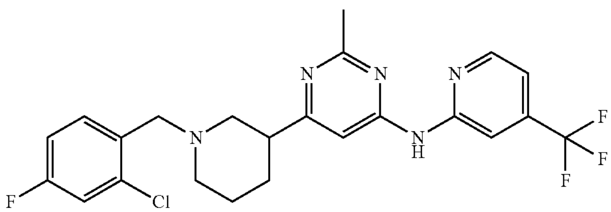 [SMILES: Cc1nc(Nc2cc(C(F)(F)F)ccn2)cc(C2CCCN(Cc3ccc(F)cc3Cl)C2)n1] | {6-[1-(2-Chloro-4-fluoro-benzyl)-piperidin-3-yl]-2-methyl-pyrimidin-4-yl}-(4-trifluoromethyl-pyridin-2-yl)-amine |
| 20 | 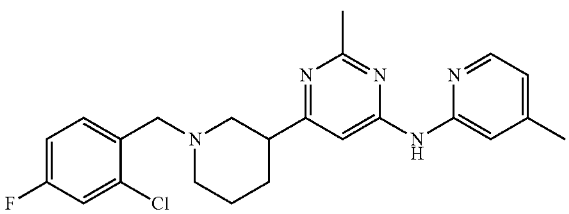 [SMILES: Cc1ccnc(Nc2cc(C3CCCN(Cc4ccc(F)cc4Cl)C3)nc(C)n2)c1] | {6-[1-(2-Chloro-4-fluoro-benzyl)-piperidin-3-yl]-2-methyl-pyrimidin-4-yl}-(4-methyl-pyridin-2-yl)-amine |
| 21 | 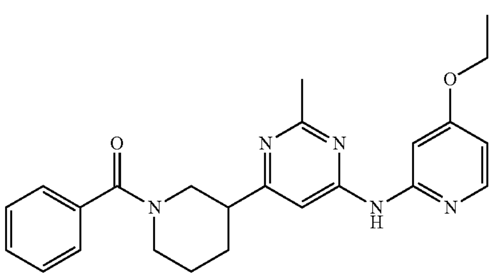 [SMILES: CCOc1ccnc(Nc2cc(C3CCCN(C(=O)c4ccccc4)C3)nc(C)n2)c1] | {3-[6-(4-Ethoxy-pyridin-2-ylamino)-2-methyl-pyrimidin-4-yl]-piperidin-1-yl}-phenyl-methanone |
| 22 | 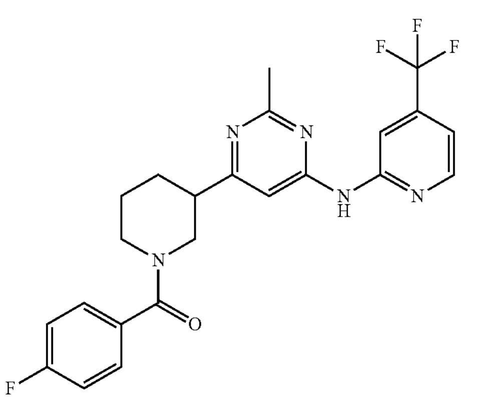 [SMILES: Cc1nc(Nc2cc(C(F)(F)F)ccn2)cc(C2CCCN(C(=O)c3ccc(F)cc3)C2)n1] | (4-Fluoro-phenyl)-{3-[2-methyl-6-(4-trifluoro-methyl-pyridin-2-ylamino)-pyrimidin-4-yl]-piperidin-1-yl}-methanone |

TABLE A-continued

| No. | Structure | Name |
| --- | --- | --- |
| 23 | 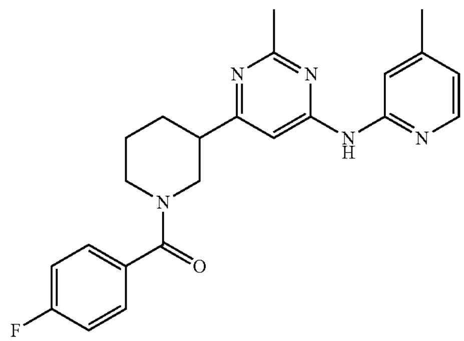 [SMILES: Cc1ccnc(Nc2cc(C3CCCN(C(=O)c4ccc(F)cc4)C3)nc(C)n2)c1] | (4-Fluoro-phenyl)-{3-[2-methyl-6-(4-methyl-pyridin-2-ylamino)-pyrimidin-4-yl]-piperidin-1-yl}-methanone |
| 24 | 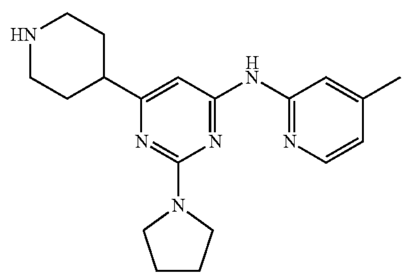 [SMILES: Cc1ccnc(Nc2cc(C3CCNCC3)nc(N3CCCC3)n2)c1] | (4-Methyl-pyridin-2-yl)-(6-piperidin-4-yl-2-pyrrolidin-1-yl-pyrimidin-4-yl)-amine |
| 25 | 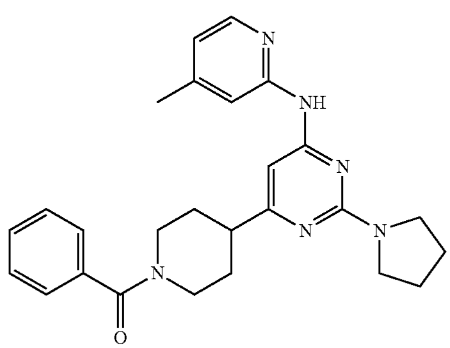 [SMILES: Cc1ccnc(Nc2cc(C3CCN(C(=O)c4ccccc4)CC3)nc(N3CCCC3)n2)c1] | {4-[6-(4-Methyl-pyridin-2-ylamino)-2-pyrrolidin-1-yl-pyrimidin-4-yl]-piperidin-1-yl}-phenyl-methanone |
| 26 | 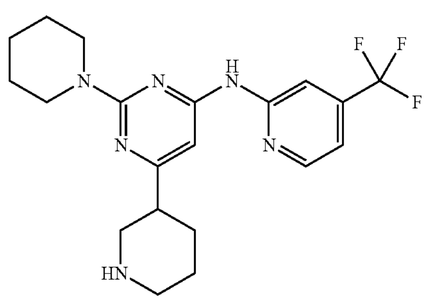 [SMILES: FC(F)(F)c1ccnc(Nc2cc(C3CCCNC3)nc(N3CCCCC3)n2)c1] | (2-Piperidin-1-yl-6-piperidin-3-yl-pyrimidin-4-yl)-(4-trifluoromethyl-pyridin-2-yl)-amine |
| 27 | 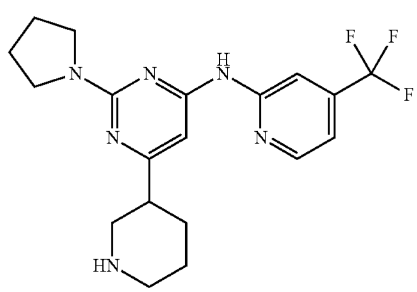 [SMILES: FC(F)(F)c1ccnc(Nc2cc(C3CCCNC3)nc(N3CCCC3)n2)c1] | (6-Piperidin-3-yl-2-pyrrolidin-1-yl-pyrimidin-4-yl)-(4-trifluoromethyl-pyridin-2-yl)-amine |

TABLE A-continued

| No. | Structure | Name |
|---|---|---|
| 28 | 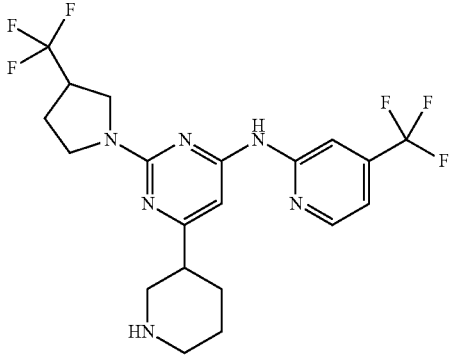 [SMILES: FC(F)(F)c1ccnc(Nc2cc(C3CCCNC3)nc(N3CCC(C(F)(F)F)C3)n2)c1] | [6-Piperidin-3-yl-2-(3-trifluoromethyl-pyrrolidin-1-yl)-pyrimidin-4-yl]-(4-trifluoromethyl-pyridin-2-yl)-amine |
| 29 | 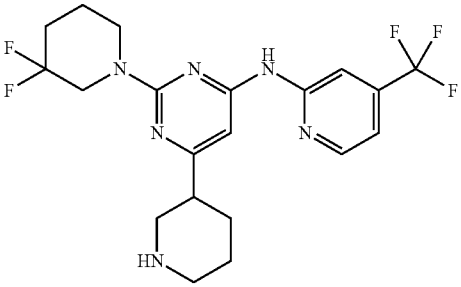 [SMILES: FC1(F)CCCN(c2nc(Nc3cc(C(F)(F)F)ccn3)cc(C3CCCNC3)n2)C1] | [2-(3,3-Difluoro-piperidin-1-yl)-6-piperidin-3-yl-pyrimidin-4-yl]-(4-trifluoromethyl-pyridin-2-yl)-amine |
| 30 | 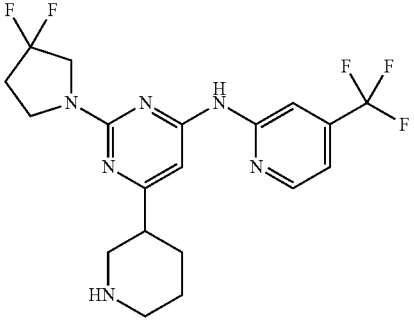 [SMILES: FC1(F)CCN(c2nc(Nc3cc(C(F)(F)F)ccn3)cc(C3CCCNC3)n2)C1] | [2-(3,3-Difluoro-pyrrolidin-1-yl)-6-piperidin-3-yl-pyrimidin-4-yl]-(4-trifluoromethyl-pyridin-2-yl)-amine |
| 31 | 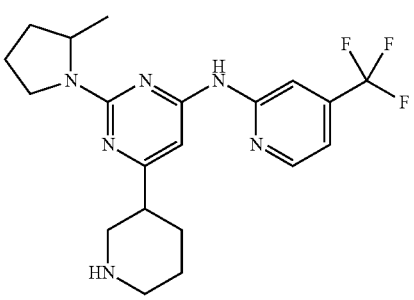 [SMILES: CC1CCCN1c1nc(Nc2cc(C(F)(F)F)ccn2)cc(C2CCCNC2)n1] | [2-(2-Methyl-pyrrolidin-1-yl)-6-piperidin-3-yl-pyrimidin-4-yl]-(4-trifluoromethyl-pyridin-2-yl)-amine |

TABLE A-continued

| No. | Structure | Name |
|---|---|---|
| 32 | 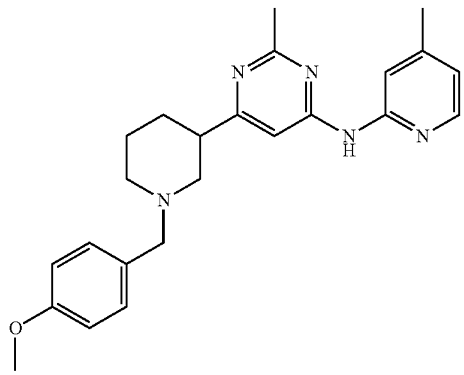 [SMILES: COc1ccc(CN2CCCC(c3cc(Nc4cc(C)ccn4)nc(C)n3)C2)cc1] | {6-[1-(4-Methoxy-benzyl)-piperidin-3-yl]-2-methyl-pyrimidin-4-yl}-(4-methyl-pyridin-2-yl)-amine |
| 33 | 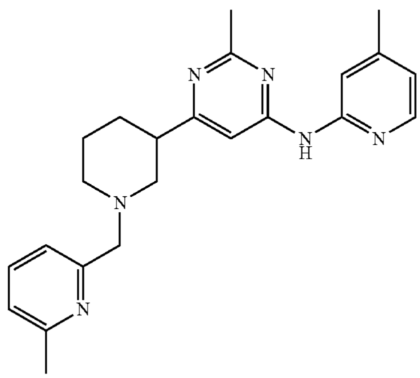 [SMILES: Cc1ccnc(Nc2cc(C3CCCN(Cc4cccc(C)n4)C3)nc(C)n2)c1] | {2-Methyl-6-[1-(6-methyl-pyridin-2-ylmethyl)-piperidin-3-yl]-pyrimidin-4-yl}-(4-methyl-pyridin-2-yl)-amine |
| 34 | 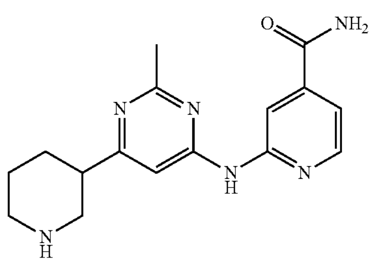 [SMILES: Cc1nc(Nc2cc(C(N)=O)ccn2)cc(C2CCCNC2)n1] | 2-(2-Methyl-6-piperidin-3-yl-pyrimidin-4-ylamino)-isonicotinamide |
| 35 | 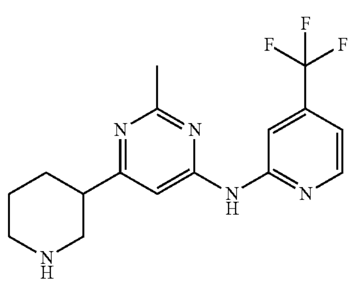 [SMILES: Cc1nc(Nc2cc(C(F)(F)F)ccn2)cc(C2CCCNC2)n1] | (2-Methyl-6-piperidin-3-yl-pyrimidin-4-yl)-(4-trifluoromethyl-pyridin-2-yl)-amine |
| 36 | 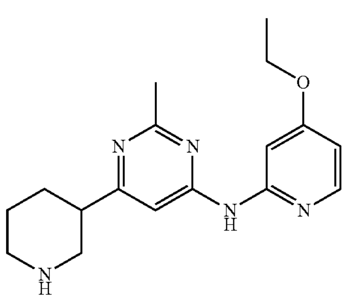 [SMILES: CCOc1ccnc(Nc2cc(C3CCCNC3)nc(C)n2)c1] | (4-Ethoxy-pyridin-2-yl)-(2-methyl-6-piperidin-3-yl-pyrimidin-4-yl)-amine |

TABLE A-continued

| No. | Structure | Name |
|---|---|---|
| 37 | 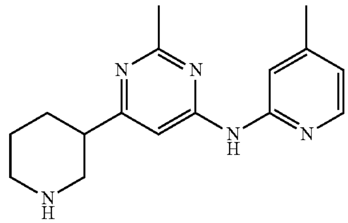 [SMILES: Cc1ccnc(Nc2cc(C3CCCNC3)nc(C)n2)c1] | (2-Methyl-6-piperidin-3-yl-pyrimidin-4-yl)-(4-methyl-pyridin-2-yl)-amine |
| 38 | 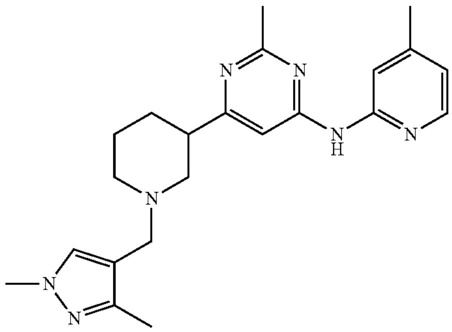 [SMILES: Cc1ccnc(Nc2cc(C3CCCN(Cc4cn(C)nc4C)C3)nc(C)n2)c1] | {6-[1-(1,3-Dimethyl-1H-pyrazol-4-ylmethyl)-piperidin-3-yl]-2-methyl-pyrimidin-4-yl}-(4-methyl-pyridin-2-yl)-amine |
| 39 | 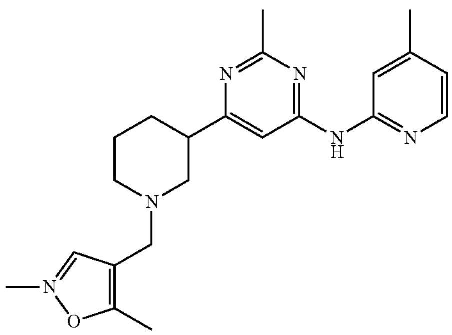 | {6-[1-(2,5-Dimethyl-oxazol-4-ylmethyl)-piperidin-3-yl]-2-methyl-pyrimidin-4-yl}-(4-methyl-pyridin-2-yl)-amine |
| 40 | 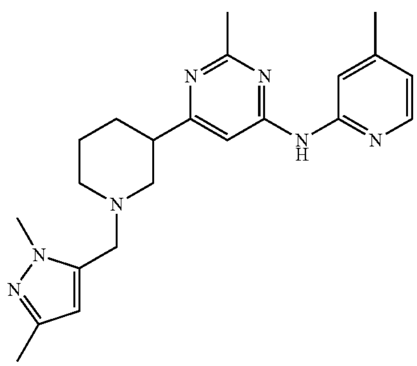 [SMILES: Cc1ccnc(Nc2cc(C3CCCN(Cc4cc(C)nn4C)C3)nc(C)n2)c1] | {6-[1-(2,5-Dimethyl-2H-pyrazol-3-ylmethyl)-piperidin-3-yl]-2-methyl-pyrimidin-4-yl}-(4-methyl-pyridin-2-yl)-amine |
| 41 | 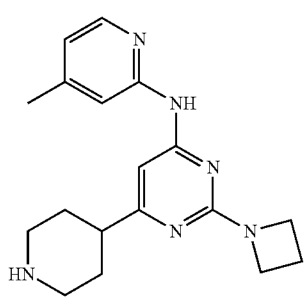 [SMILES: Cc1ccnc(Nc2cc(C3CCNCC3)nc(N3CCC3)n2)c1] | (2-Azetidin-1-yl-6-piperidin-4-yl-pyrimidin-4-yl)-(4-methyl-pyridin-2-yl)-amine |

TABLE A-continued

| No. | Structure | Name |
|---|---|---|
| 42 | 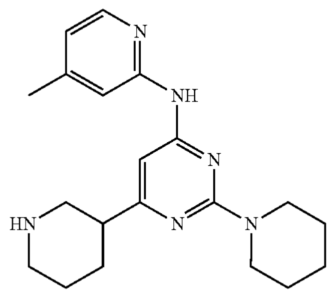 [SMILES: Cc1ccnc(Nc2cc(C3CCCNC3)nc(N3CCCCC3)n2)c1] | (4-Methyl-pyridin-2-yl)-(2-piperidin-1-yl-6-piperidin-3-yl-pyrimidin-4-yl)-amine |
| 43 | 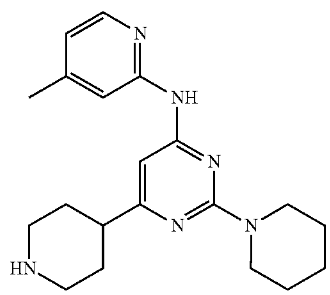 [SMILES: Cc1ccnc(Nc2cc(C3CCNCC3)nc(N3CCCCC3)n2)c1] | (4-Methyl-pyridin-2-yl)-(2-piperidin-1-yl-6-piperidin-4-yl-pyrimidin-4-yl)-amine |
| 44 | 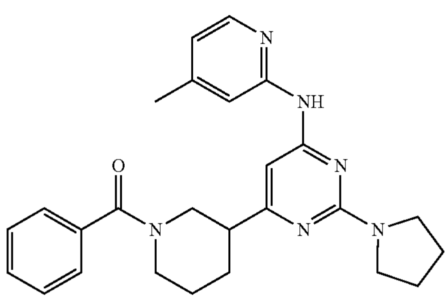 [SMILES: Cc1ccnc(Nc2cc(C3CCCN(C(=O)c4ccccc4)C3)nc(N3CCCC3)n2)c1] | {3-[6-(4-Methyl-pyridin-2-ylamino)-2-pyrrolidin-1-yl-pyrimidin-4-yl]-piperidin-1-yl}-phenyl-methanone |
| 45 | 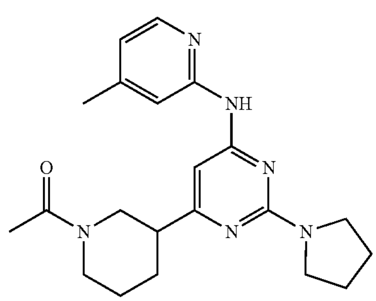 [SMILES: CC(=O)N1CCCC(c2cc(Nc3cc(C)ccn3)nc(N3CCCC3)n2)C1] | 1-{3-[6-(4-Methyl-pyridin-2-ylamino)-2-pyrrolidin-1-yl-pyrimidin-4-yl]-piperidin-1-yl}-ethanone |
| 46 | 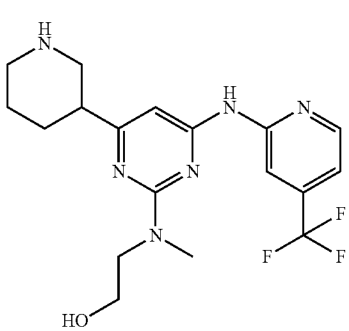 [SMILES: CN(CCO)c1nc(Nc2cc(C(F)(F)F)ccn2)cc(C2CCCNC2)n1] | 2-{Methyl-[4-piperidin-3-yl-6-(4-trifluoromethyl-pyridin-2-ylamino)-pyrimidin-2-yl]-amino}-ethanol |

TABLE A-continued

| No. | Structure | Name |
|---|---|---|
| 47 | 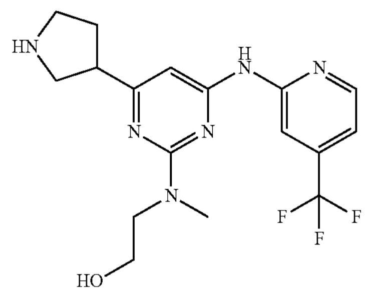 [SMILES: CN(CCO)c1nc(Nc2cc(C(F)(F)F)ccn2)cc(C2CCNC2)n1] | 2-{Methyl-[4-pyrrolidin-3-yl-6-(4-trifluoromethyl-pyridin-2-ylamino)-pyrimidin-2-yl]-amino}-ethanol |
| 48 | 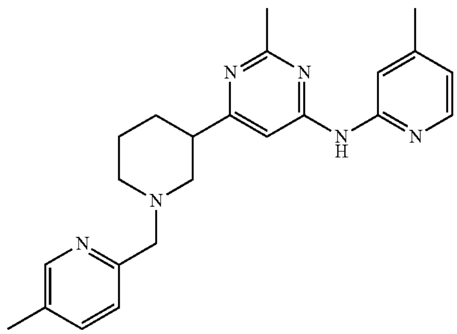 [SMILES: Cc1ccc(CN2CCCC(c3cc(Nc4cc(C)ccn4)nc(C)n3)C2)nc1] | {2-Meth-6-[1-(5-methyl-pyridin-2-ylmethyl)-piperidin-3-yl]-pyrimidin-4-yl}-(4-methyl-pyridin-2-yl)-amine |
| 49 | 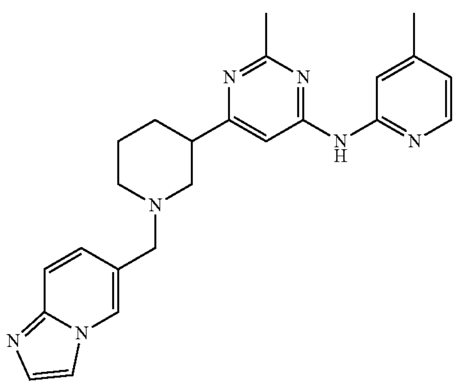 [SMILES: Cc1ccnc(Nc2cc(C3CCCN(Cc4ccc5nccn5c4)C3)nc(C)n2)c1] | [6-(1-Imidazo[1,2-a]pyridin-6-ylmethyl-piperidin-3-yl)-2-methyl-pyrimidin-4-yl]-(4-methyl-pyridin-2-yl)-amine |
| 50 | 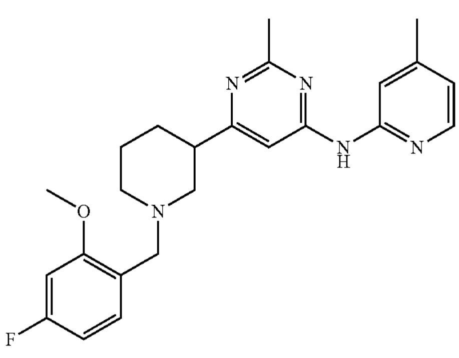 [SMILES: COc1cc(F)ccc1CN1CCCC(c2cc(Nc3cc(C)ccn3)nc(C)n2)C1] | {6-[1-(4-Fluoro-2-methoxy-benzyl)-piperidin-3-yl]-2-methyl-pyrimidin-4-yl}-(4-methyl-pyridin-2-yl)-amine |

TABLE A-continued

| No. | Structure | Name |
|---|---|---|
| 51 | 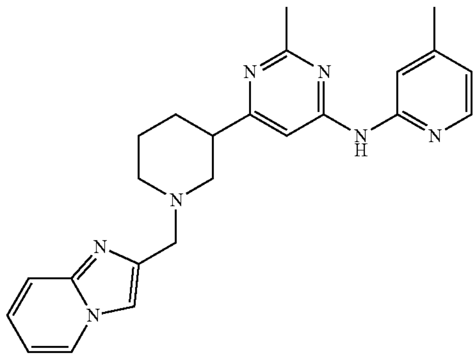 [SMILES: Cc1ccnc(Nc2cc(C3CCCN(Cc4cn5ccccc5n4)C3)nc(C)n2)c1] | [6-(1-Imidazo[1,2-a]pyridin-2-ylmethyl-piperidin-3-yl)-2-methyl-pyrimidin-4-yl]-(4-methyl-pyridin-2-yl)-amine |
| 52 | 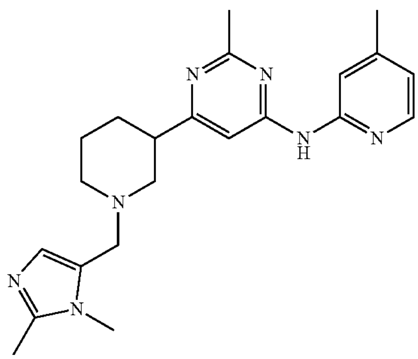 [SMILES: Cc1ccnc(Nc2cc(C3CCCN(Cc4cnc(C)n4C)C3)nc(C)n2)c1] | {6-[1-(2,3-Dimethyl-3H-imidazol-4-ylmethyl)-piperidin-3-yl]-2-methyl-pyrimidin-4-yl}-(4-methyl-pyridin-2-yl)-amine |
| 53 | 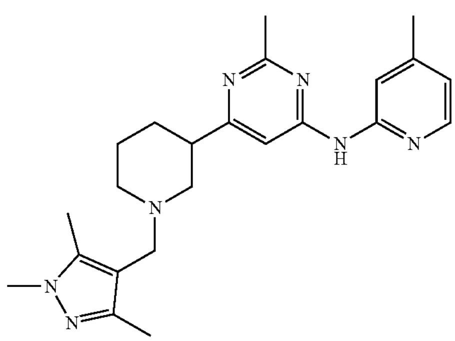 [SMILES: Cc1ccnc(Nc2cc(C3CCCN(Cc4c(C)nn(C)c4C)C3)nc(C)n2)c1] | (4-Methyl-pyridin-2-yl)-{2-methyl-6-[1-(1,3,5-trimethyl-1H-pyrazol-4-ylmethyl)-piperidin-3-yl]-pyrimidin-4-yl}-amine |
| 54 | 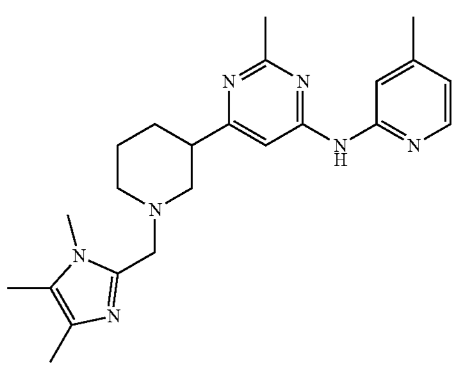 [SMILES: Cc1ccnc(Nc2cc(C3CCCN(Cc4nc(C)c(C)n4C)C3)nc(C)n2)c1] | (4-Methyl-pyridin-2-yl)-{2-methyl-6-[1-(1,4,5-trimethyl-1H-imidazol-2-ylmethyl)-piperidin-3-yl]-pyrimidin-4-yl}-amine |

TABLE A-continued

| No. | Structure | Name |
|---|---|---|
| 55 | 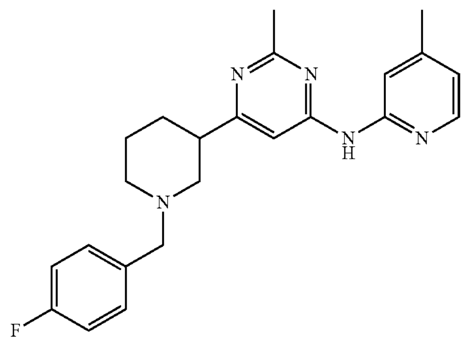 [SMILES: Cc1ccnc(Nc2cc(C3CCCN(Cc4ccc(F)cc4)C3)nc(C)n2)c1] | {6-[1-(4-Fluoro-benzyl)-piperidin-3-yl]-2-methyl-pyrimidin-4-yl}-(4-methyl-pyridin-2-yl)-amine |
| 56 | 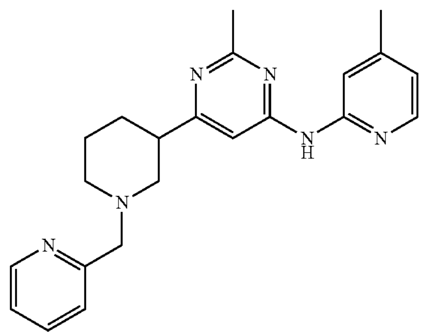 [SMILES: Cc1ccnc(Nc2cc(C3CCCN(Cc4ccccn4)C3)nc(C)n2)c1] | (4-Methyl-pyridin-2-yl)-[2-methyl-6-(1-pyridin-2-ylmethyl-piperidin-3-yl)-pyrimidin-4-yl]-amine |
| 57 | 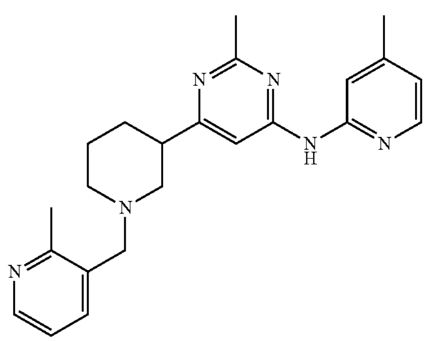 [SMILES: Cc1ccnc(Nc2cc(C3CCCN(Cc4cccnc4C)C3)nc(C)n2)c1] | {2-Methyl-6-[1-(2-methyl-pyridin-3-ylmethyl)-piperidin-3-yl]-pyrimidin-4-yl}-(4-methyl-pyridin-2-yl)-amine |
| 58 | 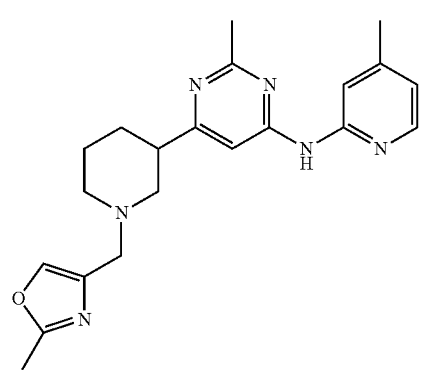 [SMILES: Cc1ccnc(Nc2cc(C3CCCN(Cc4coc(C)n4)C3)nc(C)n2)c1] | {2-Methyl-6-[1-(2-methyl-oxazol-4-ylmethyl)-piperidin-3-yl]-pyrimidin-4-yl}-(4-methyl-pyridin-2-yl)-amine |

TABLE A-continued

| No. | Structure | Name |
|---|---|---|
| 59 | 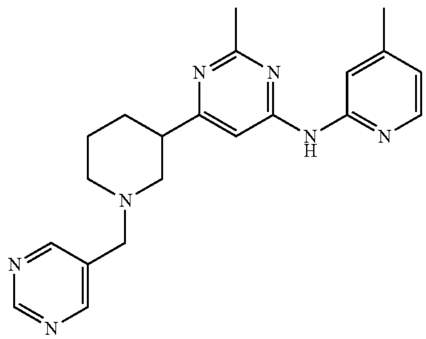 [SMILES: Cc1ccnc(Nc2cc(C3CCCN(Cc4cncnc4)C3)nc(C)n2)c1] | (4-Methyl-pyridin-2-yl)-[2-methyl-6-(1-pyrimidin-5-ylmethyl-piperidin-3-yl)-pyrimidin-4-yl]-amine |
| 60 | 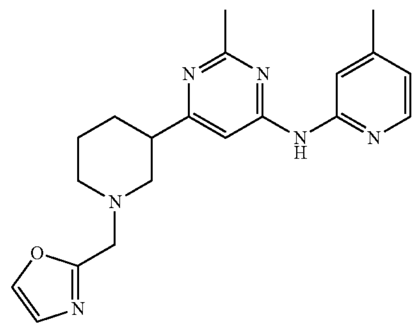 [SMILES: Cc1ccnc(Nc2cc(C3CCCN(Cc4ncco4)C3)nc(C)n2)c1] | [2-Methyl-6-(1-oxazol-2-ylmethyl-piperidin-3-yl)-pyrimidin-4-yl]-(4-methyl-pyridin-2-yl)-amine |
| 61 | 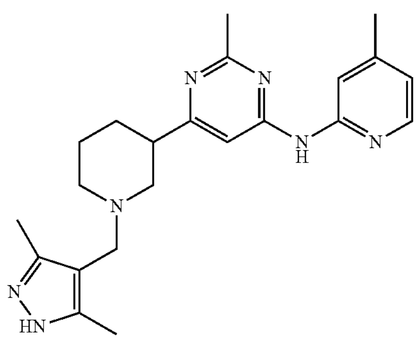 [SMILES: Cc1ccnc(Nc2cc(C3CCCN(Cc4c(C)n[nH]c4C)C3)nc(C)n2)c1] | {6-[1-(3,5-Dimethyl-1H-pyrazol-4-ylmethyl)-piperidin-3-yl]-2-methyl-pyrimidin-4-yl}-(4-methyl-pyridin-2-yl)-amine |
| 62 | 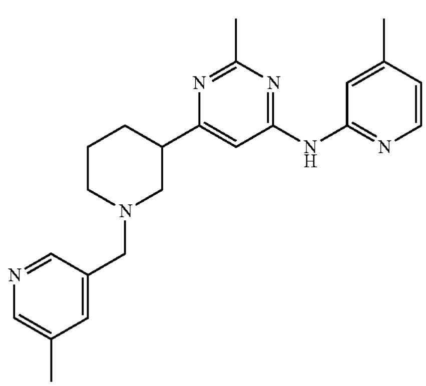 [SMILES: Cc1cncc(CN2CCCC(c3cc(Nc4cc(C)ccn4)nc(C)n3)C2)c1] | {2-Methyl-6-[1-(5-methyl-pyridin-3-ylmethyl)-piperidin-3-yl]-pyrimidin-4-yl}-(4-methyl-pyridin-2-yl)-amine |

TABLE A-continued

| No. | Structure | Name |
|-----|-----------|------|
| 63 | 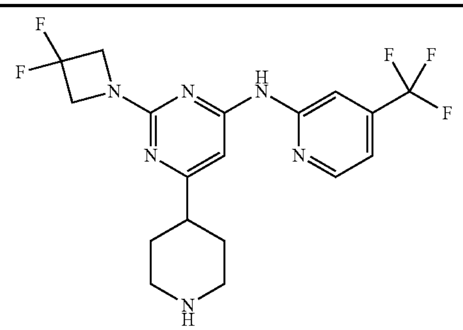 | [2-(3,3-Difluoro-azetidin-1-yl)-6-piperidin-4-yl-pyrimidin-4-yl]-(4-trifluoromethyl-pyridin-2-yl)-amine |
| 64 | 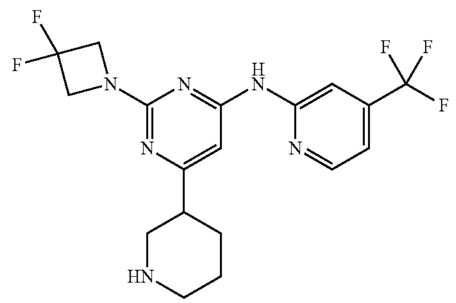 [SMILES: FC1(F)CN(c2nc(Nc3cc(C(F)(F)F)ccn3)cc(C3CCCNC3)n2)C1] | [2-(3,3-Difluoro-azetidin-1-yl)-6-piperidin-3-yl-pyrimidin-4-yl]-(4-trifluoromethyl-pyridin-2-yl)-amine |
| 65 | 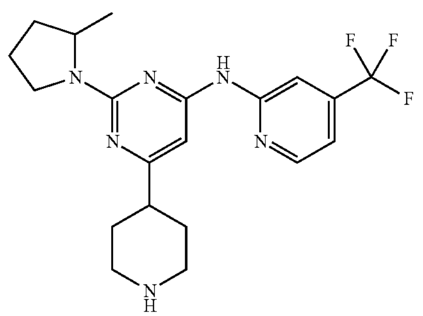 [SMILES: CC1CCCN1c1nc(Nc2cc(C(F)(F)F)ccn2)cc(C2CCNCC2)n1] | [2-(2-Methyl-pyrrolidin-1-yl)-6-piperidin-4-yl-pyrimidin-4-yl]-(4-trifluoromethyl-pyridin-2-yl)-amine |
| 66 | 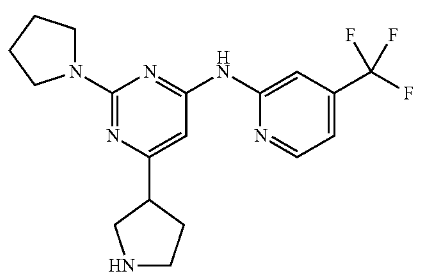 [SMILES: FC(F)(F)c1ccnc(Nc2cc(C3CCNC3)nc(N3CCCC3)n2)c1] | (2-Pyrrolidin-1-yl-6-pyrrolidin-3-yl-pyrimidin-4-yl)-(4-trifluoromethyl-pyridin-2-yl)-amine |
| 67 | 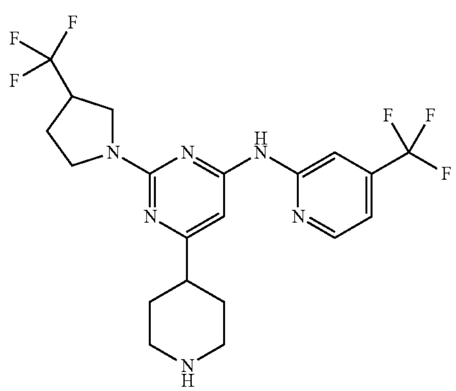 [SMILES: FC(F)(F)c1ccnc(Nc2cc(C3CCNCC3)nc(N3CCC(C(F)(F)F)C3)n2)c1] | [6-Piperidin-4-yl-2-(3-trifluoromethyl-pyrrolidin-1-yl)-pyrimidin-4-yl]-(4-trifluoromethyl-pyridin-2-yl)-amine |

TABLE A-continued

| No. | Structure | Name |
|---|---|---|
| 68 | 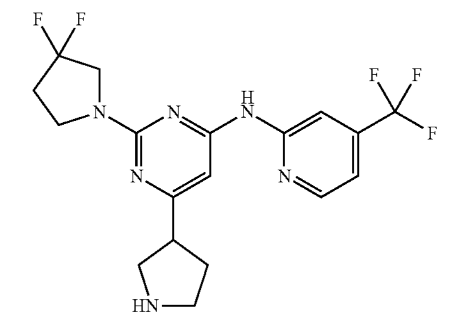 [SMILES: FC1(F)CCN(c2nc(Nc3cc(C(F)(F)F)ccn3)cc(C3CCNC3)n2)C1] | [2-(3,3-Difluoro-pyrrolidin-1-yl)-6-pyrrolidin-3-yl-pyrimidin-4-yl]-(4-trifluoromethyl-pyridin-2-yl)-amine |
| 69 | 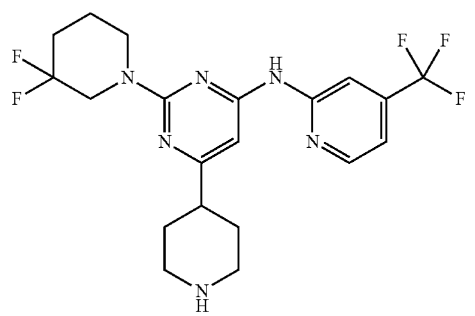 [SMILES: FC1(F)CCCN(c2nc(Nc3cc(C(F)(F)F)ccn3)cc(C3CCNCC3)n2)C1] | [2-(3,3-Difluoro-piperidin-1-yl)-6-piperidin-4-yl-pyrimidin-4-yl]-(4-trifluoromethyl-pyridin-2-yl)-amine |
| 70 | 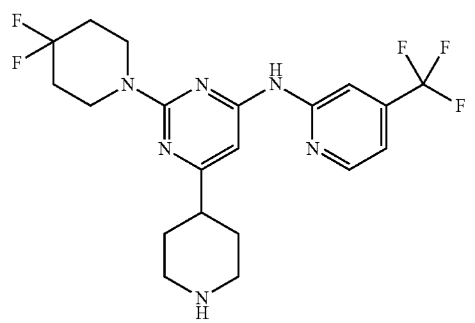 [SMILES: FC1(F)CCN(c2nc(Nc3cc(C(F)(F)F)ccn3)cc(C3CCNCC3)n2)CC1] | [2-(4,4-Difluoro-piperidin-1-yl)-6-piperidin-4-yl-pyrimidin-4-yl]-(4-trifluoromethyl-pyridin-2-yl)-amine |
| 71 | 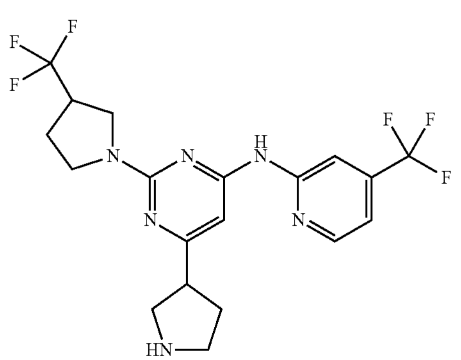 [SMILES: FC(F)(F)c1ccnc(Nc2cc(C3CCNC3)nc(N3CCC(C(F)(F)F)C3)n2)c1] | [6-Pyrrolidin-3-yl-2-(3-trifluoromethyl-pyrrolidin-1-yl)-pyrimidin-4-yl]-(4-trifluoromethyl-pyridin-2-yl)-amine |

TABLE A-continued

| No. | Structure | Name |
|---|---|---|
| 72 | 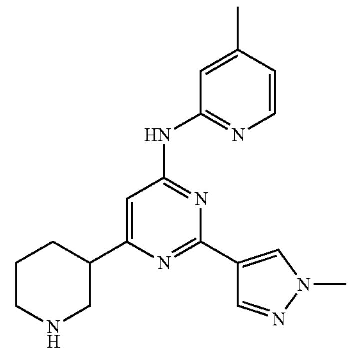 [SMILES: Cc1ccnc(Nc2cc(C3CCCNC3)nc(-c3cnn(C)c3)n2)c1] | [2-(1-Methyl-1H-pyrazol-4-yl)-6-piperidin-3-yl-pyrimidin-4-yl]-(4-methyl-pyridin-2-yl)-amine |
| 73 | 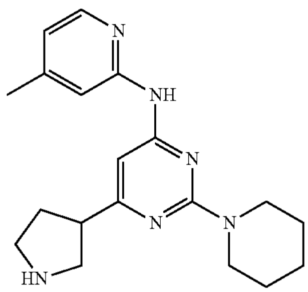 [SMILES: Cc1ccnc(Nc2cc(C3CCNC3)nc(N3CCCCC3)n2)c1] | (4-Methyl-pyridin-2-yl)-(2-piperidin-1-yl-6-pyrrolidin-3-yl-pyrimidin-4-yl)-amine |
| 74 | 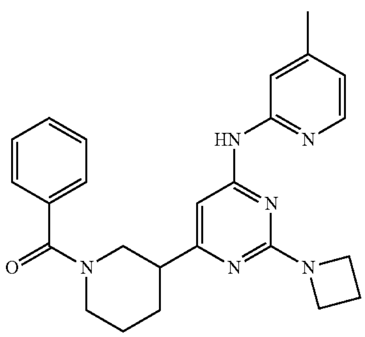 [SMILES: Cc1ccnc(Nc2cc(C3CCCN(C(=O)c4ccccc4)C3)nc(N3CCC3)n2)c1] | {3-[2-Azetidin-1-yl-6-(4-methyl-pyridin-2-ylamino)-pyrimidin-4-yl]-piperidin-1-yl}-phenyl-methanone |
| 75 | 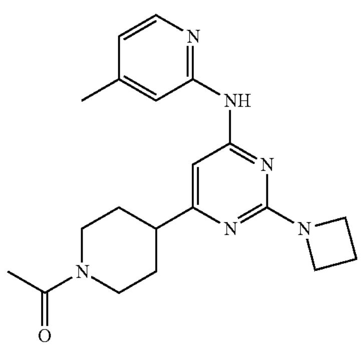 [SMILES: CC(=O)N1CCC(c2cc(Nc3cc(C)ccn3)nc(N3CCC3)n2)CC1] | 1-{4-[2-Azetidin-1-yl-6-(4-methyl-pyridin-2-ylamino)-pyrimidin-4-yl]-piperidin-1-yl}-ethanone |
| 76 | 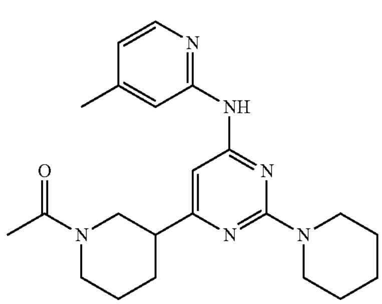 [SMILES: CC(=O)N1CCCC(c2cc(Nc3cc(C)ccn3)nc(N3CCCCC3)n2)C1] | 1-{3-[6-(4-Methyl-pyridin-2-ylamino)-2-piperidin-1-yl-pyrimidin-4-yl]-piperidin-1-yl}-ethanone |

TABLE A-continued

| No. | Structure | Name |
|-----|-----------|------|
| 77 | 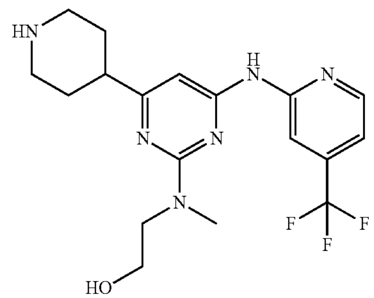 [SMILES: CN(CCO)c1nc(Nc2cc(C(F)(F)F)ccn2)cc(C2CCNCC2)n1] | 2-{Methyl-[4-piperidin-4-yl-6-(4-trifluoromethyl-pyridin-2-ylamino)-pyrimidin-2-yl]-amino}-ethanol |
| 78 | 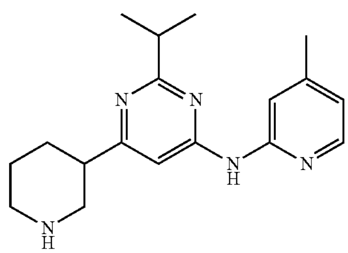 [SMILES: Cc1ccnc(Nc2cc(C3CCCNC3)nc(C(C)C)n2)c1] | (2-Isopropyl-6-piperidin-3-yl-pyrimidin-4-yl)-(4-methyl-pyridin-2-yl)-amine |
| 79 | 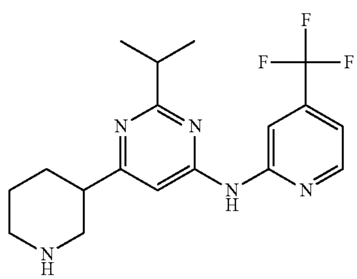 [SMILES: CC(C)c1nc(Nc2cc(C(F)(F)F)ccn2)cc(C2CCCNC2)n1] | (2-Isopropyl-6-piperidin-3-yl-pyrimidin-4-yl)-(4-trifluoromethyl-pyridin-2-yl)-amine |
| 80 | 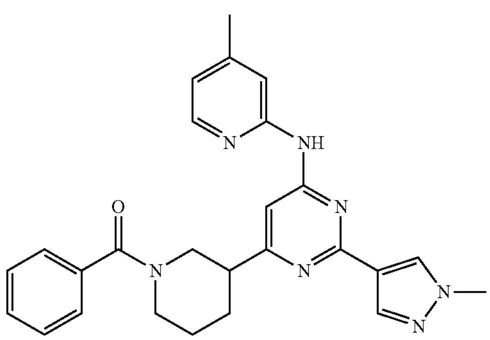 [SMILES: Cc1ccnc(Nc2cc(C3CCCN(C(=O)c4ccccc4)C3)nc(-c3cnn(C)c3)n2)c1] | {3-[2-(1-Methyl-1H-pyrazol-4-yl)-6-(4-methyl-pyridin-2-ylamino)-pyrimidin-4-yl]-piperidin-1-yl}-phenyl-methanone |
| 81 | 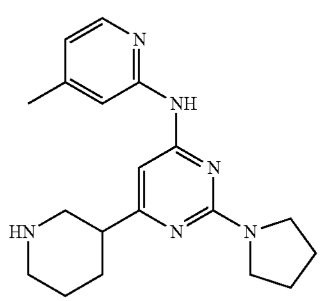 [SMILES: Cc1ccnc(Nc2cc(C3CCCNC3)nc(N3CCCC3)n2)c1] | (4-Methyl-pyridin-2-yl)-(6-piperidin-3-yl-2-pyrrolidin-1-yl-pyrimidin-4-yl)-amine |

TABLE A-continued

| No. | Structure | Name |
|---|---|---|
| 82 | 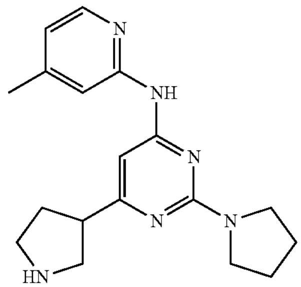 [SMILES: Cc1ccnc(Nc2cc(C3CCNC3)nc(N3CCCC3)n2)c1] | (4-Methyl-pyridin-2-yl)-(2-pyrrolidin-1-yl-6-pyrrolidin-3-yl-pyrimidin-4-yl)-amine |
| 83 | 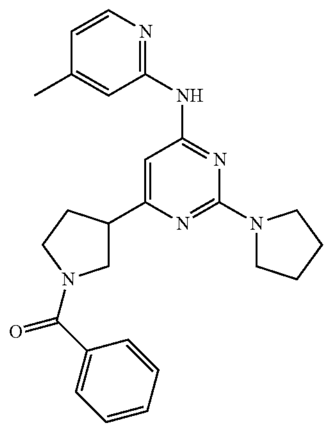 [SMILES: Cc1ccnc(Nc2cc(C3CCN(C(=O)c4ccccc4)C3)nc(N3CCCC3)n2)c1] | {3-[6-(4-Methyl-pyridin-2-ylamino)-2-pyrrolidin-1-yl-pyrimidin-4-yl]-pyrrolidin-1-yl}-phenyl-methanone |
| 84 | 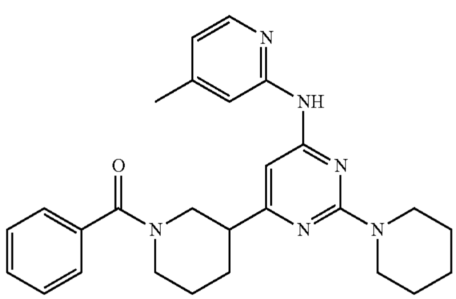 [SMILES: Cc1ccnc(Nc2cc(C3CCCN(C(=O)c4ccccc4)C3)nc(N3CCCCC3)n2)c1] | {3-[6-(4-Methyl-pyridin-2-ylamino)-2-piperidin-1-yl-pyrimidin-4-yl]-piperidin-1-yl}-phenyl-methanone |
| 85 | 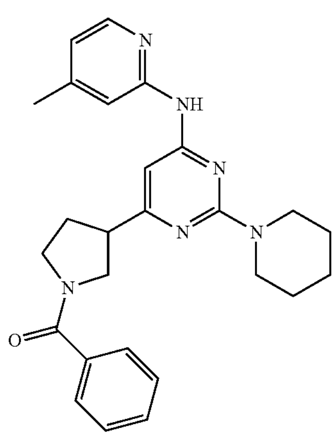 [SMILES: Cc1ccnc(Nc2cc(C3CCN(C(=O)c4ccccc4)C3)nc(N3CCCCC3)n2)c1] | {3-[6-(4-Methyl-pyridin-2-ylamino)-2-piperidin-1-yl-pyrimidin-4-yl]-pyrrolidin-1-yl}-phenyl-methanone |

TABLE A-continued

| No. | Structure | Name |
|---|---|---|
| 86 | 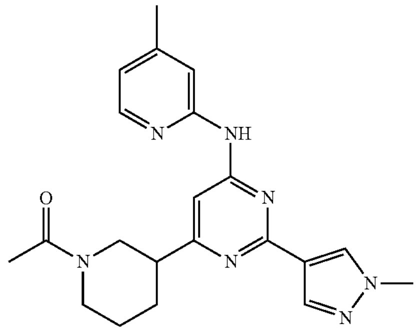 [SMILES: CC(=O)N1CCCC(c2cc(Nc3cc(C)ccn3)nc(-c3cnn(C)c3)n2)C1] | 1-{3-[2-(1-Methyl-1H-pyrazol-4-yl)-6-(4-methyl-pyridin-2-ylamino)-pyrimidin-4-yl]-piperidin-1-yl}-ethanone |
| 87 | 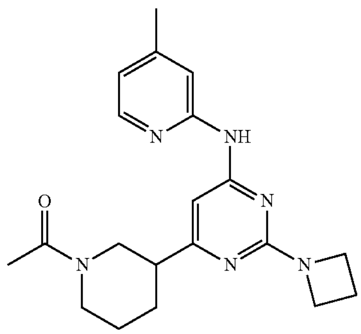 [SMILES: CC(=O)N1CCCC(c2cc(Nc3cc(C)ccn3)nc(N3CCC3)n2)C1] | 1-{3-[2-Azetidin-1-yl-6-(4-methyl-pyridin-2-ylamino)-pyrimidin-4-yl]-piperidin-1-yl}-ethanone |
| 88 | 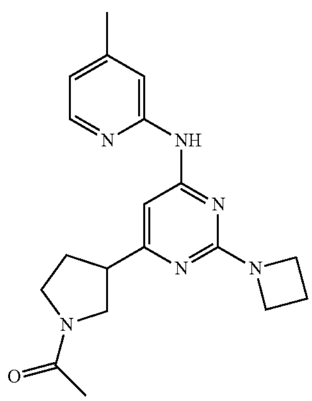 [SMILES: CC(=O)N1CCC(c2cc(Nc3cc(C)ccn3)nc(N3CCC3)n2)C1] | 1-{3-[2-Azetidin-1-yl-6-(4-methyl-pyridin-2-ylamino)-pyrimidin-4-yl]-pyrrolidin-1-yl}-ethanone |
| 89 | 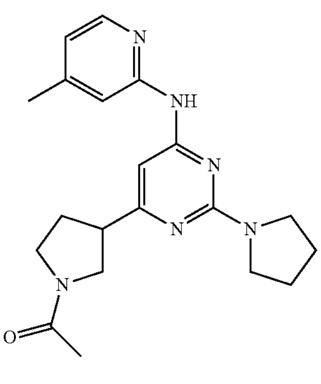 [SMILES: CC(=O)N1CCC(c2cc(Nc3cc(C)ccn3)nc(N3CCCC3)n2)C1] | 1-{3-[6-(4-Methyl-pyridin-2-ylamino)-2-pyrrolidin-1-yl-pyrimidin-4-yl]-pyrrolidin-1-yl}-ethanone |

TABLE A-continued

| No. | Structure | Name |
|---|---|---|
| 90 | 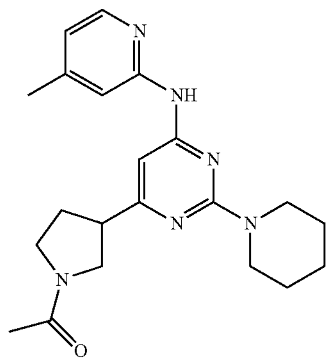 [SMILES: CC(=O)N1CCC(c2cc(Nc3cc(C)ccn3)nc(N3CCCCC3)n2)C1] | 1-{3-[6-(4-Methyl-pyridin-2-ylamino)-2-piperidin-1-yl-pyrimidin-4-yl]-pyrrolidin-1-yl}-ethanone |
| 91 | 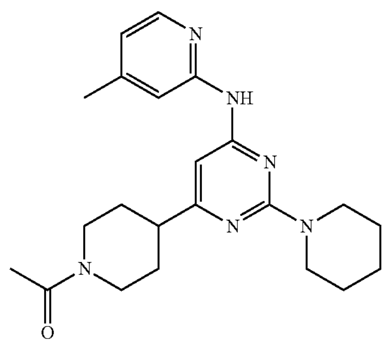 [SMILES: CC(=O)N1CCC(c2cc(Nc3cc(C)ccn3)nc(N3CCCCC3)n2)CC1] | 1-{4-[6-(4-Methyl-pyridin-2-ylamino)-2-piperidin-1-yl-pyrimidin-4-yl]-piperidin-1-yl}-ethanone |
| 92 | 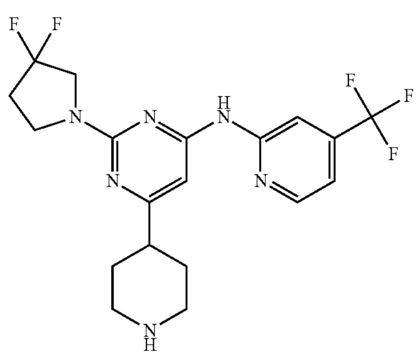 [SMILES: FC1(F)CCN(c2nc(Nc3cc(C(F)(F)F)ccn3)cc(C3CCNCC3)n2)C1] | [2-(3,3-Difluoro-pyrrolidin-din-1-yl)-6-piperidin-4-yl-pyrimidin-4-yl]-(4-trifluoromethyl-pyridin-2-yl)-amine |
| 93 | 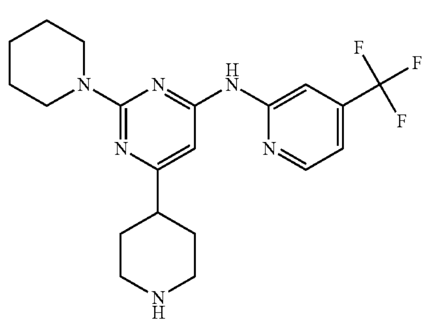 [SMILES: FC(F)(F)c1ccnc(Nc2cc(C3CCNCC3)nc(N3CCCCC3)n2)c1] | (2-Piperidin-1-yl-6-piperidin-4-yl-pyrimidin-4-yl)-(4-trifluoromethyl-pyridin-2-yl)-amine |

TABLE A-continued

| No. | Structure | Name |
|---|---|---|
| 94 | 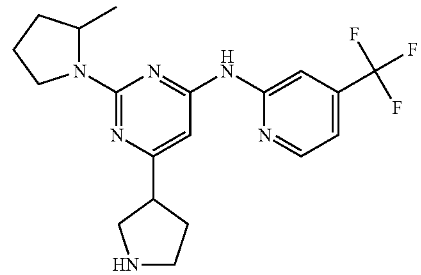 [SMILES: CC1CCCN1c1nc(Nc2cc(C(F)(F)F)ccn2)cc(C2CCNC2)n1] | [2-(2-Methyl-pyrrolidin-1-yl)-6-pyrrolidin-3-yl-pyrimidin-4-yl]-(4-trifluoromethyl-pyridin-2-yl)-amine |
| 95 | 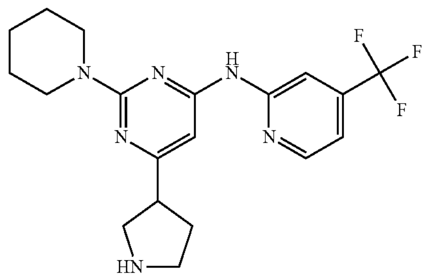 [SMILES: FC(F)(F)c1ccnc(Nc2cc(C3CCNC3)nc(N3CCCCC3)n2)c1] | (2-Piperidin-1-yl-6-pyrrolidin-3-yl-pyrimidin-4-yl)-(4-trifluoromethyl-pyridin-2-yl)-amine |
| 96 | 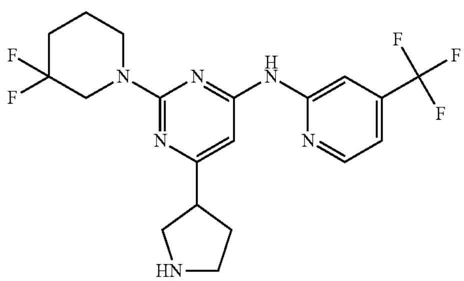 [SMILES: FC1(F)CCCN(c2nc(Nc3cc(C(F)(F)F)ccn3)cc(C3CCNC3)n2)C1] | [2-(3,3-Difluoro-piperidin-1-yl)-6-pyrrolidin-3-yl-pyrimidin-4-yl]-(4-trifluoromethyl-pyridin-2-yl)-amine |
| 97 | 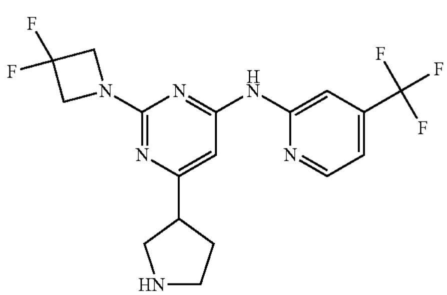 [SMILES: FC1(F)CN(c2nc(Nc3cc(C(F)(F)F)ccn3)cc(C3CCNC3)n2)C1] | [2-(3,3-Difluoro-azetidin-1-yl)-6-pyrrolidin-3-yl-pyrimidin-4-yl]-(4-trifluoromethyl-pyridin-2-yl)-amine |
| 98 | 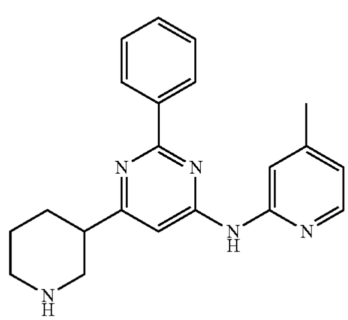 [SMILES: Cc1ccnc(Nc2cc(C3CCCNC3)nc(-c3ccccc3)n2)c1] | (4-Methyl-pyridin-2-yl)-(2-phenyl-6-piperidin-3-yl-pyrimidin-4-yl)-amine |

TABLE A-continued

| No. | Structure | Name |
|---|---|---|
| 99 | 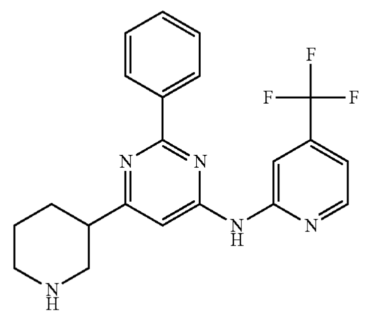 [SMILES: FC(F)(F)c1ccnc(Nc2cc(C3CCCNC3)nc(-c3ccccc3)n2)c1] | (2-Phenyl-6-piperidin-3-yl-pyrimidin-4-yl)-(4-trifluoromethyl-pyridin-2-yl)-amine |
| 100 | 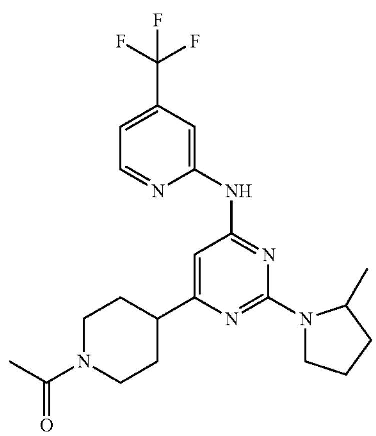 [SMILES: CC(=O)N1CCC(c2cc(Nc3cc(C(F)(F)F)ccn3)nc(N3CCCC3C)n2)CC1] | 1-{4-[2-(2-Methyl-pyrrolidin-1-yl)-6-(4-trifluoromethyl-pyridin-2-ylamino)-pyrimidin-4-yl]-piperidin-1-yl}-ethanone |
| 101 | 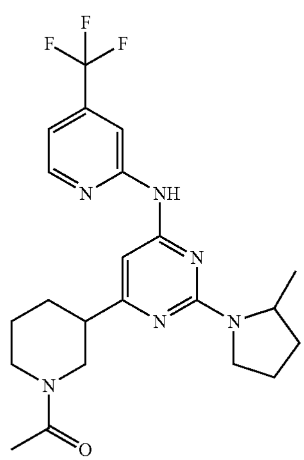 [SMILES: CC(=O)N1CCCC(c2cc(Nc3cc(C(F)(F)F)ccn3)nc(N3CCCC3C)n2)C1] | 1-{3-[2-(2-Methyl-pyrrolidin-1-yl)-6-(4-trifluoromethyl-pyridin-2-ylamino)-pyrimidin-4-yl]-piperidin-1-yl}-ethanone |
| 102 | 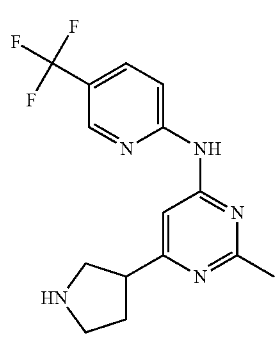 [SMILES: Cc1nc(Nc2ccc(C(F)(F)F)cn2)cc(C2CCNC2)n1] | (2-Methyl-6-pyrrolidin-3-yl-pyrimidin-4-yl)-(5-trifluoromethyl-pyridin-2-yl)-amine |

TABLE A-continued

| No. | Structure | Name |
|-----|-----------|------|
| 103 | 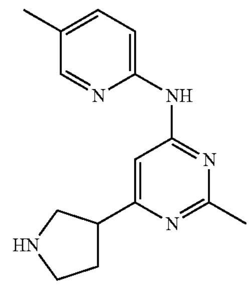 | (5-Methyl-pyridin-2-yl)-(2-methyl-6-pyrrolidin-3-yl-pyrimidin-4-yl)-amine |
| 104 | 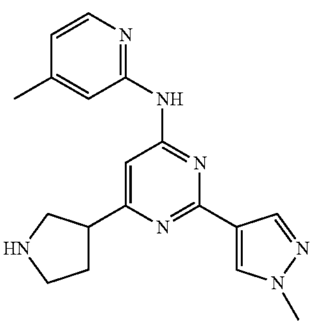 [SMILES: Cc1ccnc(Nc2cc(C3CCNC3)nc(-c3cnn(C)c3)n2)c1] | [2-(1-Methyl-1H-pyrazol-4-yl)-6-pyrrolidin-3-yl-pyrimidin-4-yl]-(4-methyl-pyridin-2-yl)-amine |
| 105 | 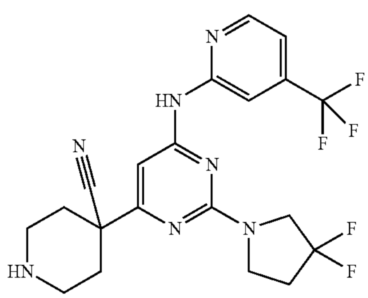 [SMILES: N#CC1(c2cc(Nc3cc(C(F)(F)F)ccn3)nc(N3CCC(F)(F)C3)n2)CCNCC1] | 4-[2-(3,3-Difluoro-pyrrolidin-1-yl)-6-(4-trifluoromethyl-pyridin-2-ylamino)-pyrimidin-4-yl]-piperidine-4-carbonitrile |
| 106 | 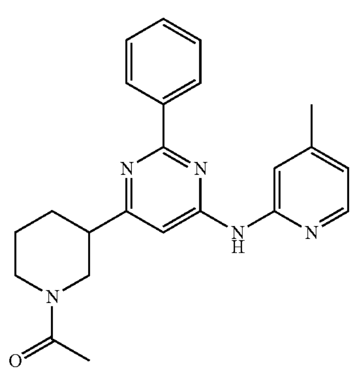 [SMILES: CC(=O)N1CCCC(c2cc(Nc3cc(C)ccn3)nc(-c3ccccc3)n2)C1] | 1-{3-[6-(4-Methyl-pyridin-2-ylamino)-2-phenyl-pyrimidin-4-yl]-piperidin-1-yl}-ethanone |

TABLE A-continued

| No. | Structure | Name |
|---|---|---|
| 107 | 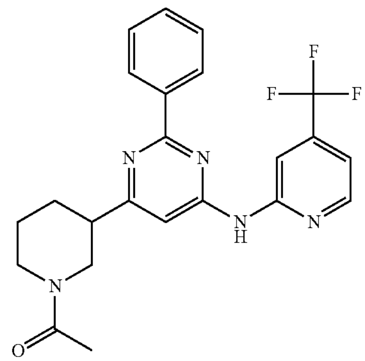 [SMILES: CC(=O)N1CCCC(c2cc(Nc3cc(C(F)(F)F)ccn3)nc(-c3ccccc3)n2)C1] | 1-{3-[2-Phenyl-6-(4-trifluoromethyl-pyridin-2-ylamino)-pyrimidin-4-yl]-piperidin-1-yl}ethanone |
| 108 | 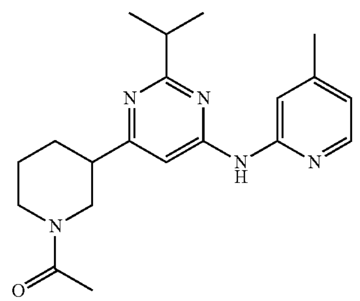 [SMILES: CC(=O)N1CCCC(c2cc(Nc3cc(C)ccn3)nc(C(C)C)n2)C1] | 1-{3-[2-Isopropyl-6-(4-methyl-pyridin-2-ylamino)-pyrimidin-4-yl]-piperidin-1-yl}-ethanone |
| 109 | 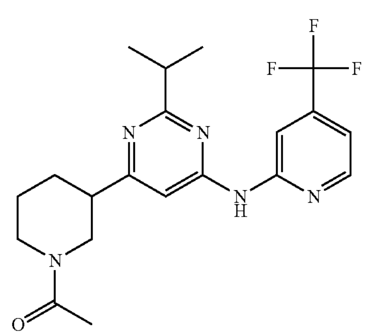 [SMILES: CC(=O)N1CCCC(c2cc(Nc3cc(C(F)(F)F)ccn3)nc(C(C)C)n2)C1] | 1-{3-[2-Isopropyl-6-(4-trifluoromethyl-pyridin-2-ylamino)-pyrimidin-4-yl]-piperidin-1-yl}-ethanone |
| 110 | 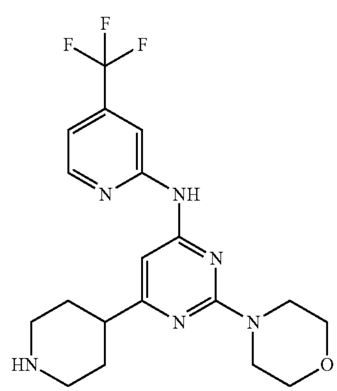 [SMILES: FC(F)(F)c1ccnc(Nc2cc(C3CCNCC3)nc(N3CCOCC3)n2)c1] | (2-Morpholin-4-yl-6-piperidin-4-yl-pyrimidin-4-yl)-(4-trifluoromethyl-pyridin-2-yl)-amine |

TABLE A-continued

| No. | Structure | Name |
|-----|-----------|------|
| 111 | 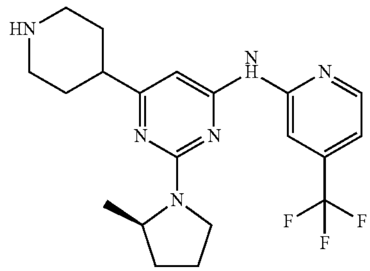 [SMILES: C[C@@H]1CCCN1c1nc(Nc2cc(C(F)(F)F)ccn2)cc(C2CCNCC2)n1] | [2-((R)-2-Methyl-pyrrolidin-1-yl)-6-piperidin-4-yl-pyrimidin-4-yl]-(4-trifluoromethyl-pyridin-2-yl)-amine |
| 112 | 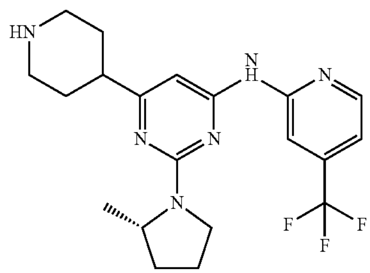 [SMILES: C[C@H]1CCCN1c1nc(Nc2cc(C(F)(F)F)ccn2)cc(C2CCNCC2)n1] | [2-((S)-2-Methyl-pyrrolidin-1-yl)-6-piperidin-4-yl-pyrimidin-4-yl]-(4-trifluoromethyl-pyridin-2-yl)-amine |
| 113 | 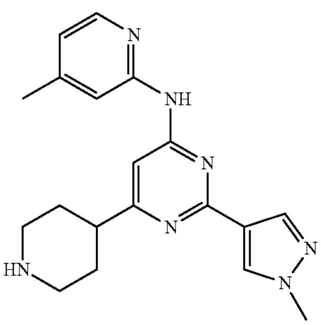 [SMILES: Cc1ccnc(Nc2cc(C3CCNCC3)nc(-c3cnn(C)c3)n2)c1] | [2-(1-Methyl-1H-pyrazol-4-yl)-6-piperidin-4-yl-pyrimidin-4-yl]-(4-methyl-pyridin-2-yl)-amine |
| 114 | 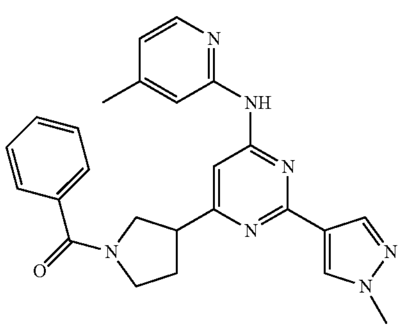 [SMILES: Cc1ccnc(Nc2cc(C3CCN(C(=O)c4ccccc4)C3)nc(-c3cnn(C)c3)n2)c1] | {3-[2-(1-Methyl-1H-pyrazol-4-yl)-6-(4-methyl-pyridin-2-ylamino)-pyrimidin-4-yl]-pyrrolidin-1-yl}-phenyl-methanone |
| 115 | 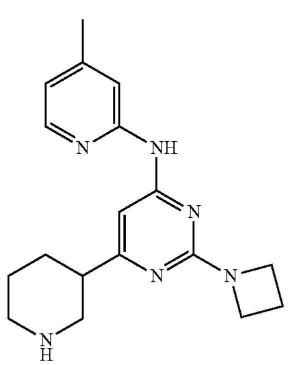 [SMILES: Cc1ccnc(Nc2cc(C3CCCNC3)nc(N3CCC3)n2)c1] | (2-Azetidin-1-yl-6-piperidin-3-yl-pyrimidin-4-yl)-(4-methyl-pyridin-2-yl)-amine |

TABLE A-continued

| No. | Structure | Name |
|---|---|---|
| 116 | 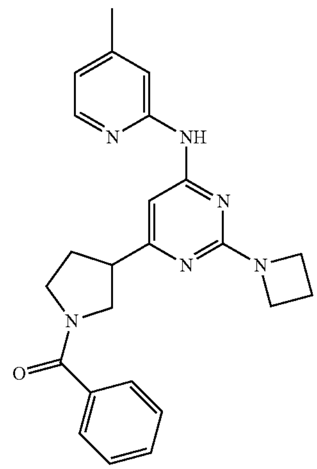 [SMILES: Cc1ccnc(Nc2cc(C3CCN(C(=O)c4ccccc4)C3)nc(N3CCC3)n2)c1] | {3-[2-Azetidin-1-yl-6-(4-methyl-pyridin-2-ylamino)-pyrimidin-4-yl]-pyrrolidin-1-yl}-phenyl-methanone |
| 117 | 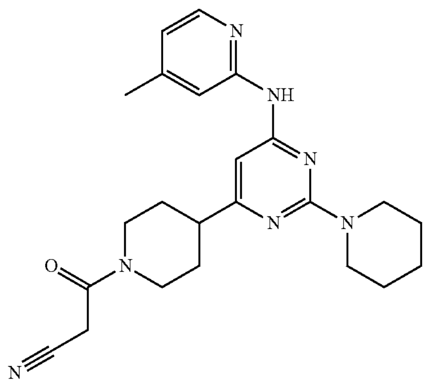 [SMILES: Cc1ccnc(Nc2cc(C3CCN(C(=O)CC#N)CC3)nc(N3CCCCC3)n2)c1] | 3-{4-[6-(4-Methyl-pyridin-2-ylamino)-2-piperidin-1-yl-pyrimidin-4-yl]-piperidin-1-yl}-3-oxo-propionitrile |
| 118 | 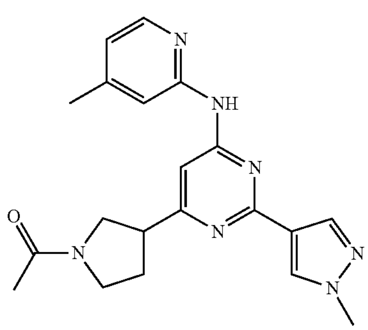 [SMILES: CC(=O)N1CCC(c2cc(Nc3cc(C)ccn3)nc(-c3cnn(C)c3)n2)C1] | 1-{3-[2-(1-Methyl-1H-pyrazol-4-yl)-6-(4-methyl-pyridin-2-ylamino)-pyrimidin-4-yl]-pyrrolidin-1-yl}-ethanone |
| 119 | 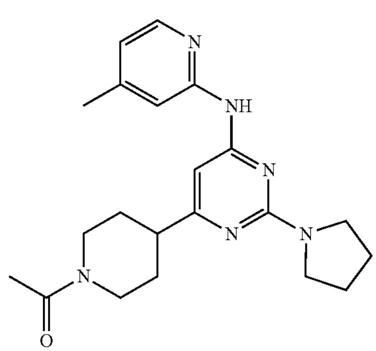 [SMILES: CC(=O)N1CCC(c2cc(Nc3cc(C)ccn3)nc(N3CCCC3)n2)CC1] | 1-{4-[6-(4-Methyl-pyridin-2-ylamino)-2-pyrrolidin-1-yl-pyrimidin-4-yl]-piperidin-1-yl}-ethanone |

TABLE A-continued

| No. | Structure | Name |
|---|---|---|
| 120 | 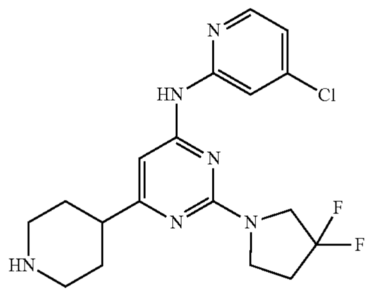 [SMILES: FC1(F)CCN(c2nc(Nc3cc(Cl)ccn3)cc(C3CCNCC3)n2)C1] | (4-Chloro-pyridin-2-yl)-[2-(3,3-difluoro-pyrrolidin-1-yl)-6-piperidin-4-yl-pyrimidin-4-yl]-amine |
| 121 | 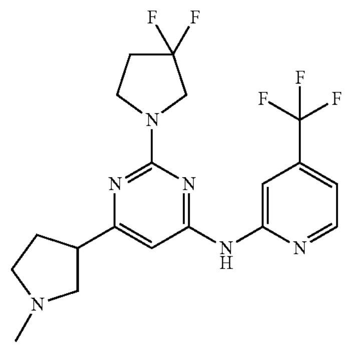 [SMILES: CN1CCC(c2cc(Nc3cc(C(F)(F)F)ccn3)nc(N3CCC(F)(F)C3)n2)C1] | [2,(3,3-Difluoro-pyrrolidin-1-yl)-6-(1-methyl-pyrrolidin-3-yl)-pyrimidin-4-yl]-(4-trifluoromethyl-pyridin-2-yl)-amine |
| 122 | 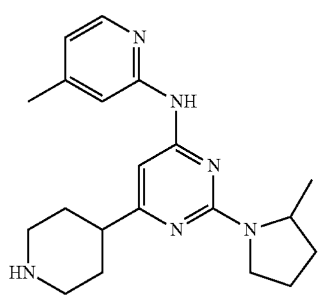 [SMILES: Cc1ccnc(Nc2cc(C3CCNCC3)nc(N3CCCC3C)n2)c1] | (4-Methyl-pyridin-2-yl)-[2-(2-methyl-pyrrolidin-1-yl)-6-piperidin-4-yl-pyrimidin-4-yl]-amine |
| 123 | 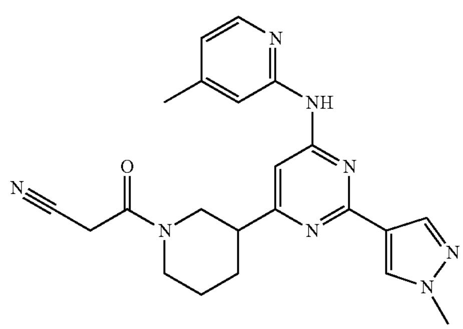 [SMILES: Cc1ccnc(Nc2cc(C3CCCN(C(=O)CC#N)C3)nc(-c3cnn(C)c3)n2)c1] | 3-{3-[2-(1-Methyl-1H-pyrazol-4-yl)-6-(4-methyl-pyridin-2-ylamino)-pyrimidin-4-yl]-piperidin-1-yl}-3-oxo-propionitrile |

TABLE A-continued

| No. | Structure | Name |
|---|---|---|
| 124 | 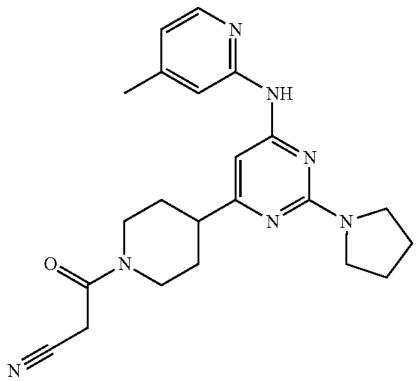 [SMILES: Cc1ccnc(Nc2cc(C3CCN(C(=O)CC#N)CC3)nc(N3CCCC3)n2)c1] | 3-{4-[6-(4-Methyl-pyridin-2-ylamino)-2-pyrrolidin-1-yl-pyrimidin-4-yl]-piperidin-1-yl}-3-oxo-propionitrile |
| 125 | 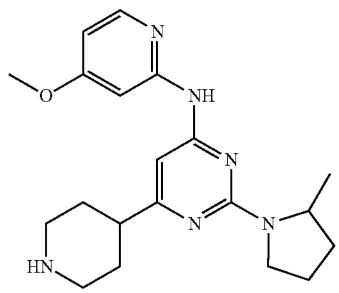 [SMILES: COc1ccnc(Nc2cc(C3CCNCC3)nc(N3CCCC3C)n2)c1] | (4-Methoxy-pyridin-2-yl)-[2-(2-methyl-pyrrolidin-1-yl)-6-piperidin-4-yl-pyrimidin-4-yl]-amine |
| 126 | 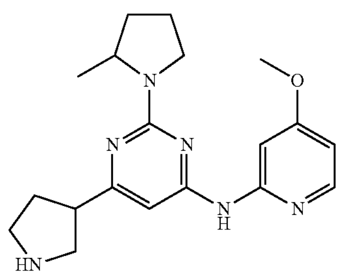 [SMILES: COc1ccnc(Nc2cc(C3CCNC3)nc(N3CCCC3C)n2)c1] | (4-Methoxy-pyridin-2-yl)-[2-(2-methyl-pyrrolidin-1-yl)-6-pyrrolidin-3-yl-pyrimidin-4-yl]-amine |
| 127 | 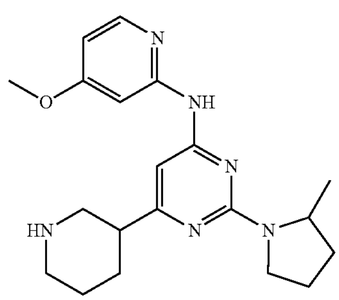 [SMILES: COc1ccnc(Nc2cc(C3CCCNC3)nc(N3CCCC3C)n2)c1] | (4-Methoxy-pyridin-2-yl)-[2-(2-methyl-pyrrolidin-1-yl)-6-piperidin-3-yl-pyrimidin-4-yl]-amine |
| 128 | 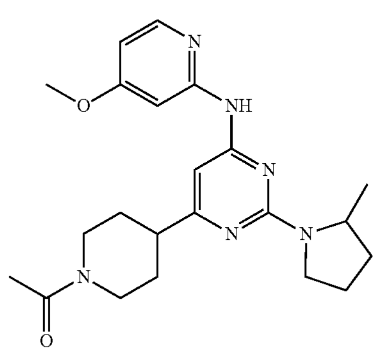 [SMILES: COc1ccnc(Nc2cc(C3CCN(C(C)=O)CC3)nc(N3CCCC3C)n2)c1] | 1-{4-[6-(4-Methoxy-pyridin-2-ylamino)-2-(2-methyl-pyrrolidin-1-yl)-pyrimidin-4-yl]-piperidin-1-yl}-ethanone |

TABLE A-continued

| No. | Structure | Name |
|---|---|---|
| 129 | 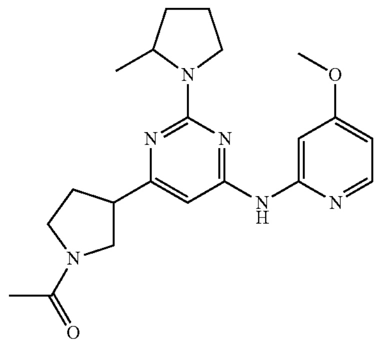 [SMILES: COc1ccnc(Nc2cc(C3CCN(C(C)=O)C3)nc(N3CCCC3C)n2)c1] | 1-{3-[6-(4-Methoxy-pyridin-2-ylamino)-2-(2-methyl-pyrrolidin-1-yl)-pyrimidin-4-yl]-pyrrolidin-1-yl}-ethanone |
| 130 | 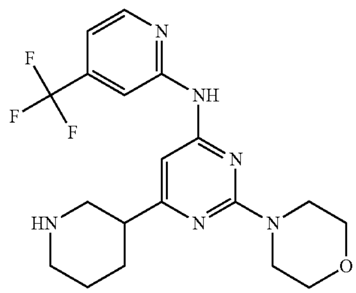 [SMILES: FC(F)(F)c1ccnc(Nc2cc(C3CCCNC3)nc(N3CCOCC3)n2)c1] | (2-Morpholin-4-yl-6-piperidin-3-yl-pyrimidin-4-yl)-(4-trifluoromethyl-pyridin-2-yl)-amine |
| 131 | 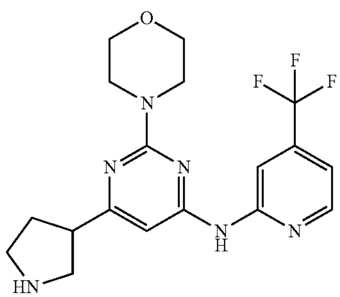 [SMILES: FC(F)(F)c1ccnc(Nc2cc(C3CCNC3)nc(N3CCOCC3)n2)c1] | (2-Morpholin-4-yl-6-pyrrolidin-3-yl-pyrimidin-4-yl)-(4-trifluoromethyl-pyridin-2-yl)-amine |
| 132 | 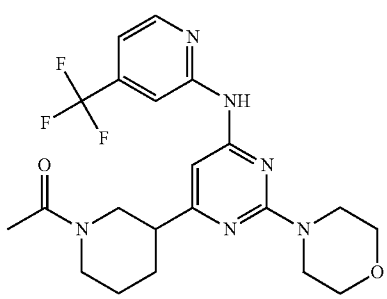 [SMILES: CC(=O)N1CCCC(c2cc(Nc3cc(C(F)(F)F)ccn3)nc(N3CCOCC3)n2)C1] | 1-{3-[2-Morpholin-4-yl-6-(4-trifluoromethyl-pyridin-2-ylamino)-pyrimidin-4-yl]-piperidin-1-yl}-ethanone |
| 133 | 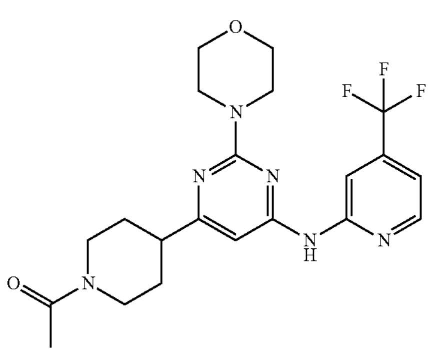 [SMILES: CC(=O)N1CCC(c2cc(Nc3cc(C(F)(F)F)ccn3)nc(N3CCOCC3)n2)CC1] | 1-{4-[2-Morpholin-4-yl-6-(4-trifluoromethyl-pyridin-2-ylamino)-pyrimidin-4-yl]-piperidin-1-yl}-ethanone |

TABLE A-continued

| No. | Structure | Name |
|---|---|---|
| 134 | 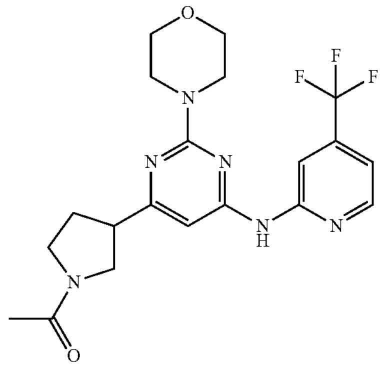 [SMILES: CC(=O)N1CCC(c2cc(Nc3cc(C(F)(F)F)ccn3)nc(N3CCOCC3)n2)C1] | 1-{3-[2-Morpholin-4-yl-6-(4-trifluoromethyl-pyridin-2-ylamino)-pyrimidin-4-yl]-pyrrolidin-1-yl}-ethanone |
| 135 | 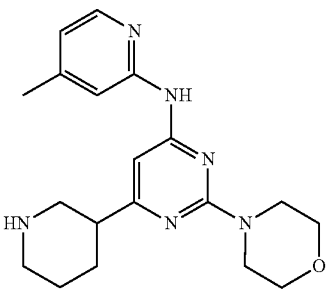 [SMILES: Cc1ccnc(Nc2cc(C3CCCNC3)nc(N3CCOCC3)n2)c1] | (4-Methyl-pyridin-2-yl)-(2-morpholin-4-yl-6-piperidin-3-yl-pyrimidin-4-yl)-amine |
| 136 | 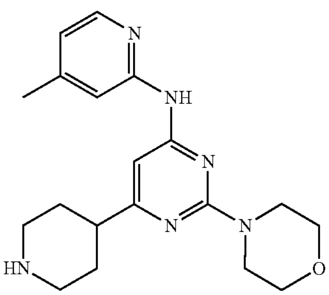 [SMILES: Cc1ccnc(Nc2cc(C3CCNCC3)nc(N3CCOCC3)n2)c1] | (4-Methyl-pyridin-2-yl)-(2-morpholin-4-yl-6-piperidin-4-yl-pyrimidin-4-yl)-amine |
| 137 | 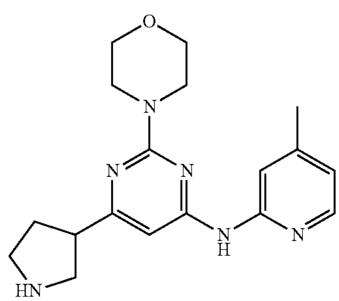 [SMILES: Cc1ccnc(Nc2cc(C3CCNC3)nc(N3CCOCC3)n2)c1] | (4-Methyl-pyridin-2-yl)-(2-morpholin-4-yl-6-pyrrolidin-3-yl-pyrimidin-4-yl)-amine |
| 138 | 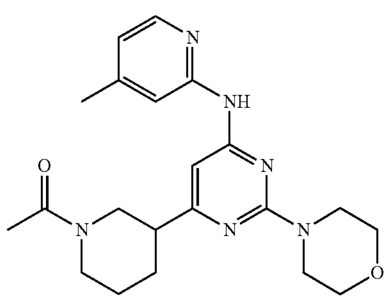 [SMILES: CC(=O)N1CCCC(c2cc(Nc3cc(C)ccn3)nc(N3CCOCC3)n2)C1] | 1-{3-[6-(4-Methyl-pyridin-2-ylamino)-2-morpholin-4-yl-pyrimidin-4-yl]-piperidin-1-yl}-ethanone |

TABLE A-continued

| No. | Structure | Name |
|---|---|---|
| 139 | 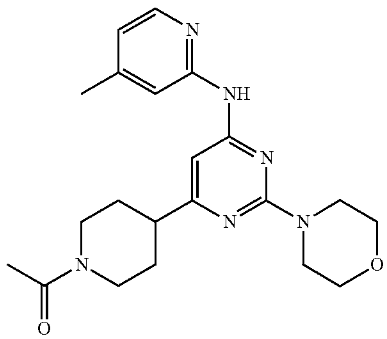 [SMILES: CC(=O)N1CCC(c2cc(Nc3cc(C)ccn3)nc(N3CCOCC3)n2)CC1] | 1-{4-[6-(4-Methyl-pyridin-2-ylamino)-2-morpholin-4-yl-pyrimidin-4-yl]-piperidin-1-yl]-ethanone |
| 140 | 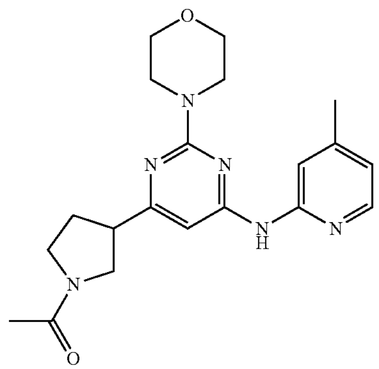 [SMILES: CC(=O)N1CCC(c2cc(Nc3cc(C)ccn3)nc(N3CCOCC3)n2)C1] | 1-{3-[6-(4-Methyl-pyridin-2-ylamino)-2-morpholin-4-yl-pyrimidin-4-yl]-pyrrolidin-1-yl]-ethanone |
| 141 | 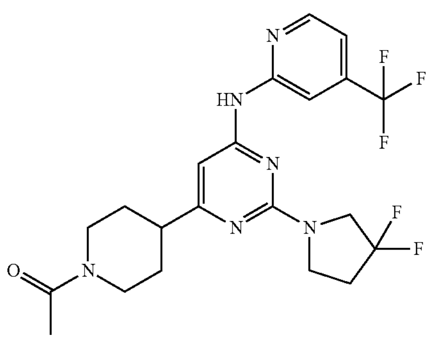 [SMILES: CC(=O)N1CCC(c2cc(Nc3cc(C(F)(F)F)ccn3)nc(N3CCC(F)(F)C3)n2)CC1] | 1-{4-[2-(3,3-Difluoro-pyrrolidin-1-yl)-6-(4-trifluoromethyl-pyridin-2-ylamino)-pyrimidin-4-yl]-piperidin-1-yl}-ethanone |
| 142 | 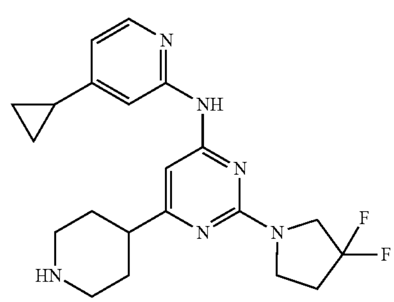 [SMILES: FC1(F)CCN(c2nc(Nc3cc(C4CC4)ccn3)cc(C3CCNCC3)n2)C1] | (4-Cyclopropyl-pyridin-2-yl)-12-(3,3-difluoro-pyrrolidin-1-yl)-6-piperidin-4-yl-pyrimidin-4-yl]-amine |

TABLE A-continued

| No. | Structure | Name |
|---|---|---|
| 143 | 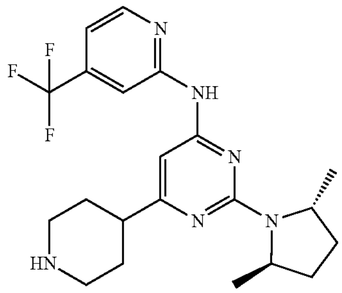 [SMILES: C[C@@H]1CC[C@@H](C)N1c1nc(Nc2cc(C(F)(F)F)ccn2)cc(C2CCNCC2)n1] | [2-((2R,5R)-2,5-Dimethyl-pyrrolidin-1-yl)-6-piperidin-4-yl-pyrimidin-4-yl]-(4-trifluoromethyl-pyridin-2-yl)-amine |
| 144 | 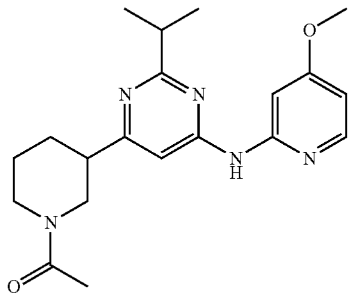 [SMILES: COc1ccnc(Nc2cc(C3CCCN(C(C)=O)C3)nc(C(C)C)n2)c1] | 1-{3-[2-Isopropyl-6-(4-methoxy-pyridin-2-ylamino)-pyrimidin-4-yl]-piperidin-1-yl}-ethanone |
| 145 | 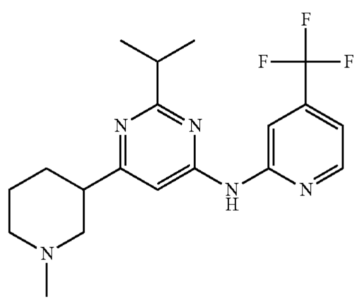 [SMILES: CC(C)c1nc(Nc2cc(C(F)(F)F)ccn2)cc(C2CCCN(C)C2)n1] | [2-Isopropyl-6-(1-methyl-piperidin-3-yl)-pyrimidin-4-yl]-(4-trifluoro-methyl-pyridin-2-yl)-amine |
| 146 | 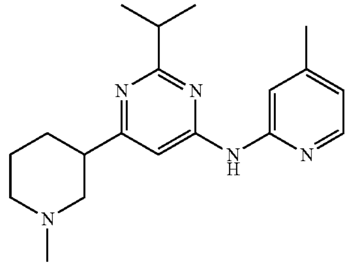 [SMILES: Cc1ccnc(Nc2cc(C3CCCN(C)C3)nc(C(C)C)n2)c1] | [2-Isopropyl-6-(1-methyl-piperidin-3-yl)-pyrimidin-4-yl]-(4-methyl-pyridin-2-yl)-amine |
| 147 | 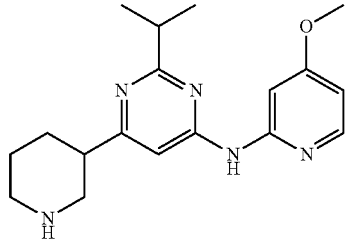 [SMILES: COc1ccnc(Nc2cc(C3CCCNC3)nc(C(C)C)n2)c1] | (2-Isopropyl-6-piperidin-3-yl-pyrimidin-4-yl)-(4-methoxy-pyridin-2-yl)-amine |

TABLE A-continued

| No. | Structure | Name |
|---|---|---|
| 148 | 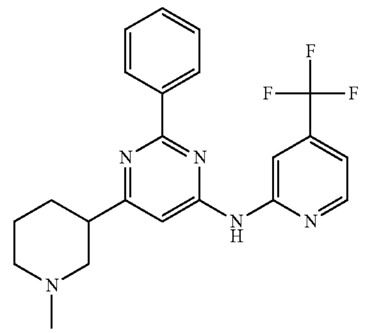 [SMILES: CN1CCCC(c2cc(Nc3cc(C(F)(F)F)ccn3)nc(-c3ccccc3)n2)C1] | [6-(1-Methyl-piperidin-3-yl)-2-phenyl-pyrimidin-4-yl]-(4-trifluoromethyl-pyridin-2-yl)-amine |
| 149 | 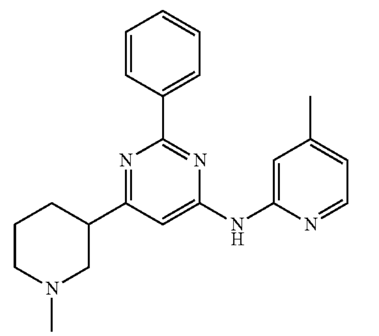 [SMILES: Cc1ccnc(Nc2cc(C3CCCN(C)C3)nc(-c3ccccc3)n2)c1] | [6-(1-Methyl-piperidin-3-yl)-2-phenyl-pyrimidin-4-yl]-(4-methyl-pyridin-2-yl)-amine |
| 150 | 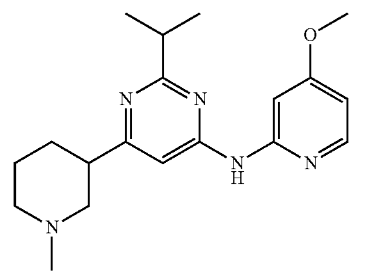 [SMILES: COc1ccnc(Nc2cc(C3CCCN(C)C3)nc(C(C)C)n2)c1] | [2-Isopropyl-6-(1-methyl-piperidin-3-yl)-pyrimidin-4-yl]-(4-methoxy-pyridin-2-yl)-amine |
| 151 | 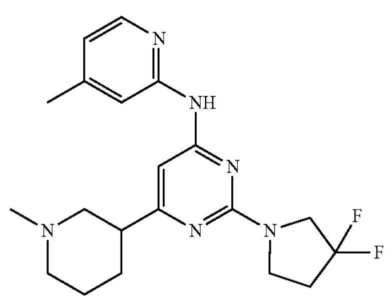 [SMILES: Cc1ccnc(Nc2cc(C3CCCN(C)C3)nc(N3CCC(F)(F)C3)n2)c1] | [2,3-Difluoro-pyrrolidin-1-yl)-6-(1-methyl-piperidin-3-yl)-pyrimidin-4-yl]-(4-methyl-pyridin-2-yl)-amine |
| 152 | 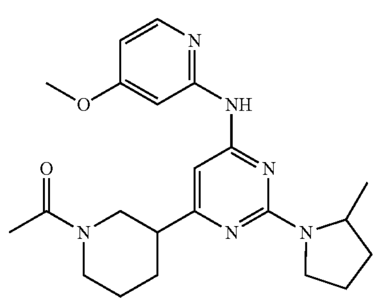 [SMILES: COc1ccnc(Nc2cc(C3CCCN(C(C)=O)C3)nc(N3CCCC3C)n2)c1] | 1-{3--[6-(4-Methoxy-pyridin-2-ylamino)-2-(2-methyl-pyrrolidin-1-yl)-pyrimidin-4-yl]-piperidin-1-yl}-ethanone |

TABLE A-continued

| No. | Structure | Name |
|---|---|---|
| 153 | 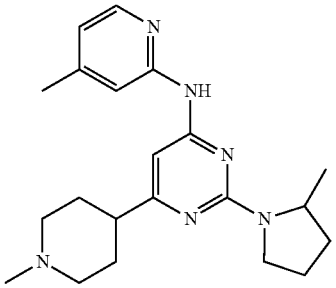 [SMILES: Cc1ccnc(Nc2cc(C3CCN(C)CC3)nc(N3CCCC3C)n2)c1] | [6-(1-Methyl-piperidin-4-yl)-2-(2-methyl-pyrrolidin-1-yl)-pyrimidin-4-yl]-(4-methyl-pyridin-2-yl)-amine |
| 154 | 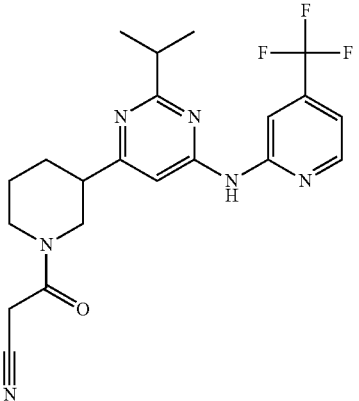 [SMILES: CC(C)c1nc(Nc2cc(C(F)(F)F)ccn2)cc(C2CCCN(C(=O)CC#N)C2)n1] | 3-{3-[2-Isopropyl-6-(4-trifluoromethyl-pyridin-2-ylamino)-pyrimidin-4-yl]-piperidin-1-yl}-3-oxo-propionitrile |
| 155 | 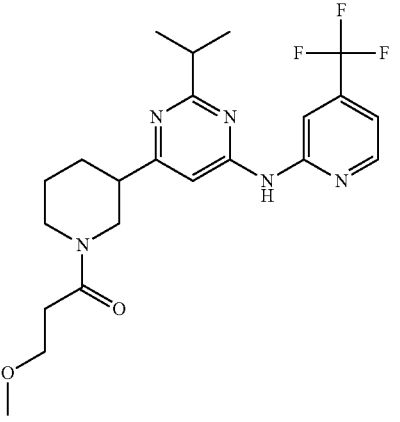 [SMILES: COCCC(=O)N1CCCC(c2cc(Nc3cc(C(F)(F)F)ccn3)nc(C(C)C)n2)C1] | 1-{3-[2-Isopropyl-6-(4-trifluoromethyl-pyridin-2-ylamino)-pyrimidin-4-yl]-piperidin-1-yl}-3-methoxy-propan-1-one |
| 156 | 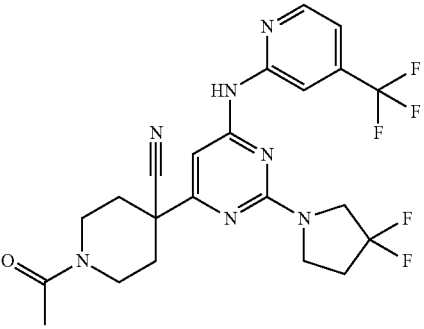 [SMILES: CC(=O)N1CCC(C#N)(c2cc(Nc3cc(C(F)(F)F)ccn3)nc(N3CCC(F)(F)C3)n2)CC1] | 1-Acetyl-4-[2-(3,3-difluoro-pyrrolidin-1-yl)-6-(4-trifluoromethyl-pyridin-2-ylamino)-pyrimidin-4-yl]-piperidine-4-carbonitrile |

TABLE A-continued

| No. | Structure | Name |
|---|---|---|
| 157 | 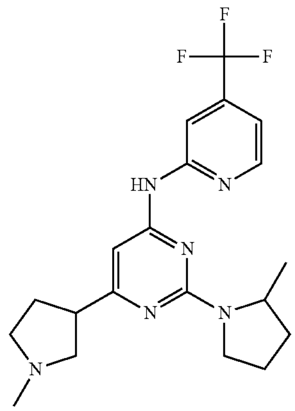 [SMILES: CC1CCCN1c1nc(Nc2cc(C(F)(F)F)ccn2)cc(C2CCN(C)C2)n1] | [2-(2-Methyl-pyrrolidin-1-yl)-6-(1-methyl-pyrrolidin-3-yl)-pyrimidin-4-yl]-(4-trifluoromethyl-pyridin-2-yl)-amine |
| 158 | 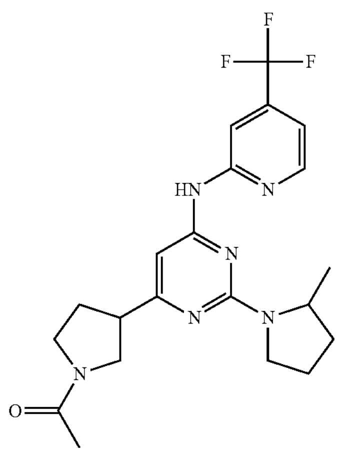 [SMILES: CC(=O)N1CCC(c2cc(Nc3cc(C(F)(F)F)ccn3)nc(N3CCCC3C)n2)C1] | 1-{3-[2-(2-Methyl-pyrrolidin-1-yl)-6-(4-trifluoromethyl-pyridin-2-ylamino)-pyrimidin-4-yl]-pyrrolidin-1-yl}-ethanone |
| 159 | 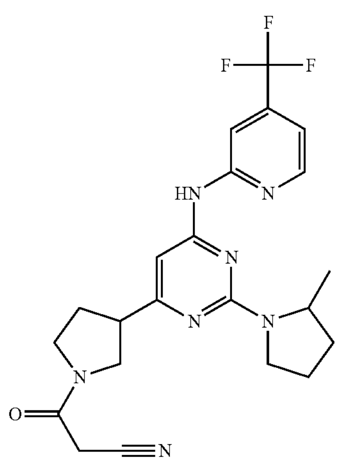 [SMILES: CC1CCCN1c1nc(Nc2cc(C(F)(F)F)ccn2)cc(C2CCN(C(=O)CC#N)C2)n1] | 3-{3-[2-(2-Methyl-pyrrolidin-1-yl)-6-(4-trifluoromethyl-pyridin-2-ylamino)-pyrimidin-4-yl]-pyrrolidin-1-yl}-3-oxo-propionitrile |
| 160 | 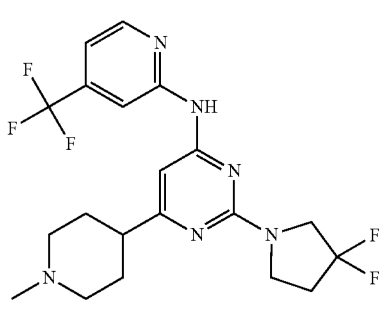 [SMILES: CN1CCC(c2cc(Nc3cc(C(F)(F)F)ccn3)nc(N3CCC(F)(F)C3)n2)CC1] | [2-(3,3-Difluoro-pyrrolidin-1-yl)-6-(1-methyl-piperidin-4-yl)-pyrimidin-4-yl]-(4-trifluoromethyl-pyridin-2-yl)-amine |

TABLE A-continued

| No. | Structure | Name |
|---|---|---|
| 161 | 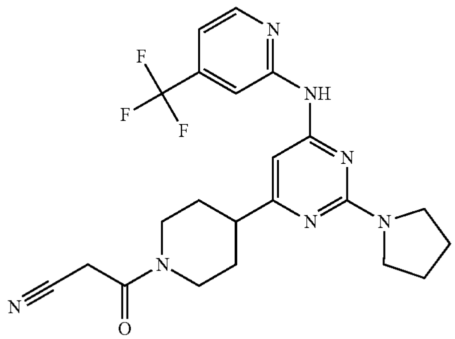 [SMILES: N#CCC(=O)N1CCC(c2cc(Nc3cc(C(F)(F)F)ccn3)nc(N3CCCC3)n2)CC1] | 3-Oxo-3-{4-[2-pyrrolidin-1-yl-6-(4-trifluoromethyl-pyridin-2-ylamino)-pyrimidin-4-yl]-piperidin-1-yl}-propionitrile |
| 162 | 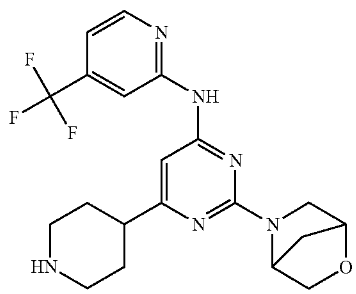 [SMILES: FC(F)(F)c1ccnc(Nc2cc(C3CCNCC3)nc(N3CC4CC3CO4)n2)c1] | [2-(2-Oxa-5-aza-bicyclo-[2.2.1]hept-5-yl)-6-piperidin-4-yl-pyrimidin-4-yl]-(4-trifluoromethyl-pyridin-2-yl)-amine |
| 163 | 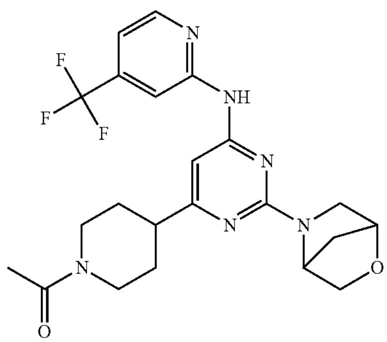 | 1-{4-[2-(2-Oxa-5-aza-bicyclo[2.2.1]hept-5-yl)-6-(4-trifluoromethyl-pyridin-2-ylamino)-pyrimidin-4-yl]-piperidin-1-yl}-ethanone |
| 164 | 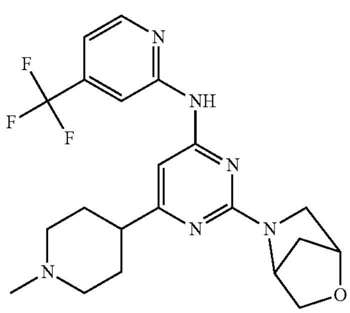 [SMILES: CN1CCC(c2cc(Nc3cc(C(F)(F)F)ccn3)nc(N3CC4CC3CO4)n2)CC1] | [6-(1-Methyl-piperidin-4-yl)-2-(2-oxa-5-aza-bicyclo[2.2.1]hept-5-yl)-pyrimidin-4-yl]-(4-trifluoromethyl-pyridin-2-yl)-amine |
| 165 | 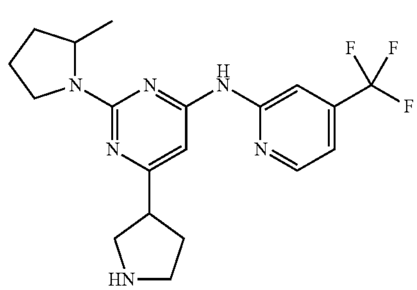 [SMILES: CC1CCCN1c1nc(Nc2cc(C(F)(F)F)ccn2)cc(C2CCNC2)n1] | [2-(2-Methyl-pyrrolidin-1-yl)-6-pyrrolidin-3-yl-pyrimidin-4-yl]-(4-trifluoromethyl-pyridin-2-yl)-amine |

TABLE A-continued

| No. | Structure | Name |
|---|---|---|
| 166 | 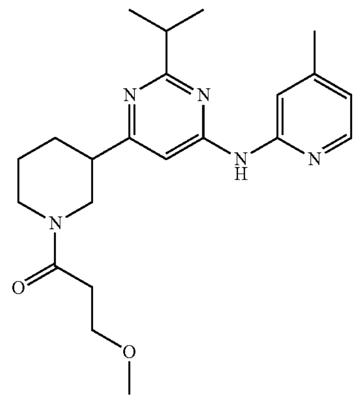 [SMILES: COCCC(=O)N1CCCC(c2cc(Nc3cc(C)ccn3)nc(C(C)C)n2)C1] | 1-{3-[2-Isopropyl-6-(4-methyl-pyridin-2-ylamino)-pyrimidin-4-yl]-piperidin-1-yl}-3-methoxy-propan-1-one |
| 167 | 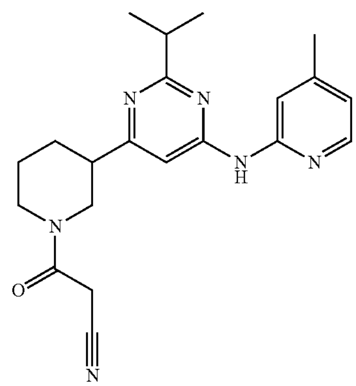 [SMILES: Cc1ccnc(Nc2cc(C3CCCN(C(=O)CC#N)C3)nc(C(C)C)n2)c1] | 3-{3-[2-Isopropyl-6-(4-methyl-pyridin-2-ylamino)-pyrimidin-4-yl]-piperidin-1-yl}-3-oxo-propionitrile |
| 168 | 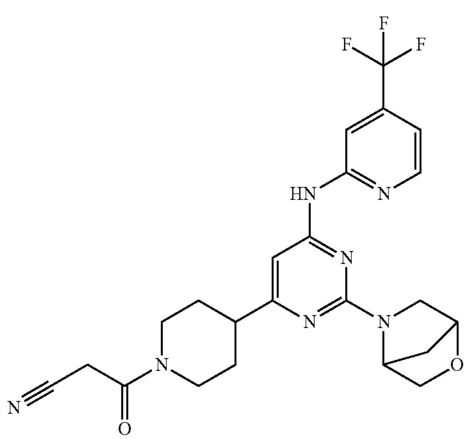 [SMILES: N#CCC(=O)N1CCC(c2cc(Nc3cc(C(F)(F)F)ccn3)nc(N3CC4CC3CO4)n2)CC1] | 3-{4-[2-(2-Oxa-5-aza-bicyclo[2.2.1]hept-5-yl)-6-(4-trifluoromethyl-pyridin-2-ylamino)-pyrimidin-4-yl]-piperidin-1-yl}-3-oxo-propionitrile |
| 169 | 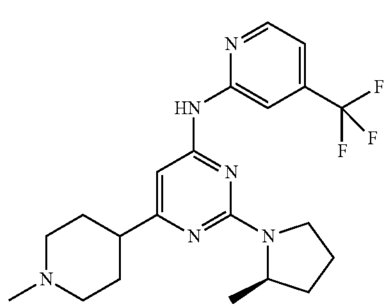 [SMILES: C[C@@H]1CCCN1c1nc(Nc2cc(C(F)(F)F)ccn2)cc(C2CCN(C)CC2)n1] | [6-(1-Methyl-piperidin-4-yl)-2-((R)-2-methyl-pyrrolidin-1-yl)-pyrimidin-4-yl]-(4-trifluoromethyl-pyridin-2-yl)-amine |

TABLE A-continued

| No. | Structure | Name |
|---|---|---|
| 170 | 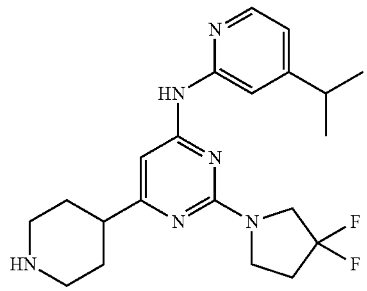 [SMILES: CC(C)c1ccnc(Nc2cc(C3CCNCC3)nc(N3CCC(F)(F)C3)n2)c1] | [2-(3,3-Difluoro-pyrrolidin-1-yl)-6-piperidin-4-yl-pyrimidin-4-yl]-(4-isopropyl-pyridin-2-yl)-amine |
| 172 | 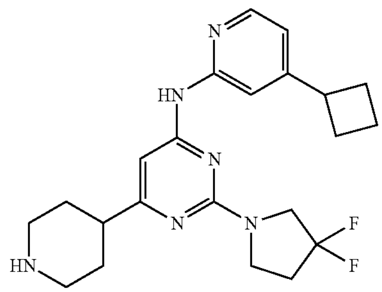 [SMILES: FC1(F)CCN(c2nc(Nc3cc(C4CCC4)ccn3)cc(C3CCNCC3)n2)C1] | (4-Cyclobutyl-pyridin-2-yl)-[2,3-difluoro-pyrrolidin-1-yl)-6-piperidin-4-yl-pyrimidin-4-yl]-amine |
| 173 | 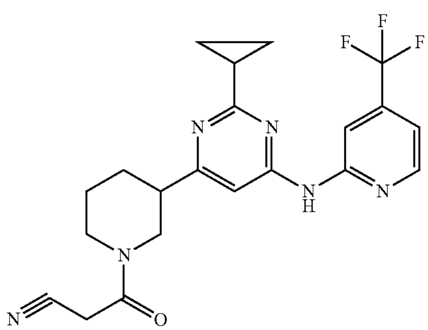 [SMILES: N#CCC(=O)N1CCCC(c2cc(Nc3cc(C(F)(F)F)ccn3)nc(C3CC3)n2)C1] | 3-{3-[2-Cyclopropyl-6-(4-trifluoromethyl-pyridin-2-ylamino)-pyrimidin-4-yl]-piperidin-1-yl}-3-oxo-propionitrile |
| 174 | 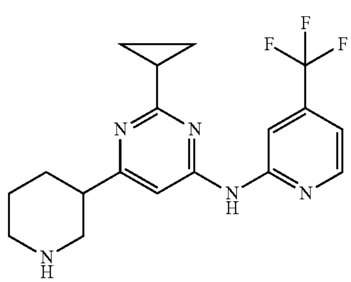 [SMILES: FC(F)(F)c1ccnc(Nc2cc(C3CCCNC3)nc(C3CC3)n2)c1] | (2-Cyclopropyl-6-piperidin-3-yl-pyrimidin-4-yl)-(4-trifluoromethyl-pyridin-2-yl)-amine |
| 175 | 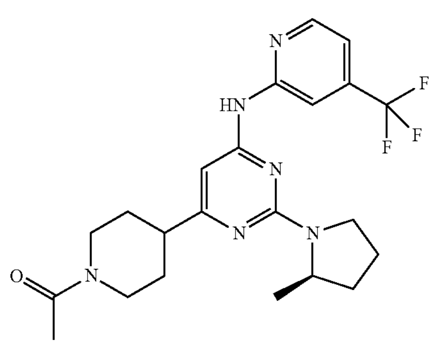 [SMILES: CC(=O)N1CCC(c2cc(Nc3cc(C(F)(F)F)ccn3)nc(N3CCC[C@H]3C)n2)CC1] | 1-{4-[2-((R)-2-Methyl-pyrrolidin-1-yl)-6-(4-trifluoromethyl-pyridin-2-ylamino)-pyrimidin-4-yl]-piperidin-1-yl}-ethanone |

TABLE A-continued
| No. | Structure | Name |
|---|---|---|
| 176 | 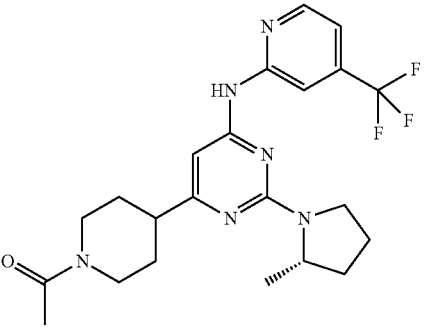 [SMILES: CC(=O)N1CCC(c2cc(Nc3cc(C(F)(F)F)ccn3)nc(N3CCC[C@@H]3C)n2)CC1] | 1-{4-[2-((S)-2-Methyl-pyrrolidin-1-yl)-6-(4-trifluoromethyl-pyridin-2-ylamino)-pyrimidin-4-yl]-piperidin-1-yl}-ethanone |
| 177 | 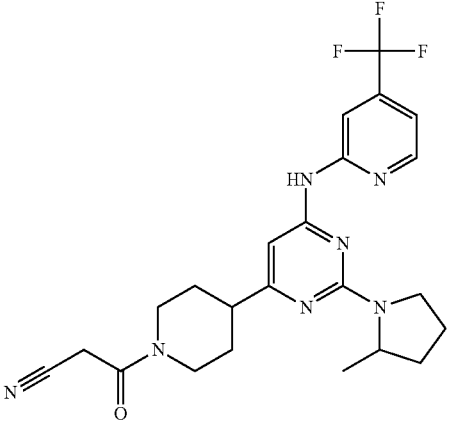 [SMILES: CC1CCCN1c1nc(Nc2cc(C(F)(F)F)ccn2)cc(C2CCN(C(=O)CC#N)CC2)n1] | 3-{4-[2-(2-Methyl-pyrrolidin-1-yl)-6-(4-trifluoromethyl-pyridin-2-ylamino)-pyrimidin-4-3yl]-piperidin-1-yl}-3-oxo-propionitrile |
| 178 | 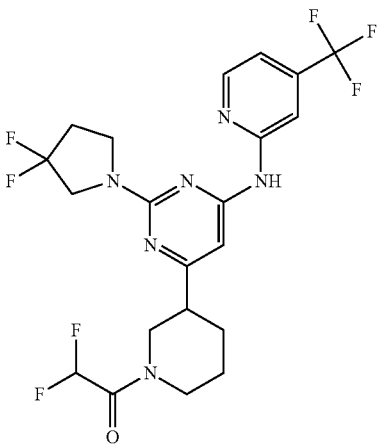 [SMILES: O=C(C(F)F)N1CCCC(c2cc(Nc3cc(C(F)(F)F)ccn3)nc(N3CCC(F)(F)C3)n2)C1] | 1-{3-[2-(3,3-Difluoro-pyrrolidin-1-yl)-6-(4-trifluoromethyl-pyridin-2-ylamino)-pyrimidin-4-yl]-piperidin-1-yl}-2,2-difluoro-ethanone |

TABLE A-continued

| No. | Structure | Name |
|---|---|---|
| 179 | 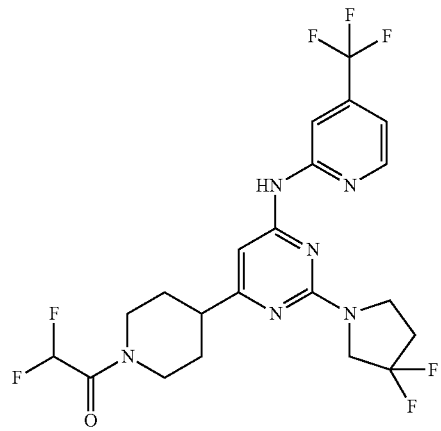 [SMILES: O=C(C(F)F)N1CCC(c2cc(Nc3cc(C(F)(F)F)ccn3)nc(N3CCC(F)(F)C3)n2)CC1] | 1-{4-[2-(3,3-Difluoro-pyrrolidin-1-yl)-6-(4-trifluoromethyl-pyridin-2-ylamino)-pyrimidin-4-yl]-piperidin-1-yl}-2,2-difluoro-ethanone |
| 180 | 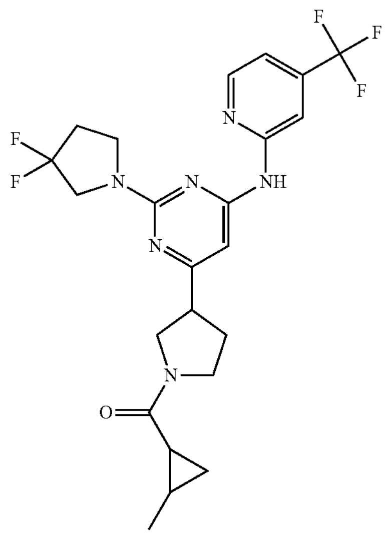 [SMILES: CC1CC1C(=O)N1CCC(c2cc(Nc3cc(C(F)(F)F)ccn3)nc(N3CCC(F)(F)C3)n2)C1] | {3-[2-(3,3-Difluoro-pyrrolidin-1-yl)-6-(4-trifluoromethyl-pyridin-2-ylamino)-pyrimidin-4-yl]-pyrrolidin-1-yl}-(2-methyl-cyclopropyanone |
| 181 | 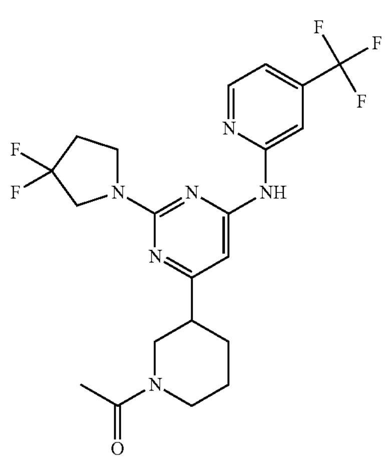 [SMILES: CC(=O)N1CCCC(c2cc(Nc3cc(C(F)(F)F)ccn3)nc(N3CCC(F)(F)C3)n2)C1] | 1-{3-[2-(3,3-Difluoro-pyrrolidin-1-yl)-6-(4-trifluoromethyl-pyridin-2-ylamino)-pyrimidin-4-yl]-piperidin-1-yl}-ethanone |

TABLE A-continued

| No. | Structure | Name |
| --- | --- | --- |
| 182 | 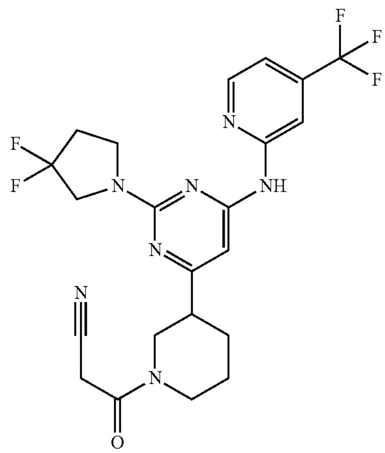 [SMILES: N#CCC(=O)N1CCCC(c2cc(Nc3cc(C(F)(F)F)ccn3)nc(N3CCC(F)(F)C3)n2)C1] | 3-{3-[2-(3,3-Difluoro-pyrrolidin-1-yl)-6-(4-trifluoromethyl-pyridin-2-ylamino)-pyrimidin-4-yl]-piperidin-1-yl}-3-oxo-propionitrile |
| 183 | 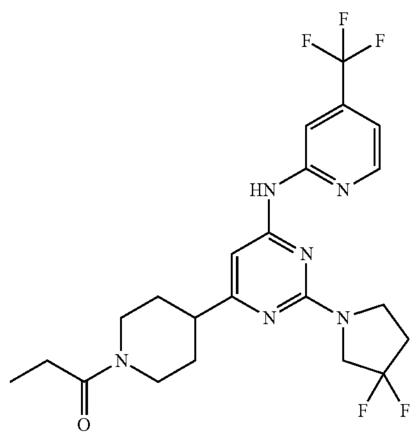 [SMILES: CCC(=O)N1CCC(c2cc(Nc3cc(C(F)(F)F)ccn3)nc(N3CCC(F)(F)C3)n2)CC1] | 1-{4-[2(3,3-Difluoro-pyrrolidin-1-yl)-6-(4-trifluoromethyl-pyridin-2-ylamino)-pyrimidin-4-yl]-piperidin-1-yl}-propan-1-one |
| 184 | 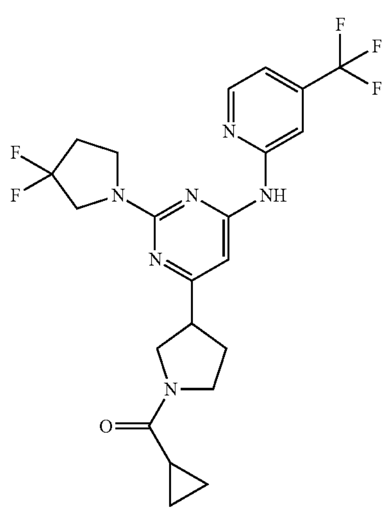 [SMILES: O=C(C1CC1)N1CCC(c2cc(Nc3cc(C(F)(F)F)ccn3)nc(N3CCC(F)(F)C3)n2)C1] | Cyclopropyl-{3-[2-(3,3-difluoro-pyrrolidin-1-yl)-6-(4-trifluoromethyl-pyridin-2-ylamino)-pyrimidin-4-yl]-pyrrolidin-1-yl}-methanone |

TABLE A-continued

| No. | Structure | Name |
|---|---|---|
| 185 | 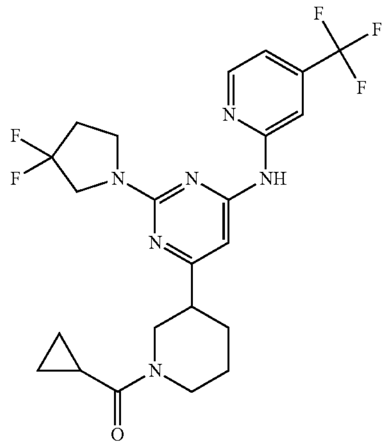 [SMILES: O=C(C1CC1)N1CCCC(c2cc(Nc3cc(C(F)(F)F)ccn3)nc(N3CCC(F)(F)C3)n2)C1] | Cyclopropyl-{3-[2-(3,3-difluoro-pyrrolidin-1-yl)-6-(4-trifluoromethyl-pyrimidin-4-yl]-piperidin-1-yl}-methanone |
| 186 | 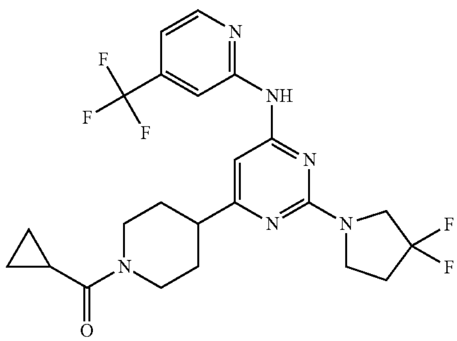 [SMILES: O=C(C1CC1)N1CCC(c2cc(Nc3cc(C(F)(F)F)ccn3)nc(N3CCC(F)(F)C3)n2)CC1] | Cyclopropyl-{4-[2-(3,3-difluoro-pyrrolidin-1-yl)-6-(4-trifluoromethyl-pyridin-2-ylamino)-pyrimidin-4-yl]-piperidin-1-yl}-methanone |
| 187 | 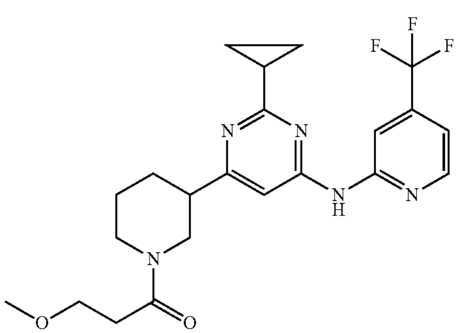 [SMILES: COCCC(=O)N1CCCC(c2cc(Nc3cc(C(F)(F)F)ccn3)nc(C3CC3)n2)C1] | 1-{3-[2-Cyclopropyl-6-(4-trifluoromethyl-pyridin-2-ylamino)-pyrimidin-4-yl]-piperidin-1-yl}-3-methoxy-propan-1-one |
| 188 | 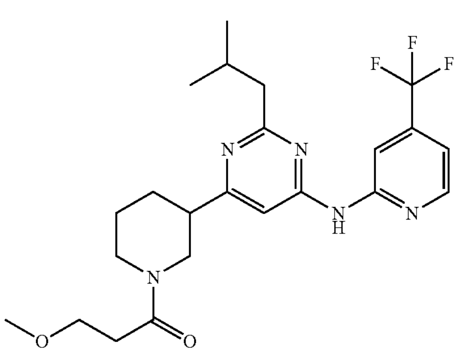 [SMILES: COCCC(=O)N1CCCC(c2cc(Nc3cc(C(F)(F)F)ccn3)nc(CC(C)C)n2)C1] | 1-{3-[2-Isobutyl-6-(4-trifluoromethyl-pyridin-2-ylamino)-pyrimidin-4-yl]-piperidin-1-yl}-3-methoxy-propan-1-one |

TABLE A-continued
| No. | Structure | Name |
|---|---|---|
| 189 | 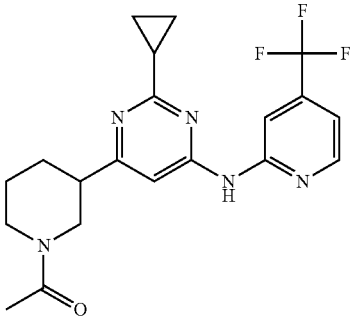 [SMILES: CC(=O)N1CCCC(c2cc(Nc3cc(C(F)(F)F)ccn3)nc(C3CC3)n2)C1] | 1-{3-[2-Cyclopropyl-6-(4-trifluoromethyl-pyridin-2-ylamino)-pyrimidin-4-yl]-piperidin-1-yl}-ethanone |
| 190 | 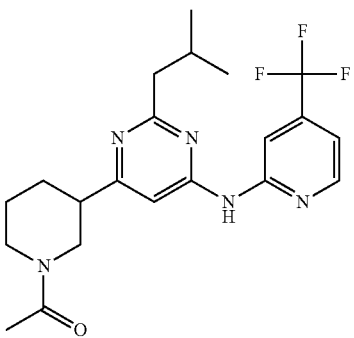 [SMILES: CC(=O)N1CCCC(c2cc(Nc3cc(C(F)(F)F)ccn3)nc(CC(C)C)n2)C1] | 1-{3-[2-Isobutyl-6-(4-trifluoromethyl-pyridin-2-ylamino)-pyrimidin-4-yl]-piperidin-1-yl}-ethanone |
| 191 | 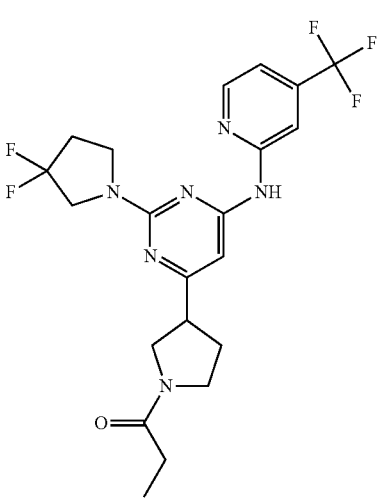 [SMILES: CCC(=O)N1CCC(c2cc(Nc3cc(C(F)(F)F)ccn3)nc(N3CCC(F)(F)C3)n2)C1] | 1-{3-[2-(3,3-Difluoro-pyrrolidin-1-yl)-6-(4-trifluoromethyl-pyridin-2-ylamino)-pyrimidin-4-yl]-pyrrolidin-1-yl}-propan-1-one |

TABLE A-continued
| No. | Structure | Name |
|---|---|---|
| 192 | 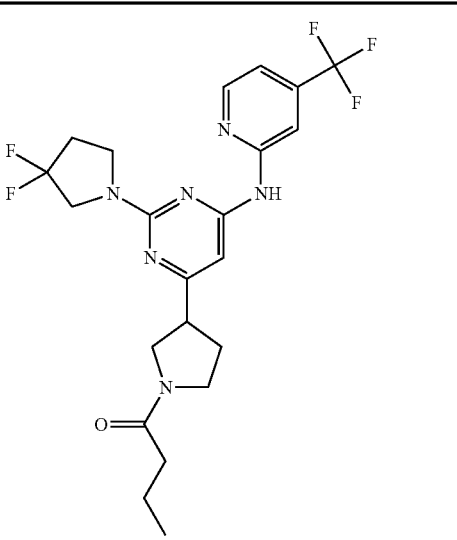 | 1-{3-[2-(3,3-Difluoro-pyrrolidin-1-yl)-6-(4-trifluoromethyl-pyridin-2-ylamino)-pyrimidin-4-yl]-pyrrolidin-1-yl}-butan-1-one |
| 193 | 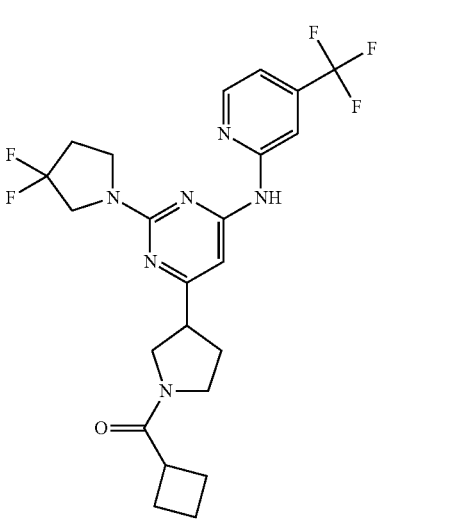 [SMILES: O=C(C1CCC1)N1CCC(c2cc(Nc3cc(C(F)(F)F)ccn3)nc(N3CCC(F)(F)C3)n2)C1] | Cyclobutyl-{3-[2-(3,3-difluoro-pyrrolidin-1-yl)-6-(4-trifluoromethyl-pyridin-2-ylamino)-pyrimidin-4-yl]-pyrrolidin-1-yl}-methanone |
| 194 | 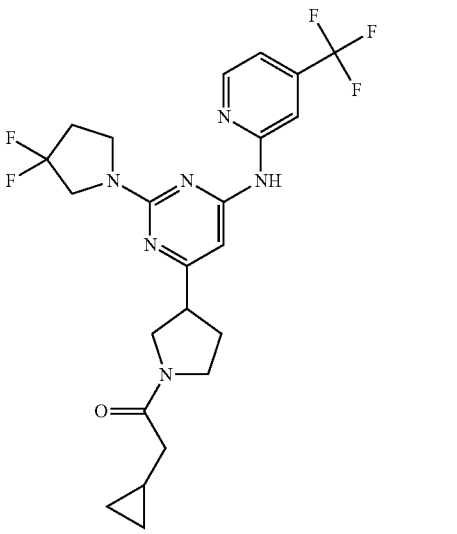 [SMILES: O=C(CC1CC1)N1CCC(c2cc(Nc3cc(C(F)(F)F)ccn3)nc(N3CCC(F)(F)C3)n2)C1] | 2-Cyclopropyl-1-{3-[2-(3,3-difluoro-pyrrolidin-1-yl)-6-(4-trifluoromethyl-pyridin-2-ylamino)-pyrimidin-4-yl]-pyrrolidin-1-yl-}-ethanone |

TABLE A-continued

| No. | Structure | Name |
|---|---|---|
| 195 | 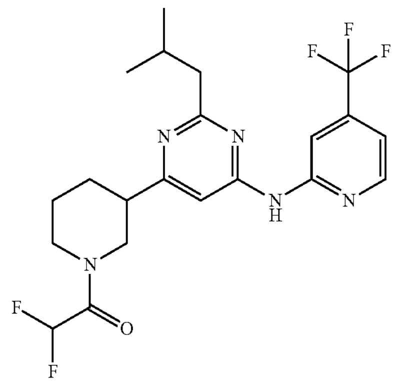 [SMILES: CC(C)Cc1nc(Nc2cc(C(F)(F)F)ccn2)cc(C2CCCN(C(=O)C(F)F)C2)n1] | 2,2-Difluoro-1-{3-[2-isobutyl-6-(4-trifluoromethyl-pyridin-2-ylamino)-pyrimidin-4-yl]-piperidin-1-yl}-ethanone |
| 196 | 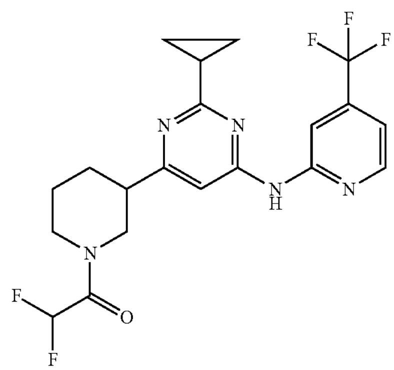 [SMILES: O=C(C(F)F)N1CCCC(c2cc(Nc3cc(C(F)(F)F)ccn3)nc(C3CC3)n2)C1] | 1-{3-[2-Cyclopropyl-6-(4-trifluoromethyl-pyridin-2-ylamino)-pyrimidin-4-yl]-piperidin-1-yl}-2,2-difluoro-ethanone |
| 197 | 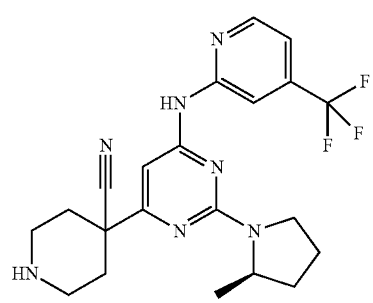 [SMILES: C[C@@H]1CCCN1c1nc(Nc2cc(C(F)(F)F)ccn2)cc(C2(C#N)CCNCC2)n1] | 4-[2-((R)-2-Methyl-pyrrolidin-1-yl)-6-(4-trifluoromethyl-pyridin-2-ylamino)-pyrimidin-4-yl]-piperidine-4-carbonitrile |
| 198 | 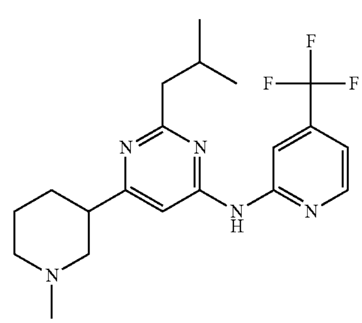 [SMILES: CC(C)Cc1nc(Nc2cc(C(F)(F)F)ccn2)cc(C2CCCN(C)C2)n1] | [2-Isobutyl-6-(1-methyl-piperidin-3-yl)-pyrimidin-4-yl]-(4-trifluoro-methylpdin-2yl)amine |

TABLE A-continued

| No. | Structure | Name |
|---|---|---|
| 199 | 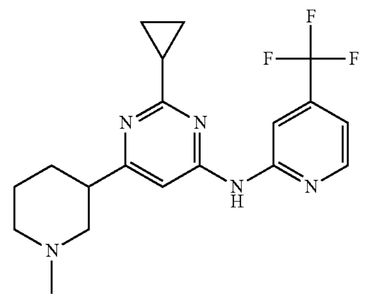 [SMILES: CN1CCCC(c2cc(Nc3cc(C(F)(F)F)ccn3)nc(C3CC3)n2)C1] | [2-Cyclopropyl-6-(1-methyl-piperidin-3-yl)-pyrimidin-4-yl]-(4-trifluoromethyl-pyridin-2-yl)-amine |
| 200 | 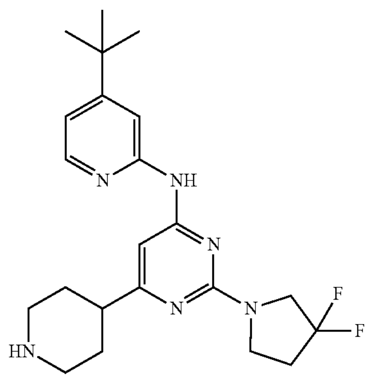 [SMILES: CC(C)(C)c1ccnc(Nc2cc(C3CCNCC3)nc(N3CCC(F)(F)C3)n2)c1] | (4-tert-Butyl-pyridin-2-yl)-[2-(3,3-difluoro-pyrrolidin-1-yl)-6-piperidin-4-yl-pyrimidin-4-yl]-amine |
| 201 | 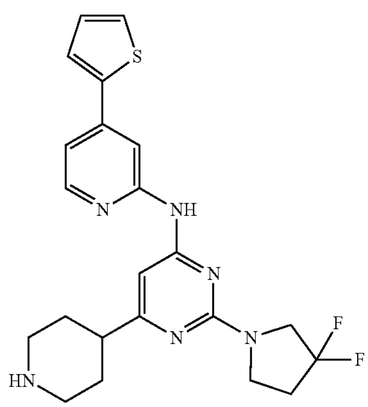 [SMILES: FC1(F)CCN(c2nc(Nc3cc(-c4cccs4)ccn3)cc(C3CCNCC3)n2)C1] | [2-(3,3-Difluoro-pyrrolidin-1-yl)-6-piperidin-4-yl-pyrimidin-4-yl]-(4-thiophen-2-yl-pyridin-2-yl)-amine |
| 202 | 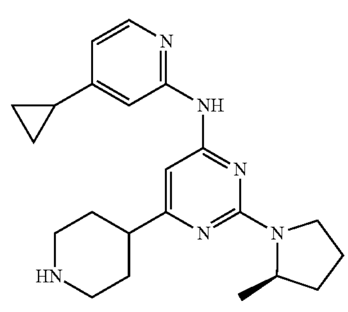 [SMILES: C[C@@H]1CCCN1c1nc(Nc2cc(C3CC3)ccn2)cc(C2CCNCC2)n1] | (4-Cyclopropyl-pyridin-2-yl)-[2-((R)-2-methyl-pyrrolidin-1-yl)-6-piperidin-4-yl-pyrimidin-4-yl]-amine |

TABLE A-continued

| No. | Structure | Name |
|---|---|---|
| 203 | 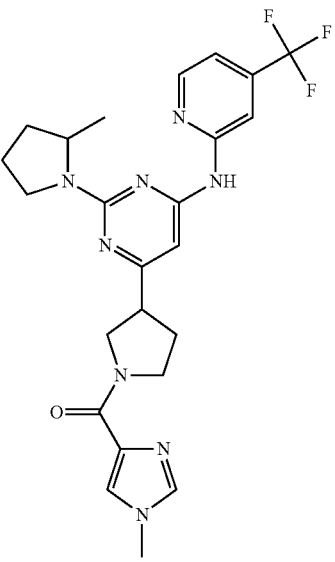 [SMILES: CC1CCCN1c1nc(Nc2cc(C(F)(F)F)ccn2)cc(C2CCN(C(=O)c3cn(C)cn3)C2)n1] | (1-Methyl-1H-imidazol-4-yl)-{3-[2-(2-methyl-pyrrolidin-1-yl)-6-(4-trifluoromethyl-pyridin-2-ylamino)-pyrimidin-4-yl]-pyrrolidin-1-yl}-methanone |
| 204 | 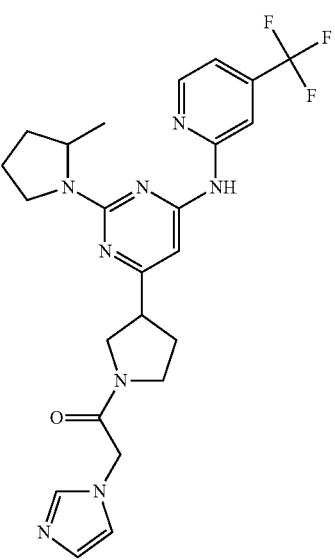 [SMILES: CC1CCCN1c1nc(Nc2cc(C(F)(F)F)ccn2)cc(C2CCN(C(=O)Cn3ccnc3)C2)n1] | 2-Imidazol-1-yl-1-{3-[2-(2-methyl-pyrrolidin-1-yl)-6-(4-trifluoromethyl-pyridin-2-ylamino)-pyrimidin-4-yl]-pyrrolidin-1-yl}-ethanone |
| 205 | 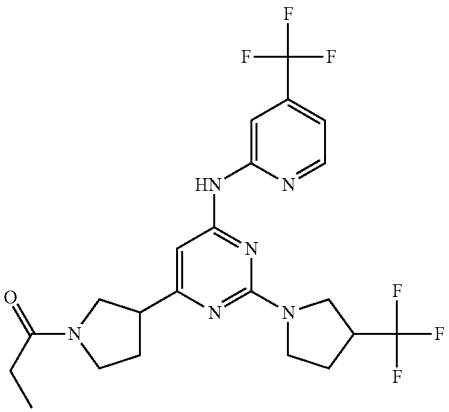 [SMILES: CCC(=O)N1CCC(c2cc(Nc3cc(C(F)(F)F)ccn3)nc(N3CCC(C(F)(F)F)C3)n2)C1] | 1-{3-[6-(4-Trifluoromethyl-pyridin-2-ylamino)-2-(3-trifluoromethyl-pyrrolidin-1-yl)-pyrimidin-4-yl]-pyrrolidin-1-yl}-propan-1-one |

TABLE A-continued

| No. | Structure | Name |
|---|---|---|
| 206 | 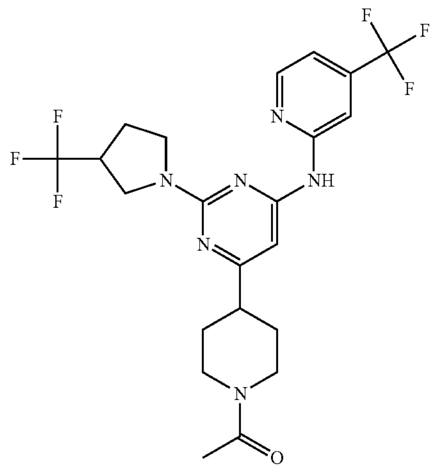 [SMILES: CC(=O)N1CCC(c2cc(Nc3cc(C(F)(F)F)ccn3)nc(N3CCC(C(F)(F)F)C3)n2)CC1] | 1-{4-[6-(4-Trifluoromethyl-pyridin-2-ylamino)-2-(3-trifluoromethyl-pyrrolidin-1-yl)-pyrimidin-4-yl]-piperidin-1-yl}-ethanone |
| 207 | 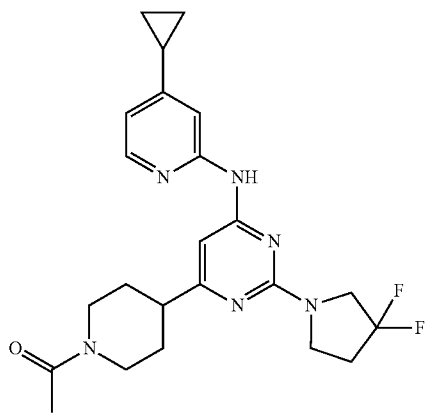 [SMILES: CC(=O)N1CCC(c2cc(Nc3cc(C4CC4)ccn3)nc(N3CCC(F)(F)C3)n2)CC1] | 1-{4-[6-(4-Cyclopropyl-pyridin-2-ylamino)-2-(3,3-difluoro-pyrrolidin-1-yl)-pyrimidin-4-yl]-piperidin-1-yl}-ethanone |
| 208 | 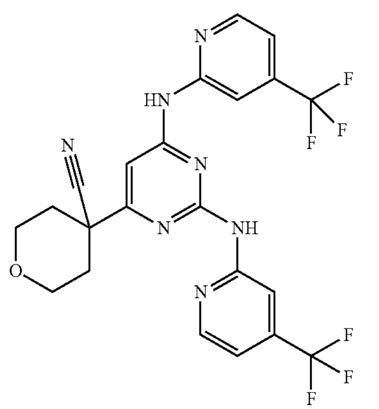 [SMILES: N#CC1(c2cc(Nc3cc(C(F)(F)F)ccn3)nc(Nc3cc(C(F)(F)F)ccn3)n2)CCOCC1] | 4-[2,6-Bis-(4-trifluoromethyl-pyridin-2-ylamino)-pyrimidin-4-yl]-tetrahydro-pyran-4-carbonitrile |
| 209 | 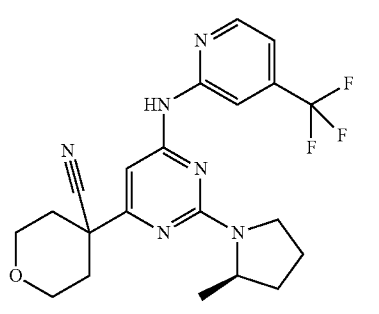 [SMILES: C[C@@H]1CCCN1c1nc(Nc2cc(C(F)(F)F)ccn2)cc(C2(C#N)CCOCC2)n1] | 4-[2-((R)-2-Methyl-pyrrolidin-1-yl)-6-(4-trifluoromethyl-pyridin-2-ylamino)-pyrimidin-4-yl]-tetrahydro-pyran-4-carbonitrile |

TABLE A-continued

| No. | Structure | Name |
|---|---|---|
| 210 | 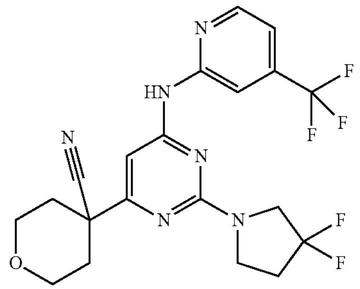 [SMILES: N#CC1(c2cc(Nc3cc(C(F)(F)F)ccn3)nc(N3CCC(F)(F)C3)n2)CCOCC1] | 4-[2-(3,3-Difluoro-pyrrolidin-1-yl)-6-(4-trifluoromethyl-pyridin-2-ylamino)-pyrimidin-4-yl]-tetrahydro-pyran-4-carbonitrile |
| 211 | 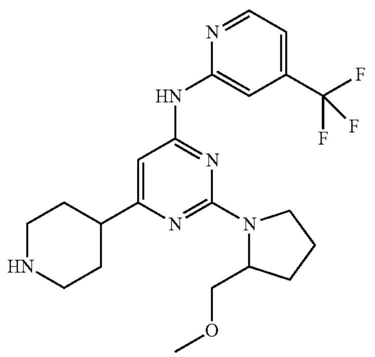 [SMILES: COCC1CCCN1c1nc(Nc2cc(C(F)(F)F)ccn2)cc(C2CCNCC2)n1] | [2-(2-Methoxymethyl-pyrrolidin-1-yl)-6-piperidin-4-yl-pyrimidin-4-yl]-(4-trifluoromethyl-pyridin-2-yl)-amine |
| 212 | 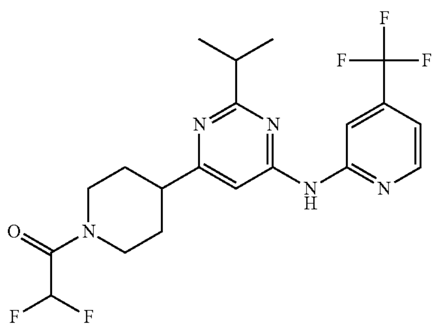 [SMILES: CC(C)c1nc(Nc2cc(C(F)(F)F)ccn2)cc(C2CCN(C(=O)C(F)F)CC2)n1] | 2,2-Difluoro-1-{4-[2-isopropyl-6-(4-trifluoro-methyl-pyridin-2-ylamino)-pyrimidin-4-yl]-piperidin-1-yl}-ethanone |
| 213 | 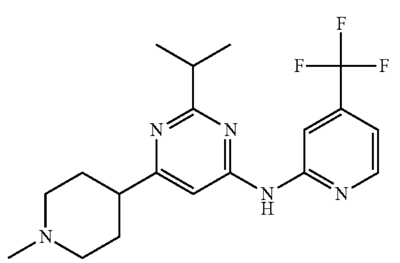 [SMILES: CC(C)c1nc(Nc2cc(C(F)(F)F)ccn2)cc(C2CCN(C)CC2)n1] | [2-Isopropyl-6-(1-methyl-piperidin-4-yl)-pyrimidin-4-yl]-(4-trifluoro-methyl-pyridin-2-yl)-amine |
| 214 | 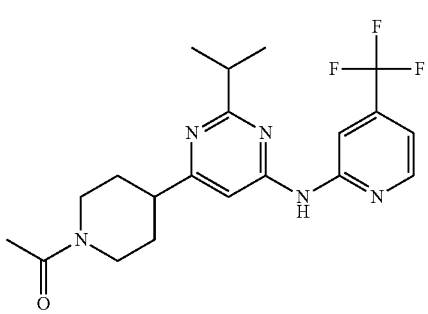 [SMILES: CC(=O)N1CCC(c2cc(Nc3cc(C(F)(F)F)ccn3)nc(C(C)C)n2)CC1] | 1-{4-[2-Isopropyl-6-(4-trifluoromethyl-pyridin-2-ylamino)-pyrimidin-4-yl]-piperidin-1-yl}-ethanone |

TABLE A-continued
| No. | Structure | Name |
|---|---|---|
| 215 | 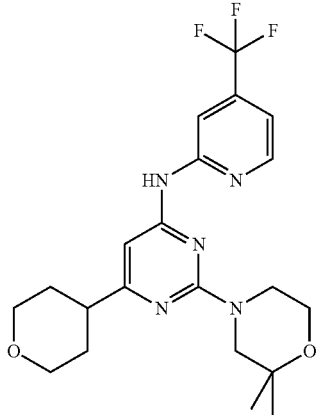 | [2-(2,2-Dimethyl-morpholin-4-yl)-6-(tetrahydro-pyran-4-yl)-pyrimidin-4-yl]-(4-trifluoromethyl-pyridin-2-yl)-amine |
| 216 | 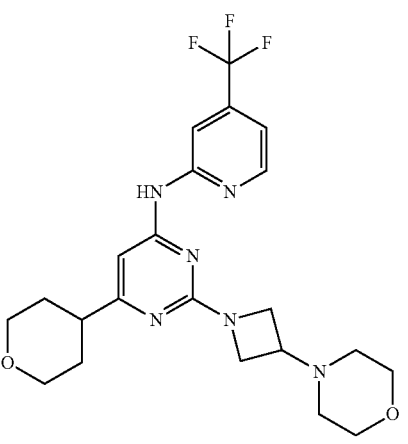 [SMILES: FC(F)(F)c1ccnc(Nc2cc(C3CCOCC3)nc(N3CC(N4CCOCC4)C3)n2)c1] | [2-(3-Morpholin-4-yl-azetidin-1-yl)-6-(tetrahydro-pyran-4-yl)-pyrimidin-4-yl]-(4-trifluoromethyl-pyridin-2-yl)-amine |
| 217 | 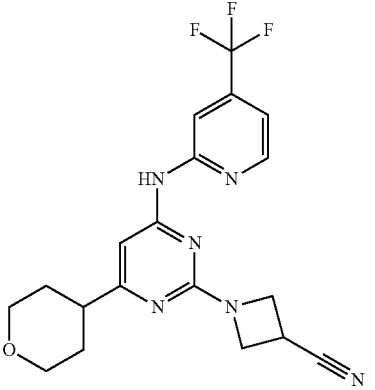 [SMILES: N#CC1CN(c2nc(Nc3cc(C(F)(F)F)ccn3)cc(C3CCOCC3)n2)C1] | 1-[4-(Tetrahydro-pyran-4-yl)-6-(4-trifluoromethyl-pyridin-2-ylamino)-pyrimidin-2-yl]-azetidine-3-carbonitrile |

TABLE A-continued

| No. | Structure | Name |
|---|---|---|
| 218 | 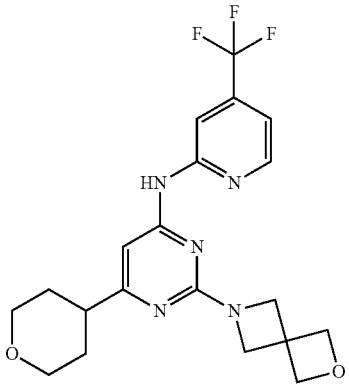 | [2-(2-Oxa-6-aza-spiro-[3.3]hept-6-yl)-6-(tetrahydro-pyran-4-yl)-pyrimidin-4-yl]-(4-trifluoromethyl-pyridin-2-yl)-amine |
| 219 | 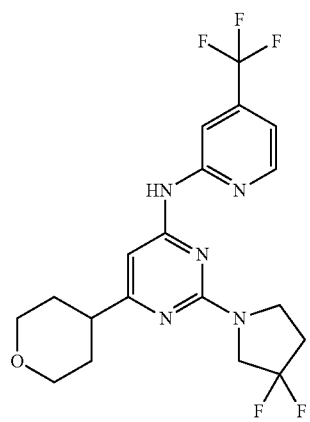 [SMILES: FC1(F)CCN(c2nc(Nc3cc(C(F)(F)F)ccn3)cc(C3CCOCC3)n2)C1] | [2-(3,3-Difluoro-pyrrolidin-1-yl)-6-(tetrahydro-pyran-4-yl)-pyrimidin-4-yl]-(4-trifluoromethyl-pyridin-2-yl)-amine |
| 220 | 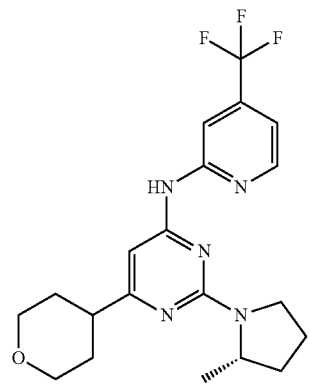 [SMILES: C[C@H]1CCCN1c1nc(Nc2cc(C(F)(F)F)ccn2)cc(C2CCOCC2)n1] | [2-((S)-2-Methyl-pyrrolidin-1-yl)-6-(tetrahydro-pyran-4-yl)-pyrimidin-4-y-(4-trifluoromethyl-pyridin-2-yl)-amine |
| 221 | 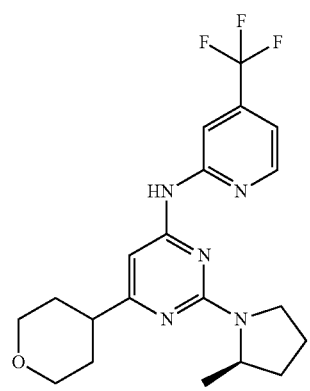 [SMILES: C[C@@H]1CCCN1c1nc(Nc2cc(C(F)(F)F)ccn2)cc(C2CCOCC2)n1] | [2-((R)-2-Methyl-pyrrolidin-1-yl)-6-(tetrahydro-pyran-4-yl)-pyrimidin-4-yl]-(4-trifluoromethyl-pyridin-2-yl)-amine |

TABLE A-continued
| No. | Structure | Name |
|---|---|---|
| 222 | 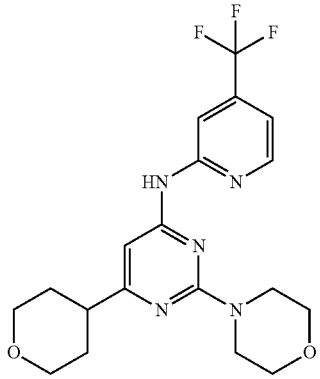 | [2-Morpholin-4-yl-6-(tetrahydro-pyran-4-yl)-pyrimidin-4-yl]-(4-trifluoromethyl-pyridin-2-yl)-amine |
| 223 | 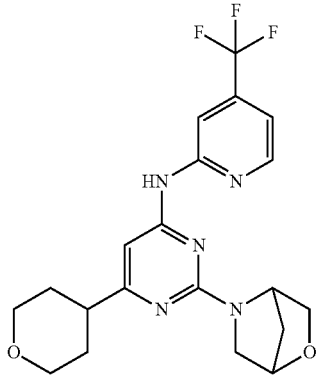 | [2-(2-Oxa-5-aza-bicyclo-[2.2.1]hept-5-yl)-6-(tetrahydro-pyran-4-yl)-pyrimidin-4-yl]-(4-trifluoromethyl-pyridin-2-yl)-amine |
| 224 | 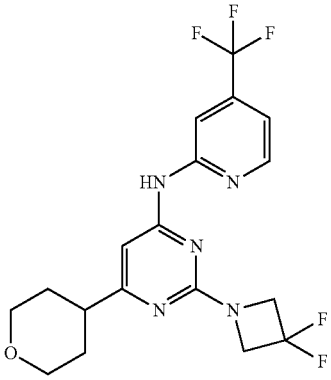 [SMILES: FC1(F)CN(c2nc(Nc3cc(C(F)(F)F)ccn3)cc(C3CCOCC3)n2)C1] | [2-(3,3-Difluoro-azetidin-1-yl)-6-(tetrahydro-pyran-4-yl)-pyrimidin-4-yl]-(4-trifluoromethyl-pyridin-2-yl)-amine |

TABLE A-continued

| No. | Structure | Name |
|---|---|---|
| 225 | 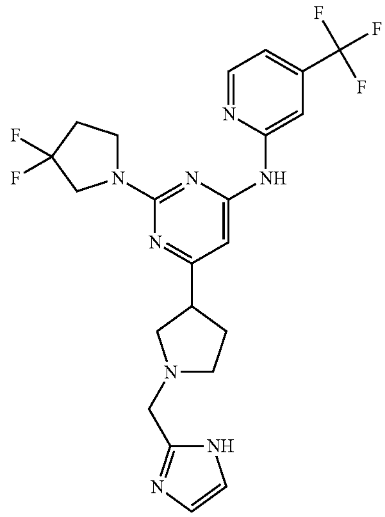 [SMILES: FC1(F)CCN(c2nc(Nc3cc(C(F)(F)F)ccn3)cc(C3CCN(Cc4ncc[nH]4)C3)n2)C1] | {2-(3,3-Difluoro-pyrrolidin-1-yl)-6-[1-(1H-imidazol-2-ylmethyl)-pyrrolidin-3-yl]-pyrimidin-4-yl}-(4-trifluoromethyl-pyridin-2-yl)-amine |
| 226 | 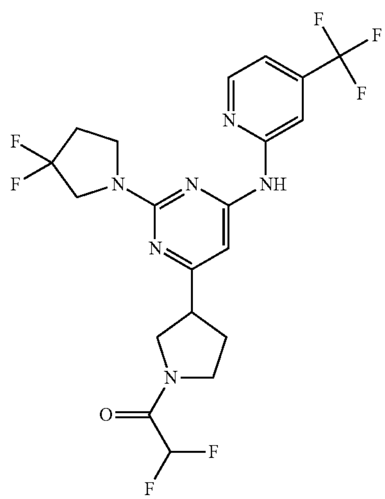 [SMILES: O=C(C(F)F)N1CCC(c2cc(Nc3cc(C(F)(F)F)ccn3)nc(N3CCC(F)(F)C3)n2)C1] | 1-{3-[2-(3,3-Difluoro-pyrrolidin-1-yl)-6-(4-trifluoromethyl-pyridin-2-ylamino)-pyrimidin-4-yl]-pyrrolidin-1-yl}-2,2-difluoro-ethanone |
| 227 | 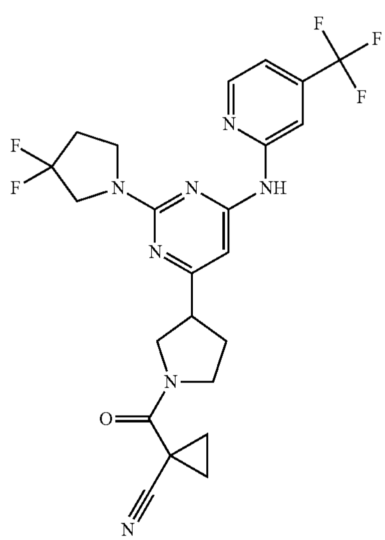 [SMILES: N#CC1(C(=O)N2CCC(c3cc(Nc4cc(C(F)(F)F)ccn4)nc(N4CCC(F)(F)C4)n3)C2)CC1] | 1-{3-[2-(3,3-Difluoro-pyrrolidin-1-yl)-6-(4-trifluoromethyl-pyridin-2-ylamino)-pyrimidin-4-yl]-pyrrolidine-1-carbonyl}-cyclopropanecarbonitrile |

TABLE A-continued

| No. | Structure | Name |
|---|---|---|
| 228 | 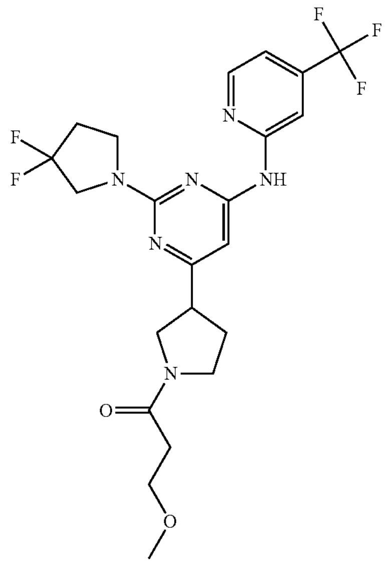 [SMILES: COCCC(=O)N1CCC(c2cc(Nc3cc(C(F)(F)F)ccn3)nc(N3CCC(F)(F)C3)n2)C1] | 1-{3-[2-(3,3-Difluoro-pyrrolidin-1-yl)-6-(4-trifluoromethyl-pyridin-2-ylamino)-pyrimidin-4-yl]-pyrrolidin-1-yl}-3-methoxy-propan-1-one |
| 229 | 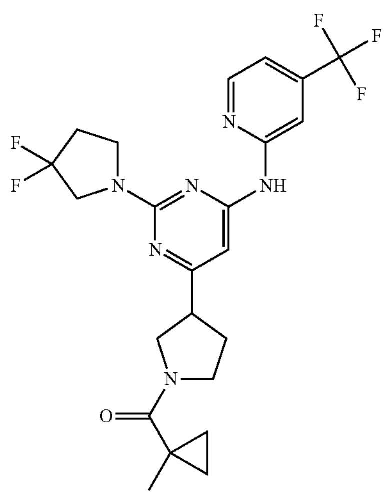 [SMILES: CC1(C(=O)N2CCC(c3cc(Nc4cc(C(F)(F)F)ccn4)nc(N4CCC(F)(F)C4)n3)C2)CC1] | {3-[2-(3,3-Difluoro-pyrrolidin-1-yl)-6-(4-trifluoromethyl-pyridin-2-ylamino)-pyrimidin-4-yl]-pyrrolidin-1-yl}-(1-methyl-cyclopropyl)-methanone |
| 230 | 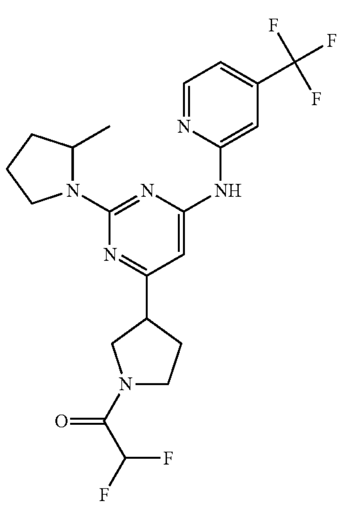 [SMILES: CC1CCCN1c1nc(Nc2cc(C(F)(F)F)ccn2)cc(C2CCN(C(=O)C(F)F)C2)n1] | 2,2-Difluoro-1-{3-[2-(2-methyl-pyrrolidin-1-yl)-6-(4-trifluoromethyl-pyridin-2-ylamino)-pyrimidin-4-yl]-pyrrolidin-1-yl}-ethanone |

TABLE A-continued
| No. | Structure | Name |
|---|---|---|
| 231 | 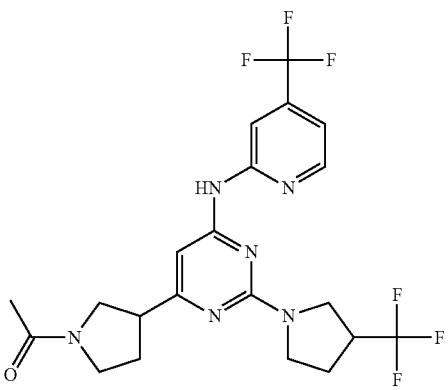 [SMILES: CC(=O)N1CCC(c2cc(Nc3cc(C(F)(F)F)ccn3)nc(N3CCC(C(F)(F)F)C3)n2)C1] | 1-{3-[6-(4-Trifluoro-methyl-pyridin-2-ylamino)-2-(3-trifluoromethyl-pyrrolidin-1-yl)-pyrimidin-4-yl]-pyrrolidin-1-yl}-ethanone |
| 232 | 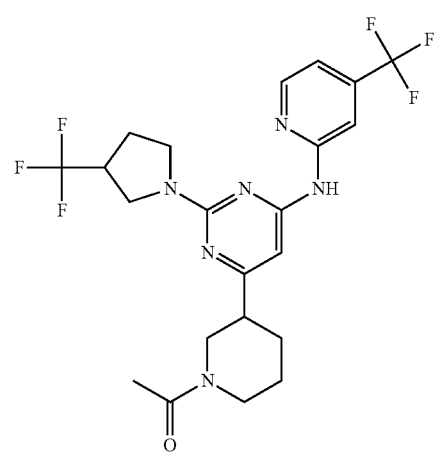 [SMILES: CC(=O)N1CCCC(c2cc(Nc3cc(C(F)(F)F)ccn3)nc(N3CCC(C(F)(F)F)C3)n2)C1] | 1-{3-[6-(4-Trifluoro-methyl-pyridin-2-ylamino)-2-(3-trifluoromethyl-pyrrolidin-1-yl)-pyrimidin-4-yl]-piperidin-1-yl}-ethanone |
| 233 | 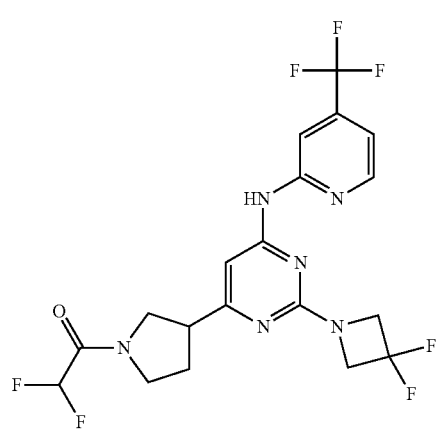 [SMILES: O=C(C(F)F)N1CCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoro-methyl-pyridin-2-ylamino)-pyrimidin-4-yl]-pyrrolidin-1-yl}-2,2-difluoro-ethanone |

TABLE A-continued

| No. | Structure | Name |
|---|---|---|
| 234 | 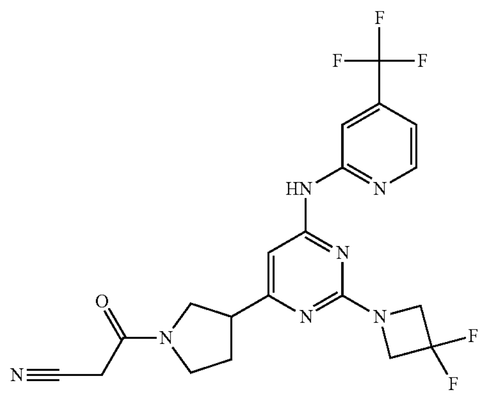 [SMILES: N#CCC(=O)N1CCC(c2cc(Nc3cc(C(F)(F)F)ccn3)nc(N3CC(F)(F)C3)n2)C1] | 3-{3-[2-(3,3-Difluoro-azetidin-1-yl)-6-(4-trifluoromethyl-pyridin-2-ylamino)-pyrimidin-4-yl]-pyrrolidin-1-yl}-3-oxo-propionitrile |
| 235 | 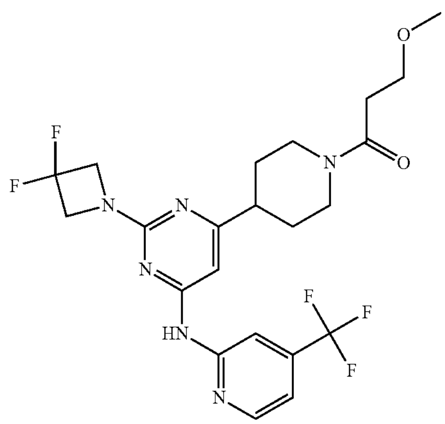 [SMILES: COCCC(=O)N1CCC(c2cc(Nc3cc(C(F)(F)F)ccn3)nc(N3CC(F)(F)C3)n2)CC1] | 1-{4-[2-(3,3-Difluoro-azetidin-1-yl)-6-(4-trifluoro-methyl-pyridin-2-ylamino)-pyrimidin-4-yl]-piperidin-1-yl}-3-methoxy-propan-1-one |
| 236 | 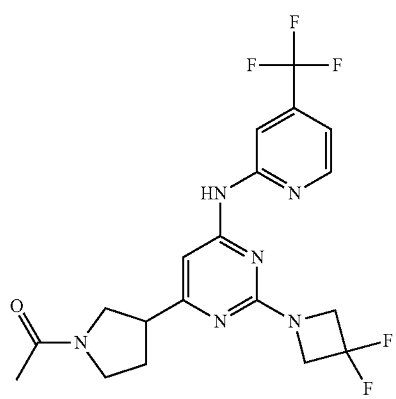 [SMILES: CC(=O)N1CCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoro-methyl-pyridin-2-ylamino)-pyrimidin-4-yl]-pyrrolidin-1-yl}-ethanone |
| 237 | 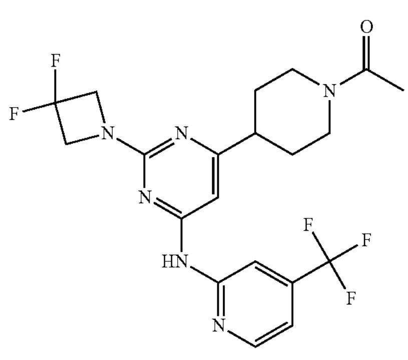 [SMILES: CC(=O)N1CCC(c2cc(Nc3cc(C(F)(F)F)ccn3)nc(N3CC(F)(F)C3)n2)CC1] | 1-{4-[2-(3,3-Difluoro-azetidin-1-yl)-6-(4-trifluoromethyl-pyridin-2-ylamino)-pyrimidin-4-yl]-piperidin-1-yl}-ethanone |

TABLE A-continued

| No. | Structure | Name |
|---|---|---|
| 238 | 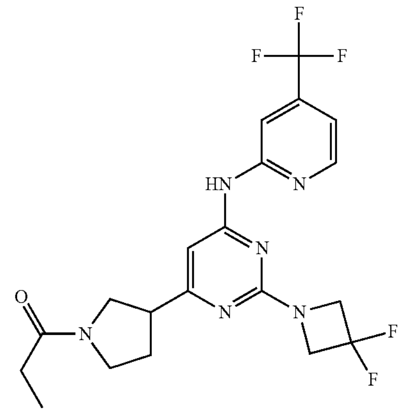 [SMILES: CCC(=O)N1CCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoromethyl-pyridin-2-ylamino)-pyrimidin-4-yl]-pyrrolidin-1-yl}-propan-1-one |
| 239 | 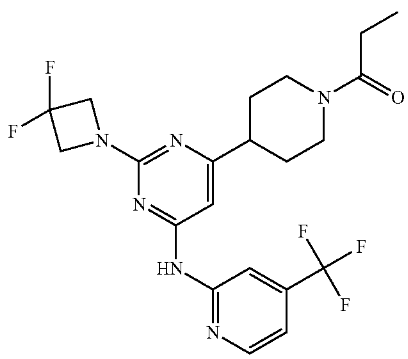 [SMILES: CCC(=O)N1CCC(c2cc(Nc3cc(C(F)(F)F)ccn3)nc(N3CC(F)(F)C3)n2)CC1] | 1-{4-[2-(3,3-Difluoro-azetidin-1-yl)-6-(4-trifluoromethyl-pyridin-2-ylamino)-pyrimidin-4-yl]-piperidin-1-yl}-propan-1-one |
| 240 | 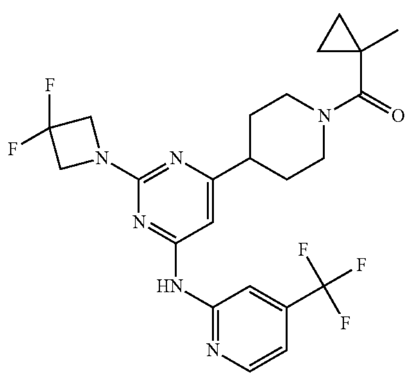 [SMILES: CC1(C(=O)N2CCC(c3cc(Nc4cc(C(F)(F)F)ccn4)nc(N4CC(F)(F)C4)n3)CC2)CC1] | {4-[2-(3,3-Difluoro-azetidin-1-yl)-6-(4-trifluoromethyl-pyridin-2-ylamino)-pyrimidin-4-yl]-piperidin-1-yl}-(1-methyl-cyclopropyl)-methanone |
| 241 | 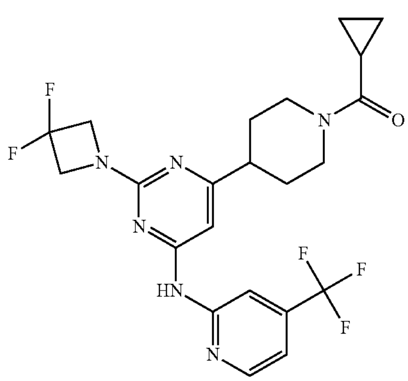 [SMILES: O=C(C1CC1)N1CCC(c2cc(Nc3cc(C(F)(F)F)ccn3)nc(N3CC(F)(F)C3)n2)CC1] | Cyclopropyl-{4-[2-(3,3-difluoro-azetidin-1-yl)-6-(4-trifluoromethyl-pyridin-2-ylamino)-pyrimidin-4-yl]-piperidin-1-yl}-methanone |

TABLE A-continued

| No. | Structure | Name |
|---|---|---|
| 242 | 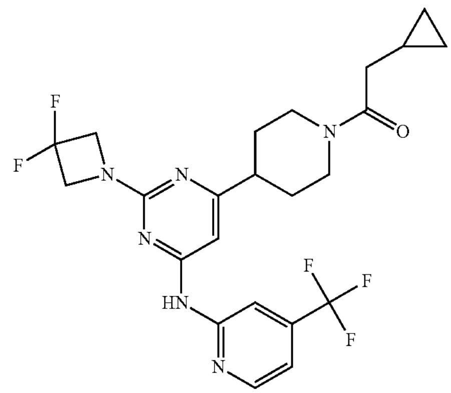 [SMILES: O=C(CC1CC1)N1CCC(c2cc(Nc3cc(C(F)(F)F)ccn3)nc(N3CC(F)(F)C3)n2)CC1] | 2-Cyclopropyl-1-{4-[2-(3,3-difluoro-azetidin-1-yl)-6-(4-trifluoromethyl-pyridin-2-ylamino)-pyrimidin-4-yl]-piperidin-1-yl}-ethanone |
| 243 | 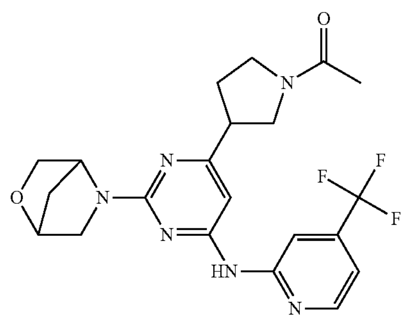 [SMILES: CC(=O)N1CCC(c2cc(Nc3cc(C(F)(F)F)ccn3)nc(N3CC4CC3CO4)n2)C1] | 1-{3-[2-(2-Oxa-5-aza-bicyclo[2.2.1]hept-5-yl)-6-(4-trifluoromethyl-pyridin-2-ylamino)-pyrimidin-4-yl]-pyrrolidin-1-yl}-ethanone |
| 244 | 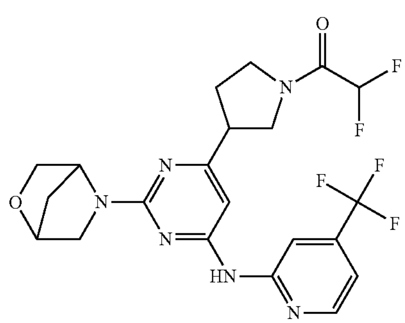 [SMILES: O=C(C(F)F)N1CCC(c2cc(Nc3cc(C(F)(F)F)ccn3)nc(N3CC4CC3CO4)n2)C1] | 2,2-Difluoro-1-{3-[2-(2-oxa-5-aza-bicyclo[2.2.1]-hept-5-yl)-6-(4-trifluoromethyl-pyridin-2-ylamino)-pyrimidin-4-yl]-pyrrolidin-1-yl}-ethanone |
| 245 | 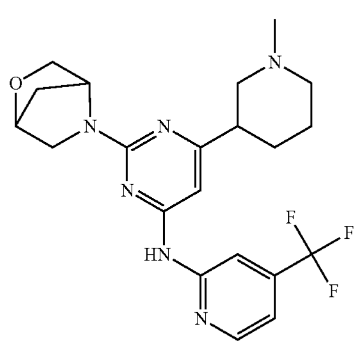 [SMILES: CN1CCCC(c2cc(Nc3cc(C(F)(F)F)ccn3)nc(N3CC4CC3CO4)n2)C1] | [6-(1-Methyl-piperidin-3-yl)-2-(2-oxa-5-aza-bicyclo[2.2.1]hept-5-yl)-pyrimidin-4-yl]-(4-trifluoromethyl-pyridin-2-yl)-amine |

TABLE A-continued

| No. | Structure | Name |
| --- | --- | --- |
| 246 | 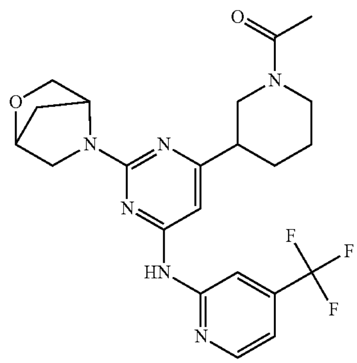 [SMILES: CC(=O)N1CCCC(c2cc(Nc3cc(C(F)(F)F)ccn3)nc(N3CC4CC3CO4)n2)C1] | 1-{3-[2-(2-Oxa-5-aza-bicyclo[2.2.1]hept-5-yl)-6-(4-trifluoromethyl-pyridin-2-ylamino)-pyrimidin-4-yl]-piperidin-1-yl}-ethanone |
| 247 | 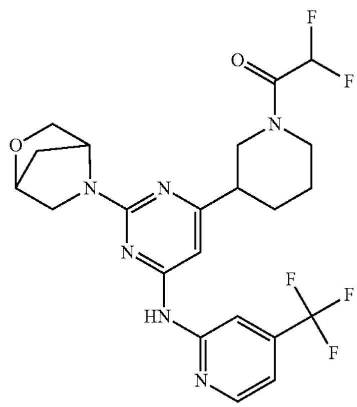 [SMILES: O=C(C(F)F)N1CCCC(c2cc(Nc3cc(C(F)(F)F)ccn3)nc(N3CC4CC3CO4)n2)C1] | 2,2-Difluoro-1-{3-[2-(2-oxa-5-aza-bicyclo[2.2.1]-hept-5-yl)-6-(4-trifluoromethyl-pyridin-2-ylamino)-pyrimidin-4-yl]-piperidin-1-yl}-ethanone |
| 248 | 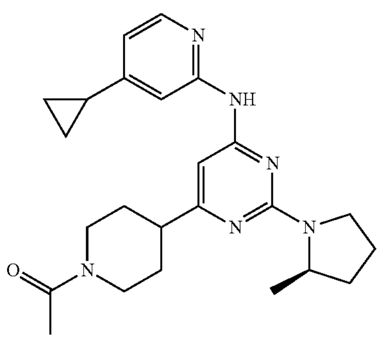 [SMILES: CC(=O)N1CCC(c2cc(Nc3cc(C4CC4)ccn3)nc(N3CCC[C@H]3C)n2)CC1] | 1-{4-[6-(4-Cyclopropyl-pyridin-2-ylamino)-2-((R)-2-methyl-pyrrolidin-1-yl)-pyrimidin-4-yl]-piperidin-1-yl1-ethanone |
| 249 | 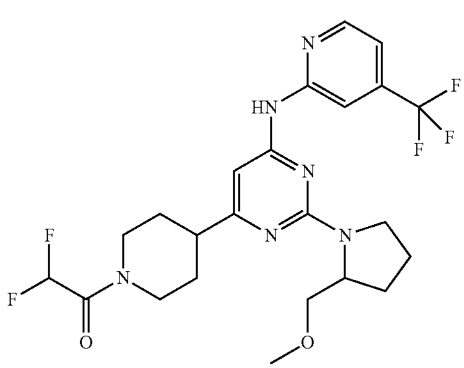 [SMILES: COCC1CCCN1c1nc(Nc2cc(C(F)(F)F)ccn2)cc(C2CCN(C(=O)C(F)F)CC2)n1] | 2,2-Difluoro-1-{4-[2-(2-methoxymethyl-pyrrolidin-1-yl)-6-(4-trifluoro-methyl-pyridin-2-ylamino)-pyrimidin-4-yl]-piperidin-1-yl}-ethanone |

TABLE A-continued

| No. | Structure | Name |
| --- | --- | --- |
| 250 | 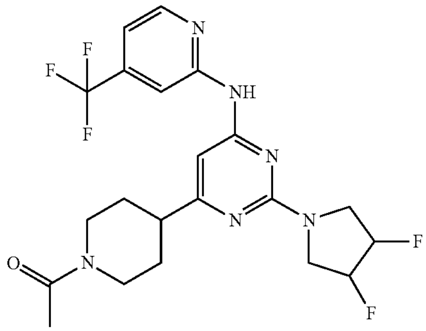 [SMILES: CC(=O)N1CCC(c2cc(Nc3cc(C(F)(F)F)ccn3)nc(N3CC(F)C(F)C3)n2)CC1] | 1-{4-[2-(3,4-Difluoro-pyrrolidin-1-yl)-6-(4-trifluoromethyl-pyridin-2-ylamino)-pyrimidin-4-yl]-piperidin-1-yl}-ethanone |
| 251 | 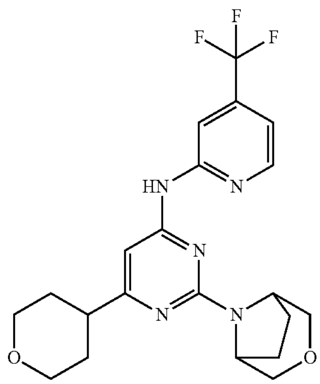 [SMILES: FC(F)(F)c1ccnc(Nc2cc(C3CCOCC3)nc(N3C4CCC3COC4)n2)c1] | [2-(3-Oxa-8-aza-bicyclo-[3.2.1]oct-8-yl)-6-(tetrahydro-pyran-4-yl)-pyrimidin-4-yl]-(4-trifluoro-methyl-pyridin-2-yl)-amine |
| 252 | 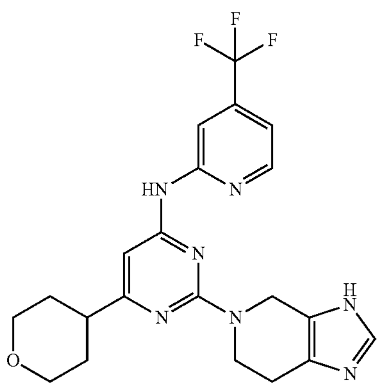 [SMILES: FC(F)(F)c1ccnc(Nc2cc(C3CCOCC3)nc(N3CCc4nc[nH]c4C3)n2)c1] | [2-(3,4,6,7-Tetrahydro-imidazo[4,5-c]pyridin-5-yl)-6-(tetrahydro-pyran-4-yl)-pyrimidin-4-yl]-(4-trifluoromethyl-pyridin-2-yl)-amine |
| 253 | 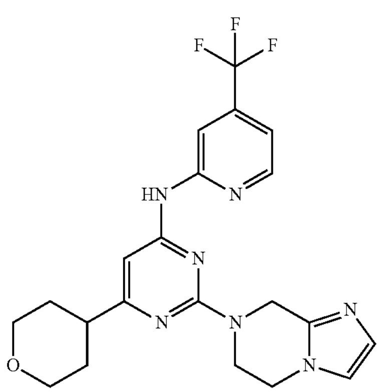 [SMILES: FC(F)(F)c1ccnc(Nc2cc(C3CCOCC3)nc(N3CCn4ccnc4C3)n2)c1] | [2-(5,6-Dihydro-8H-imidazo[1,2-a]pyrazin-7-yl)-6-(tetrahydro-pyran-4-yl)-pyrimidin-4-yl]-(4-trifluoromethyl-pyridin-2-yl)-amine |

TABLE A-continued
| No. | Structure | Name |
|-----|-----------|------|
| 254 | 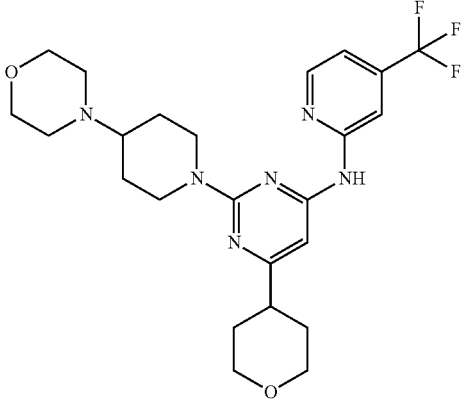 [SMILES: FC(F)(F)c1ccnc(Nc2cc(C3CCOCC3)nc(N3CCC(N4CCOCC4)CC3)n2)c1] | [2-(4-Morpholin-4-yl-piperidin-1-yl)-6-(tetrahydro-pyran-4-yl)-pyrimidin-4-yl]-(4-trifluoromethyl-pyridin-2-yl)-amine |
| 255 | 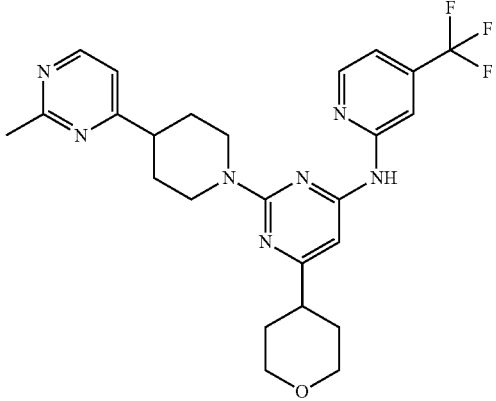 [SMILES: Cc1nccc(C2CCN(c3nc(Nc4cc(C(F)(F)F)ccn4)cc(C4CCOCC4)n3)CC2)n1] | [2-[4-(2-Methyl-pyrimidin-4-yl)-piperidin-1-yl]-6-(tetrahydro-pyran-4-yl)-pyrimidin-4-yl]-(4-trifluoromethyl-pyridin-2-yl)-amine |
| 256 | 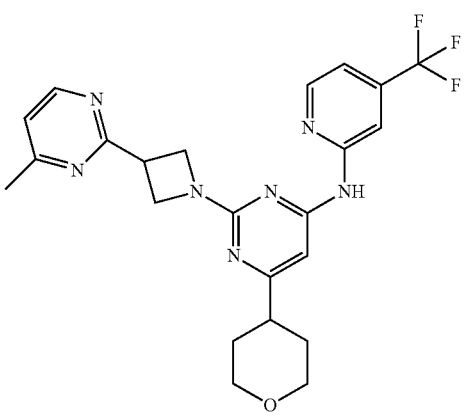 [SMILES: Cc1ccnc(C2CN(c3nc(Nc4cc(C(F)(F)F)ccn4)cc(C4CCOCC4)n3)C2)n1] | [2-[3-(4-Methyl-pyrimidin-2-yl)-azetidin-1-yl]-6-(tetrahydro-pyran-4-yl)-pyrimidin-4-yl]-(4-trifluoromethyl-pyridin-2-yl)-amine |

TABLE A-continued
| No. | Structure | Name |
|---|---|---|
| 257 | 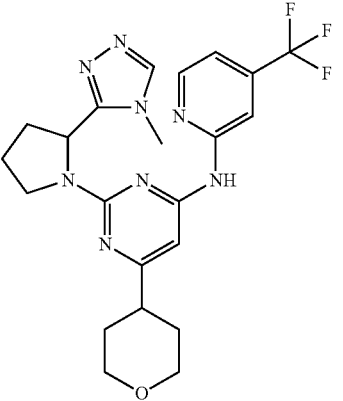 [SMILES: Cn1cnnc1C1CCCN1c1nc(Nc2cc(C(F)(F)F)ccn2)cc(C2CCOCC2)n1] | [2-[2-(4-Methyl-4H-[1,2,4]triazol-3-yl)-pyrrolidin-1-yl]-6-(tetrahydro-pyran-4-yl)-pyrimidin-4-yl]-(4-trifluoromethyl-pyridin-2-yl)-amine |
| 258 | 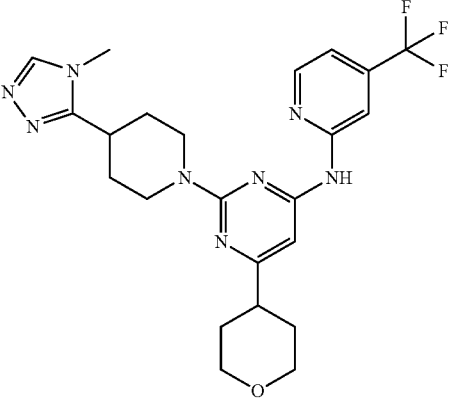 [SMILES: Cn1cnnc1C1CCN(c2nc(Nc3cc(C(F)(F)F)ccn3)cc(C3CCOCC3)n2)CC1] | [2-[4-(4-Methyl-4H-[1,2,4]triazol-3-yl)-piperidin-1-yl]-6-(tetrahydro-pyran-4-yl)-pyrimidin-4-yl]-(4-trifluoromethyl-pyridin-2-yl)-amine |
| 259 | 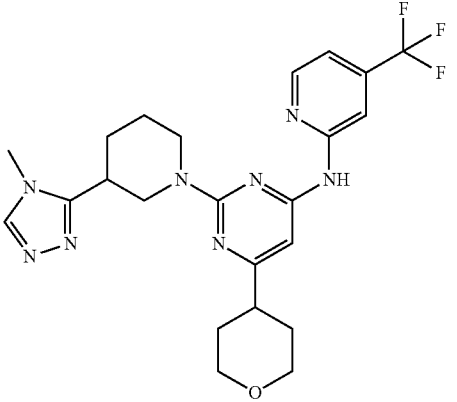 [SMILES: Cn1cnnc1C1CCCN(c2nc(Nc3cc(C(F)(F)F)ccn3)cc(C3CCOCC3)n2)C1] | [2-[3-(4-Methyl-4H-[1,2,4]triazol-3-yl)-piperidin-1-yl]-6-(tetrahydro-pyran-4-yl)-pyrimidin-4-yl]-(4-trifluoromethyl-pyridin-2-yl)-amine |

TABLE A-continued

| No. | Structure | Name |
|---|---|---|
| 260 | 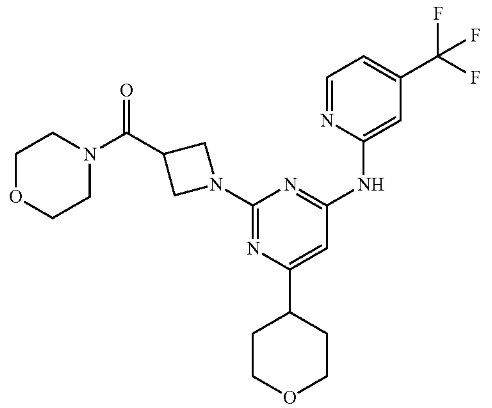 [SMILES: O=C(C1CN(c2nc(Nc3cc(C(F)(F)F)ccn3)cc(C3CCOCC3)n2)C1)N1CCOCC1] | Morpholin-4-yl-{1-[4-(tetrahydro-pyran-4-yl)-6-(4-trifluoromethyl-pyridin-2-ylamino)-pyrimidin-2-yl]-azetidin-3-yl}-methanone |
| 261 | 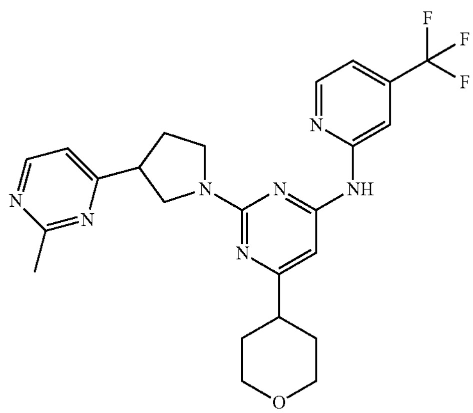 [SMILES: Cc1nccc(C2CCN(c3nc(Nc4cc(C(F)(F)F)ccn4)cc(C4CCOCC4)n3)C2)n1] | [2-[3-(2-Methyl-pyrimidin-4-yl)-pyrrolidin-1-yl]-6-(tetrahydro-pyran-4-yl)-pyrimidin-4-yl]-(4-trifluoromethyl-pyridin-2-yl)-amine |
| 262 | 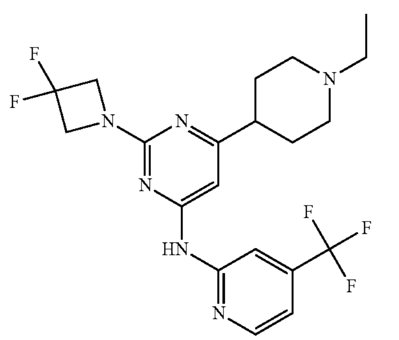 [SMILES: CCN1CCC(c2cc(Nc3cc(C(F)(F)F)ccn3)nc(N3CC(F)(F)C3)n2)CC1] | [2-(3,3-Difluoro-azetidin-1-yl)-6-(1-ethyl-piperidin-4-yl)-pyrimidin-4-yl]-(4-trifluoromethyl-pyridin-2-yl)-amine |
| 263 | 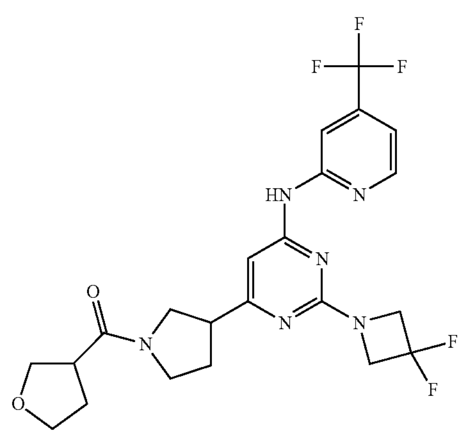 [SMILES: O=C(C1CCOC1)N1CCC(c2cc(Nc3cc(C(F)(F)F)ccn3)nc(N3CC(F)(F)C3)n2)C1] | {3-[2-(3,3-Difluoro-azetidin-1yl)-6-(4-trifluoromethyl-pyridin-2-ylamino)-pyrimidin-4-yl]-pyrrolidin-1-yl}-(tetrahydro-furan-3-yl)-methanone |

| No. | Structure | Name |
|---|---|---|
| 264 | 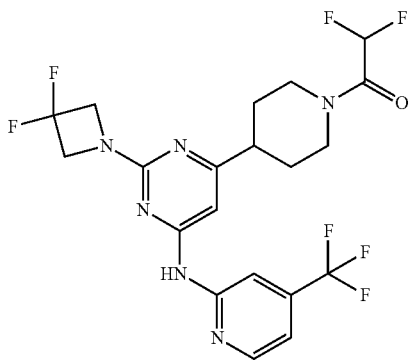 [SMILES: O=C(C(F)F)N1CCC(c2cc(Nc3cc(C(F)(F)F)ccn3)nc(N3CC(F)(F)C3)n2)CC1] | 1-{4-[2-(3,3-Difluoro-azetidin-1-yl)-6-(4-trifluoromethyl-pyridin-2-ylamino)-pyrimidin-4-yl]-piperidin-1-yl}-2,2-difluoro-ethanone |
| 265 | 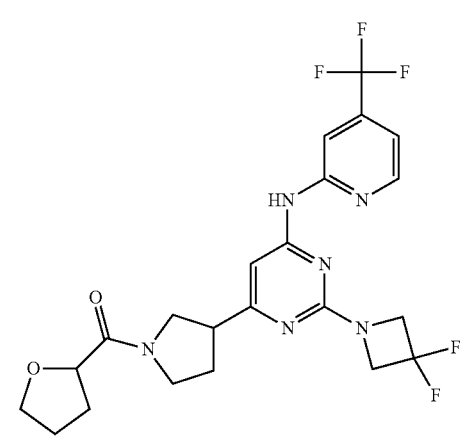 [SMILES: O=C(C1CCCO1)N1CCC(c2cc(Nc3cc(C(F)(F)F)ccn3)nc(N3CC(F)(F)C3)n2)C1] | {3-[2-(3,3-Difluoro-azetidin-1-yl)-6-(4-trifluoro-methyl-pyridin-2-ylamino)-pyrimidin-4-yl]-pyrrolidin-1-yl}-(tetrahydro-furan-2-yl)-methanone |
| 266 | 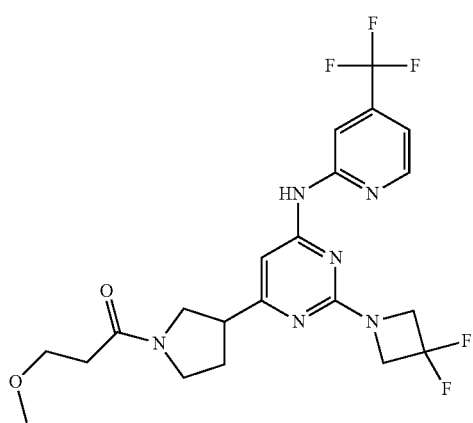 [SMILES: COCCC(=O)N1CCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoromethyl-pyridin-2-ylamino)-pyrimidin-4-yl]-pyrrolidin-1-yl}-3-methoxy-propan-1-one |

TABLE A-continued

| No. | Structure | Name |
|---|---|---|
| 267 | 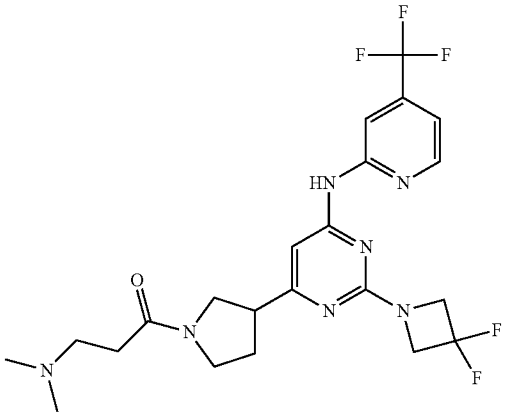 [SMILES: CN(C)CCC(=O)N1CCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoromethyl-pyridin-2-ylamino)-pyrimidin-4-yl]-pyrrolidin-1-yl}-3-dimethylamino-propan-1-one |
| 268 | 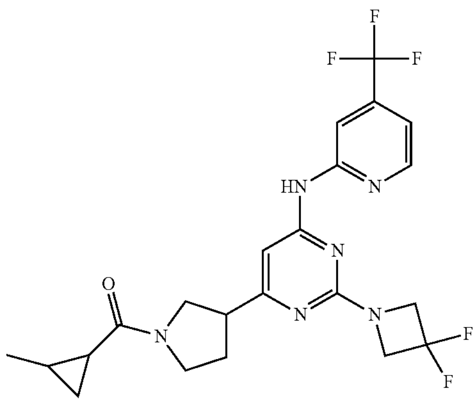 [SMILES: CC1CC1C(=O)N1CCC(c2cc(Nc3cc(C(F)(F)F)ccn3)nc(N3CC(F)(F)C3)n2)C1] | {3-[2-(3,3-Difluoro-azetidin-1-yl)-6-(4-trifluoro-methyl-pyridin-2-ylamino)-pyrimidin-4-yl]-pyrrolidin-1-yl}-(2-methyl-cyclopropyl)-methanone |
| 269 | 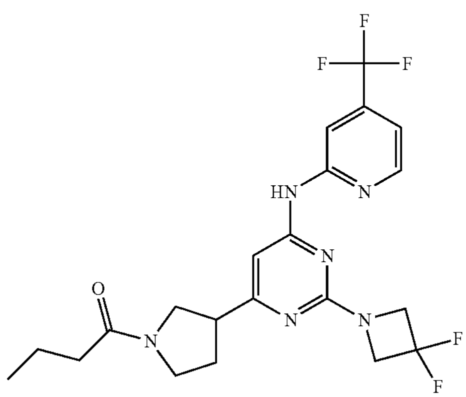 [SMILES: CCCC(=O)N1CCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoromethyl-pyridin-2-ylamino)-pyrimidin-4-yl]-pyrrolidin-1-yl}-butan-1-one |
| 270 | 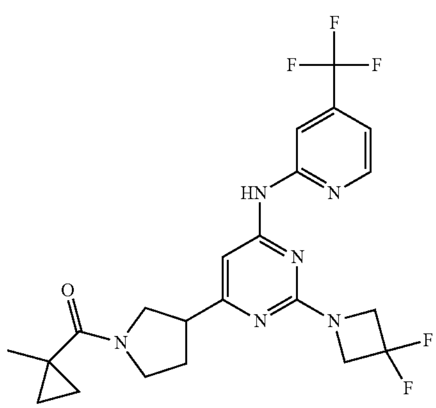 [SMILES: CC1(C(=O)N2CCC(c3cc(Nc4cc(C(F)(F)F)ccn4)nc(N4CC(F)(F)C4)n3)C2)CC1] | {3-[2-(3,3-Difluoro-azetidin-1-yl)-6-(4-trifluoro-methyl-pyridin-2-ylamino)-pyrimidin-4-yl]-pyrrolidin-1-yl}-(1-methyl-cyclopropyl)-methanone |

TABLE A-continued

| No. | Structure | Name |
|---|---|---|
| 271 | 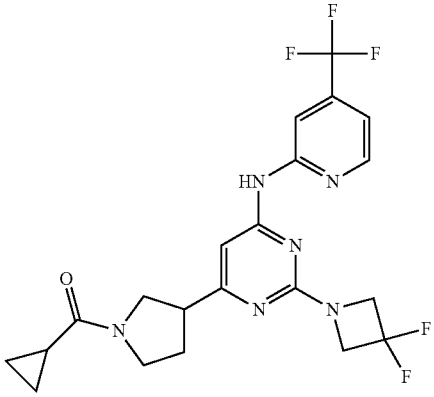 [SMILES: O=C(C1CC1)N1CCC(c2cc(Nc3cc(C(F)(F)F)ccn3)nc(N3CC(F)(F)C3)n2)C1] | Cyclopropyl-{3-[2-(3,3-difluoro-azetidin-1-yl)-6-(4-trifluoromethyl-pyridin-2-ylamino)-pyrimidin-4-yl]-pyrrolidin-1-yl}-methanone |
| 272 | 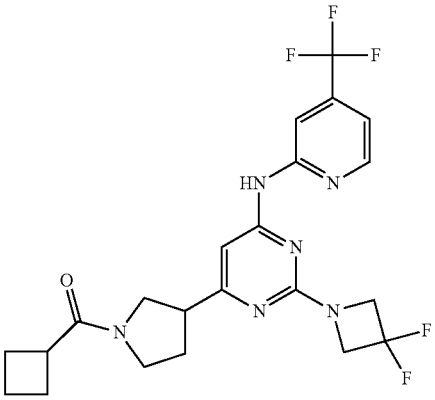 [SMILES: O=C(C1CCC1)N1CCC(c2cc(Nc3cc(C(F)(F)F)ccn3)nc(N3CC(F)(F)C3)n2)C1] | Cyclobutyl-{3-[2-(3,3-difluoro-azetidin-1-yl)-6-(4-trifluoromethyl-pyridin-2-ylamino)-pyrimidin-4-yl]-pyrrolidin-1-yl}-methanone |
| 273 | 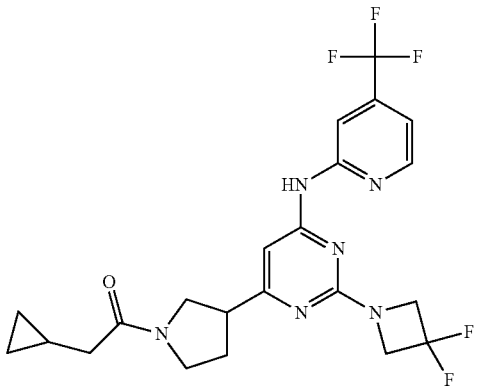 [SMILES: O=C(CC1CC1)N1CCC(c2cc(Nc3cc(C(F)(F)F)ccn3)nc(N3CC(F)(F)C3)n2)C1] | 2-Cyclopropyl-1-{3-[2-(3,3-difluoro-azetidin-1-yl)-6-(4-trifluoromethyl-pyridin-2-ylamino)-pyrimidin-4-yl]-pyrrolidin-1-yl}-ethanone |
| 274 | 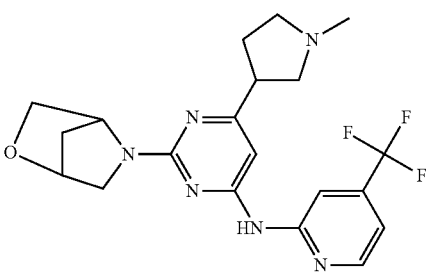 [SMILES: CN1CCC(c2cc(Nc3cc(C(F)(F)F)ccn3)nc(N3CC4CC3CO4)n2)C1] | [6-(1-Methyl-pyrrolidin-3-yl)-2-(2-oxa-5-aza-bicyclo[2.2.1]hept-5-yl)-pyrimidin-4-yl]-(4-trifluoromethyl-pyridin-2-yl)-amine |

TABLE A-continued

| No. | Structure | Name |
|---|---|---|
| 275 | 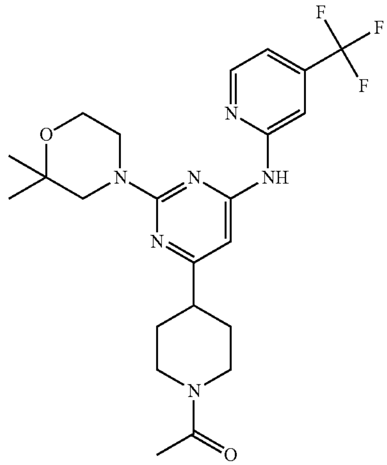 [SMILES: CC(=O)N1CCC(c2cc(Nc3cc(C(F)(F)F)ccn3)nc(N3CCOC(C)(C)C3)n2)CC1] | 1-{4-[2-(2,2-Dimethyl-morpholin-4-yl)-6-(4-trifluoromethyl-pyridin-2-ylamino)-pyrimidin-4-yl]-piperidin-1-yl}-ethanone |
| 276 | 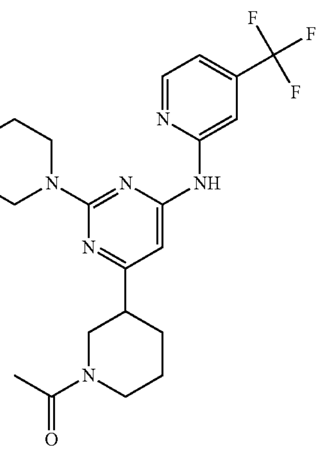 | 1-{3-[2-(2,2-Dimethyl-morpholin-4-yl)-6-(4-trifluoromethyl-pyridin-2-ylamino)-pyrimidin-4-yl]-piperidin-1-yl}-ethanone |
| 277 | 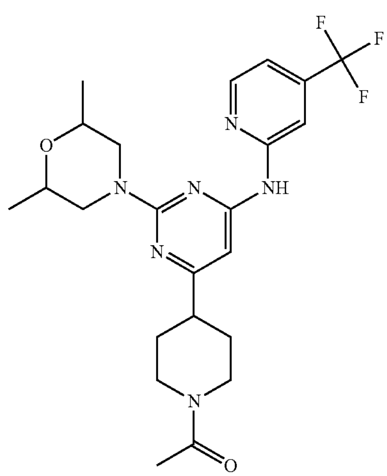 [SMILES: CC(=O)N1CCC(c2cc(Nc3cc(C(F)(F)F)ccn3)nc(N3CC(C)OC(C)C3)n2)CC1] | 1-{4-[2-(2,6-Dimethyl-morpholin-4-yl)-6-(4-trifluoromethyl-pyridin-2-ylamino)-pyrimidin-4-yl]-piperidin-1-yl}-ethanone |

TABLE A-continued

| No. | Structure | Name |
|---|---|---|
| 278 | 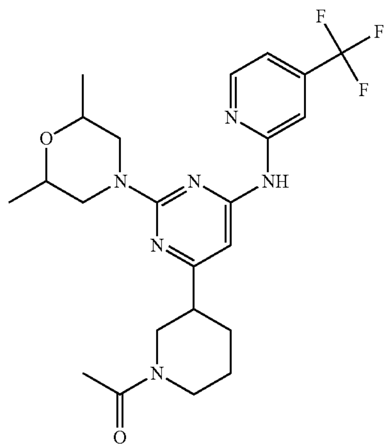 [SMILES: CC(=O)N1CCCC(c2cc(Nc3cc(C(F)(F)F)ccn3)nc(N3CC(C)OC(C)C3)n2)C1] | 1-{3-[2-(2,6-Dimethyl-morpholin-4-yl)-6-(4-trifluoromethyl-pyridin-2-ylamino)-pyrimidin-4-yl]-piperidin-1-yl}-ethanone |
| 279 | 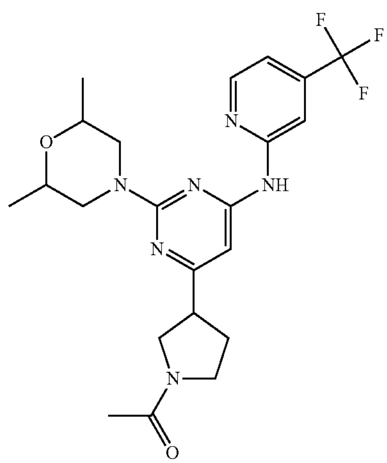 [SMILES: CC(=O)N1CCC(c2cc(Nc3cc(C(F)(F)F)ccn3)nc(N3CC(C)OC(C)C3)n2)C1] | 1-{3-[2-(2,6-Dimethyl-morpholin-4-yl)-6-(4-trifluoromethyl-pyridin-2-ylamino)-pyrimidin-4-yl]-pyrrolidin-1-yl}-ethanone |
| 280 | 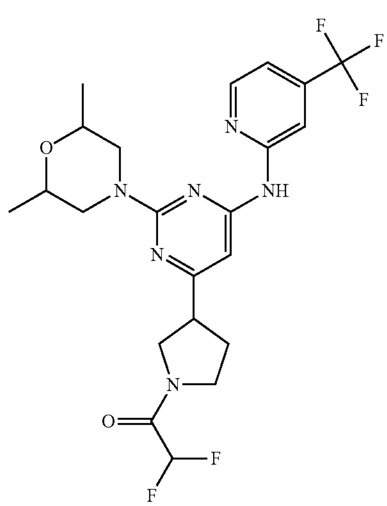 [SMILES: CC1CN(c2nc(Nc3cc(C(F)(F)F)ccn3)cc(C3CCN(C(=O)C(F)F)C3)n2)CC(C)O1] | 1-{3-[2-(2,6-Dimethyl-morpholin-4-yl)-6-(4-trifluoromethyl-pyridin-2-ylamino)-pyrimidin-4-yl]-pyrrolidin-1-yl}-2,2-difluoro-ethanone |

TABLE A-continued

| No. | Structure | Name |
|---|---|---|
| 281 | 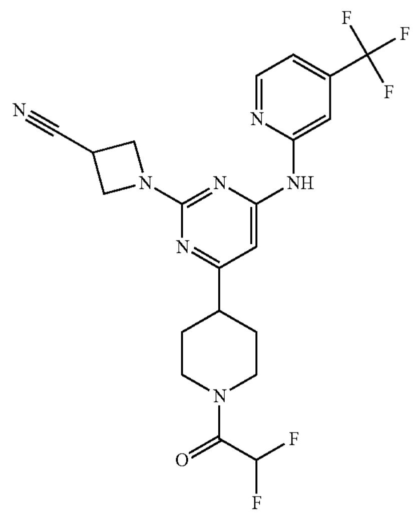 [SMILES: N#CC1CN(c2nc(Nc3cc(C(F)(F)F)ccn3)cc(C3CCN(C(=O)C(F)F)CC3)n2)C1] | 1-[4-[1-(2,2-Difluoro-acetyl)-piperidin-4-yl]-6-(4-trifluoromethyl-pyridin-2-ylamino)-pyrimidin-2-yl]-azetidine-3-carbonitrile |
| 282 | 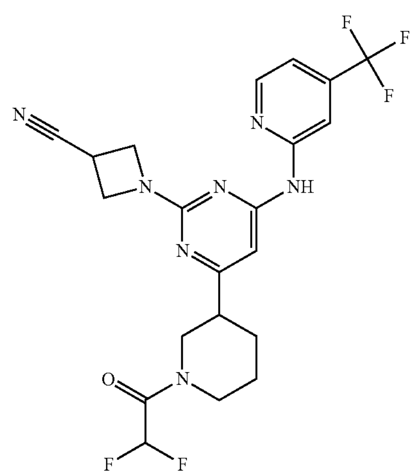 [SMILES: N#CC1CN(c2nc(Nc3cc(C(F)(F)F)ccn3)cc(C3CCCN(C(=O)C(F)F)C3)n2)C1] | 1-[4-[1-(2,2-Difluoro-acetyl)-piperidin-3-yl]-6-(4-trifluoromethyl-pyridin-2-ylamino)-pyrimidin-2-yl]-azetidine-3-carbonitrile |
| 283 | 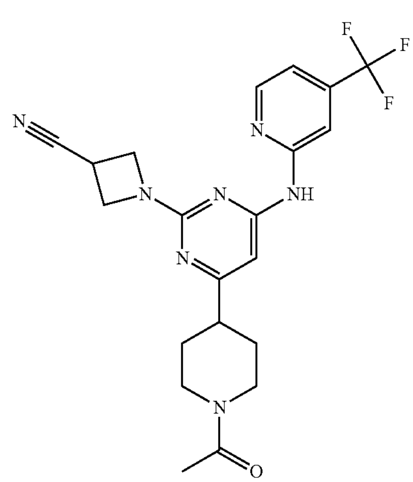 [SMILES: CC(=O)N1CCC(c2cc(Nc3cc(C(F)(F)F)ccn3)nc(N3CC(C#N)C3)n2)CC1] | 1-[4-(1-Acetyl-piperidin-4-yl)-6-(4-trifluoromethyl-pyridin-2-ylamino)-pyrimidin-2-yl]-azetidine-3-carbonitrile |

TABLE A-continued

| No. | Structure | Name |
|---|---|---|
| 284 | 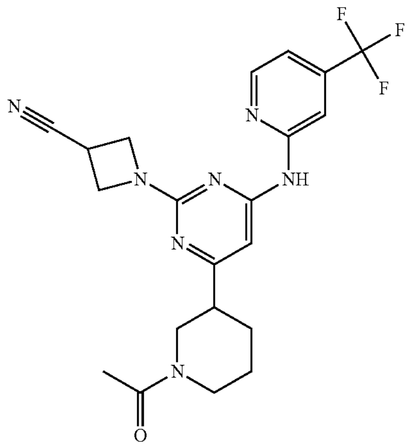 [SMILES: CC(=O)N1CCCC(c2cc(Nc3cc(C(F)(F)F)ccn3)nc(N3CC(C#N)C3)n2)C1] | 1-[4-(1-Acetyl-piperidin-3-yl)-6-(4-trifluoro-methyl-pyridin-2-ylamino)-pyrimidin-2-yl]-azetidine-3-carbonitrile |
| 285 | 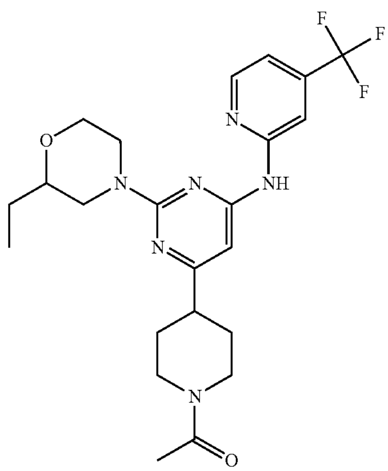 [SMILES: CCC1CN(c2nc(Nc3cc(C(F)(F)F)ccn3)cc(C3CCN(C(C)=O)CC3)n2)CCO1] | 1-{4-[2-(2-Ethyl-morph-olin-4-yl)-6-(4-trifluoro-methyl-pyridin-2-ylamino)-pyrimidin-4-yl]-piperidin-1-yl}-ethanone |
| 286 | 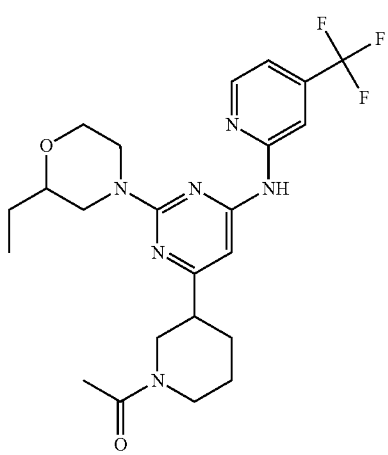 [SMILES: CCC1CN(c2nc(Nc3cc(C(F)(F)F)ccn3)cc(C3CCCN(C(C)=O)C3)n2)CCO1] | 1-{3-[2-(2-Ethyl-morph-olin-4-yl)-6-(4-trifluoro-methyl-pyridin-2-ylamino)-pyrimidin-4-yl]-piperidin-1-yl}-ethanone |

TABLE A-continued

| No. | Structure | Name |
|---|---|---|
| 287 | 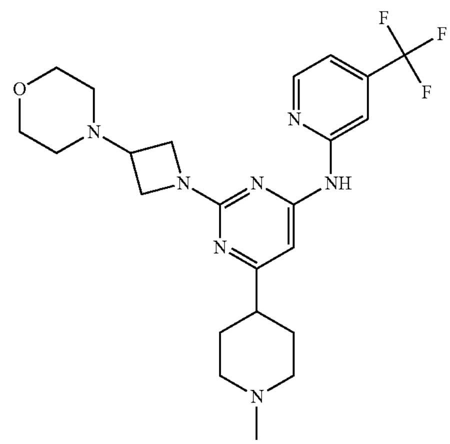 [SMILES: CN1CCC(c2cc(Nc3cc(C(F)(F)F)ccn3)nc(N3CC(N4CCOCC4)C3)n2)CC1] | 6-(1-Methyl-piperidin-4-yl)-2-(3-morpholin-4-yl-azetidin-1-yl)-pyrimidin-4-yl]-(4-trifluoromethyl-pyridin-2-yl)-amine |
| 288 | 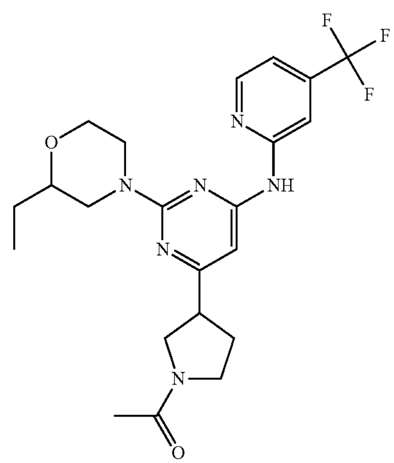 [SMILES: CCC1CN(c2nc(Nc3cc(C(F)(F)F)ccn3)cc(C3CCN(C(C)=O)C3)n2)CCO1] | 1-{3-[2-(2-Ethyl-morpholin-4-yl)-6-(4-trifluoro-methyl-pyridin-2-ylamino)-pyrimidin-4-yl]-pyrrolidin-1-yl}-ethanone |
| 289 | 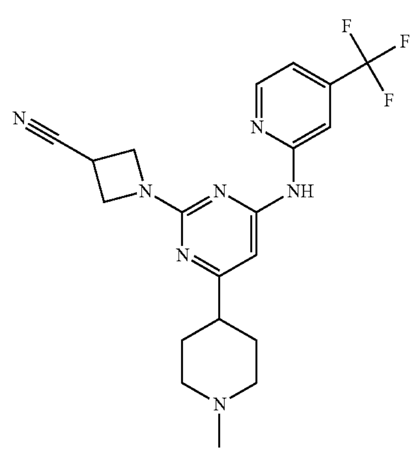 [SMILES: CN1CCC(c2cc(Nc3cc(C(F)(F)F)ccn3)nc(N3CC(C#N)C3)n2)CC1] | 1-[4-(1-Methyl-piperidin-4-yl)-6-(4-trifluoro-methyl-pyridin-2-ylamino)-pyrimidin-2-yl]-azetidine-3-carbonitrile |

| No. | Structure | Name |
|---|---|---|
| 290 | 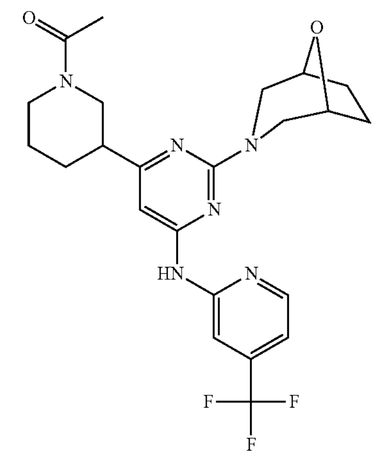 [SMILES: CC(=O)N1CCCC(c2cc(Nc3cc(C(F)(F)F)ccn3)nc(N3CC4CCC(C3)O4)n2)C1] | 1-{3-[2(8-Oxa-3-aza-bicyclo[3.2.1]oct-3-yl)-6-(4-trifluoromethyl-pyridin-2-ylamino)-pyrimidin-4-yl]-piperidin-1-yl}-ethanone |
| 291 | 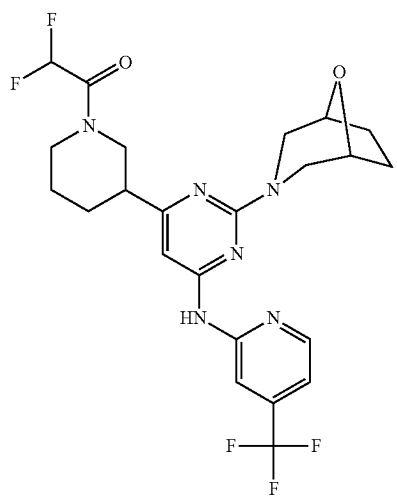 [SMILES: O=C(C(F)F)N1CCCC(c2cc(Nc3cc(C(F)(F)F)ccn3)nc(N3CC4CCC(C3)O4)n2)C1] | 2,2-Difluoro-1-{3-[2-(8-oxa-3-aza-bicyclo[3.2.1]-oct-3-yl)-6-(4-trifluoro-methyl-pyridin-2-ylamino)-pyrimidin-4-yl}-piperidin-1-yl}-ethanone |
| 292 | 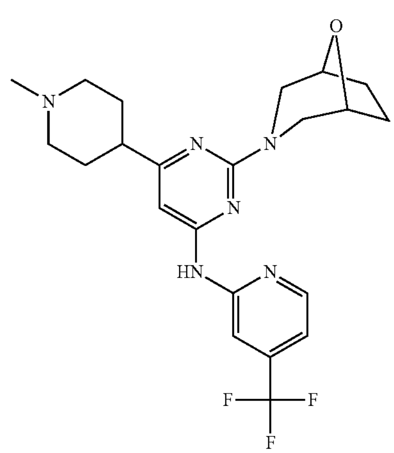 [SMILES: CN1CCC(c2cc(Nc3cc(C(F)(F)F)ccn3)nc(N3CC4CCC(C3)O4)n2)CC1] | [6-(1-Methyl-piperidin-4-yl)-2-(8-oxa-3-aza-bi-cyclo[3.2.1]oct-3-yl)-pyrimidin-4-yl]-(4-trifluoro-methyl-pyridin-2-yl)-amine |

TABLE A-continued

| No. | Structure | Name |
|---|---|---|
| 293 | 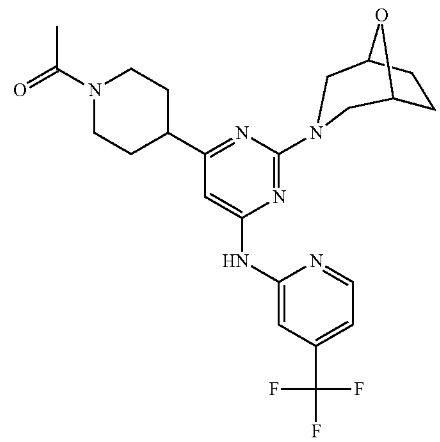 [SMILES: CC(=O)N1CCC(c2cc(Nc3cc(C(F)(F)F)ccn3)nc(N3CC4CCC(C3)O4)n2)CC1] | 1-{4-[2-(8-Oxa-3-aza-bicyclo[3.2.1]oct-3-yl)-6-(4-trifluoromethyl-pyridin-2-ylamino)-pyrimidin-4-yl]-piperidin-1-yl}-ethanone |
| 294 | 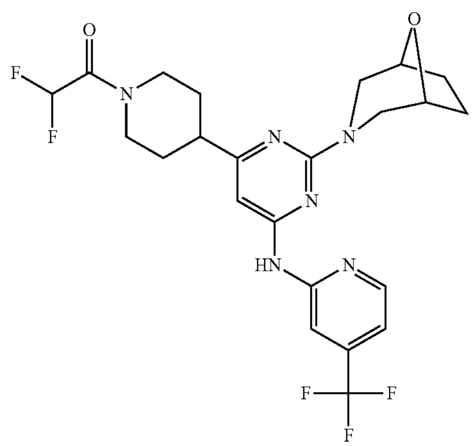 [SMILES: O=C(C(F)F)N1CCC(c2cc(Nc3cc(C(F)(F)F)ccn3)nc(N3CC4CCC(C3)O4)n2)CC1] | 2,2-Difluoro-1{-[2(8-oxa-3-aza-bicyclo[3.2.1]oct-3-yl)-6-(4-trifluoro-methyl-pyridin-2-ylamino)-pyrimidin-4-yl]-piperidin-1-yl}-ethanone |
| 295 | 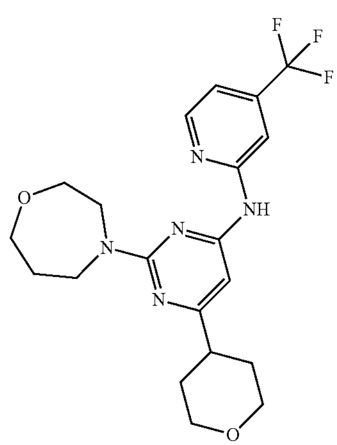 [SMILES: FC(F)(F)c1ccnc(Nc2cc(C3CCOCC3)nc(N3CCCOCC3)n2)c1] | [2-[1,4]Oxazepan-4-yl-6-(tetrahydro-pyran-4-yl)-pyrimidin-4-yl]-(4-trifluoromethyl-pyridin-2-yl)-amine |

TABLE A-continued
| No. | Structure | Name |
|---|---|---|
| 296 | 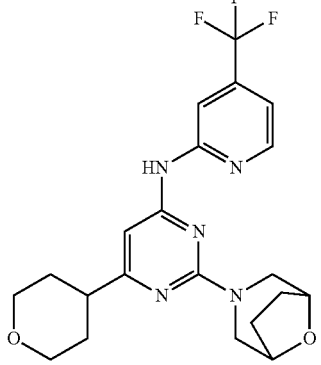 | [2-(8-Oxa-3-aza-bicyclo-[3.2.1]oct-3-yl)-6-(tetra-hydro-pyran-4-yl)-pyrimidin-4-yl]-(4-trifluoro-methyl-pyridin-2-yl)-amine |
| 297 | 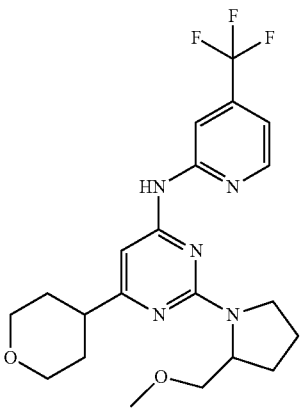 [SMILES: COCC1CCCN1c1nc(Nc2cc(C(F)(F)F)ccn2)cc(C2CCOCC2)n1] | [2-(2-Methoxymethyl-pyrrolidin-1-yl)-6-(tetra-hydro-pyran-4-yl)-pyrimidin-4-yl]-(4-trifluoromethyl-pyridin-2-yl)-amine |
| 298 | 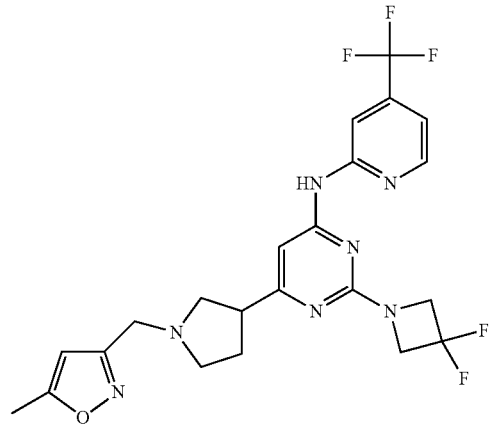 [SMILES: Cc1cc(CN2CCC(c3cc(Nc4cc(C(F)(F)F)ccn4)nc(N4CC(F)(F)C4)n3)C2)no1] | {2-(3,3-Difluoro-azetidin-1-yl)-6-[1-(5-methyl-isoxazol-3-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 299 | 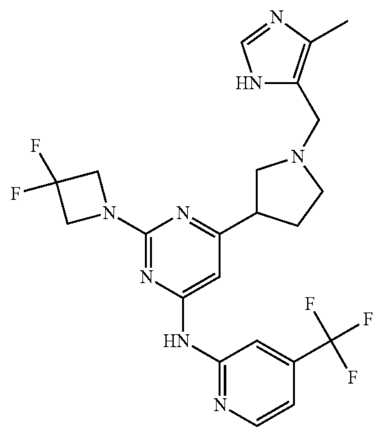 [SMILES: Cc1nc[nH]c1CN1CCC(c2cc(Nc3cc(C(F)(F)F)ccn3)nc(N3CC(F)(F)C3)n2)C1] | {2-(3,3-Difluoro-azetidin-1-yl)-6-[1-(5-methyl-3H-imidazol-4-ylmethyl)-pyrrolidin-3-yl]-pyrimidin-4-yl}-(4-trifluoro-methyl-pyridin-2-yl)-mine |
| 300 | 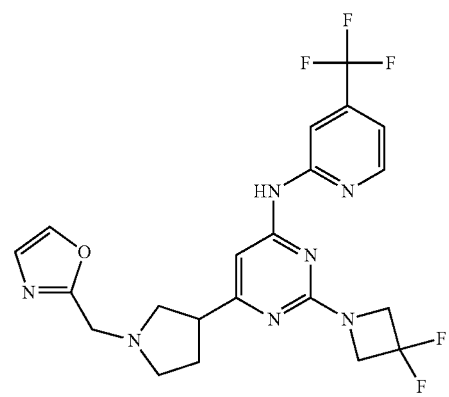 [SMILES: FC1(F)CN(c2nc(Nc3cc(C(F)(F)F)ccn3)cc(C3CCN(Cc4ncco4)C3)n2)C1] | [2-(3,3-Difluoro-azetidin-1-yl)-6-(1-oxazol-2-ylmethyl-pyrrolidin-3-yl)-pyrimidin-4-yl]-(4-trifluoromethyl-pyridin-2-yl)-amine |
| 301 | 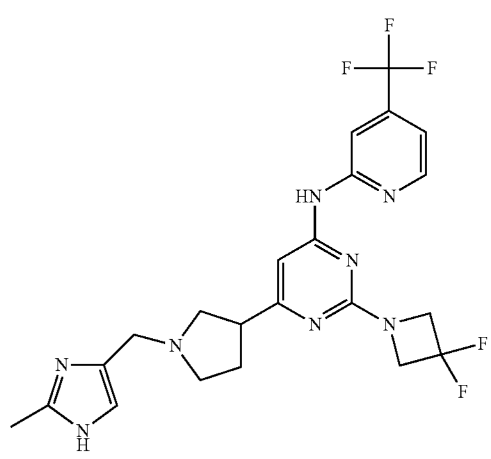 [SMILES: Cc1nc(CN2CCC(c3cc(Nc4cc(C(F)(F)F)ccn4)nc(N4CC(F)(F)C4)n3)C2)c[nH]1] | {2-(3,3-Difluoro-azetidin-1-yl)-6-[142-methyl-1H-imidazol-4-ylmethyl)-pyrrolidin-3-yl1-pyrimidin-4-yl}-(4-trifluoro-methyl-pyridin-2-yl)-amine |

TABLE A-continued
| No. | Structure | Name |
|---|---|---|
| 302 | 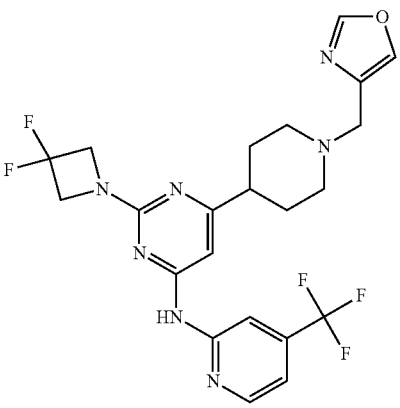 [SMILES: FC1(F)CN(c2nc(Nc3cc(C(F)(F)F)ccn3)cc(C3CCN(Cc4cocn4)CC3)n2)C1] | [2-(3,3-Difluoro-azetidin-1-yl)-6-(1-oxazol-4-ylmethyl-piperidin-4-yl)-pyrimidin-4-yl]-(4-trifluoromethyl-pyridin-2-yl)-amine |
| 303 | 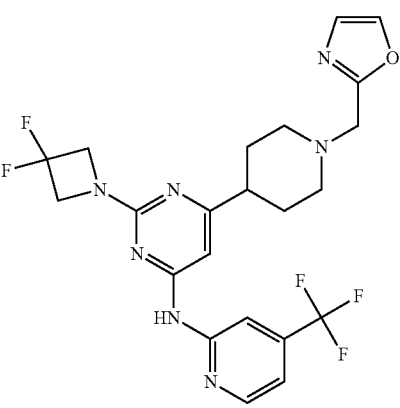 [SMILES: FC1(F)CN(c2nc(Nc3cc(C(F)(F)F)ccn3)cc(C3CCN(Cc4ncco4)CC3)n2)C1] | [2-(3,3-Difluoro-azetidin-1-yl)-6-(1-oxazol-2-ylmethyl-piperidin-4-yl)-pyrimidin-4-yl]-(4-trifluoromethyl-pyridin-2-yl)-amine |
| 304 | 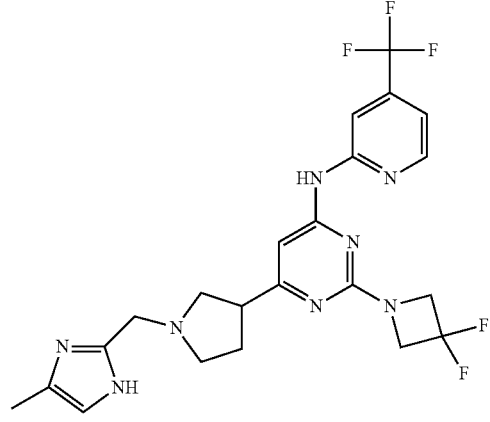 [SMILES: Cc1c[nH]c(CN2CCC(c3cc(Nc4cc(C(F)(F)F)ccn4)nc(N4CC(F)(F)C4)n3)C2)n1] | {2-(3,3-Difluoro-azetidin-1-yl)-6-[1-(4-methyl-1H-imidazol-2-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 305 | 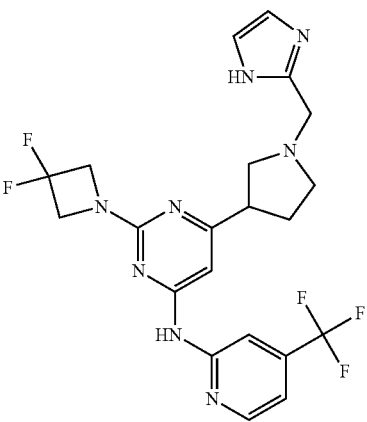 [SMILES: FC1(F)CN(c2nc(Nc3cc(C(F)(F)F)ccn3)cc(C3CCN(Cc4ncc[nH]4)C3)n2)C1] | {2-(3,3-Difluoro-azetidin-1-yl)-6-[1-(1H-imidazol-2-ylmethyl)-pyrrolidin-3-yl]-pyrimidin-4-yl}-(4-trifluoromethyl-pyridin-2-yl)-amine |
| 306 | 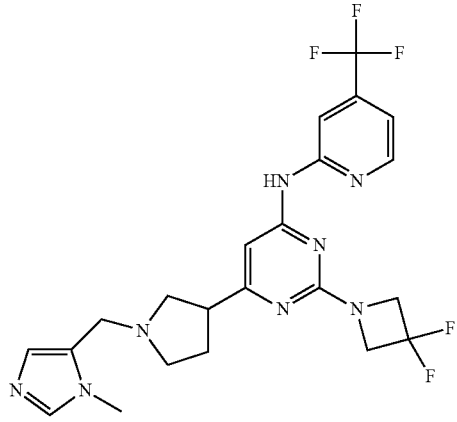 [SMILES: Cn1cncc1CN1CCC(c2cc(Nc3cc(C(F)(F)F)ccn3)nc(N3CC(F)(F)C3)n2)C1] | {2-(3,3-Difluoro-azetidin-1-yl)-6-[1-(3-methyl-3H-imidazol-4-ylmethyl)-pyrrolidin-3-yl]-pyrimidin-4-yl}-(4-trifluoro-methyl-pyridin-2-yl)-amine |
| 307 | 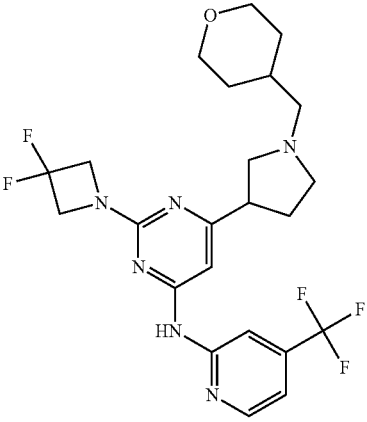 [SMILES: FC1(F)CN(c2nc(Nc3cc(C(F)(F)F)ccn3)cc(C3CCN(CC4CCOCC4)C3)n2)C1] | {2-(3,3-Difluoro-azetidin-1-yl)-6-[1-(tetrahydro-pyran-4-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 308 | 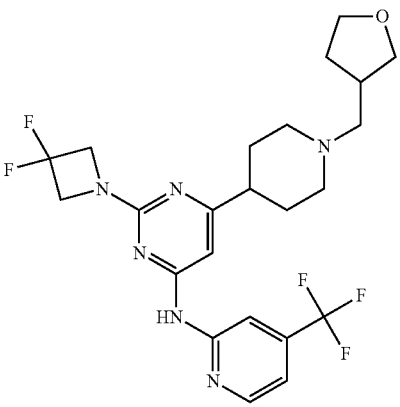 [SMILES: FC1(F)CN(c2nc(Nc3cc(C(F)(F)F)ccn3)cc(C3CCN(CC4CCOC4)CC3)n2)C1] | {2-(3,3-Difluoro-azetidin-1-yl)-6-[1-(tetrahydro-furan-3-ylmethyl)-piperidin-4-yl]-pyrimidin-4-yl}-(4-trifluoromethyl-pyridin-2-yl)-amine |
| 309 | 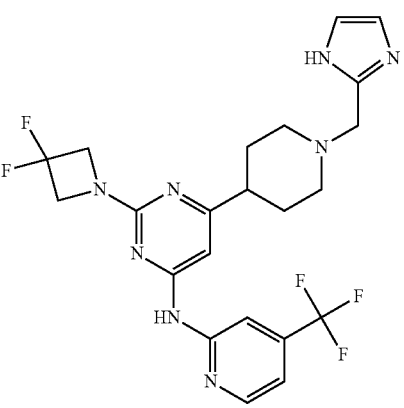 [SMILES: FC1(F)CN(c2nc(Nc3cc(C(F)(F)F)ccn3)cc(C3CCN(Cc4ncc[nH]4)CC3)n2)C1] | {2-(3,3-Difluoro-azetidin-1-yl)-6-[1-(1H-imidazol-2-ylmethyl)-piperidin-4-yl]-pyrimidin-4-yl}-(4-trifluoromethyl-pyridin-2-yl)-amine |
| 310 | 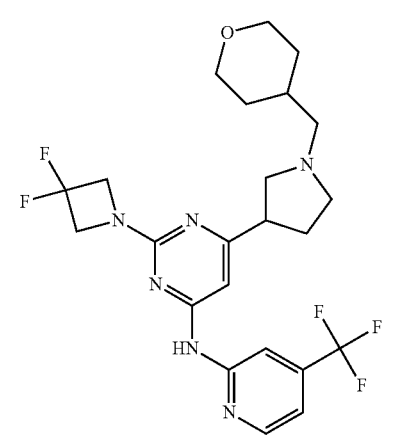 [SMILES: FC1(F)CN(c2nc(Nc3cc(C(F)(F)F)ccn3)cc(C3CCN(CC4CCOCC4)C3)n2)C1] | {2-(3,3-Difluoro-azetidin-1-yl)-6-[1-(tetrahydro-pyran-3-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 311 | 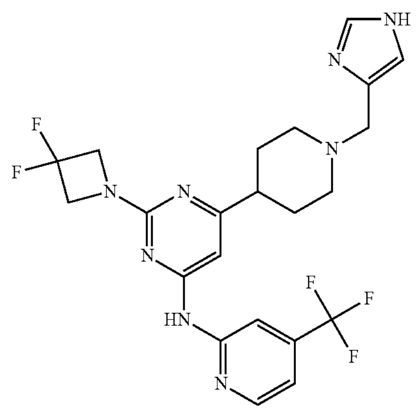 [SMILES: FC1(F)CN(c2nc(Nc3cc(C(F)(F)F)ccn3)cc(C3CCN(Cc4c[nH]cn4)CC3)n2)C1] | {2-(3,3-Difluoro-azetidin-1-yl)-6-[1-(1H-imidazol-4-ylmethyl)-piperidin-4-yl]-pyrimidin-4-yl}-(4-trifluoromethyl-pyridin-2-yl)-amine |
| 312 | 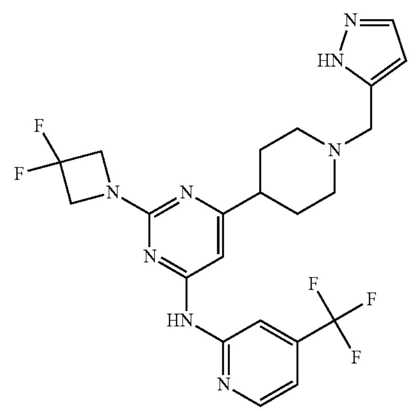 [SMILES: FC1(F)CN(c2nc(Nc3cc(C(F)(F)F)ccn3)cc(C3CCN(Cc4ccn[nH]4)CC3)n2)C1] | {2-(3,3-Difluoro-azetidin-1-yl)-6-[1-(2H-pyrazol-3-ylmethyl)-piperidin-4-yl]-pyrimidin-4-yl}-(4-trifluoromethyl-pyridin-2-yl)-amine |
| 313 | 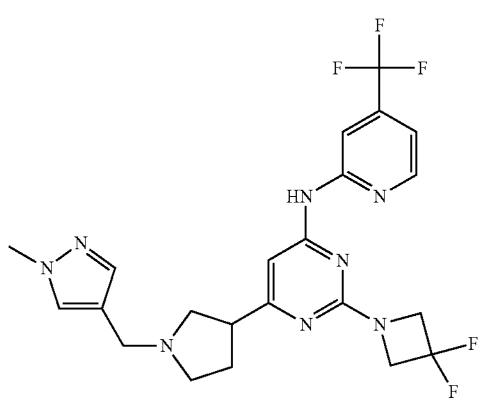 [SMILES: Cn1cc(CN2CCC(c3cc(Nc4cc(C(F)(F)F)ccn4)nc(N4CC(F)(F)C4)n3)C2)cn1] | {2-(3,3-Difluoro-azetidin-1-yl)-6-[1-(1-methyl-1H-pyrazol-4-ylmethyl)-pyrrolidin-3-yl]-pyrimidin-4-yl}-(4-trifluoromethyl-pyridin-2-yl)-amine |

TABLE A-continued
| No. | Structure | Name |
|---|---|---|
| 314 | 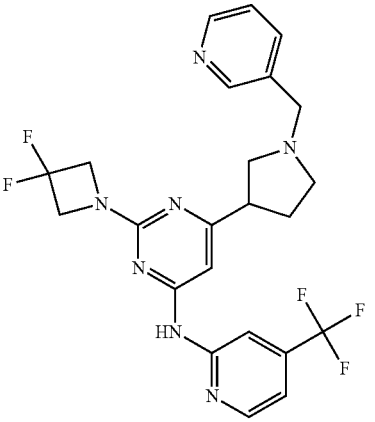 [SMILES: FC1(F)CN(c2nc(Nc3cc(C(F)(F)F)ccn3)cc(C3CCN(Cc4cccnc4)C3)n2)C1] | [2-(3,3-Difluoro-azetidin-1-yl)-6-(1-pyridin-3-ylmethyl-pyrrolidin-3-yl)-pyrimidin-4-yl]-(4-trifluoromethyl-pyridin-2-yl)-amine |
| 315 | 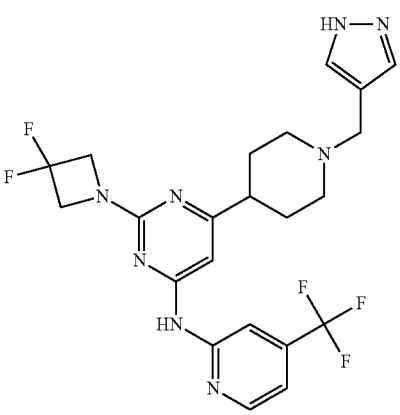 [SMILES: FC1(F)CN(c2nc(Nc3cc(C(F)(F)F)ccn3)cc(C3CCN(Cc4cn[nH]c4)CC3)n2)C1] | {2-(3,3-Difluoro-azetidin-1-yl)-6-[1-(1H-pyrazol-4-ylmethyl)-piperidin-4-yl]-pyrimidin-4-yl}-(4-trifluoromethyl-pyridin-2-yl)-amine |
| 316 | 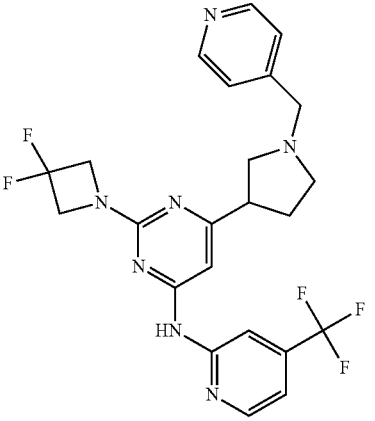 [SMILES: FC1(F)CN(c2nc(Nc3cc(C(F)(F)F)ccn3)cc(C3CCN(Cc4ccncc4)C3)n2)C1] | [2-(3,3-Difluoro-azetidin-1-yl)-6-(1-pyridin-4-ylmethyl-pyrrolidin-3-yl)-pyrimidin-4-yl]-(4-trifluoromethyl-pyridin-2-yl)-amine |

TABLE A-continued

| No. | Structure | Name |
|---|---|---|
| 317 | 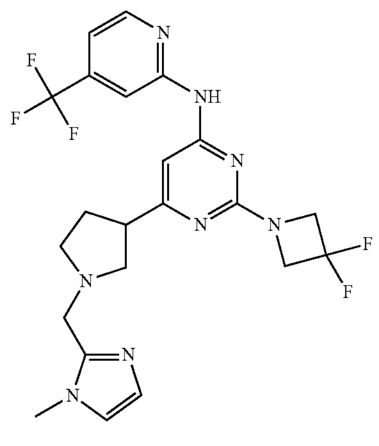 [SMILES: Cn1ccnc1CN1CCC(c2cc(Nc3cc(C(F)(F)F)ccn3)nc(N3CC(F)(F)C3)n2)C1] | {2-(3,3-Difluoro-azetidin-1-yl)-6-[1-(1-methyl-1H-imidazol-2-ylmethyl)-pyrrolidin-3-yl]-pyrimidin-4-yl}-(4-trifluoromethyl-pyridin-2-yl)-amine |
| 318 | 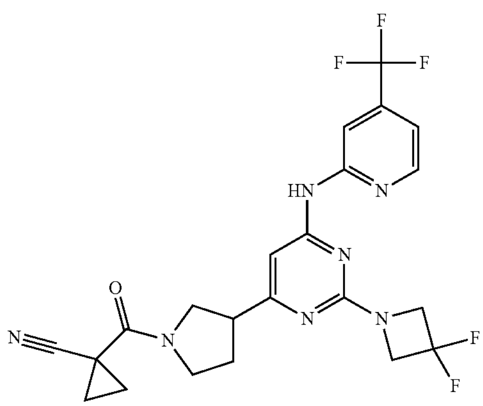 [SMILES: N#CC1(C(=O)N2CCC(c3cc(Nc4cc(C(F)(F)F)ccn4)nc(N4CC(F)(F)C4)n3)C2)CC1] | 1-{3-[2-(3,3-Difluoro-azetidin-1-yl)-6-(4-trifluoromethyl-pyridin-2-ylamino)-pyrimidin-4-yl]-pyrrolidine-1-carbonyl}-cyclopropanecarbonitrile |
| 319 | 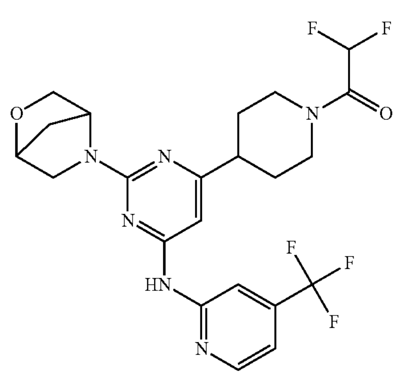 [SMILES: O=C(C(F)F)N1CCC(c2cc(Nc3cc(C(F)(F)F)ccn3)nc(N3CC4CC3CO4)n2)CC1] | 2,2-Difluoro-1-{4-[2-(2-oxa-5-aza-bicyclo[2.2.1]-hept-5-yl)-6-(4-trifluoromethyl-pyridin-2-ylamino)-pyrimidin-4-yl]-piperidin-1-yl}-ethanone |

TABLE A-continued

| No. | Structure | Name |
|---|---|---|
| 320 | 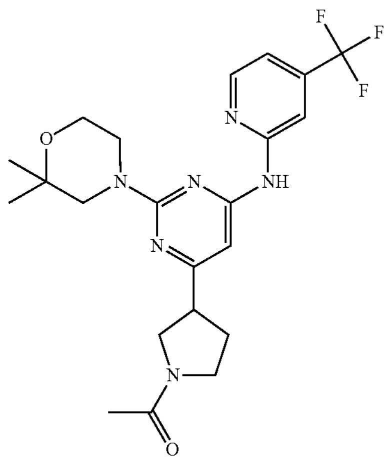 [SMILES: CC(=O)N1CCC(c2cc(Nc3cc(C(F)(F)F)ccn3)nc(N3CCOC(C)(C)C3)n2)C1] | 1-{3-[2-(2,2-Dimethyl-morpholin-4-yl)-6-(4-trifluoromethyl-pyridin-2-ylamino)-pyrimidin-4-yl]-pyrrolidin-1-yl}-ethanone |
| 321 | 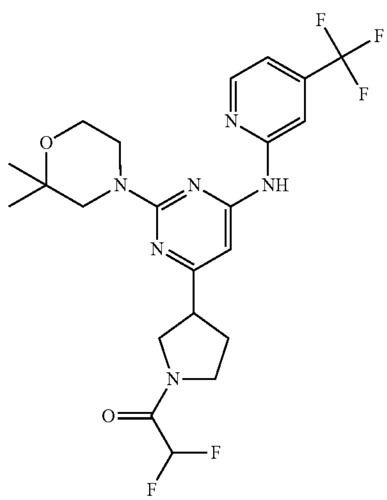 [SMILES: CC1(C)CN(c2nc(Nc3cc(C(F)(F)F)ccn3)cc(C3CCN(C(=O)C(F)F)C3)n2)CCO1] | 1-{3-[2-(2,2-Dimethyl-morpholin-4-yl)-6-(4-trifluoromethyl-pyridin-2-ylamino)-pyrimidin-4-yl]-pyrrolidin-1-yl}-2,2-difluoro-ethanone |
| 322 | 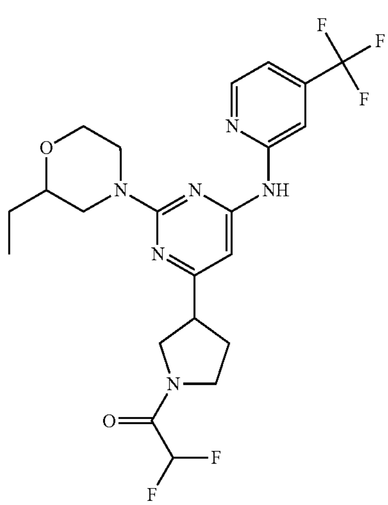 [SMILES: CCC1CN(c2nc(Nc3cc(C(F)(F)F)ccn3)cc(C3CCN(C(=O)C(F)F)C3)n2)CCO1] | 1-{3-[2-(2-Ethyl-morpholin-4-yl)-6-(4-trifluoromethyl-pyridin-2-ylamino)-pyrimidin-4-yl)-pyrrolidin-1-yl}-2,2-difluoro-ethanone |

TABLE A-continued

| No. | Structure | Name |
|---|---|---|
| 323 | 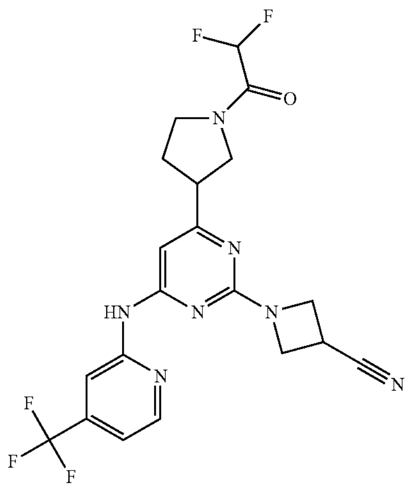 [SMILES: N#CC1CN(c2nc(Nc3cc(C(F)(F)F)ccn3)cc(C3CCN(C(=O)C(F)F)C3)n2)C1] | 1-[4-[1-(2,2-Difluoro-acetyl)-pyrrolidin-3-yl]-6-(4-trifluoromethyl-pyridin-2-ylamino)-pyrimidin-2-3yl)-azetidine-3-carbonitrile |
| 324 | 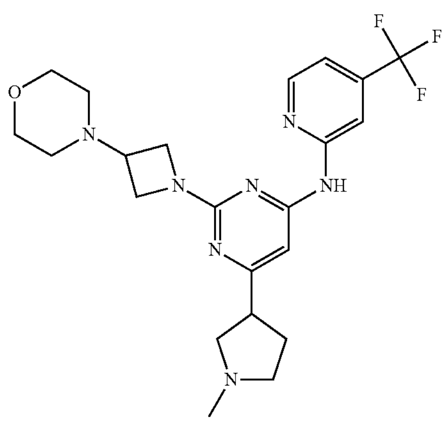 [SMILES: CN1CCC(c2cc(Nc3cc(C(F)(F)F)ccn3)nc(N3CC(N4CCOCC4)C3)n2)C1] | [6-(1-Methyl-pyrrolidin-3-yl)-2-(3-morpholin-4-yl-azetidin-1-yl)-pyrimidin-4-yl]-4-trifluoro-methyl-pyridin-2-yl)-amine |
| 325 | 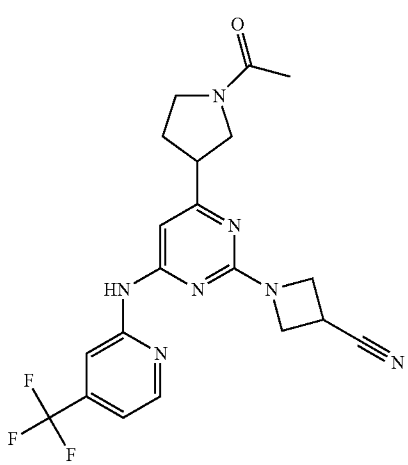 [SMILES: CC(=O)N1CCC(c2cc(Nc3cc(C(F)(F)F)ccn3)nc(N3CC(C#N)C3)n2)C1] | 1-[4-(1-Acetyl-pyrrolidin-3-yl)-6-(4-trifluoro-methyl-pyridin-2-ylamino)-pyrimidin-2-yl]-azetidine-3-carbonitrile |

TABLE A-continued

| No. | Structure | Name |
|---|---|---|
| 326 | 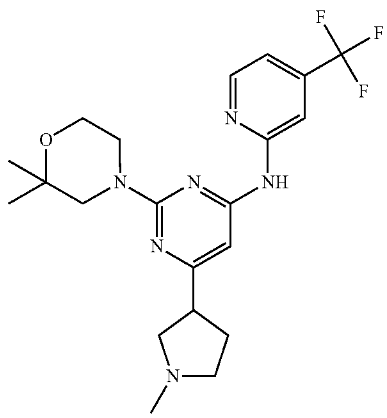 [SMILES: CN1CCC(c2cc(Nc3cc(C(F)(F)F)ccn3)nc(N3CCOC(C)(C)C3)n2)C1] | [2-(2,2-Dimethyl-morpholin-4-yl)-6-(1-methyl-pyrrolidin-3-yl)-pyrimidin-4-yl]-(4-trifluoromethyl-pyridin-2-yl)-amine |
| 327 | 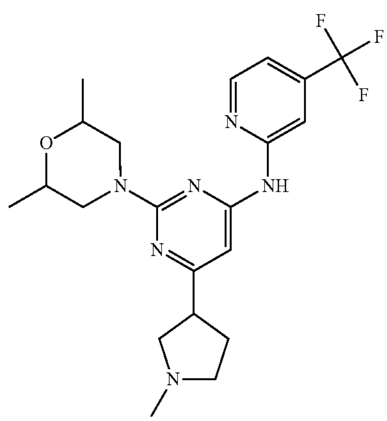 [SMILES: CC1CN(c2nc(Nc3cc(C(F)(F)F)ccn3)cc(C3CCN(C)C3)n2)CC(C)O1] | [2-(2,6-Dimethyl-morpholin-4-yl)-6-(1-methyl-pyrrolidin-3-yl)-pyrimidin-4-yl]-(4-trifluoromethyl-pyridin-2-yl)-amine |
| 328 | 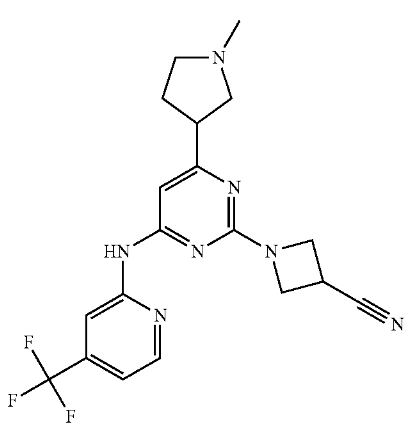 [SMILES: CN1CCC(c2cc(Nc3cc(C(F)(F)F)ccn3)nc(N3CC(C#N)C3)n2)C1] | 1-[4-(1-Methyl-pyrrolidin-3-yl)-6-(4-trifluoromethyl-pyridin-2-ylamino)-pyrimidin-2-yl]-azetidine-3-carbonitrile |

TABLE A-continued

| No. | Structure | Name |
|---|---|---|
| 329 | 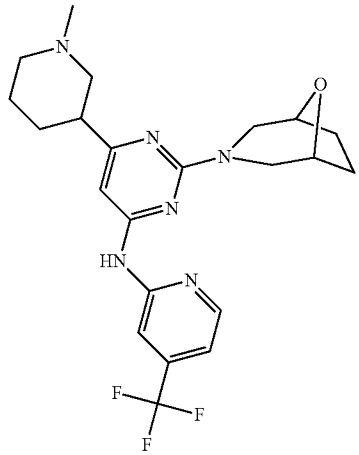 [SMILES: CN1CCCC(c2cc(Nc3cc(C(F)(F)F)ccn3)nc(N3CC4CCC(C3)O4)n2)C1] | [6-(1-Methyl-piperidin-3-yl)-2-(8-oxa-3-aza-bicyclo[3.2.1]oct-3-yl)-pyrimidin-4-yl]-(4-trifluoro-methyl-pyridin-2-yl)-amine |
| 330 | 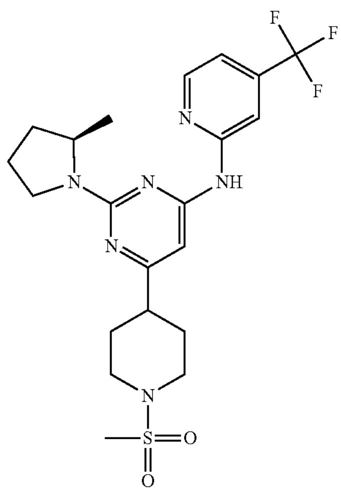 [SMILES: C[C@@H]1CCCN1c1nc(Nc2cc(C(F)(F)F)ccn2)cc(C2CCN(S(C)(=O)=O)CC2)n1] | [6-(1-Methanesulfonyl-piperidin-4-yl)-2-((R)-2-methyl-pyrrolidin-1-yl)-pyrimidin-4-yl]-(4-trifluoromethyl-pyridin-2-yl)-amine |
| 331 | 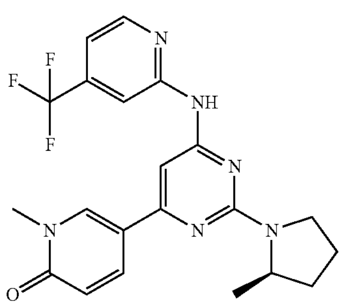 [SMILES: C[C@@H]1CCCN1c1nc(Nc2cc(C(F)(F)F)ccn2)cc(-c2ccc(=O)n(C)c2)n1] | 1-Methyl-5-[2-((R)-2-methyl-pyrrolidin-1-yl)-6-(4-trifluoromethyl-pyridin-2-ylamino)-pyrimidin-4-yl]-1H-pyridin-2-one |
| 332 | 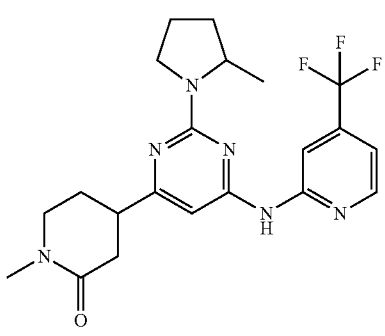 [SMILES: CC1CCCN1c1nc(Nc2cc(C(F)(F)F)ccn2)cc(C2CCN(C)C(=O)C2)n1] | 1-Methyl-4-[2-(2-methyl-pyrrolidin-1-yl)-6-(4-trifluoromethyl-pyridin-2-ylamino)-pyrimidin-4-yl]-piperidin-2-one |

TABLE A-continued

| No. | Structure | Name |
|---|---|---|
| 333 | 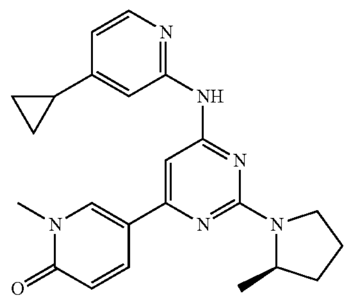 [SMILES: C[C@@H]1CCCN1c1nc(Nc2cc(C3CC3)ccn2)cc(-c2ccc(=O)n(C)c2)n1] | 5-[6-(4-Cyclopropyl-pyridin-2-ylamino)-2-((R)-2-methyl-pyrrolidin-1-yl)-pyrimidin-4-yl]-1-methyl-1H-pyridin-2-one |
| 334 | 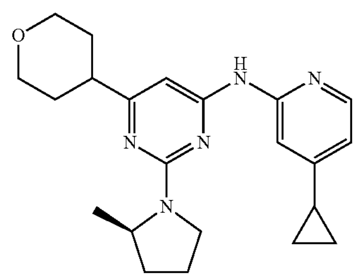 [SMILES: C[C@@H]1CCCN1c1nc(Nc2cc(C3CC3)ccn2)cc(C2CCOCC2)n1] | (4-Cyclopropyl-pyridin-2-yl)-[2-((R)-2-methyl-pyrrolidin-1-yl)-6-(tetra-hydro-pyran-4-yl)-pyrimidin-4-yl]-amine |
| 335 | 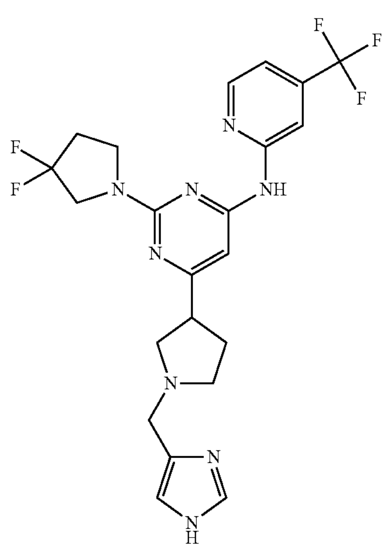 [SMILES: FC1(F)CCN(c2nc(Nc3cc(C(F)(F)F)ccn3)cc(C3CCN(Cc4c[nH]cn4)C3)n2)C1] | {2-(3,3-Difluoro-pyrrolidin-1-yl)-6-[1-(1H-imidazol-4-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 336 | 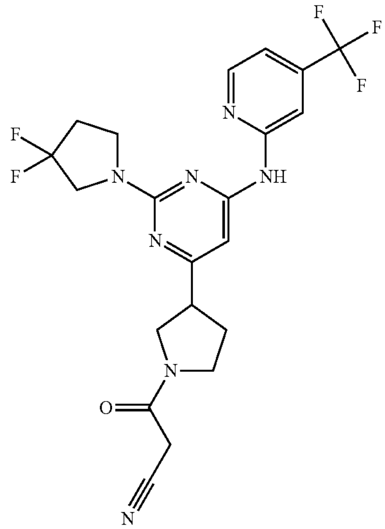 [SMILES: N#CCC(=O)N1CCC(c2cc(Nc3cc(C(F)(F)F)ccn3)nc(N3CCC(F)(F)C3)n2)C1] | 3-{3-[2-(3,3-Difluoro-pyrrolidin-1-yl)-6-(4-trifluoromethyl-pyridin-2-ylamino)-pyrimidin-4-yl]-pyrrolidin-1-yl}-3-oxo-propionitrile |
| 337 | 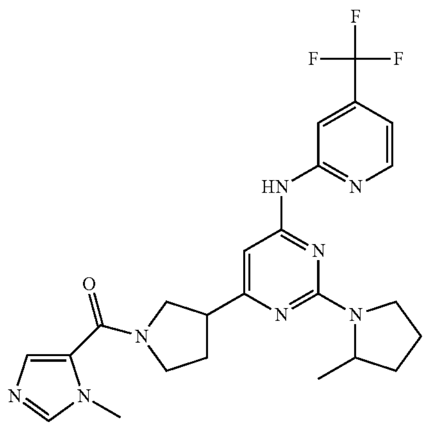 [SMILES: CC1CCCN1c1nc(Nc2cc(C(F)(F)F)ccn2)cc(C2CCN(C(=O)c3cncn3C)C2)n1] | (3-Methyl-3H-imidazol-4-yl)-{3-[2-(2-methyl-pyrrolidin-1-yl)-6-(4-trifluoromethyl-pyridin-2-ylamino)-pyrimidin-4-yl]-pyrrolidin-1-yl}-methanone |
| 338 | 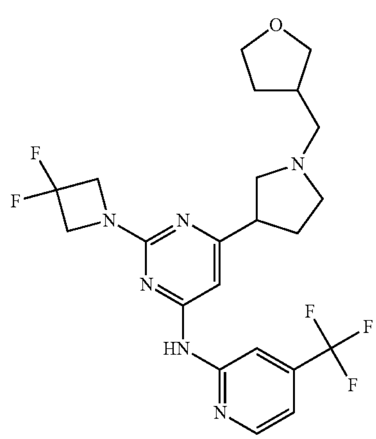 [SMILES: FC1(F)CN(c2nc(Nc3cc(C(F)(F)F)ccn3)cc(C3CCN(CC4CCOC4)C3)n2)C1] | {2-(3,3-Difluoro-azetidin-1-yl)-6-[1-(tetrahydro-furan-3-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 339 | 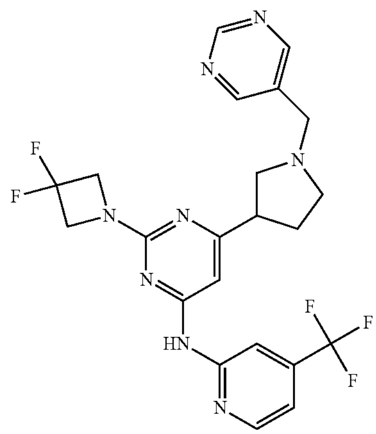 [SMILES: FC1(F)CN(c2nc(Nc3cc(C(F)(F)F)ccn3)cc(C3CCN(Cc4cncnc4)C3)n2)C1] | [2-(3,3-Difluoro-azetidin-1-yl)-6-(1-pyrimidin-5-ylmethyl-pyrrolidin-3-yl)-pyrimidin-4-yl]-(4-trifluoromethyl-pyridin-2-yl)-amine |
| 340 | 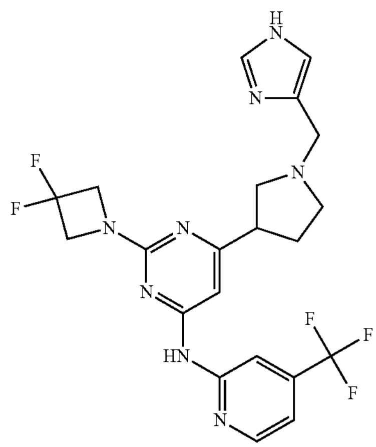 [SMILES: FC1(F)CN(c2nc(Nc3cc(C(F)(F)F)ccn3)cc(C3CCN(Cc4c[nH]cn4)C3)n2)C1] | {2-(3,3-Difluoro-azetidin-1-yl)-6-[1-(1H-imidazol-4-ylmethyl)-pyrrolidin-3-yl]-pyrimidin-4-yl}-(4-trifluoromethyl-pyridin-2-yl)-amine |
| 341 | 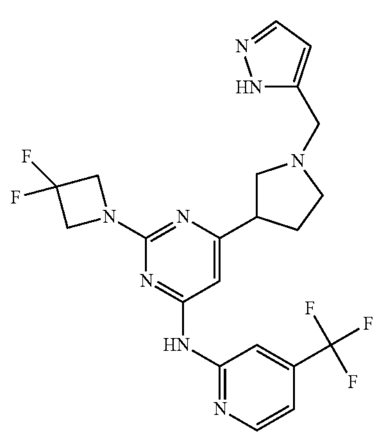 [SMILES: FC1(F)CN(c2nc(Nc3cc(C(F)(F)F)ccn3)cc(C3CCN(Cc4ccn[nH]4)C3)n2)C1] | {2-(3,3-Difluoro-azetidin-1-yl)-6-[1-(2H-pyrazol-3-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 342 | 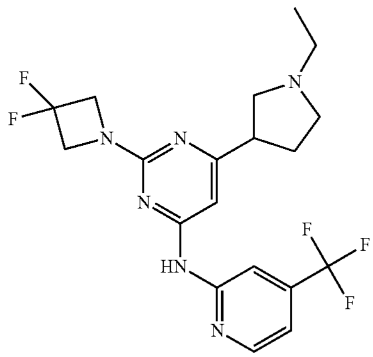 [SMILES: CCN1CCC(c2cc(Nc3cc(C(F)(F)F)ccn3)nc(N3CC(F)(F)C3)n2)C1] | [2-(3,3-Difluoro-azetidin-1-yl)-6-(1-ethyl-pyrrolidin-3-yl)-pyrimidin-4-yl]-(4-trifluoromethyl-pyridin-2-yl)-amine |
| 343 | 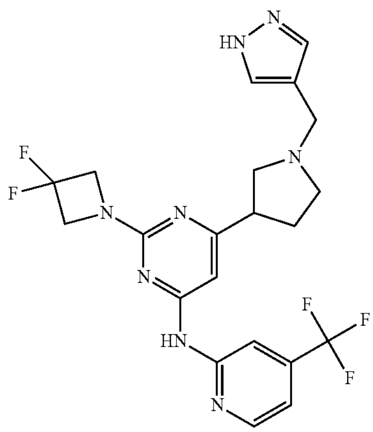 [SMILES: FC1(F)CN(c2nc(Nc3cc(C(F)(F)F)ccn3)cc(C3CCN(Cc4cn[nH]c4)C3)n2)C1] | {2-(3,3-Difluoro-azetidin-1-yl)-6-[1-(1H-pyrazol-4-ylmethyl)-pyrrolidin-3-yl]-pyrimidin-4-yl}-(4-trifluoromethyl-pyridin-2-yl)-amine |
| 344 | 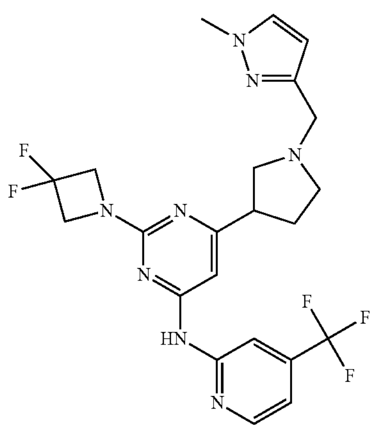 [SMILES: Cn1ccc(CN2CCC(c3cc(Nc4cc(C(F)(F)F)ccn4)nc(N4CC(F)(F)C4)n3)C2)n1] | {2-(3,3-Difluoro-azetidin-1-yl)-6-[1-(1-methyl-1H-pyrazol-3-ylmethyl)-pyrrolidin-3-yl]-pyrimidin-4-yl}-(4-trifluoro-methyl-pyridin-2-yl)-amine |
| 345 | 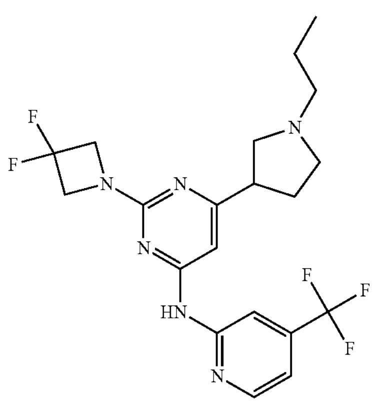 [SMILES: CCCN1CCC(c2cc(Nc3cc(C(F)(F)F)ccn3)nc(N3CC(F)(F)C3)n2)C1] | [2-(3,3-Difluoro-azetidin-1-yl)-6-(1-propyl-pyrrolidin-3-yl)-pyrimidin-4-yl]-(4-trifluoromethyl-pyridin-2-yl)-amine |

TABLE A-continued

| No. | Structure | Name |
|---|---|---|
| 346 | 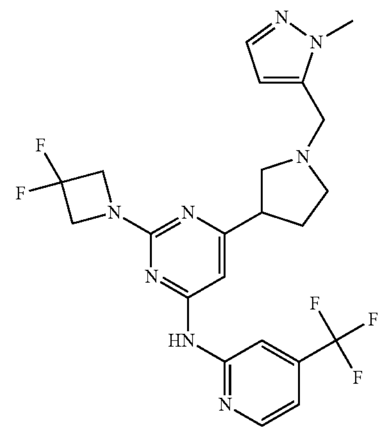 [SMILES: Cn1nccc1CN1CCC(c2cc(Nc3cc(C(F)(F)F)ccn3)nc(N3CC(F)(F)C3)n2)C1] | {2-(3,3-Difluoro-azetidin-1-yl)-6-[1-(2-methyl-2H-pyrazol-3-ylmethyl)-pyrrolidin-3-yl]-pyrimidin-4-yl}-(4-trifluoromethyl-pyridin-2-yl)-amine |
| 347 | 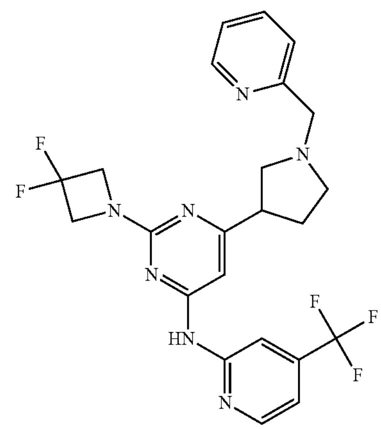 [SMILES: FC1(F)CN(c2nc(Nc3cc(C(F)(F)F)ccn3)cc(C3CCN(Cc4ccccn4)C3)n2)C1] | [2-(3,3-Difluoro-azetidin-1-yl)-6-(1-pyridin-2-ylmethyl-pyrrolidin-3-yl]-pyrimidin-4-yl}-(4-trifluoromethyl-pyridin-2-yl)-amine |
| 348 | 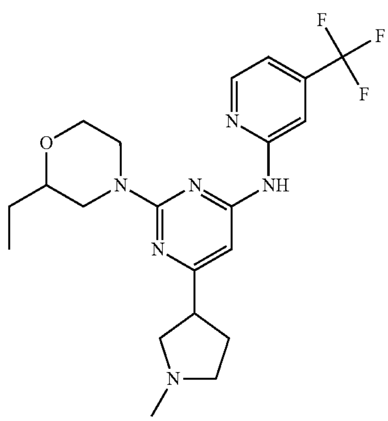 [SMILES: CCC1CN(c2nc(Nc3cc(C(F)(F)F)ccn3)cc(C3CCN(C)C3)n2)CCO1] | [2-(2-Ethyl-morpholin-4-yl)-6-(1-methyl-pyrrolidin-3-yl)-pyrimidin-4-yl]-(4-trifluoromethyl-pyridin-2-yl)-amine |
| 349 | 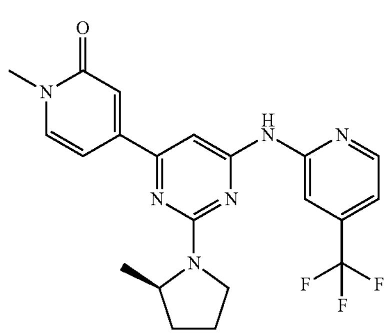 [SMILES: C[C@@H]1CCCN1c1nc(Nc2cc(C(F)(F)F)ccn2)cc(-c2ccn(C)c(=O)c2)n1] | 1-Methyl-4-[2-((R)-2-methyl-pyrrolidin-1-yl)-6-(4-trifluoromethyl-pyridin-2-ylamino)-pyrimidin-4-yl]-1H-pyridin-2-one |

TABLE A-continued
| No. | Structure | Name |
|---|---|---|
| 350 | 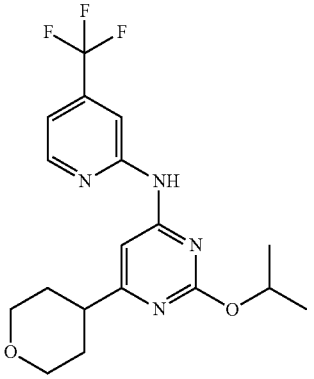 [SMILES: CC(C)Oc1nc(Nc2cc(C(F)(F)F)ccn2)cc(C2CCOCC2)n1] | [2-Isopropoxy-6-(tetrahydro-pyran-4-yl)-pyrimidin-4-yl]-(4-trifluoromethyl-pyridin-2-yl)-amine |
| 351 | 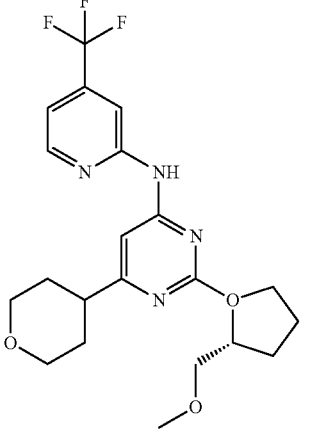 | [2-((R)-2-Methoxymethyl-pyrrolidin-1-yl)-6-(tetrahydro-pyran-4-yl)-pyrimidin-4-yl]-(4-trifluoro-methyl-pyridin-2-yl)-amine |
| 352 | 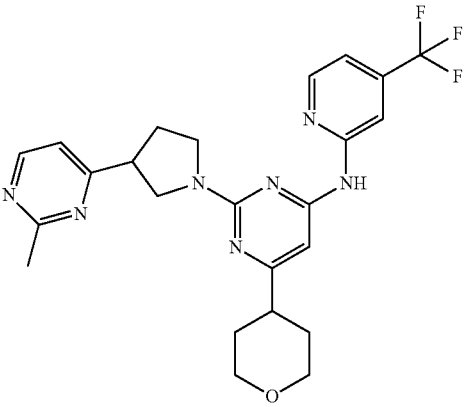 [SMILES: Cc1nccc(C2CCN(c3nc(Nc4cc(C(F)(F)F)ccn4)cc(C4CCOCC4)n3)C2)n1] | [2-[3-(2-Methyl-pyrimidin-4-yl)-pyrrolidin-1-yl]-6-(tetrahydro-pyran-4-yl)-pyrimidin-4-yl]-(4-trifluoromethyl-pyridin-2-yl)-amine |

TABLE A-continued

| No. | Structure | Name |
|---|---|---|
| 353 | 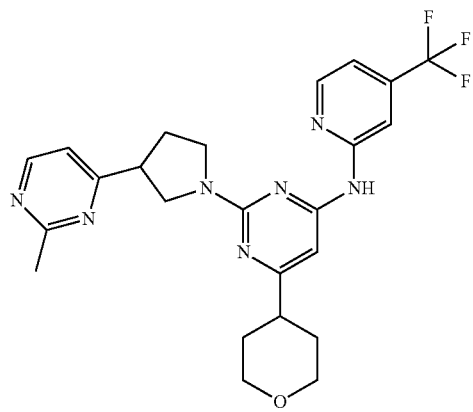 [SMILES: Cc1nccc(C2CCN(c3nc(Nc4cc(C(F)(F)F)ccn4)cc(C4CCOCC4)n3)C2)n1] | [2-[3-(2-Methyl-pyrimidin-4-yl)-pyrrolidin-1-yl]-6-(tetrahydro-pyran-4-yl)-pyrimidin-4-yl]-(4-trifluoromethyl-pyridin-2-yl)-amine |
| 354 | 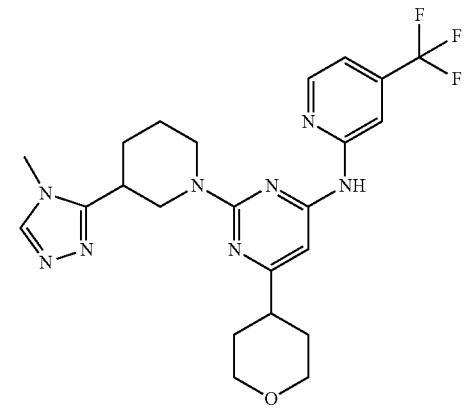 [SMILES: Cn1cnnc1C1CCCN(c2nc(Nc3cc(C(F)(F)F)ccn3)cc(C3CCOCC3)n2)C1] | [2-[3-(4-Methyl-4H-[1,1,2,4]triazol-3-yl)-piperidin-1-yl]-6-(tetrahydro-pyran-4-yl)-pyrimidin-4-yl]-(4-trifluoromethyl-pyridin-2-yl)-amine |
| 355 | 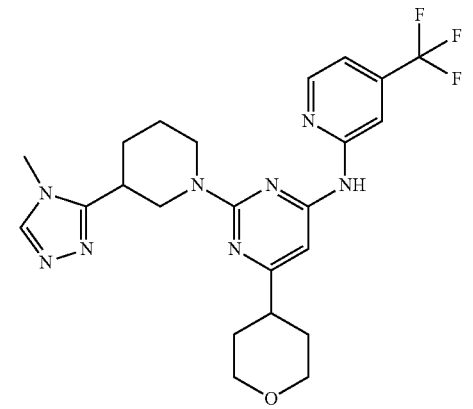 [SMILES: Cn1cnnc1C1CCCN(c2nc(Nc3cc(C(F)(F)F)ccn3)cc(C3CCOCC3)n2)C1] | [2-[3-(4-Methyl-4H-[1,2,4]triazol-3-yl)-piperidin-1-yl]-6-(tetrahydro-pyran-4-yl)-pyrimidin-4-yl]-(4-trifluoromethyl-pyridin-2-yl)-amine |
| 356 | 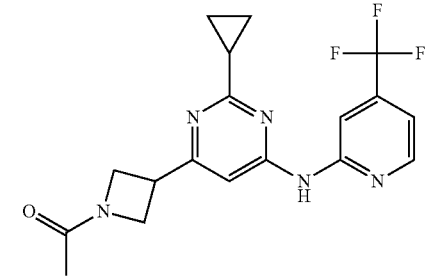 [SMILES: CC(=O)N1CC(c2cc(Nc3cc(C(F)(F)F)ccn3)nc(C3CC3)n2)C1] | 1-{3-[2-Cyclopropyl-6-(4-trifluoromethyl-pyridin-2-ylamino)-pyrimidin-4-yl]-azetidin-1-yl}-ethanone |

TABLE A-continued

| No. | Structure | Name |
|---|---|---|
| 357 | 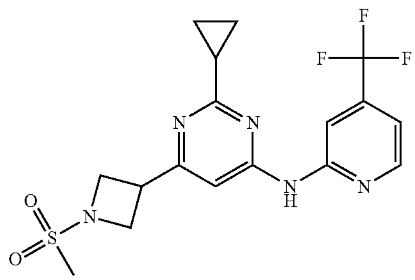 [SMILES: CS(=O)(=O)N1CC(c2cc(Nc3cc(C(F)(F)F)ccn3)nc(C3CC3)n2)C1] | [2-Cyclopropyl-6-(1-methanesulfonyl-azetidin-3-yl)-pyrimidin-4-yl]-(4-trifluoromethyl-pyridin-2-yl)-amine |
| 358 | 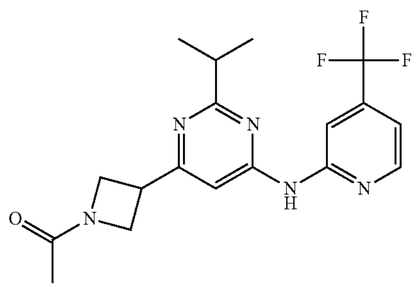 [SMILES: CC(=O)N1CC(c2cc(Nc3cc(C(F)(F)F)ccn3)nc(C(C)C)n2)C1] | 1-{3-[2-Isopropyl-6-(4-trifluoromethyl-pyridin-2-ylamino)-pyrimidin-4-yl]-azetidin-1-yl}-ethanone |
| 359 | 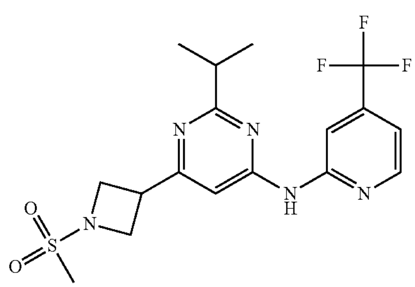 [SMILES: CC(C)c1nc(Nc2cc(C(F)(F)F)ccn2)cc(C2CN(S(C)(=O)=O)C2)n1] | [2-Isopropyl-6-(1-methanesulfonyl-azetidin-3-yl)-pyrimidin-4-yl]-4-(trifluoromethyl-pyridin-2-yl)-amine |
| 360 | 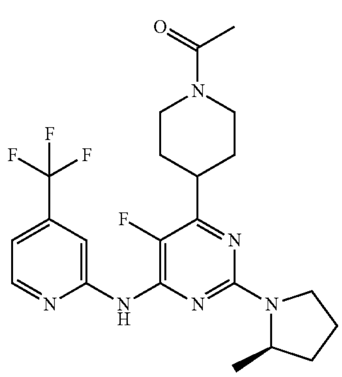 [SMILES: CC(=O)N1CCC(c2nc(N3CCC[C@H]3C)nc(Nc3cc(C(F)(F)F)ccn3)c2F)CC1] | 1-{4-[5-Fluoro-2-((R)-2-methyl-pyrrolidin-1-yl)-6-(4-trifluoromethyl-pyridin-2-ylamino)-pyrimidin-4-yl]-piperidin-1-yl}-ethanone |

TABLE A-continued
| No. | Structure | Name |
|---|---|---|
| 361 | 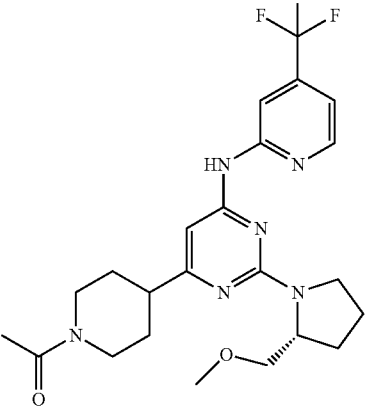 | 1-{4-[2-((R)-2-Methoxy-methyl-pyrrolidin-1-yl)-6-(4-trifluoromethyl-pyridin-2-ylamino)-pyrimidin-4-yl]-piperidin-1-yl}-ethanone |
| 362 | 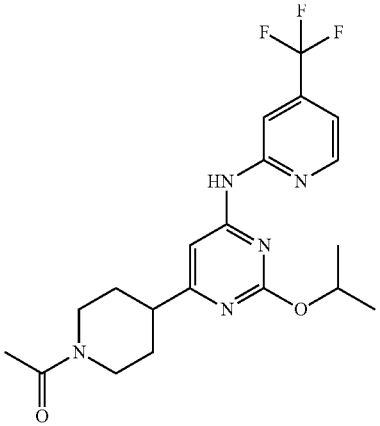 [SMILES: CC(=O)N1CCC(c2cc(Nc3cc(C(F)(F)F)ccn3)nc(OC(C)C)n2)CC1] | 1-{4-[2-Isopropoxy-6-(4-trifluoromethyl-pyridin-2-ylamino)-pyrimidin-4-yl]-piperidin-1-yl}-ethanone |
| 363 | 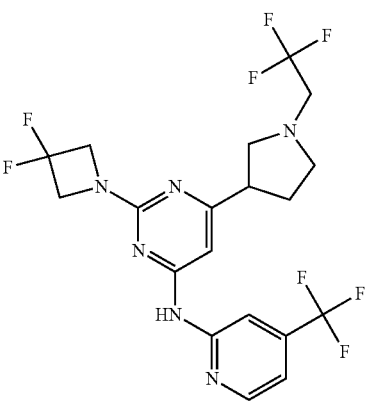 [SMILES: FC(F)(F)CN1CCC(c2cc(Nc3cc(C(F)(F)F)ccn3)nc(N3CC(F)(F)C3)n2)C1] | {2-(3,3-Difluoro-azetidin-1-yl)-6-[1-(2,2,2-trifluoro-ethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 364 | 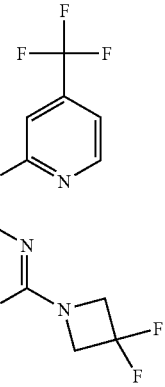 | {2-(3,3-Difluoro-azetidin-1-yl)-6-[1-(1H-imidazol-4-ylmethyl)-piperidin-3-yl]-pyrimidin-4-yl}-(4-trifluoromethyl-pyridin-2-yl)-amine |
| 365 | 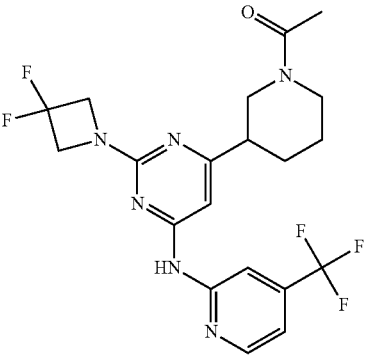 [SMILES: CC(=O)N1CCCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoromethyl-pyridin-2-ylamino)-pyrimidin-4-yl]-piperidin-1-yl}-ethanone |
| 366 | 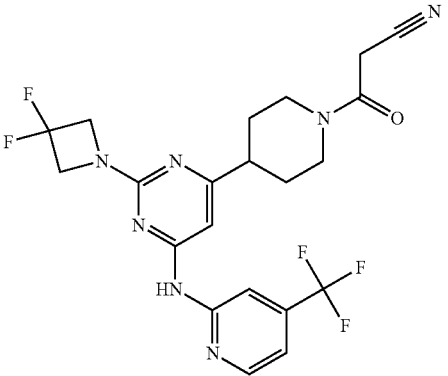 [SMILES: N#CCC(=O)N1CCC(c2cc(Nc3cc(C(F)(F)F)ccn3)nc(N3CC(F)(F)C3)n2)CC1] | 3-{4-[2-(3,3-Difluoro-azetidin-1-yl)-6-(4-trifluoromethyl-pyridin-2-ylamino)-pyrimidin-4-yl]-piperidin-1-yl}-3-oxo-propionitrile |
| 367 | 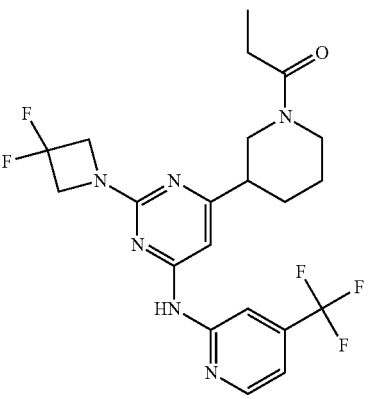 [SMILES: CCC(=O)N1CCCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoromethyl-pyridin-2-ylamino)-pyrimidin-4-yl]-piperidin-1-yl}-propan-1-one |

TABLE A-continued

| No. | Structure | Name |
|---|---|---|
| 368 | 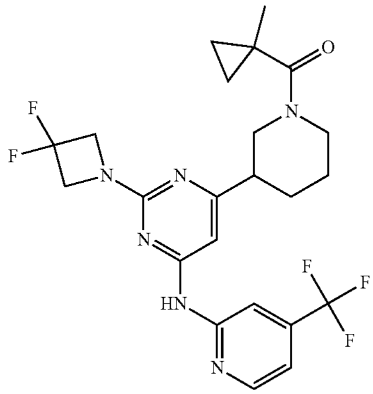 [SMILES: CC1(C(=O)N2CCCC(c3cc(Nc4cc(C(F)(F)F)ccn4)nc(N4CC(F)(F)C4)n3)C2)CC1] | {3-[2-(3,3-Difluoro-azetidin-1-yl)-6-(4-trifluoro-methyl-pyridin-2-ylamino)-pyrimidin-4-yl]-piperidin-1-yl}-(1-methyl-cyclopropyl)-methanone |
| 369 | 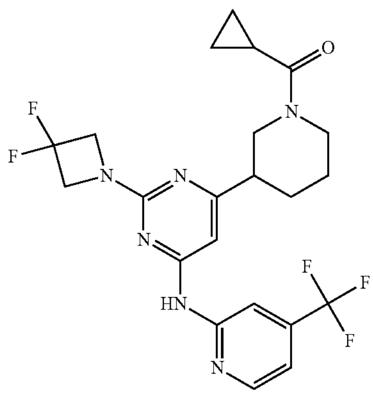 [SMILES: O=C(C1CC1)N1CCCC(c2cc(Nc3cc(C(F)(F)F)ccn3)nc(N3CC(F)(F)C3)n2)C1] | Cyclopropyl-{3-[2-(3,3-difluoro-azetidin-1-yl)-6-(4-trifluoromethyl-pyridin-2-ylamino)-pyrimidin-4-yl]-piperidin-1-yl}-methanone |
| 370 | 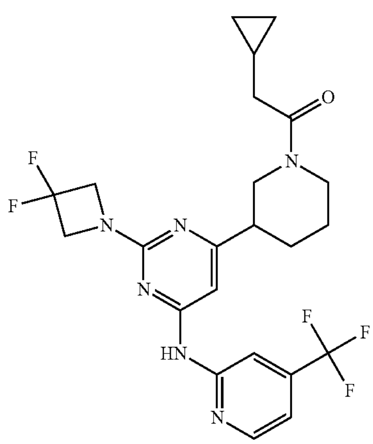 [SMILES: O=C(CC1CC1)N1CCCC(c2cc(Nc3cc(C(F)(F)F)ccn3)nc(N3CC(F)(F)C3)n2)C1] | 2-Cyclopropyl-1-{3-[2-(3,3-difluoro-azetidin-1-yl)-6-(4-trifluoromethyl-pyridin-2-ylamino)-pyrimidin-4-yl]-piperidin-1-yl}-ethanone |

TABLE A-continued

| No. | Structure | Name |
|---|---|---|
| 371 | 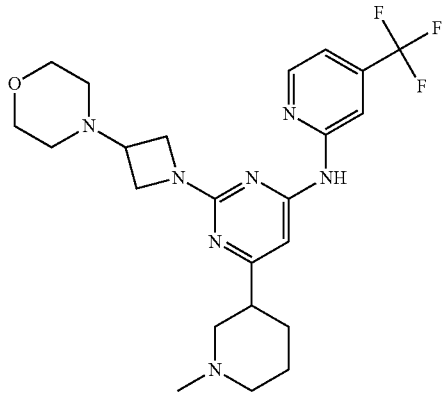 [SMILES: CN1CCCC(c2cc(Nc3cc(C(F)(F)F)ccn3)nc(N3CC(N4CCOCC4)C3)n2)C1] | [6-(1-Methyl-piperidin-3-yl)-2-(3-morpholin-4-yl-azetidin-1-yl)-pyrimidin-4-yl]-(4-trifluoromethyl-pyridin-2-yl)-amine |
| 372 | 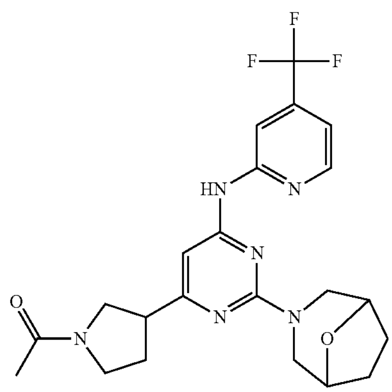 [SMILES: CC(=O)N1CCC(c2cc(Nc3cc(C(F)(F)F)ccn3)nc(N3CC4CCC(C3)O4)n2)C1] | 1-{3-[2-(8-Oxa-3-aza-bicyclo[3.2.1]oct-3-yl)-6-(4-trifluoromethyl-pyridin-2-ylamino)-pyrimidin-4-yl]-pyrrolidin-1-yl}-ethanone |
| 373 | 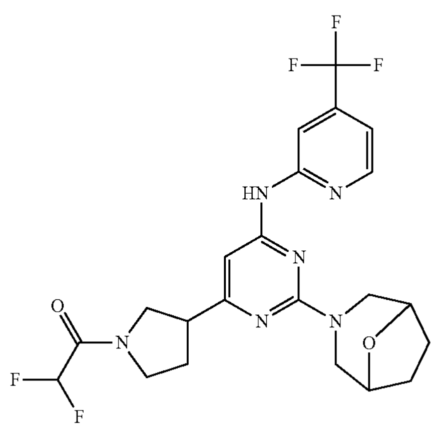 [SMILES: O=C(C(F)F)N1CCC(c2cc(Nc3cc(C(F)(F)F)ccn3)nc(N3CC4CCC(C3)O4)n2)C1] | 2,2-Difluoro-1-{3-[2-(8-oxa-3-aza-bicyclo[3.2.1]oct-3-yl)-6-(4-trifluoromethyl-pyridin-2-ylamino)-pyrimidin-4-yl]-pyrrolidin-1-yl}-ethanone |
| 374 | 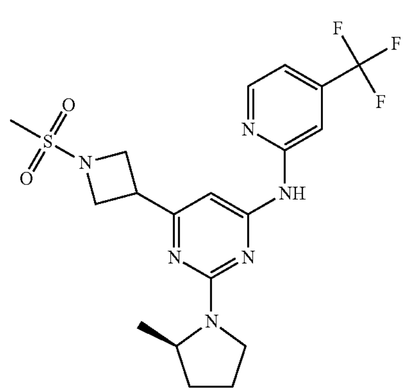 [SMILES: C[C@@H]1CCCN1c1nc(Nc2cc(C(F)(F)F)ccn2)cc(C2CN(S(C)(=O)=O)C2)n1] | [6-(1-Methanesulfonyl-azetidin-3-yl)-2-((R)-2-methyl-pyrrolidin-1-yl)-pyrimidin-4-yl]-(4-trifluoromethyl-pyridin-2-yl)-amine |

TABLE A-continued
| No. | Structure | Name |
|---|---|---|
| 375 | 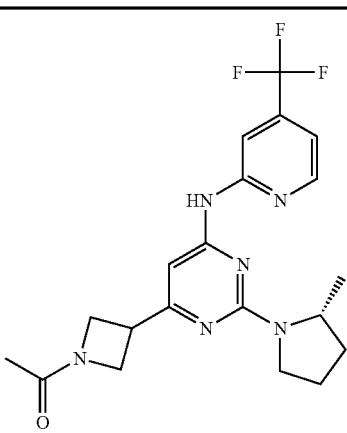 | 1-{3-[2-((R)-2-Methyl-pyrrolidin-1-yl)-6-(4-trifluoromethyl-pyridin-2-ylamino)-pyrimidin-4-yl]-azetidin-1-yl}-ethanone |
| 376 | 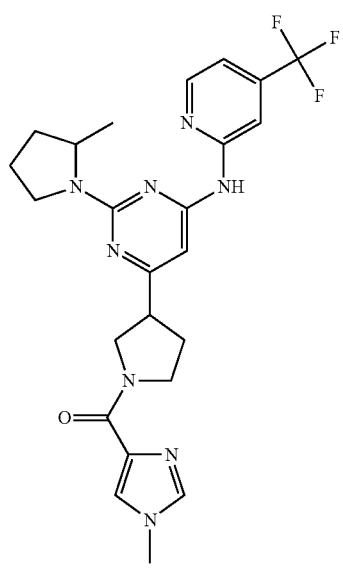 [SMILES: CC1CCCN1c1nc(Nc2cc(C(F)(F)F)ccn2)cc(C2CCN(C(=O)c3cn(C)cn3)C2)n1] | (1-Methyl-1H-imidazol-4-yl)-{3-[2-(2-methyl-pyrrolidin-1-yl)-6-(4-trifluoromethyl-pyridin-2-ylamino)-pyrimidin-4-yl]-pyrrolidin-1-yl}-methanone |
| 377 | 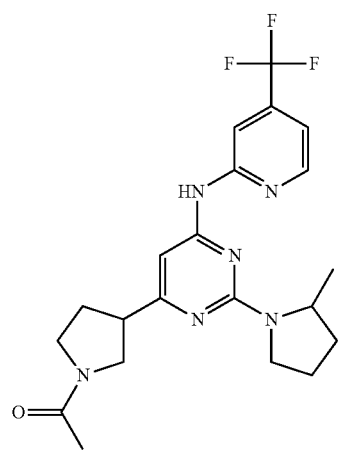 [SMILES: CC(=O)N1CCC(c2cc(Nc3cc(C(F)(F)F)ccn3)nc(N3CCCC3C)n2)C1] | 1-{3-[2-(2-Methyl-pyrrolidin-1-yl)-6-(4-trifluoro-methyl-pyridin-2-ylamino)-pyrimidin-4-yl]-pyrrolidin-1-yl}-ethanone |

TABLE A-continued

| No. | Structure | Name |
|---|---|---|
| 378 | 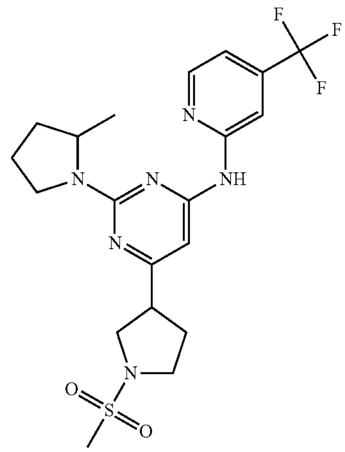 [SMILES: CC1CCCN1c1nc(Nc2cc(C(F)(F)F)ccn2)cc(C2CCN(S(C)(=O)=O)C2)n1] | [6-(1-Methanesulfonyl-pyrrolidin-3-yl)-2-(2-methyl-pyrrolidin-1-yl)-pyrimidin-4-yl]-(4-trifluoromethyl-pyridin-2-yl)-amine |
| 379 | 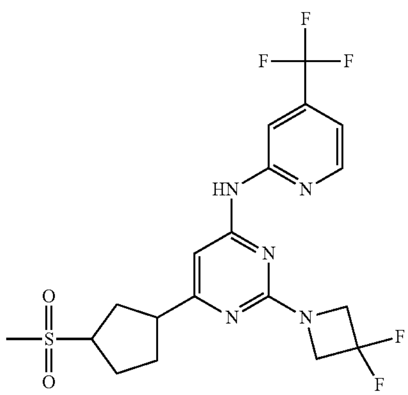 [SMILES: CS(=O)(=O)C1CCC(c2cc(Nc3cc(C(F)(F)F)ccn3)nc(N3CC(F)(F)C3)n2)C1] | [2-(3,3-Difluoro-azetidin-1-yl)-6-(1-methane-sulfonyl-pyrrolidin-3-yl)-pyrimidin-4-yl]-(4-trifluoromethyl-pyridin-2-yl)-amine |
| 380 | 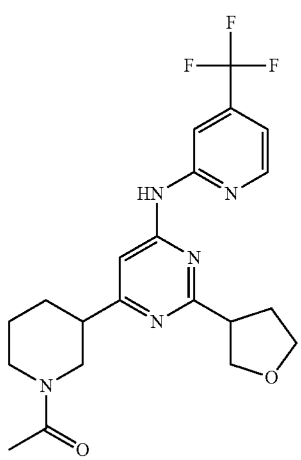 [SMILES: CC(=O)N1CCCC(c2cc(Nc3cc(C(F)(F)F)ccn3)nc(C3CCOC3)n2)C1] | 1-{3-[2-(Tetrahydro-furan-3-yl)-6-(4-trifluoro-methyl-pyridin-2-ylamino)-pyrimidin-4-yl]-piperidin-1-yl}-ethanone |

TABLE A-continued

| No. | Structure | Name |
|---|---|---|
| 381 | 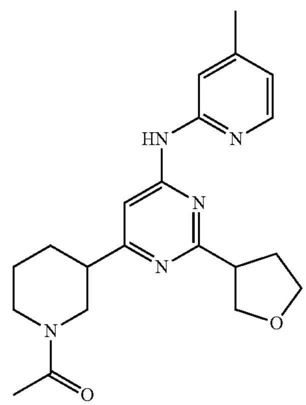 [SMILES: CC(=O)N1CCCC(c2cc(Nc3cc(C)ccn3)nc(C3CCOC3)n2)C1] | 1-{3-[6-(4-Methyl-pyridin-2-ylamino)-2-(tetrahydro-furan-3-yl)-pyrimidin-4-yl]-piperidin-1-yl}-ethanone |
| 382 | 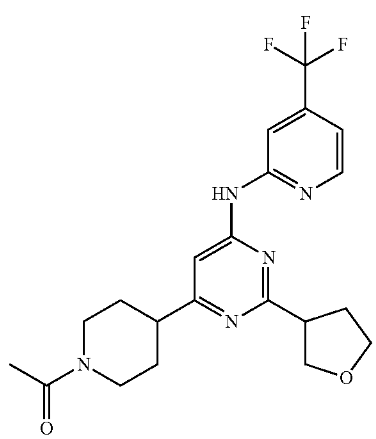 [SMILES: CC(=O)N1CCC(c2cc(Nc3cc(C(F)(F)F)ccn3)nc(C3CCOC3)n2)CC1] | 1-{4-[2-(Tetrahydro-furan-3-yl)-6-(4-trifluoromethyl-pyridin-2-ylamino)-pyrimidin-4-3yl]-piperidin-1-yl}-ethanone |
| 383 | 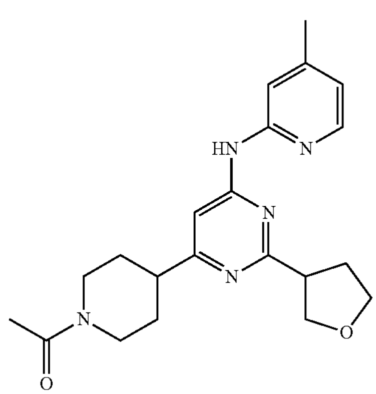 [SMILES: CC(=O)N1CCC(c2cc(Nc3cc(C)ccn3)nc(C3CCOC3)n2)CC1] | 1-{4-[6-(4-Methyl-pyridin-2-ylamino)-2-(tetrahydro-furan-3-yl)-pyrimidin-4-yl]-piperidin-1-yl}-ethanone |

TABLE A-continued

| No. | Structure | Name |
|-----|-----------|------|
| 384 | 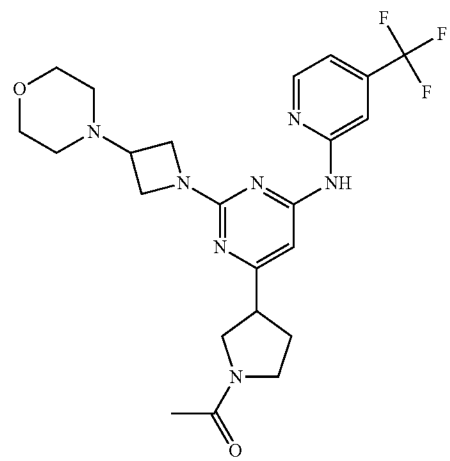 [SMILES: CC(=O)N1CCC(c2cc(Nc3cc(C(F)(F)F)ccn3)nc(N3CC(N4CCOCC4)C3)n2)C1] | 1-{3-[2-(3-Morpholin-4-yl-azetidin-1-yl)-6-(4-trifluoromethyl-pyridin-2-ylamino)-pyrimidin-4-yl]-pyrrolidin-1-yl}-ethanone |
| 385 | 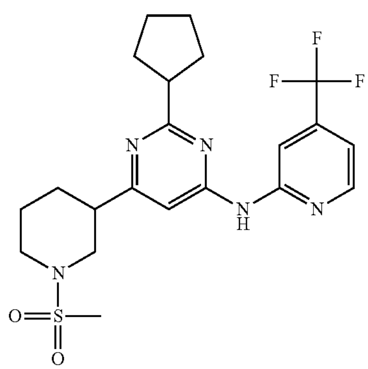 [SMILES: CS(=O)(=O)N1CCCC(c2cc(Nc3cc(C(F)(F)F)ccn3)nc(C3CCCC3)n2)C1] | [2-Cyclopentyl-6-(1-methanesulfonyl-piperidin-3-yl)-pyrimidin-4-yl]-(4-trifluoromethyl-pyridin-2-yl)-amine |
| 386 | 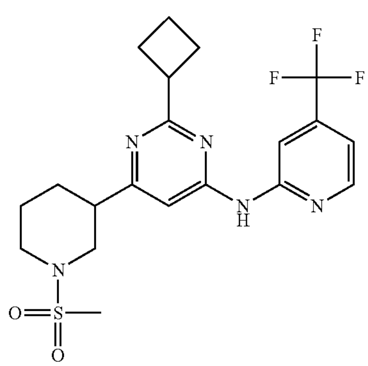 [SMILES: CS(=O)(=O)N1CCCC(c2cc(Nc3cc(C(F)(F)F)ccn3)nc(C3CCC3)n2)C1] | [2-Cyclobutyl-6-(1-methanesulfonyl-piperidin-3-yl)-pyrimidin-4-yl]-(4-trifluoromethyl-pyridin-2-yl)-amine |
| 387 | 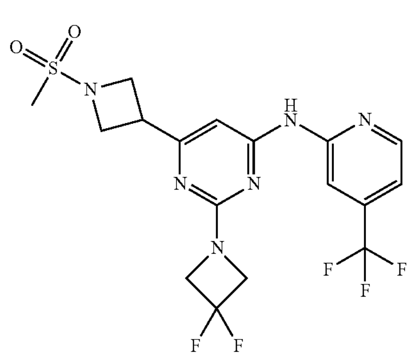 [SMILES: CS(=O)(=O)N1CC(c2cc(Nc3cc(C(F)(F)F)ccn3)nc(N3CC(F)(F)C3)n2)C1] | [2-(3,3-Difluoro-azetidin-1-yl)-6-(1-methanesulfonyl-azetidin-3-yl)-pyrimidin-4-yl]-(4-trifluoromethyl-pyridin-2-yl)-amine |

TABLE A-continued
| No. | Structure | Name |
|---|---|---|
| 388 | 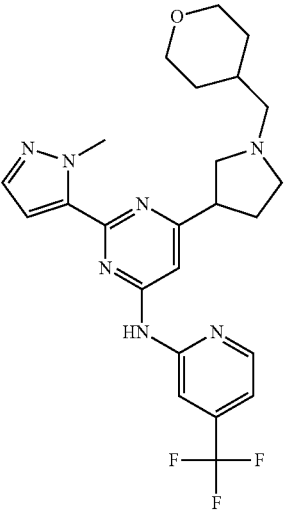 [SMILES: Cn1nccc1-c1nc(Nc2cc(C(F)(F)F)ccn2)cc(C2CCN(CC3CCOCC3)C2)n1] | {2-(2-Methyl-2H-pyrazol-3-yl)-6-[1-(tetrahydro-pyran-4-ylmethyl)-pyrrolidin-3-yl]-pyrimidin-4-yl}-(4-trifluoromethyl-pyridin-2-yl)-amine |
| 389 | 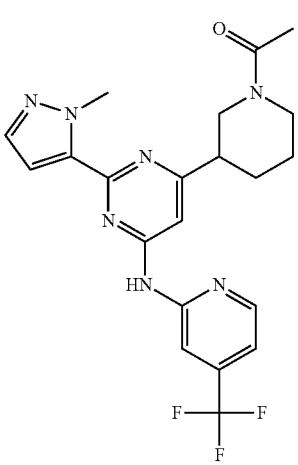 [SMILES: CC(=O)N1CCCC(c2cc(Nc3cc(C(F)(F)F)ccn3)nc(-c3ccnn3C)n2)C1] | 1-{3-[2-(2-Methyl-2H-pyrazol-3-yl)-6-(4-trifluoromethyl-pyridin-2-ylamino)-pyrimidin-4-yl]-piperidin-1-yl}-ethanone |
| 390 | 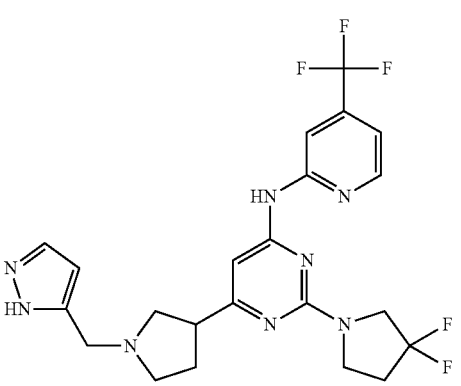 [SMILES: FC1(F)CCN(c2nc(Nc3cc(C(F)(F)F)ccn3)cc(C3CCN(Cc4ccn[nH]4)C3)n2)C1] | {2-(3,3-Difluoro-pyrrolidin-1-yl)-6-[1-(2H-pyrazol-3-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 391 | 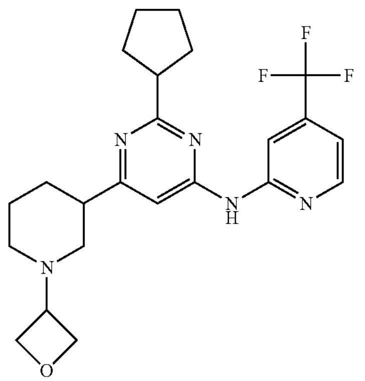 [SMILES: FC(F)(F)c1ccnc(Nc2cc(C3CCCN(C4COC4)C3)nc(C3CCCC3)n2)c1] | [2-Cyclopentyl-6-(1-oxetan-3-yl-piperidin-3-yl)-pyrimidin-4-yl]-(4-trifluoromethyl-pyridin-2-yl)-amine |
| 392 | 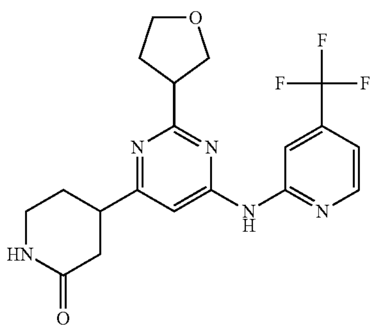 [SMILES: O=C1CC(c2cc(Nc3cc(C(F)(F)F)ccn3)nc(C3CCOC3)n2)CCN1] | 4-[2-(Tetrahydro-furan-3-yl)-6-(4-trifluoromethyl-pyridin-2-ylamino)-pyrimidin-4-yl]-piperidin-2-one |
| 393 | 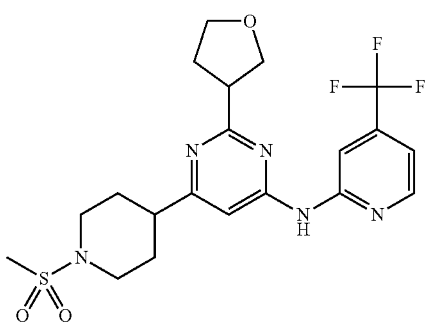 [SMILES: CS(=O)(=O)N1CCC(c2cc(Nc3cc(C(F)(F)F)ccn3)nc(C3CCOC3)n2)CC1] | [6-(1-Methanesulfonyl-piperidin-4-yl)-2-(tetra-hydro-furan-3-yl)-pyrimidin-4-yl]-(4-trifluoro-methyl-pyridin-2-yl)-amine |
| 394 | 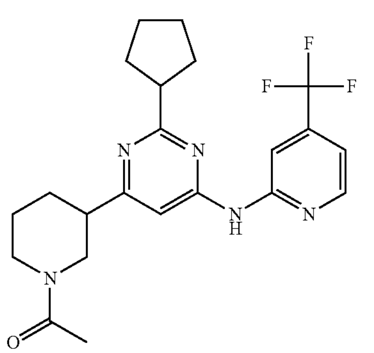 [SMILES: CC(=O)N1CCCC(c2cc(Nc3cc(C(F)(F)F)ccn3)nc(C3CCCC3)n2)C1] | 1-{3-[2-Cyclopentyl-6-(4-trifluoromethyl-pyridin-2-ylamino)-pyrimidin-4-yl]-piperidin-1-yl}-ethanone |

TABLE A-continued

| No. | Structure | Name |
|---|---|---|
| 395 | 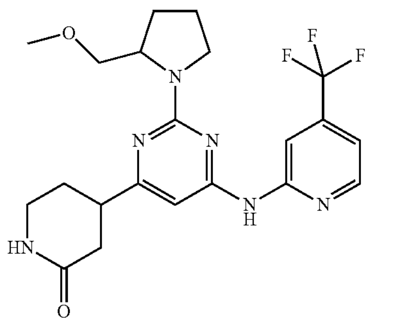 [SMILES: COCC1CCCN1c1nc(Nc2cc(C(F)(F)F)ccn2)cc(C2CCNC(=O)C2)n1] | 4-[2-(2-Methoxymethyl-pyrrolidin-1-yl)-6-(4-trifluoromethyl-pyridin-2-ylamino)-pyrimidin-4-yl]-piperidin-2-one |
| 396 | 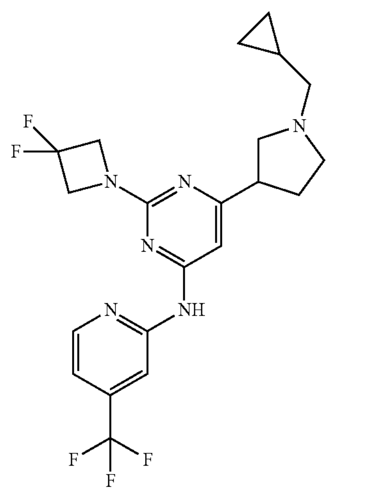 [SMILES: FC1(F)CN(c2nc(Nc3cc(C(F)(F)F)ccn3)cc(C3CCN(CC4CC4)C3)n2)C1] | [6-(1-Cyclopropylmethyl-pyrrolidin-3-yl)-2-(3,3-difluoro-azetidin-1-yl)-pyrimidin-4-yl]-(4-trifluoromethyl-pyridin-2-yl)-amine |
| 397 | 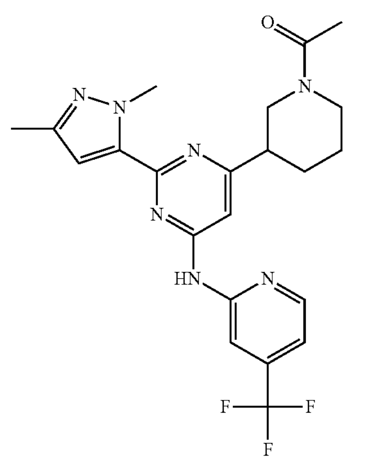 [SMILES: CC(=O)N1CCCC(c2cc(Nc3cc(C(F)(F)F)ccn3)nc(-c3cc(C)nn3C)n2)C1] | 1-{3-[2-(2,5-Dimethyl-2H-pyrazol-3-yl)-6-(4-trifluoromethyl-pyridin-2-ylamino)-pyrimidin-4-yl]-piperidin-1-yl}-ethanone |
| 398 | 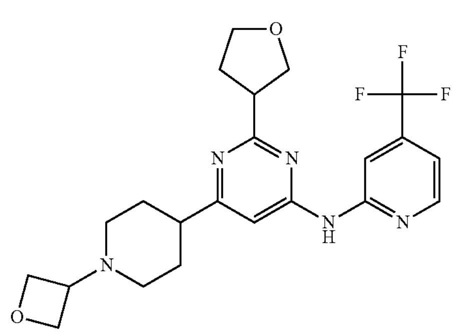 [SMILES: FC(F)(F)c1ccnc(Nc2cc(C3CCN(C4COC4)CC3)nc(C3CCOC3)n2)c1] | [6-(1-Oxetan-3-yl-piperidin-4-yl)-2-(tetrahydro-furan-3-yl)-pyrimidin-4-yl-(4-trifluoromethyl-pyridin-2-yl)-amine |

TABLE A-continued

| No. | Structure | Name |
|---|---|---|
| 399 | 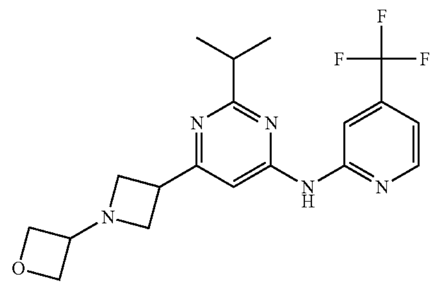 [SMILES: CC(C)c1nc(Nc2cc(C(F)(F)F)ccn2)cc(C2CN(C3COC3)C2)n1] | [2-Isopropyl-6-(1-oxetan 3-yl-azetidin-3-yl)-pyrimidin-4-yl]-(4-trifluoromethyl-pyridin-2-yl)-amine |
| 400 | 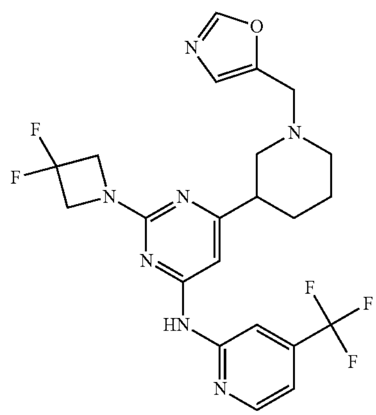 [SMILES: FC1(F)CN(c2nc(Nc3cc(C(F)(F)F)ccn3)cc(C3CCCN(Cc4cnco4)C3)n2)C1] | [2-(3,3-Difluoro-azetidin-1-yl)-6-(1-oxazol-5-ylmethyl-piperidin-3-yl)-pyrimidin-4-yl]-(4-trifluoromethyl-pyridin-2-yl)-amine |
| 401 | 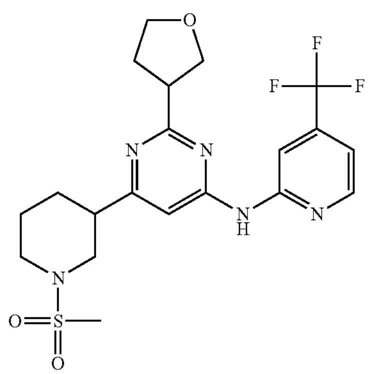 [SMILES: CS(=O)(=O)N1CCCC(c2cc(Nc3cc(C(F)(F)F)ccn3)nc(C3CCOC3)n2)C1] | [6-(1-Methanesulfonyl-piperidin-3-yl)-2-(tetrahydro-furan-3-yl)-pyrimidin-4-yl]-(4-trifluoromethyl-pyridin-2-yl)-amine |
| 402 | 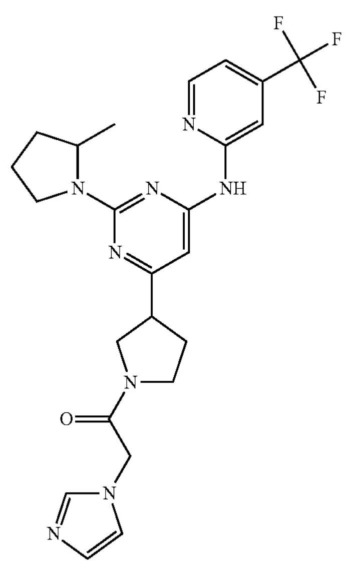 [SMILES: CC1CCCN1c1nc(Nc2cc(C(F)(F)F)ccn2)cc(C2CCN(C(=O)Cn3ccnc3)C2)n1] | 2-Imidazol-1-yl-1-{3-[2-(2-methyl-pyrrolidin-1-yl)-6-(4-trifluoromethyl-pyridin-2-ylamino)-pyrimidin-4-yl]-pyrrolidin-1-yl}-ethanone |

TABLE A-continued

| No. | Structure | Name |
| --- | --- | --- |
| 403 | 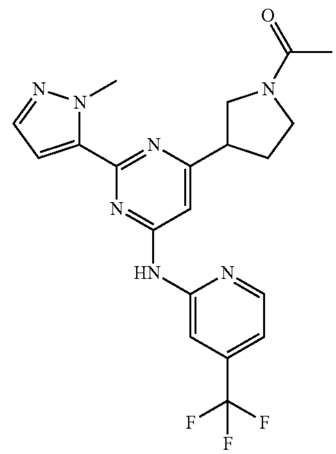 [SMILES: CC(=O)N1CCC(c2cc(Nc3cc(C(F)(F)F)ccn3)nc(-c3ccnn3C)n2)C1] | 1-{3-[2-(2-Methyl-2H-pyrazol-3-yl)-6-(4-trifluoromethyl-pyridin-2-ylamino)-pyrimidin-4-yl]-pyrrolidin-1-yl}-ethanone |
| 404 | 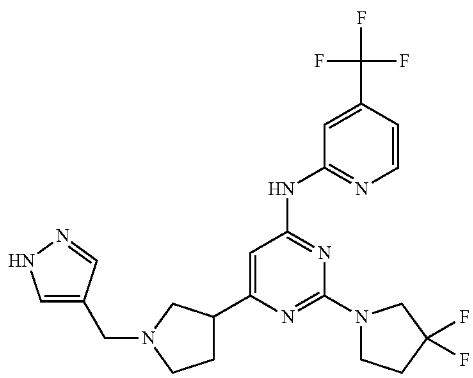 [SMILES: FC1(F)CCN(c2nc(Nc3cc(C(F)(F)F)ccn3)cc(C3CCN(Cc4cn[nH]c4)C3)n2)C1] | {2-(3,3-Difluoro-pyrrolidin-1-yl)-6-[1-(1H-pyrazol-4-ylmethyl)-pyrrolidin-3-yl]-pyrimidin-4-yl}-(4-trifluoromethyl-pyridin-2-yl)-amine |
| 405 | 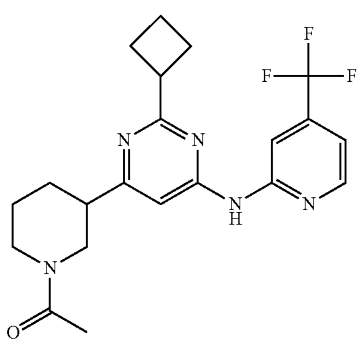 [SMILES: CC(=O)N1CCCC(c2cc(Nc3cc(C(F)(F)F)ccn3)nc(C3CCC3)n2)C1] | 1-{3-[2-Cyclobutyl-6-(4-trifluoromethyl-pyridin-2-ylamino)-pyrimidin-4-yl]-piperidin-1-yl}-ethanone |
| 406 | 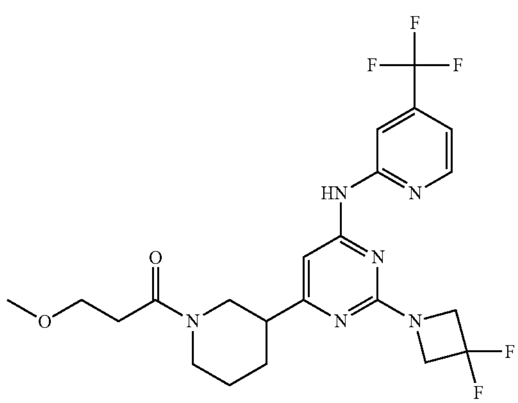 [SMILES: COCCC(=O)N1CCCC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoromethyl-pyridin-2-ylamino)-pyrimidin-4-yl]-piperidin-1-yl}-3-methoxy-propan-1-one |

TABLE A-continued

| No. | Structure | Name |
|---|---|---|
| 407 | 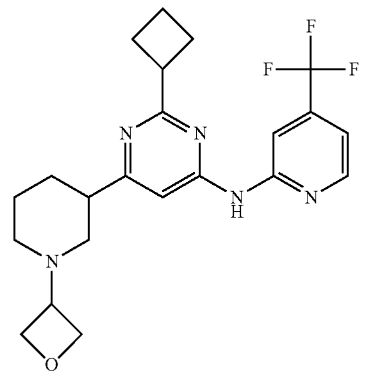 [SMILES: FC(F)(F)c1ccnc(Nc2cc(C3CCCN(C4COC4)C3)nc(C3CCC3)n2)c1] | [2-Cyclobutyl-6-(1-oxetan-3-yl-piperidin-3-yl)-pyrimidin-4-yl]-(4-trifluoro-methyl-pyridin-2-yl)-amine |
| 408 | 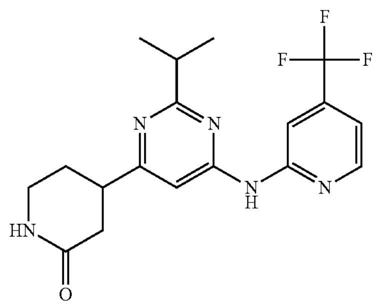 [SMILES: CC(C)c1nc(Nc2cc(C(F)(F)F)ccn2)cc(C2CCNC(=O)C2)n1] | 4-[2-Isopropyl-6-(4-trifluoro-methyl-pyridin-2-ylamino)-pyrimidin-4-yl]-piperidin-2-one |
| 409 | 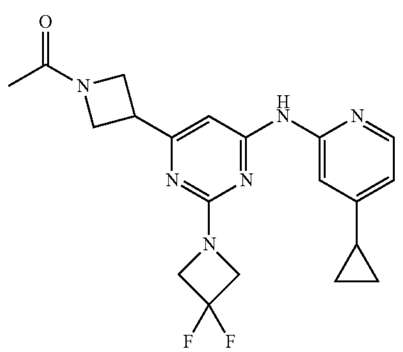 [SMILES: CC(=O)N1CC(c2cc(Nc3cc(C4CC4)ccn3)nc(N3CC(F)(F)C3)n2)C1] | 1-{3-[6-(4-Cyclopropyl-pyridin-2-ylamino)-2-(3,3-difluoro-azetidin-1-yl)-pyrimidin-4-yl]-azetidin-1-yl}-ethanone |
| 410 | 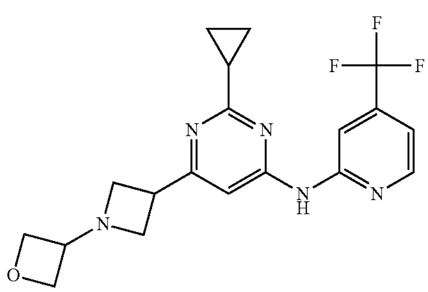 [SMILES: FC(F)(F)c1ccnc(Nc2cc(C3CN(C4COC4)C3)nc(C3CC3)n2)c1] | [2-Cyclopropyl-6-(1-oxetan-3-yl-azetidin-3-yl)-pyrimidin-4-yl]-(4-trifluoro-methyl-pyridin-2-yl)-amine |

TABLE A-continued
| No. | Structure | Name |
|---|---|---|
| 411 | 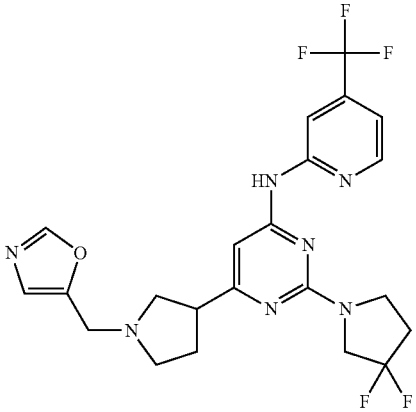 [SMILES: FC1(F)CCN(c2nc(Nc3cc(C(F)(F)F)ccn3)cc(C3CCN(Cc4cnco4)C3)n2)C1] | [2-(3,3-Difluoro-pyrrolidin-1-yl)-6-(1-oxazol-5-ylmethyl-pyrrolidin-3-yl)-pyrimidin-4-yl]-(4-trifluoromethyl-pyridin-2-yl)-amine |
| 412 | 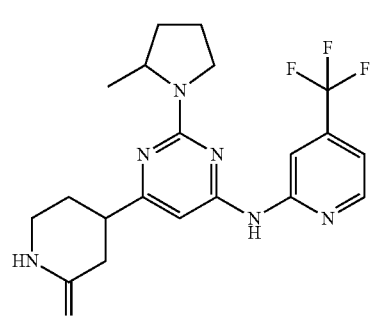 | 4-[2-(2-Methyl-pyrrolidin-1-yl)-6-(4-trifluoromethyl-pyridin-2-ylamino)-pyrimidin-4-yl]-piperidin-2-one |
| 413 | 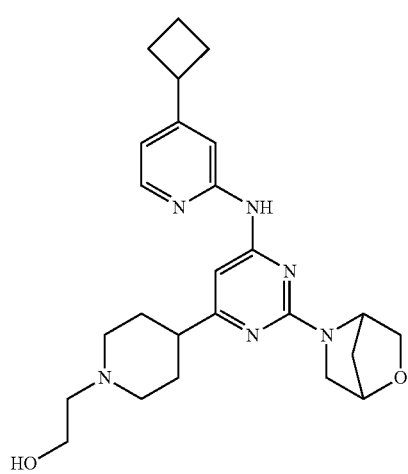 [SMILES: OCCN1CCC(c2cc(Nc3cc(C4CCC4)ccn3)nc(N3CC4CC3CO4)n2)CC1] | 2-{4-[6-(4-Cyclobutyl-pyridin-2-ylamino)-2-(2-oxa-5-aza-bicyclo[2.2.1]-hept-5-yl)-pyrimidin-4-yl]-piperidin-1-yl}-ethanol |

TABLE A-continued

| No. | Structure | Name |
|---|---|---|
| 414 | 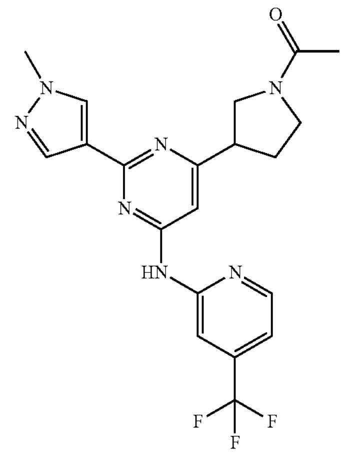 [SMILES: CC(=O)N1CCC(c2cc(Nc3cc(C(F)(F)F)ccn3)nc(-c3cnn(C)c3)n2)C1] | 1-{3-[2-(1-Methyl-1H-pyrazol-4-yl)-6-(4-trifluoromethyl-pyridin-2-ylamino)-pyrimidin-4-yl]-pyrrolidin-1-yl}-ethanone |
| 415 | 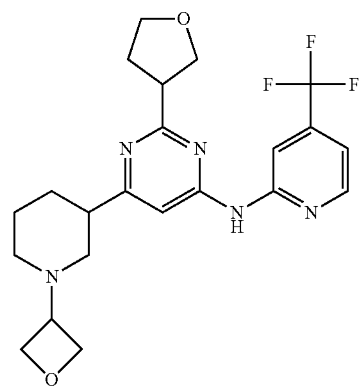 [SMILES: FC(F)(F)c1ccnc(Nc2cc(C3CCCN(C4COC4)C3)nc(C3CCOC3)n2)c1] | [6-(1-Oxetan-3-yl-piperidin-3-yl)-2-(tetrahydro-furan-3-yl)-pyrimidin-4-yl]-(4-trifluoromethyl-pyridin-2-yl)-amine |
| 416 | 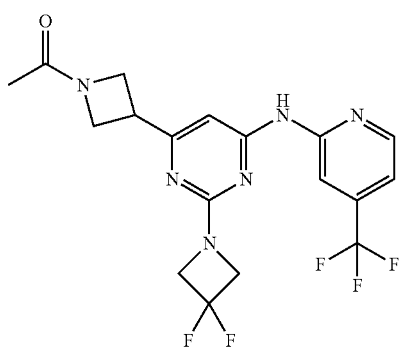 [SMILES: CC(=O)N1CC(c2cc(Nc3cc(C(F)(F)F)ccn3)nc(N3CC(F)(F)C3)n2)C1] | 1-{3-[2-(3,3-Difluoro-azetidin-1-yl)-6-(4-trifluoromethyl-pyridin-2-ylamino)-pyrimidin-4-yl]-azetidin-1-yl}-ethanone |
| 417 | 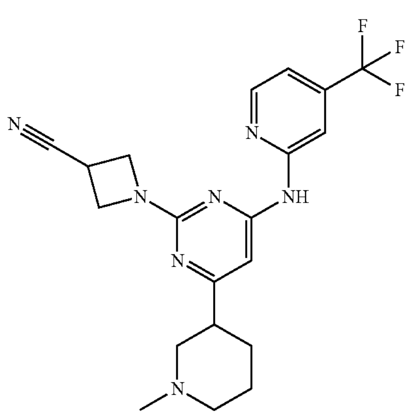 [SMILES: CN1CCCC(c2cc(Nc3cc(C(F)(F)F)ccn3)nc(N3CC(C#N)C3)n2)C1] | 1-[4-(1-Methyl-piperidin-3-yl)-6-(4-trifluoromethyl-pyridin-2-ylamino)-pyrimidin-2-yl]-azetidine-3-carbonitrile |

TABLE A-continued
| No. | Structure | Name |
|---|---|---|
| 418 | 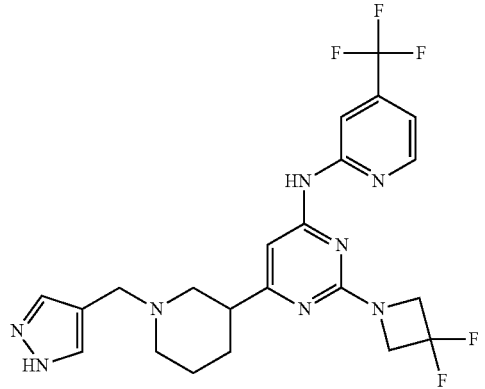 [SMILES: FC1(F)CN(c2nc(Nc3cc(C(F)(F)F)ccn3)cc(C3CCCN(Cc4cn[nH]c4)C3)n2)C1] | {2-(3,3-Difluoro-azetidin-1-yl)-6-[1-(1H-pyrazol-4-ylmethyl)-piperidin-3-yl]-pyrimidin-4-yl}-(4-trifluoromethyl-pyridin-2-yl)-amine |
| 419 | 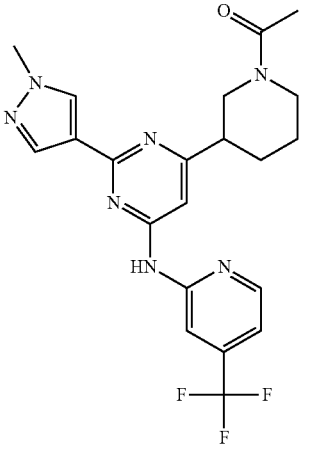 [SMILES: CC(=O)N1CCCC(c2cc(Nc3cc(C(F)(F)F)ccn3)nc(-c3cnn(C)c3)n2)C1] | 1-{3-[2-(1-Methyl-1H-pyrazol-4-yl)-6-(4-trifluoromethyl-pyridin-2-ylamino)-pyrimidin-4-yl]-piperidin-1-yl}-ethanone |
| 420 | 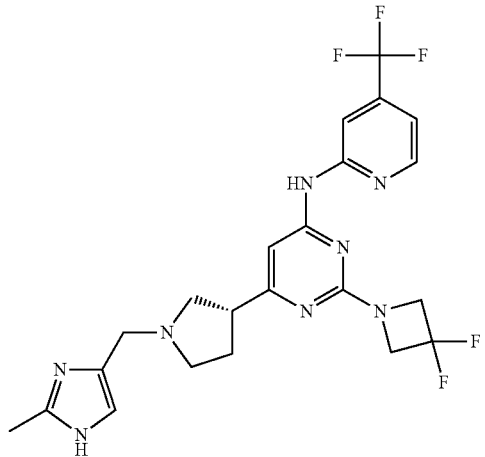 [SMILES: Cc1nc(CN2CC[C@@H](c3cc(Nc4cc(C(F)(F)F)ccn4)nc(N4CC(F)(F)C4)n3)C2)c[nH]1] | {2-(3,3-Difluoro-azetidin-1-yl)-6-1(R)-1-(2-methyl-1H-imidazol-4-ylmethyl)-pyrrolidin-3-yl]-pyrimidin-4-yl}-(4-trifluoromethyl-pyridin-2-yl)-amine |

TABLE A-continued

| No. | Structure | Name |
|---|---|---|
| 421 | 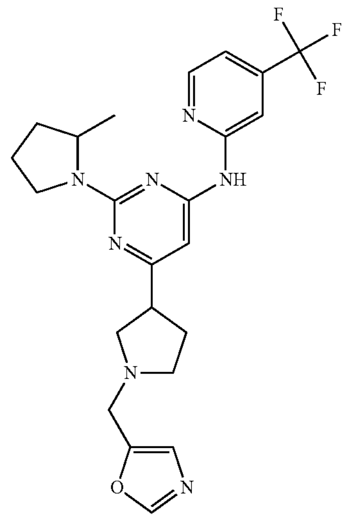 [SMILES: CC1CCCN1c1nc(Nc2cc(C(F)(F)F)ccn2)cc(C2CCN(Cc3cnco3)C2)n1] | [2-(2-Methyl-pyrrolidin-1-yl)-6-(1-oxazol-5-ylmethyl-pyrrolidin-3-yl)-pyrimidin-4-yl]-(4-trifluoromethyl-pyridin-2-yl)-amine |
| 423 | 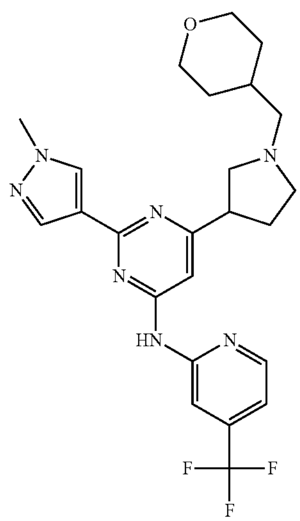 [SMILES: Cn1cc(-c2nc(Nc3cc(C(F)(F)F)ccn3)cc(C3CCN(CC4CCOCC4)C3)n2)cn1] | {2-(1-Methyl-1H-pyrazol-4-yl)-6-[1-(tetrahydro-pyran-4-ylmethyl)-pyrrolidin-3-yl]-pyrimidin-4-yl}-(4-trifluoromethyl-pyridin-2-yl)-amine |
| 424 | 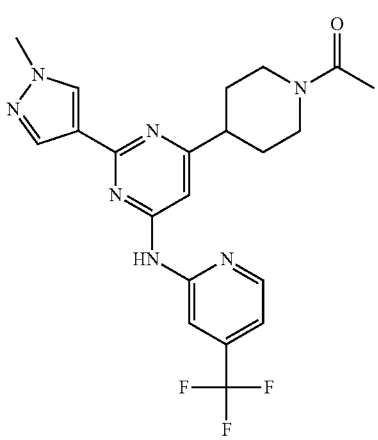 [SMILES: CC(=O)N1CCC(c2cc(Nc3cc(C(F)(F)F)ccn3)nc(-c3cnn(C)c3)n2)CC1] | 1-{4-[2-(1-Methyl-1H-pyrazol-4-yl)-6-(4-trifluoromethyl-pyridin-2-ylamino)-pyrimidin-4-yl]-piperidin-1-yl}-ethanone |

TABLE A-continued

| No. | Structure | Name |
|---|---|---|
| 425 | 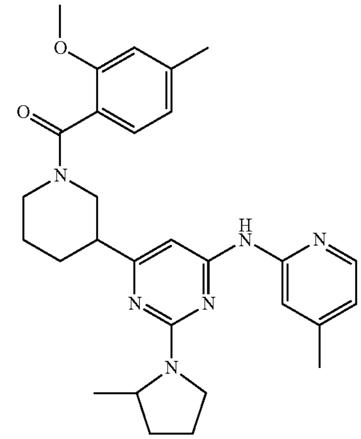 [SMILES: COc1cc(C)ccc1C(=O)N1CCCC(c2cc(Nc3cc(C)ccn3)nc(N3CCCC3C)n2)C1] | (2-Methoxy-4-methyl-phenyl)-{3-[6-(4-methyl-pyridin-2-ylamino)-2-(2-methyl-pyrrolidin-1-yl)-pyrimidin-4-yl]-piperidin-1-yl}-methanone |
| 426 | 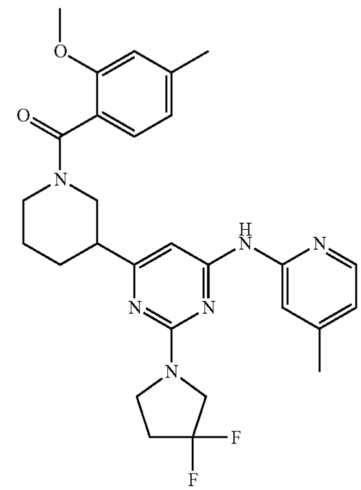 [SMILES: COc1cc(C)ccc1C(=O)N1CCCC(c2cc(Nc3cc(C)ccn3)nc(N3CCC(F)(F)C3)n2)C1] | {3-[2-(3,3-Difluoro-pyrrolidin-1-yl)-6-(4-methyl-pyridin-2-ylamino)-pyrimidin-4-yl]-piperidin-1-yl}-(2-methoxy-4-methyl-phenyl)-methanone |
| 427 | 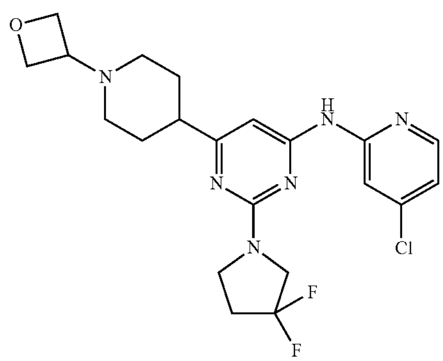 [SMILES: FC1(F)CCN(c2nc(Nc3cc(Cl)ccn3)cc(C3CCN(C4COC4)CC3)n2)C1] | N-(4-chloropyridin-2-yl)-2-(3,3-difluoropyrrolidin-1-yl)-6-(1-(oxetan-3-yl)piperidin-4-yl)pyrimidin-4-amine |

C. Synthesis of Compounds

For illustrative purposes, Schemes 1-3 show general methods for preparing the compounds of the present invention as well as key intermediates. More detailed description of the individual reaction steps, is found in the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. For example, the heterocycloalkyl rings comprising X in compounds S1-i, S2-i, and S3-i can comprise more than one heteroatom and also be further substituted with additional substituents. In addition, many of the compounds prepared by the methods described below can be further modified in light of this disclosure using conventional chemistry well known to those skilled in the art.

In preparing compounds of Formula I or I-I, protection of remote functionality (e.g., primary or secondary amine) of intermediates may be necessary. The need for such protection will vary depending on the nature of the remote functionality and the conditions of the preparation methods.

Suitable amino-protecting groups include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In Schemes 1-3 the circle containing X represents a heterocyclic ring comprising NH, O or S or substituted or oxidized variants thereof and R, R', R" represents substituents on the compounds that are non-interfering with the synthetic procedures outlined in the schemes.

Compounds of the invention can be prepared according to the synthetic process outlined in Scheme 1. In Scheme 1 a malonate derivative is acylated with cyclic acid S1-i in the presence of (CDI) carbonyl diimidazole and magnesium dichloride (MgCl2) in acetonitrile solvent (MeCN) to form ketoester S1-ii. Condensation of ketoester S1-ii with urea under basic reaction conditions produces the pyrimidindione S1-iii which can further be converted to the dichloro compound S1-iv after treatment with phosphorus oxychloride (POCl3). Palladium cross-coupling of an 2-aminopyridine with dichloropyrimidine S1-iv provides N-heteroarylated product S1-v. Displacement of the remaining chloride atom on S1-v with an alkylamine or dialkylamine under basic conditions produces compound S1-vi. In the instance where X in compound S1-vi is a nitrogen atom protected with an acid labile functional group (e.g., tBoc), treatment of such compound with acid results in loss of the protecting group to produce compound S1-vii wherein X is —N(H)— and alkylation of such S1-vii with an alkyl halide, or under reductive amination conditions with an aldehyde and hydride reducing agent, or acylation conditions (e.g., R'C(=O)Cl and Hunig's base and DMAP) can provide compounds of formula I, e.g., compound S1-viii.

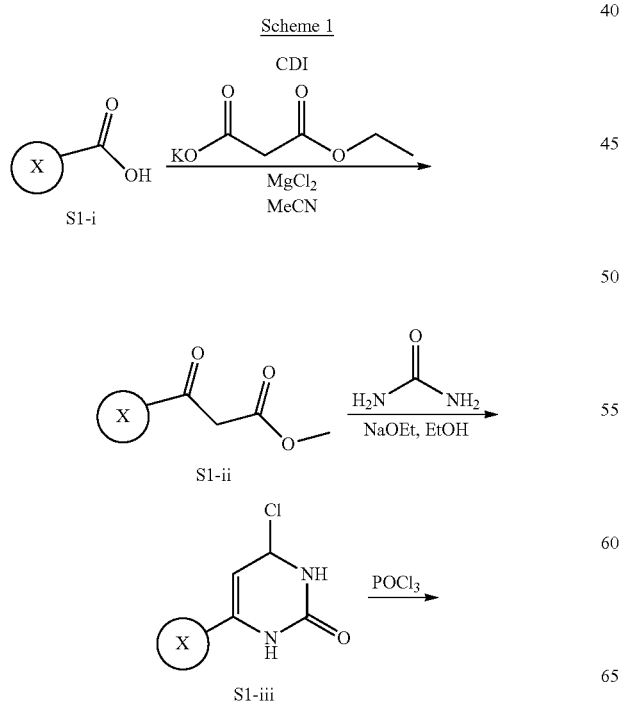

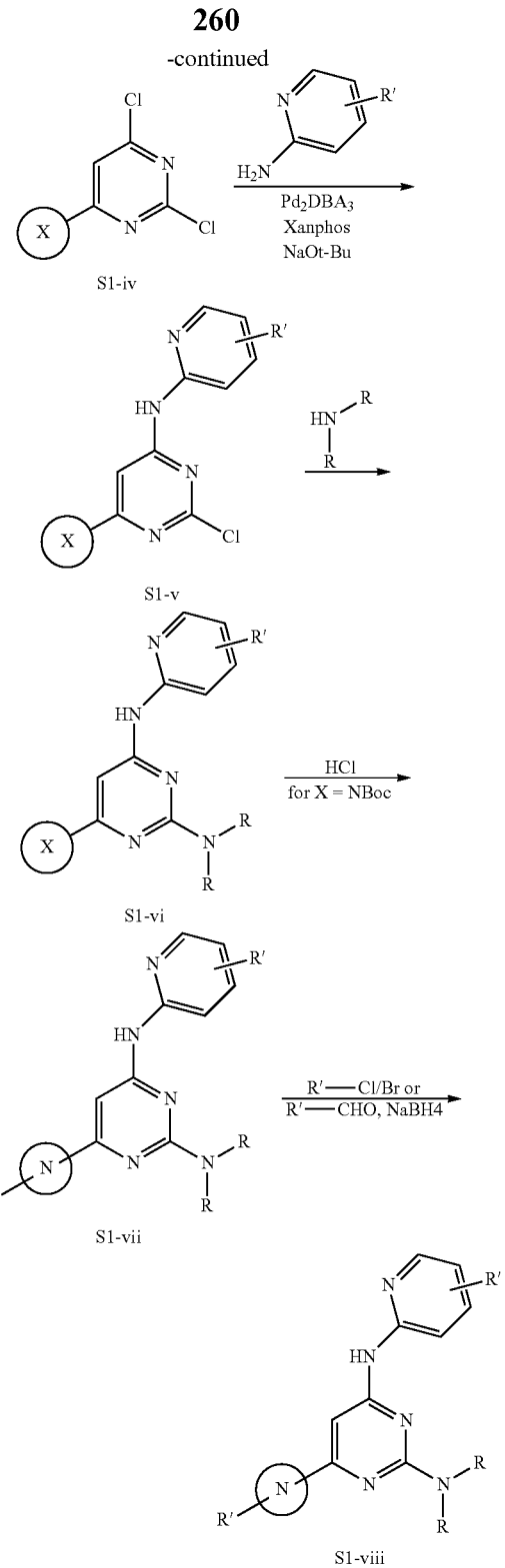

Compounds of the invention can be prepared in accordance with the synthetic process outlined in Scheme 2. In Scheme 2, ketoester S2-i is condensed with an amidine compound to form a hydroxypyrimidine compound S2-ii, which is converted to the chloro derivative S2-iii after treating with POCl3. Palladium mediated cross coupling reaction between chloride S2-iii and a 2-aminopyridine compound produces the cross coupled product S2-iv. In the instance wherein X in compound S2-iv is a nitrogen atom protected with an acid labile functional group (e.g., tBoc), treatment of such compound with acid (e.g., conc HCl solution) results in loss of the protecting group to produce compound S2-v wherein X is —N(H)— and alkylation of such S2-v compound with an alkyl halide, or under reductive amination conditions with an aldehyde and hydride reducing agent, or acylation conditions (not shown) can provide compounds of formula I, e.g., compound S2-vi.

Scheme 2

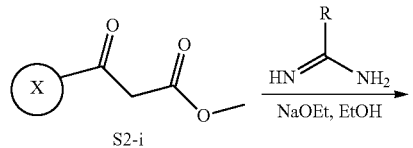

S2-i

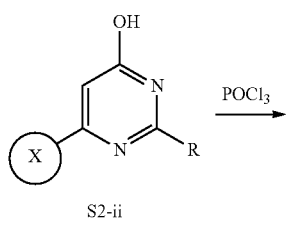

S2-ii

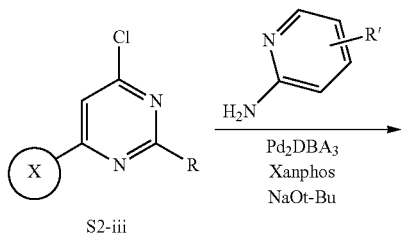

S2-iii

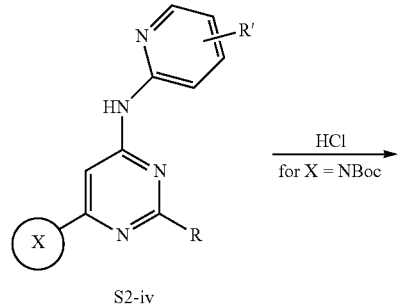

S2-iv

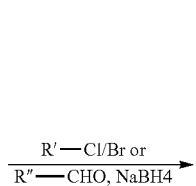

S2-v

-continued

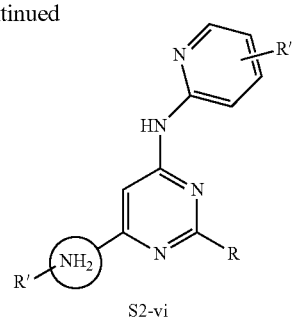

S2-vi

Compounds of the invention can be prepared as described by the process outlined in Scheme 3. 4-Cyanopipidine S3-i is deprotonated with lithium tetramethylpiperidide and undergoes a displacement/substitution reaction with trihalo pyrimidine derivative to form pyrimidine compound S3-ii. Palladium mediated cross-coupling reaction between compound S3-ii and a 2-aminopyridine provides the coupled product S3-iii. Treatment of compound S3-iii with an alkyl or dialkylamine under basic conditions can result in the displacement of the chloride atom to for the trisubstituted pyrimidine product S3-iv.

Scheme 3

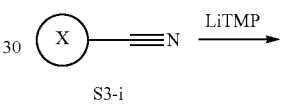

S3-i

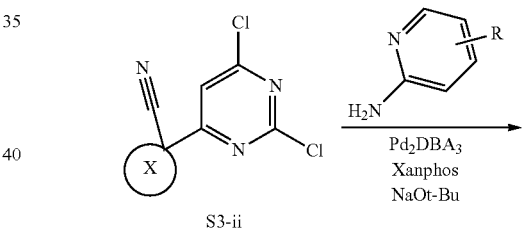

S3-ii

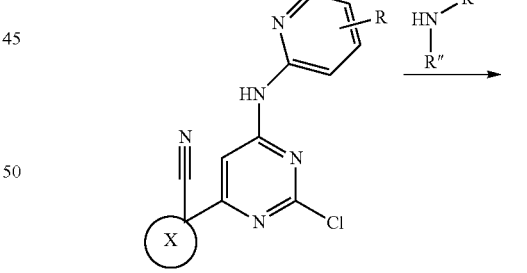

S3-iii

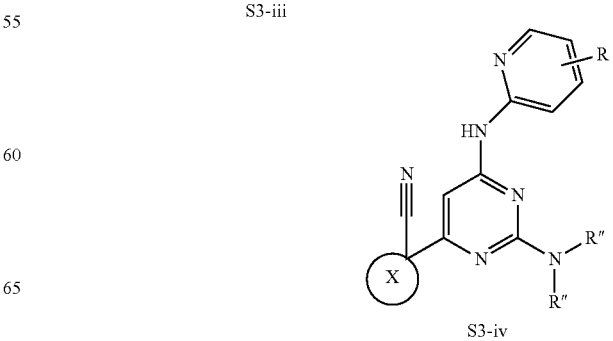

S3-iv

D. Pharmaceutical Compositions and Administrations

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I or I-I (or any embodiment thereof) and at least one pharmaceutically acceptable carrier, diluent or excipient. The compositions of the invention can be used for inhibiting DLK activity in patients (e.g, humans)

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula I or I-I (or stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I or I-I and compositions comprising compounds of Formula I or I-I to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit DLK activity as required to prevent or treat the undesired disease or disorder, such as for example, neurodegeneration, amyloidosis, formation of neurofibrillary tangles, or undesired cell growth. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of Formula I or I-I are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I or I-I) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philadelphia, Pa.

Sustained-release preparations of a compound of the invention (e.g., compound of Formula I or I-I) can be prepared. Suitable examples of sustained-release preparations include semipermeable matrices of solid hydrophobic polymers containing a compound of Formula I or I-I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(–)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I or I-I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I or I-I is formulated in an acetate buffer, at pH 5. In another embodiment, the compounds of Formula I or I-I are sterile. The compound may be stored, for example, as a solid or amorphous composition, as a lyophilized formulation or as an aqueous solution.

Formulations of a compound of the invention (e.g., compound of Formula I or I-I) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I or I-I) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I or I-I) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I or I-I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I or I-I (or an embodiment thereof) to traverse the blood-brain barrier. Certain neurodegenerative diseases are associated with an increase in permeability of the blood-brain barrier, such that a compound of formula I or I-I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I or I-I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N. Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I or I-I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I or I-I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I or I-I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I or I-I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula I or I-I (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula I or I-I (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I or I-I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 µg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 μg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula I or I-I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 μg kg to 1 mg/kg, about 1 μg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

E. Indications and Methods of Treatment

In another aspect, the invention provides for methods of inhibiting the Dual Leucine Zipper Kinase (DLK) in an ex vivo (e.g., a nerve graft of nerve transplant) or in vivo setting (e.g., in a patient) by contacting DLK present in an ex vivo or in vivo setting with compounds of Formula I or I-I (or an embodiment thereof). In these methods of the invention, the inhibition of DLK signaling or expression with a compound of formula I or I-I (or an embodiment thereof) results in a downstream decrease in JNK phosphorylation (e.g., a decrease in JNK2 and/or JNK3 phosphorylation), JNK activity (e.g., a decrease in JNK2 and/or JNK3 activity), and/or JNK expression (e.g., a decrease in JNK2 and/or JNK3 expression). Accordingly, administering one or more compounds of Formula I or I-I (or an embodiment thereof) according to the methods of the invention can result in decrease in activity of kinase targets downstream of the DLK signaling cascade, e.g, (i) a decrease in JNK phosphorylation, JNK activity, and/or JNK expression, (ii) a decrease in cJun phosphorylation, cJun activity, and/or cJun expression, and/or (iii) a decrease in p38 phosphorylation, p38 activity, and/or p38 expression.

Compounds of the invention can be used in methods for inhibiting neuron or axon degeneration. The inhibitors are, therefore, useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS demential complex (also known as HIV dementia, HIV encephalopathy, and HIV-associated dementia).

The methods of the invention can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the invention include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy.

Examples of types of pain that can be treated according to the methods of the invention include those associated with the following conditions: chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, torn ligament, and diabetes.

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine. Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the inhibitors described herein can be useful as components of culture media for use in culturing nerve cells ex vivo.

Accordingly, in another aspect, the invention provides for a method for inhibiting or preventing degeneration of a central nervous system (CNS) neuron or a portion thereof, the method comprising administering to the CNS neuron a compound of formula I-I, I, or an embodiment thereof.

In one embodiment, of the method for inhibiting or preventing degeneration of a central nervous system neuron or a portion thereof, the administering to the CNS neuron is performed ex vivo.

In another embodiment, of the method for inhibiting or preventing degeneration of a central nervous system neuron or a portion thereof, the method further comprises grafting or implanting the CNS neuron into a human patient after administration of the agent.

In another embodiment, of the method for inhibiting or preventing degeneration of a central nervous system neuron or a portion thereof, the CNS neuron is present in a human patient.

In another embodiment, of the method for inhibiting or preventing degeneration of a central nervous system neuron or a portion thereof, the administering to the CNS neuron comprises administration of said compound of formula I-I, I, or an embodiment thereof in a pharmaceutically acceptable carrier, diluent or excipient.

In another embodiment, of the method for inhibiting or preventing degeneration of a central nervous system neuron or a portion thereof, the administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

In another embodiment, of the method for inhibiting or preventing degeneration of a central nervous system neuron or a portion thereof, the method further comprises administering one or more additional pharmaceutical agents.

In another embodiment, of the method for inhibiting or preventing degeneration of a central nervous system neuron or a portion thereof, the administering of a compound of formula I-I, I, or an embodiment thereof results in a decrease in JNK phosphorylation, JNK activity and/or JNK expression.

In another embodiment, of the method for inhibiting or preventing degeneration of a central nervous system neuron or a portion thereof, the administering of a compound of formula I-I, I, or an embodiment thereof results in a decrease of cJun phosphorylation, cJun activity, and/or cJun expression.

In another embodiment, of the method for inhibiting or preventing degeneration of a central nervous system neuron or a portion thereof, the administering of a compound of formula I-I, I, or an embodiment thereof results in a decrease in p38 phosphorylation, p38 activity, and/or p38 expression.

In another embodiment, there is provided a method for inhibiting or preventing degeneration of a central nervous system (CNS) neuron in a patient having or at risk of developing a neurodegenerative disease or condition comprising administering to said patient a therapeutically effective amount of a compound of formula I-I, I, or an embodiment thereof, or a pharmaceutically acceptable salt thereof.

In another embodiment, there is provided a method for decreasing or preventing one or more symptoms of a neurodegenerative disease or condition in a patient suffering therefrom comprising administering to said patient a therapeutically effective amount of a compound of formula I-I, I, or an embodiment thereof or a pharmaceutically acceptable salt thereof.

In another embodiment, there is provided a method for decreasing the progression of a neurodegenerative disease or condition in a patient suffering therefrom comprising administering to said patient a therapeutically effective amount of a compound of formula I-I, I, or an embodiment thereof, or a pharmaceutically acceptable salt thereof.

In another embodiment, the neurodegenerative disease or condition is selected from the group consisting of Alzheimer's disease, Huntington's disease, Parkinson's disease, Parkinson's-plus diseases, amyotrophic lateral sclerosis (ALS), ischemia, stroke, intracranial hemorrhage, cerebral hemorrhage, trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie_Tooth disease, prion disease, Creutzfeldt-Jakob disease, Gerstmann-Sträussler-Scheinker syndrome (GSS), fatal familial insomnia (FFI), bovine spongiform encephalopathy, Pick's disease, epilepsy, AIDS demential complex, nerve damage caused by exposure to toxic compounds selected from the group consisting of heavy metals, industrial solvents, drugs and chemotherapeutic agents; injury to the nervous system caused by physical, mechanical or chemical trauma, glaucoma, lattice dystrophy, retinitis pigmentosa, age-related macular degeneration (AMD), photoreceptor degeneration associated with wet or dry AMD, other retinal degeneration, optic nerve drusen, optic neuropathy and optic neuritis.

In another embodiment, the compound of formula I-I is administered in combination with one or more additional pharmaceutical agents.

The inhibitors can be optionally combined with or administered in concert with each other or other agents known to be useful in the treatment of the relevant disease or condition. Thus, in the treatment of ALS, for example, inhibitors can be administered in combination with Riluzole (Rilutek), minocycline, insulin-like growth factor 1 (IGF-1), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits comprising combinations as described herein.

In addition to the combinations noted above, other combinations included in the invention are combinations of inhibitors of degeneration of different neuronal regions. Thus, the invention includes combinations of agents that (i) inhibit degeneration of the neuron cell body, and (ii) inhibit axon degeneration. For example, inhibitors of GSK and transcription are found to prevent degeneration of neuron cell bodies, while inhibitors of EGFR and p38 MAPK are found to prevent degeneration of axons. Thus, the invention includes combinations of inhibitors of GSK and EGFR (and/or p38 MAPK), combinations of transcription inhibitors and EGF (and/or p38 MAPK), and further combinations of inhibitors of dual leucine zipper-bearing kinase (DLK), glycogen synthase kinase 3β (GSK3), p38 MAPK, EGFF, phosphoinositide 3-kinase (PI3K), cyclin-dependent kinase 5 (cdk5), adenylyl cyclase, c-Jun N-terminal kinase (JNK), BCL2-associated X protein (Bax), In channel, calcium/calmodulin-dependent protein kinase kinase (CaMKK), a G-protein, a G-protein coupled receptor, transcription factor 4 (TCF4), and β-catenin. The inhibitors used in these combinations can be any of those described herein, or other inhibitors of these targets as described in WO 2011/050192, incorporated herein by reference.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

F. Examples

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Commercially available reagents were purchased from suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. $^1$H NMR spectra were recorded on a Varian instrument operating at 400 MHz. $^1$H NMR spectra were obtained in deuterated CDCl$_3$, d$_6$-DMSO, CH$_3$OD or d$_6$-acetone solutions (reported in ppm), using tetramethylsilane (TMS) as the reference standard (0 ppm). When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

When possible, product formed in the reaction mixtures were monitored by LC/MS. High Pressure Liquid Chromatography-Mass Spectrometry (LCMS) experiments to performed either on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150 EX using a Phenomenex DNYC monolithic C18 column with a linear gradient of 5%-95% acetonitrile/water (with 0.1% trifluoroacetic acid in each mobile phase) within 5 minutes and held at 95% for 1 minute to determine retention times (R$_T$) and associated mass ions.

All abbreviations used to described reagents, reaction conditions, or equipment used are consistent with the definitions set forth in the "List of standard abbreviations and acronyms" published yearly by the Journal of Organic Chemistry (an American Chemical Society journal). Thechemical names of discrete compounds of the invention were obtained using the structure naming feature ChemBioDraw Version 11.0 or from Accelrys' Pipeline Pilot IUPAC compound naming program.

Example 1

Preparation of tert-butyl 3-(2,6-dichloropyrimidin-4-yl)pyrrolidine-1-carboxylate

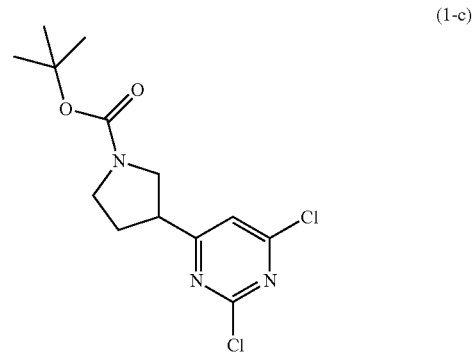 [SMILES: CC(C)(C)OC(=O)N1CCC(c2cc(Cl)nc(Cl)n2)C1]

(1-c)

Step 1—Synthesis of tert-butyl 3-(3-ethoxy-3-oxo-propanoyl)pyrrolidine-1-carboxylate

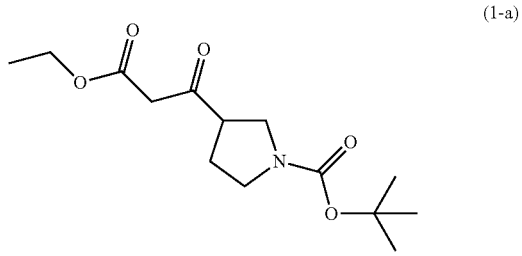 [SMILES: CCOC(=O)CC(=O)C1CCN(C(=O)OC(C)(C)C)C1]

(1-a)

To the solution of pyrrolidine-1,3-dicarboxylic acid 1-tert-butyl ester (120 g, 0.55 mols) in anhydrous acetonitrile (1200 mL), carbonyldiimidazole (110 g, 0.67 mols) was added in small portions at ambient temperature. The resulting mixture was stirred for 1 h. To the resulting vigorously stirred solutions was added the mixture of potassium monoethylmalonate (95 g, 0.55 mols) and magnesium chloride (54 g, 0.55 mols). The slurry was stirred for 16 h at ambient temperature. After the completion of the reaction, the solvent was evaporated in vacuo. The residue was diluted with cold water. The resulting mixture was neutralized with citric acid, extracted with dichloromethane (3×400 mL). Combined organic layer was evaporated to dryness. Purification by column chromatography (silica gel 60-120 mesh, ethyl acetate/hexane) afforded 3-(2-Ethoxycarbonyl-acetyl)-pyrrolidine-1-carboxylic acid tert-butyl ester (138 g, 87%): $^1$H NMR (300 MHz, DMSO-d$_6$ at 80° C.) δ 1.2 (m, 3H), 1.41

(s, 9H), 1.93-1.98 (m, 1H), 2.07-2.11 (m, 1H), 3.23-3.46 (m, 5H), 3.64 (m, 2H) and 4.09-4.15 (m, 2H).

Step 2—Synthesis of tert-butyl 3-(2,6-dioxo-1,2,3,6-tetrahydropyrimidin-4-yl)pyrrolidine-1-carboxylate

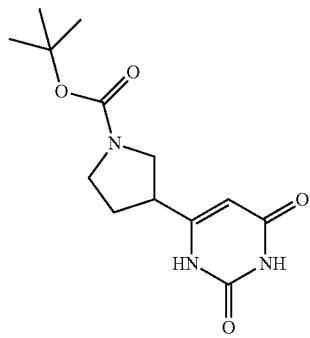

(1-b)

3-(2-Ethoxycarbonyl-acetyl)-pyrrolidine-1-carboxylic acid tert-butyl ester (100 g, 0.35 mols), and Urea (126 g, 2.1 mols) were added to sodium ethoxide (913 mL, 2.8 mols, 21% solution in ethanol) and the resulting mixture was refluxed for 72 h (TLC control). After the completion of the reaction, the solvent was evaporated in vacuo. Residue was dissolved in water. The resulting mixture was neutralized with citric acid and extracted with dichloromethane (3×300 mL). Combined organic layers were washed with water (2×300 mL) and saturated brine solution (1×300 mL) and evaporated to dryness. Purification by column chromatography (silica gel 60-120 mesh, methanol/chloroform) afforded 3-(2,6-Dihydroxy-pyrimidin-4-yl)-pyrrolidine-1-carboxylic acid tert-butyl ester (44 g, 45%): $^1$H NMR (300 MHz, DMSO-d$_6$) δ 1.38 (s, 9H), 1.91-2.10 (m, 2H), 3.00-3.23 (m, 3H), 3.32 (m, 1H), 3.56 (m, 1H), 5.31 (s, 1H), 10.83-10.85 (br, 1H) and 10.98 (broad, 1H); LCMS: 279.9 (M−1)

Step 3—Synthesis of tert-butyl 3-(2,6-dichloropyrimidin-4-yl)pyrrolidine-1-carboxylate

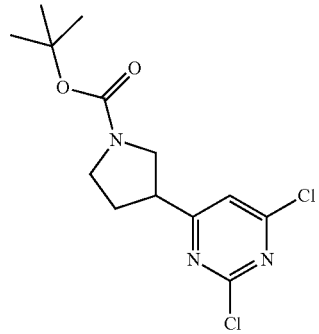

(1-c)

3-(2,6-Dihydroxy-pyrimidin-4-yl)-pyrrolidine-1-carboxylic acid tert-butyl ester (40 g, 0.142 mols), was taken in phosphorous oxychloride (200 mL) and heated to reflux for 3 h. After the completion of the reaction, the mixture was concentrated to 90% of the total volume and poured into crushed ice. pH of the solution was adjusted to 9 with slow addition of solid sodium bicarbonate. Tetrahydrofuran (500 mL) and ditert-butyl dicarbonate (46.53 g, 0.213 mols) were added and the resulting mixture was stirred at ambient temperature for 16 h (TLC control). After the completion of the reaction, the mixture was filtered and the filtrate was extracted with dichloromethane (3×200 mL). Combined organic layer was washed with water (3×200 mL), saturated brine solution (200 mL) and evaporated to dryness. Purification by column chromatography (silica gel, 60-120 mesh, ethyl acetate/hexane) afforded 3-(2,6-Dichloro-pyrimidin-4-yl)-pyrrolidine-1-carboxylic acid tert-butyl ester (20.8 g, 46%): $^1$H NMR (400 MHz, DMSO-d$_6$) δ 1.4 (s, 9H), 2.05 (m, 1H), 2.24 (m, 1H), 3.27-3.70 (m, 5H), and 7.8 (s, 1H); LCMS: 316.3 (M-2).

Additional compounds of the invention presented in Table 1 below were prepared by methods already described elsewhere in the application.

TABLE 1

| No. | Structure | $^1$H NMR | MS (M + H)+ |
|---|---|---|---|
| 1-d | 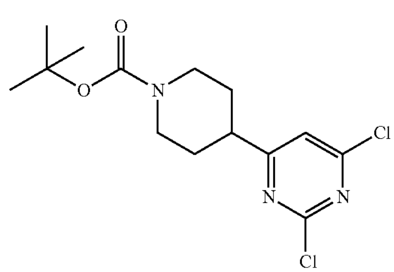 [SMILES: CC(C)(C)OC(=O)N1CCC(c2cc(Cl)nc(Cl)n2)CC1] | $^1$H NMR (400 MHz, DMSO 1.38 (m, 9 H), 1.52-1.58 (m, 2H), 1.83-1.86 (m, 2H), 2.81 (m, 2H), 2.88-2.96 (m, 1H), 4.03-4.05 (m, 2H), 7.78 (s, 1H) | 232 (M-Boc) |

TABLE 1-continued

| No. | Structure | ¹H NMR | MS (M + H)+ |
|---|---|---|---|
| 1-e | 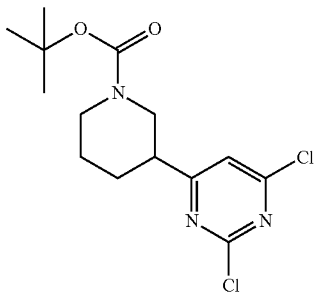 [SMILES: CC(C)(C)OC(=O)N1CCCC(c2cc(Cl)nc(Cl)n2)C1] | ¹H NMR (400 MHz, DMSO-d$_6$) δ 7.79 (s, 1H), 4.00 (s, 1H), 3.81 (d, J = 12.9 Hz, 1H), 3.00-2.75 (m, 2H), 1.95 (t, J = 14.0 Hz, 1H), 1.71 (dq, J = 19.7, 3.7 Hz, 2H), 1.39 (s, 9H). | 332 |
| 1-f | 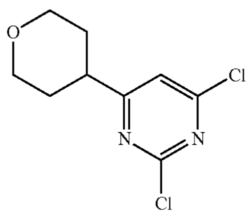 [SMILES: Clc1cc(C2CCOCC2)nc(Cl)n1] | ¹H NMR (400 MHz, DMSO-d$_6$) δ 1.6-1.82 (m, 4H), 2.99 (m, 1H), 3.38-3.44 (m, 2H), 3.92-3.96 (m, 2H), 7.77 (s, 1H) | 233 |
| 1-g | 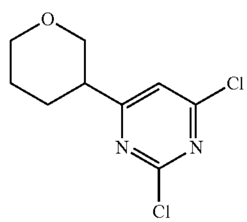 [SMILES: Clc1cc(C2CCCOC2)nc(Cl)n1] | ¹H NMR (400 MHz, DMSO-d$_6$) δ 1.55-1.75 (m, 2H), 1.78-1.90 (m, 1H), 1.98-2.02 (m, 1H), 2.97-3.01 (m, 1H), 3.35-3.41 (m, 1H), 3.47-3.53 (m, 1H), 3.81-3.84 (m, 1H), 3.93-3.96 (m, 1H), 7.80 (s, 1H) | 233 |
| 1h | 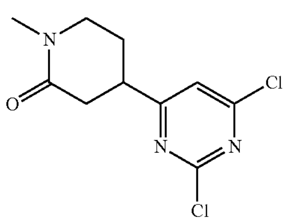 [SMILES: CN1CCC(c2cc(Cl)nc(Cl)n2)CC1=O] | | 260 |

Example 2

Preparation of (R)-2-(2-methylpyrrolidin-1-yl)-6-(piperidin-4-yl)-N-(4-(trifluoromethyl)pyridin-2-yl)pyrimidin-4-amine

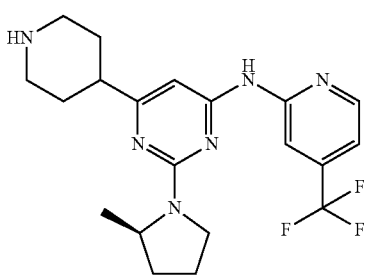
(2-c)

Step 1—Synthesis of (R)-tert-butyl 4-(2-(2-methylpyrrolidin-1-yl)-6-(4-(trifluoromethyl)pyridin-2-ylamino)pyrimidin-4-yl)piperidine-1-carboxylate

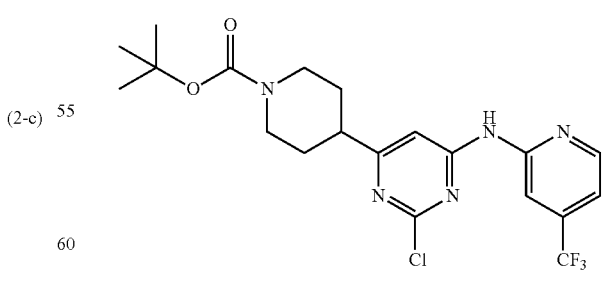
(2-a)

A vial was charged with example 1-d (1.00 g, 3.01 mmol), 2-amino-4-(trifluoromethyl)pyridine (537 mg, 3.31 mmol), tris(dibenzylideneacetone)dipalladium (0) (138 mg, 0.15 mmol), 4,5-bis(diphenylphosphino)-9,9-dimethylxanthene (180 mg, 0.30 mmol), and sodium tert-butoxide (420 mg, 4.21 mmol). The vial was capped and purged with N$_2$, followed by addition of dioxane (6 mL). The resulting mixture was heated at 60° C. for 2 h. The dark mixture was diluted with 50% DCM/EtOAc (50 mL) and filtered through paper. The filtrate was concentrated onto Celite, and purified by chromatography (24 g SiO$_2$ column, 0-50% ethyl acetate-heptane) to afford 820 mg (53%) of the title compound as an off-white solid: $^1$H NMR (400 MHz, CDCl$_3$) δ 8.16 (d, J=5.3 Hz, 1H), 7.94 (s, 1H), 7.55 (s, 1H), 7.04 (s, 1H), 6.66 (d, J=5.2 Hz, 1H), 4.25 (s, 2H), 2.97-2.59 (m, 3H), 2.00-1.79 (m, 3H), 1.79-1.56 (m, 3H), 1.47 (s, 9H), 1.36-1.17 (m, 3H), 1.17-1.01 (m, 2H), 0.98-0.72 (m, 4H); MS m/z=459 (M+H$^+$).

Step 2—Synthesis of (R)-tert-butyl 4-(2-(2-methyl-pyrrolidin-1-yl)-6-(4-(trifluoromethyl)pyridin-2-ylamino)pyrimidin-4-yl)piperidine-1-carboxylate (2-b)

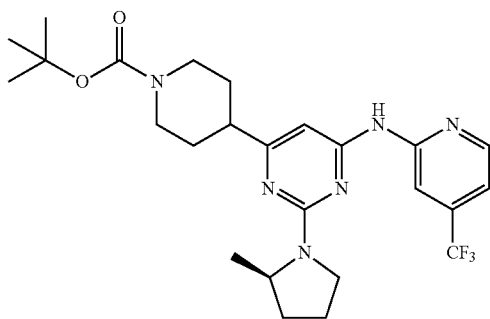

A solution of example 2-a (1.25 g, 2.73 mmol), (2R)-2-methylpyrrolidine (465 mg, 5.46 mmol) and dimethylformamide (5.0 mL) was heated in a sealed vial at 80° C. for 5 h. The reaction was diluted with sat. aqueous NH$_4$Cl (50 mL) and extracted with ethyl acetate (3×20 mL). The combined organic phases were washed with water (1×10 mL), brine (1×10 mL), dried (Na$_2$SO$_4$), filtered and concentrated onto Celite. Purification by chromatography (SiO$_2$, 40 g column 0-40% ethyl acetate-heptane) afforded 1.00 g (72%) of the title compound as a colorless solid: $^1$H NMR (400 MHz, CDCl$_3$) δ 8.85 (s, 1H), 8.36 (d, J=5.2 Hz, 1H), 7.24 (s, 1H), 7.08 (d, J=5.2 Hz, 1H), 5.85 (s, 1H), 4.40-4.26 (m, 1H), 4.26-4.09 (m, 2H), 3.67 (ddd, J=10.5, 7.3, 3.2 Hz, 1H), 3.62-3.44 (m, 1H), 2.82 (t, J=12.4 Hz, 2H), 2.54 (tt, J=11.6, 3.6 Hz, 1H), 2.20-1.99 (m, 2H), 1.99-1.91 (m, 1H), 1.87 (d, J=13.4 Hz, 2H), 1.72 (dd, J=15.2, 9.9 Hz, 3H), 1.48 (s, 9H), 1.28 (d, J=6.3 Hz, 4H); MS m/z=507 (M+H$^+$).

Step 3—Synthesis of (R)-2-(2-methylpyrrolidin-1-yl)-6-(piperidin-4-yl)-N-(4-(trifluoromethyl)pyridin-2-yl)pyrimidin-4-amine (2-c)

A solution of 2-b (100 mg, 0.22 mmol) in dioxane (2 mL) and MeOH (1 mL) was treated with a stream of HCl(g) for 10 sec. The vial was capped and maintained at rt for 2 h. The solvents were removed under reduced pressure and the residue purified by HPLC to afford the title compound as a colorless solid: $^1$H NMR (400 MHz, MeOD) δ 8.62 (d, J=5.1 Hz, 1H), 7.45 (d, J=5.1 Hz, 1H), 4.63-4.44 (m, 1H), 3.84 (t, J=8.5 Hz, 1H), 3.58 (d, J=13.0 Hz, 2H), 3.25-3.05 (m, 3H), 2.36-2.06 (m, 5H), 2.06-1.80 (m, 3H), 1.36 (d, J=6.4 Hz, 3H); MS m/z=407 (M+H$^+$).

Additional compounds of the invention presented in Table 2 below were prepared by methods already described elsewhere in the application.

TABLE 2

| No. | Structure | $^1$H NMR | MS (M + H)+ |
|---|---|---|---|
| 2-d | 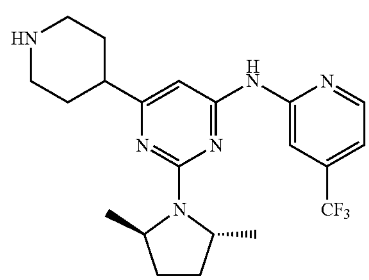 [SMILES: C[C@@H]1CC[C@@H](C)N1c1nc(Nc2cc(C(F)(F)F)ccn2)cc(C2CCNCC2)n1] | $^1$H NMR (400 MHz, CDCl$_3$) δ 8.84 (s, 1H), 8.45 (s, 1H), 8.36 (d, J = 5.2 Hz, 1H), 7.49 (s, 1H), 7.10 (d, J = 5.2 Hz, 1H), 5.86 (s, 1H), 4.42-4.22 (m, 2H), 3.51 (t, J = 11.8 Hz, 3H), 3.06-2.90 (m, 3H), 2.72-2.61 (m, 3H), 2.32-2.20 (m, 3H), 2.20-1.98 (m, 6H), 1.66 (s, 2H), 1.33-1.14 (m, 6H) | 421 |
| 2-e | 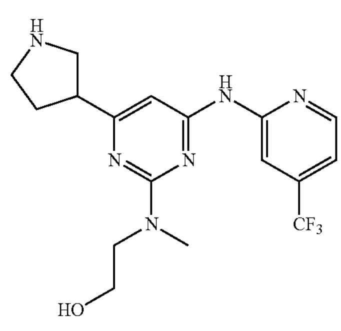 [SMILES: CN(CCO)c1nc(Nc2cc(C(F)(F)F)ccn2)cc(C2CCNC2)n1] | $^1$H NMR (400 MHz, DMSO-d$_6$) δ 10.11 (s, 1H), 8.50 (d, J = 5.1 Hz, 1H), 7.25 (d, J = 4.7 Hz, 1H), 6.35 (s, 1H), 3.71-3.51 (m, 5H), 3.16 (s, 4H), 3.11-3.03 (m, 1H), 3.03-2.88 (m, 2H), 2.88-2.74 (m, 2H), 2.06-1.94 (m, 1H), 1.94-1.78 (m, 1H) | 383 |

TABLE 2-continued

| No. | Structure | ¹H NMR | MS (M + H)+ |
|---|---|---|---|
| 2-f | 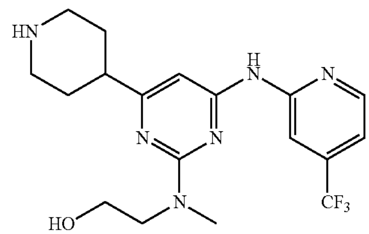 [SMILES: CN(CCO)c1nc(Nc2cc(C(F)(F)F)ccn2)cc(C2CCNCC2)n1] | ¹H NMR (400 MHz, DMSO-d₆) δ 10.17 (s, 1H), 8.51 (d, J = 5.1 Hz, 1H), 7.26 (d, J = 5.1 Hz, 1H), 6.34 (s, 1H), 3.71-3.58 (m, 5H), 2.76 (dd, J = 12.3, 9.9 Hz, 2H), 1.87-1.55 (m, 4H) | 3.97 |
| 2-g | 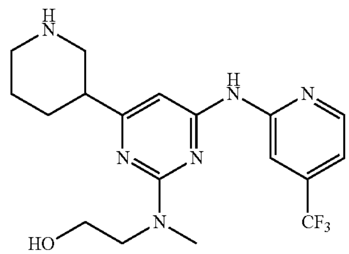 [SMILES: CN(CCO)c1nc(Nc2cc(C(F)(F)F)ccn2)cc(C2CCCNC2)n1] | ¹H NMR (400 MHz, DMSO-d₆) δ 10.11 (s, 1H), 8.68 (s, 1H), 8.50 (d, J = 5.1 Hz, 1H), 7.25 (d, J = 4.9 Hz, 1H), 6.32 (s, 1H), 4.66 (s, 1H), 3.79-3.54 (m, 4H), 3.16 (s, 3H), 3.04 (d, J = 11.5 Hz, 1H), 2.91 (d, J = 12.4 Hz, 1H), 2.56 (t, J = 11.2 Hz, 1H), 2.45-2.38 (m, 1H), 1.89 (d, J = 12.3 Hz, 1H), 1.78-1.51 (m, 3H), 1.44 (dt, J = 7.6, 6.0 Hz, 1H) | 397 |
| 2-h | 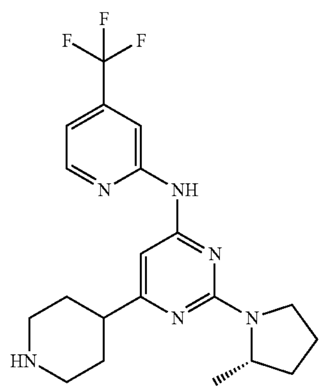 [SMILES: C[C@H]1CCCN1c1nc(Nc2cc(C(F)(F)F)ccn2)cc(C2CCNCC2)n1] | ¹H NMR (400 MHz, MeOD) δ 8.62 (d, J = 5.1 Hz, 1H), 7.45 (d, J = 5.1 Hz, 1H), 4.63-4.44 (m, 1H), 3.84 (t, J = 8.5 Hz, 1H), 3.58 (d, J = 13.0 Hz, 2H), 3.25-3.05 (m, 3H), 2.36-2.06 (m, 5H), 2.06-1.80 (m, 3H), 1.36 (d, J = 6.4 Hz, 3H) | 407 |
| 2-i | 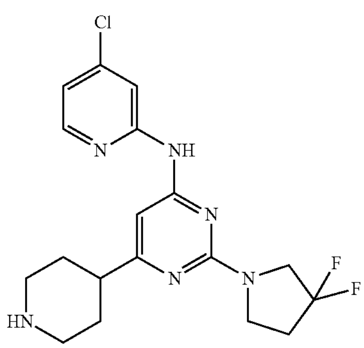 [SMILES: FC1(F)CCN(c2nc(Nc3cc(Cl)ccn3)cc(C3CCNCC3)n2)C1] | ¹H NMR (400 MHz, CDCl₃) δ 8.30 (s, 1H), 8.14 (d, J = 5.4 Hz, 1H), 7.19 (s, 1H), 6.92 (dd, J = 5.4, 1.7 Hz, 1H), 6.10 (s, 1H), 3.97 (t, J = 13.3 Hz, 2H), 3.86 (t, J = 7.3 Hz, 2H), 3.18 (d, J = 12.1 Hz, 2H), 2.78-2.68 (m, 2H), 2.65-2.36 (m, 4H), 1.86 (d, J = 12.4 Hz, 2H), 1.69 (ddd, J = 24.9, 12.4, 3.9 Hz, 2H). | 395 |
| 2-j | 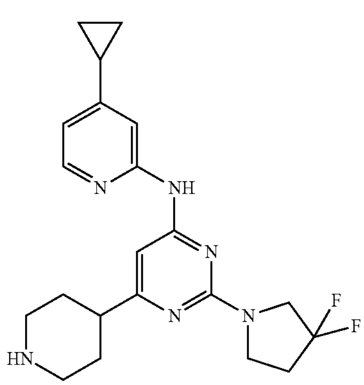 [SMILES: FC1(F)CCN(c2nc(Nc3cc(C4CC4)ccn3)cc(C3CCNCC3)n2)C1] | ¹H NMR (400 MHz, DMSO-d₆) δ 9.62 (s, 1H), 8.06 (d, J = 5.2 Hz, 1H), 7.85 (s, 1H), 6.73 (s, 1H), 6.72 (dd, J = 5.2, 1.1 Hz, 1H), 6.52 (s, 1H), 3.90 (t, J = 13.3 Hz, 2H), 3.74 (t, J = 7.3 Hz, 2H), 2.99 (d, J = 12.1 Hz, 2H), 2.56 (dd, J = 13.6, 7.1 Hz, 3H), 2.40 (tt, J = 11.7, 3.6 Hz, 1H), 2.10 (s, 1H), 1.94-1.85 (m, 1H), 1.70 (d, J = 11.0 Hz, 2H), 1.51 (qd, J = 12.3, 3.9 Hz, 2H), 1.10-1.02 (m, 2H), 0.79-0.73 (m, 2H). | 401 |

| No. | Structure | ¹H NMR | MS (M + H)+ |
|---|---|---|---|
| 2-k | 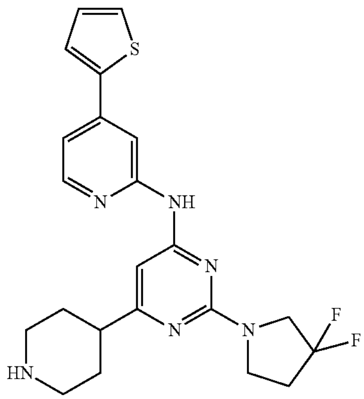 [SMILES: FC1(F)CCN(c2nc(Nc3cc(-c4cccs4)ccn3)cc(C3CCNCC3)n2)C1] | ¹H NMR (400 MHz, CDCl₃) δ 8.50 (d, J = 12.6 Hz, 2H), 8.19 (d, J = 5.4 Hz, 1H), 7.96 (s, 1H), 7.51 (d, J = 3.8 Hz, 1H), 7.44 (d, J = 5.1 Hz, 1H), 7.20-7.12 (m, 2H), 6.21 (s, 1H), 4.04 (t, J = 13.1 Hz, 2H), 3.91 (t, J = 7.2 Hz, 2H), 3.55-3.46 (m, 2H), 3.03-2.92 (m, 2H), 2.76-2.66 (m, 1H), 2.55-2.42 (m, 2H), 2.19-2.06 (m, 4H). | 443 |
| 2-l | 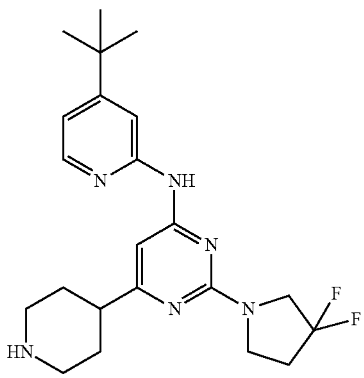 [SMILES: CC(C)(C)c1ccnc(Nc2cc(C3CCNCC3)nc(N3CCC(F)(F)C3)n2)c1] | ¹H NMR (400 MHz, CDCl₃) δ 8.17 (d, J = 5.4 Hz, 1H), 8.02 (s, 1H), 7.17 (s, 1H), 6.93 (dd, J = 5.4, 1.5 Hz, 1H), 6.26 (s, 1H), 3.98 (t, J = 13.3 Hz, 2H), 3.86 (t, J = 7.3 Hz, 2H), 3.27 (d, J = 12.3 Hz, 2H), 2.84-2.75 (m, 2H), 2.63-2.53 (m, 1H), 2.50-2.38 (m, 2H), 1.98-1.89 (m, 2H), 1.88-1.75 (m, 2H), 1.33 (s, 9H). | 417 |
| 2-m | 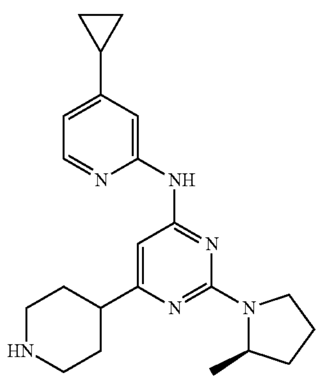 [SMILES: C[C@@H]1CCCN1c1nc(Nc2cc(C3CC3)ccn2)cc(C2CCNCC2)n1] | ¹H NMR (400 MHz, DMSO-d₆) δ 9.42 (s, 1H), 8.04 (d, J = 5.2 Hz, 1H), 8.01 (s, 1H), 6.67 (d, J = 4.8 Hz, 1H), 6.31 (s, 1H), 4.26-4.17 (m, 1H), 3.61-3.44 (m, 3H), 2.98 (d, J = 12.1 Hz, 2H), 2.57-2.51 (m, 2H), 2.40-2.30 (m, 1H), 2.10-1.95 (m, 2H), 1.93-1.82 (m, 2H), 1.73-1.62 (m, 3H), 1.58-1.45 (m, 2H), 1.24 (d, J = 6.2 Hz, 3H), 1.08-1.01 (m, 2H), 0.79-0.72 (m, 2H). | 379 |
| 2-n | 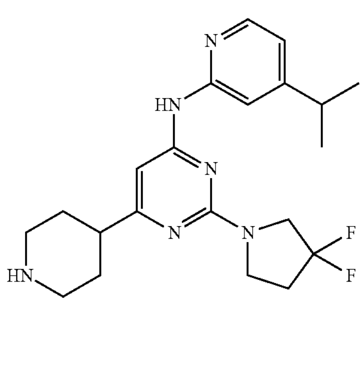 [SMILES: CC(C)c1ccnc(Nc2cc(C3CCNCC3)nc(N3CCC(F)(F)C3)n2)c1] | ¹H NMR (400 MHz, CDCl₃) δ 8.53 (s, 1H), 8.12 (d, J = 5.2 Hz, 1H), 7.94 (s, 1H), 6.81 (d, J = 5.3 Hz, 1H), 6.32 (s, 1H), 3.96 (t, J = 13.2 Hz, 2H), 3.85 (t, J = 7.3 Hz, 2H), 3.45 (d, J = 12.8 Hz, 2H), 3.00-2.82 (m, 3H), 2.74-2.63 (m, 1H), 2.54-2.40 (m, 2H), 2.12-2.00 (m, 4H), 1.28 (d, J = 6.9 Hz, 6H) | 403 |

TABLE 2-continued

| No. | Structure | ¹H NMR | MS (M + H)+ |
|---|---|---|---|
| 2-o | 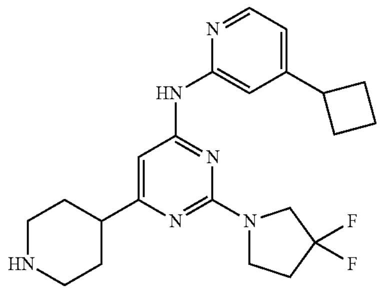 [SMILES: FC1(F)CCN(c2nc(Nc3cc(C4CCC4)ccn3)cc(C3CCNCC3)n2)C1] | ¹H NMR (400 MHz, DMSO-d₆) δ 9.77 (s, 1H), 8.34 (s, 1H), 8.14 (s, 1H), 6.79 (d, J = 5.8 Hz, 1H), 6.51 (s, 1H), 3.92 (t, J = 13.2 Hz, 2H), 3.75 (t, J = 7.3 Hz, 2H), 3.55-3.50 (m, 2H), 3.22 (d, J = 12.3 Hz, 2H), 2.83 (t, J = 11.6 Hz, 2H), 2.62-2.52 (m, 2H), 2.38-2.26 (m, 2H), 2.18-1.93 (m, 3H), 1.91-1.62 (m, 5H) | 415 |
| 2-p | 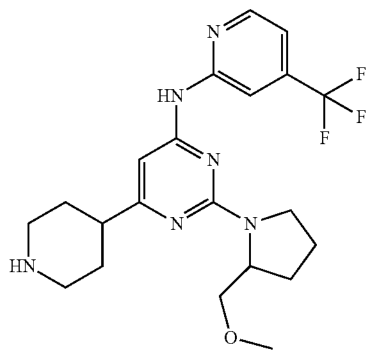 [SMILES: COCC1CCCN1c1nc(Nc2cc(C(F)(F)F)ccn2)cc(C2CCNCC2)n1] | ¹H NMR (400 MHz, CDCl₃) δ 8.50 (s, 1H), 8.37 (d, J = 5.1 Hz, 1H), 7.57 (s, 1H), 7.10 (d, J = 5.1 Hz, 1H), 6.03 (s, 1H), 4.34 (s, 1H), 3.84-3.27 (m, 7H), 3.36 (s, 3H), 3.05-2.90 (m, 2H), 2.75-2.65 (m, 1H), 2.05 (m, 8H). | 437 |
| 2-q | 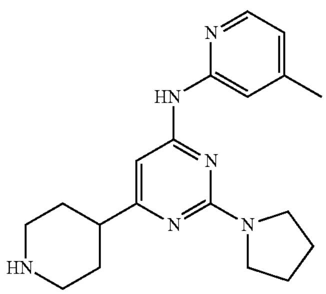 [SMILES: Cc1ccnc(Nc2cc(C3CCNCC3)nc(N3CCCC3)n2)c1] | ¹H NMR (400 MHz, MeOD) δ 8.50 (d, J = 6.0 Hz, 1H), 7.66 (s, 1H), 7.53 (d, J = 5.6 Hz, 1 H), 6.53 (s, 1 H), 3.89 (br, 2 H), 3.77 (br, 2 H), 3.58-3.55 (m, 2 H), 3.32-3.31 (m, 1 H), 3.29-3.18 (m, 2 H), 2.64 (s, 3 H), 2.28-2.02 (m, 8 H). | 339 |
| 2-r | 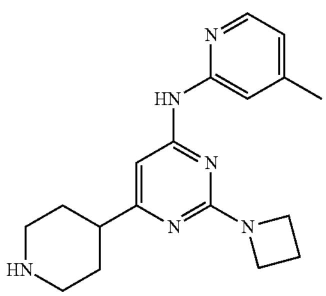 [SMILES: Cc1ccnc(Nc2cc(C3CCNCC3)nc(N3CCC3)n2)c1] | ¹H NMR (400 MHz, MeOD) δ 8.31 (d, J = 6.4 Hz, 1 H), 7.50-7.30 (m, 2 H), 6.50 (br, 1 H), 4.37 (t, J = 7.6 Hz, 3 H), 3.54-3.33 (m, 3 H), 3.30-3.10 (m, 3 H), 2.54-2.49 (m, 5 H), 2.21-1.94 (m, 4 H) | 325 |
| 2-s | 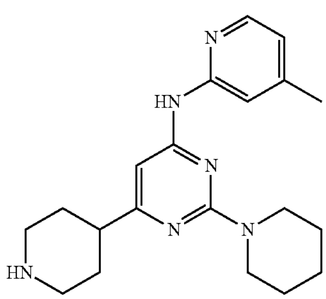 [SMILES: Cc1ccnc(Nc2cc(C3CCNCC3)nc(N3CCCCC3)n2)c1] | ¹H NMR (400 MHz, MeOD) δ 8.48 (d, J = 5.6 Hz, 1 H), 7.67 (s, 1 H), 7.54 (d, J = 5.2 Hz, 1 H), 6.53 (s, 1 H), 3.89 (s, 4 H), 3.67-3.65 (m, 1 H), 3.47-3.40 (m, 2 H), 3.31-3.30 (m, 1 H), 3.14-3.08 (m, 1 H), 2.64 (s, 3 H), 2.24-2.21 (m, 1 H), 2.11-2.07 (m, 1 H), 1.98-1.86 (m, 2 H), 1.77 (s, 6 H) | 353 |

TABLE 2-continued

| No. | Structure | ¹H NMR | MS (M + H)+ |
|---|---|---|---|
| 2-t | 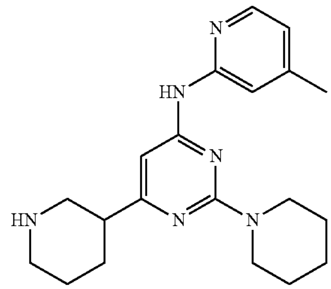 [SMILES: Cc1ccnc(Nc2cc(C3CCCNC3)nc(N3CCCCC3)n2)c1] | ¹H NMR (400 MHz, MeOD) δ 8.30 (d, J = 6.4 Hz, 1 H), 7.31 (s, 1 H), 7.26 (d, J = 7.2 Hz, 1 H), 6.32 (s, 1 H), 3.82 (t, J = 5.6 Hz, 5 H), 3.52-3.49 (m, 1 H), 3.49-3.46 (m, 1 H), 3.16-3.10 (m, 2 H), 2.51 (s, 3 H), 2.18-2.14 (m, 2 H), 2.06-1.96 (m, 2 H), 1.75-1.74 (m, 6 H) | 353 |
| 2-u | 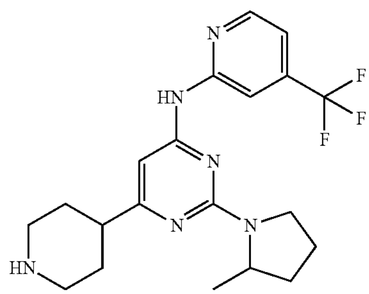 [SMILES: CC1CCCN1c1nc(Nc2cc(C(F)(F)F)ccn2)cc(C2CCNCC2)n1] | ¹H NMR (400 MHz, MeOD) δ 8.86-8.45 (m, 2 H), 7.45 (d, J = 5.2 Hz, 1 H), 6.62-6.39 (br, 1 H), 4.54 (s, 1 H), 3.81 (s, 1 H), 3.71-3.55 (m, 3 H), 3.20-3.13 (m, 3 H), 2.27-2.18 (m, 5 H), 2.01-1.87 (m, 3 H), 1.35 (d, J = 5.6 Hz, 3 H). | 407 |
| 2-v | 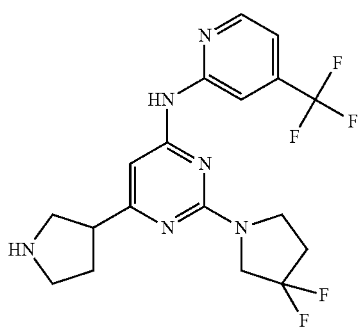 [SMILES: FC1(F)CCN(c2nc(Nc3cc(C(F)(F)F)ccn3)cc(C3CCNC3)n2)C1] | ¹H NMR (400 MHz, MeOD) δ 8.58-8.57 (m, 1H), 8.30-8.20 (m, 1H), 7.42-7.40 (m, 1H), 6.70-6.60 (m, 1H), 4.10-4.07 (m, 2H), 3.96-3.92 (m, 2H), 3.70-3.68 (m, 2H), 3.54-3.49 (m, 2H), 3.40-3.36 (m, 1H) 2.61-2.49 (m, 3H), 2.22-2.12 (m, 1H) | 415 |
| 2-w | 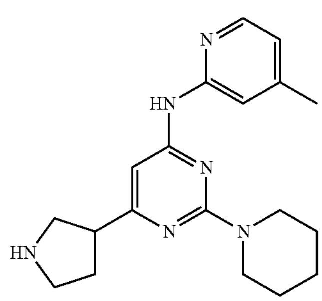 [SMILES: Cc1ccnc(Nc2cc(C3CCNC3)nc(N3CCCCC3)n2)c1] | ¹H NMR (400 MHz, MeOD) δ 8.04 (d, J = 5.2 Hz, 1 H), 7.70 (s, 1 H), 6.80 (s, 1 H), 6.46 (s, 1 H), 3.76 (d, J = 6.4 Hz, 4 H), 3.60-3.36 (m, 4 H), 3.29-3.25 (m, 1 H), 2.40-2.30 (m, 1 H), 2.29 (s, 3 H), 2.20-2.10 (m, 1 H), 1.70-1.60 (m, 2 H), 1.57-1.54 (m, 4 H) | 339 |
| 2-x | 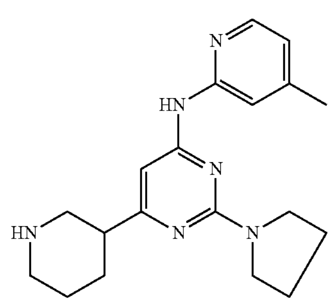 [SMILES: Cc1ccnc(Nc2cc(C3CCCNC3)nc(N3CCCC3)n2)c1] | ¹H NMR (400 MHz, MeOD) δ 8.53 (d, J = 6.0 Hz, 1 H), 7.68 (s, 1 H), 7.56 (d, J = 6.0 Hz, 1 H), 6.58 (s, 1 H), 3.90-3.76 (m, 4 H), 3.71-3.68 (m, 1 H), 3.52-3.36 (m, 2 H), 3.33-3.32 (m, 1 H), 3.18-3.12 (m, 1 H), 2.67 (s, 3 H), 2.28-2.11 (m, 6 H), 2.00-1.88 (m, 2 H) | 339 |

TABLE 2-continued

| No. | Structure | ¹H NMR | MS (M + H)+ |
|---|---|---|---|
| 2-y | 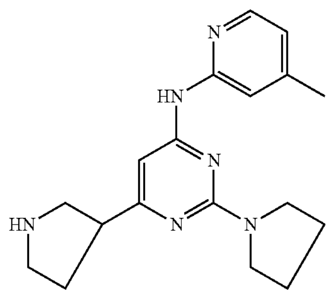 [SMILES: Cc1ccnc(Nc2cc(C3CCNC3)nc(N3CCCC3)n2)c1] | ¹H NMR (400 MHz, MeOD) δ 8.07 (d, J = 4.2 Hz, 1 H), 7.98 (s, 1 H), 6.86 (d, J = 6.0 Hz, 1 H), 6.45 (s, 1 H), 3.65-3.31 (m, 9 H), 2.50-2.40 (m, 1 H), 2.35 (s, 3 H), 2.25-2.15 (m, 1 H), 2.03-2.00 (m, 4 H) | 325 |
| 2-z | 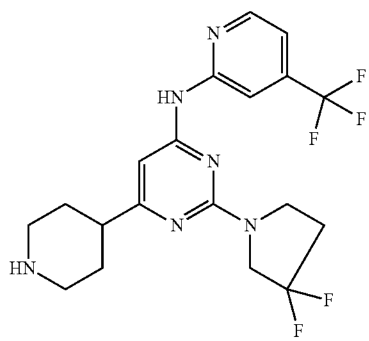 [SMILES: FC1(F)CCN(c2nc(Nc3cc(C(F)(F)F)ccn3)cc(C3CCNCC3)n2)C1] | ¹H NMR (400 MHz, MeOD) δ 8.65 (d, J = 5.2 Hz, 1 H), 7.55 (br, 1 H), 7.49 (d, J =5.2 Hz, 1 H), 6.66 (br, 1 H), 4.19-4.12 (m, 2 H), 4.06-4.02 (m, 2 H), 3.60 (d, J = 12.8 Hz, 2 H), 2.23-2.17 (m, 3 H), 2.70-2.67 (m, 2 H), 2.32 (d, J = 13.6 Hz, 2 H), 2.02-1.98 (m, 2 H) | 429 |
| 2-aa | 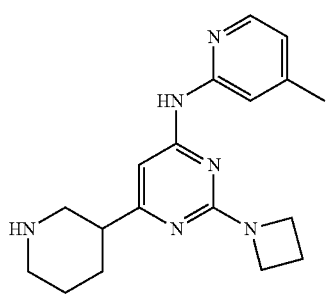 [SMILES: Cc1ccnc(Nc2cc(C3CCCNC3)nc(N3CCC3)n2)c1] | ¹H NMR (400 MHz, MeOD) δ 8.01 (d, J = 5.2 Hz, 1 H), 7.80 (s, 1 H), 6.76 (d, J = 5.2 Hz, 1 H), 6.49 (s, 1 H), 4.52 (br, 1 H), 4.09-4.06 (m, 4 H), 3.15-3.12 (m, 2 H), 2.92-2.85 (m, 1 H), 2.78-2.75 (m, 1 H), 2.45-2.35 (m, 5 H), 2.05-1.98 (m, 1 H), 1.90-1.86 (m, 1 H), 1.75-1.70 (m, 2 H) | 325 |
| 2-ab | 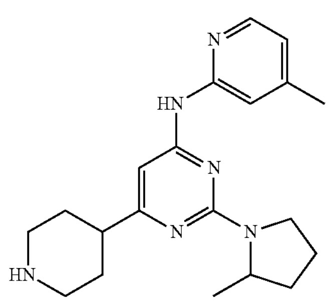 [SMILES: Cc1ccnc(Nc2cc(C3CCNCC3)nc(N3CCCC3C)n2)c1] | ¹H NMR (400 MHz, MeOD) δ 8.56 (d, J = 6.4 Hz, 1 H), 7.83-7.60 (m, 2 H), 6.60 (s, 1 H), 4.72 (d, J = 6.0 Hz, 1 H), 3.93-3.74 (m, 2 H), 3.62-3.19 (m, 5 H), 2.69 (s, 3 H), 2.35-2.20 (m, 5 H), 2.10-1.92 (m, 3 H), 1.34 (d, J = 8.0 Hz, 3 H) | 353 |
| 2-ac | 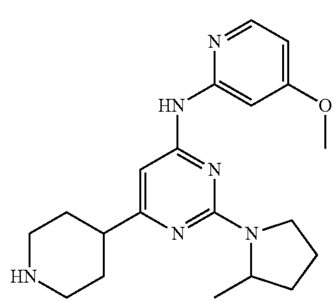 [SMILES: COc1ccnc(Nc2cc(C3CCNCC3)nc(N3CCCC3C)n2)c1] | ¹H NMR (400 MHz, MeOD) δ 8.54 (d, J = 6.8 Hz, 1 H), 7.51-7.18 (m, 2 H), 6.59 (s, 1 H), 4.61 (s, 1 H), 4.18 (s, 3 H), 4.36-3.20 (m, 7 H), 2.72-1.79 (m, 8 H), 1.38 (s, 3 H). | 369 |

TABLE 2-continued

| No. | Structure | ¹H NMR | MS (M + H)+ |
|---|---|---|---|
| 2-ad | 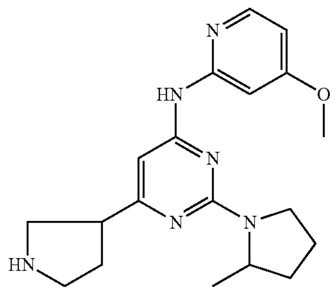 [SMILES: COc1ccnc(Nc2cc(C3CCNC3)nc(N3CCCC3C)n2)c1] | ¹H NMR (400 MHz, MeOD) δ 8.33 (d, J = 6.8 Hz, 1 H), 7.25-7.05 (m, 2 H), 6.49 (s, 1 H), 4.51-4.48 (m, 1 H), 4.00 (s, 3 H), 3.85-3.55 (m, 4 H), 3.55-3.30 (m, 3 H), 2.54-2.46 (m, 1 H), 2.20-1.96 (m, 4 H), 1.80-1.70 (m, 1 H), 1.20 (d, J = 6.4 Hz, 3 H). | 355 |
| 2-ae | 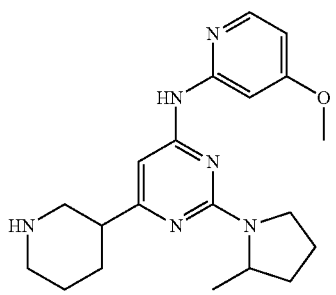 [SMILES: COc1ccnc(Nc2cc(C3CCCNC3)nc(N3CCCC3C)n2)c1] | ¹H NMR (400 MHz, MeOD) δ 8.49 (d, J = 6.8 Hz, 1 H), 7.37-7.27 (m, 2 H), 6.58 (s, 1 H), 4.65 (s, 1 H), 4.17 (s, 3 H), 3.94 (s, 1 H), 3.75-3.68 (m, 2 H), 3.54-3.46 (m, 2 H), 3.40-3.33 (m, 1 H), 3.17-3.11 (m, 1 H), 2.27-2.11 (m, 5 H), 2.05-1.36 (m, 3 H), 1.35 (d, J = 5.2 Hz, 3 H) | 369 |
| 2-af | 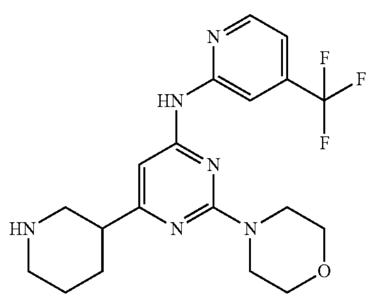 [SMILES: FC(F)(F)c1ccnc(Nc2cc(C3CCCNC3)nc(N3CCOCC3)n2)c1] | ¹H NMR (400 MHz, MeOD) δ 8.65 (d, J = 4.8 Hz, 1 H), 8.20 (s, 1 H), 7.46 (d, J = 4.4 Hz, 1 H), 6.82-6.78 (m, 1 H), 3.92-3.87 (m, 3 H), 3.83 (m, 4 H), 3.69-3.63 (m, 1 H), 3.46-3.43 (m, 2 H), 3.30-3.29 (m, 2 H), 3.23-3.19 (m, 1 H), 3.15-3.09 (m, 1 H), 2.24-2.22 (m, 1 H), 2.09-2.06 (m, 1 H), 2.00-1.86 (m, 2 H) | 409 |
| 2-ag | 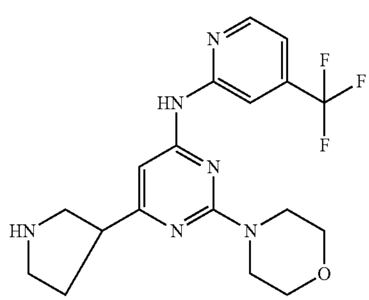 [SMILES: FC(F)(F)c1ccnc(Nc2cc(C3CCNC3)nc(N3CCOCC3)n2)c1] | ¹H NMR (400 MHz, MeOD) δ 8.56 (d, J = 6.0 Hz, 1 H), 8.07-8.33 (m, 1 H), 7.38 (d, J = 5.2 Hz, 1 H), 6.71-6.68 (br, 1 H), 3.77-3.67 (m, 10 H), 3.54-3.45 (m, 2 H), 3.40-3.32 (m, 1 H), 2.52-2.45 (m, 1 H), 2.19-2.15 (m, 1 H) | 395 |
| 2-ah | 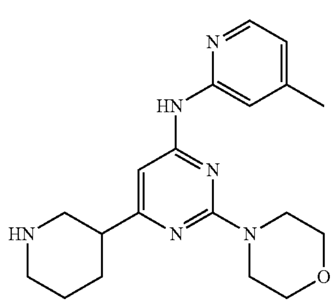 [SMILES: Cc1ccnc(Nc2cc(C3CCCNC3)nc(N3CCOCC3)n2)c1] | ¹H NMR (400 MHz, MeOD) δ 8.37 (d, J = 6.0 Hz, 1 H), 7.40-7.34 (m, 2 H), 6.43 (s, 1 H), 3.89-3.83 (m, 8 H), 3.59-3.57 (m, 1 H), 3.43-3.37 (m, 1 H), 3.24-3.23 (m, 2 H), 3.10-3.04 (m, 1 H), 2.59 (s, 3 H), 2.17-2.14 (m, 1 H), 2.07-2.03 (m, 1 H), 1.94-1.83 (m, 2 H) | 355 |

TABLE 2-continued

| No. | Structure | ¹H NMR | MS (M + H)+ |
|---|---|---|---|
| 2-ai | 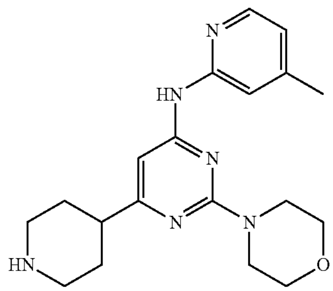 [SMILES: Cc1ccnc(Nc2cc(C3CCNCC3)nc(N3CCOCC3)n2)c1] | ¹H NMR (400 MHz, MeOD) δ 8.39 (d, J = 6.4 Hz, 1 H), 7.42-7.36 (m, 2 H), 6.45 (s, 1 H), 3.86-3.85 (m, 8 H), 3.55 (d, J = 13.2 Hz, 2 H), 3.21-3.07 (m, 2 H), 2.68 (s, 1 H), 2.61 (s, 3 H), 2.22 (d, J = 13.2 Hz, 2 H), 2.11-2.02 (m, 2 H) | 355 |
| 2-aj | 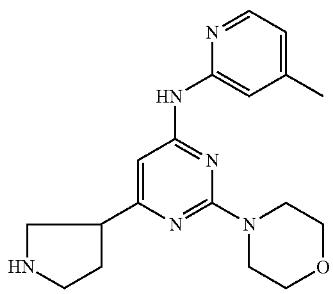 [SMILES: Cc1ccnc(Nc2cc(C3CCNC3)nc(N3CCOCC3)n2)c1] | ¹H NMR (400 MHz, MeOD) δ 8.25 (d, J = 6.4 Hz, 1 H), 7.31-7.23 (m, 2 H), 6.35 (s, 1 H), 3.74-3.70 (m, 8 H), 3.64-3.55 (m, 2 H), 3.50-3.40 (m, 2 H), 3.32-3.28 (m, 1 H), 2.50 (s, 3 H), 2.36-2.26 (m, 1 H), 2.12-2.10 (m, 1 H) | 341 |
| 2-ak | 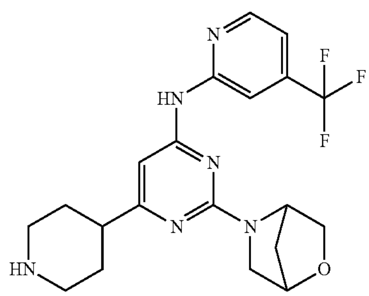 [SMILES: FC(F)(F)c1ccnc(Nc2cc(C3CCNCC3)nc(N3CC4CC3CO4)n2)c1] | ¹H NMR (400 MHz, MeOD) δ 8.68-8.64 (m, 2H), 7.51-7.48 (m, 1H), 6.56 (br, 1H), 4.66 (s, 1H), 4.03-3.94 (m, 3H), 3.82-3.58 (m, 4H), 3.24-3.17 (m, 3H), 2.38-2.30 (m, 3H), 2.15 (s, 1H), 2.07-1.95 (m, 2H) | 421 |
| 2-al | 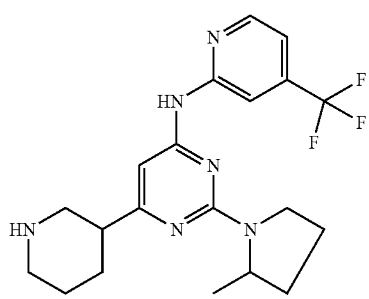 [SMILES: CC1CCCN1c1nc(Nc2cc(C(F)(F)F)ccn2)cc(C2CCCNC2)n1] | ¹H NMR (400 MHz, MeOD) δ 8.76 (d, J = 5.2 Hz, 1 H), 7.59-7.49 (m, 2 H), 6.58-6.49 (m, 1H), 4.60-4.39 (m, 1 H), 3.89-3.50 (m, 4 H), 3.50-3.32 (m, 2 H), 3.28-3.12 (m, 1 H), 2.31-1.86 (m, 8 H), 1.38-1.32 (m, 3 H) | 407 |
| 2-am | 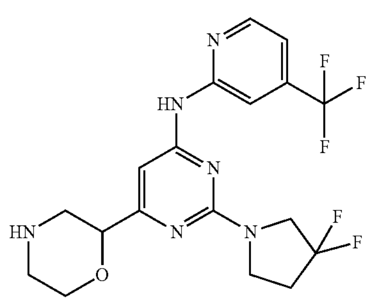 [SMILES: FC1(F)CCN(c2nc(Nc3cc(C(F)(F)F)ccn3)cc(C3CNCCO3)n2)C1] | ¹H NMR (400 MHz, MeOD) δ 8.61 (d, J = 5.2 Hz, 1 H), 8.35 (s, 1 H), 7.44 (d, J = 5.6 Hz, 1 H), 6.82 (s, 1 H), 4.32-4.25 (m, 1 H), 4.07-4.03 (m, 3 H), 3.97-3.93 (m, 2 H), 3.83-3.81 (m, 1 H), 3.40-3.35 (m, 3 H), 3.14-3.12 (m, 1 H), 2.65-2.61 (m, 2 H) | 431 |

TABLE 2-continued

| No. | Structure | ¹H NMR | MS (M + H)+ |
|---|---|---|---|
| 2-an | 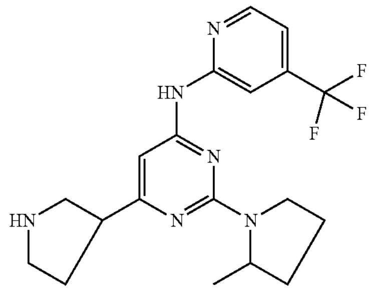 [SMILES: CC1CCCN1c1nc(Nc2cc(C(F)(F)F)ccn2)cc(C2CCNC2)n1] | ¹H NMR (400 MHz, MeOD) δ 8.58-8.56 (m, 2 H), 7.41 (d, J = 4.8 Hz, 1 H), 6.47-6.46 (br, 1 H), 4.90-4.80 (m, 1 H), 3.77-3.68 (m, 3 H), 3.57-3.50 (m, 2 H), 3.49-3.42 (m, 2 H), 2.52-2.49 (m, 1 H), 2.26-2.11 (m, 4 H), 1.87-1.82 (m, 1 H), 1.29-1.32 (m, 3 H). | 393 |
| 2-ao | 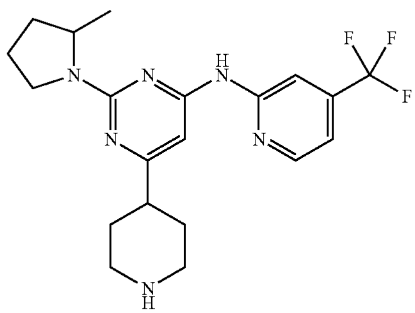 [SMILES: CC1CCCN1c1nc(Nc2cc(C(F)(F)F)ccn2)cc(C2CCNCC2)n1] | ¹H NMR (400 MHz, DMSO) δ 9.17-8.47 (m, 1H), 7.44-7.02 (m, 3H), 3.05-2.89 (m, 1H), 2.16-1.69 (m, 2H), 1.24 (d, J = 5.9 Hz, 1H). | 407.5 |
| 2-ap | 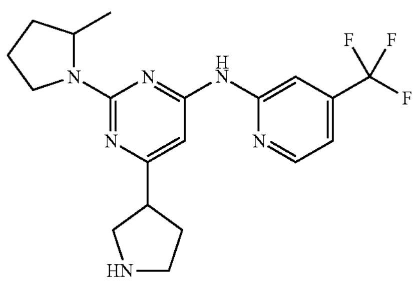 [SMILES: CC1CCCN1c1nc(Nc2cc(C(F)(F)F)ccn2)cc(C2CCNC2)n1] | ¹H NMR (400 MHz, DMSO-d₆) δ 10.20 (s, 1H), 8.83 (s, 1H), 8.51 (d, J = 5.1 Hz, 1H), 7.27 (d, J = 4.8 Hz, 1H), 6.33 (s, 1H), 4.22 (s, 1H), 3.67-3.37 (m, 1H), 3.30-3.00 (m, 3H), 2.28-1.65 (m, 6H), 1.22 (d, J = 6.2 Hz, 3H), 0.03--0.07 (m, 4H). | 393.4 |
| 2-aq | 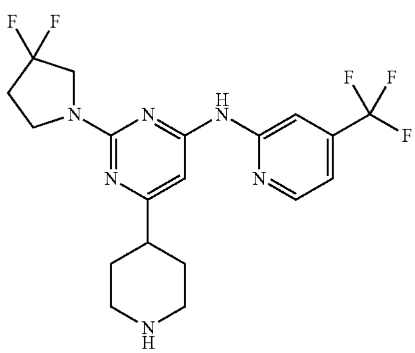 [SMILES: FC1(F)CCN(c2nc(Nc3cc(C(F)(F)F)ccn3)cc(C3CCNCC3)n2)C1] | ¹H NMR (400 MHz, DMSO) δ 10.29 (s, 1H), 8.71 (s, 1H), 8.52 (d, J = 5.1 Hz, 1H), 7.29 (d, J = 5.1 Hz, 1H), 6.48 (s, 1H), 3.89 (t, J = 13.2 Hz, 2H), 3.73 (t, J = 7.3 Hz, 2H), 3.06 (d, J = 12.1 Hz, 2H), 2.67-2.52 (m, 4H), 1.92-1.68 (m, 2H), 1.58 (qd, J = 12.4, 3.9 Hz, 2H). | 429.4 |
| 2-ar | 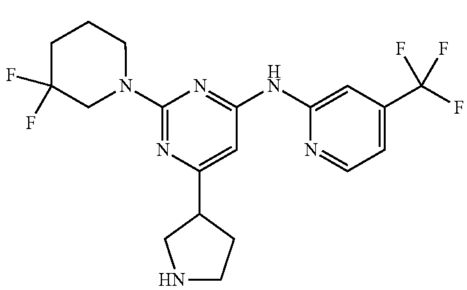 [SMILES: FC1(F)CCCN(c2nc(Nc3cc(C(F)(F)F)ccn3)cc(C3CCNC3)n2)C1] | ¹H NMR (400 MHz, DMSO) δ 10.34-10.24 (m, 1H), 8.61-8.30 (m, 2H), 7.28 (d, J = 5.1 Hz, 1H), 6.53 (d, J = 15.7 Hz, 1H), 4.07 (t, J = 12.1 Hz, 2H), 3.79 (s, 2H), 3.18-2.61 (m, 5H), 2.18-1.98 (m, 3H), 2.03-1.87 (m, 1H), 1.95-1.76 (m, 1H), 1.71 (s, 2H). | 429.4 |

TABLE 2-continued

| No. | Structure | ¹H NMR | MS (M + H)+ |
|---|---|---|---|
| 2-as | 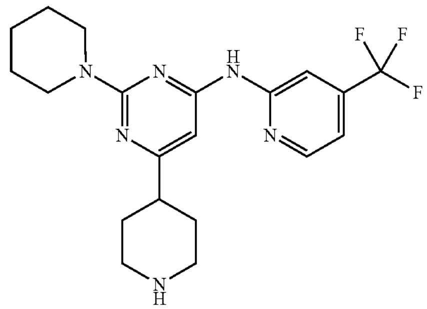 [SMILES: FC(F)(F)c1ccnc(Nc2cc(C3CCNCC3)nc(N3CCCCC3)n2)c1] | ¹H NMR (400 MHz, DMSO) δ 10.18 (s, 1H), 8.59-8.50 (m, 2H), 7.26 (d, J = 5.2 Hz, 1H), 6.37 (s, 1H), 3.80-3.67 (m, 4H), 3.14 (d, J = 12.3 Hz, 2H), 2.78-2.66 (m, 2H), 2.53 (dd, J = 7.7, 4.0 Hz, 1H), 1.80 (d, J = 11.6 Hz, 2H), 1.75-1.66 (m, 1H), 1.64-1.47 (m, 7H). | 407.5 |
| 2-at | 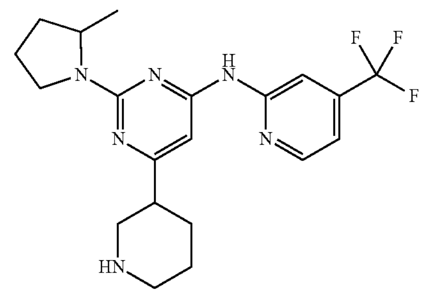 [SMILES: CC1CCCN1c1nc(Nc2cc(C(F)(F)F)ccn2)cc(C2CCCNC2)n1] | ¹H NMR (400 MHz, DMSO) δ 10.17 (s, 1H), 8.84 (s, 1H), 8.65-8.19 (m, 2H), 7.26 (d, J = 5.1 Hz, 1H), 6.29 (s, 1H), 4.28-4.08 (m, 2H), 3.30-2.60 (m, 7H), 2.09-1.81 (m, 5H), 1.22 (d, J = 6.2 Hz, 4H). | 407.5 |
| 2-au | 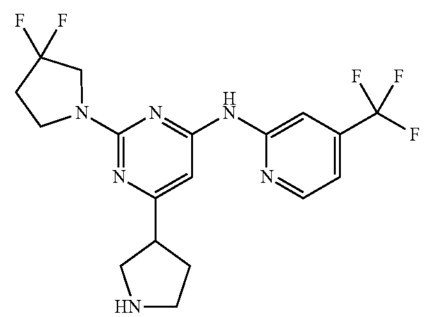 [SMILES: FC1(F)CCN(c2nc(Nc3cc(C(F)(F)F)ccn3)cc(C3CCNC3)n2)C1] | ¹H NMR (400 MHz, DMSO) δ 10.37 (s, 1H), 8.68 (s, 1H), 8.54 (d, J = 7.1 Hz, 1H), 8.36 (d, J = 18.6 Hz, 1H), 6.54 (s, 1H), 4.07-3.85 (m, 4H), 3.74 (t, J = 7.3 Hz, 4H), 2.63-2.53 (m, 2H), 2.24-2.10 (m, 2H), 1.97 (dt, J = 13.8, 7.1 Hz, 2H). | 415.4 |
| 2-av | 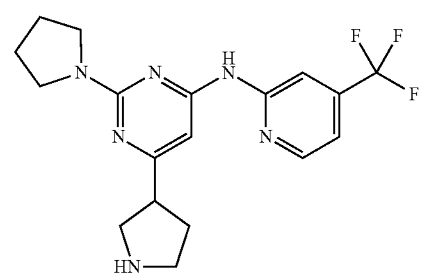 [SMILES: FC(F)(F)c1ccnc(Nc2cc(C3CCNC3)nc(N3CCCC3)n2)c1] | ¹H NMR (400 MHz, DMSO-d₆) δ 10.28 (s, 1H), 8.83 (s, 1H), 8.52 (d, J = 5.1 Hz, 1H), 7.28 (d, J = 5.3 Hz, 1H), 6.39 (s, 1H), 3.70-3.40 (m, 9H), 2.22 (dt, J = 13.2, 6.7 Hz, 1H), 2.06-1.96 (m, 2H), 1.94 (s, 4H). | 379.4 |
| 2-aw | 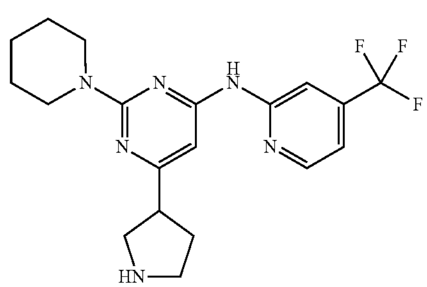 [SMILES: FC(F)(F)c1ccnc(Nc2cc(C3CCNC3)nc(N3CCCCC3)n2)c1] | ¹H NMR (400 MHz, DMSO) δ 10.17-10.12 (m, 1H), 8.63-8.42 (m, 2H), 7.25 (d, J = 5.0 Hz, 1H), 6.41 (d, J = 15.1 Hz, 1H), 3.79-3.62 (m, 4H), 3.14-2.66 (m, 5H), 2.11-1.76 (m, 2H), 1.68-1.44 (m, 6H). | 393.4 |

TABLE 2-continued

| No. | Structure | ¹H NMR | MS (M + H)+ |
|---|---|---|---|
| 2-ax | 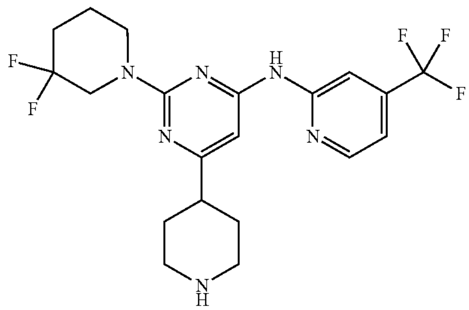 [SMILES: FC1(F)CCCN(c2nc(Nc3cc(C(F)(F)F)ccn3)cc(C3CCNCC3)n2)C1] | ¹H NMR (400 MHz, DMSO-d₆) δ 10.32 (s, 1H), 8.63-8.39 (d, J = 5.2 Hz, 1H), 8.31 (s, 1H), 7.30 (d, J = 5.2 Hz, 1H), 6.50 (s, 1H), 4.09 (t, J = 12.1 Hz, 3H), 3.81 (d, J = 5.0 Hz, 3H), 2.86 (t, J = 11.2 Hz, 3H), 2.67 (t, J = 11.6 Hz, 2H), 2.26-1.94 (m, 3H), 1.93-1.67 (m, 3H). | 443.4 |
| 2-ay | 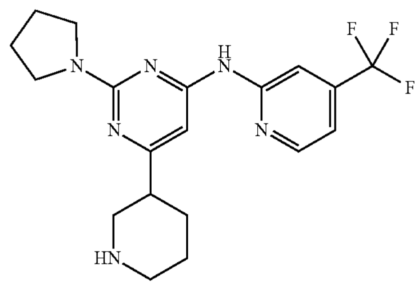 [SMILES: FC(F)(F)c1ccnc(Nc2cc(C3CCCNC3)nc(N3CCCC3)n2)c1] | ¹H NMR (400 MHz, DMSO-d₆) δ 10.18 (s, 1H), 8.85 (s, 1H), 8.50 (d, J = 5.1 Hz, 1H), 7.26 (d, J = 4.7 Hz, 1H), 6.32 (s, 1H), 3.19 (d, J = 12.4 Hz, 2H), 3.04 (s, 2H), 2.78 (t, J = 11.5 Hz, 1H), 2.64 (dd, J = 15.1, 6.7 Hz, 2H), 1.94 (s, 5H), 1.80-1.46 (m, 4H). | 393.4 |
| 2-az | 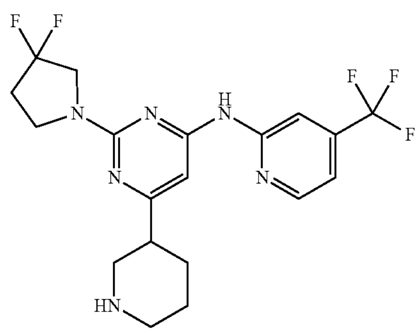 [SMILES: FC1(F)CCN(c2nc(Nc3cc(C(F)(F)F)ccn3)cc(C3CCCNC3)n2)C1] | ¹H NMR (400 MHz, DMSO) δ 10.29 (d, J = 17.8 Hz, 1H), 8.69 (s, 1H), 8.53 (d, J = 5.1 Hz, 1H), 7.29 (d, J = 5.1 Hz, 1H), 6.48 (s, 1H), 3.90 (t, J = 13.2 Hz, 3H), 3.73 (t, J = 7.3 Hz, 3H), 3.03 (d, J = 12.6 Hz, 2H), 2.82-2.56 (m, 4H), 1.92 (d, J = 13.7 Hz, 1H), 1.77-1.50 (m, 3H). | 429.4 |
| 2-ba | 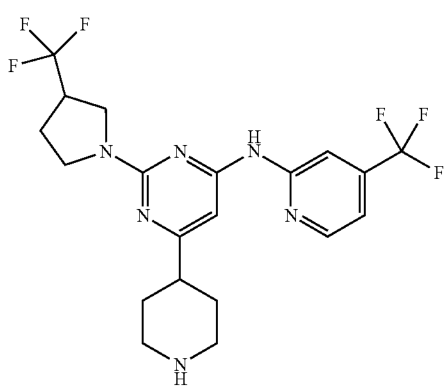 [SMILES: FC(F)(F)c1ccnc(Nc2cc(C3CCNCC3)nc(N3CCC(C(F)(F)F)C3)n2)c1] | ¹H NMR (400 MHz, DMSO) δ 10.35 (s, 1H), 8.86 (s, 1H), 8.79 (d, J = 5.1 Hz, 1H), 8.53 (d, J = 5.1 Hz, 1H), 6.42 (s, 1H), 3.88-3.76 (m, 2H), 3.06-2.91 (m, 4H), 2.83-2.69 (m, 2H), 2.36-2.32 (m, 2H), 2.19-2.03 (m, 2H), 2.04-1.74 (m, 4H). | 461.4 |

TABLE 2-continued

| No. | Structure | ¹H NMR | MS (M + H)+ |
|---|---|---|---|
| 2-bb | 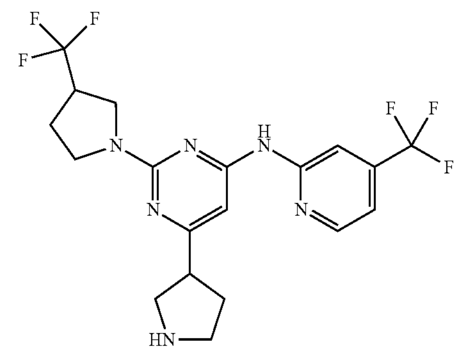 [SMILES: FC(F)(F)c1ccnc(Nc2cc(C3CCNC3)nc(N3CCC(C(F)(F)F)C3)n2)c1] | ¹H NMR (400 MHz, DMSO-d₆) δ 10.36 (s, 1H), 9.03-9.01 (m, 1H), 8.78 (s, 1H), 8.53 (d, J = 5.1 Hz, 1H), 8.23 (s, 1H), 7.30 (d, J = 5.1 Hz, 1H), 6.46 (s, 1H), 3.90-3.65 (m, 4H), 3.63-3.54 (m, 4H), 2.34-2.15 (m, 2H), 2.15-1.92 (m, 2H). | 447.4 |
| 2-bc | 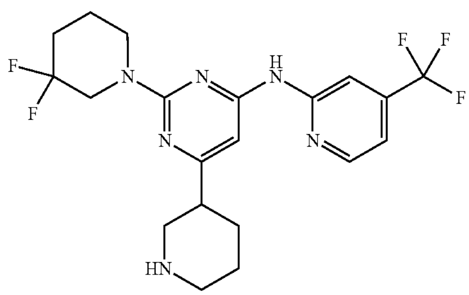 [SMILES: FC1(F)CCCN(c2nc(Nc3cc(C(F)(F)F)ccn3)cc(C3CCCNC3)n2)C1] | ¹H NMR (400 MHz, DMSO) δ 10.29 (s, 1H), 8.54 (d, J = 5.1 Hz, 1H), 8.45 (s, 1H), 7.30 (d, J = 6.1 Hz, 1H), 6.49 (s, 1H), 3.18 (d, J = 9.0 Hz, 2H), 3.05 (d, J = 12.2 Hz, 2H), 2.73 (t, J = 11.6 Hz, 1H), 2.67-2.57 (m, 2H), 2.09 (td, J = 13.9, 7.0 Hz, 3H), 1.92 (d, J = 11.0 Hz, 1H), 1.77-1.67 (m, 3H), 1.66-1.50 (m, 3H). | 443.4 |
| 2-bd | 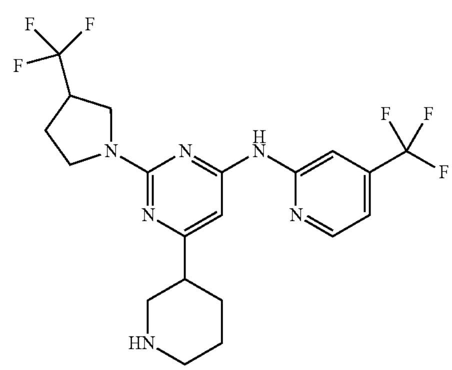 [SMILES: FC(F)(F)c1ccnc(Nc2cc(C3CCCNC3)nc(N3CCC(C(F)(F)F)C3)n2)c1] | ¹H NMR (400 MHz, DMSO) δ 10.27 (s, 1H), 8.79 (s, 1H), 8.52 (d, J = 5.1 Hz, 1H), 8.37 (s, 1H), 7.28 (d, J = 5.1 Hz, 1H), 6.39 (s, 1H), 3.17 (d, J = 11.5 Hz, 2H), 3.03 (d, J = 12.5 Hz, 2H), 2.77-2.56 (m, 4H), 2.28 (dd, J = 18.8, 11.2 Hz, 2H), 2.15-2.05 (m, 1H), 1.92 (d, J = 11.7 Hz, 1H), 1.76-1.47 (m, 4H). | 461.4 |
| 2-be | 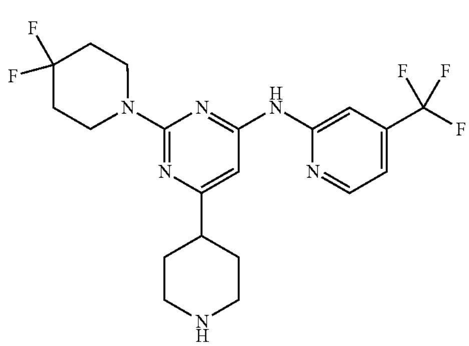 [SMILES: FC1(F)CCN(c2nc(Nc3cc(C(F)(F)F)ccn3)cc(C3CCNCC3)n2)CC1] | ¹H NMR (400 MHz, DMSO-d₆) δ 10.31 (s, 1H), 8.56 (d, J = 17.8 Hz, 1H), 8.40 (s, 1H), 7.29 (d, J = 5.0 Hz, 1H), 6.57 (s, 1H), 3.89 (d, J = 4.5 Hz, 3H), 3.21 (s, 2H), 2.84 (t, J = 11.3 Hz, 2H), 2.66 (dd, J = 13.5, 9.6 Hz, 1H), 2.06-1.67 (m, 9H). | 443.4 |

TABLE 2-continued

| No. | Structure | ¹H NMR | MS (M + H)+ |
|---|---|---|---|
| 2-bf | 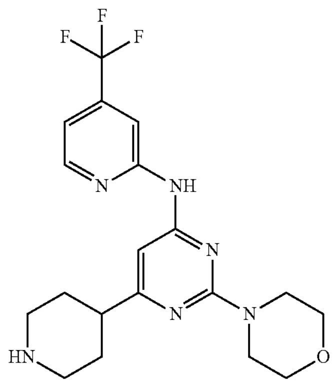 [SMILES: FC(F)(F)c1ccnc(Nc2cc(C3CCNCC3)nc(N3CCOCC3)n2)c1] | ¹H NMR (400 MHz, DMSO) δ 10.27 (s, 1H), 8.54-8.42 (m, 3H), 7.28 (d, J = 5.2 Hz, 1H), 6.52 (s, 1H), 3.19 (d, J = 12.8 Hz, 2H), 2.78 (dd, J = 12.3, 10.3 Hz, 2H), 2.68-2.56 (m, 1H), 1.85 (d, J = 11.6 Hz, 2H), 1.71 (qd, J = 12.7, 3.7 Hz, 2H). | 490.4 |
| 2-bg | 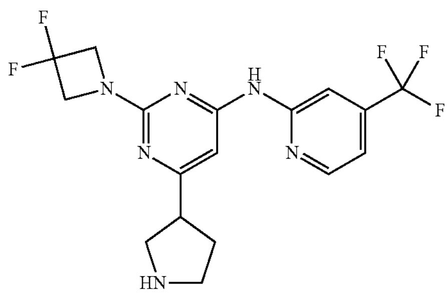 [SMILES: FC1(F)CN(c2nc(Nc3cc(C(F)(F)F)ccn3)cc(C3CCNC3)n2)C1] | ¹H NMR (400 MHz, DMSO-d$_6$) δ 10.34 (s, 1H), 8.59-8.43 (m, 2H), 7.29 (d, J = 5.0 Hz, 1H), 6.79 (d, J = 18.5 Hz, 1H), 4.42 (t, J = 12.5 Hz, 4H), 3.11-2.72 (m, 5H), 2.07-1.76 (m, 2H). | 401.4 |
| 2-bh | 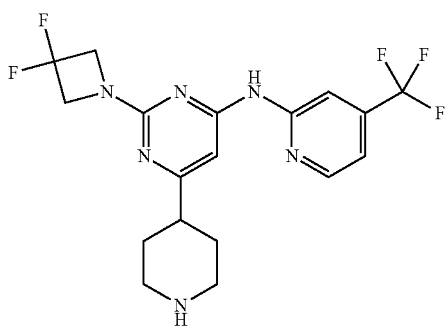 [SMILES: FC1(F)CN(c2nc(Nc3cc(C(F)(F)F)ccn3)cc(C3CCNCC3)n2)C1] | ¹H NMR (400 MHz, DMSO-d$_6$) δ 10.45 (s, 1H), 8.58-8.40 (m, 2H), 8.24 (s, 1H), 7.31 (d, J = 5.0 Hz, 1H), 6.76 (s, 1H), 4.44 (t, J = 12.4 Hz, 4H), 3.01-2.61 (m, 4H), 1.99-1.65 (m, 4H). | 415.4 |
| 2-bi | 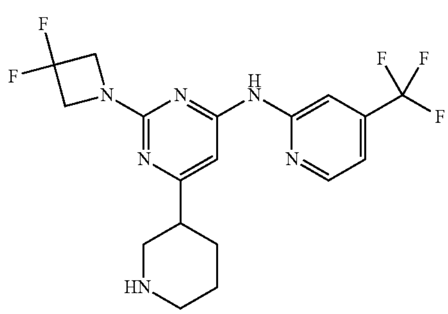 [SMILES: FC1(F)CN(c2nc(Nc3cc(C(F)(F)F)ccn3)cc(C3CCCNC3)n2)C1] | ¹H NMR (400 MHz, DMSO) δ 10.48 (s, 1H), 8.55 (d, J = 5.2 Hz, 1H), 8.45 (s, 1H), 6.79 (s, 1H), 4.45 (t, J = 12.4 Hz, 5H), 3.03-2.79 (m, 4H), 2.04-1.57 (m, 5H). | 415.4 |

Example 3

Preparation of (R)-1-(4-(2-(2-methylpyrrolidin-1-yl)-6-(4-(trifluoromethyl)pyridin-2-ylamino)pyrimidin-4-yl)piperidin-1-yl)ethanone (3-a)

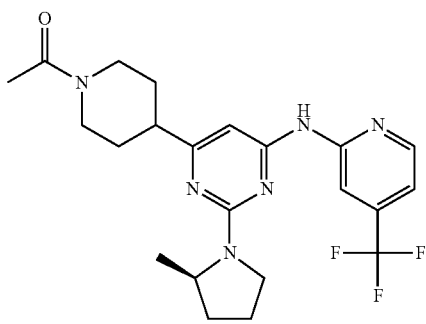

To a cool (0° C.) solution of example 2-c (1.97 mmol), 4-(dimethylamino)pyridine (49 mg, 0.40 mmol) and N,N-diisopropylethylamine (1.72 mL, 9.90 mmol) in acetonitrile (10 ml) and dichloromethane (10 mL) was added acetic anhydride (0.211 mL, 2.17 mmol). The solution was maintained for at 0° C. for 1 h, then poured into 100 mL of sat. aqueous NH$_4$Cl, and extracted with ethyl acetate (3×20 mL). The combined organic phases were washed brine (1×10 mL), dried (Na$_2$SO$_4$), filtered and concentrated to a colorless solid. Purification by HPLC afforded 430 mg (49%) of the title compound as a colorless solid: $^1$H NMR (400 MHz, CDCl$_3$) δ 8.83 (s, 1H), 8.37 (d, J=5.2 Hz, 1H), 7.24 (s, 1H), 7.09 (d, J=5.1 Hz, 1H), 5.90 (d, J=30.7 Hz, 1H), 4.70 (d, J=12.6 Hz, 1H), 4.39-4.22 (m, 1H), 3.91 (d, J=13.5 Hz, 1H), 3.67 (ddd, J=10.2, 7.3, 3.1 Hz, 1H), 3.62-3.44 (m, 1H), 3.25-3.08 (m, 1H), 2.79-2.50 (m, 2H), 2.13 (s, 3H), 2.07 (ddd, J=13.5, 9.1, 4.4 Hz, 2H), 2.01-1.82 (m, 3H), 1.82-1.62 (m, 3H), 1.28 (d, J=6.3 Hz, 3H); MS m/z=449 (M+H$^+$).

Additional compounds of the invention presented in Table 3 below were prepared by methods already described in the application

TABLE 3

| No. | Structure | $^1$H NMR | MS (M + H)+ |
|---|---|---|---|
| 3-b | 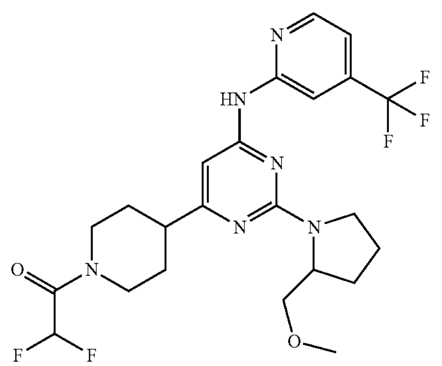 [SMILES: COCC1CCCN1c1nc(Nc2cc(C(F)(F)F)ccn2)cc(C2CCN(C(=O)C(F)F)CC2)n1] | $^1$H NMR (400 MHz, CDCl$_3$) δ 8.72 (bs, 1H), 8.38 (d, J = 5.2 Hz, 1H), 7.28 (s, 1H), 7.10 (d, J = 5.1 Hz, 1H), 6.13 (t, J = 53.8 Hz, 1H), 5.98 (s, 1H), 4.57 (d, J = 13.4 Hz, 1H), 4.34 (s, 1H), 4.19 (d, J = 13.6 Hz, 1H), 3.70-3.61 (m, 2H), 3.56 (dd, J = 18.3, 7.7 Hz, 1H), 3.44 (s, 1H), 3.35 (s, 3H), 3.23 (t, J = 12.8 Hz, 1H), 2.89 (t, J = 12.4 Hz, 1H), 2.72 (tt, J = 11.2, 3.8 Hz, 1H), 2.15-1.73 (m, 8H). | 515 |
| 3-c | 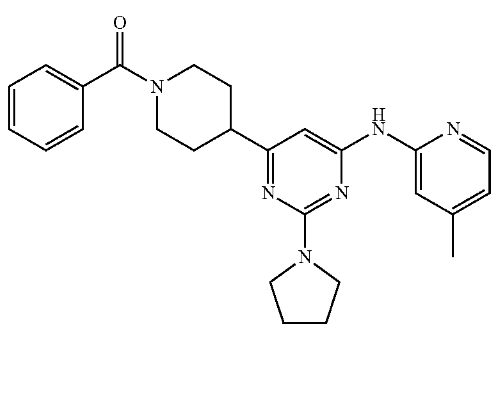 [SMILES: Cc1ccnc(Nc2cc(C3CCN(C(=O)c4ccccc4)CC3)nc(N3CCCC3)n2)c1] | H NMR (400 MHz, MeOD) δ 8.54 (d, J = 8.0 Hz, 1 H), 7.69 (s, 1 H), 7.57 (d, J = 6.4 Hz, 1 H), 7.52-7.48 (m, 5 H), 6.55 (s, 1 H), 3.93-3.77 (m, 5 H), 3.27-3.24 (m, 3 H), 3.02 (br, 1 H), 2.67 (s, 3 H), 2.21-2.04 (m, 6 H), 1.81-1.70 (m, 2 H). | 443 |

TABLE 3-continued

| No. | Structure | ¹H NMR | MS (M + H)+ |
|---|---|---|---|
| 3-d | 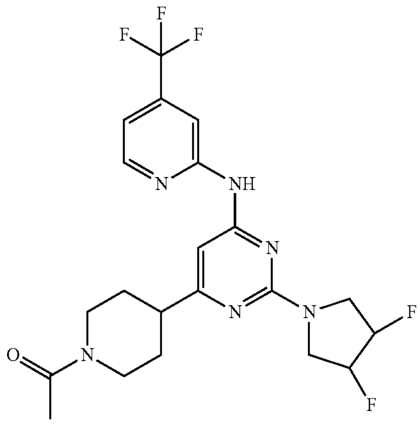 [SMILES: CC(=O)N1CCC(c2cc(Nc3cc(C(F)(F)F)ccn3)nc(N3CC(F)C(F)C3)n2)CC1] | ¹H NMR (400 MHz, DMSO-d₆) δ 10.27 (s, 1H), 8.67 (s, 1H), 8.53 (d, J = 5.1 Hz, 1H), 7.29 (d, J = 5.1 Hz, 1H), 6.52 (s, 1H), 5.54 (s, 1H), 5.41 (s, 1H), 4.47 (d, J = 12.8 Hz, 1H), 3.97-3.68 (m, 5H), 3.14 (t, J = 12.3 Hz, 1H), 2.72-2.57 (m, 2H), 2.02 (s, 3H), 1.84 (t, J = 14.3 Hz, 2H), 1.68-1.42 (m, 2H). | 471 |
| 3-e | 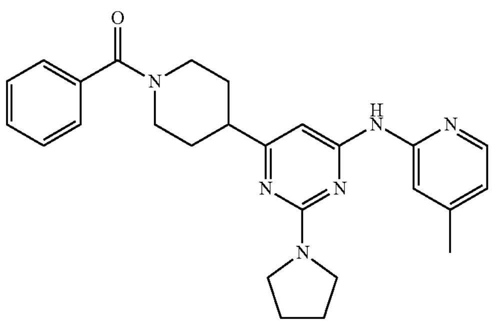 [SMILES: Cc1ccnc(Nc2cc(C3CCN(C(=O)c4ccccc4)CC3)nc(N3CCCC3)n2)c1] | ¹H NMR (400 MHz, CDCl₃) δ 8.08-7.93 (m, 2 H), 7.40 (s, 5 H), 6.74 (d, J = 4.8 Hz, 1 H), 6.23-6.07 (m, 1 H), 4.80-4.71 (m, 1 H), 3.95-3.73 (m, 1 H), 3.61-3.48 (m, 4 H), 3.26-3.08 (m, 1 H), 2.82-2.60 (m, 1H), 2.34 (s, 3 H), 2.17-2.10 (m, 1 H), 2.07-1.97 (m, 6 H), 1.70-1.56 (m, 2 H) | 443 |
| 3-f | 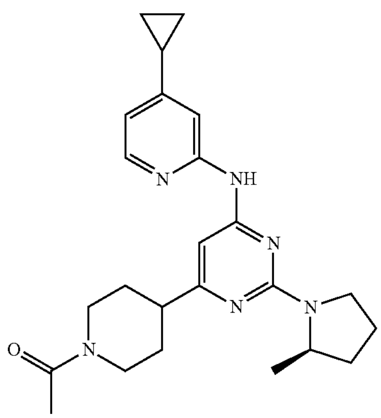 [SMILES: CC(=O)N1CCC(c2cc(Nc3cc(C4CC4)ccn3)nc(N3CCC[C@H]3C)n2)CC1] | ¹H NMR (400 MHz, DMSO-d₆) δ 9.46 (s, 1H), 8.04 (d, J = 5.2 Hz, 1H), 7.99 (s, 1H), 6.68 (d, J = 5.0 Hz, 1H), 6.34 (s, 1H), 4.44 (d, J = 12.8 Hz, 1H), 4.26-4.16 (m, 1H), 3.88 (d, J = 12.8 Hz, 1H), 3.62-3.43 (m, 2H), 3.12 (t, J = 12.0 Hz, 1H), 2.69-2.52 (m, 2H), 2.10-1.94 (m, 5H), 1.92-1.73 (m, 4H), 1.70-1.39 (m, 3H), 1.24 (d, J = 6.1 Hz, 3H), 1.09-1.02 (m, 2H), 0.79-0.73 (m, 2H). | 421 |
| 3-g | 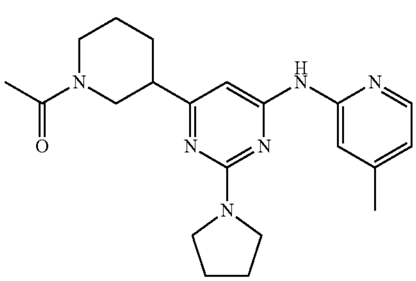 [SMILES: CC(=O)N1CCCC(c2cc(Nc3cc(C)ccn3)nc(N3CCCC3)n2)C1] | ¹H NMR (400 MHz, CDCl₃) δ 8.07-8.04 (m, 2 H), 6.76-6.73 (m, 1 H), 6.21-6.16 (m, 1 H), 4.72-4.54 (m, 1 H), 3.96-3.77 (m, 1 H), 3.60-3.58 (m, 4 H), 3.36-3.29 (m, 1 H), 3.11-2.82 (m, 1 H), 2.68-2.55 (m, 1 H), 2.36 (d, J = 3.2 Hz, 3 H), 2.11 (s, 3 H), 2.01-1.96 (m, 5 H), 1.87-1.80 (m, 2 H), 1.65-1.55 (m, 1 H) | 381 |

TABLE 3-continued

| No. | Structure | ¹H NMR | MS (M + H)+ |
|---|---|---|---|
| 3-h | 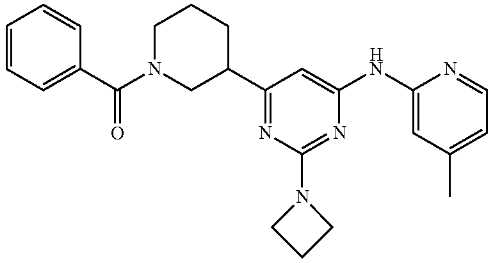 [SMILES: Cc1ccnc(Nc2cc(C3CCCN(C(=O)c4ccccc4)C3)nc(N3CCC3)n2)c1] | ¹H NMR (400 MHz, MeOD), δ ppm: 8.08-8.07 (m, 1H), 7.81-7.75 (m, 1H), 7.40-7.31 (m, 6H), 6.76-6.75 (m, 1H), 6.40-6.26 (m, 1H), 4.80-4.60 (m, 1H), 4.20-4.06 (m, 4H), 3.92-3.74 (m, 1H), 3.25-3.11 (m, 1H), 2.85-2.60 (m, 1H), 2.30-2.20 (m, 4H), 2.10-2.00 (m, 2H), 1.90-1.60 (m, 4 H). | 429 |
| 3-i | 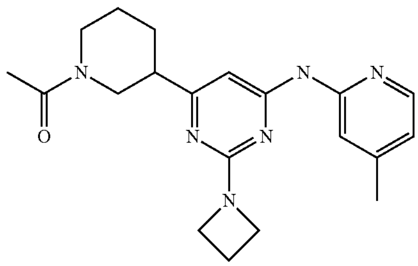 [SMILES: CC(=O)N1CCCC(c2cc(Nc3cc(C)ccn3)nc(N3CCC3)n2)C1] | ¹H NMR (400 MHz, MeOD) δ 8.44 (d, J = 6.4 Hz, 1 H), 7.59 (s, 1 H), 7.52-7.51 (m, 1 H), 6.40 (s, 1 H), 4.72-4.69 (m, 1 H), 4.50 (t, J = 8.0 Hz, 4 H), 4.12-4.08 (m, 1 H), 4.29-4.24 (m, 1 H), 3.02 (m, 1 H), 2.75-2.71 (m, 1 H), 2.62 (s, 3 H), 2.60-2.54 (m, 2 H), 2.14 (s, 3 H), 2.09-2.00 (m, 2 H), 1.74-1.59 (m, 2 H) | 367 |
| 3-j | 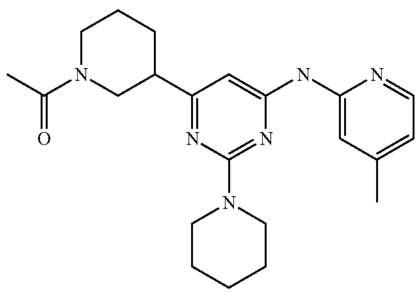 [SMILES: CC(=O)N1CCCC(c2cc(Nc3cc(C)ccn3)nc(N3CCCCC3)n2)C1] | ¹H NMR (400 MHz, CDCl₃) δ 8.05 (t, J = 5.2 Hz, 1H), 7.86-7.82 (d, J = 16.0 Hz, 1H), 6.74 (t, J = 6.0 Hz, 1 H), 6.25-6.19 (m, 1 H), 4.72-4.53 (m, 1 H), 3.93-3.89 (m, 1 H), 3.78 (m, 4 H), 3.33-3.04 (m, 1 H), 2.86-2.80 (m, 1 H), 2.67-2.54 (m, 2 H), 2.34 (s, 3 H), 2.10 (s, 3 H), 2.01-1.81 (m, 1 H), 1.78-1.75 (m, 2 H), 1.67-1.65 (m, 6 H) | 395 |
| 3-k | 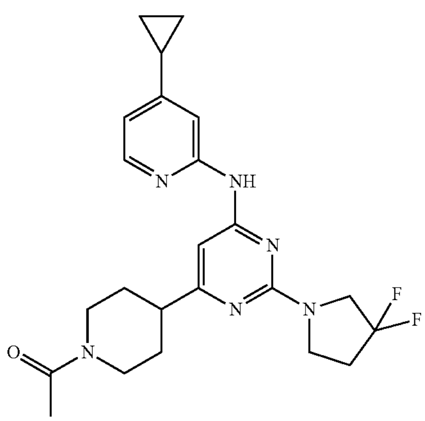 [SMILES: CC(=O)N1CCC(c2cc(Nc3cc(C4CC4)ccn3)nc(N3CCC(F)(F)C3)n2)CC1] | ¹H NMR (400 MHz, DMSO-d₆) δ 9.67 (s, 1H), 8.07 (d, J = 5.2 Hz, 1H), 7.82 (s, 1H), 6.73 (d, J = 5.1 Hz, 1H), 6.54 (s, 1H), 4.46 (d, J = 13.2 Hz, 1H), 3.91 (t, J = 13.3 Hz, 3H), 3.74 (t, J = 7.3 Hz, 2H), 3.12 (t, J = 11.8 Hz, 1H), 2.68-2.51 (m, 4H), 2.02 (s, 3H), 1.95-1.75 (m, 3H), 1.66-1.53 (m, 1H), 1.53-1.39 (m, 1H), 1.10-1.03 (m, 2H), 0.80-0.73 (m, 2H). | 443 |
| 3-l | 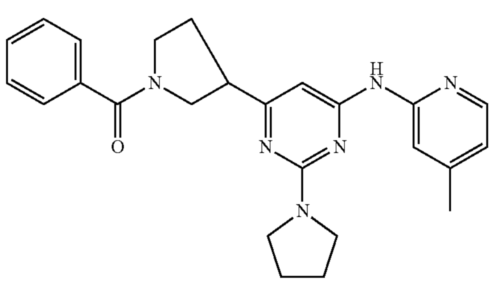 [SMILES: Cc1ccnc(Nc2cc(C3CCN(C(=O)c4ccccc4)C3)nc(N3CCCC3)n2)c1] | ¹H NMR (400 MHz, MeOD) δ 8.10 (m, 1 H), 7.75-7.65 (m, 1 H), 7.55-7.53 (m, 2 H), 7.47-7.44 (m, 3 H), 6.91 (br, 1 H), 6.45-6.33 (m, 1 H), 3.96-3.92 (m, 1 H), 3.80-3.77 (m, 1 H), 3.70-3.65 (m, 1 H), 3.63-3.57 (m, 6 H), 2.39 (d, J = 7.2 Hz, 3 H), 2.35-2.15 (m, 2 H), 2.05-1.99 (m, 4 H) | 429 |

TABLE 3-continued

| No. | Structure | ¹H NMR | MS (M + H)+ |
|---|---|---|---|
| 3-m | 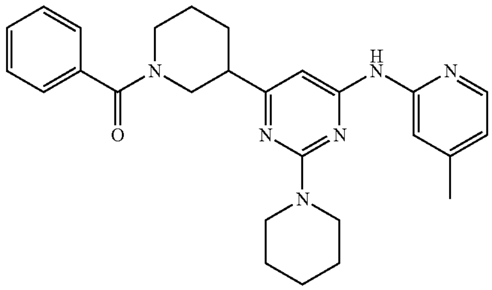 [SMILES: Cc1ccnc(Nc2cc(C3CCCN(C(=O)c4ccccc4)C3)nc(N3CCCCC3)n2)c1] | ¹H NMR (400 MHz, MeOD), δ ppm: 8.45 (s, 1H), 7.66 (s, 1H), 7.47-7.41 (m, 6H), 6.58-6.37 (m, 1H), 4.73-4.55 (m, 1H), 3.94-3.70 (m, 5H), 3.29-3.06 (m, 2H), 2.62 (s, 3H), 2.24-2.21 (m, 1H), 2.04-1.90 (m, 10H) | 457 |
| 3-n | 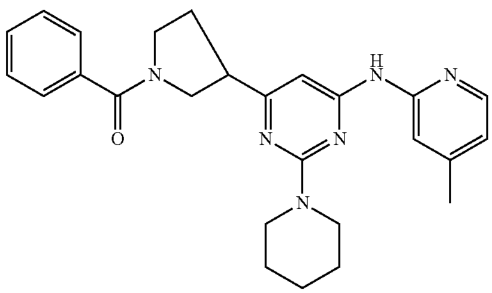 [SMILES: Cc1ccnc(Nc2cc(C3CCN(C(=O)c4ccccc4)C3)nc(N3CCCCC3)n2)c1] | ¹H NMR (400 MHz, MeOD) δ 8.15-8.10 (m, 1 H), 7.70-7.65 (m, 1 H), 7.55-7.52 (m, 2 H), 7.47-7.46 (m, 3 H), 6.90 (br, 1 H), 6.45-6.35 (m, 1 H), 3.90 (s, 1 H), 3.83-3.81 (m, 2 H), 3.77-3.74 (m, 3 H), 3.70-3.60 (m, 2 H), 3.50-3.40 (m, 1 H), 2.37 (d, J = 7.2 Hz, 3 H), 2.30-2.15 (m, 2 H), 1.70-1.65 (m, 2 H), 1.63-1.59 (m, 4 H) | 443 |
| 3-o | 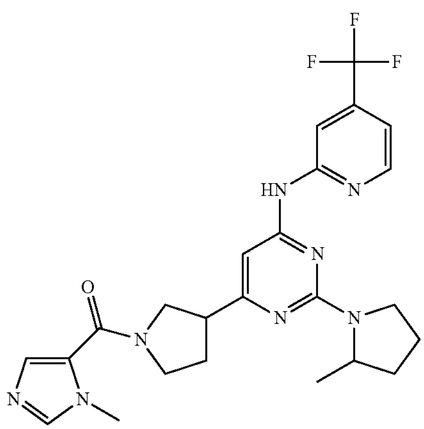 [SMILES: CC1CCCN1c1nc(Nc2cc(C(F)(F)F)ccn2)cc(C2CCN(C(=O)c3cncn3C)C2)n1] | ¹H NMR (400 MHz, MeOD), δ ppm: 8.87 (d, J = 5.6 Hz, 1H), 8.41 (d, J = 5.2 Hz, 1H), 7.76 (s, 1H), 7.47 (d, J = 3.6 Hz, 1H), 7.16 (d, J = 4.8 Hz, 1H), 6.25 (d, J = 13.2 Hz, 1H), 4.58 (s, 2H), 4.30 (s, 1H), 4.10-4.03 (m, 1H), 3.91-3.85 (m, 3H), 3.70-3.38 (m, 4H), 2.25-2.42 (m, 2H), 2.15-2.10 (m, 2H), 2.03-1.90 (m, 1H), 1.70 (s, 1H), 1.35-1.24 (m, 3H) | 501 |
| 3-p | 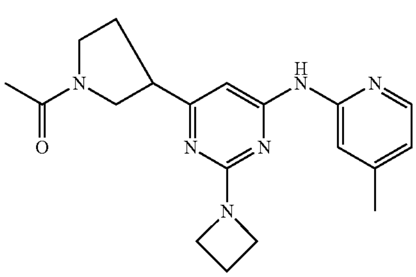 [SMILES: CC(=O)N1CCC(c2cc(Nc3cc(C)ccn3)nc(N3CCC3)n2)C1] | ¹H NMR (400 MHz, CDCl₃), δ ppm: 8.04-7.96 (m, 2H), 6.78-6.76 (m, 1H), 6.37-6.32 (m, 1H), 4.68-4.50 (m, 1H), 4.17-4.14 (m, 4H), 3.91-3.76 (m, 1H), 3.36-3.09 (m, 1H), 2.88-2.60 (m, 2H), 2.48-2.35 (m, 5H), 2.11 (s, 3H), 2.04-1.99 (m, 1H), 1.81-1.80 (m, 2H), 1.60-1.50 (m, 1H) | 367 |
| 3-q | 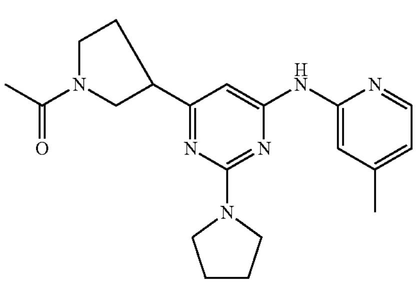 [SMILES: CC(=O)N1CCC(c2cc(Nc3cc(C)ccn3)nc(N3CCCC3)n2)C1] | ¹H NMR (400 MHz, CDCl₃), δ ppm: 8.05-8.03 (m, 1H), 7.98-7.96 (m, 1H), 6.78-6.75 (m, 1H), 6.40-6.35 (m, 1H), 4.16-4.11 (m, 4H), 3.85-3.82 (m, 1H), 3.76-3.65 (m, 3H), 3.51-3.47 (m, 1H), 3.32-3.23 (m, 1H), 2.38-2.32 (m, 4H), 2.19-2.18 (m, 1H), 2.17-2.14 (m, 1H), 2.07 (s, 3H) | 353 |

TABLE 3-continued

| No. | Structure | ¹H NMR | MS (M + H)+ |
|---|---|---|---|
| 3-r | 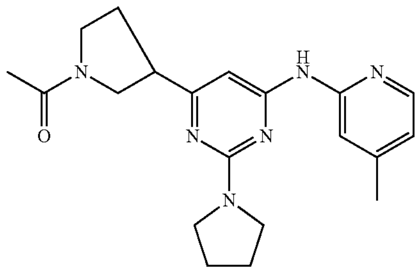 [SMILES: CC(=O)N1CCC(c2cc(Nc3cc(C)ccn3)nc(N3CCCC3)n2)C1] | ¹H NMR (400 MHz, MeOD) δ 8.14-8.12 (m, 1 H), 7.82-7.75 (m, 1 H), 6.93 (br, 1 H), 6.39 (d, J = 6.8 Hz, 1 H), 3.90-3.78 (m, 2 H), 3.68-3.65 (m, 1 H), 3.64-3.62 (m, 4 H), 3.50-3.40 (m, 1 H), 3.35-3.30 (m, 1 H), 2.40 (s, 3 H), 2.39-2.28 (m, 2 H), 2.09 (d, J = 4.0 Hz, 3 H), 2.05-2.01 (m, 4 H) | 367 |
| 3-s | 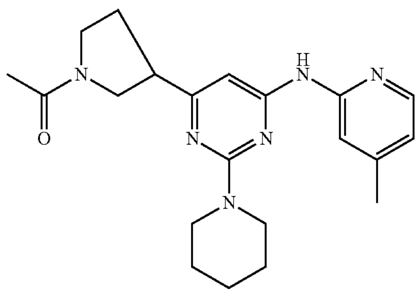 [SMILES: CC(=O)N1CCC(c2cc(Nc3cc(C)ccn3)nc(N3CCCCC3)n2)C1] | ¹H NMR (400 MHz, MeOD) δ 8.16-8.13 (m, 1 H), 7.60-7.55 (m, 1 H), 6.97 (br, 1 H), 6.40 (d, J = 6.8 Hz, 1 H), 3.82-3.74 (m, 4 H), 3.69-3.67 (m, 1 H), 3.63-3.60 (m, 2 H), 3.36-3.30 (m, 2 H), 2.41 (s, 3 H), 2.40-2.10 (m, 2 H), 2.09 (d, J = 4.0 Hz, 3 H), 1.73-1.72 (m, 2 H), 1.64-1.63 (m, 4 H) | 381 |
| 3-t | 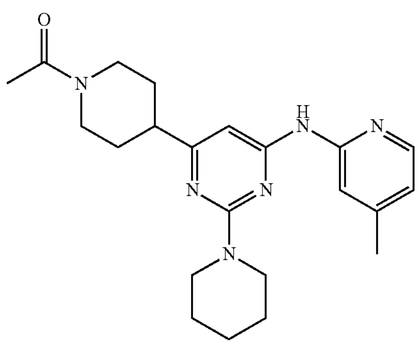 [SMILES: CC(=O)N1CCC(c2cc(Nc3cc(C)ccn3)nc(N3CCCCC3)n2)CC1] | ¹H NMR (400 MHz, MeOD) δ 8.43 (d, J = 6.4 Hz, 1 H), 7.62 (s, 1 H), 7.49-7.47 (m, 1 H), 6.43 (s, 1 H), 4.77-4.67 (m, 1 H), 4.11-4.07 (m, 1 H), 3.86-3.85 (m, 4 H), 3.29-3.09 (m, 2 H), 2.76-2.70 (m, 1 H), 2.64 (s, 3 H), 2.14 (s, 3 H), 2.13-2.04 (m, 2 H), 1.80-1.70 (m, 7 H), 1.65-1.55 (m, 1H) | 395 |
| 3-u | 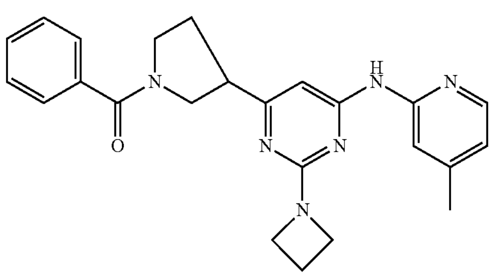 [SMILES: Cc1ccnc(Nc2cc(C3CCN(C(=O)c4ccccc4)C3)nc(N3CCC3)n2)c1] | ¹H NMR (400 MHz, CDCl₃) δ 8.02-7.99 (m, 1H), 7.60-7.70 (m, 1H), 7.48-7.46 (m, 2H), 7.34-7.30 (m, 3H), 6.68-6.60 (m, 1H), 6.39-6.30 (m, 1H), 4.12-3.90 (m, 5H), 3.85-3.75 (m, 1H), 3.68-3.55 (m, 3H), 3.30-3.10 (m, 1H), 2.30-2.21 (m, 6H) | 415 |
| 3-v | 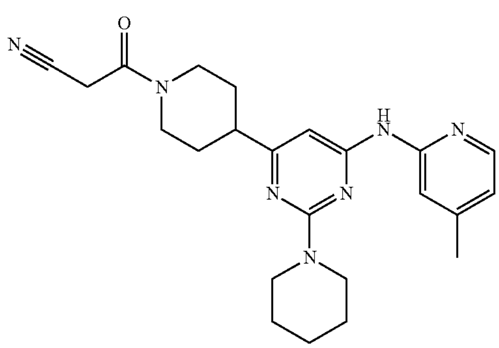 [SMILES: Cc1ccnc(Nc2cc(C3CCN(C(=O)CC#N)CC3)nc(N3CCCCC3)n2)c1] | ¹H NMR (400 MHz, MeOD), δ ppm: 8.45-8.42 (m, 1H), 7.62 (s, 1H), 7.50-7.48 (m, 1H), 6.43-6.17 (m, 1H), 4.72-4.63 (m, 1H), 4.01-3.67 (m, 7H), 3.27-3.29 (m, 1H), 3.24-3.11 (m, 1H), 2.83-2.77 (m, 1H), 2.61 (s, 3H), 2.09-2.04 (m, 2H), 1.85-1.70 (m, 7H), 1.68-1.60 (m, 1H) | 420 |

TABLE 3-continued

| No. | Structure | ¹H NMR | MS (M + H)+ |
|---|---|---|---|
| 3-w | 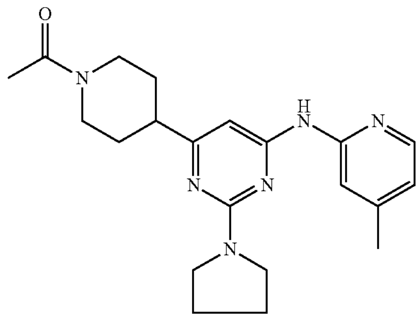 [SMILES: CC(=O)N1CCC(c2cc(Nc3cc(C)ccn3)nc(N3CCCC3)n2)CC1] | ¹H NMR (400 MHz, MeOD) δ 8.48 (d, J = 6.4 Hz, 1 H), 7.60 (s, 1 H), 7.51 (d, J = 6.4 Hz, 1 H), 6.43 (s, 1 H), 4.73-4.69 (m, 1 H), 4.12-4.08 (m, 1 H), 3.87 (s, 2 H), 3.72 (s, 2 H), 3.25-3.10 (m, 1 H), 2.81-2.65 (m, 1 H), 2.62 (s, 3 H), 2.17-2.09 (m, 10 H), 2.08-2.03 (m, 2 H). | 381 |
| 3-x | 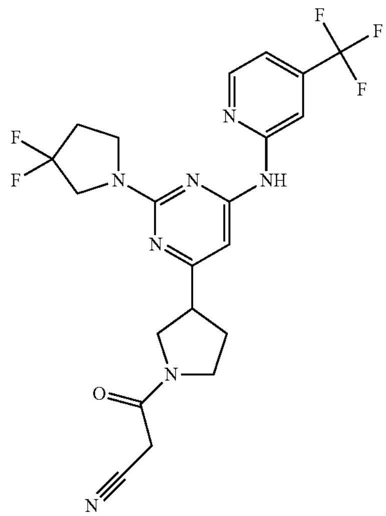 [SMILES: N#CCC(=O)N1CCC(c2cc(Nc3cc(C(F)(F)F)ccn3)nc(N3CCC(F)(F)C3)n2)C1] | ¹H NMR (400 MHz, MeOD), δ ppm: 8.58-8.56 (m, 1H), 8.47 (br, 1H), 7.39-7.36 (m, 1H), 6.66 (br, 1H), 4.08-4.01 (m, 2H), 3.96-3.83 (m, 3H), 3.77 (s, 2H), 3.76-3.70 (m, 1H), 3.69-3.51 (m, 3H), 2.67-2.60 (m, 2H), 2.58-2.30 (m, 1H), 2.29-2.16 (m, 1H). | 482 |
| 3-y | 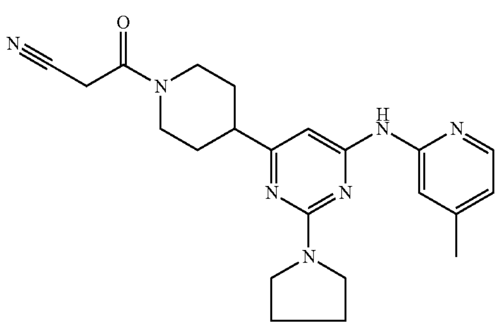 [SMILES: Cc1ccnc(Nc2cc(C3CCN(C(=O)CC#N)CC3)nc(N3CCCC3)n2)c1] | ¹H NMR (400 MHz, MeOD) δ 8.54 (d, J = 6.4 Hz, 1 H), 7.67-7.58 (m, 2 H), 6.47 (s, 1 H), 4.78 (d, J = 8.4 Hz, 1 H), 4.16-3.76 (m, 5 H), 3.34-3.20 (m, 3 H), 2.91-2.79 (m, 1 H), 2.68 (s, 4 H), 2.23-2.14 (m, 6 H), 1.87-1.84 (m, 2 H). | 406 |
| 3-z | 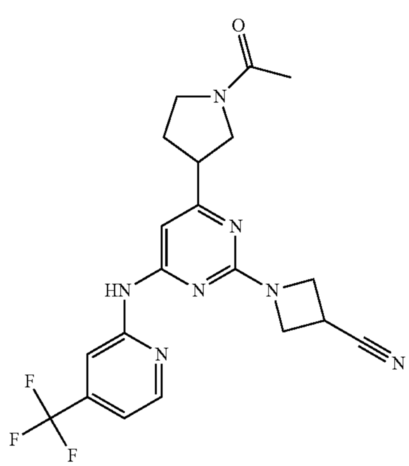 [SMILES: CC(=O)N1CCC(c2cc(Nc3cc(C(F)(F)F)ccn3)nc(N3CC(C#N)C3)n2)C1] | ¹H NMR (400 MHz, MeOD) δ 8.55 (s, 1 H), 8.46 (d, J = 5.2 Hz, 1 H), 7.21 (d, J = 5.2 Hz, 1 H), 6.61 (d, J = 7.2 Hz, 1 H), 4.43 (t, J = 8.4 Hz, 2 H), 4.26 (t, J = 6.4 Hz, 2 H), 3.32-3.88 (m, 6 H), 2.28-2.38 (m, 2 H), 2.27 (s, 3 H). | 432 |

TABLE 3-continued

| No. | Structure | ¹H NMR | MS (M + H)+ |
|---|---|---|---|
| 3-aa | 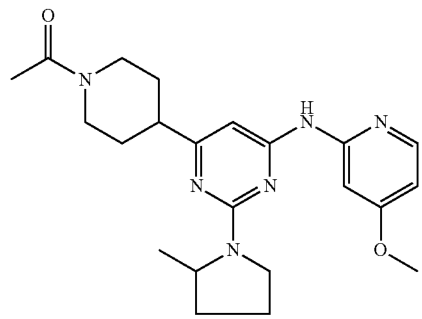 [SMILES: COc1ccnc(Nc2cc(C3CCN(C(C)=O)CC3)nc(N3CCCC3C)n2)c1] | ¹H NMR (400 MHz, MeOD) δ 8.48 (d, J = 7.2 Hz, 1 H), 7.32-7.25 (m, 2 H), 6.47 (s, 1 H), 4.80-4.34 (m, 2 H), 4.16-3.64 (m, 6 H), 3.34-3.16 (m, 2 H), 2.80-2.68 (m, 2 H), 2.34-1.82 (m, 11 H), 1.47 (s, 3H). | 411 |
| 3-ab | 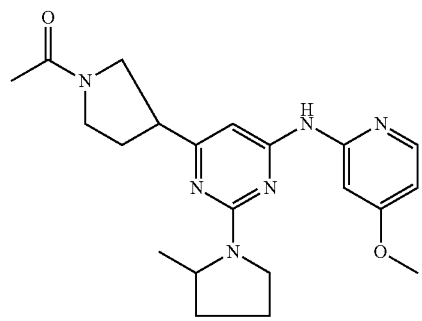 [SMILES: COc1ccnc(Nc2cc(C3CCN(C(C)=O)C3)nc(N3CCCC3C)n2)c1] | ¹H NMR (400 MHz, CDCl₃), δ ppm: 13.2 (br, 1H), 8.37 (br, 1H), 7.94-7.90 (m, 1H), 6.97 (br, 1H), 6.75 (br, 1H), 4.90-3.40 (m, 11H), 2.66-2.49 (m, 1H), 2.23-2.02 (m, 7H), 1.81-1.61 (m, 1H), 1.30-1.23 (m, 3H) | 397 |
| 3-ac | 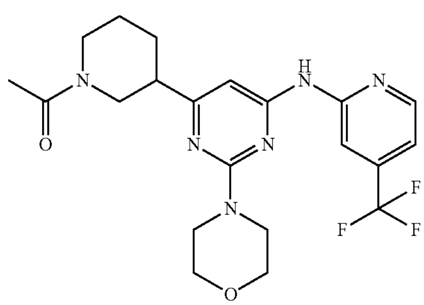 [SMILES: CC(=O)N1CCCC(c2cc(Nc3cc(C(F)(F)F)ccn3)nc(N3CCOCC3)n2)C1] | ¹H NMR (400 MHz, MeOD) δ 8.71 (d, J = 5.6 Hz, 1 H), 8.29 (s, 1 H), 7.56 (d, J = 5.2 Hz, 1 H), 6.88 (s, 1 H), 4.64-4.57 (m, 1 H), 4.34-4.31 (m, 1 H), 3.04-2.94 (m, 4 H), 3.87-3.85 (m, 4 H), 3.52-3.38 (m, 1 H), 3.21-2.98 (m, 2 H), 2.45-2.25 (m, 4 H), 1.99-1.68 (m, 3 H) | 451 |
| 3-ad | 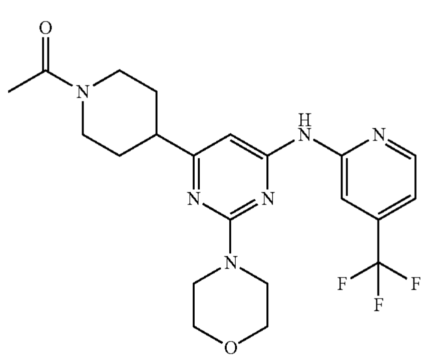 [SMILES: CC(=O)N1CCC(c2cc(Nc3cc(C(F)(F)F)ccn3)nc(N3CCOCC3)n2)CC1] | ¹H NMR (400 MHz, CDCl₃), δ ppm: 8.54-8.43 (m, 2 H), 7.31-7.26 (m, 2H), 6.90-6.60 (br, 1H), 4.90-4.60 (m, 1H), 4.18-3.87 (m, 8H), 3.60-3.40 (m, 1H), 2.80-2.70 (m, 1H), 2.52-2.50 (m, 1H), 2.30-2.26 (m, 4H), 2.10-1.96 (m, 1H), 1.80-1.40 (m, 3H), | 451 |

TABLE 3-continued

| No. | Structure | ¹H NMR | MS (M + H)+ |
|---|---|---|---|
| 3-ae | 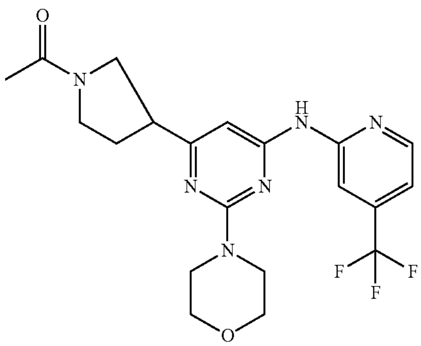 [SMILES: CC(=O)N1CCC(c2cc(Nc3cc(C(F)(F)F)ccn3)nc(N3CCOCC3)n2)C1] | ¹H NMR (400 MHz, CDCl₃), δ ppm: 8.49 (br, 2H), 7.31-7.26 (m, 2H), 4.24-4.20 (m, 3H), 3.98-3.76 (m, 5H), 3.70-3.66 (m, 3H), 2.90-2.80 (m, 1H), 2.16-2.10 (m, 6H) | 437 |
| 3-af | 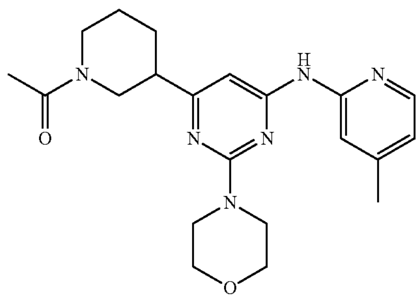 [SMILES: CC(=O)N1CCCC(c2cc(Nc3cc(C)ccn3)nc(N3CCOCC3)n2)C1] | ¹H NMR (400 MHz, MeOD) δ 8.57 (d, J = 6.0 Hz 1 H), 7.75 (s, 1 H), 7.63 (d, J = 6.0 Hz, 1 H), 6.69 (d, J = 7.2 Hz, 1 H), 4.62-4.59 (m, 1 H), 4.34-4.32 (m, 1 H), 3.99-3.95 (m, 4 H), 3.89 (m, 4 H), 3.48-3.34 (m, 2 H), 3.24-3.20 (m, 1 H), 2.69 (s, 3 H), 2.40-1.95 (m, 4 H), 1.78-1.66 (m, 3 H) | 397 |
| 3-ag | 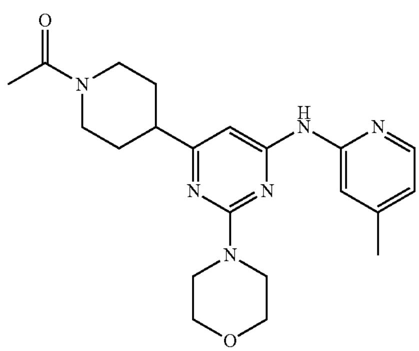 [SMILES: CC(=O)N1CCC(c2cc(Nc3cc(C)ccn3)nc(N3CCOCC3)n2)CC1] | ¹H NMR (400 MHz, MeOD) δ 8.42 (d, J = 6.4 Hz, 1 H), 7.49-7.45 (m, 2 H), 6.42 (s, 1 H), 4.74-4.69 (m, 1 H) 4.12 (d, J = 14.8 Hz, 1 H), 3.92-3.87 (m, 8 H), 3.37-3.32 (m, 1 H), 3.26-2.60 (m, 5 H) 2.18 (s, 3 H), 2.12-1.57 (m, 4 H) | 397 |
| 3-ah | 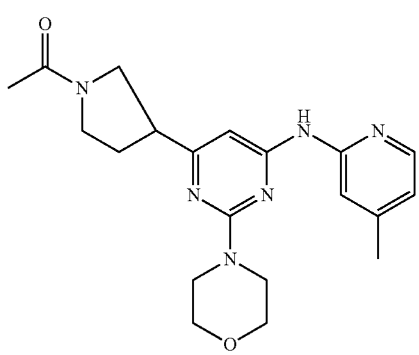 [SMILES: CC(=O)N1CCC(c2cc(Nc3cc(C)ccn3)nc(N3CCOCC3)n2)C1] | ¹H NMR (400 MHz, MeOD) δ 8.29 (d, J = 6.4 Hz, 1 H), 7.31-7.27 (m, 2 H), 6.32 (d, J = 6.0 Hz, 1 H), 3.87-3.85 (m, 1 H), 3.79-3.69 (m, 9 H), 3.68-3.47 (m, 3 H), 2.50 (s, 3 H), 2.40-2.05 (m, 5 H) | 383 |

TABLE 3-continued

| No. | Structure | ¹H NMR | MS (M + H)+ |
|---|---|---|---|
| 3-ai | 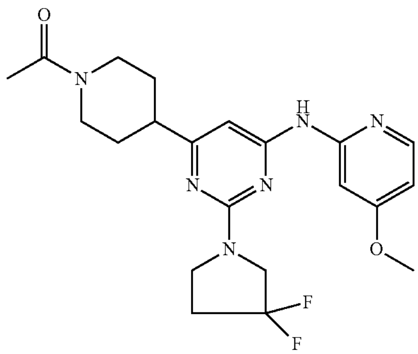 [SMILES: COc1ccnc(Nc2cc(C3CCN(C(C)=O)CC3)nc(N3CCC(F)(F)C3)n2)c1] | ¹H NMR (400 MHz, MeOD) δ 8.65 (d, J = 5.2 Hz, 2 H), 7.49 (s, 1 H), 6.56 (br, 1 H), 4.77-4.54 (m, 2 H), 4.19-4.02 (m, 4 H), 3.34-3.30 (m, 1 H), 3.27-3.09 (m, 1 H), 2.82-2.66 (m, 3H), 2.20-2.13 (m, 5 H), 1.83-1.62 (m, 2H) | 471 |
| 3-aj | 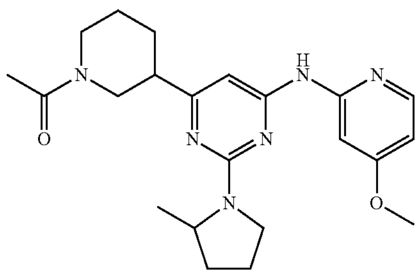 [SMILES: COc1ccnc(Nc2cc(C3CCCN(C(C)=O)C3)nc(N3CCCC3C)n2)c1] | ¹H NMR (400 MHz, MeOD) δ 8.53 (d, J = 7.2 Hz, 1 H), 7.43-7.30 (m, 2 H), 6.63 (d, J = 4.4 Hz, 1 H), 4.70-4.59 (m, 2 H), 4.18 (s, 3 H), 4.01-3.70 (m, 3 H), 3.44-3.39 (m, 1 H), 3.12-2.84 (m, 2 H), 2.33-2.24 (m, 7 H), 1.99-1.90 (m, 3 H), 1.72-1.68 (m, 1 H), 1.36 (d, J = 6.4 Hz, 3 H) | 411 |
| 3-ak | 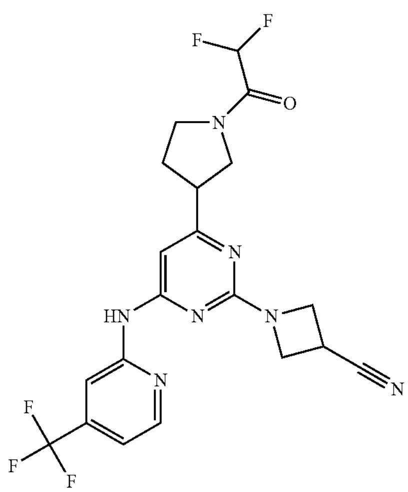 [SMILES: N#CC1CN(c2nc(Nc3cc(C(F)(F)F)ccn3)cc(C3CCN(C(=O)C(F)F)C3)n2)C1] | ¹H NMR (400 MHz, MeOD), δ ppm: 8.55 (d, J = 4.4 Hz, 1H), 8.44 (d, J = 5.2 Hz, 1H), 7.20 (d, J = 4.8 Hz, 1H), 6.62 (d, J = 4.8 Hz, 1H), 6.42 (t, J = 12.8 Hz, 1H), 4.41 (t, J = 8.4 Hz, 2H), 4.24 (t, J = 6.4 Hz, 2H), 3.32-4.00 (m, 6H), 2.15-2.39 (m, 2H). | 468 |
| 3-al | 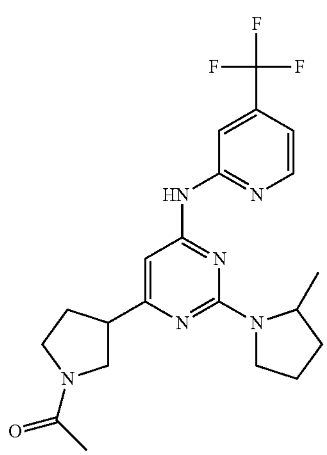 [SMILES: CC(=O)N1CCC(c2cc(Nc3cc(C(F)(F)F)ccn3)nc(N3CCCC3C)n2)C1] | ¹H NMR (400 MHz, MeOD) δ 8.86 (s, 1 H), 8.41 (d, J = 4.8 Hz, 1 H), 7.14 (d, J = 5.2 Hz, 1 H), 6.23-6.21 (m, 1 H), 4.59 (s, 1 H), 4.30 (s, 1 H), 3.81-3.53 (m, 6 H), 2.28-2.45 (m, 1 H), 2.20-2.07 (m, 6 H), 1.95 (s, 1 H), 1.74-1.73 (m, 1 H), 1.25 (d, J = 6.4 Hz, 3 H) | 435 |

TABLE 3-continued

| No. | Structure | ¹H NMR | MS (M + H)+ |
|---|---|---|---|
| 3-am | 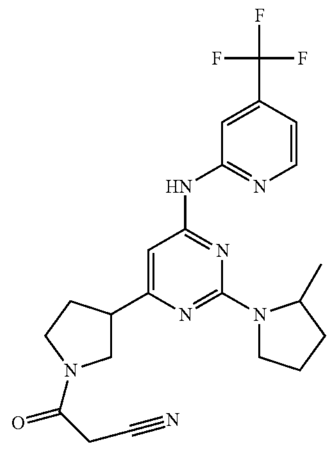 [SMILES: CC1CCCN1c1nc(Nc2cc(C(F)(F)F)ccn2)cc(C2CCN(C(=O)CC#N)C2)n1] | ¹H NMR (400 MHz, MeOD) δ 8.90-8.57 (m, 2H), 7.46-7.40 (m, 1H), 6.50-6.39 (br, 1H), 4.56-4.46 (m, 1H), 3.98-3.60 (m, 9H), 2.53-2.49 (m, 1H), 2.40-2.20 (m, 4H), 1.90-1.82 (m, 1H), 1.40-1.30 (m, 3H) | 460 |
| 3-an | 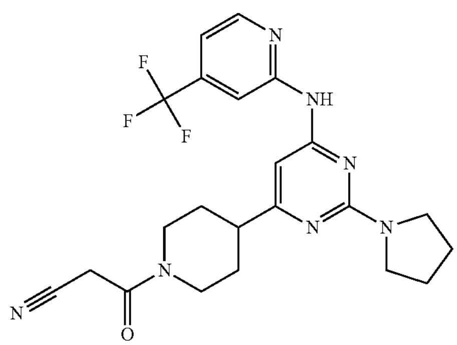 [SMILES: N#CCC(=O)N1CCC(c2cc(Nc3cc(C(F)(F)F)ccn3)nc(N3CCCC3)n2)CC1] | ¹H NMR (400 MHz, MeOD) δ 8.66 (d, J = 5.2 Hz, 1 H), 8.52 (br, 1 H), 7.50 (d, J = 4.8 Hz, 1 H), 6.72 (br, 1 H), 4.77-4.72 (m, 1 H), 4.21-4.11 (m, 2 H), 4.07-3.92 (m, 4 H), 3.29-3.21 (m, 3 H), 2.88-2.82 (m, 1 H), 2.72-2.66 (m, 2 H), 2.28-2.11 (m, 2 H), 1.84-1.57 (m, 2 H), 1.44-1.38 (m, 2 H) | 460 |
| 3-ao | 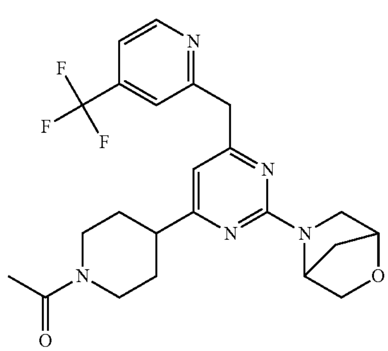 [SMILES: CC(=O)N1CCC(c2cc(Cc3cc(C(F)(F)F)ccn3)nc(N3CC4CC3CO4)n2)CC1] | ¹H NMR (400 MHz, MeOD), δ ppm: 8.58-8.50 (m, 2H), 7.74-7.37 (m, 1H), 6.45 (br, 1H), 5.13 (s, 1H), 4.88-4.80 (m, 3H), 4.75-4.72 (m, 1H), 4.14-4.11 (m, 1H), 4.02-3.65 (m, 3H), 3.26-3.22 (m, 2H), 3.00-2.92 (m, 1H), 2.77-2.70 (m, 1H), 2.14 (s, 3H), 2.11-2.04 (m, 4H), 1.85-1.60 (m, 2H) | 463 |
| 3-ap | 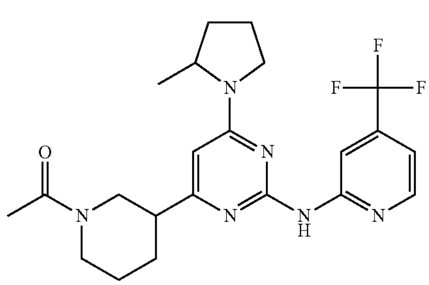 [SMILES: CC(=O)N1CCCC(c2cc(N3CCCC3C)nc(Nc3cc(C(F)(F)F)ccn3)n2)C1] | ¹H NMR (400 MHz, MeOD) δ 8.67 (d, J = 5.6 Hz, 1 H), 7.52-7.46 (m, 2 H), 6.50-6.40 (m, 1 H), 4.57-4.15 (m, 2 H), 3.89-3.30 (m, 4 H), 3.29-2.80 (m, 2 H), 2.26-2.16 (m, 7 H), 2.02-1.84 (m, 3 H), 1.73-1.60 (m, 1 H), 1.37-1.27 (m, 3 H) | 449 |

TABLE 3-continued

| No. | Structure | ¹H NMR | MS (M + H)+ |
|---|---|---|---|
| 3-aq | 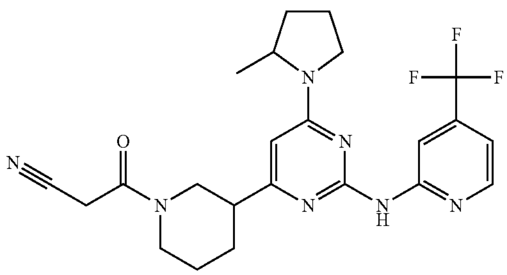 [SMILES: CC1CCCN1c1cc(C2CCCN(C(=O)CC#N)C2)nc(Nc2cc(C(F)(F)F)ccn2)n1] | ¹H NMR (400 MHz, MeOD) δ 8.69 (d, J = 4.0 Hz, 1 H), 7.54-7.46 (m, 2 H), 6.49-6.41 (m, 1 H), 4.56-4.35 (m, 2 H), 4.02-3.34 (m, 6 H), 3.12-2.86 (m, 1 H), 2.24-1.65 (m, 9 H), 1.36-1.29 (m, 3 H) | 474 |
| 3-ar | 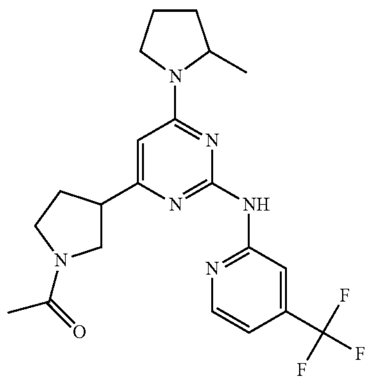 [SMILES: CC(=O)N1CCC(c2cc(N3CCCC3C)nc(Nc3cc(C(F)(F)F)ccn3)n2)C1] | ¹H NMR (400 MHz, MeOD) δ 8.58-8.57 (m, 1H), 7.44-7.38 (m, 2H), 6.43-6.31 (m, 1H), 4.53-4.20 (m, 1H), 4.02-3.92 (m, 1H), 3.75-2.48 (m, 6H), 2.55-2.40 (m, 1H), 2.80-2.60 (m, 1H), 2.28-1.96 (m, 7H), 1.89-1.72 (m, 1H), 1.28-1.20 (m, 3H) | 435 |
| 3-as | 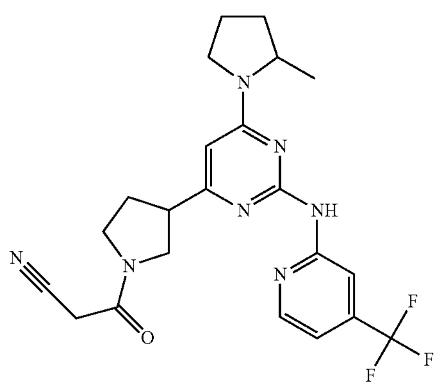 [SMILES: CC1CCCN1c1cc(C2CCN(C(=O)CC#N)C2)nc(Nc2cc(C(F)(F)F)ccn2)n1] | ¹H NMR (400 MHz, MeOD) δ 8.61-8.60 (m, 1H), 7.46-7.40 (m, 2H), 6.42-6.35 (m, 1H), 4.53-4.25 (m, 1H), 4.01-3.99 (m, 1H), 3.82-3.62 (m, 8H), 2.59-2.49 (m, 1H), 2.18-2.07 (m, 4H), 1.83-1.75 (m, 1H), 1.30-1.23 (m, 3H) | 460 |
| 3-at | 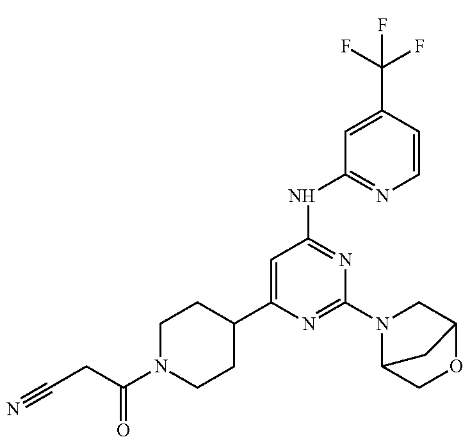 [SMILES: N#CCC(=O)N1CCC(c2cc(Nc3cc(C(F)(F)F)ccn3)nc(N3CC4CC3CO4)n2)CC1] | ¹H NMR (400 MHz, MeOD), δ ppm: 8.66-8.63 (m, 1H), 7.89-7.69 (m, 1H), 7.47-7.26 (m, 2H), 5.19 (br, 1H), 4.90-4.86 (m, 1H), 4.72-4.69 (m, 1H), 4.03-3.89 (m, 5H), 3.80-3.67 (m, 2H), 3.12-3.08 (m, 1H), 2.86-2.80 (m, 1H), 2.19-2.11 (m, 4H), 1.80-1.68 (m, 3H) | 488 |

TABLE 3-continued

| No. | Structure | ¹H NMR | MS (M + H)+ |
|---|---|---|---|
| 3-au | 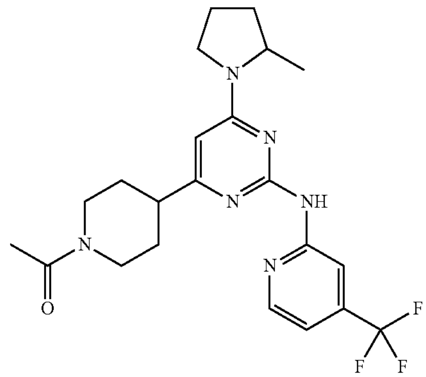 [SMILES: CC(=O)N1CCC(c2cc(N3CCCC3C)nc(Nc3cc(C(F)(F)F)ccn3)n2)CC1] | ¹H NMR (400 MHz, MeOD), δ ppm: 8.71-8.68 (d, J = 5.2 Hz, 1H), 7.54-7.48 (m, 2H), 6.46-6.36 (d, J = 38.0 Hz, 1H), 4.80-4.70 (m, 1H), 4.60-4.32 (m, 1H), 4.20-4.10 (m, 1H), 3.95-3.72 (m, 1H), 3.70-3.41 (m, 1H), 3.22-3.10 (m, 1H), 2.89-2.81 (m, 1H), 2.20-2.14 (m, 9H), 1.90-1.68 (m, 3H), 1.37-1.30 (m, 3H) | 449 |
| 3-av | 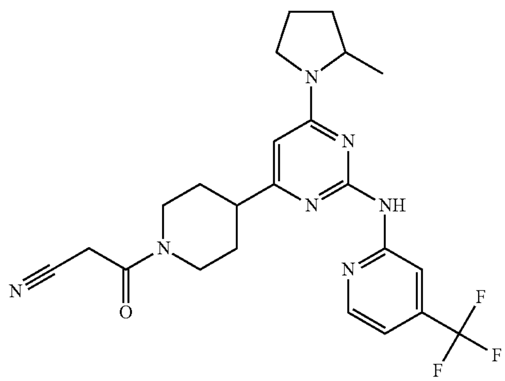 [SMILES: CC1CCCN1c1cc(C2CCN(C(=O)CC#N)CC2)nc(Nc2cc(C(F)(F)F)ccn2)n1] | ¹H NMR (400 MHz, MeOD), δ ppm: 8.78-8.69 (m, 1H), 7.55-7.47 (m, 2H), 6.48-6.37 (m, 1H), 4.87-4.58 (m, 2H), 4.38-3.51 (m, 4H), 3.36-3.31 (m, 2H), 3.17-2.87 (m, 2H), 2.21-1.86 (m, 8H), 1.37-1.31 (m, 3H) | 474 |
| 3-aw | 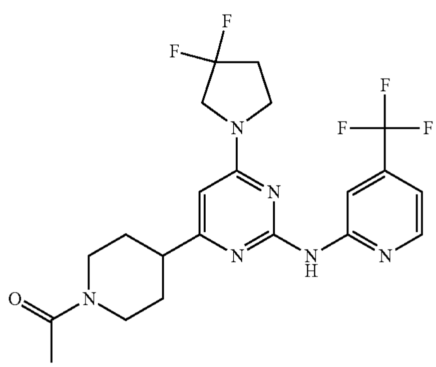 [SMILES: CC(=O)N1CCC(c2cc(N3CCC(F)(F)C3)nc(Nc3cc(C(F)(F)F)ccn3)n2)CC1] | ¹H NMR (400 MHz, MeOD), δ ppm: 8.71-8.69 (d, J = 5.2 Hz, 1H), 7.53-7.50 (m, 2H), 6.53-6.44 (d, J = 38.0 Hz, 1H), 4.89-4.74 (m, 1H), 4.23-3.93 (m, 5H), 3.38-3.32 (m, 1H), 3.19-3.14 (m, 1H), 2.86-2.79 (m, 1H), 2.73-2.56 (m, 2H), 2.18-2.10 (m, 5H), 1.90-1.68 (m, 2H) | 471 |
| 3-ax | 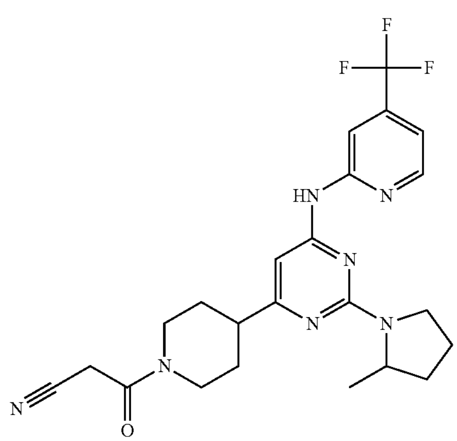 [SMILES: CC1CCCN1c1nc(Nc2cc(C(F)(F)F)ccn2)cc(C2CCN(C(=O)CC#N)CC2)n1] | ¹H NMR (400 MHz, MeOD) δ 8.68-8.61 (m, 2 H), 7.45 (d, J = 5.2 Hz, 1 H), 6.44 (s, 1 H), 4.75-4.67 (m, 1 H), 4.54 (s, 1 H), 4.01-3.31 (m, 5 H), 3.13-3.02 (m, 2 H), 2.84-2.78 (m, 1 H), 2.24-1.62 (m, 8 H), 1.36 (d, J = 6.0 Hz, 3 H). | 474 |

TABLE 3-continued

| No. | Structure | ¹H NMR | MS (M + H)+ |
|---|---|---|---|
| 3-ay | 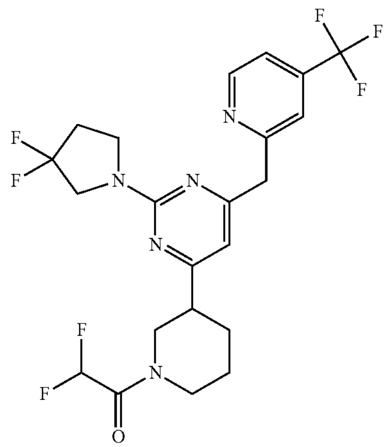 [SMILES: O=C(C(F)F)N1CCCC(c2cc(Cc3cc(C(F)(F)F)ccn3)nc(N3CCC(F)(F)C3)n2)C1] | ¹H NMR (400 MHz, MeOD) δ 8.64 (d, J = 5.2 Hz, 1 H), 7.47 (d, J = 4.8 Hz, 1 H), 6.68-6.39 (m, 2 H), 4.59-4.45 (m, 1 H), 4.22-3.97 (m, 5 H), 3.57-3.36 (m, 2 H), 3.13-2.94 (m, 2 H), 2.71-2.63 (m, 2 H), 2.26-2.22 (m, 1 H), 1.99-1.55 (m, 3 H). | 507 |
| 3-az | 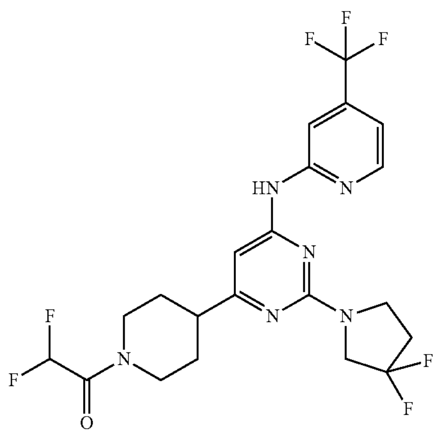 [SMILES: O=C(C(F)F)N1CCC(c2cc(Nc3cc(C(F)(F)F)ccn3)nc(N3CCC(F)(F)C3)n2)CC1] | ¹H NMR (400 MHz, MeOD) δ 8.73 (s, 1 H), 8.46 (d, J = 5.2 Hz, 1 H), 7.19 (d, J = 4.8 Hz, 1 H), 6.53-6.37 (m, 2 H), 4.57 (d, J = 13.2 Hz, 1 H), 4.13 (d, J = 13.6 Hz, 1 H), 3.96-3.81 (m, 4 H), 3.32-3.28 (m, 1 H), 2.98-2.79 (m, 2 H), 2.57-2.46 (m, 2 H), 2.05-1.71 (m, 4 H). | 507 |
| 3-ba | 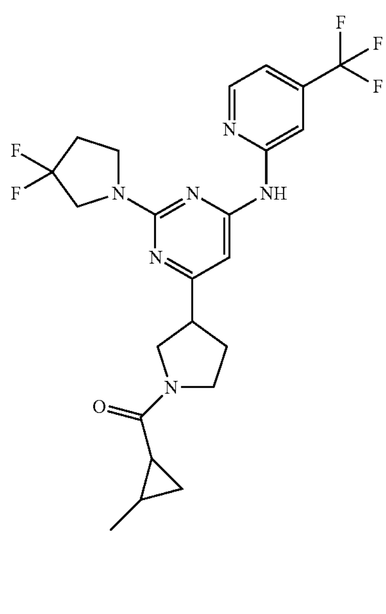 [SMILES: CC1CC1C(=O)N1CCC(c2cc(Nc3cc(C(F)(F)F)ccn3)nc(N3CCC(F)(F)C3)n2)C1] | ¹H NMR (400 MHz, MeOD) δ 8.73-8.35 (m, 2 H), 7.50 (d, J = 4.8 Hz, 1 H), 6.82-6.45 (br, 1 H), 4.22-3.60 (m, 9 H), 2.74-2.10 (m, 4 H), 1.59-1.57 (m, 1 H), 1.40-1.33 (m, 1 H), 1.19-1.15 (m, 4 H), 0.76-0.71 (m, 1 H). | 497 |

TABLE 3-continued

| No. | Structure | ¹H NMR | MS (M + H)+ |
|---|---|---|---|
| 3-bb | 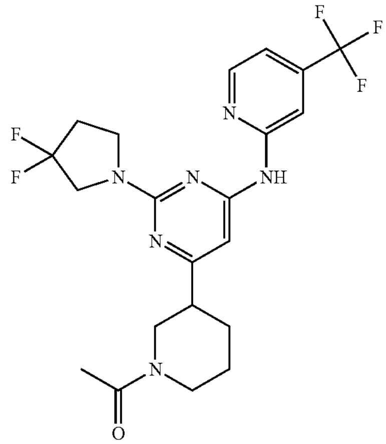 [SMILES: CC(=O)N1CCCC(c2cc(Nc3cc(C(F)(F)F)ccn3)nc(N3CCC(F)(F)C3)n2)C1] | ¹H NMR (400 MHz, MeOD) δ 8.73 (d, J = 8.4 Hz, 1 H), 8.47-8.45 (m, 1 H), 7.20 (s, 1 H), 6.44 (d, J = 18.0 Hz, 1 H), 4.62-4.40 (m, 1 H), 4.06-3.83 (m, 5 H), 3.47-3.19 (m, 1 H), 2.99-2.47 (m, 4 H), 2.15-2.07 (m, 4 H), 1.93-1.55 (m, 3 H). | 471 |
| 3-bc | 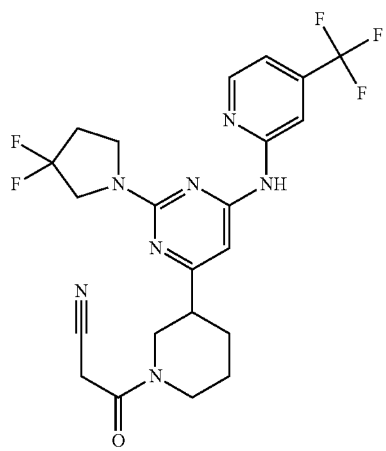 [SMILES: N#CCC(=O)N1CCCC(c2cc(Nc3cc(C(F)(F)F)ccn3)nc(N3CCC(F)(F)C3)n2)C1] | ¹H NMR (400 MHz, MeOD) δ 8.73 (d, J = 8.4 Hz, 1 H), 8.47-8.45 (m, 1 H), 7.20 (s, 1 H), 6.44 (d, J = 18.0 Hz, 1 H), 4.62-4.40 (m, 1 H), 4.06-3.83 (m, 5 H), 3.47-3.19 (m, 1 H), 2.99-2.47 (m, 4 H), 2.15-2.07 (m, 4 H), 1.93-1.55 (m, 3 H). | 496 |
| 3-bd | 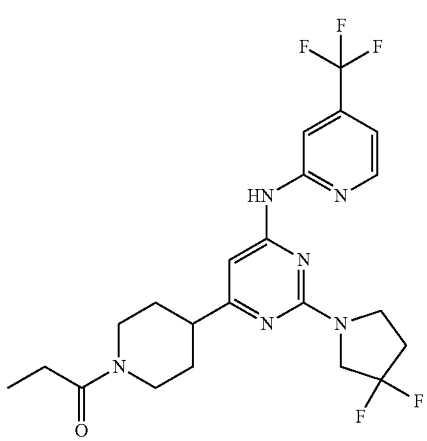 [SMILES: CCC(=O)N1CCC(c2cc(Nc3cc(C(F)(F)F)ccn3)nc(N3CCC(F)(F)C3)n2)CC1] | ¹H NMR (400 MHz, MeOD) δ 8.70-8.45 (m, 2 H), 7.48 (d, J = 5.6 Hz, 1 H), 6.89-6.62 (br, 1 H), 4.78-4.75 (m, 1 H), 4.19-4.00 (m, 5 H), 3.27-3.20 (m, 1 H), 3.07-3.01 (m, 1 H), 2.77-2.67 (m, 3 H), 2.51-2.46 (m, 2 H), 2.05-2.05 (m, 2 H), 1.72-1.56 (m, 2 H), 1.15 (t, J = 12.4 Hz, 3 H). | 485 |

TABLE 3-continued
| No. | Structure | ¹H NMR | MS (M + H)+ |
|---|---|---|---|
| 3-be | 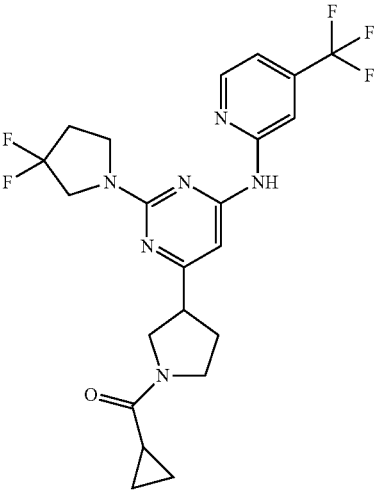 [SMILES: O=C(C1CC1)N1CCC(c2cc(Nc3cc(C(F)(F)F)ccn3)nc(N3CCC(F)(F)C3)n2)C1] | ¹H NMR (400 MHz, MeOD) δ 8.70-8.45 (m, 2 H), 7.48 (d, J = 5.6 Hz, 1 H), 6.89-6.62 (br, 1 H), 4.78-4.75 (m, 1 H), 4.19-4.00 (m, 5 H), 3.27-3.20 (m, 1 H), 3.07-3.01 (m, 1 H), 2.77-2.67 (m, 3 H), 2.51-2.46 (m, 2 H), 2.05-2.05 (m, 2 H), 1.72-1.56 (m, 2 H), 1.15 (t, J = 12.4 Hz, 3 H). | 483 |
| 3-bf | 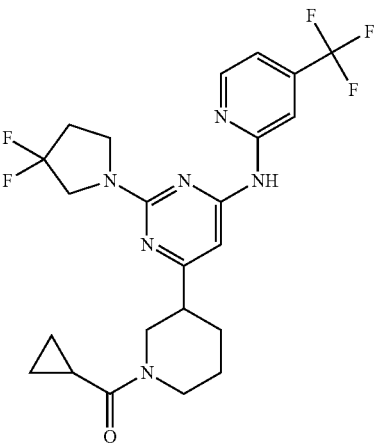 [SMILES: O=C(C1CC1)N1CCCC(c2cc(Nc3cc(C(F)(F)F)ccn3)nc(N3CCC(F)(F)C3)n2)C1] | ¹H NMR (400 MHz, MeOD) δ 8.70-8.45 (m, 2 H), 7.50 (d, J = 5.2 Hz, 1 H), 6.89-6.62 (m, 1 H), 4.58-4.33 (m, 2 H), 4.18-4.03 (m, 4 H), 3.43-3.37 (m, 1 H), 3.07-2.90 (m, 2 H), 2.74-2.64 (m, 2 H), 2.27-2.23 (m, 1 H), 2.06-1.61 (m, 4 H), 0.97-0.94 (m, 4 H). | 497 |
| 3-bg | 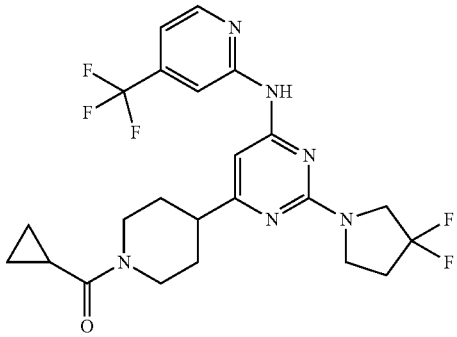 [SMILES: O=C(C1CC1)N1CCC(c2cc(Nc3cc(C(F)(F)F)ccn3)nc(N3CCC(F)(F)C3)n2)CC1] | ¹H NMR (400 MHz, MeOD) δ 8.70-8.45 (m, 2 H), 7.50 (d, J = 5.2 Hz, 1 H), 6.89-6.62 (m, 1 H), 4.58-4.33 (m, 2 H), 4.18-4.03 (m, 4 H), 3.43-3.37 (m, 1 H), 3.07-2.90 (m, 2 H), 2.74-2.64 (m, 2 H), 2.27-2.23 (m, 1 H), 2.06-1.61 (m, 4 H), 0.97-0.94 (m, 4 H). | 497 |

TABLE 3-continued

| No. | Structure | ¹H NMR | MS (M + H)+ |
|---|---|---|---|
| 3-bh | 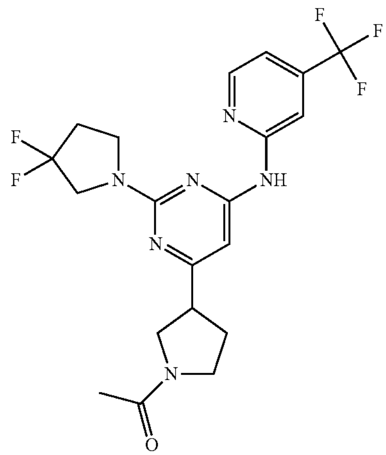 [SMILES: CC(=O)N1CCC(c2cc(Nc3cc(C(F)(F)F)ccn3)nc(N3CCC(F)(F)C3)n2)C1] | ¹H NMR (400 MHz, MeOD) δ 8.65-8.38 (m, 2 H), 7.47 (d, J = 4.4 Hz, 1 H), 6.83-6.64 (br, 1 H), 4.16-3.61 (m, 9 H), 2.68-2.43 (m, 3 H), 2.27-2.09 (m, 4 H). | 457 |
| 3-bi | 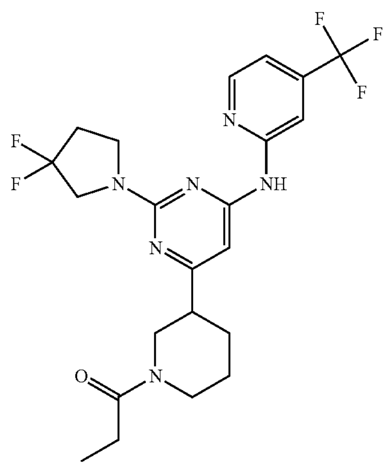 [SMILES: CCC(=O)N1CCCC(c2cc(Nc3cc(C(F)(F)F)ccn3)nc(N3CCC(F)(F)C3)n2)C1] | ¹H NMR (400 MHz, MeOD) δ 8.65-8.45 (m, 2 H), 7.48 (d, J = 5.6 Hz, 1 H), 6.62-6.54 (br, 1 H), 4.61-4.54 (m, 1 H), 4.19-3.97 (m, 5 H), 3.25-3.15 (m, 1 H), 3.02-2.48 (m, 6 H), 2.23-2.19 (m, 1 H), 1.98-1.55 (m, 3 H), 1.18-1.14 (m, 3 H). | 485 |
| 3-bj | 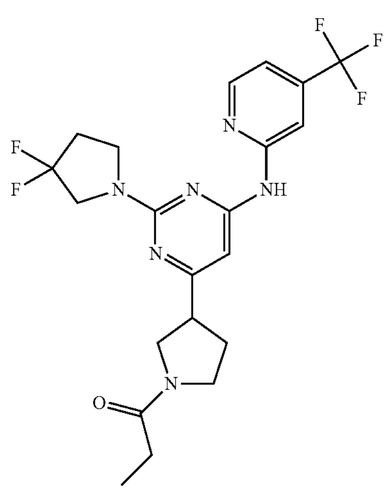 [SMILES: CCC(=O)N1CCC(c2cc(Nc3cc(C(F)(F)F)ccn3)nc(N3CCC(F)(F)C3)n2)C1] | ¹H NMR (400 MHz, MeOD) δ 8.65-8.45 (m, 2 H), 7.47 (d, J = 5.2 Hz, 1 H), 6.64-6.56 (m, 1 H), 4.16-3.85 (m, 5 H), 3.78-3.60 (m, 4 H), 2.70-2.48 (m, 5 H), 2.29-2.11 (m, 1 H), 1.09-1.04 (m, 3 H). | 471 |

| No. | Structure | ¹H NMR | MS (M + H)+ |
|---|---|---|---|
| 3-bk | 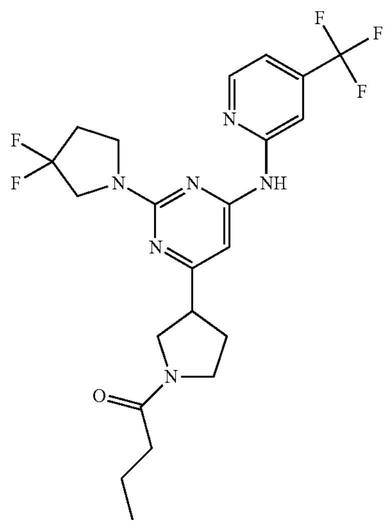 [SMILES: CCCC(=O)N1CCC(c2cc(Nc3cc(C(F)(F)F)ccn3)nc(N3CCC(F)(F)C3)n2)C1] | ¹H NMR (400 MHz, MeOD) δ 8.65-8.48 (m, 2 H), 7.47 (d, J = 5.2 Hz, 1 H), 6.64-6.56 (m, 1 H), 4.15-3.85 (m, 5 H), 3.75-3.57 (m, 4 H), 2.70-2.14 (m, 6 H), 1.68-1.61 (m, 2 H), 0.98-0.95 (m, 3 H). | 485 |
| 3-bl | 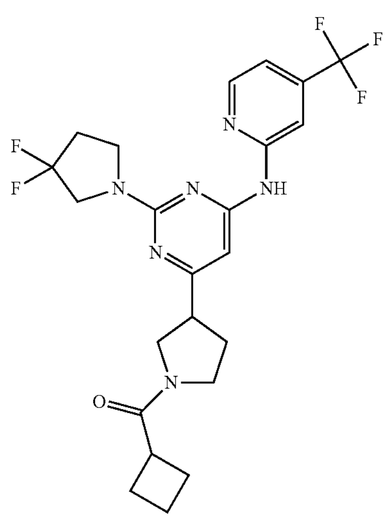 [SMILES: O=C(C1CCC1)N1CCC(c2cc(Nc3cc(C(F)(F)F)ccn3)nc(N3CCC(F)(F)C3)n2)C1] | ¹H NMR (400 MHz, MeOD) δ 8.65-8.25 (m, 2 H), 7.50 (d, J = 4.8 Hz, 1 H), 6.64-6.56 (m, 1 H), 4.16-3.85 (m, 5 H), 3.75-3.39 (m, 5 H), 2.74-2.64 (m, 2 H), 2.56-1.88 (m, 8 H). | 497 |
| 3-bm | 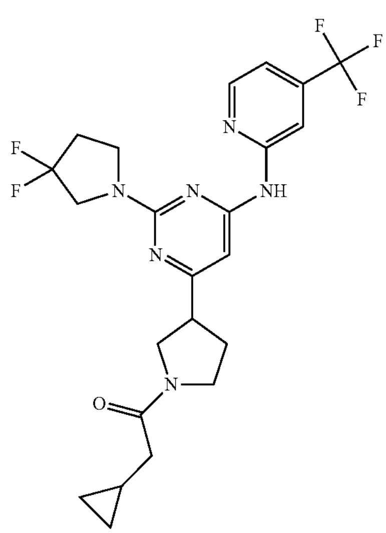 [SMILES: O=C(CC1CC1)N1CCC(c2cc(Nc3cc(C(F)(F)F)ccn3)nc(N3CCC(F)(F)C3)n2)C1] | ¹H NMR (400 MHz, MeOD) δ 8.65-8.25 (m, 2 H), 7.29 (d, J = 5.2 Hz, 1 H), 6.64-6.56 (m, 1 H), 4.18-3.90 (m, 5 H), 3.76-3.62 (m, 4 H), 2.72-2.21 (m, 6 H), 1.11-1.06 (m, 1 H), 0.60-0.54 (m, 2 H), 0.24-0.20 (m, 2 H). | 497 |

TABLE 3-continued
| No. | Structure | ¹H NMR | MS (M + H)+ |
|---|---|---|---|
| 3-bn | 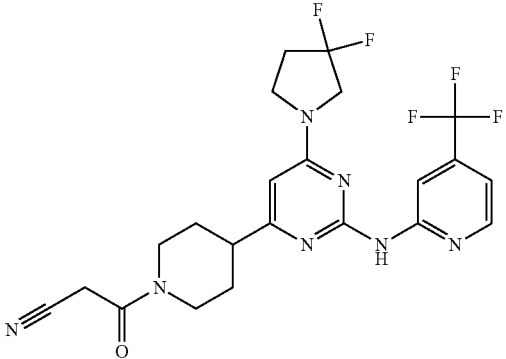 [SMILES: N#CCC(=O)N1CCC(c2cc(N3CCC(F)(F)C3)nc(Nc3cc(C(F)(F)F)ccn3)n2)CC1] | ¹H NMR (400 MHz, MeOD) δ 8.71-8.63 (m, 1 H), 7.50-7.47 (m, 2 H), 6.47 (d, J = 40.0 Hz, 1 H), 4.14-3.83 (m, 5 H), 2.92-2.57 (m, 8 H), 2.17-2.07 (m, 2 H), 1.89-1.73 (m, 1H), 1.40-1.28 (m, 1 H) | 496 |
| 3-bo | 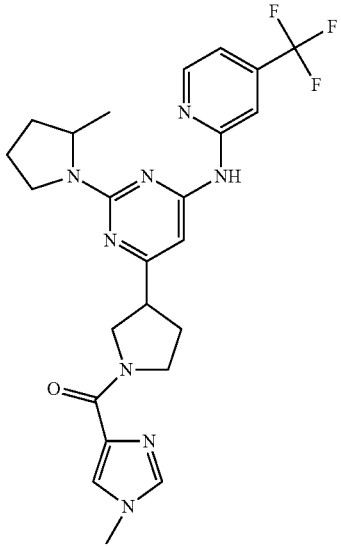 [SMILES: CC1CCCN1c1nc(Nc2cc(C(F)(F)F)ccn2)cc(C2CCN(C(=O)c3cn(C)cn3)C2)n1] | ¹H NMR (400 MHz, MeOD), δ ppm: 9.07-9.00 (m, 1H), 8.62-8.58 (m, 1H), 8.25-8.20 (m, 1H), 7.50-7.45 (m, 1H), 6.50 (br, 2H), 4.65-4.52 (m, 1H), 4.40-4.10 (m, 2H), 4.02 (s, 3H), 3.98-3.85 (m, 1H), 3.80-3.62 (m, 3H), 2.70-2.15 (m, 6H), 1.90 (s, 1H), 1.50-1.35 (m, 3H) | 501 |
| 3-bp | 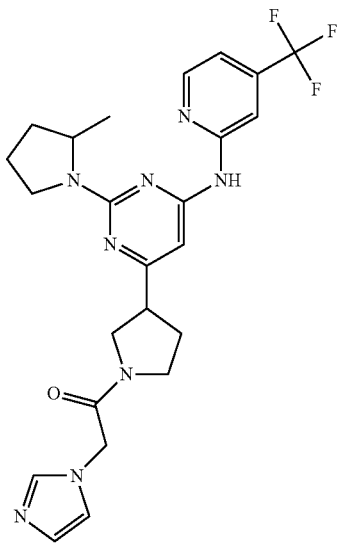 [SMILES: CC1CCCN1c1nc(Nc2cc(C(F)(F)F)ccn2)cc(C2CCN(C(=O)Cn3ccnc3)C2)n1] | ¹H NMR (400 MHz, MeOD), δ ppm: 8.94 (s, 1H), 8.65 (s, 2H), 7.62-7.61 (m, 2H), 7.40 (s, 1H), 6.60 (br, 1H), 5.35-5.40 (m, 2H), 4.58 (s, 1H), 4.22-4.00 (m, 1H), 3.96-3.58 (m, 6H), 2.70-2.15 (m, 5H), 1.90 (s, 1H), 1.33-1.38 (m, 3H) | 501 |

TABLE 3-continued
| No. | Structure | ¹H NMR | MS (M + H)+ |
|---|---|---|---|
| 3-bq | 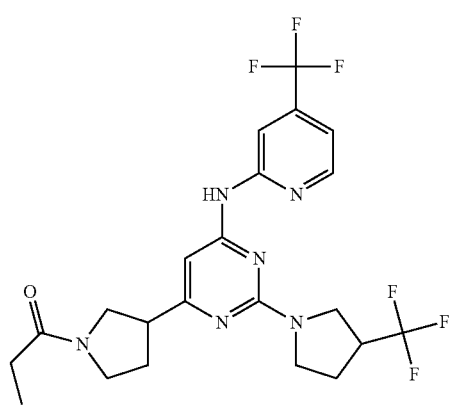 [SMILES: CCC(=O)N1CCC(c2cc(Nc3cc(C(F)(F)F)ccn3)nc(N3CCC(C(F)(F)F)C3)n2)C1] | ¹H NMR (400 MHz, MeOD) δ 8.62 (d, J = 5.2 Hz, 2 H), 7.46 (d, J = 5.2 Hz, 1 H), 6.55 (br, 1 H), 4.15-3.68 (m, 5 H), 3.71-3.61 (m, 4 H), 3.42 (s, 1 H), 2.60-2.12 (m, 6 H), 1.18-1.13 (m, 3 H) | 503 |
| 3-br | 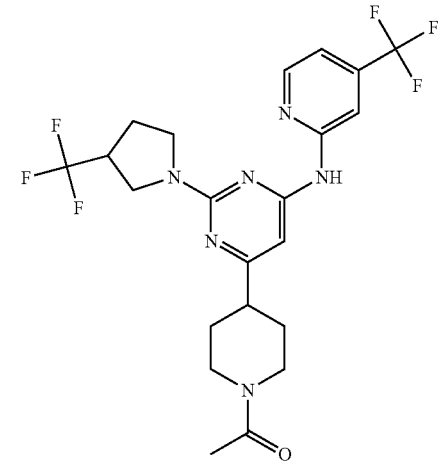 [SMILES: CC(=O)N1CCC(c2cc(Nc3cc(C(F)(F)F)ccn3)nc(N3CCC(C(F)(F)F)C3)n2)CC1] | ¹H NMR (400 MHz, MeOD) δ 8.64 (d, J = 5.2 Hz, 2 H), 7.47 (d, J = 5.2 Hz, 1 H), 6.58 (br, 1 H), 4.75-4.72 (m, 1 H), 4.15-3.88 (m, 5 H), 3.43 (s, 1 H), 3.14-3.12 (m, 2 H), 2.82-2.76 (m, 1 H), 2.49-2.35 (m, 2 H), 2.19-2.03 (m, 5 H), 1.76-1.61 (m, 2 H) | 503 |
| 3-bs | 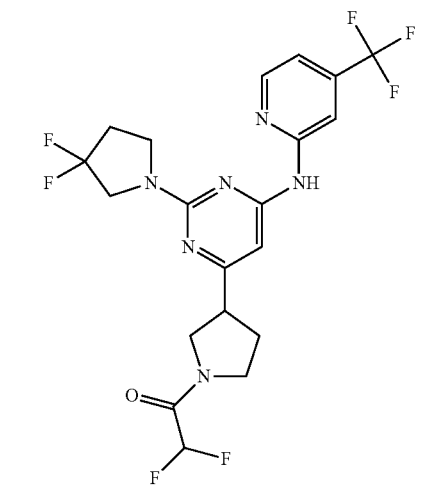 [SMILES: O=C(C(F)F)N1CCC(c2cc(Nc3cc(C(F)(F)F)ccn3)nc(N3CCC(F)(F)C3)n2)C1] | ¹H NMR (400 MHz, MeOD) δ 8.65-8.30 (m, 2H), 7.60-7.50 (m, 1H), 7.60-6.60 (br, 1H), 6.55-6.30 (m, 1H), 4.70-4.60 (m, 2H), 4.10-4.00 (m, 2H), 3.92-3.60 (m, 5H), 2.80-2.20 (m, 4H) | 493 |

TABLE 3-continued

| No. | Structure | ¹H NMR | MS (M + H)+ |
|---|---|---|---|
| 3-bt | 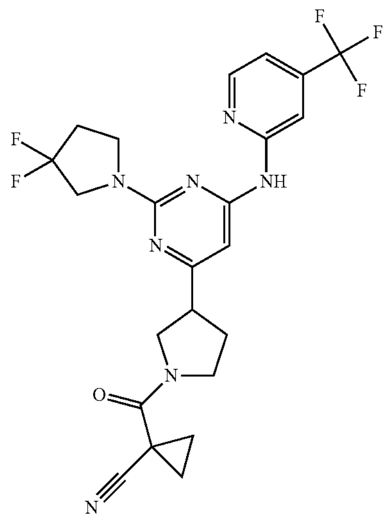 [SMILES: N#CC1(C(=O)N2CCC(c3cc(Nc4cc(C(F)(F)F)ccn4)nc(N4CCC(F)(F)C4)n3)C2)CC1] | ¹H NMR (400 MHz, MeOD) δ 8.65-8.30 (m, 2H), 7.60-7.50 (m, 1H), 7.60-6.60 (br, 1H), 4.25-3.90 (m, 6H), 4.10-4.00 (m, 2H), 3.80-3.60 (m, 3H), 2.80-2.20 (m, 4H), 1.70-1.50 (m, 4H) | 508 |
| 3-bu | 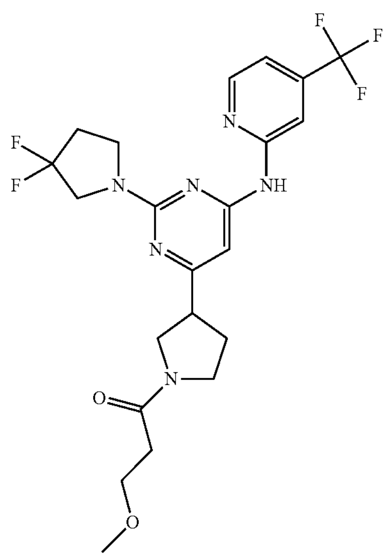 [SMILES: COCCC(=O)N1CCC(c2cc(Nc3cc(C(F)(F)F)ccn3)nc(N3CCC(F)(F)C3)n2)C1] | ¹H NMR (400 MHz, MeOD) δ 8.65-8.39 (m, 2 H), 7.50 (d, J = 4.8 Hz, 1 H), 6.68 (br, 1 H), 4.18-4.00 (m, 4 H), 3.80-3.60 (m, 7 H), 3.30 (s, 3 H), 2.80-2.20 (m, 6 H) | 501 |
| 3-bv | 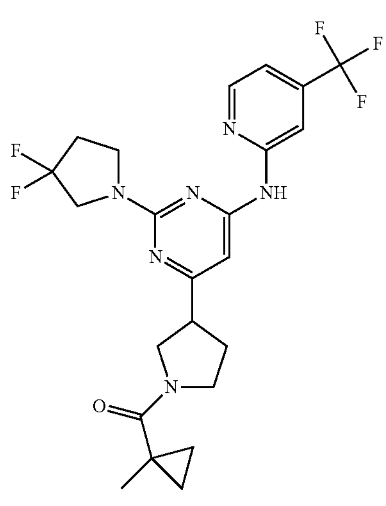 [SMILES: CC1(C(=O)N2CCC(c3cc(Nc4cc(C(F)(F)F)ccn4)nc(N4CCC(F)(F)C4)n3)C2)CC1] | ¹H NMR (400 MHz, MeOD) δ 8.65-8.30 (m, 2 H), 7.47 (d, J = 4.0 Hz, 1 H), 6.70 (br, 1 H), 4.24-4.09 (m, 2 H), 4.02-3.92 (m, 2 H), 3.88-3.64 (m, 5 H), 2.73-2.19 (m, 4 H), 1.35 (s, 3 H), 0.99-0.98 (m, 2 H), 0.68-0.60 (m, 2 H) | 497 |

TABLE 3-continued

| No. | Structure | ¹H NMR | MS (M + H)+ |
|---|---|---|---|
| 3-bw | 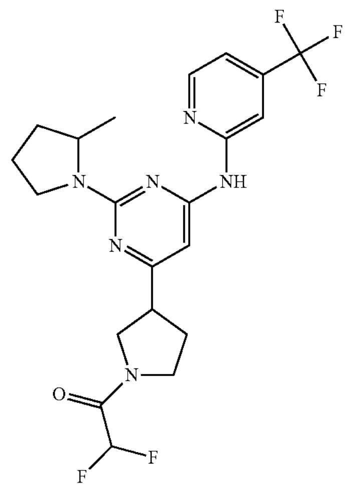 [SMILES: CC1CCCN1c1nc(Nc2cc(C(F)(F)F)ccn2)cc(C2CCN(C(=O)C(F)F)C2)n1] | ¹H NMR (400 MHz, MeOD) δ 8.82 (s, 1 H), 7.46 (d, J = 5.2 Hz, 1 H), 7.72-7.69 (m, 1 H), 6.48-6.20 (m, 2 H), 4.30 (s, 1 H), 4.02-3.45 (m, 7 H), 2.40-1.95 (m, 5 H), 1.84-1.72 (m, 1 H), 1.33-1.25 (m, 3 H) | 471 |
| 3-bx | 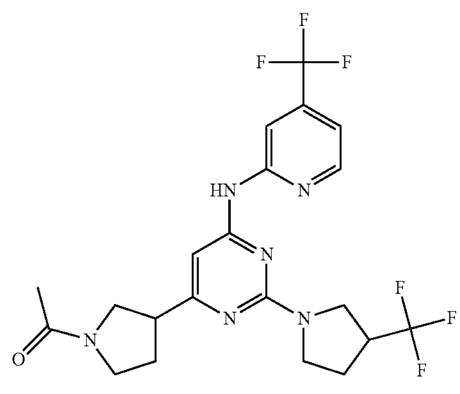 [SMILES: CC(=O)N1CCC(c2cc(Nc3cc(C(F)(F)F)ccn3)nc(N3CCC(C(F)(F)F)C3)n2)C1] | ¹H NMR (400 MHz, MeOD) δ 8.62 (d, J = 5.2 Hz, 2 H), 7.46 (d, J = 4.8 Hz, 1 H), 6.60 (br, 1 H), 4.08-3.65 (m, 9 H), 3.45-3.43 (m, 1 H), 3.04 (s, 1 H), 2.54-2.28 (m, 3 H), 2.23-2.12 (m, 3 H) | 489 |
| 3-by | 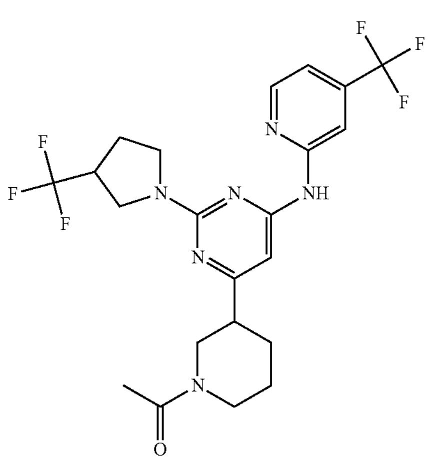 [SMILES: CC(=O)N1CCCC(c2cc(Nc3cc(C(F)(F)F)ccn3)nc(N3CCC(C(F)(F)F)C3)n2)C1] | ¹H NMR (400 MHz, MeOD) δ 8.62 (d, J = 4.8 Hz, 2 H), 7.45 (d, J = 5.2 Hz, Hz, 1 H), 6.49-6.37 (m, 1 H), 4.57-4.48 (m, 1 H), 4.16-3.83 (m, 5 H), 3.47-3.29 (m, 2 H), 3.00-2.83 (m, 2 H), 2.46-2.32 (m, 2 H), 2.25-2.16 (m, 4 H), 1.95-1.62 (m, 3 H) | 503 |

TABLE 3-continued

| No. | Structure | ¹H NMR | MS (M + H)+ |
|---|---|---|---|
| 3-bz | 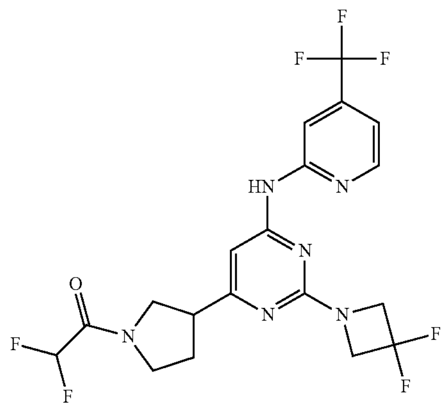 [SMILES: O=C(C(F)F)N1CCC(c2cc(Nc3cc(C(F)(F)F)ccn3)nc(N3CC(F)(F)C3)n2)C1] | ¹H NMR (400 MHz, MeOD), δ ppm: 8.49-8.45 (m, 2H), 7.21-7.20 (m, 1H), 6.69 (s, 1H), 6.49-6.22 (m, 1H), 4.45-4.39 (m, 4H), 3.98-3.74 (m, 3H), 3.47-3.31 (m, 2H), 2.10-2.48 (m, 2H) | 479 |
| 3-ca | 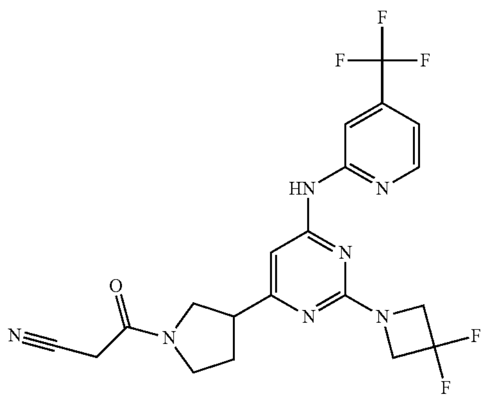 [SMILES: N#CCC(=O)N1CCC(c2cc(Nc3cc(C(F)(F)F)ccn3)nc(N3CC(F)(F)C3)n2)C1] | ¹H NMR (400 MHz, MeOD), δ ppm: 8.50-8.48 (m, 2H), 7.25 (s, 1H), 6.72 (s, 1H), 4.51-4.43 (m, 4H), 3.83 (s, 3H), 3.72-3.40 (m, 4H), 2.48-2.10 (m, 2H) | 468 |
| 3-cb | 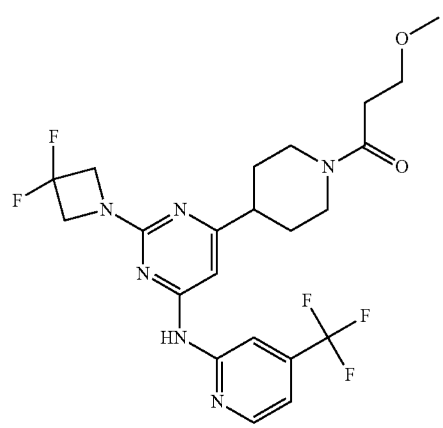 [SMILES: COCCC(=O)N1CCC(c2cc(Nc3cc(C(F)(F)F)ccn3)nc(N3CC(F)(F)C3)n2)CC1] | ¹H NMR (400 MHz, MeOD) δ 8.55 (s, 1 H), 8.49 (d, J = 4.8 Hz, 1 H), 7.24 (d, J = 5.2 Hz, 1 H), 6.63 (s, 1 H), 4.70-4.67 (m, 1 H), 4.47 (t, J = 12.0 Hz, 4 H), 4.17-4.14 (m, 1 H), 3.70 (t, J = 6.4 Hz, 2 H), 3.36 (s, 3 H), 3.25-3.19 (m, 1 H), 2.83-2.65 (m, 4 H), 2.03-1.95 (m, 2 H), 1.80-1.73 (m, 2 H) | 501 |
| 3-cc | 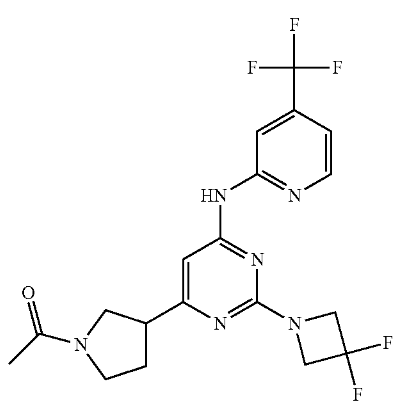 [SMILES: CC(=O)N1CCC(c2cc(Nc3cc(C(F)(F)F)ccn3)nc(N3CC(F)(F)C3)n2)C1] | ¹H NMR (400 MHz, MeOD), δ ppm: 8.48-8.47 (m, 2H), 7.24-7.22 (m, 1H), 6.71-6.69 (m, 1H), 4.49-4.43 (m, 3H), 3.87-3.61 (m, 4H), 3.48-3.43 (m, 1H), 3.31-3.20 (m, 1H), 2.36-2.27 (m, 2H), 2.20-2.10 (m, 3H) | 443 |

TABLE 3-continued

| No. | Structure | ¹H NMR | MS (M + H)+ |
|---|---|---|---|
| 3-cd | 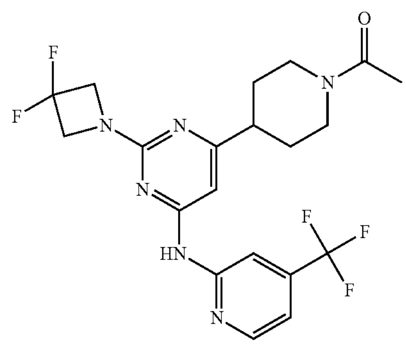 [SMILES: CC(=O)N1CCC(c2cc(Nc3cc(C(F)(F)F)ccn3)nc(N3CC(F)(F)C3)n2)CC1] | ¹H NMR (400 MHz, MeOD) δ 8.53 (s, 1 H), 8.46 (d, J = 5.6 Hz, 1 H), 7.21 (d, J = 4.8 Hz, 1 H), 6.60 (s, 1 H), 4.65-4.61 (m, 1 H), 4.44 (t, J = 12.0 Hz, 4 H), 4.05-4.01 (m, 1 H), 3.29-3.19 (m, 1 H), 2.79-2.69 (m, 2 H), 2.12 (s, 3 H), 2.00-1.91 (m, 2 H), 1.75-1.66 (m, 2H) | 457 |
| 3-ce | 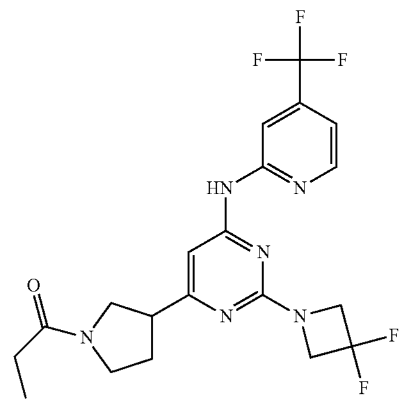 [SMILES: CCC(=O)N1CCC(c2cc(Nc3cc(C(F)(F)F)ccn3)nc(N3CC(F)(F)C3)n2)C1] | ¹H NMR (400 MHz, MeOD), δ ppm: 8.48 (s, 2H), 7.25 (s, 1H), 6.72 (s, 1H), 4.52-4.45 (m, 4H), 3.86-3.60 (m, 4H), 3.50-3.31 (m, 1H), 2.41-2.27 (m, 4H), 1.20-1.10 (m, 3H) | 457 |
| 3-cf | 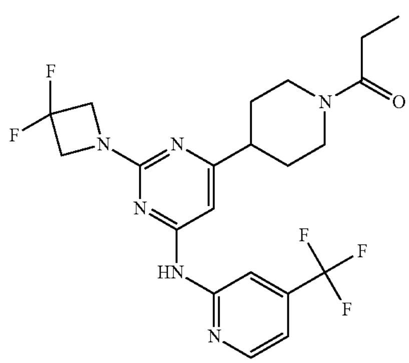 [SMILES: CCC(=O)N1CCC(c2cc(Nc3cc(C(F)(F)F)ccn3)nc(N3CC(F)(F)C3)n2)CC1] | ¹H NMR (400 MHz, MeOD) δ 8.57 (s, 1 H), 8.48 (d, J = 5.2 Hz, 1 H), 7.22-7.21 (m, 1 H), 6.60 (s, 1 H), 4.68-4.59 (m, 1 H), 4.47-4.41 (m, 4 H), 4.09 (d, J = 13.2 Hz, 1 H), 3.33-3.18 (m, 1 H), 2.81-2.72 (m, 2 H), 2.49-2.22 (m, 2 H), 2.03-1.74 (m, 4 H), 1.25-1.09 (m, 3 H). | 471 |
| 3-cg | 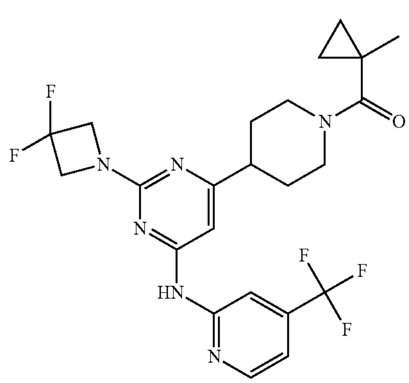 [SMILES: CC1(C(=O)N2CCC(c3cc(Nc4cc(C(F)(F)F)ccn4)nc(N4CC(F)(F)C4)n3)CC2)CC1] | ¹H NMR (400 MHz, MeOD) δ 8.56 (s, 1 H), 8.45 (d, J = 5.2 Hz, 1 H), 7.20-7.18 (m, 1 H), 6.58 (s, 1 H), 4.55-4.39 (m, 6 H), 3.00-2.73 (m, 3 H), 2.03-1.97 (m, 2 H), 1.74-1.63 (m, 2 H), 1.34 (s, 3 H), 0.94-0.90 (m, 2 H), 0.65-0.64 (m, 2 H) | 497 |

TABLE 3-continued
| No. | Structure | ¹H NMR | MS (M + H)+ |
|---|---|---|---|
| 3-ch | 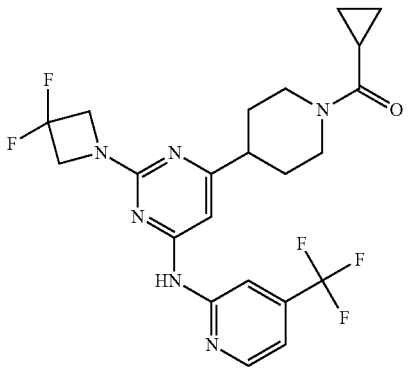 [SMILES: O=C(C1CC1)N1CCC(c2cc(Nc3cc(C(F)(F)F)ccn3)nc(N3CC(F)(F)C3)n2)CC1] | ¹H NMR (400 MHz, MeOD) δ 8.56 (s, 1 H), 8.45 (d, J = 5.2 Hz, 1 H), 7.20-7.18 (m, 2 H), 6.59 (s, 1 H), 4.63-4.57 (m, 1 H), 4.45-4.39 (m, 4 H), 3.30-3.29 (m, 1 H), 2.80-2.77 (m, 2 H), 2.04-1.63 (m, 5 H), 0.90-0.85 (m, 4 H). | 483 |
| 3-ci | 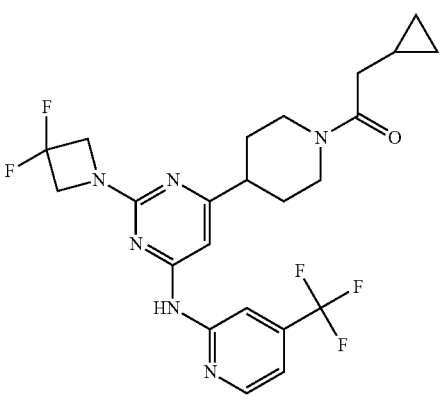 [SMILES: O=C(CC1CC1)N1CCC(c2cc(Nc3cc(C(F)(F)F)ccn3)nc(N3CC(F)(F)C3)n2)CC1] | ¹H NMR (400 MHz, MeOD) δ 8.35 (s, 1 H), 8.26 (d, J = 5.2 Hz, 1 H), 7.01-6.99 (m, 1 H), 6.39 (s, 1 H), 4.48-4.45 (m, 1 H), 4.23-4.20 (m, 4 H), 3.88 (d, J = 13.6 Hz, 1 H), 3.01-2.98 (m, 1 H), 2.60-2.51 (m, 2 H), 2.18-2.16 (m, 2 H), 1.81-1.73 (m, 2 H), 1.54-1.43 (m, 2 H), 0.84-0.83 (m, 1 H), 0.48-0.10 (m, 4 H). | 497 |
| 3-cj | 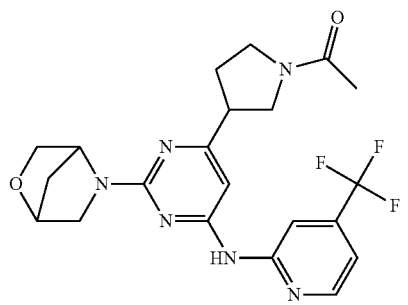 [SMILES: CC(=O)N1CCC(c2cc(Nc3cc(C(F)(F)F)ccn3)nc(N3CC4CC3CO4)n2)C1] | ¹H NMR (400 MHz, CDCl₃,), δ ppm: 8.71-8.69 (m, 1H), 8.38-8.37 (m, 1H), 7.54 (s, 1H), 7.12-7.09 (m, 1H), 6.07-6.04 (m, 1H), 5.02-4.94 (m, 1H), 4.70 (s, 1H), 3.93-3.80 (m, 2H), 3.79-3.44 (m, 5H), 3.33-3.20 (m, 1H), 2.30-2.15 (m, 2 H), 2.13-2.08 (m, 3H), 2.07-1.96 (m, 2H) | 449 |
| 3-ck | 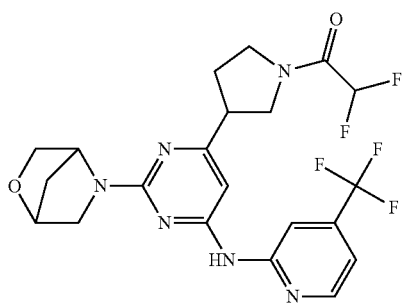 [SMILES: O=C(C(F)F)N1CCC(c2cc(Nc3cc(C(F)(F)F)ccn3)nc(N3CC4CC3CO4)n2)C1] | ¹H NMR (400 MHz, MeOD), δ ppm: 8.61-8.60 (m, 2H), 7.46-7.44 (m, 1H), 6.52-6.30 (m, 1H), 5.52 (s, 1H), 4.75 (s, 1H), 4.00-3.67 (m, 8H), 3.03 (s, 1H), 2.70-2.00 (m, 5H) | 485 |

TABLE 3-continued

| No. | Structure | ¹H NMR | MS (M + H)+ |
|---|---|---|---|
| 3-cl | 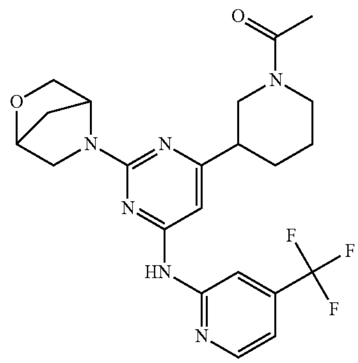 [SMILES: CC(=O)N1CCCC(c2cc(Nc3cc(C(F)(F)F)ccn3)nc(N3CC4CC3CO4)n2)C1] | ¹H NMR (400 MHz, MeOD) δ 8.74 (s, 1 H), 8.48-8.46 (m, 1 H), 7.21-7.19 (m, 1 H), 6.40 (d, J = 18.8 Hz, 1 H), 5.05-5.02 (m, 1 H), 4.74-4.40 (m, 2 H), 4.10-3.88 (m, 3 H), 3.64-3.43 (m, 2 H), 3.34-3.16 (m, 1 H), 3.05-2.85 (m, 1 H), 2.70-2.58 (m, 1 H), 2.16-2.15 (m, 3 H), 2.11-1.85 (m, 5 H), 1.66-1.58 (m, 1 H) | 463 |
| 3-cm | 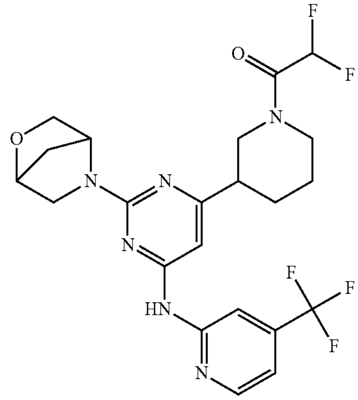 [SMILES: O=C(C(F)F)N1CCCC(c2cc(Nc3cc(C(F)(F)F)ccn3)nc(N3CC4CC3CO4)n2)C1] | ¹H NMR (400 MHz, CDCl₃), δ ppm: 8.80-8.50 (m, 1H), 8.40-8.31 (m, 1H), 7.51 (s, 1H), 7.05-7.02 (m, 1H), 6.22-5.93 (m, 2H), 5.01-4.80 (m, 1H), 4.64 (s, 1H), 4.50-4.40 (m, 1H), 4.13-3.98 (m, 1H), 3.84 (s, 2H), 3.57-3.49 (m, 2H), 3.31-2.97 (m, 1H), 2.72-2.54 (m, 1H), 2.00-1.97 (m, 1H), 1.95-1.90 (m, 2H), 1.84-1.74 (m, 2H), 1.67-1.52 (m, 1H) | 499 |
| 3-cn | 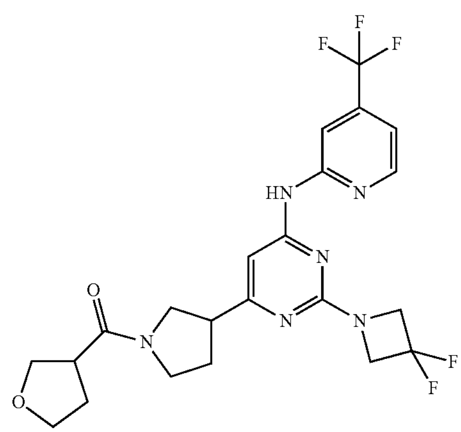 [SMILES: O=C(C1CCOC1)N1CCC(c2cc(Nc3cc(C(F)(F)F)ccn3)nc(N3CC(F)(F)C3)n2)C1] | ¹H NMR(400 MHz, MeOD) δ 8.51-8.44 (m, 2 H), 7.19 (d, J = 5.2 Hz, 1 H), 6.68-6.65 (m, 1 H), 4.47-4.41 (m, 4 H), 4.02-3.79 (m, 6 H), 3.60-3.70 (m, 2 H), 3.40-3.50 (m, 2 H), 2.40-2.02 (m, 4 H). | 499 |
| 3-co | 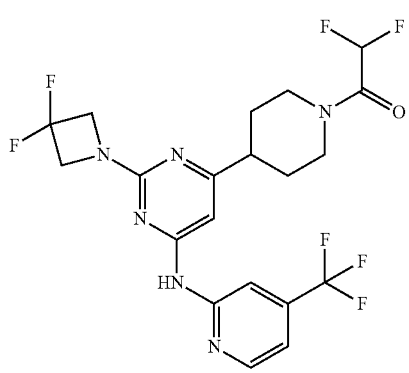 [SMILES: O=C(C(F)F)N1CCC(c2cc(Nc3cc(C(F)(F)F)ccn3)nc(N3CC(F)(F)C3)n2)CC1] | ¹H NMR (400 MHz, MeOD) δ 8.57-8.47 (m, 2 H), 7.22 (d, J = 6.4 Hz, 1 H), 6.65-6.38 (m, 2 H), 4.62-4.61 (m, 1 H), 4.47-4.41 (m, 4 H), 4.17-4.16 (m, 1 H), 3.30-3.20 (m, 1 H), 2.97-2.81 (m, 2 H), 2.15-2.06 (m, 2 H), 1.86-1.73 (m, 2 H) | 493 |

TABLE 3-continued
| No. | Structure | ¹H NMR | MS (M + H)+ |
|---|---|---|---|
| 3-cp | 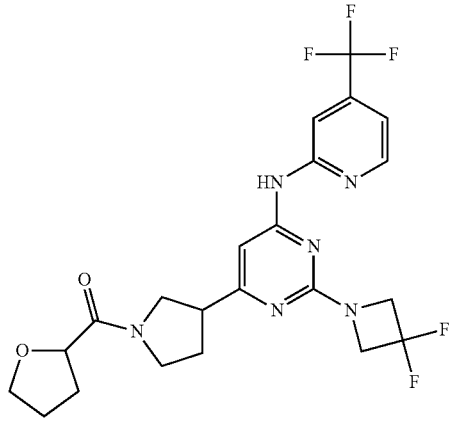 [SMILES: O=C(C1CCCO1)N1CCC(c2cc(Nc3cc(C(F)(F)F)ccn3)nc(N3CC(F)(F)C3)n2)C1] | ¹H NMR (400 MHz, MeOD) δ 8.51-8.44 (m, 2 H), 7.19 (d, J = 5.2 Hz, 1 H), 6.68-6.65 (m, 1 H), 4.67-4.61 (m, 2 H), 4.45-4.16 (m, 4 H), 3.98-3.97 (m, 1 H), 3.88-3.85 (m, 2 H), 3.77-3.31 (m, 3 H), 2.40-1.95 (m, 6 H). | 499 |
| 3-cq | 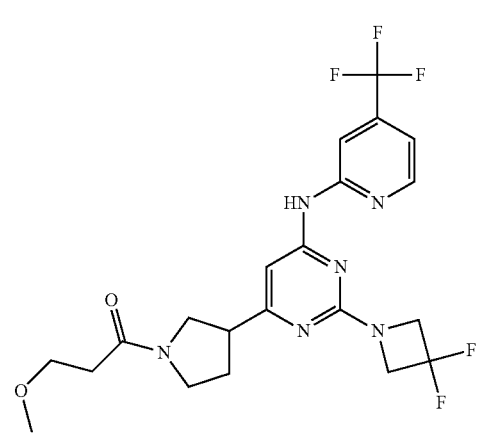 [SMILES: COCCC(=O)N1CCC(c2cc(Nc3cc(C(F)(F)F)ccn3)nc(N3CC(F)(F)C3)n2)C1] | ¹H NMR (400 MHz, MeOD) δ 8.51-8.45 (m, 2 H), 7.20 (d, J = 6.0 Hz, 1 H), 6.67 (d, J = 8.8 Hz, 1 H), 4.43 (t, J = 12.0 Hz, 5 H), 3.90-3.63 (m, 7 H), 3.49-3.30 (m, 2 H), 2.63-2.60 (m, 2 H), 2.26-2.15 (m, 2 H). | 487 |
| 3-cr | 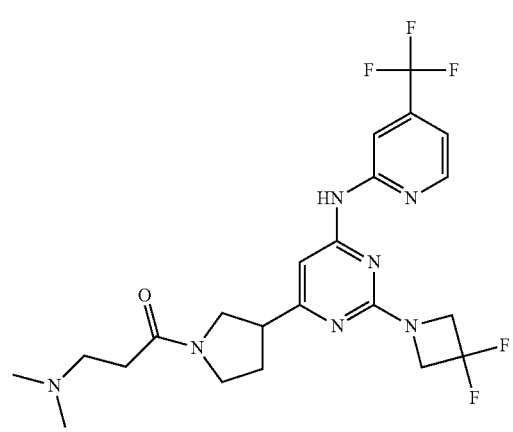 [SMILES: CN(C)CCC(=O)N1CCC(c2cc(Nc3cc(C(F)(F)F)ccn3)nc(N3CC(F)(F)C3)n2)C1] | ¹H NMR (400 MHz, MeOD) δ 8.51-8.44 (m, 2 H), 7.24-7.21 (m, 1 H), 6.73 (s, 1 H), 4.45-4.16 (m, 4 H), 3.77-3.75 (m, 2 H), 3.69-3.52 (m, 3 H), 3.00 (s, 10 H), 2.44-2.30 (m, 2 H) | 500 |

TABLE 3-continued

| No. | Structure | ¹H NMR | MS (M + H)+ |
|---|---|---|---|
| 3-cs | 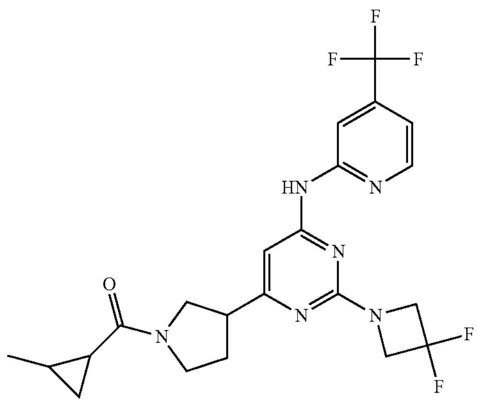 [SMILES: CC1CC1C(=O)N1CCC(c2cc(Nc3cc(C(F)(F)F)ccn3)nc(N3CC(F)(F)C3)n2)C1] | ¹H NMR (400 MHz, MeOD) δ 8.51-8.44 (m, 2 H), 7.20-7.19 (m, 1 H), 6.69-6.65 (m, 1 H), 4.46-4.38 (m, 4 H), 4.14-3.60 (m, 4 H), 3.50-3.40 (m, 1 H), 2.44-2.30 (m, 2 H), 1.55-1.50 (m, 1 H), 1.40-1.30 (m, 1 H), 1.12-0.92 (m, 4 H), 0.72-0.70 (m, 1 H) | 483 |
| 3-ct | 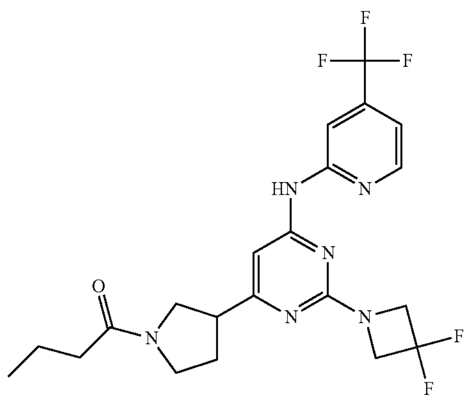 [SMILES: CCCC(=O)N1CCC(c2cc(Nc3cc(C(F)(F)F)ccn3)nc(N3CC(F)(F)C3)n2)C1] | ¹H NMR (400 MHz, MeOD) δ 8.51-8.44 (m, 2 H), 7.19 (d, J = 4.8 Hz, 1 H), 6.68-6.65 (m, 1 H), 4.45-4.36 (m, 4 H), 3.90-3.60 (m, 4 H), 3.50-3.40 (m, 1 H), 2.44-2.10 (m, 4 H), 1.70-1.60 (m, 2 H), 1.02-0.98 (m, 3 H) | 471 |
| 3-cu | 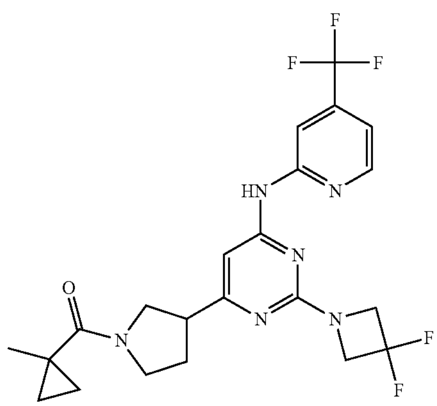 [SMILES: CC1(C(=O)N2CCC(c3cc(Nc4cc(C(F)(F)F)ccn4)nc(N4CC(F)(F)C4)n3)C2)CC1] | ¹H NMR (400 MHz, MeOD) δ 8.51-8.44 (m, 2 H), 7.43 (d, J = 5.2 Hz, 1 H), 6.68-6.65 (m, 1 H), 4.72-4.66 (m, 4 H), 4.10-3.50 (m, 5 H), 2.50-2.10 (m, 2 H), 1.31 (s, 3 H), 0.98-0.90 (m, 2 H), 0.64-0.63 (m, 2 H) | 483 |
| 3-cv | 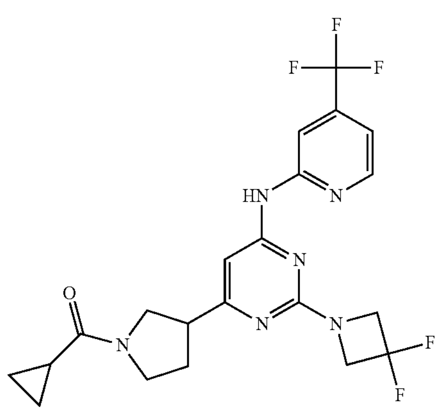 [SMILES: O=C(C1CC1)N1CCC(c2cc(Nc3cc(C(F)(F)F)ccn3)nc(N3CC(F)(F)C3)n2)C1] | ¹H NMR (400 MHz, MeOD) δ 8.51-8.44 (m, 2 H), 7.19 (d, J = 4.8 Hz, 1 H), 6.68-6.65 (m, 1 H), 4.45-4.40 (m, 4 H), 4.14-3.60 (m, 4 H), 3.50-3.40 (m, 1 H), 2.44-2.30 (m, 3H), 0.98-0.80 (m, 4 H) | 469 |

TABLE 3-continued
| No. | Structure | ¹H NMR | MS (M + H)+ |
|---|---|---|---|
| 3-cw | 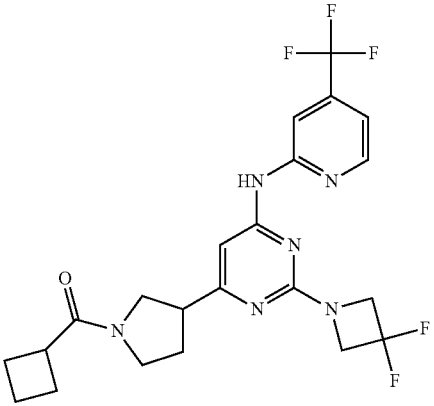 [SMILES: O=C(C1CCC1)N1CCC(c2cc(Nc3cc(C(F)(F)F)ccn3)nc(N3CC(F)(F)C3)n2)C1] | ¹H NMR (400 MHz, MeOD) δ 8.50-8.46 (m, 2 H), 7.21-7.20 (m, 1 H), 6.67 (d, J = 6.0 Hz, 1 H), 4.42 (t, J = 12.4 Hz, 4 H), 3.80-3.65 (m, 3 H), 3.64-3.31 (m, 3 H), 2.44-2.30 (m, 6 H), 2.10-2.00 (m, 1 H), 2.00-1.98 (m, 1 H) | 483 |
| 3-cx | 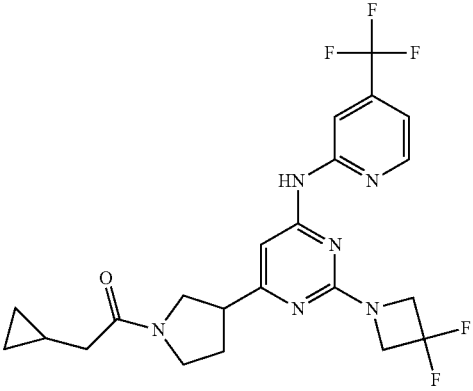 [SMILES: O=C(CC1CC1)N1CCC(c2cc(Nc3cc(C(F)(F)F)ccn3)nc(N3CC(F)(F)C3)n2)C1] | ¹H NMR (400 MHz, MeOD) δ 8.51-8.44 (m, 2 H), 7.22 (d, J = 5.2 Hz, 1 H), 6.68-6.65 (m, 1 H), 4.45-4.40 (m, 4 H), 3.80-3.60 (m, 4 H), 3.50-3.40 (m, 1 H), 2.44-2.20 (m, 4 H), 1.10-1.00 (m, 1 H), 0.55-0.50 (m, 2 H), 0.20-0.12 (m, 2 H) | 483 |
| 3-cy | 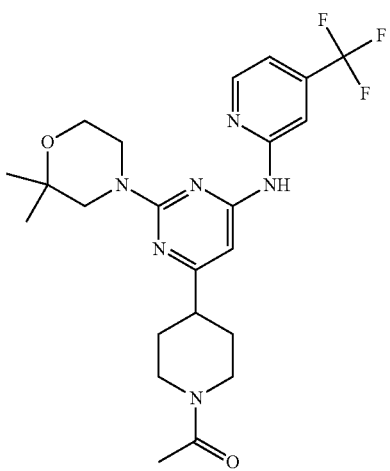 [SMILES: CC(=O)N1CCC(c2cc(Nc3cc(C(F)(F)F)ccn3)nc(N3CCOC(C)(C)C3)n2)CC1] | ¹H NMR (400 MHz, MeOD) δ 8.57 (s, 1 H), 8.44 (d, J = 5.2 Hz, 1 H), 7.17 (d, J = 5.2 Hz, 1 H), 6.30 (s, 1 H), 4.62-4.57 (m, 1 H), 4.03-4.00 (m, 1 H), 3.80 (s, 4 H), 3.65 (s, 2 H), 3.25-3.16 (m, 1 H), 2.78-2.71 (m, 2 H), 2.12 (s, 3 H), 1.99-1.90 (m, 2 H), 1.79-1.71 (m, 2 H), 1.24 (s, 6 H) | 479 |

TABLE 3-continued

| No. | Structure | ¹H NMR | MS (M + H)+ |
|---|---|---|---|
| 3-cz | 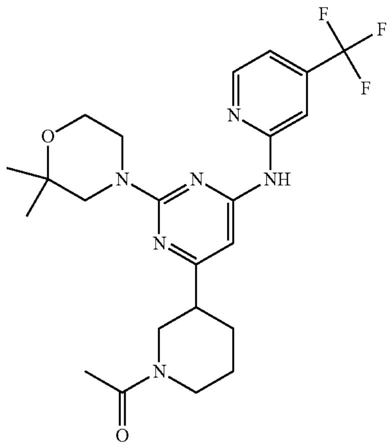 [SMILES: CC(=O)N1CCCC(c2cc(Nc3cc(C(F)(F)F)ccn3)nc(N3CCOC(C)(C)C3)n2)C1] | ¹H NMR (400 MHz, MeOD) δ 8.65 (d, J = 5.2 Hz, 1 H), 8.30 (s, 1 H), 7.47 (d, J = 5.2 Hz, 1 H), 6.70 (s, 1 H), 4.60-4.50 (m, 1 H), 4.20-3.70 (m, 7 H), 3.40- 3.35 (m, 1 H), 3.25-3.10 (m, 1 H), 3.25-3.10 (m, 1 H), 3.0-2.80 (m, 1 H), 2.24-2.18 (m, 3 H), 2.0-1.80 (m, 2 H), 1.80-1.50 (m, 1 H), 1.29 (s, 6 H) | 479 |
| 3-da | 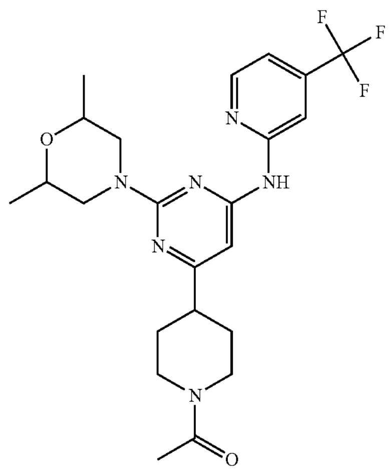 [SMILES: CC(=O)N1CCC(c2cc(Nc3cc(C(F)(F)F)ccn3)nc(N3CC(C)OC(C)C3)n2)CC1] | ¹H NMR (400 MHz, MeOD) δ 8.57 (s, 1 H), 8.44 (d, J = 5.2 Hz, 1 H), 7.17 (d, J = 5.2 Hz, 1 H), 6.30 (s, 1 H), 4.62-4.50 (m, 3 H), 4.03-4.00 (m, 1 H), 3.70-3.60 (m, 2 H), 3.25-3.16 (m, 1 H), 2.78-2.71 (m, 2 H), 2.60-2.50 (m, 2 H) 2.12 (s, 3 H), 1.99-1.90 (m, 2 H), 1.79-1.71 (m, 2 H), 1.22 (d, J = 8.0 Hz, 6 H) | 479 |
| 3-db | 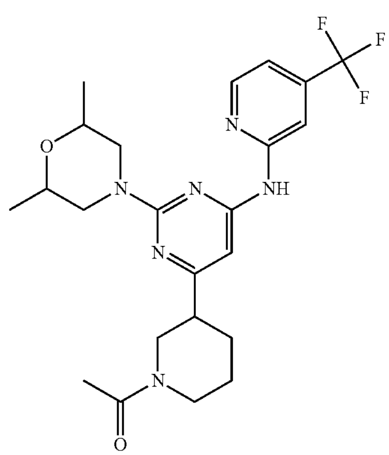 [SMILES: CC(=O)N1CCCC(c2cc(Nc3cc(C(F)(F)F)ccn3)nc(N3CC(C)OC(C)C3)n2)C1] | ¹H NMR (400 MHz, MeOD) δ 8.64 (d, J = 5.2 Hz, 1 H), 8.50-8.40 (br, 1 H), 7.46 (d, J = 4.8 Hz, 1 H), 6.70-6.50 (br, 1 H), 4.55-4.35 (m, 3 H), 4.20-3.90 (m, 1 H), 3.80-3.70 (m, 2 H), 3.35-3.26 (m, 1 H), 3.10-2.70 (m, 4 H), 2.21-2.16 (m, 3 H), 2.08-1.60 (m, 4 H), 1.26 (d, J = 8.0 Hz, 6 H) | 479 |

| No. | Structure | ¹H NMR | MS (M + H)+ |
|---|---|---|---|
| 3-dc | 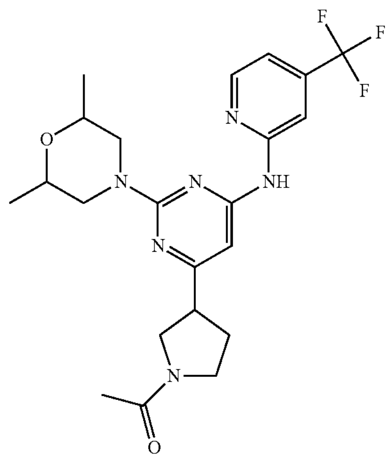 [SMILES: CC(=O)N1CCC(c2cc(Nc3cc(C(F)(F)F)ccn3)nc(N3CC(C)OC(C)C3)n2)C1] | ¹H NMR (400 MHz, DMSO-d₆) δ 10.03 (s, 1 H), 8.57 (s, 1 H), 8.52 (d, J = 5.2 Hz, 1 H), 7.30 (s, 1 H), 6.47 (d, J = 8.0 Hz, 1 H), 4.41 (s, 2 H), 3.78-3.40 (m, 6 H), 3.32-3.20 (m, 1 H), 2.51-2.50 (m, 2 H), 2.37-1.95 (m, 2 H), 1.94 (m, 3 H), 1.15 (s, 6 H). | 465 |
| 3-dd | 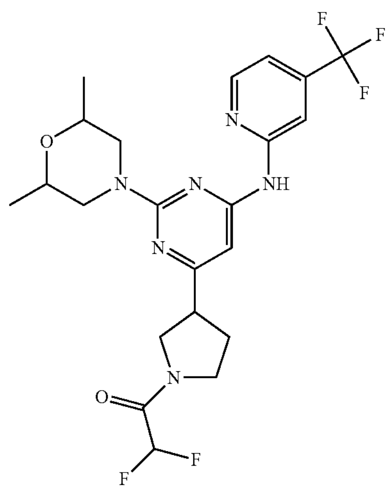 [SMILES: CC1CN(c2nc(Nc3cc(C(F)(F)F)ccn3)cc(C3CCN(C(=O)C(F)F)C3)n2)CC(C)O1] | ¹H NMR (400 MHz, DMSO-d₆) δ 10.33 (d, J = 3.2 Hz, 1 H), 8.56-8.52 (m, 2 H), 7.30-7.28 (d, J = 8.0 Hz, 1 H), 6.72-6.45 (m, 2 H), 4.40-4.37 (m, 2 H), 3.90-3.41 (m, 6 H), 2.52-2.51 (m, 2 H), 2.33-2.19 (m, 3 H), 1.16 (s, 6 H). | 501 |
| 3-de | 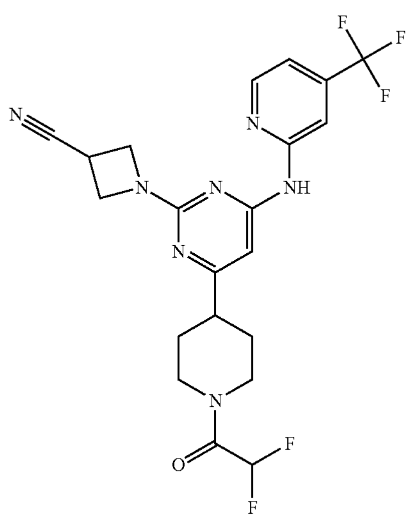 [SMILES: N#CC1CN(c2nc(Nc3cc(C(F)(F)F)ccn3)cc(C3CCN(C(=O)C(F)F)CC3)n2)C1] | ¹H NMR (400 MHz, MeOD) δ 8.57 (s, 1 H), 8.44 (d, J = 5.2 Hz, 1 H), 7.17 (d, J = 5.2 Hz, 1 H), 6.60-6.35 (m, 2 H), 4.62-4.50 (m, 1 H), 4.45-4.40 (m, 2 H), 4.26-4.22 (m, 2 H), 4.15-4.05 (m, 1 H), 3.80-3.70 (m, 1 H), 3.25-3.16 (m, 1 H), 2.95-2.88 (m, 1 H), 2.87-2.75 (m, 1 H) 2.06-1.98 (m, 2 H), 1.81-1.69 (m, 2 H) | 482 |

TABLE 3-continued

| No. | Structure | ¹H NMR | MS (M + H)+ |
|---|---|---|---|
| 3-df | 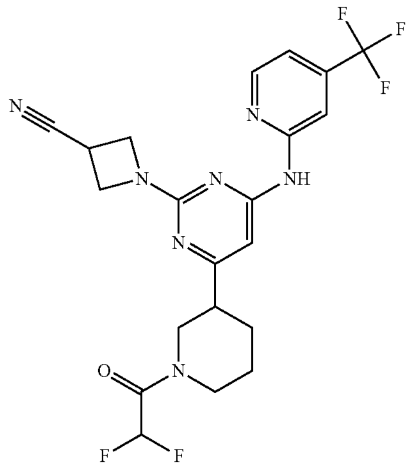 [SMILES: N#CC1CN(c2nc(Nc3cc(C(F)(F)F)ccn3)cc(C3CCCN(C(=O)C(F)F)C3)n2)C1] | ¹H NMR (400 MHz, MeOD) δ 8.61-8.47 (m, 2 H), 7.23 (d, J = 4.8 Hz, 1 H), 6.68-6.38 (m, 2 H), 4.56-4.25 (m, 5 H), 4.08-3.77 (m, 2 H), 3.52-3.23 (m, 2 H), 2.75-2.68 (m, 1 H), 2.13-1.64 (m, 4 H). | 482 |
| 3-dg | 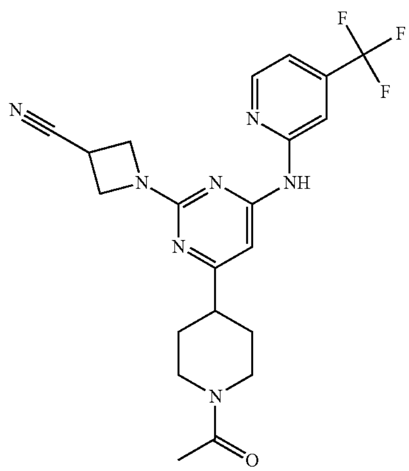 [SMILES: CC(=O)N1CCC(c2cc(Nc3cc(C(F)(F)F)ccn3)nc(N3CC(C#N)C3)n2)CC1] | ¹H NMR (400 MHz, MeOD) δ 8.62 (s, 1 H), 8.47 (d, J = 5.2 Hz, 1 H), 7.21 (d, J = 5.2 Hz, 1 H), 6.53 (s, 1 H), 4.63-4.86 (m, 1 H), 4.43 (t, J = 8.4 Hz, 2 H), 4.27-4.24 (m, 2 H), 4.06-4.03 (m, 1 H), 3.80-3.75 (m, 1 H), 3.28-3.21 (m, 1 H), 2.78-2.71 (m, 2 H), 2.15 (s, 3 H), 2.01-1.92 (m, 2 H), 1.77-1.64 (m, 2 H) | 446 |
| 3-dh | 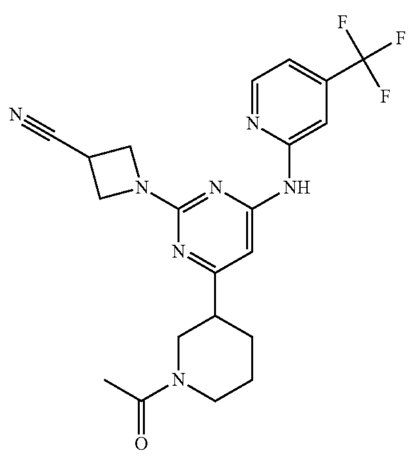 [SMILES: CC(=O)N1CCCC(c2cc(Nc3cc(C(F)(F)F)ccn3)nc(N3CC(C#N)C3)n2)C1] | ¹H NMR (400 MHz, MeOD), δ ppm: 8.56-8.51 (m, 2H), 7.32-7.27 (m, 1H), 6.65 (s, 1H), 4.60-4.32 (m, 5 H), 4.05-3.83 (m, 2H), 3.44-3.20 (m, 1H), 3.00-2.67 (m, 2H), 2.14-2.11 (m, 4H), 1.96-1.39 (m, 3H). | 446 |

| No. | Structure | ¹H NMR | MS (M + H)+ |
|---|---|---|---|
| 3-di | 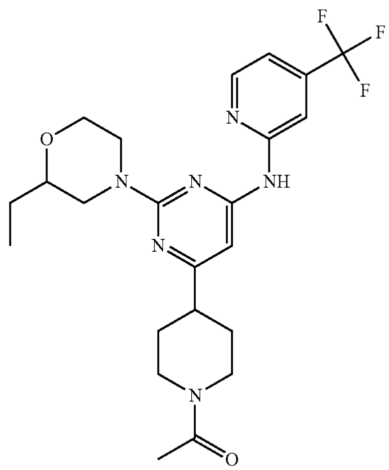 [SMILES: CCC1CN(c2nc(Nc3cc(C(F)(F)F)ccn3)cc(C3CCN(C(C)=O)CC3)n2)CCO1] | ¹H NMR (400 MHz, MeOD) δ 8.57 (s, 1 H), 8.44 (d, J = 5.2 Hz, 1 H), 7.17 (d, J = 5.2 Hz, 1 H), 6.35 (s, 1 H), 4.61-4.57 (m, 1 H), 4.56-4.48 (m, 2 H), 4.02-3.95 (m, 2 H), 3.62-3.58 (m, 1 H), 3.40-3.20 (m, 2 H), 3.02-2.98 (m, 1 H), 2.75-2.65 (m, 3 H), 2.16 (s, 3 H), 1.98-1.88 (m, 2 H), 1.81-1.51 (m, 4 H), 1.00-0.98 (m, 3 H) | 479 |
| 3-dj | 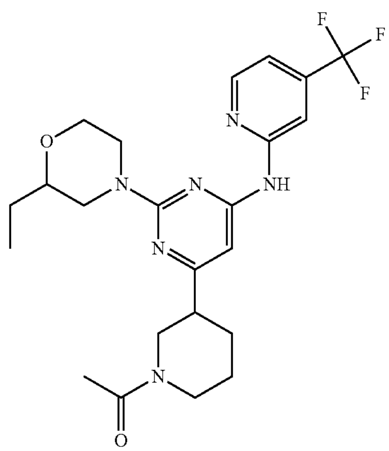 [SMILES: CCC1CN(c2nc(Nc3cc(C(F)(F)F)ccn3)cc(C3CCCN(C(C)=O)C3)n2)CCO1] | ¹H NMR (400 MHz, MeOD), δ ppm: 8.56-8.46 (m, 2H), 7.20-7.18 (m, 1H), 6.44-6.40 (m, 1H), 4.79-4.51 (m, 4 H), 4.04-3.92 (m, 2H), 3.66-3.38 (m, 2H), 3.22-2.58 (m, 5H), 2.15-1.05 (m, 6H), 1.55-1.02 (m, 3H). | 479 |
| 3-dk | 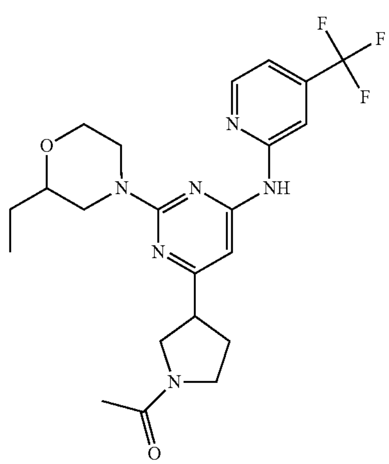 [SMILES: CCC1CN(c2nc(Nc3cc(C(F)(F)F)ccn3)cc(C3CCN(C(C)=O)C3)n2)CCO1] | ¹H NMR (400 MHz, MeOD) δ 8.60-8.40 (m, 2 H), 7.20 (d, J = 5.2 Hz, 1 H), 6.46 (d, J = 5.2 Hz, 1 H), 4.60-4.40 (m, 2 H), 4.00-3.95 (m, 1 H), 3.90-3.60 (m, 5 H), 3.55-3.40 (m, 2 H), 3.10-3.00 (m, 1 H), 2.80-2.70 (m, 1 H), 2.40-2.20 (m, 2 H), 2.10 (s, 3 H), 1.60-1.50 (m, 2 H), 1.10-1.00 (m, 3 H) | 465 |

TABLE 3-continued

| No. | Structure | ¹H NMR | MS (M + H)+ |
|---|---|---|---|
| 3-dl | 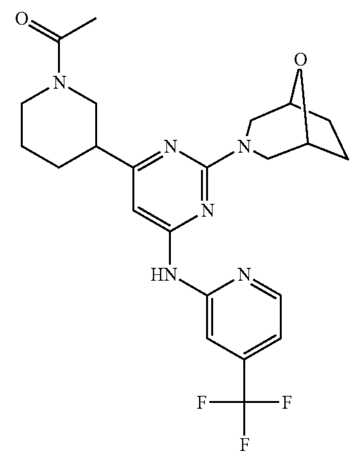 [SMILES: CC(=O)N1CCCC(c2cc(Nc3cc(C(F)(F)F)ccn3)nc(N3CC4CCC(C3)O4)n2)C1] | ¹H NMR (400 MHz, DMSO-d₆) δ 10.25 (d, J = 5.2 Hz, 1 H), 8.52-8.50 (m, 2 H), 7.27 (d, J = 8.0 Hz, 1 H), 6.54-6.50 (m, 1 H), 4.51-4.22 (m, 3 H), 4.16-4.13 (m, 2 H), 3.88-3.79 (m, 1 H), 3.10-3.00 (m, 3 H), 2.51-2.50 (m, 2 H), 2.18-1.93 (m, 4 H), 1.88 (s, 2 H), 1.82-1.63 (m, 4 H), 1.54-1.38 (m, 1 H). | 477 |
| 3-dm | 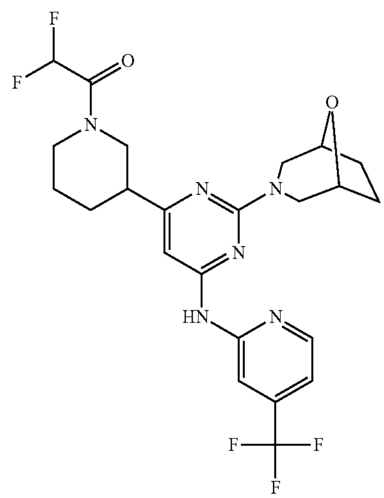 [SMILES: O=C(C(F)F)N1CCCC(c2cc(Nc3cc(C(F)(F)F)ccn3)nc(N3CC4CCC(C3)O4)n2)C1] | ¹H NMR (400 MHz, DMSO-d₆) δ 10.27 (d, J = 3.2 Hz, 1 H), 8.50 (d, J = 6.0 Hz, 2 H), 7.28 (d, J = 5.6 Hz, 1 H), 6.89-6.62 (m, 1 H), 6.51 (d, J = 2.8 Hz, 1 H), 4.40-4.25 (m, 3 H), 4.21-4.13 (m, 2 H), 3.18-3.07 (m, 3 H), 2.51-2.50 (m, 3 H), 1.98-1.95 (m, 1 H), 1.82-1.71 (m, 4 H), 1.68-1.65 (m, 2 H), 1.57 (s, 1 H). | 513 |
| 3-dn | 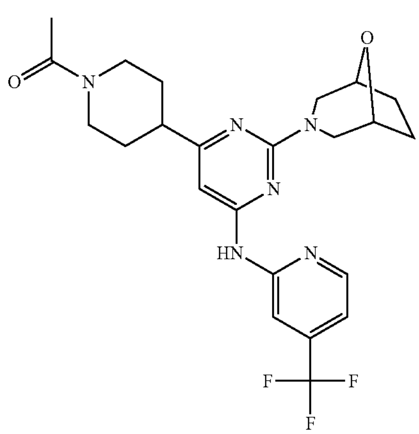 [SMILES: CC(=O)N1CCC(c2cc(Nc3cc(C(F)(F)F)ccn3)nc(N3CC4CCC(C3)O4)n2)CC1] | ¹H NMR (400 MHz, MeOD) δ 8.56 (s, 1 H), 8.46 (d, J = 5.2 Hz, 1 H), 7.19-7.17 (m, 1 H), 6.41 (s, 1 H), 4.86-4.02 (m, 6 H), 3.30-3.26 (m, 1 H), 3.20-3.10 (m, 2 H), 2.80-2.71 (m, 2 H), 2.12 (s, 3 H), 2.10-1.90 (m, 4 H), 1.80-1.60 (m, 4 H) | 477 |

TABLE 3-continued

| No. | Structure | ¹H NMR | MS (M + H)+ |
|---|---|---|---|
| 3-do | 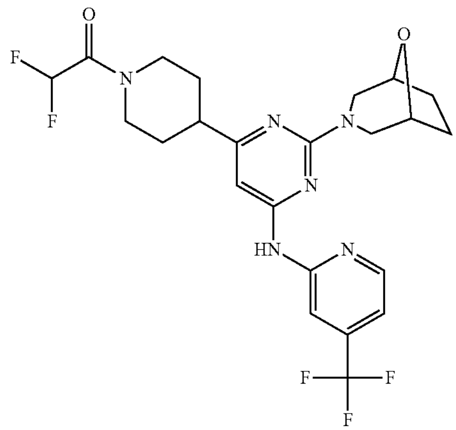 [SMILES: O=C(C(F)F)N1CCC(c2cc(Nc3cc(C(F)(F)F)ccn3)nc(N3CC4CCC(C3)O4)n2)CC1] | ¹H NMR (400 MHz, MeOD) δ 8.56 (s, 1 H), 8.46 (d, J = 5.2 Hz, 1 H), 7.19-7.17 (m, 1 H), 6.65-6.38 (m, 2 H), 4.60-4.56 (m, 1 H), 4.46-4.40 (m, 2 H), 4.32-4.22 (m, 2 H), 4.15-4.10 (m, 1 H), 3.30-3.26 (m, 1 H), 3.20-3.10 (m, 2 H), 2.99-2.90 (m, 1 H), 2.90-2.80 (m, 1 H), 2.10-1.90 (m, 4 H), 1.80-1.60 (m, 4 H) | 513 |
| 3-dp | 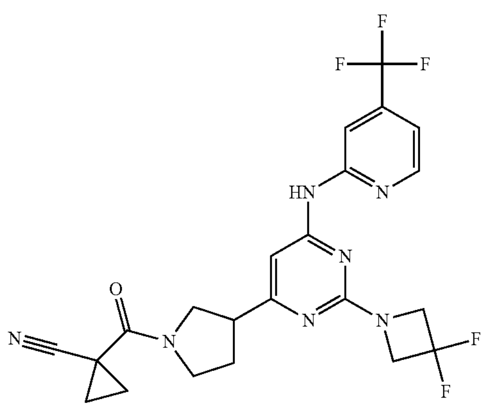 [SMILES: N#CC1(C(=O)N2CCC(c3cc(Nc4cc(C(F)(F)F)ccn4)nc(N4CC(F)(F)C4)n3)C2)CC1] | ¹H NMR (400 MHz, MeOD) δ 8.52-8.45 (m, 2 H), 7.20 (d, J = 4.8 Hz, 1 H), 6.70 (d, J = 15.2 Hz, 1 H), 4.45-4.38 (m, 4 H), 4.19-4.14 (m, 1 H), 4.00-3.70 (m, 2 H), 3.55-3.31 (m, 2 H), 2.32-2.29 (m, 2 H), 1.66-1.55 (m, 4 H). | 494 |
| 3-dq | 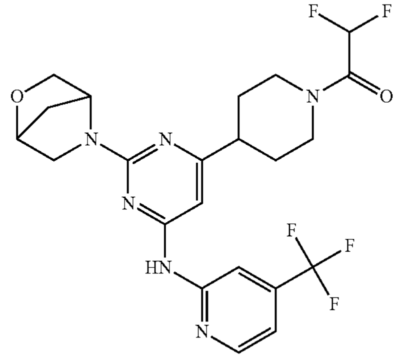 [SMILES: O=C(C(F)F)N1CCC(c2cc(Nc3cc(C(F)(F)F)ccn3)nc(N3CC4CC3CO4)n2)CC1] | ¹H NMR (400 MHz, MeOD) δ 8.74 (d, J = 9.2 Hz, 1 H), 8.46 (d, J = 4.8 Hz, 1 H), 7.19 (d, J = 4.8 Hz, 2 H), 6.65-6.36 (m, 2 H), 5.02 (d, J = 2.8 Hz, 1 H), 4.72-4.56 (m, 2 H), 4.16-4.12 (m, 1 H), 3.91-3.86 (m, 2 H), 3.63-3.55 (m, 2 H), 3.29 (d, J = 2.4 Hz, 1 H), 2.98-2.77 (m, 1 H), 2.06-1.97 (m, 4 H), 1.85-1.79 (m, 2 H). | 499 |

TABLE 3-continued
| No. | Structure | ¹H NMR | MS (M + H)+ |
|---|---|---|---|
| 3-dr | 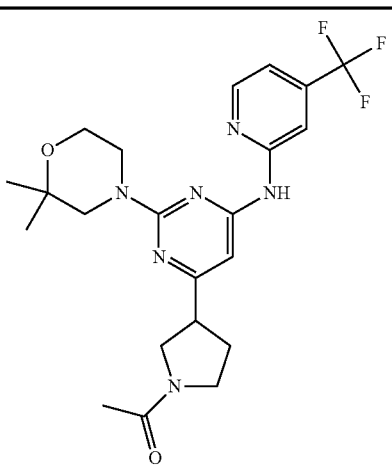 | ¹H NMR (400 MHz, MeOD) δ 8.52 (s, 1 H), 8.43 (d, J = 5.2 Hz, 1 H), 7.17 (s, 1 H), 7.16 (s, 1 H), 3.85-3.60 (m, 6 H), 3.59-3.56 (m, 4 H), 3.48-3.32 (m, 1 H), 2.34-2.23 (m, 2 H), 2.08 (d, J = 4.0 Hz, 3 H), 1.25 (s, 6 H). | 465 |
| 3-ds | 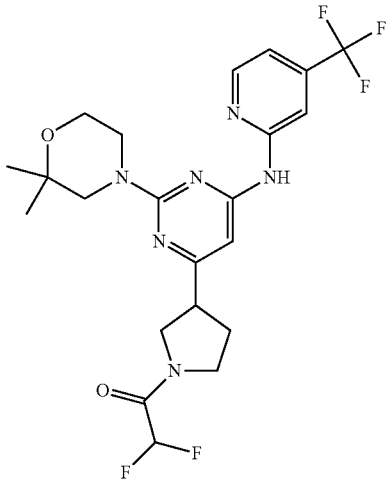 [SMILES: CC1(C)CN(c2nc(Nc3cc(C(F)(F)F)ccn3)cc(C3CCN(C(=O)C(F)F)C3)n2)CCO1] | ¹H NMR (400 MHz, MeOD) δ 8.51 (s, 1 H), 8.45 (d, J = 5.2 Hz, 1 H), 7.20 (s, 1 H), 6.49-6.21 (m, 2 H), 3.95-3.80 (m, 2 H), 3.78-3.54 (m, 6 H), 3.48-3.40 (m, 2 H), 3.38-3.29 (m, 1 H), 2.65-2.28 (m, 2 H), 1.22 (s, 6 H). | 501 |
| 3-dt | 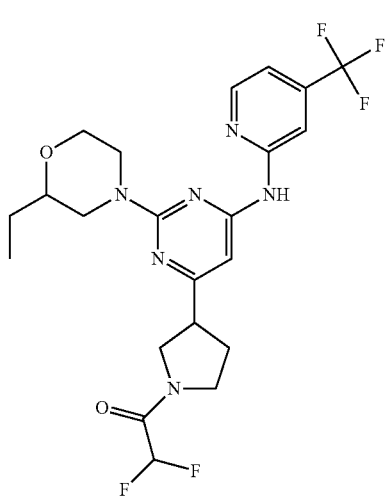 [SMILES: CCC1CN(c2nc(Nc3cc(C(F)(F)F)ccn3)cc(C3CCN(C(=O)C(F)F)C3)n2)CCO1] | ¹H NMR (400 MHz, MeOD) δ 8.48 (s, 1 H), 8.44 (d, J = 6.4 Hz, 1 H), 7.18-7.17 (m, 1 H), 6.48-6.45 (m, 1 H), 6.35-6.21 (m, 1 H), 4.51-4.44 (m, 2 H), 3.96-3.35 (m, 8 H), 3.04-2.97 (m, 1 H), 2.72-2.66 (m, 1 H), 2.39-2.09 (m, 2 H), 1.57-1.51 (m, 2 H), 1.02-0.98 (m, 3 H). | 501 |

TABLE 3-continued

| No. | Structure | ¹H NMR | MS (M + H)+ |
|---|---|---|---|
| 3-du | 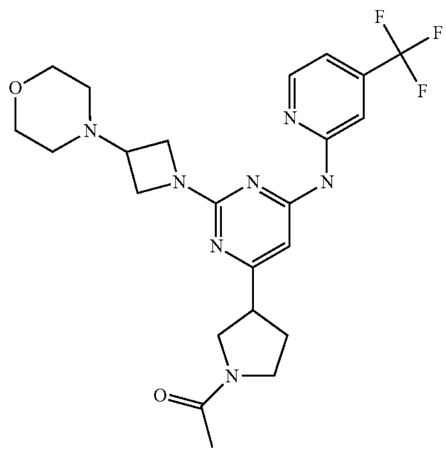 [SMILES: CC(=O)N1CCC(c2cc(Nc3cc(C(F)(F)F)ccn3)nc(N3CC(N4CCOCC4)C3)n2)C1] | ¹H NMR (400 MHz, MeOD) δ 8.70 (s, 1 H), 8.43 (d, J = 4.2 Hz, 1 H), 7.17 (d, J = 4.2 Hz, 1 H), 6.44 (d, J = 8.8 Hz, 1 H), 4.18-4.44 (m, 2 H), 3.98-3.95 (m, 2 H), 3.86-3.80 (m, 1 H), 3.78-3.71 (m, 5 H), 3.67-3.56 (m, 2 H), 3.47-3.41 (m, 1 H), 3.39-3.33 (m, 1 H), 2.47 (s, 4 H), 2.45-2.11 (m, 2 H), 2.08-2.07 (d, J = 2.8 Hz, 3 H) | 492 |
| 3-dv | 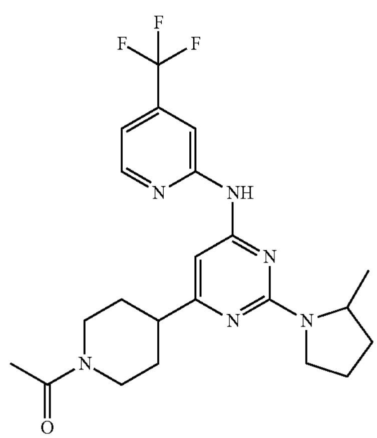 [SMILES: CC(=O)N1CCC(c2cc(Nc3cc(C(F)(F)F)ccn3)nc(N3CCCC3C)n2)CC1] | ¹H NMR (400 MHz, DMSO) δ 10.15 (s, 1H), 8.84 (s, 1H), 8.50 (d, J = 5.1 Hz, 1H), 7.26 (d, J = 5.0 Hz, 1H), 6.29 (s, 1H), 4.45 (d, J = 13.3 Hz, 1H), 4.24-4.12 (m, 1H), 3.89 (d, J = 12.9 Hz, 1H), 3.61-3.50 (m, 2H), 3.19-3.04 (m, 3H), 2.73-2.53 (m, 2H), 1.97-1.73 (m, 3H), 1.74-1.37 (m, 3H), 1.22 (d, J = 6.2 Hz, 3H). | 449.5 |
| 3-dw | 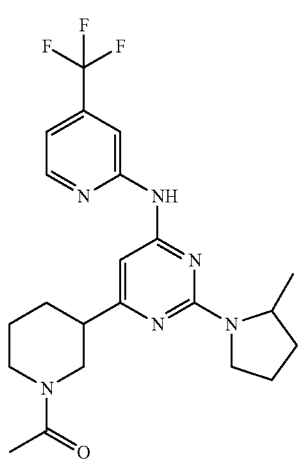 [SMILES: CC(=O)N1CCCC(c2cc(Nc3cc(C(F)(F)F)ccn3)nc(N3CCCC3C)n2)C1] | ¹H NMR (400 MHz, DMSO) δ 10.17 (d, J = 4.3 Hz, 1H), 8.84 (s, 1H), 8.50 (d, J = 5.1 Hz, 1H), 7.26 (d, J = 5.1 Hz, 1H), 6.32 (d, J = 14.6 Hz, 1H), 4.51 (d, J = 12.7 Hz, 1H), 4.35-4.04 (m, 2H), 3.96-3.77 (m, 2H), 2.74-2.53 (m, 1H), 2.38-2.72 (m, 1H), 2.07-1.81 (m, 7H), 1.71 (d, J = 14.4 Hz, 3H), 1.56-1.34 (m, 1H), 1.23 (d, J = 6.2 Hz, 3H). | 449.5 |

TABLE 3-continued

| No. | Structure | ¹H NMR | MS (M + H)+ |
|---|---|---|---|
| 3-dx | 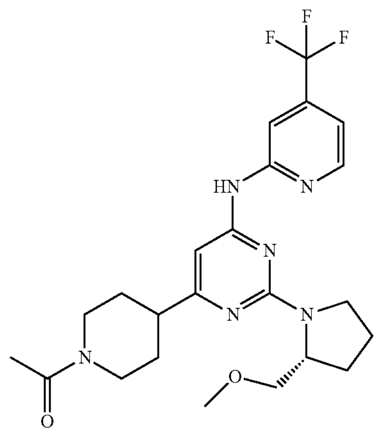 [SMILES: COC[C@H]1CCCN1c1nc(Nc2cc(C(F)(F)F)ccn2)cc(C2CCN(C(C)=O)CC2)n1] | ¹H NMR (400 MHz, DMSO) δ 10.15 (s, 1H), 8.50 (d, J = 5.1 Hz, 1H), 7.25 (d, J = 5.1 Hz, 1H), 6.38 (s, 1H), 4.45 (d, J = 13.1 Hz, 1H), 4.23 (s, 1H), 3.89 (d, J = 13.2 Hz, 1H), 3.68-3.36 (m, 4H), 3.12 (d, J = 11.3 Hz, 1H), 2.64 (t, J = 12.2 Hz, 2H), 2.03-1.72 (m, 9H), 1.70-1.50 (m, 3H). | 479.5 |

Example 4

Synthesis of (R)-6-(1-methylpiperidin-4-yl)-2-(2-methylpyrrolidin-1-yl)-N-(4-(trifluoromethyl)pyridin-2-yl)pyrimidin-4-amine

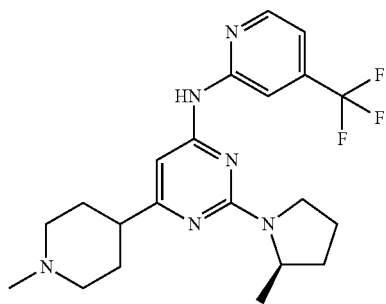

(4-a)

To a suspension of formic acid; 2-[(2R)-2-methylpyrrolidin-1-yl]-6-(4-piperidyl)-N-[4-(trifluoromethyl)-2-pyridyl]pyrimidin-4-amine (18 mg; 0.03978 mmol) in 1,4-dioxane (300 equiv.; 11.93 mmol) was added formaldehyde (37 mass %) in aqueous solution (10.0 equiv.; 0.3978 mmol) at 25° C., and the reaction was stirred at 60° C. for 2 h, resulting in a clear solution. The desired product (12.9 mg, 78% yield) was obtained as white powder after HPLC purification: ¹H NMR (400 MHz, DMSO-d$_6$) δ 10.11 (s, 1H), 8.85 (s, 1H), 8.50 (d, J=5.1 Hz, 1H), 7.25 (d, J=5.1 Hz, 1H), 6.29 (s, 1H), 4.28-4.13 (m, 1H), 3.51 (dt, J=16.1, 7.8 Hz, 2H), 2.83 (d, J=11.3 Hz, 2H), 2.28 (m, 1H), 2.17 (s, 3H), 2.10-1.83 (m, 5H), 1.79-1.61 (m, 5H), 1.22 (d, J=6.3 Hz, 3H); MS m/z=421 (M+H⁺).

Additional compounds of the invention presented in Table 4 below were prepared by methods already described in the application.

TABLE 4

| No. | Structure | 1H NMR | MS (M + H)+ |
|---|---|---|---|
| 4-a | 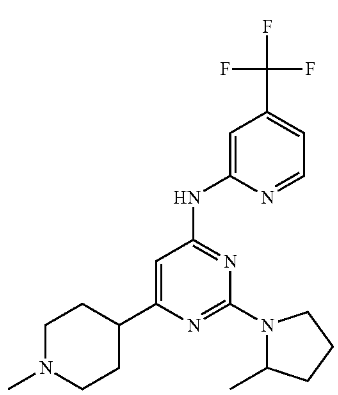 [SMILES: CC1CCCN1c1nc(Nc2cc(C(F)(F)F)ccn2)cc(C2CCN(C)CC2)n1] | ¹H NMR (400 MHz, MeOD) δ 8.76-8.53 (m, 2H), 7.46 (d, J = 4.8 Hz, 1H), 6.65-6.41 (br, 1H), 4.56 (s, 1H), 3.86 (s, 1H), 3.69-3.40 (m, 3H), 3.30-3.20 (m, 2H), 2.94 (s, 3H), 2.32-2.11 (m, 8H), 1.89 (s, 1H), 1.35 (s, 3H). | 421 |

TABLE 4-continued

| No. | Structure | 1H NMR | MS (M + H)+ |
|---|---|---|---|
| 4-b | 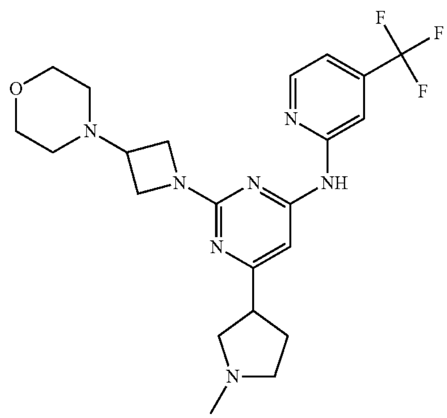 [SMILES: CN1CCC(c2cc(Nc3cc(C(F)(F)F)ccn3)nc(N3CC(N4CCOCC4)C3)n2)C1] | ¹H NMR (400 MHz, MeOD) δ 8.69 (s, 1H), 8.44 (d, J = 4.8 Hz, 1H), 7.18 (d, J = 5.2 Hz, 1H), 6.45 (s, 1H), 4.21-4.16 (m, 2H), 4.01-3.98 (m, 2H), 3.74-3.72 (m, 4H), 3.51-3.34 (m, 6H), 2.88 (s, 3H), 2.47 (s, 5H), 2.21-2.19 (m, 1H). | 464 |
| 4-c | 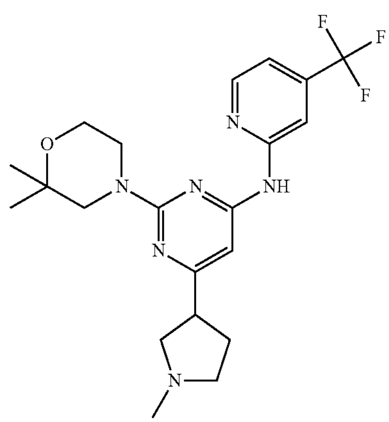 [SMILES: CN1CCC(c2cc(Nc3cc(C(F)(F)F)ccn3)nc(N3CCOC(C)(C)C3)n2)C1] | ¹H NMR (400 MHz, MeOD) δ 8.16 (s, 1H), 8.45 (d, J = 5.2 Hz, 1H), 7.19 (d, J = 5.2 Hz, 1H), 6.39 (s, 1H), 3.82-3.79 (m, 4H), 3.66 (s, 2H), 3.64-3.61 (m, 3H), 3.59-3.41 (m, 2H), 2.96 (s, 3H), 2.50-2.44 (m, 1H), 2.32-2.25 (m, 1H), 1.24 (s, 6H). | 437 |
| 4-d | 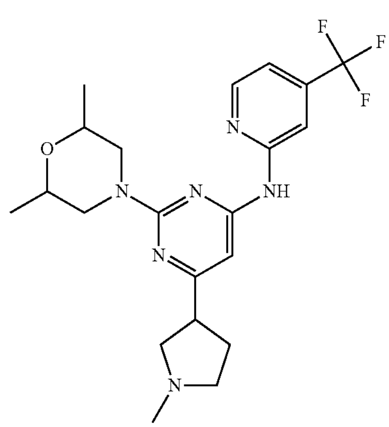 [SMILES: CC1CN(c2nc(Nc3cc(C(F)(F)F)ccn3)cc(C3CCN(C)C3)n2)CC(C)O1] | ¹H NMR (400 MHz, MeOD) δ 8.55 (s, 1H), 8.45 (d, J = 5.2 Hz, 1H), 7.20 (d, J = 5.2 Hz, 1H), 6.39 (s, 1H), 4.56-4.53 (m, 2H), 3.67-3.62 (m, 5H), 3.51-3.45 (m, 2H), 2.96 (s, 3H), 2.65-2.60 (m, 2H), 2.47 (s, 1H), 2.28 (s, 1H), 1.22 (s, 6H). | 437 |

TABLE 4-continued

| No. | Structure | 1H NMR | MS (M + H)+ |
|---|---|---|---|
| 4-e | 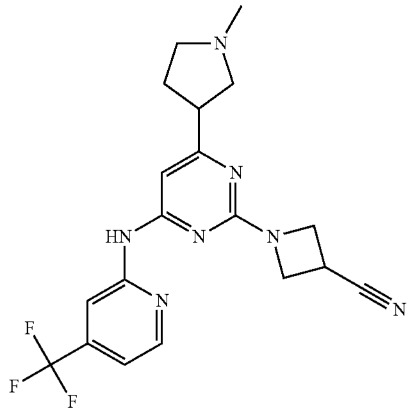 [SMILES: CN1CCC(c2cc(Nc3cc(C(F)(F)F)ccn3)nc(N3CC(C#N)C3)n2)C1] | ¹H NMR (400 MHz, MeOD) δ 8.54 (s, 1H), 8.46 (d, J = 4.8 Hz, 1H), 7.21 (d, J = 5.2 Hz, 1H), 6.62 (s, 1H), 4.43 (t, J = 8.4 Hz, 2H), 4.26 (m, 2H), 3.32-3.81 (m, 6H), 2.97 (s, 3H), 2.22-2.53 (m, 2H). | 404 |
| 4-f | 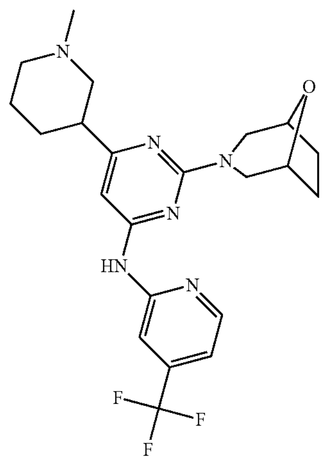 [SMILES: CN1CCCC(c2cc(Nc3cc(C(F)(F)F)ccn3)nc(N3CC4CCC(C3)O4)n2)C1] | ¹H NMR (400 MHz, MeOD) δ 8.45 (d, J = 4.0 Hz, 2H), 7.18 (d, J = 5.2 Hz, 1H), 6.50 (s, 1H), 4.56 (s, 1H), 4.43-4.40 (m, 2H), 4.30-4.24 (m, 2H), 3.52-3.49 (m, 1H), 3.38-3.30 (m, 1H), 3.18-3.12 (m, 2H), 2.97 (s, 2H), 2.84 (s, 3H), 2.07-1.80 (m, 8H). | 449 |
| 4-g | 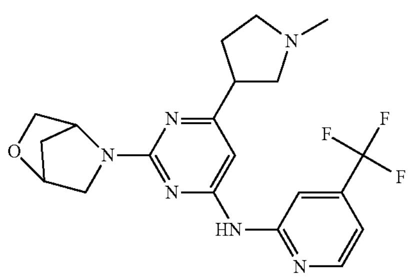 [SMILES: CN1CCC(c2cc(Nc3cc(C(F)(F)F)ccn3)nc(N3CC4CC3CO4)n2)C1] | ¹H NMR (400 MHz, MeOD), δ ppm: 8.63-8.52 (m, 1H), 7.60-7.59 (m, 1H), 7.19-7.09 (m, 2H), 6.42 (s, 1H), 5.01-4.99 (m, 1H), 4.71 (s, 1H), 3.90-3.84 (m, 2H), 3.61-3.41 (m, 6H), 2.90-2.89 (m, 3H), 2.49-2.43 (m, 1H), 2.27-2.20 (m, 1H), 2.02-1.97 (m, 2H) | 421 |
| 4-h | 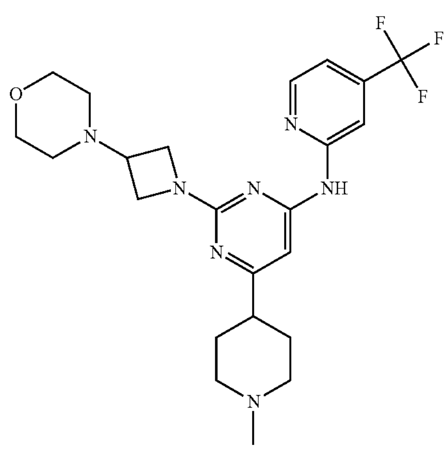 [SMILES: CN1CCC(c2cc(Nc3cc(C(F)(F)F)ccn3)nc(N3CC(N4CCOCC4)C3)n2)CC1] | ¹H NMR (400 MHz, DMSO-d₆) δ 10.21 (s, 1H), 8.67 (s, 1H), 8.49 (d, J = 5.2 Hz, 1H), 7.22 (d, J = 5.2 Hz, 1H), 6.48 (s, 1H), 4.01-3.99 (m, 2H), 3.83-3.82 (m, 2H), 3.59-3.57 (m, 4H), 3.21-3.20 (m, 1H), 2.88-2.80 (m, 2H), 2.38-2.30 (m, 5H), 2.16 (s, 3H), 1.98-1.88 (m, 2H), 1.75-1.70 (m, 2H), 1.65-1.55 (m, 2H) | 478 |

TABLE 4-continued

| No. | Structure | 1H NMR | MS (M + H)+ |
|---|---|---|---|
| 4-i | 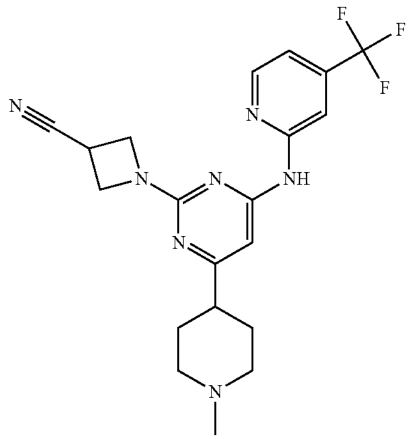 [SMILES: CN1CCC(c2cc(Nc3cc(C(F)(F)F)ccn3)nc(N3CC(C#N)C3)n2)CC1] | ¹H NMR (400 MHz, MeOD) δ 8.64 (d, J = 5.2 Hz, 1H), 8.46-8.40 (br, 1H), 7.47 (d, J = 4.8 Hz, 1H), 6.83-6.73 (br, 1H), 4.71-4.67 (m, 2H), 4.45-4.40 (m, 2H), 4.00-3.98 (m, 1H), 3.75-3.68 (m, 2H), 3.28-3.20 (m, 2H) 3.16-3.00 (m, 1H), 2.96 (s, 3H), 2.30-2.25 (m, 2H), 2.12-2.00 (m, 2H) | 418 |
| 4-j | 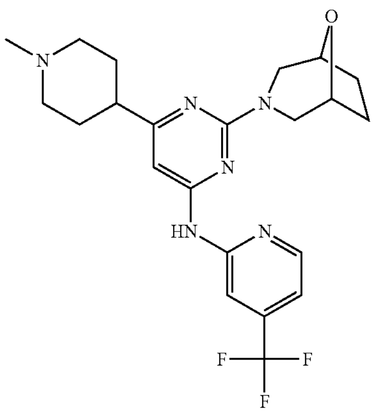 [SMILES: CN1CCC(c2cc(Nc3cc(C(F)(F)F)ccn3)nc(N3CC4CCC(C3)O4)n2)CC1] | ¹H NMR (400 MHz, MeOD) δ 8.67 (d, J = 6.4 Hz, 1H), 8.50-8.10 (br, 1H), 7.50 (d, J = 5.2 Hz, 1H), 7.00-6.60 (br, 1H), 4.60-4.50 (m, 2H), 4.20-4.10 (m, 2H), 3.80-3.70 (m, 2H), 3.60-3.50 (m, 2H), 3.30-3.20 (m, 3H), 2.91 (s, 3H), 2.40-2.30 (m, 2H), 2.20-2.00 (m, 4H), 1.96-1.86 (m, 2H) | 449 |
| 4-k | 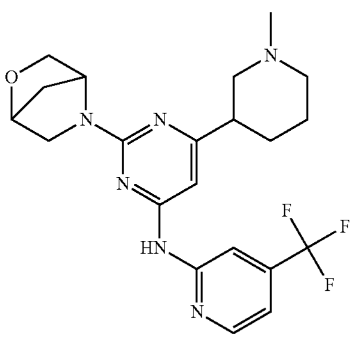 [SMILES: CN1CCCC(c2cc(Nc3cc(C(F)(F)F)ccn3)nc(N3CC4CC3CO4)n2)C1] | ¹H NMR (400 MHz, CDCl₃) δ 8.76-8.67 (m, 1H), 8.37 (d, J = 4.8 Hz, 1H), 7.33 (s, 1H), 7.09-7.08 (m, 1H), 5.99 (s, 1H), 4.70 (s, 1H), 3.90-3.88 (m, 2H), 3.64-3.56 (m, 2H), 3.02-3.00 (m, 1H), 2.90-2.72 (m, 2H), 2.33 (s, 3H), 2.17-2.14 (m, 1H), 2.03-1.89 (m, 4H), 1.78-1.64 (m, 2H), 1.55-1.48 (m, 1H) | 435 |
| 4-l | 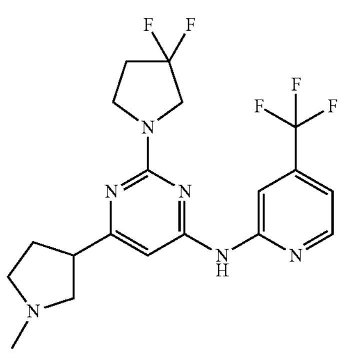 [SMILES: CN1CCC(c2cc(Nc3cc(C(F)(F)F)ccn3)nc(N3CCC(F)(F)C3)n2)C1] | ¹H NMR (400 MHz, MeOD) δ 8.55 (d, J = 5.2 Hz, 1H), 8.32 (s, 1H), 7.36 (s, 1H), 6.62 (s, 1H), 4.07-4.00 (m, 2H), 3.95-3.71 (m, 5H), 3.65-3.26 (m, 2H), 3.03 (d, J = 17.2 Hz, 3H), 2.64-2.51 (m, 3H), 2.40-2.20 (m, 1H) | 429 |

| No. | Structure | 1H NMR | MS (M + H)+ |
|---|---|---|---|
| 4-m | 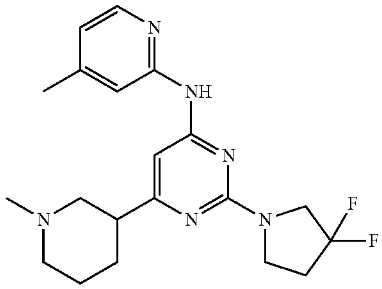 [SMILES: Cc1ccnc(Nc2cc(C3CCCN(C)C3)nc(N3CCC(F)(F)C3)n2)c1] | ¹H NMR (400 MHz, MeOD), δ ppm: 8.43-8.33 (m, 1H), 7.49-7.33 (m, 2H), 6.53 (s, 1H), 4.22-3.92 (m, 4H), 3.75-3.48 (m, 3H), 3.41-3.413 (m, 4H), 3.12-2.93 (m, 5H), 2.17-1.83 (m, 4H) | 389 |
| 4-n | 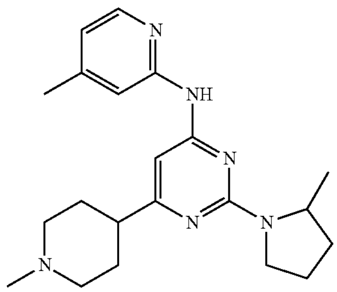 [SMILES: Cc1ccnc(Nc2cc(C3CCN(C)CC3)nc(N3CCCC3C)n2)c1] | ¹H NMR (400 MHz, MeOD) δ 8.50 (d, J = 6.4 Hz, 1H), 7.77-7.54 (m, 2H), 6.52 (s, 1H), 4.64 (s, 1H), 3.89-3.65 (m, 4H), 3.38-3.19 (m, 3H), 2.92 (s, 3H), 2.66 (s, 3H), 2.35-2.09 (m, 8H), 1.39 (s, 3H). | 367 |
| 4-o | 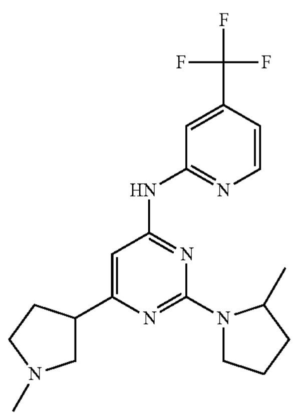 [SMILES: CC1CCCN1c1nc(Nc2cc(C(F)(F)F)ccn2)cc(C2CCN(C)C2)n1] | ¹H NMR (400 MHz, MeOD) δ 8.90-8.57 (m, 2H), 7.40-7.30 (m, 1H), 6.50-6.39 (br, 1H), 4.56-4.40 (m, 1H), 3.98-3.70 (m, 4H), 3.70-3.30 (m, 3H), 3.00-2.96 (m, 3H), 2.63-2.49 (m, 1H), 2.40-2.20 (m, 4H), 1.85-1.72 (m, 1H), 1.40-1.30 (m, 3H) | 407 |
| 4-p | 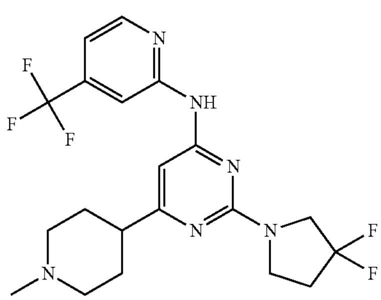 [SMILES: CN1CCC(c2cc(Nc3cc(C(F)(F)F)ccn3)nc(N3CCC(F)(F)C3)n2)CC1] | ¹H NMR (400 MHz, MeOD) δ 8.80 (d, J = 4.4 Hz, 1H), 8.66 (br, 1H), 7.50 (d, J = 5.2 Hz, 1H), 6.68 (br, 1H), 4.21-4.15 (m, 2H), 4.08-4.04 (m, 2H), 3.76-3.62 (m, 2H), 3.34-3.23 (m, 3H), 3.05 (s, 3H), 2.78-2.64 (m, 2H), 2.41-2.35 (m, 2H), 2.19-2.03 (m, 2H) | 443 |
| 4-q | 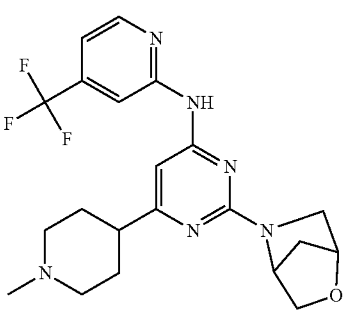 [SMILES: CN1CCC(c2cc(Nc3cc(C(F)(F)F)ccn3)nc(N3CC4CC3CO4)n2)CC1] | ¹H NMR (400 MHz, MeOD) δ 8.68-8.64 (m, 2H), 7.52-7.48 (m, 2H), 4.66 (s, 1H), 4.04-3.94 (m, 3H), 3.82-3.69 (m, 4H), 2.96 (s, 4H), 2.37-2.34 (m, 4H), 2.15-2.08 (m, 4H) | 435 |

TABLE 4-continued

| No. | Structure | 1H NMR | MS (M + H)+ |
|---|---|---|---|
| 4-r | 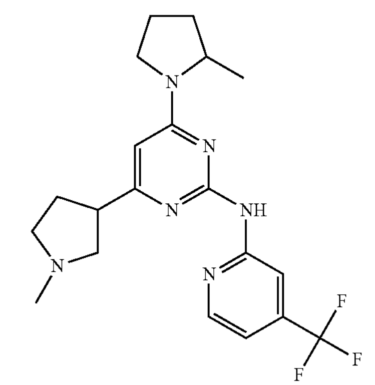 [SMILES: CC1CCCN1c1cc(C2CCN(C)C2)nc(Nc2cc(C(F)(F)F)ccn2)n1] | $^1$H NMR (400 MHz, MeOD) δ 8.68-8.64 (m, 1H), 7.54-7.40 (m, 2H), 6.68-6.47 (m, 1H), 4.53-4.30 (m, 1H), 4.12-3.99 (m, 1H), 3.86-3.80 (m, 3H), 3.69-3.28 (m, 3H), 3.05-2.96 (m, 3H), 2.80-2.60 (m, 1H), 2.49-2.23 (m, 1H), 2.19-1.96 (m, 3H), 1.89-1.72 (m, 1H), 1.30-1.26 (m, 3H) | 407 |
| 4-s | 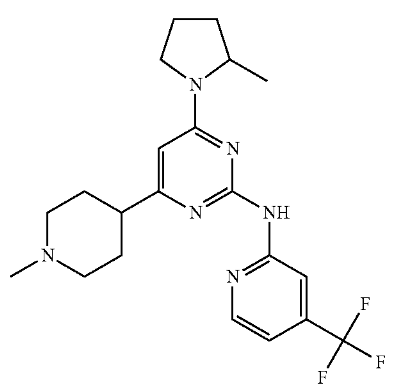 [SMILES: CC1CCCN1c1cc(C2CCN(C)CC2)nc(Nc2cc(C(F)(F)F)ccn2)n1] | $^1$H NMR (400 MHz, MeOD), δ ppm: 8.92-8.90 (m, 1H), 7.54-7.48 (m, 2H), 6.54-6.45 (d, J = 38.8 Hz, 1H), 4.60-4.38 (m, 1H), 3.88-3.58 (m, 4H), 3.33-3.29 (m, 2H), 2.96 (s, 3H), 2.32-2.10 (m, 8H), 1.93-1.86 (m, 1H), 1.37-1.30 (m, 3H) | 421 |
| 4-t | 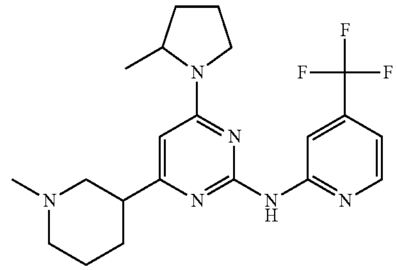 [SMILES: CC1CCCN1c1cc(C2CCCN(C)C2)nc(Nc2cc(C(F)(F)F)ccn2)n1] | $^1$H NMR (400 MHz, MeOD), δ ppm: 8.80-8.79 (d, J = 5.2 Hz, 1H), 7.60-7.57 (m, 1H), 7.50-7.49 (d, J = 5.2 Hz, 1H), 6.61-6.51 (m, 1H), 4.60-4.42 (m, 1H), 3.91-3.81 (m, 2H), 3.76-3.66 (m, 2H), 3.63-3.40 (m, 2H), 3.23-3.18 (m, 1H), 3.00 (s, 3H), 1.85-2.30 (m, 8H), 1.92-1.80 (m, 3H) | 421 |

TABLE 4-continued

| No. | Structure | 1H NMR | MS (M + H)+ |
|---|---|---|---|
| 4-u | 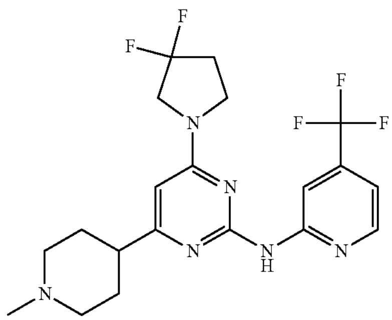 [SMILES: CN1CCC(c2cc(N3CCC(F)(F)C3)nc(Nc3cc(C(F)(F)F)ccn3)n2)CC1] | ¹H NMR (400 MHz, MeOD), δ ppm: 8.87-8.81 (m, 1H), 7.54-7.52 (m, 2H), 6.58-6.49 (m, 1H), 4.19-4.13 (m, 2H), 4.10-3.97 (m, 2H), 3.75-3.72 (d, J = 13.6 Hz, 2H), 3.32-3.23 (m, 3H), 2.97 (s, 3H), 2.73-2.65 (m, 2H), 2.38-2.34 (m, 2H), 2.27-2.15 (m, 2H) | 443 |
| 4-v | 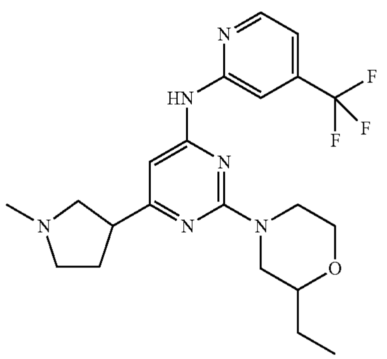 [SMILES: CCC1CN(c2nc(Nc3cc(C(F)(F)F)ccn3)cc(C3CCN(C)C3)n2)CCO1] | ¹H NMR (400 MHz, MeOD) δ 8.51 (s, 1H), 8.46-8.43 (m, 1H), 7.23-7.16 (m, 1H), 6.45 (s, 1H), 4.50-4.47 (m, 2H), 3.98-3.94 (m, 1H), 3.68-3.47 (m, 6H), 3.37-3.32 (m, 1H), 3.05-2.98 (m, 4H), 2.73-2.70 (m, 1H), 2.51-2.46 (m, 1H), 2.34-2.22 (m, 1H), 1.61-1.49 (m, 2H), 1.01-0.96 (m, 3H). | 437 |

Example 5

Preparation of (R)—N-(4-cyclopropylpyridin-2-yl)-2-(2-methylpyrrolidin-1-yl)-6-(tetrahydro-2H-pyran-4-yl)pyrimidin-4-amine

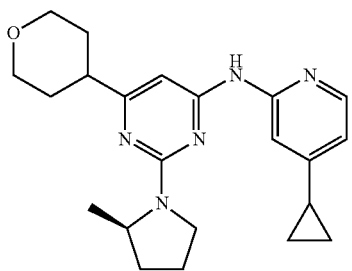

(5-b)

Step 1—Synthesis of 2-Chloro-N-(4-cyclopropylpyridin-2-yl)-6-(tetrahydro-2H-pyran-4-yl)pyrimidin-4-amine

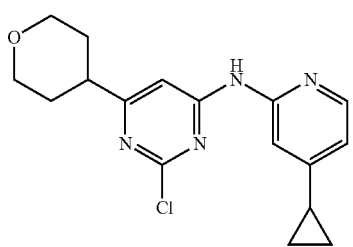

(5-a)

A vial was charged with example 1-f (250 mg, 1.07 mmol), 2-amino-4-(cyclopropyl)pyridine (160 mg, 1.18 mmol), tris(dibenzylideneacetone)dipalladium (0) (50 mg, 0.054 mmol), 4,5-bis(diphenylphosphino)-9,9-dimethylxanthene (64 mg, 0.11 mmol), and sodium tert-butoxide (150 mg, 1.5 mmol). The vial was capped and purged with $N_2$, followed by addition of dioxane (2 mL). The resulting mixture was heated at 60° C. for 2 h. The dark mixture was diluted with 50% DCM/EtOAc (20 mL) and filtered through paper. The filtrate was concentrated onto Celite, and purified by chromatography (12 g $SiO_2$ column, 0-50% ethyl acetate-heptane) to afford 106 mg (30%) of the title compound as an off-white solid: ¹H NMR (400 MHz, $CDCl_3$) δ 8.16 (d, J=5.3 Hz, 1H), 8.13-8.02 (m, 2H), 7.52 (s, 1H), 7.08 (s, 1H), 6.66 (d, J=5.3 Hz, 1H), 4.18-3.97 (m, 2H), 3.65-3.34 (m, 2H), 2.91-2.68 (m, 1H), 2.18 (s, 1H), 1.98-1.76 (m, 6H), 1.38-1.18 (m, 2H), 1.18-1.02 (m, 2H), 0.96-0.74 (m, 2H); MS m/z=329 (M+H⁺).

Step 2—Synthesis of (R)—N-(4-cyclopropylpyridin-2-yl)-2-(2-methylpyrrolidin-1-yl)-6-(tetrahydro-2H-pyran-4-yl)pyrimidin-4-amine A solution of example 5-a (100 mg, 0.30 mmol), (2R)-2-methylpyrrolidine (51 mg, 0.60 mmol) and dimethylformamide (1.0 mL) was heated in a sealed vial at 80° C. for 7 h. The mixture was directly purified by HPLC to afford 62 mg (54%) of the title compound as a colorless solid: ¹H NMR (400 MHz, DMSO-$d_6$) δ 9.45 (s, 1H), 8.04 (d, J=5.2 Hz, 1H), 8.00 (s, 1H), 6.68 (d, J=5.0 Hz, 1H), 6.34 (s, 1H), 4.23 (s, 1H), 3.92 (d, J=11.3 Hz, 2H), 3.64-3.46 (m, 2H), 3.40 (dt, J=17.6, 7.0 Hz, 2H), 2.62-2.52 (m, 1H), 2.15-1.95 (m, 2H), 1.95-1.80 (m, 2H), 1.79-1.56 (m, 5H), 1.24 (d, J=6.2 Hz, 3H), 1.14-0.95 (m, 2H), 0.76 (d, J=4.5 Hz, 2H); MS m/z=380.2 (M+H⁺).

Additional compounds of the invention presented in Table 5 below were prepared by methods already described in the application.

TABLE 5

| No. | Structure | $^1$H NMR | MS (M + H)+ |
|---|---|---|---|
| 5-c | 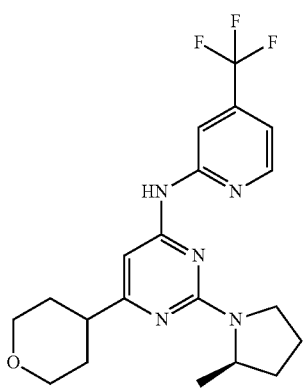 [SMILES: C[C@@H]1CCCN1c1nc(Nc2cc(C(F)(F)F)ccn2)cc(C2CCOCC2)n1] | $^1$H NMR (400 MHz, DMSO-d$_6$) δ 10.12 (s, 1H), 8.85 (s, 1H), 8.50 (d, J = 5.1 Hz, 1H), 7.25 (d, J = 5.1 Hz, 1H), 6.30 (s, 1H), 4.26-4.15 (m, 1H), 3.92 (d, J = 11.4 Hz, 2H), 3.62-3.35 (m, 4H), 2.71-2.54 (m, 1H), 2.15-1.84 (m, 3H), 1.78-1.60 (m, 5H), 1.22 (d, J = 6.3 Hz, 3H). | 408.4 |
| 5-d | 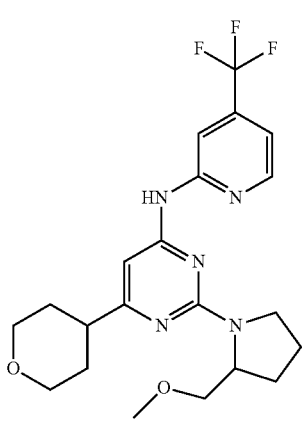 [SMILES: COCC1CCCN1c1nc(Nc2cc(C(F)(F)F)ccn2)cc(C2CCOCC2)n1] | $^1$H NMR (400 MHz, DMSO-d$_6$) δ 10.14 (s, 1H), 8.50 (d, J = 5.1 Hz, 1H), 7.25 (d, J = 5.1 Hz, 1H), 6.38 (s, 1H), 4.24 (s, 1H), 3.93 (d, J = 11.7 Hz, 3H), 3.64-3.40 (m, 6H), 2.71-2.57 (m, 1H), 2.06-1.85 (m, 5H), 1.72 (d, J = 4.7 Hz, 5H). | 438.5 |
| 5-e | 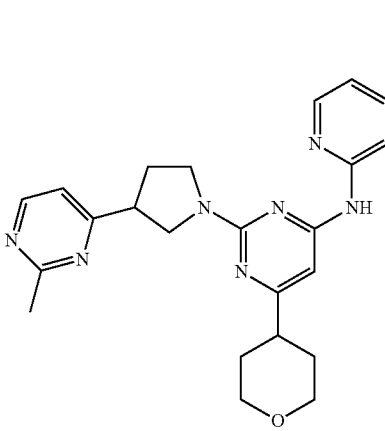 | $^1$H NMR (400 MHz, DMSO) δ 10.18 (s, 1H), 8.84 (s, 1H), 8.62 (d, J = 5.2 Hz, 1H), 8.50 (d, J = 5.1 Hz, 1H), 7.35-7.27 (m, 2H), 6.38 (s, 1H), 4.10-3.36 (m, 11H), 3.17 (d, J = 3.8 Hz, 2H), 2.69-2.57 (m, 4H), 2.37 (t, J = 12.4 Hz, 1H), 2.20 (s, 1H), 1.77-1.64 (m, 4H). | 486.5 |

TABLE 5-continued

| No. | Structure | ¹H NMR | MS (M + H)+ |
|---|---|---|---|
| 5-f | 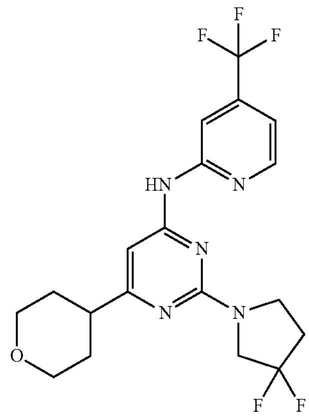 [SMILES: FC1(F)CCN(c2nc(Nc3cc(C(F)(F)F)ccn3)cc(C3CCOCC3)n2)C1] | ¹H NMR (400 MHz, DMSO-d₆) δ 10.28 (s, 1H), 8.70 (s, 1H), 8.52 (d, J = 5.2 Hz, 1H), 7.28 (d, J = 4.9 Hz, 1H), 6.50 (s, 1H), 3.97-3.84 (m, 4H), 3.73 (dd, J = 16.6, 9.2 Hz, 2H), 3.43 (td, J = 11.1, 3.5 Hz, 2H), 2.72-2.54 (m, 2H), 1.69 (ddd, J = 16.4, 10.7, 3.4 Hz, 5H). | 430.4 |
| 5-g | 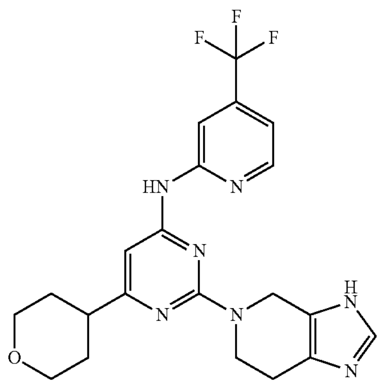 [SMILES: FC(F)(F)c1ccnc(Nc2cc(C3CCOCC3)nc(N3CCc4nc[nH]c4C3)n2)c1] | ¹H NMR (400 MHz, DMSO) δ 10.21 (s, 1H), 8.64-8.47 (m, 2H), 7.47 (s, 1H), 7.30 (t, J = 11.6 Hz, 1H), 6.49 (s, 1H), 4.71 (s, 2H), 4.10-3.89 (m, 4H), 3.46-3.38 (m, 2H), 2.73-2.60 (m, 3H), 1.80-1.60 (m, 4H). | 446.4 |
| 5-h | 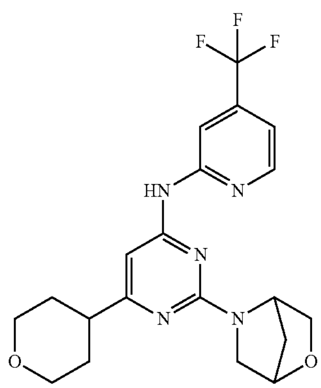 [SMILES: FC(F)(F)c1ccnc(Nc2cc(C3CCOCC3)nc(N3CC4CC3CO4)n2)c1] | ¹H NMR (400 MHz, DMSO) δ 10.20 (s, 1H), 8.51 (d, J = 5.1 Hz, 1H), 7.26 (d, J = 5.1 Hz, 1H), 6.44 (s, 1H), 4.67 (s, 1H), 3.93 (d, J = 11.1 Hz, 2H), 3.87-3.66 (m, 2H), 3.57-3.36 (m, 4H), 3.17 (d, J = 5.2 Hz, 1H), 2.71-2.57 (m, 1H), 2.00-1.58 (m, 7H). | 422.4 |
| 5-i | 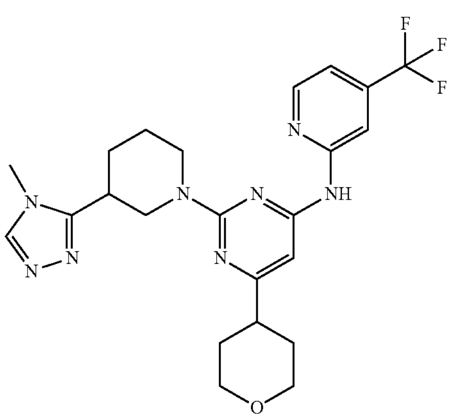 [SMILES: Cn1cnnc1C1CCCN(c2nc(Nc3cc(C(F)(F)F)ccn3)cc(C3CCOCC3)n2)C1] | ¹H NMR (400 MHz, DMSO-d₆) δ 10.18 (s, 1H), 8.53 (t, J = 9.3 Hz, 1H), 8.35 (s, 1H), 7.25 (d, J = 5.0 Hz, 1H), 6.49 (s, 1H), 4.79 (d, J = 12.3 Hz, 1H), 3.92 (d, J = 10.6 Hz, 2H), 3.61 (s, 3H), 3.46-3.38 (m, 2H), 3.19-2.92 (m, 3H), 2.69-2.58 (m, 1H), 2.07 (d, J = 12.2 Hz, 1H), 1.91-1.53 (m, 7H). | 489.5 |

TABLE 5-continued

| No. | Structure | ¹H NMR | MS (M + H)+ |
|---|---|---|---|
| 5-j | 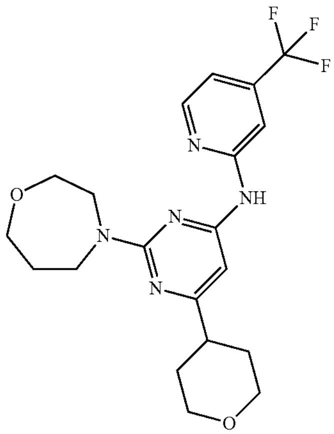 [SMILES: FC(F)(F)c1ccnc(Nc2cc(C3CCOCC3)nc(N3CCCOCC3)n2)c1] | ¹H NMR (400 MHz, DMSO-d₆) δ 10.18 (s, 1H), 8.51 (d, J = 5.2 Hz, 1H), 7.26 (d, J = 5.1 Hz, 1H), 6.38 (s, 1H), 4.03-3.79 (m, 6H), 3.73 (t, J = 5.0 Hz, 2H), 3.68-3.58 (m, 2H), 3.42 (td, J = 11.1, 3.5 Hz, 2H), 2.63 (ddd, J = 15.5, 10.3, 5.1 Hz, 1H), 1.94-1.81 (m, 2H), 1.68 (ddd, J = 17.3, 11.2, 4.0 Hz, 4H). | 424.4 |
| 5-k | 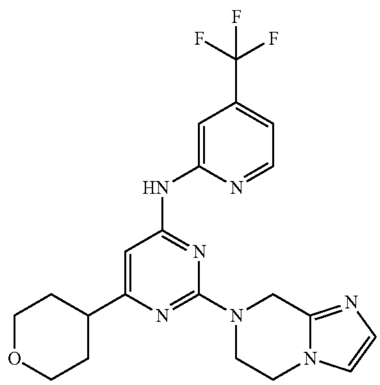 [SMILES: FC(F)(F)c1ccnc(Nc2cc(C3CCOCC3)nc(N3CCn4ccnc4C3)n2)c1] | ¹H NMR (400 MHz, DMSO) δ 10.30 (s, 1H), 8.54 (d, J = 5.2 Hz, 1H), 8.48 (s, 1H), 7.30 (d, J = 5.2 Hz, 1H), 7.11 (s, 1H), 6.89 (s, 1H), 6.62 (s, 1H), 4.89 (s, 2H), 4.25-4.05 (m, 4H), 4.00-3.89 (m, 2H), 3.47-3.39 (m, 2H), 2.70 (ddd, J = 15.5, 10.3, 5.0 Hz, 1H), 1.87-1.63 (m, 4H). | 446.4 |
| 5-l | 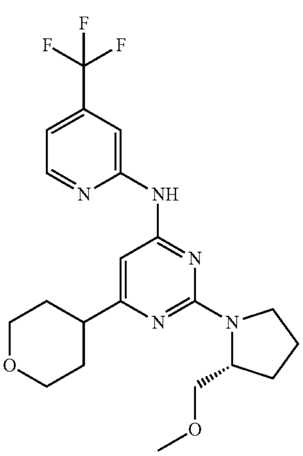 | ¹H NMR (400 MHz, DMSO-d₆) δ 10.14 (s, 1H), 8.50 (d, J = 5.1 Hz, 1H), 7.25 (d, J = 5.1 Hz, 1H), 6.38 (s, 1H), 4.24 (s, 1H), 3.93 (d, J = 12.1 Hz, 2H), 3.62-3.36 (m, 6H), 2.68-2.56 (m, 1H), 2.06-1.84 (m, 4H), 1.76-1.66 (m, 4H). | 438.5 |

TABLE 5-continued

| No. | Structure | ¹H NMR | MS (M + H)+ |
|---|---|---|---|
| 5-m | 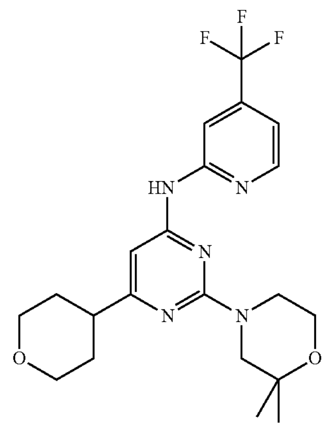 [SMILES: CC1(C)CN(c2nc(Nc3cc(C(F)(F)F)ccn3)cc(C3CCOCC3)n2)CCO1] | ¹H NMR (400 MHz, DMSO-d₆) δ 10.23 (s, 1H), 8.64-8.45 (m, 2H), 7.38-7.23 (m, 2H), 6.42 (s, 1H), 3.93 (dd, J = 10.4, 3.1 Hz, 2H), 3.69 (s, 3H), 3.56 (s, 2H), 3.42 (td, J = 11.3, 2.8 Hz, 2H), 2.63 (td, J = 11.1, 5.7 Hz, 1H), 1.78-1.57 (m, 4H), 1.17 (s, 6H). | 438.5 |
| 5-n | 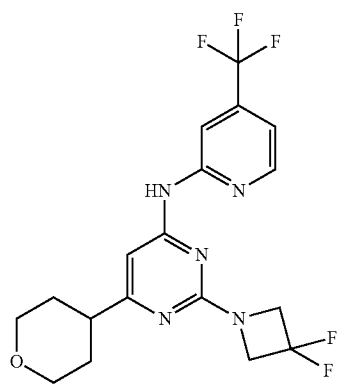 [SMILES: FC1(F)CN(c2nc(Nc3cc(C(F)(F)F)ccn3)cc(C3CCOCC3)n2)C1] | ¹H NMR (400 MHz, DMSO-d₆) δ 10.37 (s, 1H), 8.53 (d, J = 5.2 Hz, 1H), 8.47 (s, 1H), 7.29 (d, J = 5.2 Hz, 1H), 6.77 (s, 1H), 4.43 (t, J = 12.5 Hz, 4H), 3.93 (dd, J = 10.5, 3.1 Hz, 2H), 3.42 (td, J = 11.3, 2.8 Hz, 2H), 2.69 (tt, J = 8.8, 4.4 Hz, 1H), 1.82-1.60 (m, 4H). | 416.4 |
| 5-o | 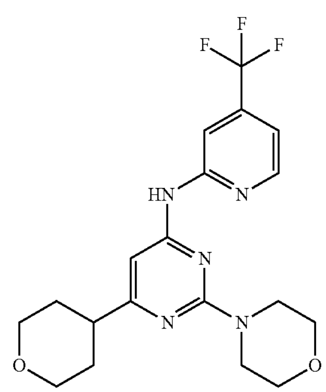 [SMILES: FC(F)(F)c1ccnc(Nc2cc(C3CCOCC3)nc(N3CCOCC3)n2)c1] | ¹H NMR (400 MHz, DMSO-d₆) δ 10.22 (s, 1H), 8.53 (t, J = 9.5 Hz, 1H), 8.47 (s, 1H), 7.27 (d, J = 5.2 Hz, 1H), 6.53 (s, 1H), 3.93 (dd, J = 10.2, 2.9 Hz, 2H), 3.67 (t, J = 5.1 Hz, 8H), 3.42 (td, J = 11.2, 3.1 Hz, 2H), 2.65 (dt, J = 9.8, 5.3 Hz, 1H), 1.76-1.64 (m, 4H). | 410.4 |
| 5-p | 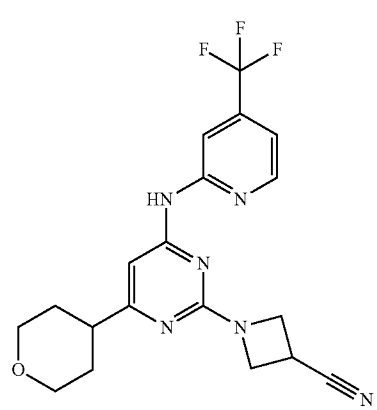 [SMILES: N#CC1CN(c2nc(Nc3cc(C(F)(F)F)ccn3)cc(C3CCOCC3)n2)C1] | ¹H NMR (400 MHz, DMSO) δ 10.32 (s, 1H), 8.52 (dd, J = 10.6, 5.4 Hz, 2H), 7.27 (t, J = 7.8 Hz, 1H), 6.74-6.54 (m, 1H), 4.32 (t, J = 8.6 Hz, 2H), 4.14 (dt, J = 13.1, 6.5 Hz, 2H), 3.96-3.80 (m, 3H), 3.42 (td, J = 11.3, 2.8 Hz, 2H), 2.71-2.61 (m, 1H), 1.75-1.61 (m, 4H). | 405.4 |

TABLE 5-continued

| No. | Structure | ¹H NMR | MS (M + H)+ |
|---|---|---|---|
| 5-q | 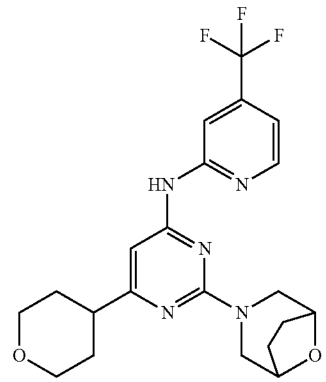 [SMILES: FC(F)(F)c1ccnc(Nc2cc(C3CCOCC3)nc(N3CC4CCC(C3)O4)n2)c1] | ¹H NMR (400 MHz, DMSO-d₆) δ 10.19 (s, 1H), 8.51 (d, J = 5.0 Hz, 2H), 7.26 (d, J = 5.4 Hz, 1H), 6.50 (s, 1H), 4.39 (s, 2H), 4.15 (d, J = 12.7 Hz, 2H), 3.92 (d, J = 10.7 Hz, 2H), 3.06 (s, 2H), 2.71-2.60 (m, 1H), 1.85-1.62 (m, 9H). | 436.4 |
| 5-r | 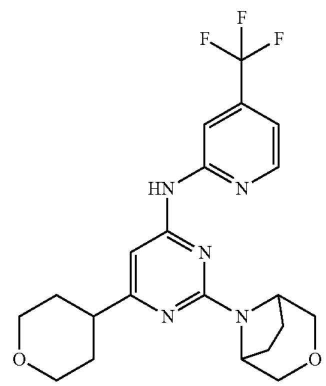 [SMILES: FC(F)(F)c1ccnc(Nc2cc(C3CCOCC3)nc(N3C4CCC3COC4)n2)c1] | ¹H NMR (400 MHz, DMSO) δ 10.23 (s, 1H), 8.56-8.45 (m, 2H), 7.26 (s, 1H), 6.50 (s, 1H), 4.54 (s, 2H), 3.98-3.87 (m, 2H), 3.75-3.38 (m, 4H), 3.41 (dt, J = 11.2, 5.8 Hz, 2H), 2.64 (td, J = 11.0, 5.4 Hz, 1H), 2.01-1.81 (m, 3H), 1.78-1.62 (m, 4H). | 436.4 |
| 5-s | 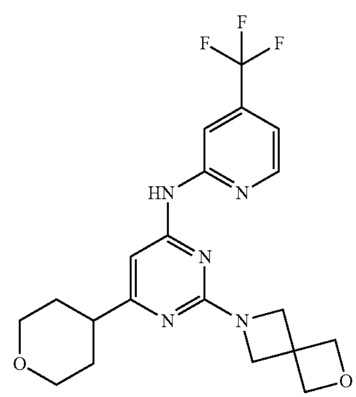 [SMILES: FC(F)(F)c1ccnc(Nc2cc(C3CCOCC3)nc(N3CC4(COC4)C3)n2)c1] | ¹H NMR (400 MHz, DMSO-d₆) δ 10.23 (s, 1H), 8.65 (s, 1H), 8.51 (d, J = 5.2 Hz, 1H), 7.27 (d, J = 4.6 Hz, 1H), 6.54 (s, 1H), 4.72 (s, 4H), 4.18 (s, 4H), 3.92 (dd, J = 10.2, 2.9 Hz, 2H), 3.48-3.36 (m, 2H), 2.68-2.58 (m, 1H), 1.77-1.57 (m, 4H). | 422.4 |
| 5-t | 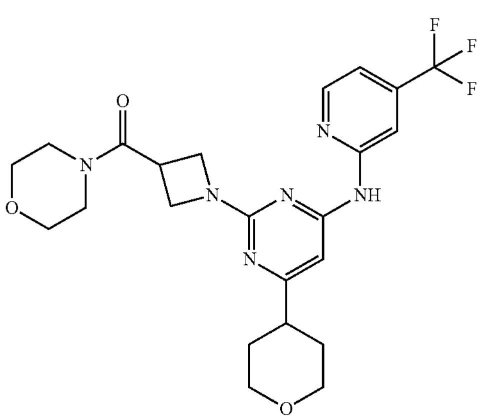 [SMILES: O=C(C1CN(c2nc(Nc3cc(C(F)(F)F)ccn3)cc(C3CCOCC3)n2)C1)N1CCOCC1] | ¹H NMR (400 MHz, DMSO) δ 10.26 (s, 1H), 8.72 (d, J = 6.2 Hz, 1H), 8.55-8.48 (m, 1H), 7.27 (d, J = 4.9 Hz, 1H), 6.51 (s, 1H), 4.18 (dd, J = 14.0, 13.5 Hz, 5H), 3.92 (d, J = 10.7 Hz, 3H), 3.81 (dd, J = 14.6, 8.4 Hz, 1H), 3.44 (ddd, J = 14, 19.3, 14.2 Hz, 7H), 2.72-2.56 (m, 2H), 1.80-1.60 (m, 4H). | 493.5 |

TABLE 5-continued
| No. | Structure | ¹H NMR | MS (M + H)+ |
|---|---|---|---|
| 5-u | 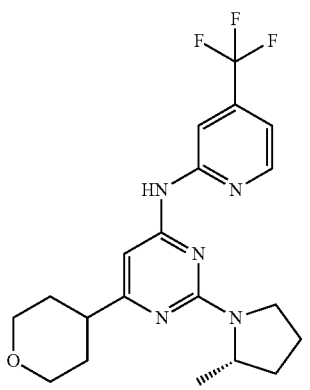 [SMILES: C[C@H]1CCCN1c1nc(Nc2cc(C(F)(F)F)ccn2)cc(C2CCOCC2)n1] | ¹H NMR (400 MHz, DMSO-d₆) δ 10.12 (s, 1H), 8.85 (s, 1H), 8.52 (t, J = 13.4 Hz, 1H), 7.25 (d, J = 5.3 Hz, 1H), 6.30 (s, 1H), 4.25-4.16 (m, 1H), 3.92 (d, J = 11.4 Hz, 2H), 3.61-3.36 (m, 4H), 2.69-2.54 (m, 1H), 2.04 (ddd, J = 58.3, 31.3, 23.6 Hz, 3H), 1.75-1.65 (m, 5H), 1.22 (d, J = 6.3 Hz, 3H). | 408.4 |
| 5-v | 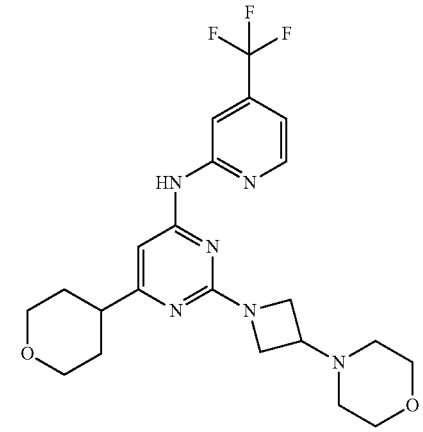 [SMILES: FC(F)(F)c1ccnc(Nc2cc(C3CCOCC3)nc(N3CC(N4CCOCC4)C3)n2)c1] | ¹H NMR (400 MHz, DMSO) δ 10.23 (s, 1H), 8.69 (s, 1H), 8.52 (t, J = 10.8 Hz, 1H), 7.26 (d, J = 5.2 Hz, 1H), 6.51 (s, 1H), 4.16-3.36 (m, 12H), 3.24-3.18 (m, 1H), 2.63 (ddd, J = 15.6, 10.5, 5.0 Hz, 1H), 2.35 (s, 4H), 1.73-1.56 (m, 4H). | 465.5 |
| 5-w | 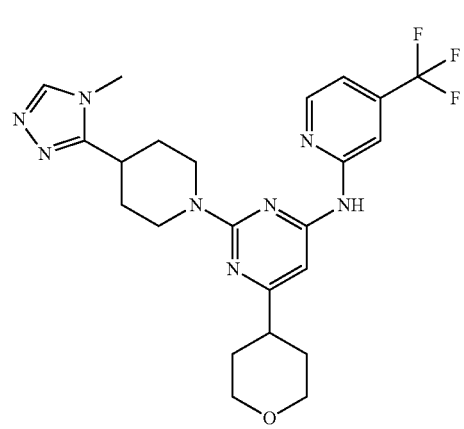 [SMILES: Cn1cnnc1C1CCN(c2nc(Nc3cc(C(F)(F)F)ccn3)cc(C3CCOCC3)n2)CC1] | ¹H NMR (400 MHz, DMSO-d₆) δ 10.20 (s, 1H), 8.57-8.46 (m, 2H), 8.32 (s, 1H), 7.26 (d, J = 5.0 Hz, 1H), 6.46 (s, 1H), 4.67 (d, J = 13.1 Hz, 1H), 3.91 (s, 1H), 3.65 (s, 3H), 3.42 (td, J = 11.1, 3.0 Hz, 3H), 3.15 (q, J = 11.7 Hz, 3H), 2.65 (tt, J = 9.7, 4.8 Hz, 1H), 1.92 (d, J = 10.6 Hz, 2H), 1.80-1.61 (m, 7H). | 489.5 |

TABLE 5-continued

| No. | Structure | ¹H NMR | MS (M + H)+ |
|---|---|---|---|
| 5-x | 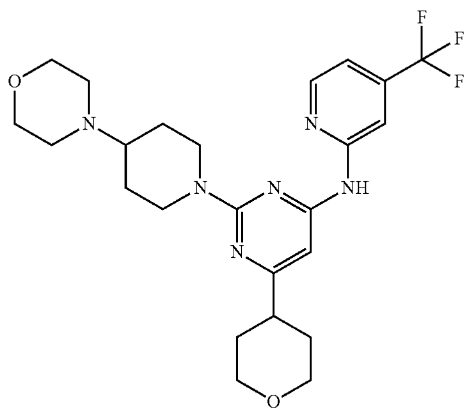 [SMILES: FC(F)(F)c1ccnc(Nc2cc(C3CCOCC3)nc(N3CCC(N4CCOCC4)CC3)n2)c1] | ¹H NMR (400 MHz, DMSO-$d_6$) δ 10.16 (s, 1H), 8.51 (d, J = 5.7 Hz, 2H), 7.26 (d, J = 5.1 Hz, 1H), 6.43 (s, 1H), 4.64 (d, J = 13.1 Hz, 2H), 3.97-3.86 (m, 2H), 3.55 (d, J = 4.5 Hz, 3H), 3.41 (td, J = 11.2, 3.0 Hz, 2H), 2.90 (t, J = 11.8 Hz, 2H), 2.68-2.58 (m, 1H), 1.83 (d, J = 10.8 Hz, 2H), 1.78-1.59 (m, 4H), 1.34 (dt, J = 11.8, 8.3 Hz, 2H). | 493.5 |
| 5-y | 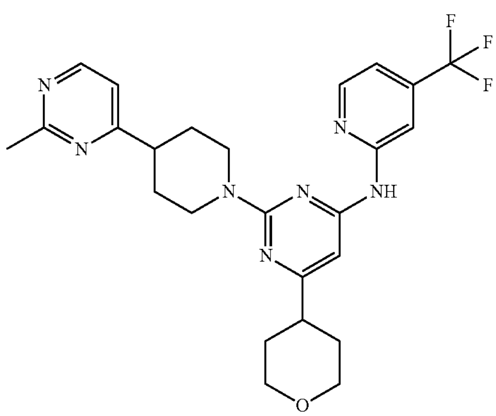 [SMILES: Cc1nccc(C2CCN(c3nc(Nc4cc(C(F)(F)F)ccn4)cc(C4CCOCC4)n3)CC2)n1] | ¹H NMR (400 MHz, DMSO-$d_6$) δ 10.19 (s, 1H), 8.66-8.45 (m, 3H), 7.32-7.15 (m, 2H), 6.46 (s, 1H), 4.79 (d, J = 13.0 Hz, 2H), 3.97-3.86 (m, 2H), 3.42 (td, J = 11.2, 3.0 Hz, 2H), 3.17 (d, J = 4.4 Hz, 1H), 3.09-2.87 (m, 3H), 2.67 (dt, J = 10.5, 8.7 Hz, 1H), 2.56 (s, 3H), 1.89 (d, J = 10.9 Hz, 2H), 1.79-1.60 (m, 5H) | 500.5 |
| 5-z | 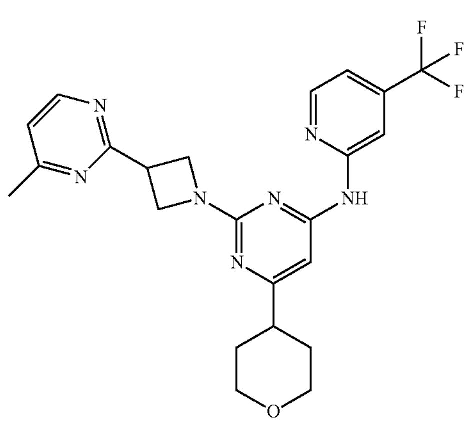 [SMILES: Cc1ccnc(C2CN(c3nc(Nc4cc(C(F)(F)F)ccn4)cc(C4CCOCC4)n3)C2)n1] | ¹H NMR (400 MHz, DMSO-$d_6$) δ 10.25 (s, 1H), 8.72-8.48 (m, 3H), 7.31-7.22 (m, 2H), 6.53 (s, 1H), 4.40 (t, J = 8.4 Hz, 2H), 4.31-4.21 (m, 2H), 4.13 (td, J = 8.5, 4.2 Hz, 1H), 3.95-3.88 (m, 2H), 3.42 (td, J = 11.3, 2.8 Hz, 2H), 2.69-2.58 (m, 1H), 2.47 (s, 3H), 1.76-1.62 (m, 4H). | 472.5 |

TABLE 5-continued
| No. | Structure | ¹H NMR | MS (M + H)+ |
|---|---|---|---|
| 5-aa | 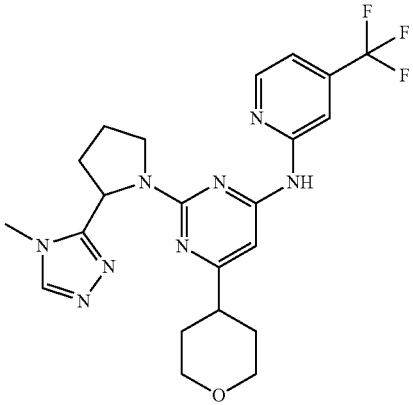 [SMILES: Cn1cnnc1C1CCCN1c1nc(Nc2cc(C(F)(F)F)ccn2)cc(C2CCOCC2)n1] | ¹H NMR (400 MHz, DMSO) δ 10.19 (s, 1H), 8.51 (d, J = 5.1 Hz, 1H), 8.31 (d, J = 7.0 Hz, 1H), 7.27 (d, J = 5.0 Hz, 1H), 6.50-6.20 (m, 1H), 5.26 (d, J = 4.3 Hz, 1H), 3.91-3.65 (m, 7H), 3.41-3.34 (m, 2H), 2.38-2.25 (m, 2H), 2.13-1.94 (m, 2H), 1.60-1.30 (m, 4H). | 475.5 |
| 5-ab | 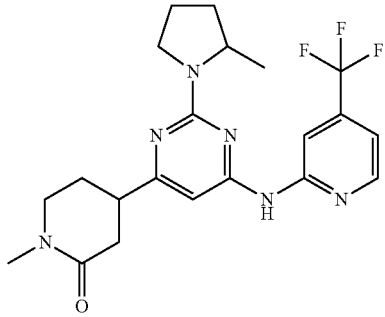 [SMILES: CC1CCCN1c1nc(Nc2cc(C(F)(F)F)ccn2)cc(C2CCN(C)C(=O)C2)n1] | ¹H NMR (400 MHz, DMSO-d₆) δ 10.19 (s, 1H), 8.83 (s, 1H), 8.51 (d, J = 5.1 Hz, 1H), 7.27 (d, J = 5.2 Hz, 1H), 6.38 (s, 1H), 2.96 (s, 3H), 2.42-2.16 (m, 4H), 2.14-1.81 (m, 6H), 1.67 (s, 1H), 1.22 (d, J = 6.2 Hz, 4H). | 435.5 |

Example 6

Preparation of 6-(1-((1H-imidazol-2-yl)methyl)pyrrolidin-3-yl)-2-(3,3-difluoropyrrolidin-1-yl)-N-(4-(trifluoromethyl)pyridin-2-yl)pyrimidin-4-amine (6-a)

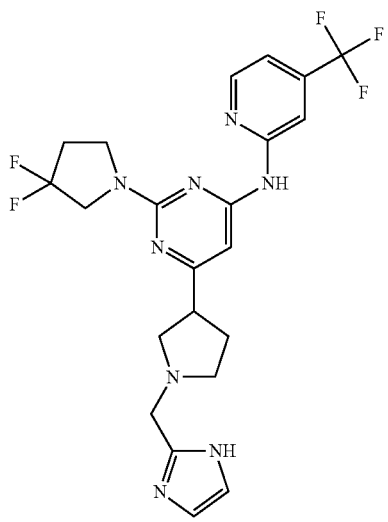

Compound 2-v (50 mg, 0.11 mmol), 1H-imidazole-2-carbaldehyde (13 mg, 0.14 mmol) and NaBH(CN)$_3$ (35 mg, 0.56 mmol) in DMF (5.0 mL) was stirred at 80° C. for 16 h. The mixture was directly purified by HPLC to give the title compound (3.5 mg, 5.0%): $^1$H NMR (400 MHz, MeOD) δ 8.65 (d, J=5.2 Hz, 1H), 8.42 (s, 1H), 7.70 (s, 2H), 6.84 (s, 1H), 7.47-7.44 (m, 1H), 6.83 (s, 1H), 4.74-4.70 (m, 2H), 4.15-4.05 (m, 2H), 4.04-3.98 (m, 2H), 3.90-3.80 (m, 1H), 3.75-3.65 (m, 2H), 3.64-3.55 (m, 1H), 3.50-3.40 (m, 1H), 2.75-2.65 (m, 3H), 2.35-2.25 (m, 1H); MS m/z=495 (M+H$^+$).

Additional compounds of the invention presented in Table 6 below were prepared by methods already described in the application.

TABLE 6

| No. | Structure | NMR | MS (M + H)+ |
|---|---|---|---|
| 6-b | 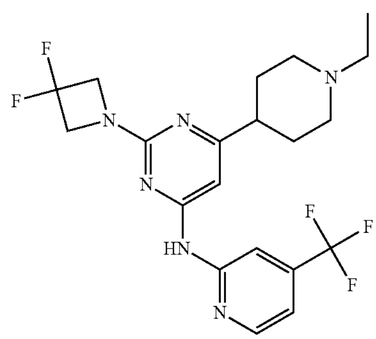 [SMILES: CCN1CCC(c2cc(Nc3cc(C(F)(F)F)ccn3)nc(N3CC(F)(F)C3)n2)CC1] | $^1$H NMR (400 MHz, MeOD) δ 8.54 (d, J = 8.0 Hz, 1 H), 8.48 (d, J = 5.2 Hz, 1 H), 7.23 (d, J = 4.8 Hz, 1 H), 6.69 (s, 1 H), 4.47-4.41 (m, 4 H), 3.64-3.61 (m, 2 H), 3.18-2.84 (m, 5 H), 2.17-2.11 (m, 4 H), 1.39-1.36 (m, 3 H) | 443 |
| 6-c | 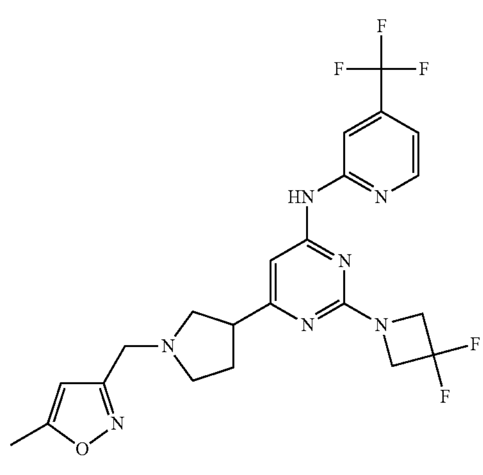 [SMILES: Cc1cc(CN2CCC(c3cc(Nc4cc(C(F)(F)F)ccn4)nc(N4CC(F)(F)C4)n3)C2)no1] | $^1$H NMR (400 MHz, MeOD) δ 8.52 (s, 1 H), 8.46 (d, J = 5.2 Hz, 1 H), 7.21-7.19 (m, 1 H), 6.66 (s, 1 H), 6.26 (s, 1 H), 4.47-4.41 (m, 4 H), 4.16-4.07 (m, 2 H), 3.50-3.45 (m, 1 H), 3.49-3.31 (m, 1 H), 3.24-3.16 (m, 3 H), 2.44-2.35 (m, 4 H), 2.20-2.12 (m, 1 H) | 496 |

TABLE 6-continued

| No. | Structure | NMR | MS (M + H)+ |
|---|---|---|---|
| 6-d | 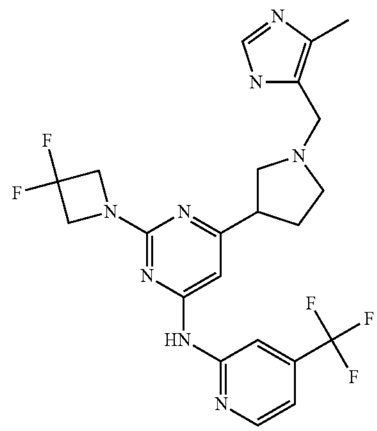 [SMILES: Cc1nc[nH]c1CN1CCC(c2cc(Nc3cc(C(F)(F)F)ccn3)nc(N3CC(F)(F)C3)n2)C1] | ¹H NMR (400 MHz, MeOD) δ 8.46 (s, 1 H), 8.48-8.42 (m, 2 H), 7.70 (s, 1 H), 7.18-7.16 (m, 1 H), 6.62 (s, 1 H), 4.44-4.36 (m, 6 H), 3.70-3.67 (m, 2 H), 3.62-3.46 (m, 3 H), 2.50-2.44 (m, 1 H), 2.33 (s, 3 H), 2.24-2.16 (m, 1 H) | 495 |
| 6-e | 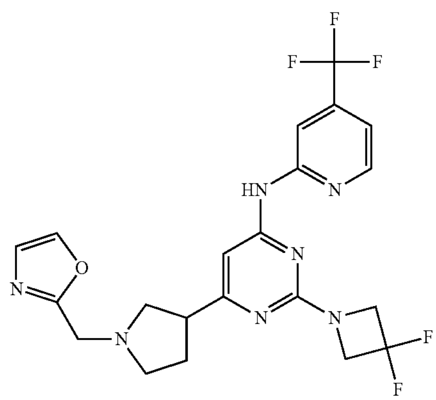 [SMILES: FC1(F)CN(c2nc(Nc3cc(C(F)(F)F)ccn3)cc(C3CCN(Cc4ncco4)C3)n2)C1] | ¹H NMR (400 MHz, MeOD) δ 8.55 (s, 1 H), 8.47 (d, J = 5.2 Hz, 1 H), 7.99 (s, 1 H), 7.24-7.24 (m, 2 H), 6.67 (s, 1 H), 4.49-4.22 (m, 5 H), 3.48-3.37 (m, 2 H), 3.27-3.19 (m, 3 H), 2.41-1.96 (m, 2 H), 1.30 (s, 1 H) | 482 |
| 6-f | 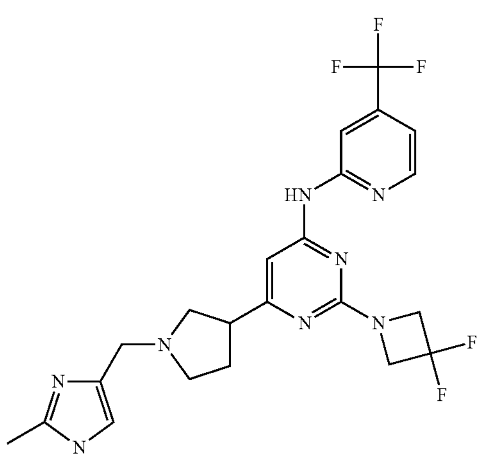 [SMILES: Cc1nc(CN2CCC(c3cc(Nc4cc(C(F)(F)F)ccn4)nc(N4CC(F)(F)C4)n3)C2)c[nH]1] | ¹H NMR (400 MHz, MeOD) δ 8.64 (s, 1 H), 8.46 (d, J = 5.2 Hz, 1 H), 7.28-7.20 (m, 2 H), 6.66 (s, 1 H), 4.48-4.33 (m, 6 H), 3.69-3.47 (m, 5 H), 2.60-2.43 (m, 4 H), 2.26-2.20 (m, 1 H) | 495 |

TABLE 6-continued

| No. | Structure | NMR | MS (M + H)+ |
|---|---|---|---|
| 6-g | 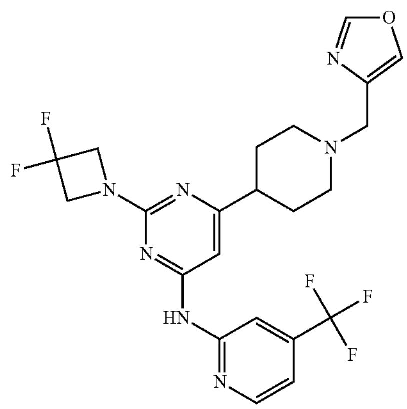 [SMILES: FC1(F)CN(c2nc(Nc3cc(C(F)(F)F)ccn3)cc(C3CCN(Cc4cocn4)CC3)n2)C1] | ¹H NMR (400 MHz, MeOD) δ 8.55 (s, 1 H), 8.44 (d, J = 5.2 Hz, 1 H), 7.19 (d, J = 5.2 Hz, 1 H), 7.88 (s, 1 H), 7.19-7.17 (m, 1 H), 6.58 (s, 1 H), 4.44-4.38 (m, 4 H), 3.58 (s, 2 H), 3.09 (d, J = 12.0 Hz, 2 H), 2.5-2.4 (m, 1 H), 2.24-2.23 (m, 2 H), 1.93-1.84 (m, 4 H) | 496 |
| 6-h | 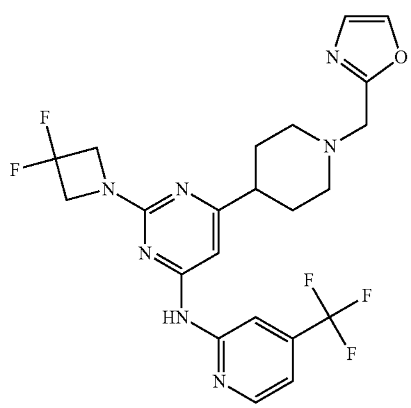 [SMILES: FC1(F)CN(c2nc(Nc3cc(C(F)(F)F)ccn3)cc(C3CCN(Cc4ncco4)CC3)n2)C1] | ¹H NMR (400 MHz, MeOD) δ 8.63 (d, J = 5.2 Hz, 1 H), 8.35 (s, 1 H), 8.09 (s, 1 H), 7.47 (d, J = 5.2 Hz, 1 H), 7.34 (s, 1 H), 6.85 (s, 1 H), 4.81-4.75 (m, 4 H), 4.68 (s, 2 H), 3.82-3.64 (m, 2 H), 3.50-3.30 (m, 2 H), 3.20-3.10 (m, 1 H), 2.38-2.35 (m, 2 H), 2.25-2.10 (m, 2 H) | 496 |
| 6-i | 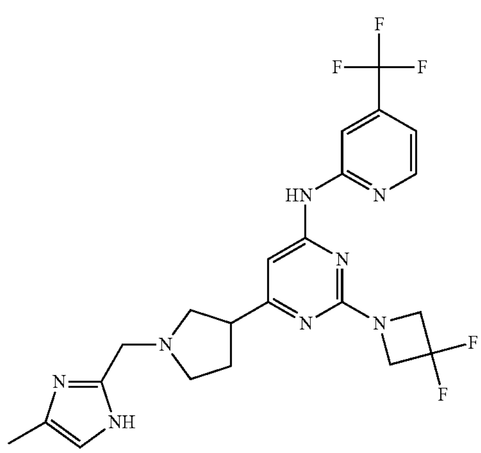 [SMILES: Cc1c[nH]c(CN2CCC(c3cc(Nc4cc(C(F)(F)F)ccn4)nc(N4CC(F)(F)C4)n3)C2)n1] | ¹H NMR (400 MHz, MeOD) δ 8.48-8.45 (m, 2 H), 7.23-7.21 (m, 1 H), 6.98 (s, 1 H), 6.67 (s, 1 H), 4.48-4.42 (m, 4 H), 4.17 (s, 2 H), 3.50-3.44 (m, 2 H), 3.22-3.13 (m, 3 H), 2.40-2.13 (m, 5 H) | 495 |

TABLE 6-continued

| No. | Structure | NMR | MS (M + H)+ |
|---|---|---|---|
| 6-j | 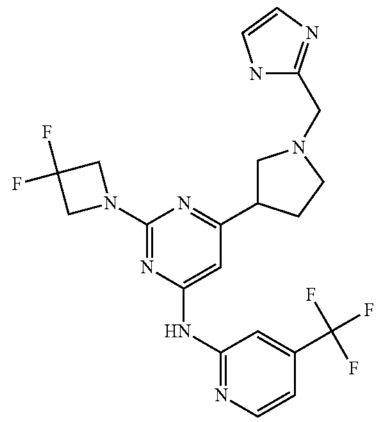 [SMILES: FC1(F)CN(c2nc(Nc3cc(C(F)(F)F)ccn3)cc(C3CCN(Cc4ncc[nH]4)C3)n2)C1] | ¹H NMR (400 MHz, MeOD) δ 8.50 (s, 1 H), 8.43-8.41 (m, 1 H), 7.19-7.16 (m, 3 H), 6.62 (s, 1 H), 4.44-4.38 (m, 4 H), 4.31 (s, 2 H), 3.50-3.42 (m, 2 H), 3.38-3.32 (m, 1 H), 3.30-3.21 (m, 2 H), 2.41-2.33 (m, 1 H), 2.20-2.14 (m, 1 H) | 481 |
| 6-k | 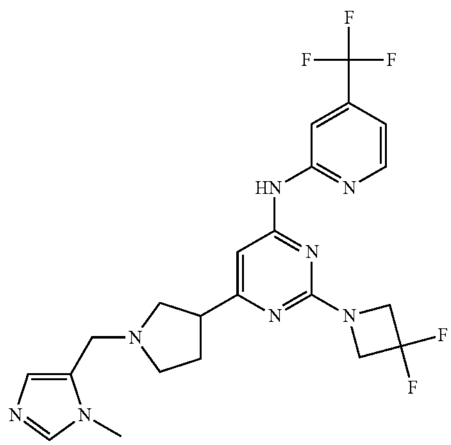 [SMILES: Cn1cncc1CN1CCC(c2cc(Nc3cc(C(F)(F)F)ccn3)nc(N3CC(F)(F)C3)n2)C1] | ¹H NMR (400 MHz, MeOD) δ 8.52 (s, 1 H), 8.48-8.46 (m, 1 H), 7.98 (br, 1 H), 7.28-7.22 (m, 2 H), 6.70 (s, 1 H), 4.48-4.30 (m, 6 H), 3.85 (s, 3 H), 3.54-3.46 (m, 3 H), 3.37-3.27 (m, 2 H), 2.42 (br, 1 H), 2.24-2.20 (m, 1 H) | 495 |
| 6-l | 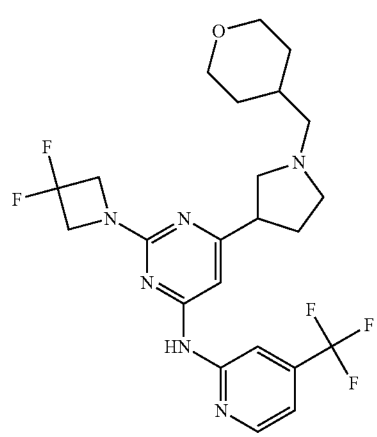 [SMILES: FC1(F)CN(c2nc(Nc3cc(C(F)(F)F)ccn3)cc(C3CCN(CC4CCOCC4)C3)n2)C1] | ¹H NMR (400 MHz, MeOD) δ 8.46 (d, J = 6.0 Hz, 2 H), 7.22-7.20 (m, 1 H), 6.70 (s, 1 H), 4.48-4.42 (m, 4 H), 3.99-3.95 (m, 2 H), 3.70-3.31 (m, 7 H), 3.17-3.16 (m, 2 H), 2.51-2.46 (m, 1 H), 2.26-2.21 (m, 1 H), 2.13-2.06 (m, 1 H), 1.77-1.73 (m, 2 H), 1.46-1.34 (m, 2 H) | 499 |

TABLE 6-continued

| No. | Structure | NMR | MS (M + H)+ |
|---|---|---|---|
| 6-m | 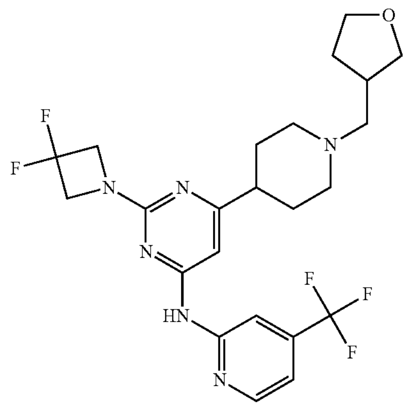 [SMILES: FC1(F)CN(c2nc(Nc3cc(C(F)(F)F)ccn3)cc(C3CCN(CC4CCOC4)CC3)n2)C1] | $^1$H NMR (400 MHz, MeOD) δ 8.55 (d, J = 5.2 Hz, 1 H), 8.42 (s, 1 H), 7.40-7.30 (m, 1 H), 6.80 (s, 1 H), 4.65-4.59 (m, 4 H), 4.00-3.90 (m, 1 H), 3.90-3.80 (m, 1 H), 3.80-3.75 (m, 1 H), 3.55-3.50 (m, 1 H), 3.30-3.24 (m, 2 H), 3.24 (s, 1 H), 3.05-2.95 (m, 1 H), 2.80-2.70 (m, 1 H), 2.65-2.45 (m, 1 H), 3.23-3.22 (m, 4 H), 2.0-1.65 (m, 4 H) | 499 |
| 6-n | 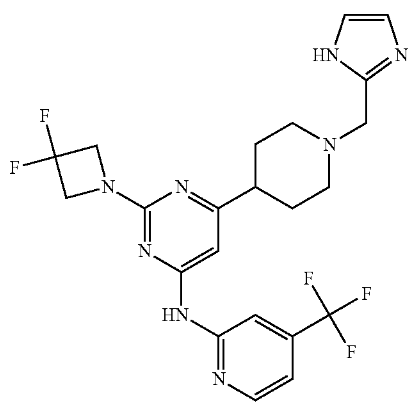 [SMILES: FC1(F)CN(c2nc(Nc3cc(C(F)(F)F)ccn3)cc(C3CCN(Cc4ncc[nH]4)CC3)n2)C1] | $^1$H NMR (400 MHz, MeOD) δ 8.47 (d, J = 5.2 Hz, 1 H), 8.42 (s, 1 H), 7.22-7.21 (m, 1 H), 7.17 (s, 2 H), 6.63 (s, 1 H), 4.46-4.40 (m, 4 H), 3.87 (s, 2 H), 3.14-3.11 (m, 2 H), 2.59-2.53 (m, 1 H), 2.46-2.40 (m, 2 H), 2.00-1.88 (m, 4 H). | 495 |
| 6-o | 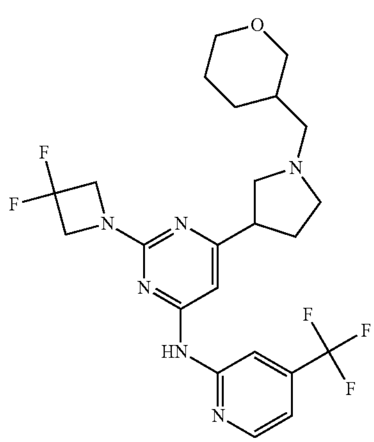 [SMILES: FC1(F)CN(c2nc(Nc3cc(C(F)(F)F)ccn3)cc(C3CCN(CC4CCCOC4)C3)n2)C1] | $^1$H NMR (400 MHz, MeOD) δ 8.46 (d, J = 3.6 Hz, 2 H), 7.21-7.20 (m, 1 H), 6.70 (s, 1 H), 4.48-4.42 (m, 4 H), 3.96-3.93 (m, 1 H), 3.84-3.81 (m, 1 H), 3.65-3.60 (m, 3 H), 3.52-3.50 (m, 3 H), 3.34-3.28 (m, 1 H), 3.21-3.05 (m, 2 H), 2.49-2.44 (m, 1 H), 2.24-1.96 (m, 3 H), 1.72-1.62 (m, 2 H), 1.47-1.40 (m, 1 H) | 499 |

TABLE 6-continued

| No. | Structure | NMR | MS (M + H)+ |
|---|---|---|---|
| 6-p | 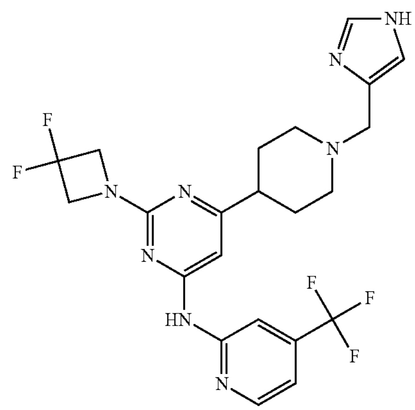 [SMILES: FC1(F)CN(c2nc(Nc3cc(C(F)(F)F)ccn3)cc(C3CCN(Cc4c[nH]cn4)CC3)n2)C1] | ¹H NMR (400 MHz, MeOD) δ 8.47 (d, J = 5.2 Hz, 1 H), 8.34 (s, 1 H), 7.86 (s, 1 H), 7.41 (s, 1 H), 7.23-7.21 (m, 1 H), 6.68 (s, 1 H), 4.46-4.40 (m, 4 H), 4.30 (s, 2 H), 3.64-3.61 (m, 2 H), 3.17-3.10 (m, 2 H), 2.87-2.79 (m, 1 H), 2.21-2.06 (m, 4 H). | 495 |
| 6-q | 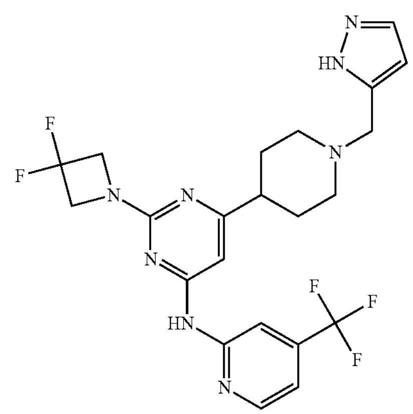 [SMILES: FC1(F)CN(c2nc(Nc3cc(C(F)(F)F)ccn3)cc(C3CCN(Cc4ccn[nH]4)CC3)n2)C1] | ¹H NMR (400 MHz, MeOD) δ 8.47 (d, J = 5.2 Hz, 1 H), 8.45 (s, 1 H), 7.75 (s, 1 H), 7.23-7.22 (m, 1 H), 6.67 (s, 1 H), 6.51 (s, 1 H), 4.48-4.40 (m, 4 H), 4.24 (s, 2 H), 3.54-3.51 (m, 2 H), 3.04-2.95 (m, 2 H), 2.80-2.74 (m, 1 H), 2.17-2.02 (m, 4 H). | 495 |
| 6-r | 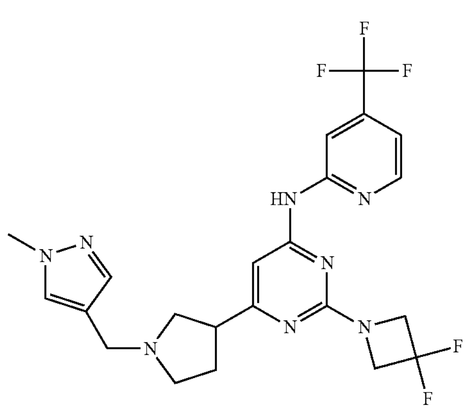 [SMILES: Cn1cc(CN2CCC(c3cc(Nc4cc(C(F)(F)F)ccn4)nc(N4CC(F)(F)C4)n3)C2)cn1] | ¹H NMR (400 MHz, MeOD) δ 8.50-8.47 (m, 2 H), 7.86 (s, 1 H), 7.67 (s, 1 H), 7.23-7.22 (m, 1 H), 6.69 (s, 1 H), 4.50-4.30 (m, 6 H), 3.94 (s, 3 H), 3.66-3.32 (m, 5 H), 2.50-2.46 (m, 1 H), 2.27-1.96 (m, 1 H). | 495 |

TABLE 6-continued

| No. | Structure | NMR | MS (M + H)+ |
|---|---|---|---|
| 6-s | 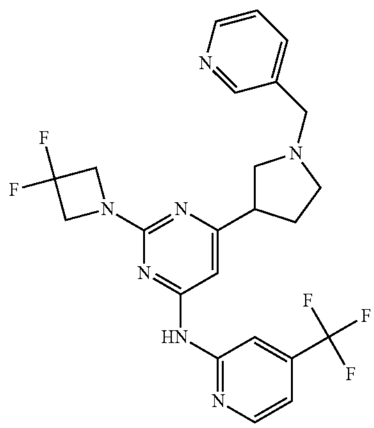 [SMILES: FC1(F)CN(c2nc(Nc3cc(C(F)(F)F)ccn3)cc(C3CCN(Cc4cccnc4)C3)n2)C1] | ¹H NMR (400 MHz, MeOD) δ 8.55-8.54 (m, 2 H), 8.46-8.44 (m, 2 H), 7.89-7.87 (m, 1 H), 7.44-7.40 (m, 1 H), 7.19-7.18 (m, 1 H), 6.65 (s, 1 H), 4.44-4.38 (m, 4 H), 3.82-3.72 (m, 2 H), 3.37-3.31 (m, 1 H), 3.04-3.00 (m, 1 H), 2.84-2.73 (m, 3 H), 2.30-2.25 (m, 1 H), 2.24-2.13 (m, 1 H). | 492 |
| 6-t | 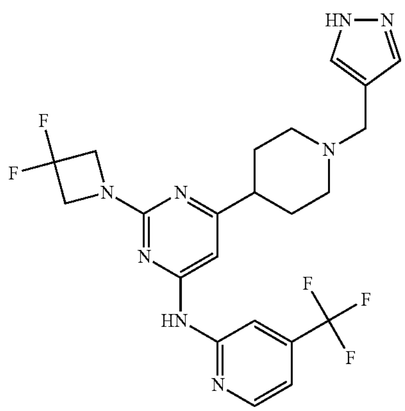 [SMILES: FC1(F)CN(c2nc(Nc3cc(C(F)(F)F)ccn3)cc(C3CCN(Cc4cn[nH]c4)CC3)n2)C1] | ¹H NMR (400 MHz, MeOD) δ 8.51 (s, 1 H), 8.47 (d, J = 5.2 Hz, 1 H), 7.78 (s, 2 H), 7.23-7.22 (m, 1 H), 6.69 (s, 1 H), 4.59-4.40 (m, 4 H), 4.15 (s, 2 H), 3.49 (d, J = 12.4 Hz, 2 H), 2.92-2.71 (m, 3 H), 2.16-1.96 (m, 4 H). | 495 |
| 6-u | 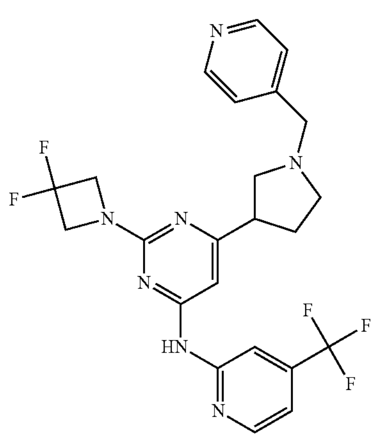 [SMILES: FC1(F)CN(c2nc(Nc3cc(C(F)(F)F)ccn3)cc(C3CCN(Cc4ccncc4)C3)n2)C1] | ¹H NMR (400 MHz, MeOD) δ 8.54-8.44 (m, 4 H), 7.48 (d, J = 6.0 Hz, 2 H), 7.20-7.18 (m, 1 H), 6.68 (s, 1 H), 4.45-4.39 (m, 4 H), 3.85-3.75 (m, 2 H), 3.39-3.36 (m, 1 H), 3.06-3.01 (m, 1 H), 2.86-2.79 (m, 3 H), 2.33-2.24 (m, 1 H), 2.14-2.08 (m, 1 H). | 492 |

TABLE 6-continued

| No. | Structure | NMR | MS (M + H)+ |
|---|---|---|---|
| 6-v | 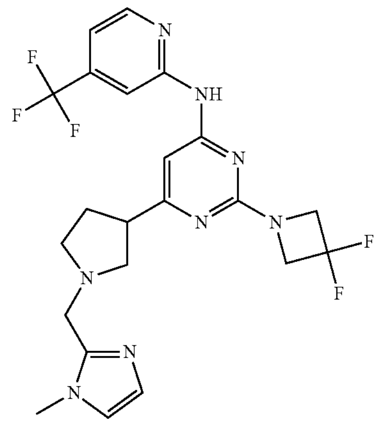 [SMILES: Cn1ccnc1CN1CCC(c2cc(Nc3cc(C(F)(F)F)ccn3)nc(N3CC(F)(F)C3)n2)C1] | ¹H NMR (400 MHz, MeOD) δ 8.55 (s, 1 H), 8.45 (d, J = 5.2 Hz, 1 H), 7.20 (d, J = 4.0 Hz, 1 H), 7.06 (s, 1 H), 6.89 (d, J = 1.6 Hz, 1 H), 6.64 (s, 1 H), 4.42 (t, J = 12.0 Hz, 4 H), 3.83 (s, 2 H), 3.76 (s, 3 H), 3.30 (m, 1 H), 2.77-3.05 (m, 4 H), 2.03-2.30 (m, 2 H). | 495 |
| 6-w | 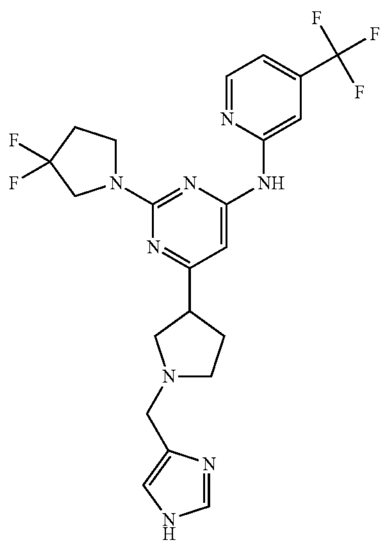 [SMILES: FC1(F)CCN(c2nc(Nc3cc(C(F)(F)F)ccn3)cc(C3CCN(Cc4c[nH]cn4)C3)n2)C1] | ¹H NMR (400 MHz, MeOD) δ 8.63 (s, 1 H), 8.52 (s, 1 H), 8.44 (d, J = 5.2 Hz, 1 H), 7.79 (s, 1 H), 7.37 (s, 1 H), 7.19-7.18 (m, 1 H), 6.46 (s, 1 H), 4.43 2 H), 3.94-3.87 (m, 2 H), 3.81-3.78 (m, 2 H), 3.74-3.44 (m, 5 H), 2.56-2.43 (m, 3 H), 2.41-2.23 (m, 1 H). | 495 |
| 6-x | 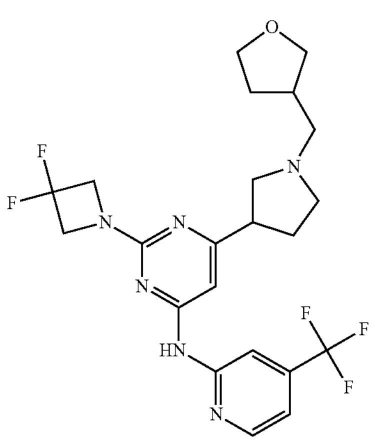 [SMILES: FC1(F)CN(c2nc(Nc3cc(C(F)(F)F)ccn3)cc(C3CCN(CC4CCOC4)C3)n2)C1] | ¹H NMR (400 MHz, MeOD) δ 8.46 (t, J = 4.8 Hz, 2 H), 7.21-7.19 (m, 1 H), 6.69 (s, 1 H), 4.47-4.41 (m, 4 H), 3.97-3.87 (m, 2 H), 3.80-3.76 (m, 1 H), 3.74-3.70 (m, 1 H), 3.67-3.59 (m, 2 H), 3.56-3.48 (m, 3 H), 3.30-3.29 (m, 1 H), 3.27-3.25 (m, 1 H), 2.68-2.64 (m, 1 H), 2.49-2.44 (m, 1 H), 2.30-2.23 (m, 2 H), 1.80-1.70 (m, 1 H) | 485 |

| No. | Structure | NMR | MS (M + H)+ |
|---|---|---|---|
| 6-y | 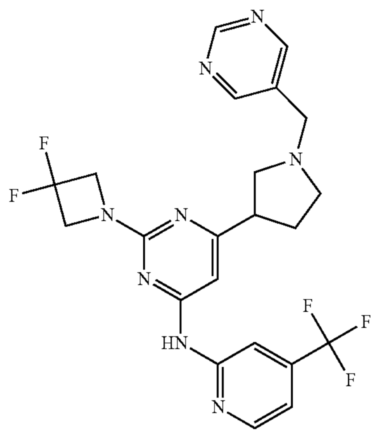 [SMILES: FC1(F)CN(c2nc(Nc3cc(C(F)(F)F)ccn3)cc(C3CCN(Cc4cncnc4)C3)n2)C1] | ¹H NMR (400 MHz, MeOD), δ ppm: 9.14 (s, 1H), 8.90 (s, 1H), 8.50-8.44 (m, 2H), 8.34 (s, 1H), 7.21-7.19 (m, 1H), 6.69-6.67 (m, 1H), 4.48-4.39 (m, 4H), 4.16-4.07 (m, 2H), 3.67-3.33 (m, 2H), 3.29-3.02 (m, 3H), 2.49-2.41 (m, 1H), 2.22-2.14 (m, 1H). | 493 |
| 6-z | 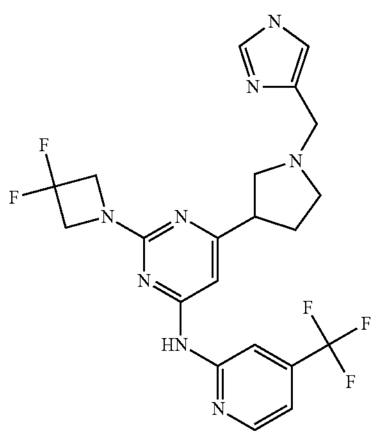 [SMILES: FC1(F)CN(c2nc(Nc3cc(C(F)(F)F)ccn3)cc(C3CCN(Cc4c[nH]cn4)C3)n2)C1] | ¹H NMR (400 MHz, MeOD) δ 8.45 (d, J = 6.0 Hz, 2 H), 7.80 (s, 1 H), 7.37 (s, 1 H), 7.21 (d, J = 6.0 Hz, 1 H), 6.68 (s, 1 H), 4.47 (s, 1 H), 4.44 (s, 2 H), 4.40-4.35 (m, 3 H), 3.70-3.56 (m, 4 H), 3.50-3.45 (m, 1 H), 2.49-2.44 (m, 1 H), 2.22-2.17 (m, 1 H). | 481 |
| 6-aa | 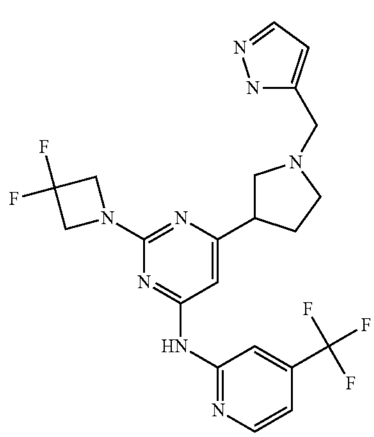 [SMILES: FC1(F)CN(c2nc(Nc3cc(C(F)(F)F)ccn3)cc(C3CCN(Cc4ccn[nH]4)C3)n2)C1] | ¹H NMR (400 MHz, MeOD) δ 8.45 (d, J = 6.0 Hz, 2 H), 7.72 (d, J = 2.0 Hz, 1 H), 7.21 (d, J = 6.0 Hz, 1 H), 6.68 (s, 1 H), 6.48 (d, J = 2.4 Hz, 1 H), 4.48 (s, 1 H), 4.45 (d, J = 8.0 Hz, 2 H), 4.42 (d, J = 4.0 Hz, 3 H), 3.62-3.50 (m, 4 H), 3.44-3.38 (m, 1 H), 2.49-2.44 (m, 1 H), 2.22-2.17 (m, 1 H). | 481 |

TABLE 6-continued

| No. | Structure | NMR | MS (M + H)+ |
|---|---|---|---|
| 6-ab | 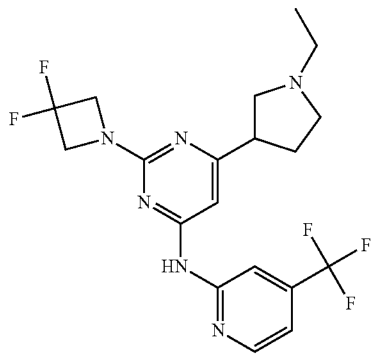 [SMILES: CCN1CCC(c2cc(Nc3cc(C(F)(F)F)ccn3)nc(N3CC(F)(F)C3)n2)C1] | ¹H NMR (400 MHz, MeOD) δ 8.46 (d, J = 4.0 Hz, 2 H), 7.22-7.20 (m, 1 H), 6.71 (s, 1 H), 4.45 (t, J = 12.0 Hz, 4 H), 3.66-3.60 (m, 4 H), 3.52-3.46 (m, 1 H), 3.35-3.30 (m, 2 H), 2.53-2.45 (m, 1 H), 2.28-2.21 (m, 1 H), 1.40-1.26 (m, 3 H) | 429 |
| 6-ac | 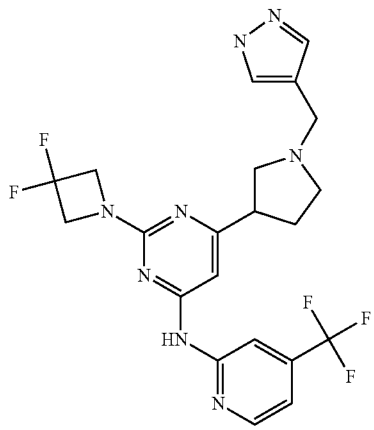 [SMILES: FC1(F)CN(c2nc(Nc3cc(C(F)(F)F)ccn3)cc(C3CCN(Cc4cn[nH]c4)C3)n2)C1] | ¹H NMR (400 MHz, MeOD) δ 8.54 (s, 1 H), 8.44 (d, J = 5.2 Hz, 1 H), 7.60 (s, 2 H), 7.18 (d, J = 5.2 Hz, 1 H), 6.61 (s, 1 H), 4.44 (s, 1 H), 4.42 (d, J = 8.0 Hz, 2 H), 4.38 (s, 1 H), 3.73-3.64 (m, 2 H), 3.35-3.30 (m, 1 H), 3.11-3.06 (m, 1 H), 2.89-2.86 (m, 1 H), 2.78-2.73 (m, 2 H), 2.27-2.23 (m, 1 H), 2.21-2.02 (m, 1 H). | 481 |
| 6-ad | 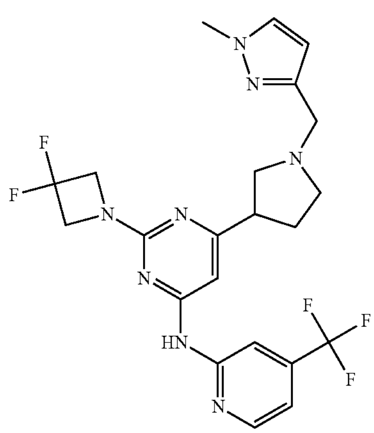 [SMILES: Cn1ccc(CN2CCC(c3cc(Nc4cc(C(F)(F)F)ccn4)nc(N4CC(F)(F)C4)n3)C2)n1] | ¹H NMR (400 MHz, MeOD) δ 8.46 (d, J = 5.2 Hz, 2 H), 7.64 (s, 1 H), 7.21 (d, J = 5.2 Hz, 1 H), 6.68 (s, 1 H), 6.43 (s, 1 H), 4.48 (s, 1 H), 4.45 (s, 2 H), 4.42-4.35 (m, 3 H), 3.91 (s, 3 H), 3.62-3.52 (m, 4 H), 3.47-3.40 (m, 1 H), 2.49-2.44 (m, 1 H), 2.24-2.18 (m, 1 H). | 495 |
| 6-ae | 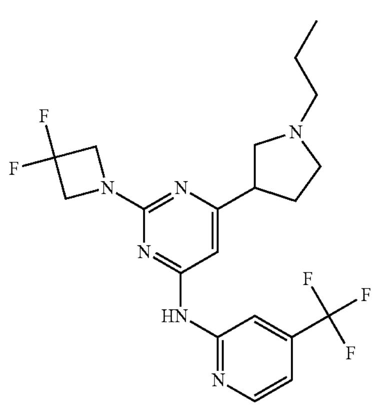 [SMILES: CCCN1CCC(c2cc(Nc3cc(C(F)(F)F)ccn3)nc(N3CC(F)(F)C3)n2)C1] | ¹H NMR (400 MHz, MeOD) δ 8.46 (d, J = 6.0 Hz, 2 H), 7.22-7.20 (m, 1 H), 6.69 (s, 1 H), 4.48-4.42 (m, 4 H), 3.65-3.47 (m, 5 H), 3.23-3.19 (m, 2 H), 2.50-2.45 (m, 1 H), 2.27-2.20 (m, 1 H), 1.84-1.74 (m, 2 H), 1.11-1.06 (m, 3 H). | 443 |

US 9,868,720 B2

431 432

TABLE 6-continued

| No. | Structure | NMR | MS (M + H)+ |
|---|---|---|---|
| 6-af | 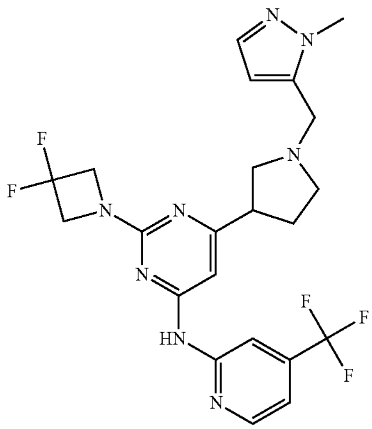 [SMILES: Cn1nccc1CN1CCC(c2cc(Nc3cc(C(F)(F)F)ccn3)nc(N3CC(F)(F)C3)n2)C1] | $^1$H NMR (400 MHz, MeOD) δ 8.52 (s, 1 H), 8.44 (d, J = 5.2 Hz, 1 H), 7.38 (m, 1 H), 7.19-7.18 (m, 1 H), 6.65 (s, 1 H), 6.27 (d, J = 6.0 Hz, 1 H), 4.44-4.38 (m, 4 H), 3.88 (s, 3 H), 3.83 (d, J = 2.8 Hz, 2 H), 3.36-3.31 (m, 1 H), 3.07-3.03 (m, 1 H), 2.86-2.80 (m, 3 H), 2.31-2.26 (m, 1 H), 2.25-2.10 (m, 1 H). | 495 |
| 6-ag | 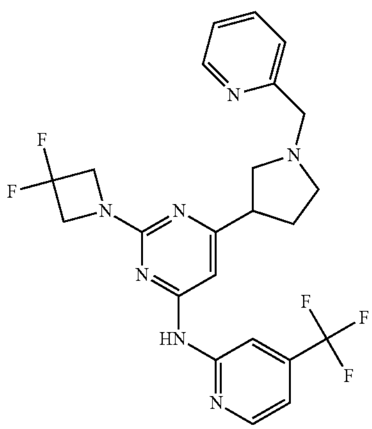 [SMILES: FC1(F)CN(c2nc(Nc3cc(C(F)(F)F)ccn3)cc(C3CCN(Cc4ccccn4)C3)n2)C1] | $^1$H NMR (400 MHz, MeOD) δ 8.63-8.61 (m, 1 H), 8.49-8.45 (m, 2 H), 7.91-7.86 (m, 1 H), 7.52-7.50 (m, 1 H), 7.44-7.41 (m, 1 H), 7.22-7.20 (m, 1 H), 6.69 (s, 1 H), 4.52-4.47 (m, 6 H), 3.61-3.56 (m, 4 H), 3.42-3.37 (m, 1 H), 2.57-2.48 (m, 1 H), 2.24-2.20 (m, 1 H). | 492 |

Example 7

Synthesis of 1-(3-(2-(1-methyl-1H-pyrazol-4-yl)-6-(4-methylpyridin-2-ylamino)pyrimidin-4-yl)piperidin-1-yl)ethanone Step 1—Synthesis of tert-butyl 3-(2-(1-methyl-1H-pyrazol-4-yl)-6-(4-methylpyridin-2-ylamino)pyrimidin-4-yl)piperidine-1-carboxylate

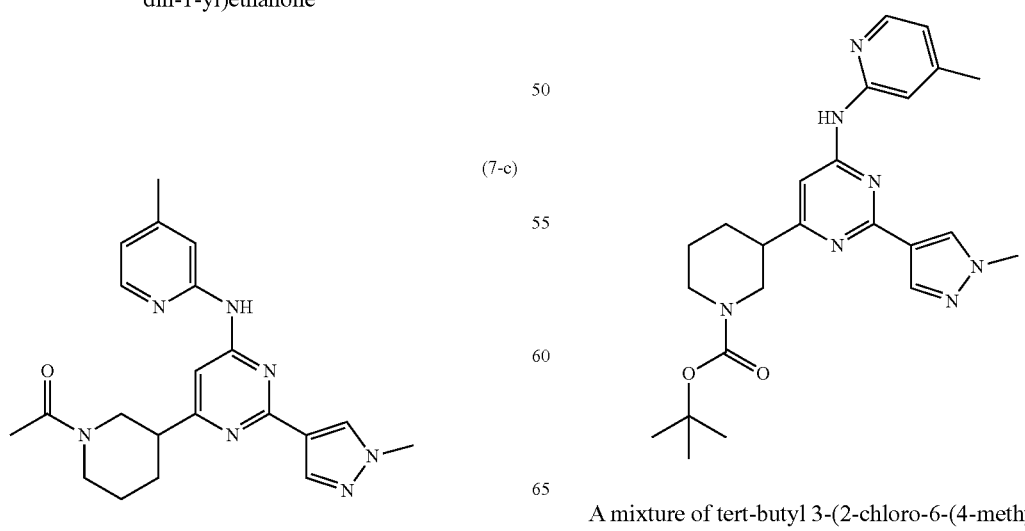

A mixture of tert-butyl 3-(2-chloro-6-(4-methylpyridin-2-ylamino)pyrimidin-4-yl)piperidine-1-carboxylate (180 mg, 0.45 mmol), 1-methyl-4-(4,4,5,5-tetramethyl-1,3,2-dioxaborolan-2-yl)-1H-pyrazole (187 mg, 0.90 mmol), Cs$_2$CO$_3$ (293 mg, 0.90 mmol), Pd(dppf)Cl$_2$ (16 mg, 0.0225 mmol) and dioxane/H$_2$O (6:1) (8.0 mL) was heated at 160° C. under microwave for 30 mins. After removal of the solvent, the residue was purified by column (PE:EA=2:3) to give the title compound (170 mg, yield: 74.9%): MS m/z=450.2 (M+H$^+$).

Step 2—Synthesis of 2-(1-methyl-1H-pyrazol-4-yl)-N-(4-methylpyridin-2-yl)-6-(piperidin-3-yl)pyrimidin-4-amine (7-b)

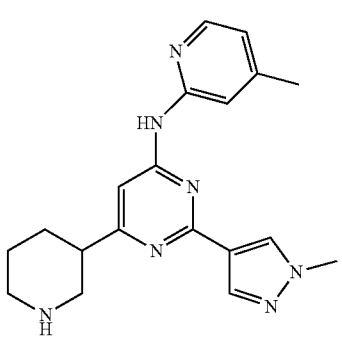

To a solution of compound 7-a (180 mg, 040 mmol) in EA (30.0 mL) was added 4M HCl/EA (20 mL). The mixture was stirred at r.t. for 3 h. After removal of the solvent, the residue was lyophilized o give the desired product in quantitative yield: $^1$H NMR (400 MHz, MeOD) δ 8.52 (s, 1H), 8.40 (d, J=6.4 Hz, 1H), 8.23 (s, 1H), 7.30-7.26 (m, 2H), 6.86 (s, 1H), 3.93 (s, 3H), 3.56-3.53 (m, 1H), 3.39-3.31 (m, 2H), 3.24-3.22 (m, 1H), 3.05-3.02 (m, 1H), 2.51 (s, 3H), 2.12-2.06 (m, 1H), 1.97-1.96 (m, 1H), 1.87-1.80 (m, 2H); MS m/z=349.9 (M+H$^+$). Alternatively, the compound could be purified by HPLC.

Step 3—Synthesis of 1-(3-(2-(1-methyl-1H-pyrazol-4-yl)-6-(4-methylpyridin-2-ylamino)pyrimidin-4-yl)piperidin-1-yl)ethanone To a mixture of Example 7-b (30 mg, 0.068 mmol), DCM (20 mL) and Et$_3$N (0.5 mL). was added acetyl chloride (5.3 mg, 0.068 mmol). The mixture was stirred at r.t. for 15 min. The solvents were removed and the residue purified by HPLC to give the title compound (12.9 mg, 48.7%): $^1$H NMR (400 MHz, CDCl$_3$) δ 8.18-8.12 (m, 2H), 8.05 (d, J=2.4 Hz, 1H), 7.54-7.51 (m, 1H), 7.42-7.13 (m, 1H), 6.80 (t, J=6.0 Hz, 1H), 4.76-4.53 (m, 1H), 3.99-3.81 (m, 4H), 3.48-3.12 (m, 1H), 2.98-2.79 (m, 2H), 2.38 (s, 3H), 2.14 (s, 3H), 2.09-2.13 (m, 1H), 1.90-1.82 (m, 2H), 1.64-1.58 (m, 1H); MS m/z=392 (M+H$^+$).

Additional compounds of the invention presented in Table 7 below were prepared by methods already described in the application.

TABLE 7

| No. | Structure | NMR | MS (M + H)+ |
|---|---|---|---|
| 7-c | 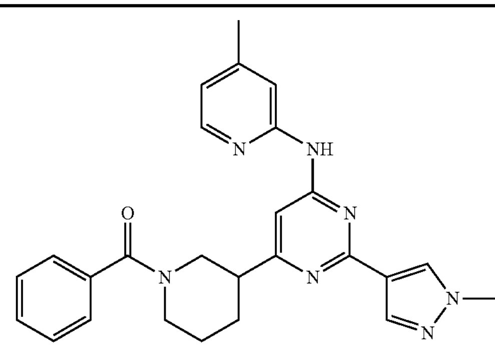 | $^1$H NMR (400 MHz, CDCl$_3$), δ ppm: 8.33-7.94 (m, 3H), 7.94-7.50 (m, 1H), 7.50 (s, 5H), 7.17-7.07 (m, 1H), 6.80-6.79 (m, 1H), 4.83-4.74 (m, 1H), 3.95-3.74 (m, 4H), 3.34-3.22 (m, 1H), 3.11-2.78 (m, 2H), 2.38 (s, 3H), 2.16-2.13 (m, 1H), 1.87-1.60 (m, 3H) | 454 |
| 7-d | 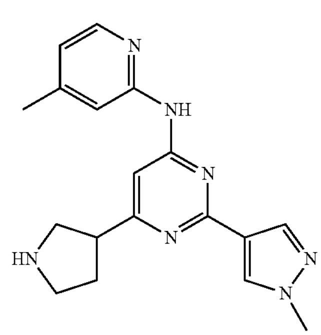 [SMILES: Cc1ccnc(Nc2cc(C3CCNC3)nc(-c3cnn(C)c3)n2)c1] | $^1$H NMR (400 MHz, MeOD) δ 8.66 (s, 1 H), 8.51 (d, J = 6.4 Hz, 1 H), 8.38 (s, 1 H), 7.40-7.36 (m, 2 H), 6.96 (s, 1 H), 4.03 (s, 3 H), 3.89-3.79 (m, 1 H), 3.70-3.75 (m, 2 H), 3.68-3.60 (m, 1 H), 3.55-3.48 (m, 1 H), 2.61 (s, 3 H), 2.59-2.50 (m, 1 H), 2.32-2.23 (m, 1 H) | 336 |

TABLE 7-continued

| No. | Structure | NMR | MS (M + H)+ |
|---|---|---|---|
| 7-e | 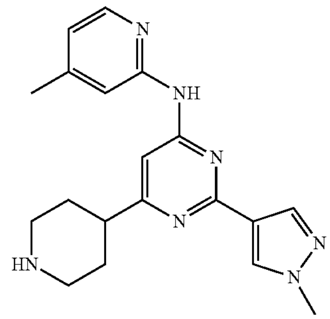 [SMILES: Cc1ccnc(Nc2cc(C3CCNCC3)nc(-c3cnn(C)c3)n2)c1] | $^1$H NMR (400 MHz, MeOD) δ 8.61-8.58 (m, 1 H), 8.51-8.50 (m, 1 H), 8.33-8.31 (m, 1 H), 7.39 (s, 2 H), 6.96 (s, 1 H), 4.04 (s, 3 H), 3.58 (d, J = 12.4 Hz, 2 H), 3.25-3.14 (m, 3 H), 2.62 (s, 3 H), 2.28-2.09 (m, 4 H) | 350 |
| 7-f | 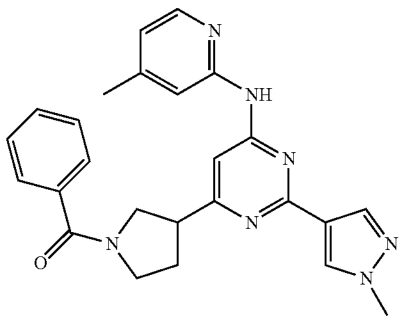 [SMILES: Cc1ccnc(Nc2cc(C3CCN(C(=O)c4ccccc4)C3)nc(-c3cnn(C)c3)n2)c1] | $^1$H NMR (400 MHz, MeOD) δ 8.40-8.33 (m, 2 H), 8.18 (d, J = 16.0 Hz, 1 H), 7.56-7.53 (m, 2 H), 7.49-7.43 (m, 3 H), 7.36-7.33 (m, 1 H), 7.21-6.90 (m, 2 H), 4.01-3.95 (m, 3 H), 3.90-3.83 (m, 2 H), 3.74-3.65 (m, 2 H), 3.55-3.52 (m, 1 H), 2.52-2.46 (m, 3 H), 2.38-2.25 (m, 2 H). | 440 |
| 7-g | 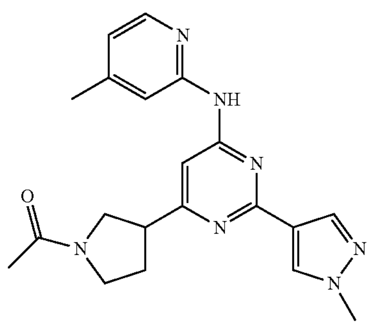 [SMILES: CC(=O)N1CCC(c2cc(Nc3cc(C)ccn3)nc(-c3cnn(C)c3)n2)C1] | $^1$H NMR (400 MHz, CDCl$_3$) δ 8.12-8.06 (m, 3 H), 7.93-7.90 (m, 1 H), 7.10-7.06 (m, 1 H), 6.86-6.85 (m, 1 H), 3.99 (d, J = 3.2 Hz, 3 H), 3.87-3.69 (m, 3 H), 3.60-3.38 (m, 2 H), 2.92-2.83 (m, 1 H), 2.44 (s, 3 H), 2.41-2.20 (m, 2 H), 2.11 (s, 3 H) | 378 |
| 7-h | 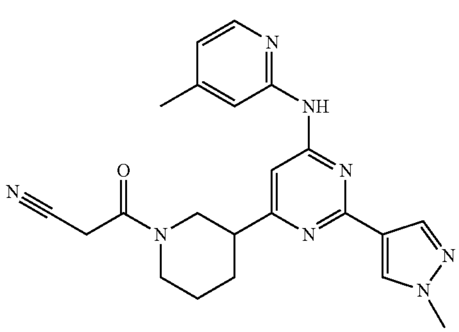 [SMILES: Cc1ccnc(Nc2cc(C3CCCN(C(=O)CC#N)C3)nc(-c3cnn(C)c3)n2)c1] | $^1$H NMR (400 MHz, MeOD) δ 8.31-8.11 (m, 3 H), 7.53 (s, 1 H), 7.21 (s, 1 H), 7.02 (d, J = 5.2 Hz, 1 H), 4.67-4.64 (m, 1 H), 4.03-3.81 (m, 5 H), 3.32-3.29 (m, 2 H), 2.98-2.85 (m, 2 H), 2.46 (d, J = 9.6 Hz, 3 H), 2.17-1.80 (m, 4 H) | 417 |

TABLE 7-continued

| No. | Structure | NMR | MS (M + H)+ |
|---|---|---|---|
| 7-i | 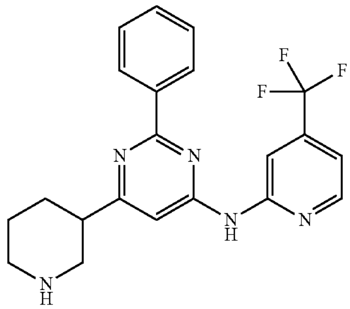 [SMILES: FC(F)(F)c1ccnc(Nc2cc(C3CCCNC3)nc(-c3ccccc3)n2)c1] | $^1$H NMR (400 MHz, DMSO) δ 10.62 (s, 1H), 8.66-8.52 (m, 2H), 8.44-8.30 (m, 2H), 7.57-7.46 (m, 2H), 7.40-7.21 (m, 2H), 3.04-2.91 (m, 2H), 2.76 (t, J = 9.6 Hz, 2H), 2.03 (d, J = 14.0 Hz, 1H), 1.83-1.54 (m, 2H), 1.57-1.49 (m, 2H). | 400.4 |
| 7-j | 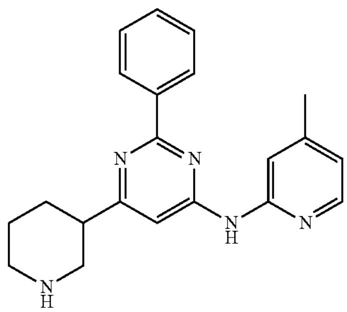 [SMILES: Cc1ccnc(Nc2cc(C3CCCNC3)nc(-c3ccccc3)n2)c1] | $^1$H NMR (400 MHz, DMSO-d$_6$) δ 10.05 (s, 1H), 8.46-8.33 (m, 2H), 8.19 (d, J = 5.1 Hz, 1H), 7.77 (s, 1H), 7.57-7.43 (m, 4H), 6.87 (d, J = 5.1 Hz, 1H), 3.19 (d, J = 8.0 Hz, 1H), 2.98 (d, J = 11.8 Hz, 1H), 2.78-2.64 (m, 2H), 2.59-2.55 (m, 1H), 2.01 (d, J = 14.1 Hz, 1H), 1.81-1.65 (m, 2H), 1.61-1.45 (m, 1H). | 346.4 |
| 7-k | 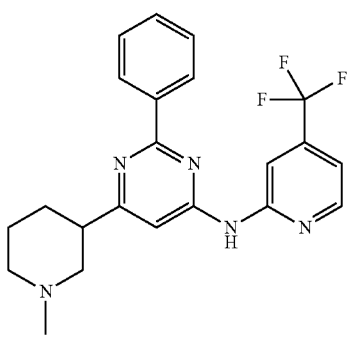 [SMILES: CN1CCCC(c2cc(Nc3cc(C(F)(F)F)ccn3)nc(-c3ccccc3)n2)C1] | $^1$H NMR (400 MHz, DMSO) δ 10.74 (s, 1H), 8.67-8.53 (m, 2H), 8.39 (dd, J = 6.6, 3.0 Hz, 2H), 7.58-7.48 (m, 3H), 7.43-7.33 (m, 2H), 6.51 (s, 1H), 3.55 (s, 1H), 3.16 (s, 2H), 2.81-2.63 (m, 4H), 2.09-1.57 (m, 4H). | 414.4 |
| 7-l | 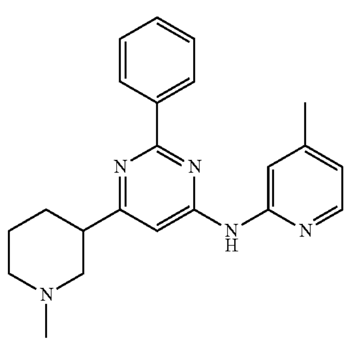 [SMILES: Cc1ccnc(Nc2cc(C3CCCN(C)C3)nc(-c3ccccc3)n2)c1] | $^1$H NMR (400 MHz, DMSO) δ 10.19 (s, 1H), 8.45-8.36 (m, 2H), 8.20 (d, J = 5.1 Hz, 1H), 7.72 (s, 1H), 7.64-7.52 (m, 4H), 6.88 (t, J = 9.0 Hz, 1H), 6.51 (s, 1H), 3.62-3.42 (m, 1H), 3.12 (s, 1H), 2.83-2.61 (m, 3H), 2.34 (d, J = 11.0 Hz, 3H), 2.05-1.60 (m, 4H). | 360.5 |

TABLE 7-continued

| No. | Structure | NMR | MS (M + H)+ |
|---|---|---|---|
| 7-m | 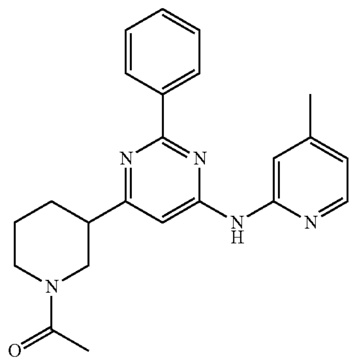 [SMILES: CC(=O)N1CCCC(c2cc(Nc3cc(C)ccn3)nc(-c3ccccc3)n2)C1] | $^1$H NMR (400 MHz, DMSO) δ 10.11 (d, J = 3.0 Hz, 1H), 8.40 (dd, J = 7.7, 3.3 Hz, 2H), 8.19 (d, J = 5.1 Hz, 1H), 7.76 (s, 1H), 7.60-7.47 (m, 4H), 6.88 (d, J = 5.1 Hz, 1H), 4.68-3.79 (m, 2H), 3.45 (dd, J = 13.3, 10.5 Hz, 1H), 3.11 (t, J = 11.7 Hz, 1H), 2.92-2.58 (m, 2H), 2.36 (s, 3H), 2.05 (d, J = 2.8 Hz, 3H), 1.90-1.45 (m, 3H). | 388.5 |
| 7-n | 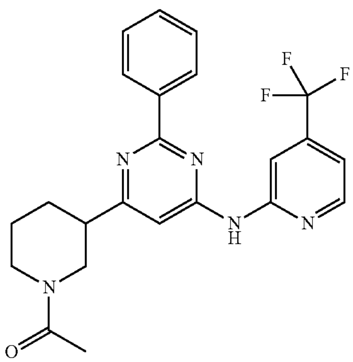 [SMILES: CC(=O)N1CCCC(c2cc(Nc3cc(C(F)(F)F)ccn3)nc(-c3ccccc3)n2)C1] | $^1$H NMR (400 MHz, DMSO) δ 10.67 (d, J = 4.8 Hz, 1H), 8.60 (d, J = 5.2 Hz, 2H), 8.42-8.35 (m, 2H), 7.58-7.51 (m, 3H), 7.41-7.32 (m, 2H), 4.70-3.79 (m, 3H), 3.46 (dd, J = 13.3, 10.5 Hz, 1H), 3.12 (t, J = 11.7 Hz, 1H), 2.92-2.66 (m, 2H), 2.05 (d, J = 2.2 Hz, 2H), 1.92-1.73 (m, 2H), 1.68-1.41 (m, 1H). | 442.5 |

Example 8

Synthesis of tert-butyl 3-(6-chloro-2-cyclopentylpyrimidin-4-yl)azetidine-1-carboxylate (8-b)

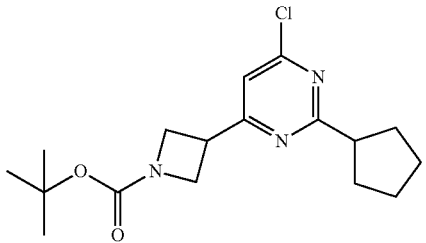

Step 1—Synthesis of tert-butyl 3-(2-cyclopentyl-6-hydroxypyrimidin-4-yl)azetidine-1-carboxylate

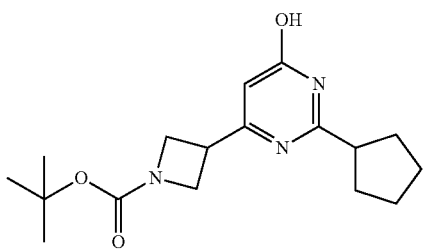

(8-a)

A mixture of tert-butyl 3-(3-ethoxy-3-oxopropanoyl)azetidine-1-carboxylate (3.25 g, 12.0 mmol), Cyclopentanecarboxamidine hydrochloride salt (4.45 g, 30.0 mmol), NaOMe (1.95 g, 3 eq) and anhydrous MeOH (200 mL) was heated at reflux under N$_2$ overnight. TLC (DCM:MeOH=20:1, R$_f$=0.35) showed the reaction was completed and MeOH was removed under reduced pressure. Water was added and the pH adjusted to 5-6 with critic acid, extracted with DCM (60 mL×3), dried over Na$_2$SO$_4$ and concentrated. The residue was purified by silica gel flash-chromatography to give the desired product. (2.8 g, yield: 45.0%): $^1$H NMR (CDCl$_3$, 400 MHz), δ: 12.56 (s, 1H), 6.17 (s, 1H), 4.19-4.15 (t, J=8.4 Hz, 2H), 4.10-4.07 (m, 2H), 3.61-3.55 (m, 1H), 3.08-3.00 (m, 1H), 2.09-1.61 (m, 8H), 1.46 (s, 9H).

Step 2—Synthesis of tert-butyl 3-(6-chloro-2-cyclopentylpyrimidin-4-yl)azetidine-1-carboxylate A mixture of compound 8-a (20 mmol), PPh$_3$ (80 mmol) and CCl$_4$ (0.2 mol) in DCE (100 mL) was stirred at reflux under N$_2$ atmosphere for 2-3 hours. LCMS and TLC (PE:EA=5:1, R$_f$=0.75) showed the reaction was completed. The solvent was removed under reduced pressure and the residue was purified by silica gel flash-chromatography to give the pure product of (1226.5 mg, 35%): $^1$H NMR (400 MHz, MeOD), δ ppm: 7.05 (s, 1H), 4.29-4.24 (m, 2H), 4.15-4.12 (m, 2H), 3.77-3.72 (m, 1H), 3.37-3.31 (m, 1H), 2.10-2.04 (m, 2H), 1.94-1.87 (m, 4H), 1.72-1.65 (m, 2H), 1.47 (s, 9H).

Additional compounds of the invention presented in Table 8 below were prepared by methods already described in the application.

TABLE 8

| No. | Structure | NMR | MS (M + H)+ |
|---|---|---|---|
| 8-b | 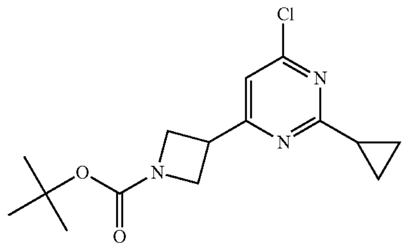 [SMILES: CC(C)(C)OC(=O)N1CC(c2cc(Cl)nc(C3CC3)n2)C1] | ¹H NMR (400 MHz, CDCl₃) δ 6.98 (s, 1 H), 4.24 (t, J = 8.8 Hz, 2 H), 4.12-4.08 (m, 2 H), 3.71-3.65 (m, 1 H), 2.25-2.19 (m, 1 H), 1.46 (s, 9 H), 1.18-1.07 (m, 4 H). | 310 |
| 8-c | 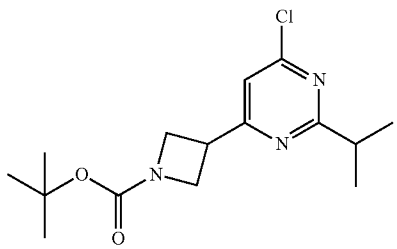 [SMILES: CC(C)c1nc(Cl)cc(C2CN(C(=O)OC(C)(C)C)C2)n1] | ¹H NMR (400 MHz, CDCl₃) δ 7.07 (s, 1 H), 4.27 (t, J = 8.8 Hz, 2 H), 4.12-4.16 (q, 2 H), 3.72-3.79 (m, 1 H), 3.14-3.21 (m, 1 H), 1.46 (s, 9 H), 1.33 (d, J = 6.8 Hz, 6 H). | 312 |
| 8-d | 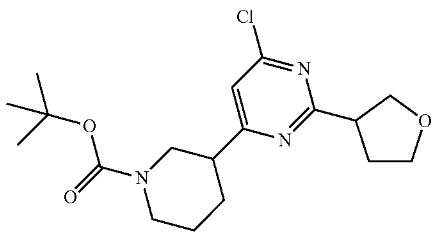 [SMILES: CC(C)(C)OC(=O)N1CCCC(c2cc(Cl)nc(C3CCOC3)n2)C1] | ¹H NMR (400 MHz, DMSO-d₆) δ 1.3-1.5 (m, 10H), 1.65-1.8 (m, 2H), 1.93-1.96 (m, 1H), 2.20-2.27 (m, 2H), 2.79-2.89 (m, 2H), 2.9-3.2 (broad, 1H), 3.61-3.65 (m, 1H), 3.76-3.89 (m, 4H), 3.90-4.08 (broad, 2H), and 7.53 (s, 1H) | 369 |
| 8-e | 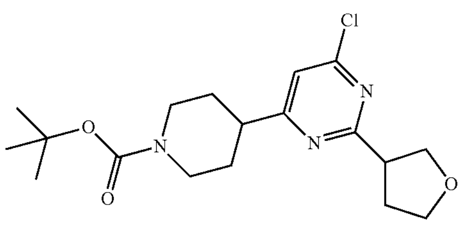 [SMILES: CC(C)(C)OC(=O)N1CCC(c2cc(Cl)nc(C3CCOC3)n2)CC1] | ¹H NMR (400 MHz, DMSO-d₆) δ 1.38 (m, 9H), 1.54-1.58 (m, 2H), 1.82-1.84 (m, 2H), 2.20-2.27 (m, 2H), 2.80-2.90 (m, 3H), 3.61-3.65 (m, 1H), 3.78-3.87 (m, 3H), 4.0-4.09 (m, 3H), and 7.50 (s, 1H) | 269 (M − Boc) |
| 8-f | 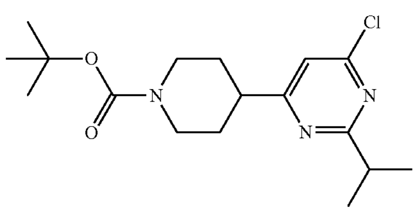 [SMILES: CC(C)c1nc(Cl)cc(C2CCN(C(=O)OC(C)(C)C)CC2)n1] | ¹H NMR (400 MHz, DMSO-d₆) δ 1.25 (m, 6H), 1.41 (s, 9H), 1.52-1.62 (m, 2H), 1.82-1.85 (m, 2H), 2.83-2.89 (broad, 3H), 3.04-3.09 (m, 1H), 4.03-4.05 (broad, 2H), and 7.45 (s, 1H). | 242 |
| 8-g | 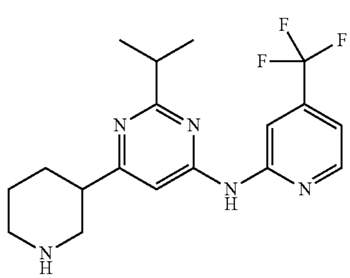 [SMILES: CC(C)c1nc(Nc2cc(C(F)(F)F)ccn2)cc(C2CCCNC2)n1] | ¹H NMR (400 MHz, DMSO) δ 10.55-10.39 (m, 1H), 8.70-8.57 (m, 2H), 8.35 (s, 1H), 7.30 (t, J = 7.3 Hz, 1H), 7.12 (s, 1H), 3.17 (d, J = 6.9 Hz, 1H), 3.03-2.91 (m, 2H), 2.79-2.53 (m, 4H), 1.74-1.45 (m, 3H), 1.27 (d, J = 6.1 Hz, 6H). | 366.4 |

TABLE 8-continued

| No. | Structure | NMR | MS (M + H)+ |
|---|---|---|---|
| 8-h | 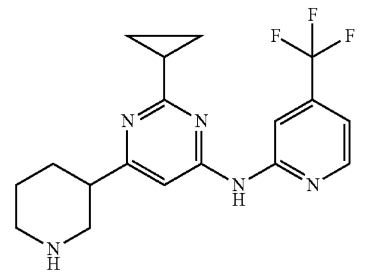 [SMILES: FC(F)(F)c1ccnc(Nc2cc(C3CCCNC3)nc(C3CC3)n2)c1] | ¹H NMR (400 MHz, DMSO-d₆) δ 10.46 (s, 1H), 8.58-8.41 (m, 2H), 7.31 (d, J = 4.6 Hz, 1H), 7.08 (s, 1H), 3.17 (d, J = 8.8 Hz, 2H), 3.01 (d, J = 9.5 Hz, 2H), 2.76-2.58 (m, 3H), 2.08-1.88 (m, 3H), 1.76-1.50 (m, 5H). | 364.4 |
| 8-i | 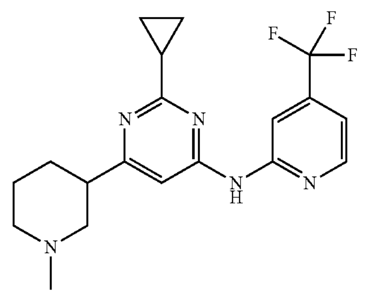 [SMILES: CN1CCCC(c2cc(Nc3cc(C(F)(F)F)ccn3)nc(C3CC3)n2)C1] | | 378 |
| 8-j | 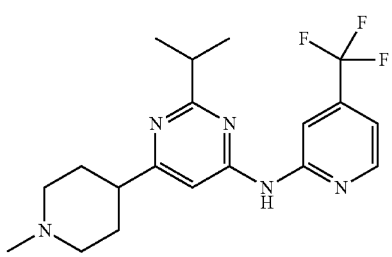 [SMILES: CC(C)c1nc(Nc2cc(C(F)(F)F)ccn2)cc(C2CCN(C)CC2)n1] | ¹H NMR (400 MHz, DMSO-d₆) δ 10.42 (s, 1H), 8.63 (s, 1H), 8.54 (d, J = 5.1 Hz, 1H), 7.30 (d, J = 5.0 Hz, 1H), 7.12 (s, 1H), 3.00 (dt, J = 13.8, 6.9 Hz, 1H), 2.85 (d, J = 11.4 Hz, 2H), 1.96 (dd, J = 11.6, 9.5 Hz, 2H), 1.82 (d, J = 11.1 Hz, 2H), 1.76-1.59 (m, 3H), 1.28 (d, J = 6.9 Hz, 6H). | 380.4 |
| 8-k | 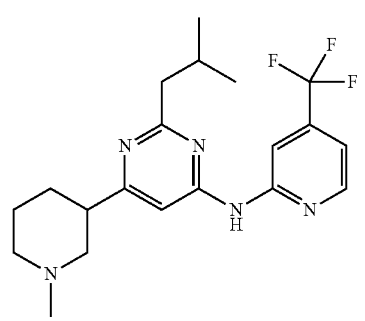 [SMILES: CC(C)Cc1nc(Nc2cc(C(F)(F)F)ccn2)cc(C2CCCN(C)C2)n1] | | 394.5 |
| 8-l | 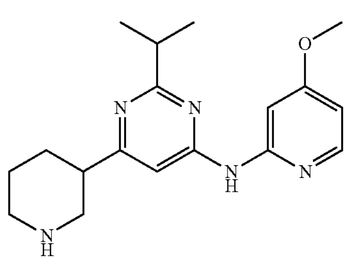 [SMILES: COc1ccnc(Nc2cc(C3CCCNC3)nc(C(C)C)n2)c1] | ¹H NMR (400 MHz, DMSO-d₆) δ 11.32 (s, 1H), 8.94 (d, J = 3.8 Hz, 1H), 7.97 (s, 1H), 7.49 (s, 1H), 4.37 (dd, J = 114.9, 12.7 Hz, 2H), 3.17-3.03 (m, 2H), 2.77 (ddd, J = 33.6, 29.8, 18.9 Hz, 3H), 1.87-1.67 (m, 3H), 1.49 (dd, J = 47.2, 12.6 Hz, 1H), 1.32 (dd, J = 6.8, 1.9 Hz, 6H). | 328.4 |

TABLE 8-continued

| No. | Structure | NMR | MS (M + H)+ |
|---|---|---|---|
| 8-m | 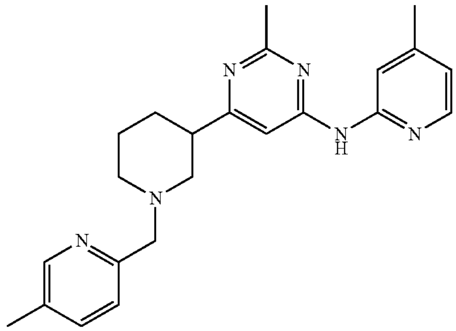 [SMILES: Cc1ccc(CN2CCCC(c3cc(Nc4cc(C)ccn4)nc(C)n3)C2)nc1] | $^1$H NMR (400 MHz, DMSO) δ 9.92 (s, 1H), 8.30 (s, 1H), 8.13 (d, J = 5.1 Hz, 1H), 7.59-7.54 (m, 2H), 7.43 (s, 1H), 7.34 (d, J = 7.9 Hz, 1H), 6.80 (d, J = 5.1 Hz, 1H), 6.51 (s, 1H), 3.63-3.52 (m, 2H), 2.97-2.74 (m, 2H), 2.75-2.64 (m, 1H), 2.43 (s, 3H), 2.27 (d, J = 7.3 Hz, 6H), 2.21-1.98 (m, 2H), 1.86 (d, J = 12.4 Hz, 1H), 1.71 (d, J = 12.7 Hz, 1H), 1.64-1.42 (m, 2H). | 389.5 |
| 8-n | 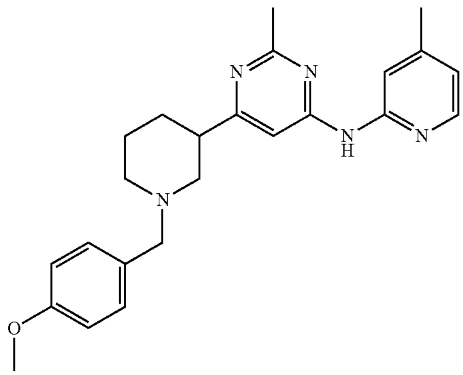 [SMILES: COc1ccc(CN2CCCC(c3cc(Nc4cc(C)ccn4)nc(C)n3)C2)cc1] | $^1$H NMR (400 MHz, DMSO) δ 9.91 (s, 1H), 8.13 (d, J = 5.1 Hz, 1H), 7.56 (s, 1H), 7.43 (s, 1H), 7.21 (d, J = 8.5 Hz, 2H), 6.86 (d, J = 8.5 Hz, 2H), 6.80 (d, J = 5.1 Hz, 1H), 3.72 (s, 3H), 3.43 (q, J = 13.0 Hz, 1H), 3.17 (s, 2H), 2.97-2.73 (m, 2H), 2.66 (dd, J = 14.7, 7.1 Hz, 1H), 2.43 (s, 3H), 2.28 (s, 3H), 2.97-2.73 (m, 3H), 1.72-1.42 (m, 3H). | 404.5 |
| 8-o | 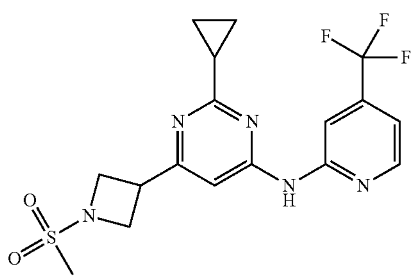 [SMILES: CS(=O)(=O)N1CC(c2cc(Nc3cc(C(F)(F)F)ccn3)nc(C3CC3)n2)C1] | $^1$H NMR (400 MHz, DMSO-d$_6$) δ 10.51 (s, 1H), 8.55 (d, J = 5.1 Hz, 1H), 8.38 (s, 1H), 7.32 (d, J = 5.1 Hz, 1H), 7.20 (s, 1H), 4.17-4.03 (m, 4H), 3.86 (tt, J = 15.5, 7.9 Hz, 1H), 3.09 (s, 3H), 2.11 (dq, J = 7.5, 5.4 Hz, 1H), 1.04 (dd, J = 9.7, 4.0 Hz, 4H). | 414.4 |
| 8-p | 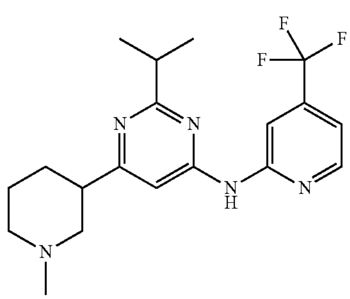 [SMILES: CC(C)c1nc(Nc2cc(C(F)(F)F)ccn2)cc(C2CCCN(C)C2)n1] | $^1$H NMR (400 MHz, DMSO) δ 10.05 (s, 1H), 8.86 (s, 1H), 8.51 (d, J = 5.1 Hz, 1H), 7.27 (d, J = 5.0 Hz, 1H), 6.89 (s, 1H), 3.10-2.70 (dddd, J = m, 4H), 2.19 (s, 3H), 2.15-2.01 (m, 1H), 2.00-1.79 (m, 2H), 1.77-1.37 (m, 3H), 1.24 (d, J = 6.9 Hz, 6H). | 380.4 |
| 8-q | 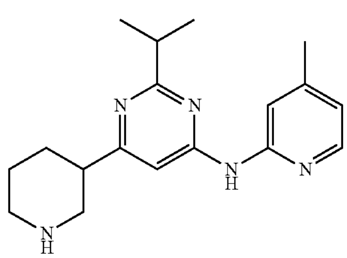 [SMILES: Cc1ccnc(Nc2cc(C3CCCNC3)nc(C(C)C)n2)c1] | $^1$H NMR (400 MHz, DMSO) δ 9.88 (s, 1H), 8.14 (d, J = 5.1 Hz, 1H), 7.72 (s, 1H), 7.35 (s, 1H), 6.82 (d, J = 5.1 Hz, 1H), 3.03-2.56 (m, 5H), 2.29 (s, 3H), 2.00-1.86 (m, 2H), 1.78-1.39 (m, 4H), 1.27 (d, J = 6.9 Hz, 6H). | 312.4 |

TABLE 8-continued

| No. | Structure | NMR | MS (M + H)+ |
|---|---|---|---|
| 8-r | 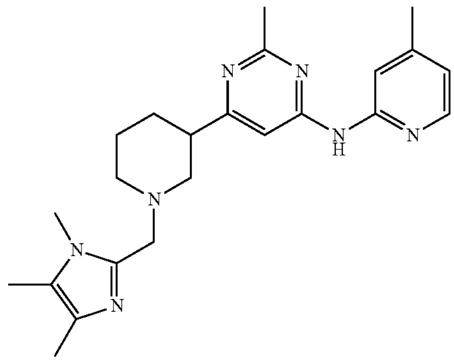 [SMILES: Cc1ccnc(Nc2cc(C3CCCN(Cc4nc(C)c(C)n4C)C3)nc(C)n2)c1] | ¹H NMR (400 MHz, DMSO) δ 9.93 (s, 1H), 8.14 (d, J = 5.1 Hz, 1H), 7.56 (s, 1H), 7.43 (s, 1H), 6.81 (d, J = 5.1 Hz, 1H), 3.45 (s, 3H), 2.99-2.72 (m, 2H), 2.69-2.57 (m, 1H), 2.44 (s, 3H), 2.28 (s, 3H), 2.40-2.07 (m, 1H), 2.06-2.02 (m, 3H), 1.95 (s, 3H), 1.84-1.67 (m, 2H), 1.59-1.41 (m, 2H). | 406.5 |
| 8-s | 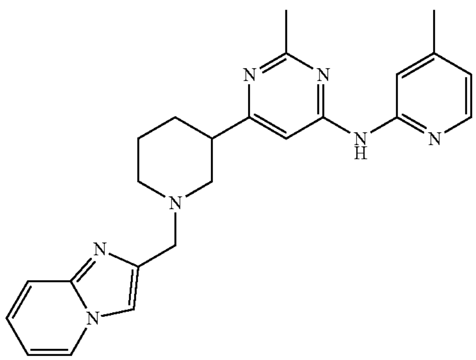 [SMILES: Cc1ccnc(Nc2cc(C3CCCN(Cc4cn5ccccc5n4)C3)nc(C)n2)c1] | ¹H NMR (400 MHz, DMSO) δ 9.91 (s, 1H), 8.46 (t, J = 8.1 Hz, 1H), 8.12 (d, J = 5.1 Hz, 1H), 7.80 (s, 1H), 7.56 (s, 1H), 7.50-7.42 (m, 2H), 7.17 (dd, J = 8.5, 7.2 Hz, 1H), 6.87-6.77 (m, 2H), 3.68-3.58 (m, 2H), 3.12-2.86 (m, 2H), 2.69 (dd, J = 15.1, 6.6 Hz, 1H), 2.43 (s, 3H), 2.27 (s, 3H), 2.19-2.00 (m, 2H), 1.92-1.63 (m, 2H), 1.62-1.41 (m, 2H). | 414.5 |
| 8-t | 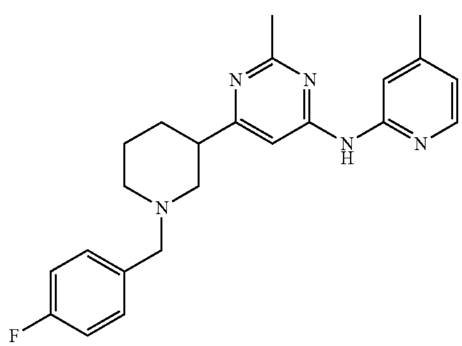 [SMILES: Cc1ccnc(Nc2cc(C3CCCN(Cc4ccc(F)cc4)C3)nc(C)n2)c1] | ¹H NMR (400 MHz, DMSO) δ 9.92 (s, 1H), 8.13 (d, J = 5.1 Hz, 1H), 7.57 (s, 1H), 7.43 (s, 1H), 7.34 (dd, J = 8.5, 5.8 Hz, 2H), 7.12 (t, J = 8.8 Hz, 2H), 6.81 (d, J = 5.1 Hz, 1H), 3.57-3.44 (m, 2H), 2.97-2.59 (m, 2H), 2.75-2.62 (m, 1H), 2.43 (s, 3H), 2.28 (s, 3H), 2.10 (t, J = 10.8 Hz, 1H), 2.03-1.92 (m, 1H), 1.88-1.65 (m, 2H), 1.61-1.39 (m, 2H). | 392.5 |
| 8-u | 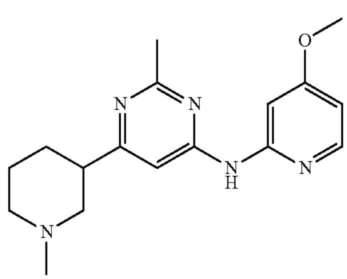 [SMILES: COc1ccnc(Nc2cc(C3CCCN(C)C3)nc(C)n2)c1] | ¹H NMR (400 MHz, DMSO) δ 10.40-9.93 (m, 1H), 8.09 (t, J = 6.0 Hz, 1H), 7.74 (s, 1H), 7.20 (s, 1H), 6.59 (dd, J = 5.8, 2.3 Hz, 1H), 3.83 (s, 3H), 3.00-2.85 (m, 2H), 2.79-2.63 (m, 2H), 2.19-2.17 (m, 1H), 2.07 (s, 1H), 1.99 (t, J = 10.8 Hz, 1H), 1.92-1.78 (m, 2H), 1.75-1.64 (m, 1H), 1.63-1.36 (m, 2H), 1.28 (t, J = 7.9 Hz, 7H). | 342.5 |

TABLE 8-continued

| No. | Structure | NMR | MS (M + H)+ |
|---|---|---|---|
| 8-v | 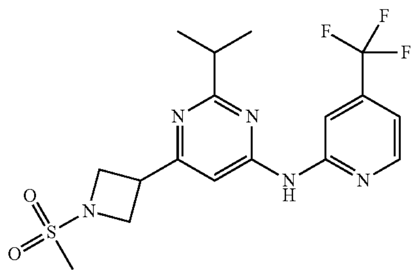 [SMILES: CC(C)c1nc(Nc2cc(C(F)(F)F)ccn2)cc(C2CN(S(C)(=O)=O)C2)n1] | $^1$H NMR (400 MHz, DMSO-d$_6$) δ 10.55 (d, J = 14.9 Hz, 1H), 8.56 (d, J = 5.2 Hz, 2H), 7.33 (d, J = 5.8 Hz, 1H), 7.23 (s, 1H), 4.20-4.06 (m, 4H), 4.00-3.83 (m, 1H), 3.09 (d, J = 11.1 Hz, 3H), 3.08-2.99 (m, 1H), 1.30 (t, J = 7.4 Hz, 6H). | 416.4 |
| 8-w | 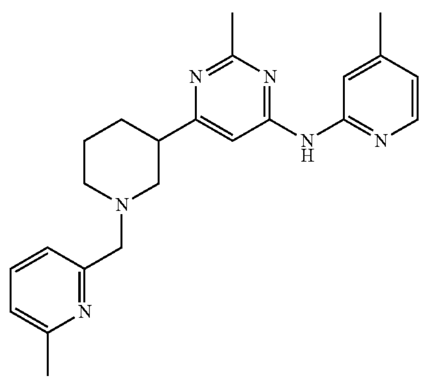 [SMILES: Cc1ccnc(Nc2cc(C3CCCN(Cc4cccc(C)n4)C3)nc(C)n2)c1] | $^1$H NMR (400 MHz, DMSO) δ 9.92 (s, 1H), 8.13 (d, J = 5.1 Hz, 1H), 7.70-7.52 (m, 2H), 7.43 (s, 1H), 7.25 (d, J = 7.7 Hz, 1H), 7.09 (d, J = 7.6 Hz, 1H), 6.80 (d, J = 5.1 Hz, 1H), 3.57 (s, 2H), 3.17 (s, 3H), 3.03-2.60 (m, 3H), 2.43 (d, J = 3.9 Hz, 4H), 2.28 (s, 3H), 2.25-1.98 (m, 2H), 1.92-1.68 (m, 2H), 1.68-1.44 (m, 2H). | 389.5 |
| 8-x | 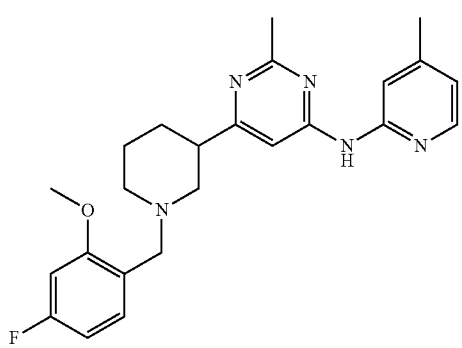 [SMILES: COc1cc(F)ccc1CN1CCCC(c2cc(Nc3cc(C)ccn3)nc(C)n2)C1] | $^1$H NMR (400 MHz, DMSO) δ 9.92 (s, 1H), 8.14 (d, J = 5.1 Hz, 1H), 7.57 (s, 1H), 7.43 (s, 1H), 7.35-7.27 (m, 1H), 6.91-6.67 (m, 3H), 3.46 (s, 2H), 3.01-2.62 (m, 2H), 2.70 (dd, J = 12.7, 9.1 Hz, 1H), 2.43 (s, 3H), 2.28 (s, 3H), 2.17-1.93 (m, 2H), 1.90-1.67 (m, 2H), 1.63-1.40 (m, 2H). | 422.5 |
| 8-y | 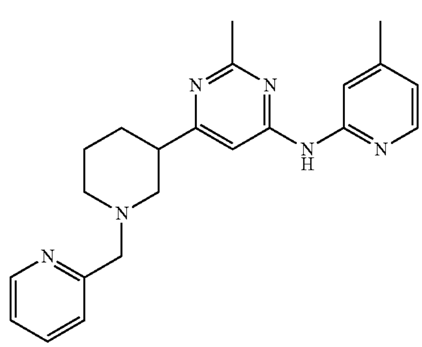 [SMILES: Cc1ccnc(Nc2cc(C3CCCN(Cc4ccccn4)C3)nc(C)n2)c1] | $^1$H NMR (400 MHz, DMSO-d$_6$) δ 9.92 (s, 1H), 8.47 (d, J = 4.3 Hz, 1H), 8.13 (d, J = 5.1 Hz, 1H), 7.75 (td, J = 7.7, 1.8 Hz, 1H), 7.57 (s, 1H), 7.51-7.38 (m, 2H), 7.24 (dd, J = 7.0, 5.2 Hz, 1H), 6.80 (d, J = 5.1 Hz, 1H), 3.63 (s, 2H), 2.98-2.63 (m, 3H), 2.43 (s, 3H), 2.38-2.26 (m, 3H), 2.23-2.02 (m, 2H), 1.92-1.68 (m, 2H), 1.69-1.41 (m, 2H). | 375.5 |

TABLE 8-continued

| No. | Structure | NMR | MS (M + H)+ |
|---|---|---|---|
| 8-z | 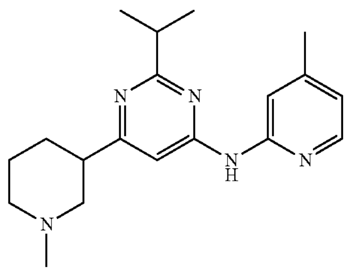 [SMILES: Cc1ccnc(Nc2cc(C3CCCN(C)C3)nc(C(C)C)n2)c1] | ¹H NMR (400 MHz, DMSO) δ 9.98 (s, 1H), 8.21-8.04 (m, 1H), 7.69 (s, 1H), 7.42 (s, 1H), 6.83 (d, J = 5.1 Hz, 1H), 3.01-2.90 (m, 2H), 2.70 (d, J = 14.4 Hz, 1H), 2.58 (s, 3H), 2.29 (s, 3H), 1.83 (ddd, J = 12.0, 19.4, 10.3 Hz, 3H), 1.57 (tt, J = 11.9, 6.1 Hz, 1H), 1.27 (d, J = 6.9 Hz, 6H). | 326.5 |
| 8-aa | 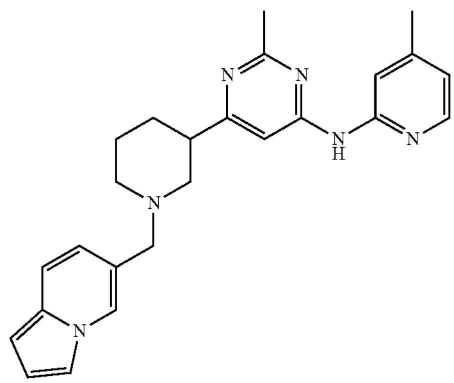 [SMILES: Cc1ccnc(Nc2cc(C3CCCN(Cc4ccc5cccn5c4)C3)nc(C)n2)c1] | ¹H NMR (400 MHz, DMSO) δ 9.91 (s, 1H), 8.42 (d, J = 12.5 Hz, 1H), 8.11 (d, J = 5.1 Hz, 1H), 7.88 (s, 1H), 7.58 (s, 1H), 7.54-7.48 (m, 2H), 7.42 (s, 1H), 7.21 (d, J = 9.3 Hz, 1H), 6.80 (d, J = 5.0 Hz, 1H), 3.56-3.45 (m, 2H), 2.90 (dd, J = 11.3, 11.1 Hz, 2H), 2.70 (dd, J = 12.7, 9.0 Hz, 1H), 2.42 (s, 3H), 2.27 (s, 3H), 2.09 (dt, J = 11, 9.8 Hz, 2H), 1.91-1.67 (m, 2H), 1.67-1.44 (m, 2H). | 414.5 |
| 8-ab | 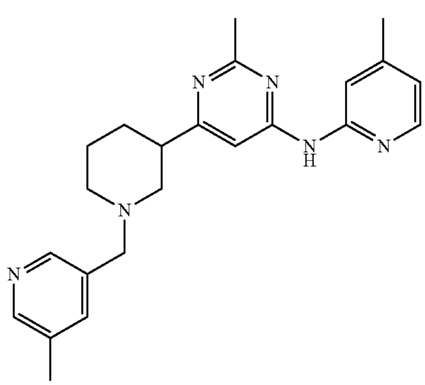 [SMILES: Cc1cncc(CN2CCCC(c3cc(Nc4cc(C)ccn4)nc(C)n3)C2)c1] | ¹H NMR (400 MHz, DMSO) δ 9.92 (s, 1H), 8.29 (s, 2H), 8.14 (d, J = 5.1 Hz, 1H), 7.60-7.38 (m, 3H), 6.81 (t, J = 5.7 Hz, 1H), 3.55-3.45 (m, 2H), 2.84 (dd, J = 11.2, 10.9 Hz, 2H), 2.70 (dd, J = 12.5, 9.0 Hz, 1H), 2.44 (d, J = 7.2 Hz, 3H), 2.27 (d, J = 6.9 Hz, 6H), 2.06 (dt, J = 11.9, 9.7 Hz, 2H), 1.78 (dd, J = 10.0, 12.5 Hz, 2H), 1.51 (ddd, J = 11.4, 18.4, 10.1 Hz, 2H). | 389.5 |
| 8-ac | 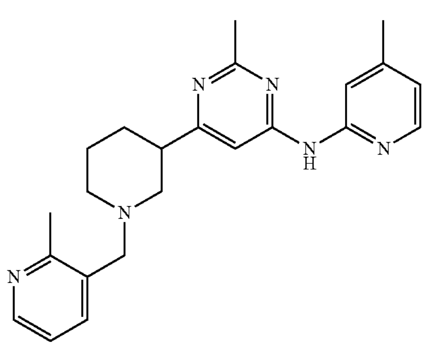 [SMILES: Cc1ccnc(Nc2cc(C3CCCN(Cc4cccnc4C)C3)nc(C)n2)c1] | ¹H NMR (400 MHz, DMSO) δ 9.92 (s, 1H), 8.31 (dd, J = 4.8, 1.5 Hz, 1H), 8.14 (d, J = 5.1 Hz, 1H), 7.59 (dd, J = 8.0, 6.7 Hz, 2H), 7.42 (s, 1H), 7.15 (dd, J = 7.5, 4.8 Hz, 1H), 6.80 (d, J = 5.1 Hz, 1H), 3.52-3.44 (m, 2H), 3.00-2.70 (m, 2H), 2.73-2.63 (m, 1H), 2.43 (s, 3H), 2.28 (s, 3H), 2.23-1.97 (m, 2H), 1.91-1.68 (m, 2H), 1.64-1.45 (m, 2H). | 389.5 |

TABLE 8-continued

| No. | Structure | NMR | MS (M + H)+ |
|---|---|---|---|
| 8-ad | 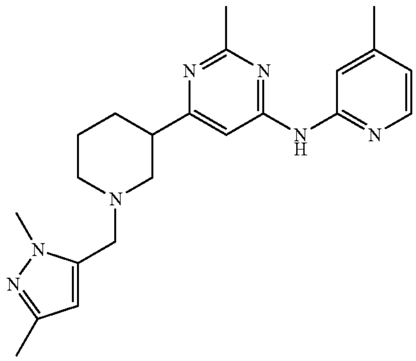 [SMILES: Cc1ccnc(Nc2cc(C3CCCN(Cc4cc(C)nn4C)C3)nc(C)n2)c1] | ¹H NMR (400 MHz, DMSO) δ 9.93 (s, 1H), 8.14 (d, J = 5.1 Hz, 1H), 7.58 (d, J = 9.4 Hz, 1H), 7.42 (s, 1H), 6.81 (d, J = 5.1 Hz, 1H), 5.89 (s, 1H), 4.08 (s, 1H), 3.70 (s, 3H), 3.47 (d, J = 1.7 Hz, 2H), 2.90-2.80 (m, 2H), 2.72-2.60 (m, 1H), 2.44 (s, 3H), 2.28 (s, 3H), 2.07 (s, 3H), 2.01-1.79 (m, 2H), 1.77-1.39 (m, 3H). | 392.5 |
| 8-ae | 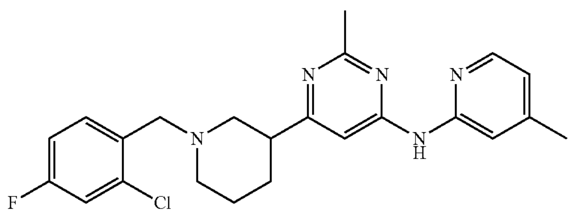 [SMILES: Cc1ccnc(Nc2cc(C3CCCN(Cc4ccc(F)cc4Cl)C3)nc(C)n2)c1] | ¹H NMR (400 MHz, DMSO) δ 9.90 (s, 1H), 8.13 (d, J = 5.1 Hz, 1H), 7.69-7.36 (m, 4H), 7.19 (td, J = 8.5, 2.6 Hz, 1H), 6.80 (d, J = 5.1 Hz, 1H), 3.57 (s, 2H), 3.00-2.75 (m, 2H), 2.70 (dd, J = 14.8, 7.3 Hz, 1H), 2.43 (s, 3H), 2.28 (s, 3H), 2.22 (t, J = 10.8 Hz, 1H), 2.08 (t, J = 9.9 Hz, 1H), 1.95-1.70 (m, 2H), 1.64-1.43 (m, 2H). | 426.9 |
| 8-af | 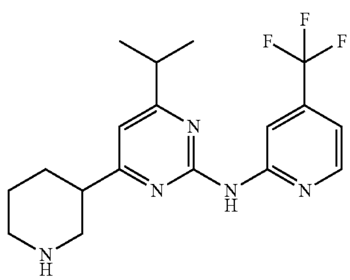 [SMILES: CC(C)c1cc(C2CCCNC2)nc(Nc2cc(C(F)(F)F)ccn2)n1] | ¹H NMR (400 MHz, DMSO-d₆) δ 10.25 (s, 1H), 8.84 (s, 1H), 8.53 (d, J = 5.1 Hz, 1H), 7.29 (d, J = 5.0 Hz, 1H), 6.90 (s, 1H), 3.18 (d, J = 6.2 Hz, 1H), 3.00 (d, J = 5.9 Hz, 1H), 2.94-2.84 (m, 2H), 2.09-1.52 (m, 7H), 1.25 (d, J = 6.9 Hz, 6H). | 366.4 |
| 8-ag | 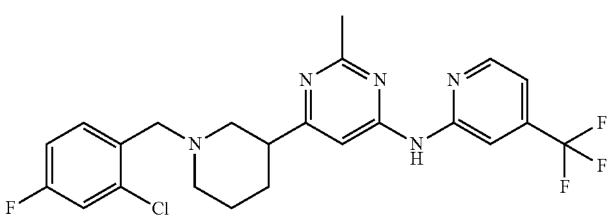 [SMILES: Cc1nc(Nc2cc(C(F)(F)F)ccn2)cc(C2CCCN(Cc3ccc(F)cc3Cl)C2)n1] | ¹H NMR (400 MHz, DMSO) δ 10.43 (s, 1H), 8.54 (d, J = 5.2 Hz, 1H), 8.17 (s, 1H), 7.54 (dd, J = 7.7, 5.9 Hz, 1H), 7.46-7.13 (m, 4H), 3.58 (s, 2H), 2.90-2.65 (m, 3H), 2.47 (s, 3H), 2.29-1.43 (m, 6H). | 480.9 |
| 8-ah | 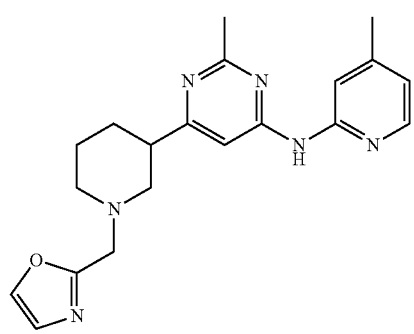 [SMILES: Cc1ccnc(Nc2cc(C3CCCN(Cc4ncco4)C3)nc(C)n2)c1] | ¹H NMR (400 MHz, DMSO) δ 9.93 (s, 1H), 8.14 (d, J = 5.1 Hz, 1H), 8.06 (s, 1H), 7.57 (s, 1H), 7.43 (s, 1H), 7.15 (s, 1H), 6.81 (d, J = 5.1 Hz, 1H), 3.71 (s, 2H), 3.10-2.80 (m, 2H), 2.74-2.61 (m, 1H), 2.44 (s, 3H), 2.33-2.18 (m, 4H), 2.09 (t, J = 10.3 Hz, 1H), 1.77 (dd, J = 51.5, 12.4 Hz, 2H), 1.64-1.35 (m, 2H). | 365.4 |

TABLE 8-continued

| No. | Structure | NMR | MS (M + H)+ |
|---|---|---|---|
| 8-ai | 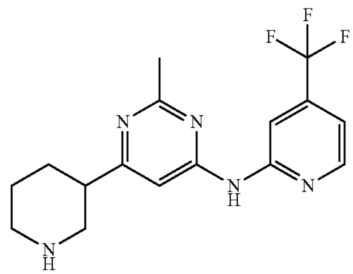 [SMILES: Cc1nc(Nc2cc(C(F)(F)F)ccn2)cc(C2CCCNC2)n1] | ¹H NMR (400 MHz, DMSO-d₆) δ 10.44 (s, 1H), 8.55 (d, J = 5.2 Hz, 1H), 8.19 (s, 1H), 7.44-7.20 (m, 2H), 3.17 (s, 3H), 3.05 (d, J = 7.8 Hz, 1H), 2.92 (d, J = 12.0 Hz, 1H), 2.58 (dd, J = 12.9, 6.6 Hz, 1H), 1.99-1.36 (m, 6H). | 338.3 |
| 8-aj | 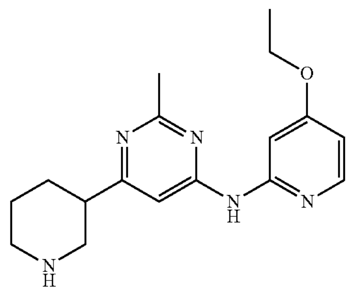 [SMILES: CCOc1ccnc(Nc2cc(C3CCCNC3)nc(C)n2)c1] | ¹H NMR (400 MHz, DMSO) δ 9.88 (s, 1H), 8.09 (d, J = 5.8 Hz, 1H), 7.51-7.29 (m, 2H), 6.57 (dd, J = 5.8, 2.3 Hz, 1H), 4.09 (q, J = 7.0 Hz, 2H), 3.04 (d, J = 8.9 Hz, 1H), 2.92 (d, J = 11.7 Hz, 1H), 2.70-2.55 (m, 3H), 1.94-1.82 (m, 5H), 1.68-1.30 (m, 6H). | 314.4 |
| 8-ak | 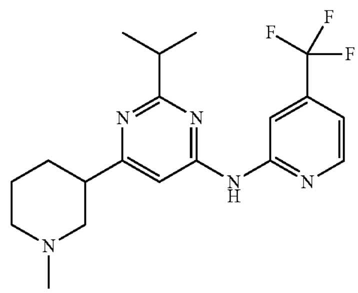 [SMILES: CC(C)c1nc(Nc2cc(C(F)(F)F)ccn2)cc(C2CCCN(C)C2)n1] | ¹H NMR (400 MHz, DMSO-d₆) δ 10.05 (s, 1H), 8.86 (s, 1H), 8.51 (d, J = 5.1 Hz, 1H), 7.27 (d, J = 5.0 Hz, 1H), 6.89 (s, 1H), 2.86 (dddd, J = 24.2, 20.4, 15.0, 9.7 Hz, 4H), 2.19 (s, 3H), 2.09 (dd, J = 26.7, 15.9 Hz, 1H), 2.00-1.79 (m, 2H), 1.77-1.37 (m, 3H), 1.24 (d, J = 6.9 Hz, 6H). | 380.4 |
| 8-al | 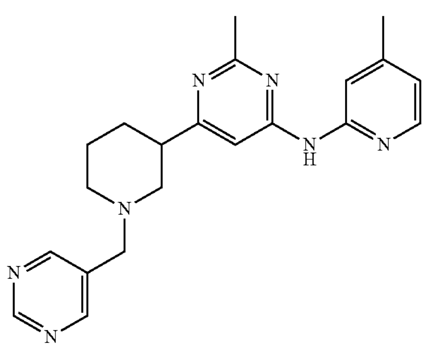 [SMILES: Cc1ccnc(Nc2cc(C3CCCN(Cc4cncnc4)C3)nc(C)n2)c1] | ¹H NMR (400 MHz, DMSO) δ 9.96 (d, J = 14.6 Hz, 1H), 9.08 (s, 1H), 8.74 (s, 2H), 8.14 (t, J = 4.8 Hz, 1H), 7.59 (s, 1H), 7.43 (s, 1H), 6.81 (d, J = 5.0 Hz, 1H), 3.58 (s, 2H), 3.00-2.60 (m, 3H), 2.43-2.40 (m, 2H), 2.35-2.22 (m, 3H), 2.22-1.44 (m, 6H). | 376.5 |
| 8-am | 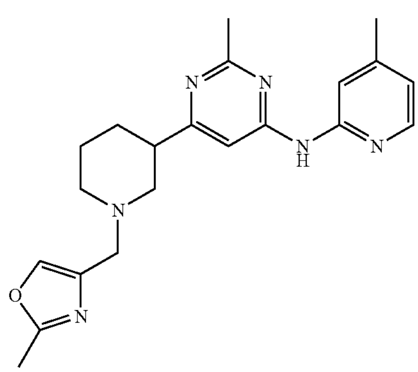 [SMILES: Cc1ccnc(Nc2cc(C3CCCN(Cc4coc(C)n4)C3)nc(C)n2)c1] | ¹H NMR (400 MHz, DMSO) δ 8.49 (s, 1H), 8.41 (s, 1H), 7.90 (d, J = 7.4 Hz, 1H), 7.55 (s, 1H), 7.34-7.14 (d, 1H), 4.60-4.42 (m, 3H), 4.29-4.13 (m, 3H), 3.00 (t, J = 5.4 Hz, 3H), 2.83 (d, J = 5.5 Hz, 2H), 2.34 (d, J = 11.0 Hz, 4H), 1.64 (s, 2H), 1.11 (s, 1H). | 379.5 |

TABLE 8-continued

| No. | Structure | NMR | MS (M + H)+ |
|---|---|---|---|
| 8-an | 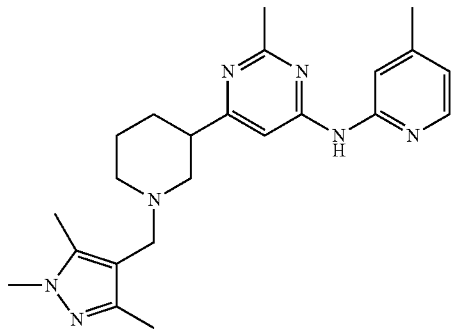 [SMILES: Cc1ccnc(Nc2cc(C3CCCN(Cc4c(C)nn(C)c4C)C3)nc(C)n2)c1] | ¹H NMR (400 MHz, DMSO) δ 9.92 (s, 1H), 8.14 (d, J = 5.1 Hz, 1H), 7.56 (s, 1H), 7.42 (s, 1H), 6.82 (t, J = 7.5 Hz, 1H), 3.60 (s, 3H), 3.22 (d, J = 2.4 Hz, 2H), 3.00-2.75 (m, 2H), 2.67-2.56 (m, 1H), 2.44 (s, 3H), 2.28 (s, 3H), 2.14 (s, 3H), 2.07-1.95 (m, 4H), 1.87 (t, J = 11.2 Hz, 2H), 1.68 (d, J = 12.6 Hz, 1H), 1.57-1.35 (m, 2H). | 406.5 |
| 8-ao | 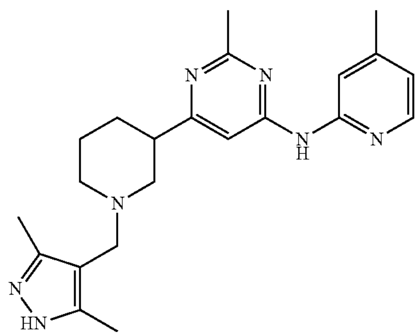 [SMILES: Cc1ccnc(Nc2cc(C3CCCN(Cc4c(C)n[nH]c4C)C3)nc(C)n2)c1] | | 392.5 |
| 8-ap | 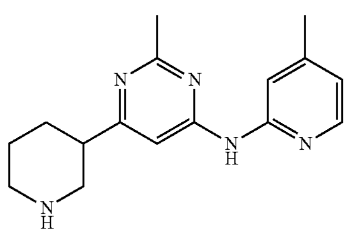 [SMILES: Cc1ccnc(Nc2cc(C3CCCNC3)nc(C)n2)c1] | ¹H NMR (400 MHz, DMSO-d₆) δ 9.91 (s, 1H), 8.15 (d, J = 5.1 Hz, 1H), 7.55 (s, 1H), 7.43 (s, 1H), 6.80 (s, 1H), 3.17 (s, 2H), 3.04 (d, J = 8.8 Hz, 1H), 2.90 (s, 1H), 2.61-2.55 (m, 2H), 2.44 (d, J = 5.1 Hz, 3H), 2.28 (s, 3H), 1.93-1.83 (m, 1H), 1.68-1.56 (m, 2H), 1.51-1.39 (m, 1H). | 284.4 |
| 8-aq | 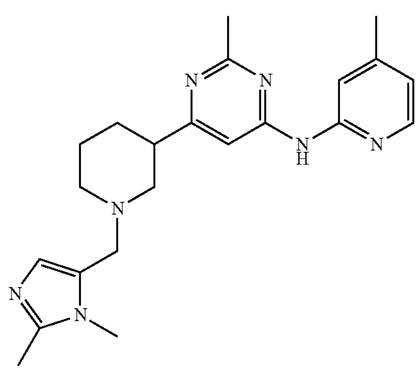 [SMILES: Cc1ccnc(Nc2cc(C3CCCN(Cc4cnc(C)n4C)C3)nc(C)n2)c1] | ¹H NMR (400 MHz, DMSO-d₆) δ 9.93 (d, J = 4.7 Hz, 1H), 8.14 (d, J = 5.1 Hz, 1H), 7.57 (d, J = 7.9 Hz, 1H), 7.43 (s, 1H), 6.81 (d, J = 5.1 Hz, 1H), 6.56 (s, 1H), 3.68-3.37 (m, 5H), 3.02-2.59 (m, 3H), 2.44 (s, 3H), 2.37-1.42 (m, 14H). | 392.5 |

TABLE 8-continued

| No. | Structure | NMR | MS (M + H)+ |
|---|---|---|---|
| 8-ar | 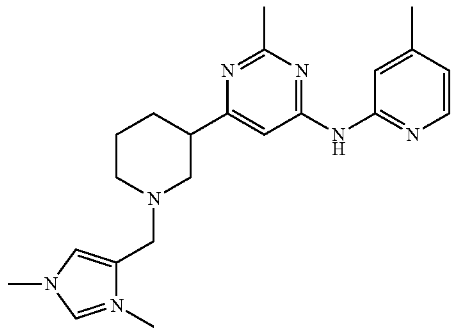 | ¹H NMR (400 MHz, DMSO) δ 9.92 (s, 1H), 8.14 (d, J = 5.1 Hz, 1H), 7.56 (s, 1H), 7.42 (d, J = 3.6 Hz, 2H), 6.81 (d, J = 5.0 Hz, 1H), 4.08 (q, J = 5.1 Hz, 2H), 3.69 (s, 3H), 3.10-2.71 (m, 2H), 2.63 (ddd, J = 14.7, 7.5, 3.8 Hz, 1H), 2.44 (s, 3H), 2.28 (s, 3H), 2.09 (s, 3H), 2.00 (t, J = 10.8 Hz, 1H), 1.94-1.79 (m, 2H), 1.69 (d, J = 12.5 Hz, 1H), 1.59-1.38 (m, 2H). | 392.5 |
| 8-as | 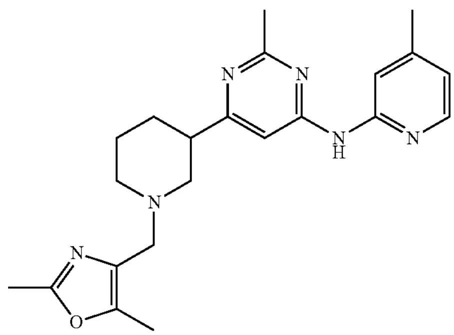 [SMILES: Cc1ccnc(Nc2cc(C3CCCN(Cc4nc(C)oc4C)C3)nc(C)n2)c1] | ¹H NMR (400 MHz, DMSO-d₆) δ 9.93 (s, 1H), 8.13 (s, 1H), 7.56 (s, 1H), 7.43 (s, 1H), 6.81 (d, J = 5.3 Hz, 1H), 3.17 (s, 3H), 2.98-2.78 (m, 2H), 2.64 (ddd, J = 17.2, 9.6, 5.8 Hz, 1H), 2.44 (s, 3H), 2.29 (d, J = 6.4 Hz, 6H), 2.23 (s, 3H), 2.10-1.20 (m, 5H). ¹H NMR (400 MHz, DMSO) δ 9.93 (s, 1H), 8.13 (s, 1H), 7.56 (s, 1H), 7.43 (s, 1H), 6.81 (d, J = 5.3 Hz, 1H), 3.17 (s, 3H), 2.98-2.78 (m, 2H), 2.64 (ddd, J = 14.2, 9.6, 5.8 Hz, 1H), 2.44 (s, 3H), 2.29 (d, J = 6.4 Hz, 6H), 2.23 (s, 3H), 2.10-1.20 (m, 5H). | 393.5 |
| 8-at | 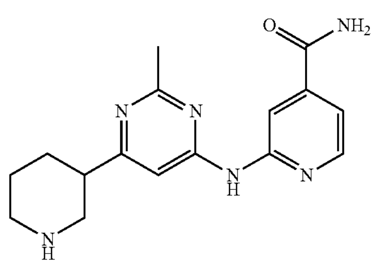 [SMILES: Cc1nc(Nc2cc(C(N)=O)ccn2)cc(C2CCCNC2)n1] | ¹H NMR (400 MHz, DMSO) δ 10.18 (s, 1H), 8.39 (d, J = 5.2 Hz, 1H), 8.11 (s, 1H), 8.01 (s, 1H), 7.62 (s, 1H), 7.52 (s, 1H), 7.31 (d, J = 5.2 Hz, 1H), 3.04 (t, J = 8.9 Hz, 1H), 2.92 (d, J = 11.8 Hz, 1H), 2.80-2.60 (m, 2H), 2.46 (s, 3H), 1.95-1.87 (m, 1H), 1.63 (dd, J = 12.2, 11.1 Hz, 2H), 1.46 (dd, J = 16.9, 8.8 Hz, 1H), 1.23 (s, 1H). | 313.4 |
| 8-au | 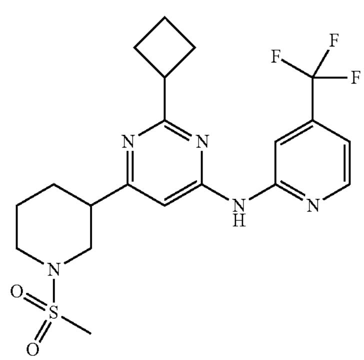 [SMILES: CS(=O)(=O)N1CCCC(c2cc(Nc3cc(C(F)(F)F)ccn3)nc(C3CCC3)n2)C1] | ¹H NMR (400 MHz, DMSO-d₆) δ 10.63 (s, 1H), 8.58 (d, J = 5.3 Hz, 1H), 7.34 (d, J = 5.1 Hz, 1H), 7.13 (s, 1H), 7.01 (s, 1H), 3.77-3.55 (m, 4H), 2.90-2.70 (m, 6H), 2.40-2.24 (m, 5H), 2.13-1.96 (m, 2H), 1.96-1.81 (m, 2H), 1.64 (d, J = 8.5 Hz, 2H). | 456.5 |

TABLE 8-continued

| No. | Structure | NMR | MS (M + H)+ |
|---|---|---|---|
| 8-av | 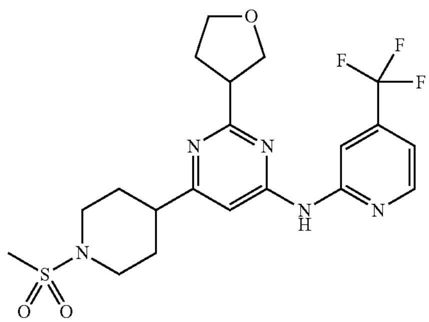 [SMILES: CS(=O)(=O)N1CCC(c2cc(Nc3cc(C(F)(F)F)ccn3)nc(C3CCOC3)n2)CC1] | $^1$H NMR (400 MHz, DMSO-d$_6$) δ 10.52 (s, 1H), 8.56 (d, J = 5.1 Hz, 1H), 8.44 (s, 1H), 7.31 (s, 1H), 7.10 (s, 1H), 4.09 (t, J = 8.0 Hz, 1H), 3.93-3.78 (m, 3H), 3.68 (d, J = 11.9 Hz, 2H), 3.60-3.48 (m, 2H), 2.84 (t, J = 10.8 Hz, 3H), 2.76-2.66 (m, 1H), 2.35-2.24 (m, 2H), 1.96 (s, 1H), 1.71 (dt, J = 12.3, 8.4 Hz, 2H). | 472.5 |
| 8-aw | 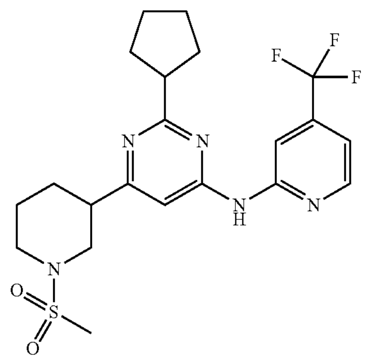 [SMILES: CS(=O)(=O)N1CCCC(c2cc(Nc3cc(C(F)(F)F)ccn3)nc(C3CCCC3)n2)C1] | $^1$H NMR (400 MHz, DMSO) δ 10.47 (s, 1H), 8.55 (d, J = 4.4 Hz, 2H), 7.31 (d, J = 5.6 Hz, 1H), 6.98 (s, 1H), 3.80-3.60 (mz, 2H), 3.23-3.16 (m, 1H), 2.89-2.70 (m, 6H), 2.06-1.93 (m, 3H), 1.88 (dd, J = 10.8, 6.4 Hz, 3H), 1.75 (dd, J = 10.7, 7.0 Hz, 2H), 1.66 (dt, J = 12.1, 10.4 Hz, 4H). | 470.5 |
| 8-ax | 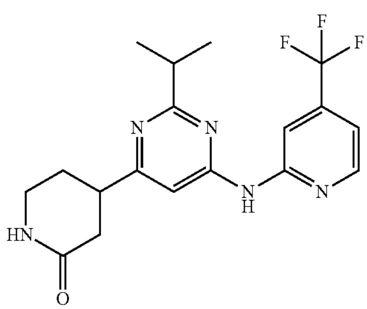 [SMILES: CC(C)c1nc(Nc2cc(C(F)(F)F)ccn2)cc(C2CCNC(=O)C2)n1] | $^1$H NMR (400 MHz, DMSO-d$_6$) δ 10.46 (s, 1H), 8.60 (s, 1H), 8.55 (d, J = 5.1 Hz, 1H), 7.30 (d, J = 5.1 Hz, 1H), 7.16 (s, 1H), 3.27-3.17 (m, 3H), 3.12-2.96 (m, 2H), 2.41 (t, J = 9.5 Hz, 2H), 2.07-1.96 (m, 1H), 1.89-1.74 (m, 1H), 1.28 (d, J = 6.9 Hz, 6H). | 380.4 |
| 8-ay | 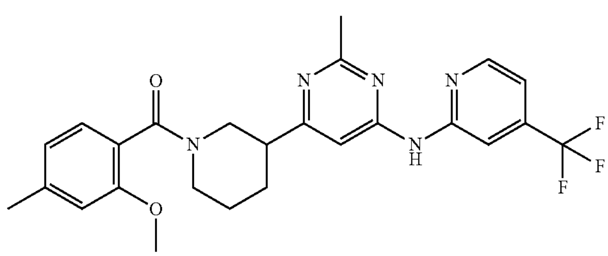 [SMILES: COc1cc(C)ccc1C(=O)N1CCCC(c2cc(Nc3cc(C(F)(F)F)ccn3)nc(C)n2)C1] | $^1$H NMR (400 MHz, DMSO) δ 10.57-10.39 (s, 1H), 8.62-8.48 (m, 1H), 8.13 (d, J = 29.3 Hz, 1H), 7.47 (d, J = 41.2 Hz, 1H), 7.30 (s, 1H), 7.20-6.68 (m, 3H), 4.73-4.44 (m, 1H), 3.91-3.70 (m, 3H), 3.22-2.52 (m, 4H), 2.44-2.24 (m, 5H), 1.86-1.42 (m, 5H). | 486.5 |
| 8-az | 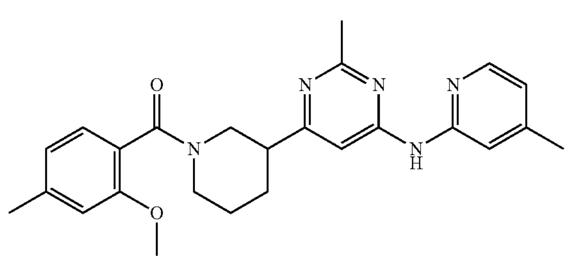 | $^1$H NMR (400 MHz, DMSO) δ 10.04-9.88 (m, 1H), 8.21-8.08 (m, 1H), 7.71-6.71 (m, 6H), 4.65 (d, J = 11.8 Hz, 1H), 4.52 (d, J = 13.9 Hz, 1H), 4.12-3.71 (m, 3H), 3.40 (d, J = 13.8 Hz, 1H), 3.24-2.55 (m, 3H), 2.40-2.22 (m, 8H), 1.81-1.44 (m, 4H). | 432.5 |

TABLE 8-continued

| No. | Structure | NMR | MS (M + H)+ |
|---|---|---|---|
| 8-ba | 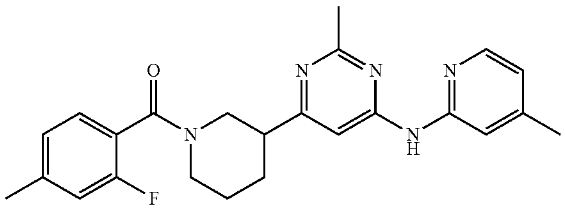 | ¹H NMR (400 MHz, DMSO) δ 10.40-9.88 (m, 1H), 8.14 (dd, J = 15.0, 5.1 Hz, 1H), 7.67 (s, 1H), 7.55-7.01 (m, 5H), 6.82 (s, 1H), 4.56 (dd, J = 71.9, 13.0 Hz, 1H), 3.62-3.47 (m, 1H), 3.16-2.61 (m, 3H), 2.43-2.23 (m, 8H), 2.07-1.39 (m, 4H). | 420.5 |
| 8-bb | 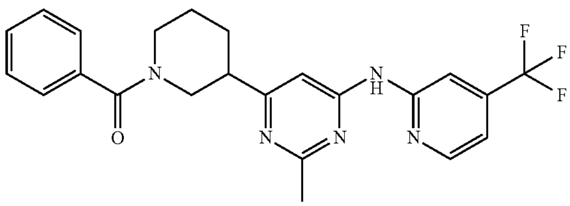 [SMILES: Cc1nc(Nc2cc(C(F)(F)F)ccn2)cc(C2CCCN(C(=O)c3ccccc3)C2)n1] | ¹H NMR (400 MHz, DMSO-d₆) δ 11.87 (s, 1H), 9.21 (s, 1H), 8.03-7.59 (m, 4H), 6.72-5.81 (m, 4H), 3.55 (d, J = 8.0 Hz, 1H), 3.09 (s, 3H), 1.52 (s, 2H), 1.29-0.75 (m, 6H). | 442.5 |
| 8-bc | 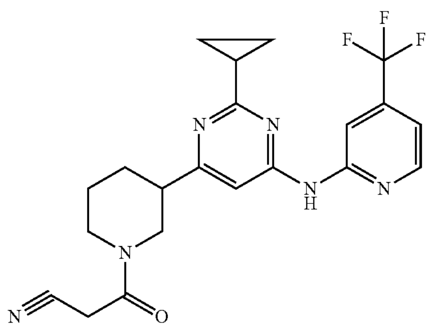 [SMILES: N#CCC(=O)N1CCCC(c2cc(Nc3cc(C(F)(F)F)ccn3)nc(C3CC3)n2)C1] | ¹H NMR (400 MHz, DMSO) δ 10.50 (d, J = 9.6 Hz, 1H), 8.60-8.49 (m, 1H), 8.42 (d, J = 5.3 Hz, 1H), 7.32 (d, J = 5.2 Hz, 1H), 7.13 (d, J = 8.0 Hz, 1H), 4.51-4.01 (m, 2H), 3.79-3.60 (m, 1H), 3.07 (t, J = 11.8 Hz, 1H), 2.85-2.56 (m, 2H), 2.13-1.88 (m, 2H), 1.82-1.20 (m, 4H), 1.08-0.89 (m, 4H). | 431.4 |
| 8-bd | 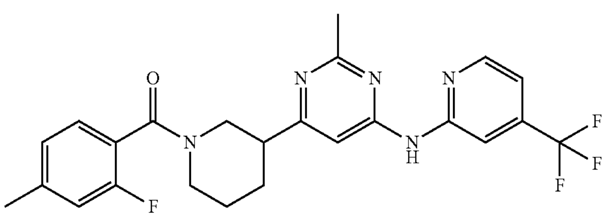 [SMILES: Cc1ccc(C(=O)N2CCCC(c3cc(Nc4cc(C(F)(F)F)ccn4)nc(C)n3)C2)c(F)c1] | ¹H NMR (400 MHz, DMSO) δ 10.54-10.40 (m, 1H), 8.55 (dd, J = 13.4, 5.2 Hz, 1H), 8.14 (d, J = 21.1 Hz, 1H), 7.57-7.01 (m, 4H), 4.70-4.40 (m, 1H), 3.58-3.35 (m, 2H), 3.14-2.65 (m, 3H), 2.43-2.26 (m, 5H), 2.01 (d, J = 12.7 Hz, 1H), 1.91-1.44 (m, 4H). | 474.5 |
| 8-be | 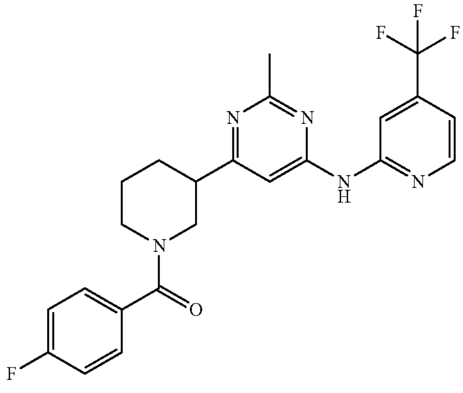 [SMILES: Cc1nc(Nc2cc(C(F)(F)F)ccn2)cc(C2CCCN(C(=O)c3ccc(F)cc3)C2)n1] | ¹H NMR (400 MHz, DMSO) δ 10.51 (s, 1H), 8.54 (d, J = 5.2 Hz, 1H), 8.14 (s, 1H), 7.49 (dd, J = 8.5, 5.6 Hz, 3H), 7.31-7.23 (m, 3H), 4.68-4.27 (m 1H), 4.08 (q, J = 5.2 Hz, 1H), 3.83-3.48 (m, 1H), 3.20-2.64 (m, 4H), 2.30-1.08 (m, 5H). | 460.4 |

TABLE 8-continued

| No. | Structure | NMR | MS (M + H)+ |
|---|---|---|---|
| 8-bf | 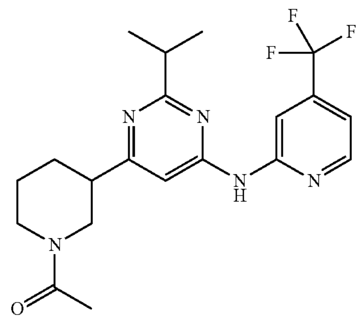 [SMILES: CC(=O)N1CCCC(c2cc(Nc3cc(C(F)(F)F)ccn3)nc(C(C)C)n2)C1] | ¹H NMR (400 MHz, DMSO) δ 10.49 (s, 1H), 8.68-8.49 (m, 2H), 7.31 (d, J = 5.2 Hz, 1H), 7.17 (d, J = 15.4 Hz, 1H), 4.60-4.18 (m, 1H), 3.95-3.77 (m, 1H), 3.40-3.35 (m, 1H), 3.11-2.95 (m, 2H), 2.82-2.63 (m, 2H), 2.63-2.52 (m, 1H), 1.84-1.64 (m, 2H), 1.60-1.36 (m, 1H), 1.29 (d, J = 6.8 Hz, 6H). | 408.4 |
| 8-bg | 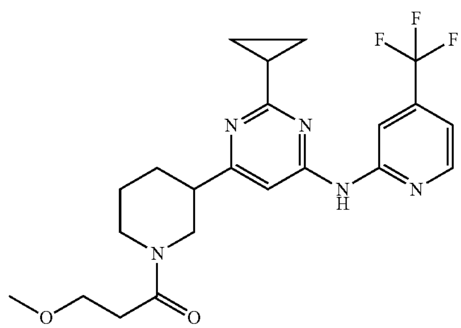 [SMILES: COCCC(=O)N1CCCC(c2cc(Nc3cc(C(F)(F)F)ccn3)nc(C3CC3)n2)C1] | ¹H NMR (400 MHz, DMSO) δ 10.43 (s, 1H), 8.54 (d, J = 5.2 Hz, 1H), 8.41 (s, 1H), 7.30 (d, J = 5.2 Hz, 1H), 7.13 (d, J = 10.4 Hz, 1H), 4.62-4.38 (m, 1H), 4.06 (m, 1H), 4.01-3.86 (m, 1H), 3.57 (t, J = 6.5 Hz, 2H), 3.24-3.14 (m, 3H), 3.03 (t, J = 12.3 Hz, 1H), 2.76-2.56 (m, 3H), 2.13-1.91 (m, 2H), 1.77 (d, J = 10.4 Hz, 2H), 1.61-1.34 (m, 1H), 1.08-0.95 (m, 4H). | 450.5 |
| 8-bh | 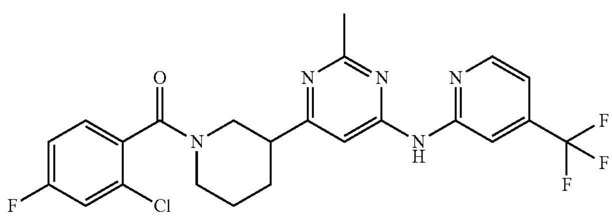 [SMILES: Cc1nc(Nc2cc(C(F)(F)F)ccn2)cc(C2CCCN(C(=O)c3ccc(F)cc3Cl)C2)n1] | ¹H NMR (400 MHz, DMSO) δ 10.60-10.38 (m, 1H), 8.61-8.47 (m, 1H), 8.21-8.07 (m, 1H), 7.63-7.24 (m, 7H), 4.71-4.38 (m, 1H), 3.15-2.62 (m, 3H), 2.41 (s, 1H), 2.01 (d, J = 12.8 Hz, 1H), 1.90-1.45 (m, 4H). | 494.9 |
| 8-bi | 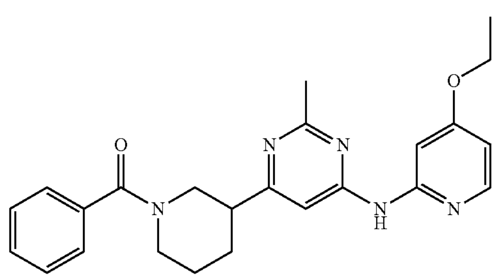 [SMILES: CCOc1ccnc(Nc2cc(C3CCCN(C(=O)c4ccccc4)C3)nc(C)n2)c1] | ¹H NMR (400 MHz, DMSO) δ 9.94 (s, 1H), 8.09 (d, J = 5.7 Hz, 1H), 7.42 (d, J = 9.4 Hz, 4H), 6.58 (dd, J = 5.8, 1.9 Hz, 1H), 4.74-4.33 (m, 1H), 4.09 (q, J = 6.8 Hz, 2H), 3.81-3.44 (m, 1H), 3.12-2.69 (m, 3H), 1.92-1.47 (m, 5H), 1.35 (t, J = 6.9 Hz, 3H). | 418.5 |
| 8-bj | 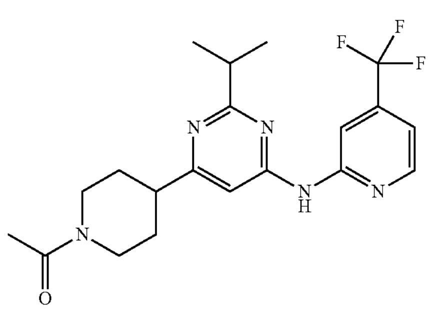 [SMILES: CC(=O)N1CCC(c2cc(Nc3cc(C(F)(F)F)ccn3)nc(C(C)C)n2)CC1] | ¹H NMR (400 MHz, DMSO-d₆) δ 10.45 (s, 1H), 8.61 (s, 1H), 8.55 (d, J = 5.2 Hz, 1H), 7.30 (d, J = 5.1 Hz, 1H), 7.13 (s, 1H), 4.49 (d, J = 12.9 Hz, 1H), 4.06 (q, J = 5.2 Hz, 1H), 3.91 (d, J = 13.4 Hz, 1H), 3.15 (dd, J = 14.1, 8.0 Hz, 2H), 3.00 (dt, J = 13.7, 6.9 Hz, 1H), 2.80 (ddd, J = 11.6, 8.1, 3.6 Hz, 1H), 2.71-2.59 (m, 1H), 2.03 (s, 3H), 1.67-1.41 (m, 2H), 1.28 (d, J = 6.9 Hz, 6H). | 408.4 |

TABLE 8-continued

| No. | Structure | NMR | MS (M + H)+ |
|---|---|---|---|
| 8-bk | 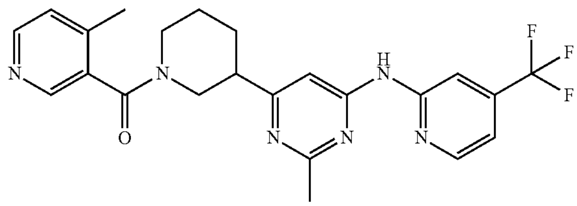 [SMILES: Cc1nc(Nc2cc(C(F)(F)F)ccn2)cc(C2CCCN(C(=O)c3cnccc3C)C2)n1] | ¹H NMR (400 MHz, DMSO) δ 10.58-10.38 (m, 1H), 8.65-8.29 (m, 2H), 8.24-8.05 (m, 1H), 7.54 (s, 1H), 7.37-7.27 (m, 2H), 4.77-4.36 (m, 1H), 3.53-3.34 (m, 1H), 3.16-2.74 (m, 2H), 2.40 (s, 1H), 2.36-1.43 (m, 8H). | 457.5 |
| 8-bl | 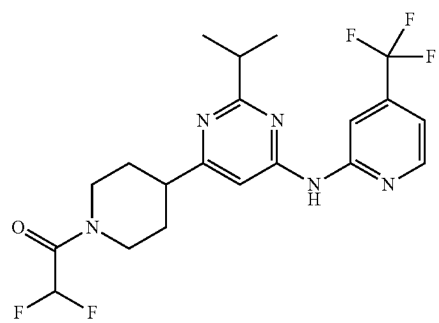 [SMILES: CC(C)c1nc(Nc2cc(C(F)(F)F)ccn2)cc(C2CCN(C(=O)C(F)F)CC2)n1] | ¹H NMR (400 MHz, DMSO-d₆) δ 10.47 (s, 1H), 8.61 (s, 1H), 8.55 (d, J = 5.2 Hz, 1H), 7.31 (d, J = 5.1 Hz, 1H), 7.14 (s, 1H), 4.41 (d, J = 13.1 Hz, 1H), 4.06 (q, J = 5.2 Hz, 1H), 3.99 (d, J = 13.5 Hz, 1H), 3.17 (d, J = 5.2 Hz, 1H), 2.99 (dq, J = 13.8, 6.9 Hz, 1H), 2.93-2.83 (m, 2H), 1.94 (d, J = 12.3 Hz, 2H), 1.74-1.49 (m, 2H), 1.28 (t, J = 5.4 Hz, 6H). | 444.4 |
| 8-bm | 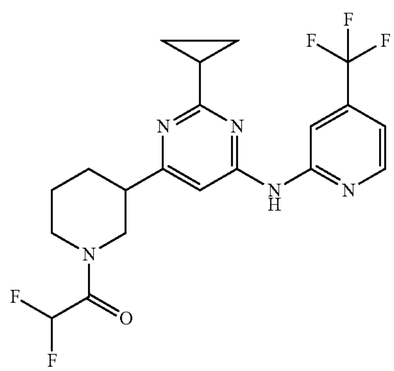 [SMILES: O=C(C(F)F)N1CCCC(c2cc(Nc3cc(C(F)(F)F)ccn3)nc(C3CC3)n2)C1] | ¹H NMR (400 MHz, DMSO) δ 10.45 (s, 1H), 8.54 (d, J = 5.2 Hz, 1H), 8.41 (s, 1H), 7.31 (d, J = 5.2 Hz, 1H), 7.14 (d, J = 3.7 Hz, 1H), 4.49-3.81 (m, 2H), 3.40 (ddd, J = 13.5, 10.9, 11.3 Hz, 1H), 2.98-2.60 (m, 2H), 2.11-1.45 (m, 6H), 1.03-0.98 (m, 4H). | 442.4 |
| 8-bn | 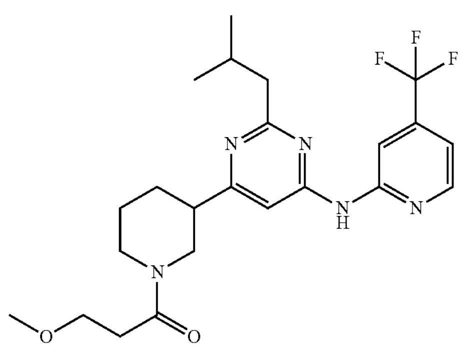 [SMILES: COCCC(=O)N1CCCC(c2cc(Nc3cc(C(F)(F)F)ccn3)nc(CC(C)C)n2)C1] | ¹H NMR (400 MHz, DMSO) δ 10.49 (s, 1H), 8.55 (d, J = 5.1 Hz, 1H), 8.37 (s, 1H), 7.31 (t, J = 6.1 Hz, 1H), 4.59-3.76 (m, 4H), 3.56 (t, J = 6.6 Hz, 2H), 2.75-2.55 (m, 6H), 2.23 (dt, J = 13.5, 6.7 Hz, 1H), 1.85-1.64 (m, 2H), 1.58-1.38 (m, 2H), 0.95 (t, J = 7.5 Hz, 6H). | 466.5 |
| 8-bo | 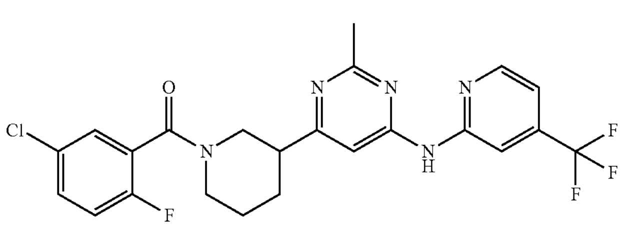 [SMILES: Cc1nc(Nc2cc(C(F)(F)F)ccn2)cc(C2CCCN(C(=O)c3cc(Cl)ccc3F)C2)n1] | ¹H NMR (400 MHz, DMSO) δ 10.60-10.38 (m, 1H), 8.55 (dd, J = 12.5, 5.2 Hz, 1H), 8.15 (d, J = 13.9 Hz, 1H), 7.52 (t, J = 13.5 Hz, 2H), 7.63-7.24 (m, 4H), 4.62-3.53 (dd, J = 12.7, 12.8 Hz, .8 Hz, 1H), 3.43-3.34 (m, 1H), 3.17-2.95 (m, 1H), 2.86-2.60 (m, 1H), 2.41 (s, 1H), 2.02 (d, J = 12.8 Hz, 1H), 1.88-1.46 (m, 4H). | 494.9 |

TABLE 8-continued

| No. | Structure | NMR | MS (M + H)+ |
|---|---|---|---|
| 8-bp | 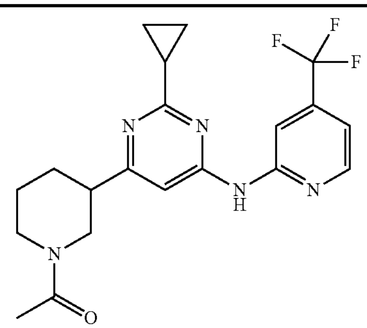 | $^1$H NMR (400 MHz, DMSO) δ 10.42 (s, 1H), 8.54 (d, J = 5.2 Hz, 1H), 8.42 (s, 1H), 7.30 (d, J = 5.1 Hz, 1H), 7.13 (d, J = 14.2 Hz, 1H), 4.58-4.20 (m, 1H), 4.06 (q, J = 5.2 Hz, 1H), 3.95-3.75 (m, 1H), 3.17 (d, J = 4.9 Hz, 1H), 3.06 (t, J = 12.1 Hz, 1H), 2.67 (t, J = 11.9 Hz, 1H), 2.12-1.92 (m, 5H), 1.80-1.66 (m, 2H), 1.59-1.31 (m, 1H), 1.01 (d, J = 7.1 Hz, 4H). | 406.4 |
| 8-bq | 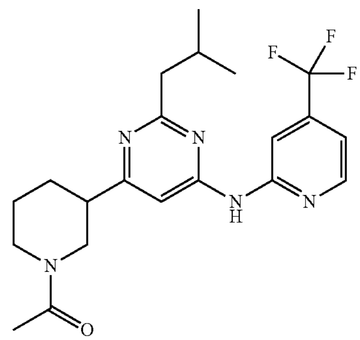 [SMILES: CC(=O)N1CCCC(c2cc(Nc3cc(C(F)(F)F)ccn3)nc(CC(C)C)n2)C1] | $^1$H NMR (400 MHz, DMSO-d$_6$) δ 10.46 (s, 1H), 8.55 (d, J = 5.2 Hz, 1H), 8.41 (s, 1H), 7.29 (dd, J = 13.1, 8.6 Hz, 1H), 4.64 (t, J = 5.5 Hz, 1H), 4.54-4.14 (m, 3H), 2.87-2.59 (m, 4H), 2.37-2.17 (m, 2H), 2.05-1.91 (m, 4H), 1.80-1.66 (m, 2H), 0.99-0.90 (m, 6H). | 422.5 |
| 8-br | 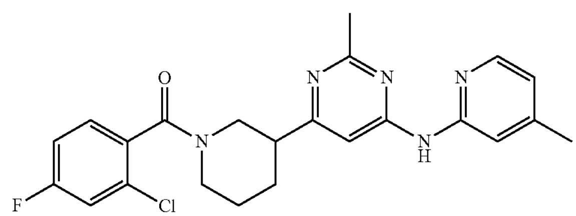 [SMILES: Cc1ccnc(Nc2cc(C3CCCN(C(=O)c4ccc(F)cc4Cl)C3)nc(C)n2)c1] | $^1$H NMR (400 MHz, DMSO) δ 10.08-9.85 (m, 1H), 8.20-8.10 (m, 1H), 7.67 (s, 1H), 7.62-7.22 (m, 4H), 6.82 (t, J = 5.4 Hz, 1H), 4.70-4.40 (m, 1H), 3.15-2.64 (m, 3H), 2.38 (s, 1H), 2.28 (d, J = 8.6 Hz, 3H), 2.00 (d, J = 13.0 Hz, 1H), 1.90-1.40 (m, 3H). | 440.9 |
| 8-bs | 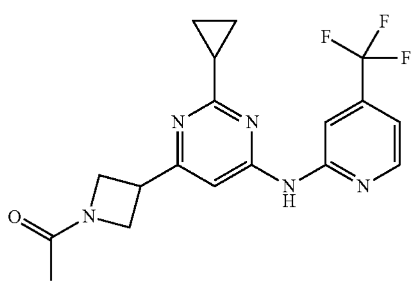 [SMILES: CC(=O)N1CC(c2cc(Nc3cc(C(F)(F)F)ccn3)nc(C3CC3)n2)C1] | $^1$H NMR (400 MHz, DMSO-d$_6$) δ 10.48 (s, 1H), 8.54 (d, J = 5.2 Hz, 1H), 8.41 (s, 1H), 7.31 (d, J = 4.9 Hz, 1H), 7.16 (s, 1H), 4.42 (t, J = 8.5 Hz, 1H), 4.22 (dd, J = 8.0, 6.0 Hz, 1H), 4.13 (t, J = 9.0 Hz, 1H), 3.95 (dd, J = 9.1, 6.0 Hz, 1H), 3.78 (tt, J = 8.8, 5.9 Hz, 1H), 3.17 (d, J = 5.2 Hz, 1H), 2.12-2.05 (m, 1H), 1.79 (s, 3H), 1.06-0.98 (m, 4H). | 378.4 |
| 8-bt | 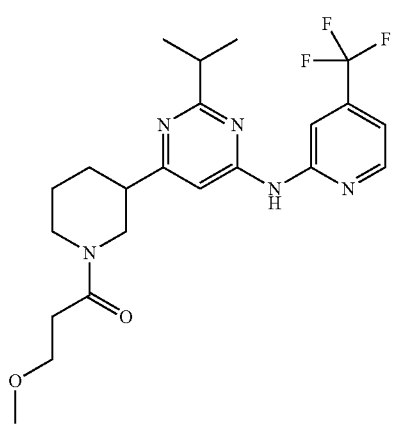 [SMILES: COCCC(=O)N1CCCC(c2cc(Nc3cc(C(F)(F)F)ccn3)nc(C(C)C)n2)C1] | $^1$H NMR (400 MHz, DMSO) δ 8.62 (s, 1H), 7.44 (s, 1H), 7.30-7.01 (m, 1H), 4.60-3.84 (m, 2H), 3.60-3.53 (m, 4H), 3.23 (s, 2H), 3.18-3.04 (m, 2H), 2.89-2.54 (m, 4H), 2.02 (s, 1H), 1.80 (d, J = 12.0 Hz, 2H), 1.61-1.36 (m, 1H), 1.31 (d, J = 6.8 Hz, 6H). | 452.5 |

TABLE 8-continued

| No. | Structure | NMR | MS (M + H)+ |
|---|---|---|---|
| 8-bu | 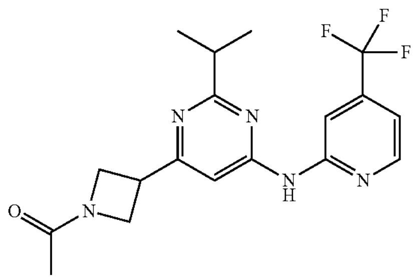 [SMILES: CC(=O)N1CC(c2cc(Nc3cc(C(F)(F)F)ccn3)nc(C(C)C)n2)C1] | ¹H NMR (400 MHz, DMSO-d₆) δ 10.53 (s, 1H), 8.60 (s, 1H), 8.55 (d, J = 5.2 Hz, 1H), 7.32 (d, J = 5.0 Hz, 1H), 7.20 (s, 1H), 4.44 (t, J = 8.5 Hz, 1H), 4.27-4.20 (m, 1H), 4.15 (t, J = 9.0 Hz, 1H), 3.97 (dd, J = 9.1, 6.1 Hz, 1H), 3.90-3.76 (m, 1H), 3.11-3.00 (m, 1H), 1.79 (s, 3H), 1.30 (d, J = 6.9 Hz, 6H). | 380.4 |
| 8-bv | 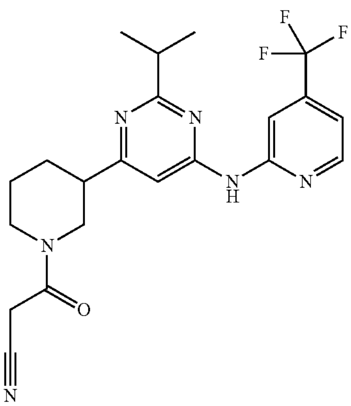 [SMILES: CC(C)c1nc(Nc2cc(C(F)(F)F)ccn2)cc(C2CCCN(C(=O)CC#N)C2)n1] | ¹H NMR (400 MHz, DMSO) δ 8.60 (s, 1H), 7.40 (s, 1H), 7.31-6.97 (m, 1H), 4.47 (d, J = 15.0 Hz, 1H), 4.29-3.95 (m, 2H), 3.83-3.64 (m, 1H), 3.10 (s, 1H), 2.94-2.65 (m, 1H), 2.00 (s, 1H), 1.74 (d, J = 12.9 Hz, 1H), 1.65-1.40 (m, 1H), 1.30 (d, J = 6.8 Hz, 4H). | 433.4 |
| 8-bw | 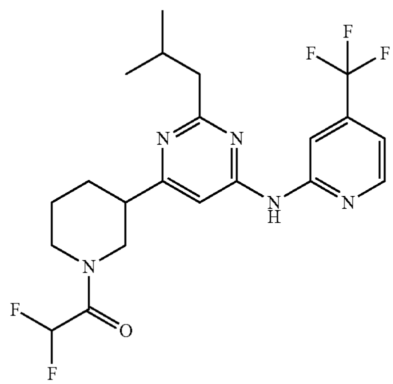 [SMILES: CC(C)Cc1nc(Nc2cc(C(F)(F)F)ccn2)cc(C2CCCN(C(=O)C(F)F)C2)n1] | | 458.4 |
| 8-bx | 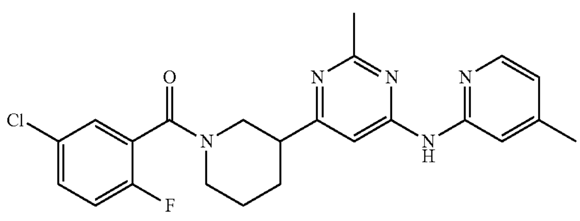 [SMILES: Cc1ccnc(Nc2cc(C3CCCN(C(=O)c4cc(Cl)ccc4F)C3)nc(C)n2)c1] | ¹H NMR (400 MHz, DMSO) δ 10.05-9.86 (m, 1H), 8.14 (dd, J = 13.4, 5.1 Hz, 1H), 7.67 (s, 1H), 7.59-7.48 (m, 2H), 7.47-7.28 (m, 2H), 6.82 (t, J = 5.0 Hz, 1H), 4.66-4.35 (m, 1H), 3.60-3.34 (m, 2H), 3.20-2.91 (m, 1H), 2.82-2.62 (m, 1H), 2.38 (s, 1H), 2.28 (d, J = 7.7 Hz, 3H), 2.00 (d, J = 9.6 Hz, 1H), 1.88-1.45 (m, 3H). | 440.9 |
| 8-by | 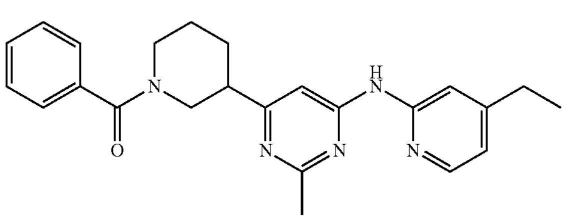 [SMILES: CCc1ccnc(Nc2cc(C3CCCN(C(=O)c4ccccc4)C3)nc(C)n2)c1] | ¹H NMR (400 MHz, DMSO) δ 9.98 (s, 1H), 8.33 (s, 1H), 8.16 (d, J = 4.8 Hz, 1H), 7.42 (d, J = 8.8 Hz, 7H), 6.85 (d, J = 5.1 Hz, 1H), 2.80-2.60 (m, 2H), 2.59 (q, J = 7.5 Hz, 3H), 2.05-1.50 (m, 5H), 1.25-1.14 (m, 4H). | 402.5 |

TABLE 8-continued

| No. | Structure | NMR | MS (M + H)+ |
|---|---|---|---|
| 8-bz | 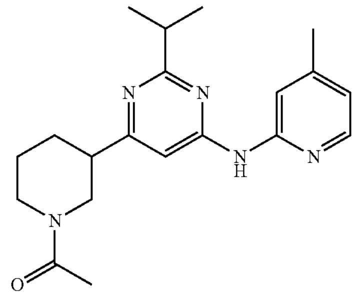 [SMILES: CC(=O)N1CCCC(c2cc(Nc3cc(C)ccn3)nc(C(C)C)n2)C1] | $^1$H NMR (400 MHz, DMSO) δ 9.92 (d, J = 3.4 Hz, 1H), 8.14 (d, J = 5.1 Hz, 1H), 7.72 (s, 1H), 7.40 (d, J = 15.8 Hz, 1H), 6.82 (d, J = 5.1 Hz, 1H), 4.58-4.14 (m, 1H), 3.94-3.72 (m, 1H), 3.13-2.90 (m, 2H), 2.79-2.61 (m, 2H), 2.29 (s, 3H), 2.05-1.89 (m, 4H), 1.82-1.63 (m, 2H), 1.28 (dd, J = 6.9, 1.4 Hz, 6H). | 354.5 |
| 8-ca | 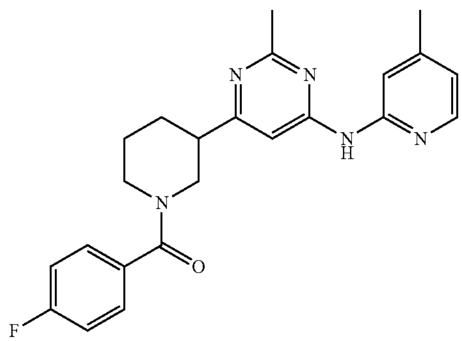 [SMILES: Cc1ccnc(Nc2cc(C3CCCN(C(=O)c4ccc(F)cc4)C3)nc(C)n2)c1] | $^1$NMR (400 MHz, DMSO) δ 8.27 (d, J = 5.2 Hz, 1H), 7.49 (dd, J = 8.6, 5.6 Hz, 2H), 7.38-7.24 (m, 3H), 7.18-6.91 (m, 2H), 5.75 (s, 1H), 2.98 (s, 1H), 2.69-2.59 (m, 3H), 2.42-2.26 (m, 4H), 2.07 (s, 1H), 1.97-1.46 (m, 4H). | 406.5 |
| 8-cb | 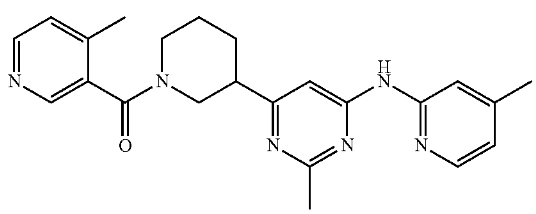 [SMILES: Cc1ccnc(Nc2cc(C3CCCN(C(=O)c4cnccc4C)C3)nc(C)n2)c1] | $^1$H NMR (400 MHz, DMSO) δ 10.08-9.86 (m, 1H), 8.50-8.35 (m, 1H), 8.14 (dd, J = 15.6, 5.1 Hz, 1H), 7.69 (s, 1H), 7.52-7.25 (m, 3H), 6.82 (t, J = 5.1 Hz, 1H), 4.81-4.33 (m, 1H), 3.49-3.33 (m, 1H), 3.17-2.90 (m, 2H), 2.67 (s, 1H), 2.36 (s, 1H), 2.28 (d, J = 9.3 Hz, 4H), 2.24-2.10 (m, 1H), 2.06-1.38 (m, 5H). | 403.5 |
| 8-cc | 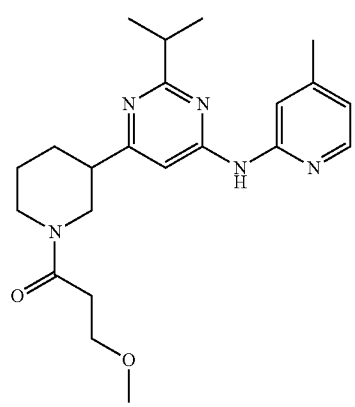 [SMILES: COCCC(=O)N1CCCC(c2cc(Nc3cc(C)ccn3)nc(C(C)C)n2)C1] | $^1$H NMR (400 MHz, DMSO) δ 9.95 (s, 1H), 8.15 (s, 1H), 7.71 (s, 1H), 7.41 (s, 1H), 6.84 (d, J = 4.0 Hz, 1H), 4.60-3.79 (m, 1H), 4.00-3.87 (m, 1H), 3.60-3.49 (m, 2H), 3.23 (d, J = 3.2 Hz, 3H), 3.08-2.85 (m, 2H), 2.77-2.55 (m, 4H), 2.30 (s, 3H), 1.97 (d, J = 12.4 Hz, 1H), 1.85-1.67 (m, 2H), 1.28 (d, J = 6.9 Hz, 6H). | 398.5 |

TABLE 8-continued

| No. | Structure | NMR | MS (M + H)+ |
|---|---|---|---|
| 8-cd | 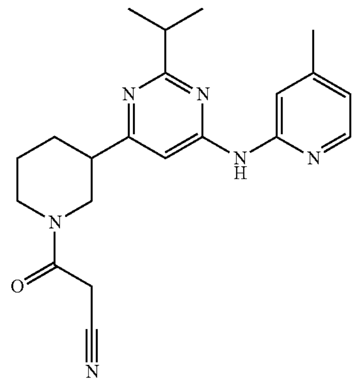 [SMILES: Cc1ccnc(Nc2cc(C3CCCN(C(=O)CC#N)C3)nc(C(C)C)n2)c1] | ¹H NMR (400 MHz, DMSO) δ 9.94 (d, J = 6.9 Hz, 1H), 8.15 (d, J = 5.1 Hz, 1H), 7.70 (d, J = 7.8 Hz, 1H), 7.41 (d, J = 11.8 Hz, 1H), 6.82 (d, J = 5.1 Hz, 1H), 4.60-4.20 (m, 1H), 3.78-3.63 (m, 1H), 3.38 (dd, J = 13.5, 10.4 Hz, 1H), 3.19-2.92 (m, 2H), 2.80 (t, J = 12.0 Hz, 2H), 2.68-2.54 (m, 1H), 2.29 (s, 3H), 1.95 (d, J = 10.5 Hz, 1H), 1.80-1.70 (m, 2H), 1.65-1.49 (m, 1H), 1.27 (d, J = 6.9 Hz, 6H). | 379.5 |
| 8-ce | 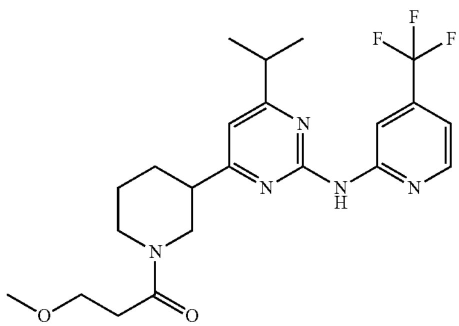 [SMILES: COCCC(=O)N1CCCC(c2cc(C(C)C)nc(Nc3cc(C(F)(F)F)ccn3)n2)C1] | ¹H NMR (400 MHz, DMSO) δ 10.06 (s, 1H), 8.90-8.60 (mz, 1H), 8.52 (d, J = 5.1 Hz, 1H), 7.28 (d, J = 5.2 Hz, 1H), 6.92 (d, J = 12.8 Hz, 1H), 4.64 (t, J = 5.4 Hz, 1H), 4.60-4.40 (m, 2H), 4.05-3.90 (m, 2H), 3.22 (d, J = 7.7 Hz, 2H), 3.06-2.75 (m, 3H), 2.69-2.57 (m, 2H), 2.01 (s, 1H), 2.00-1.60 (m, 2H), 1.25 (d, J = 6.8 Hz, 4H). | 452.5 |
| 8-cf | 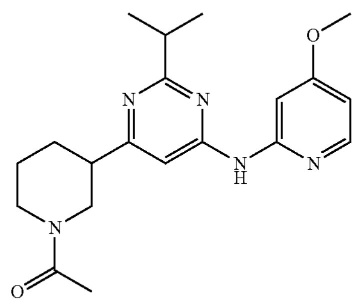 [SMILES: COc1ccnc(Nc2cc(C3CCCN(C(C)=O)C3)nc(C(C)C)n2)c1] | ¹H NMR (400 MHz, DMSO) δ 9.94 (d, J = 2.7 Hz, 1H), 8.10 (d, J = 5.8 Hz, 1H), 7.70 (s, 1H), 7.25 (d, J = 14.9 Hz, 1H), 6.64-6.48 (m, 1H), 4.50-4.25 (m, 1H), 3.14-2.90 (m, 2H), 2.80-2.59 (m, 2H), 2.11-1.23 (m, 15H). | 370.5 |
| 8-cg | 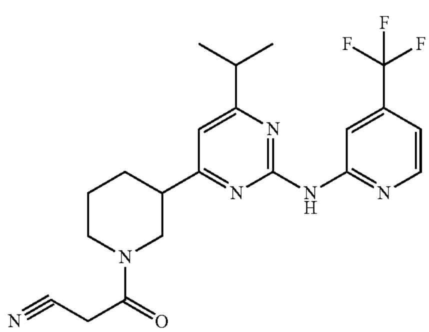 [SMILES: CC(C)c1cc(C2CCCN(C(=O)CC#N)C2)nc(Nc2cc(C(F)(F)F)ccn2)n1] | ¹H NMR (400 MHz, DMSO) δ 10.14 (d, J = 7.2 Hz, 1H), 8.83 (s, 1H), 8.52 (d, J = 5.0 Hz, 1H), 7.29 (s, 1H), 6.92 (d, J = 5.6 Hz, 1H), 4.52-3.64 (m, 4H), 3.09-2.63 (m, 3H), 2.06-1.14 (m, 11H). | 433.4 |
| 8-ch | 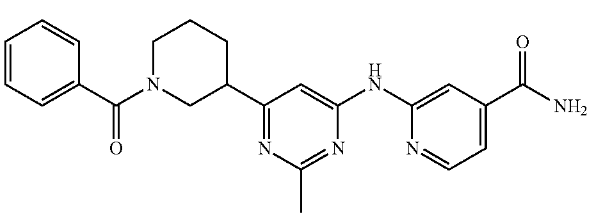 [SMILES: Cc1nc(Nc2cc(C(N)=O)ccn2)cc(C2CCCN(C(=O)c3ccccc3)C2)n1] | ¹H NMR (400 MHz, DMSO) δ 10.24 (s, 1H), 8.38 (d, J = 5.0 Hz, 1H), 8.10 (s, 1H), 7.98 (s, 1H), 7.61 (s, 1H), 7.42 (d, J = 7.8 Hz, 3H), 7.32 (t, J = 5.3 Hz, 1H), 4.20-3.90 (m, 2H), 3.15-2.95 (m, 2H), 2.76 (t, J = 11.1 Hz, 1H), 2.06-0.98 (m, 7H). | 417.5 |

TABLE 8-continued

| No. | Structure | NMR | MS (M + H)+ |
|---|---|---|---|
| 8-ci | 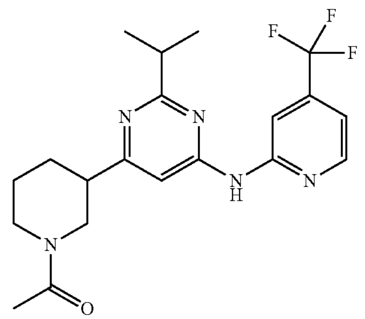 [SMILES: CC(=O)N1CCCC(c2cc(Nc3cc(C(F)(F)F)ccn3)nc(C(C)C)n2)C1] | $^1$H NMR (400 MHz, DMSO) δ 10.12 (s, 1H), 8.84 (s, 1H), 8.52 (d, J = 5.0 Hz, 1H), 7.38 (d, J = 4.6 Hz, 1H), 7.28 (d, J = 5.1 Hz, 1H), 4.60-4.44 (m, 1H), 4.00-3.78 (m, 1H), 3.16-2.62 (m, 4H), 2.03 (d, J = 4.3 Hz, 4H), 1.81-1.37 (m, 4H), 1.26 (dd, J = 6.9, 1.8 Hz, 6H). | 408.4 |
| 8-cj | 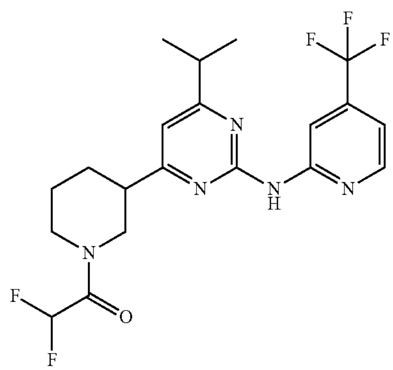 [SMILES: CC(C)c1cc(C2CCCN(C(=O)C(F)F)C2)nc(Nc2cc(C(F)(F)F)ccn2)n1] | $^1$H NMR (400 MHz, DMSO) δ 10.14 (s, 1H), 8.82 (d, J = 6.5 Hz, 1H), 8.52 (d, J = 5.1 Hz, 1H), 7.29 (d, J = 5.1 Hz, 1H), 6.93 (t, J = 6.2 Hz, 1H), 4.60-4.20 (m, 1H), 4.10-3.80 (m, 1H), 3.46 (dd, J = 13.6, 10.9 Hz, 1H), 3.16-2.69 (m, 4H), 2.07 (d, J = 9.6 Hz, 1H), 1.83 (tt, J = 10.1, 7.4 Hz, 2H), 1.55 (dt, J = 12.5, 10.8 Hz, 1H), 1.26 (d, J = 6.8 Hz, 6H). | 444.4 |
| 8-ck | 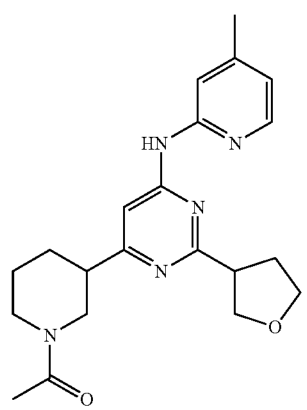 [SMILES: CC(=O)N1CCCC(c2cc(Nc3cc(C)ccn3)nc(C3CCOC3)n2)C1] | $^1$H NMR (400 MHz, DMSO-d$_6$) δ 9.97 (s, 1H), 8.15 (d, J = 5.1 Hz, 1H), 7.66 (s, 1H), 7.45 (d, J = 14.8 Hz, 1H), 6.83 (d, J = 5.1 Hz, 1H), 4.38 (dd, J = 113.5, 12.8 Hz, 1H), 4.08 (t, J = 8.0 Hz, 1H), 3.86 (dq, J = 13.9, 6.4 Hz, 4H), 3.58-3.44 (m, 1H), 3.06 (t, J = 11.7 Hz, 1H), 2.69 (dd, J = 21.6, 10.1 Hz, 1H), 2.29-2.18 (m, 3H), 1.98 (d, J = 21.2 Hz, 3H), 1.77-1.64 (m, 2H), 1.47 (dd, J = 45.7, 12.5 Hz, 1H). | 382.5 |
| 8-cl | 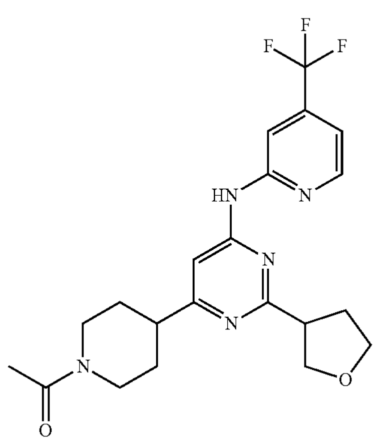 [SMILES: CC(=O)N1CCC(c2cc(Nc3cc(C(F)(F)F)ccn3)nc(C3CCOC3)n2)CC1] | $^1$H NMR (400 MHz, DMSO) δ 10.53 (d, J = 4.4 Hz, 1H), 8.56 (d, J = 5.2 Hz, 1H), 8.44 (s, 1H), 7.32 (d, J = 5.2 Hz, 1H), 7.27 (d, J = 14.8 Hz, 1H), 4.45-4.30 (m, 1H), 4.08 (d, J = 8.0 Hz, 1H), 3.95-3.80 (m, 4H), 3.60-3.51 (m, 1H), 3.06 (t, J = 11.8 Hz, 1H), 2.80-2.60 (m, 2H), 2.40-2.50 (m, 2H), 2.00 (t, J = 11.7 Hz, 4H), 1.84-1.70 (m, 2H), 1.55-1.40 (m, 1H). | 436.4 |

TABLE 8-continued

| No. | Structure | NMR | MS (M + H)+ |
|---|---|---|---|
| 8-cm | 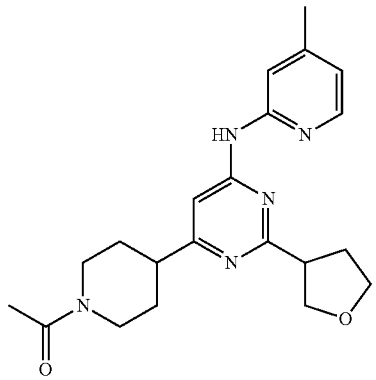 [SMILES: CC(=O)N1CCC(c2cc(Nc3cc(C)ccn3)nc(C3CCOC3)n2)CC1] | ¹H NMR (400 MHz, DMSO) δ 9.97 (s, 1H), 8.15 (d, J = 5.1 Hz, 1H), 7.66 (s, 1H), 7.45 (d, J = 11.8 Hz, 1H), 6.83 (d, J = 5.1 Hz, 1H), 4.50-4.30 (m, 1H), 4.08 (t, J = 8.0 Hz, 1H), 3.86 (m, 4H), 3.58-3.44 (m, 1H), 3.06 (t, J = 11.7 Hz, 1H), 2.80-2.60 (m, 1H), 2.29-2.18 (m, 3H), 1.98 (d, J = 11 Hz, 3H), 1.77-1.64 (m, 2H), 1.50-1.40 (m, 1H). | 382.5 |
| 8-cn | 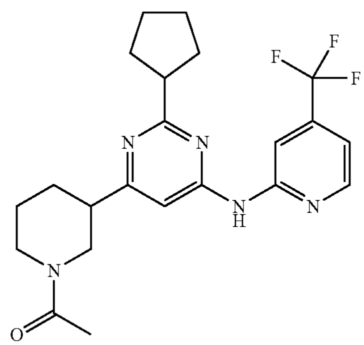 [SMILES: CC(=O)N1CCCC(c2cc(Nc3cc(C(F)(F)F)ccn3)nc(C3CCCC3)n2)C1] | ¹H NMR (400 MHz, DMSO) δ 10.48 (s, 1H), 7.31 (d, J = 5.4 Hz, 1H), 7.24 (s, 1H), 7.15 (s, 1H), 6.98 (s, 1H), 4.50-4.40 (m, 2H), 3.90-3.81 (m, 1H), 3.12-3.01 (m, 1H), 2.71 (dd, J = 11.4, 10.1 Hz, 1H), 2.56 (s, 1H), 2.01 (t, J = 10.0 Hz, 5H), 1.94-1.82 (m, 2H), 1.82-1.61 (m, 6H), 1.59-1.38 (m, 1H). | 434.5 |
| 8-co | 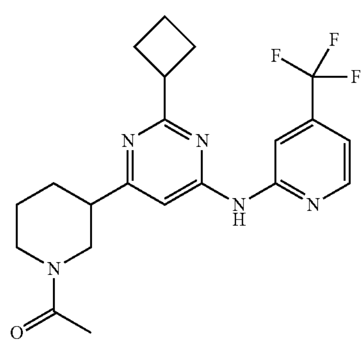 [SMILES: CC(=O)N1CCCC(c2cc(Nc3cc(C(F)(F)F)ccn3)nc(C3CCC3)n2)C1] | ¹H NMR (400 MHz, DMSO) δ 10.52 (s, 1H), 8.61 (s, 1H), 8.56 (d, J = 5.2 Hz, 1H), 7.32 (d, J = 5.2 Hz, 1H), 7.01 (s, 1H), 4.50-4.30 (m, 1H), 3.95-3.80 (m, 1H), 3.80-3.60 (m, 1H), 3.07 (t, J = 11.8 Hz, 1H), 2.80-2.65 (m, 2H), 2.42-2.26 (m, 4H), 2.05-1.96 (m, 5H), 1.95-1.88 (m, 1H), 1.82-1.68 (m, 2H), 1.55-1.40 (m, 1H). | 420.4 |
| 8-cp | 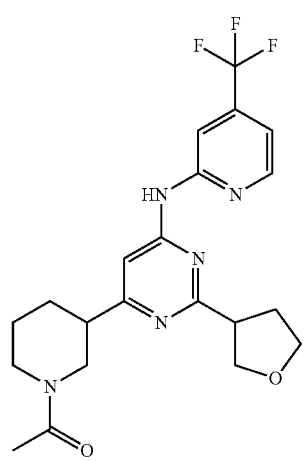 [SMILES: CC(=O)N1CCCC(c2cc(Nc3cc(C(F)(F)F)ccn3)nc(C3CCOC3)n2)C1] | ¹H NMR (400 MHz, DMSO-d₆) δ 10.53 (d, J = 4.4 Hz, 1H), 8.56 (d, J = 5.2 Hz, 1H), 8.44 (s, 1H), 7.32 (d, J = 5.2 Hz, 1H), 7.27 (d, J = 14.8 Hz, 1H), 4.38 (dd, J = 115.4, 12.5 Hz, 1H), 4.08 (d, J = 8.0 Hz, 1H), 3.86 (dt, J = 14.1, 8.0 Hz, 4H), 3.60-3.51 (m, 1H), 3.06 (t, J = 11.8 Hz, 1H), 2.69 (ddd, J = 49.9, 26.4, 10.7 Hz, 2H), 2.30 (dd, J = 12.9, 6.5 Hz, 2H), 2.00 (t, J = 11.7 Hz, 4H), 1.74 (dd, J = 23.9, 13.6 Hz, 2H), 1.48 (dd, J = 45.4, 12.2 Hz, 1H). | 436.4 |

TABLE 8-continued

| No. | Structure | NMR | MS (M + H)+ |
|---|---|---|---|
| 8-cq | 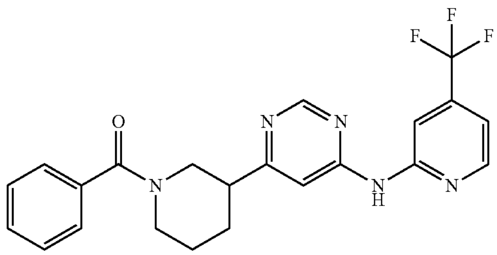 [SMILES: O=C(c1ccccc1)N1CCCC(c2cc(Nc3cc(C(F)(F)F)ccn3)ncn2)C1] | ¹H NMR (400 MHz, DMSO) δ 10.60 (s, 1H), 8.85-8.61 (m, 1H), 8.56 (d, J = 4.5 Hz, 1H), 8.19 (s, 1H), 7.67-7.39 (m, 6H), 7.33 (d, J = 5.1 Hz, 1H), 4.75-4.40 (m, 1H), 3.84-3.53 (m, 1H), 3.11-2.84 (m, 2H), 2.03 (s, 1H), 1.87-1.49 (m, 3H), 1.23 (s, 1H). | 428.4 |
| 8-cr | 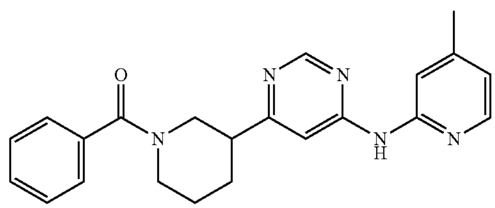 [SMILES: Cc1ccnc(Nc2cc(C3CCCN(C(=O)c4ccccc4)C3)ncn2)c1] | ¹H NMR (400 MHz, DMSO) δ 10.09 (s, 1H), 8.74-8.47 (m, 1H), 8.15 (s, 1H), 7.6-7.40 (m, 8H), 6.84 (d, J = 5.0 Hz, 1H), 4.55 (d, J = 55.2 Hz, 1H), 3.67 (d, J = 14 Hz, 1H), 3.17 (d, J = 5.1 Hz, 1H), 2.78 (t, J = 11.2 Hz, 2H), 2.29 (s, 3H), 2.10-1.47 (m, 2H), 1.19 (dd, J = 15.1, 10.9 Hz, 2H). | 374.5 |
| 8-cs | 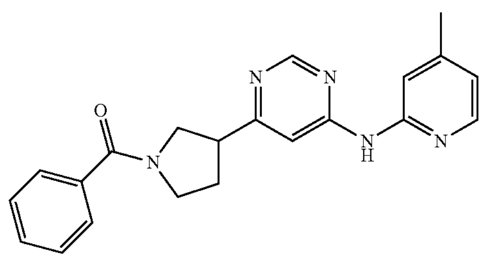 [SMILES: Cc1ccnc(Nc2cc(C3CCN(C(=O)c4ccccc4)C3)ncn2)c1] | ¹H NMR (400 MHz, DMSO) δ 10.09 (d, J = 15.2 Hz, 1H), 9.40-9.20 (m, 1H), 8.15 (dd, J = 9.2, 5.1 Hz, 1H), 7.78-7.37 (m, 6H), 6.84 (d, J = 4.3 Hz, 1H), 4.16-3.42 (m, 6H), 2.39-2.27 (m, 3H), 2.24-1.93 (m, 1H), 1.23 (s, 1H). | 360.4 |

Example 9

Preparation of 1-acetyl-4-(2-(3,3-difluoropyrrolidin-1-yl)-6-(4-(trifluoromethyl)pyridin-2-ylamino)pyrimidin-4-yl) piperidine-4-carbonitrile (10-e)

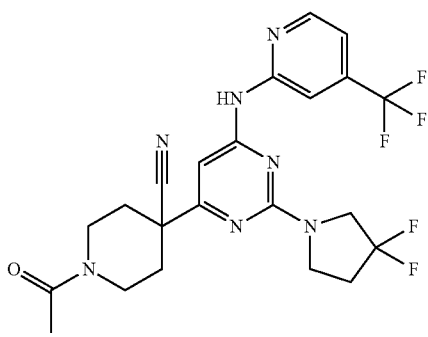

Step 1—Synthesis of tert-butyl 4-cyano-4-(2,6-dichloropyrimidin-4-yl)piperidine-1-carboxylate

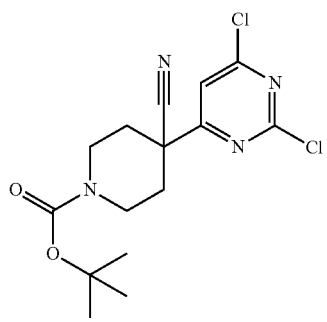

(10-a)

To a solution of n-butyllithium (1.6 mol/l in hexanes; 4.5 mL, 7.13 mmol, 1.5 equiv.) in tetrahydrofuran (50 mL) at −78° C. was added 2,2,6,6-tetramethylpiperidine (1.07 mL, 6.18 mmol, 1.3 equiv.), and the reaction was maintained at −78° C. for 5 min and then 0° C. for 5 min, then recooled to −78° C. A solution of 1-N-Boc-4-cyano-piperidine (1.00 g; 4.76 mmol) in tetrahydrofuran (50 mL) was added dropwise in 5 min the temperature was allowed to rise up to −40° C., and a solution of 2,4,6-trichloropyrimidine (2.23 mL, 19.0 mmol, 4 equiv.) in tetrahydrofuran (20 mL) was added rapidly. The reaction was allowed to warm to 25° C., and stirred for 4 h. The reaction was diluted with EtOAc and 10% citric acid, and washed by water (2×) and brine until pH 7. After evaporation, the residue was purified by chromatography (24 g SiO$_2$ column, 0-50% ethyl acetate-heptane) and afforded 705 mg (41% yield) of the title compounds as a film, which solidified during storage. $^1$H NMR (400 MHz, CDCl$_3$) δ 7.65 (s, 1H), 4.34 (d, J=7.1 Hz, 2H), 3.15 (s, 2H), 2.22 (d, J=4.3 Hz, 2H), 2.00 (d, J=13.2 Hz, 2H), 1.48 (s, 9H); MS (M+H$^+$) m/z=357.

Step 2—Synthesis of tert-butyl 4-(2-chloro-6-(4-(trifluoromethyl)pyridin-2-ylamino)pyrimidin-4-yl)-4-cyanopiperidine-1-carboxylate

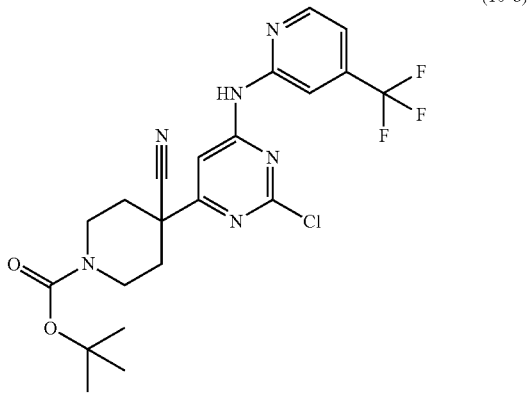

(10-b)

A mixture of tert-butyl 4-cyano-4-(2,6-dichloropyrimidin-4-yl)piperidine-1-carboxylate (200 mg, 0.55 mmol), 2-amino-4-(trifluoromethyl)pyridine (180 mg, 1.1 mmol), Pd$_2$(dba)$_3$ (50 mg, 0.10 eq), 4,5-Bis(diphenylphosphino)-9,9-dimethylxanthene (XantPhos, 68 mg, 0.21 eq), sodium tert-butoxide (109 mg, 2.0 eq) and 1,4-dioxane (2.8 mL), was heated at 80° C. for 30 min. The reaction was diluted with EtOAc and water, and 10% citric acid water solution was used to adjust the final pH around 7. The EtOAc layer was washed by water twice and brine once, then dried over MgSO$_4$. After evaporation of the organic solvents, the residue was purified by chromatography (12 g SiO$_2$ column, 0-30% EtOAc/DCM) and afforded 163 mg (53% yield) of the title compounds as a yellow solid. $^1$H NMR (400 MHz, CDCl$_3$) δ 8.55 (d, J=5.2 Hz, 1H), 8.00 (s, 1H), 7.83 (s, 1H), 7.74 (s, 1H), 4.31 (s, 2H), 3.16 (s, 2H), 2.27 (td, J=13.2, 4.3 Hz, 2H), 2.00 (d, J=13.2 Hz, 2H), 1.49 (s, 9H); MS (M+H$^+$) m/z=483.

Step 3—Synthesis of tert-butyl 4-cyano-4-(2-(3,3-difluoropyrrolidin-1-yl)-6-(4-(trifluoromethyl)pyridin-2-ylamino)pyrimidin-4-yl)piperidine-1-carboxylate

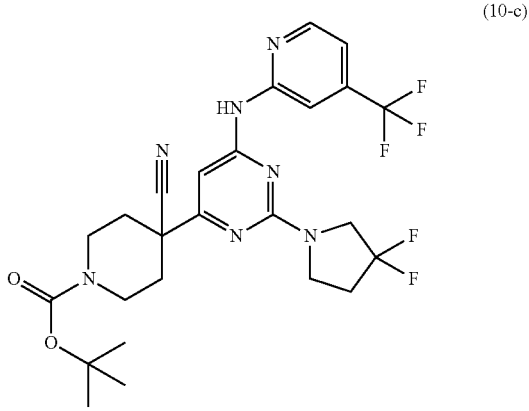 [SMILES: CC(C)(C)OC(=O)N1CCC(C#N)(c2cc(Nc3cc(C(F)(F)F)ccn3)nc(N3CCC(F)(F)C3)n2)CC1]

(10-c)

A solution of tert-butyl 4-[2-chloro-6-[[4-(trifluoromethyl)-2-pyridyl]amino]pyrimidin-4-yl]-4-cyano-piperidine-1-carboxylate (163 mg, 0.29 mmol), 3,3-difluoropyrrolidine hydrochloride (64 mg, 1.5 eq), N,N-diisopropylethylamine (0.15 ml, 3.0 eq), and 1,4-dioxane (1.5 ml), was heated at 65° C. for 2 h while LCMS indicated the reaction was completed. The crude was used directly in next step without further purification. MS (M+H$^+$) m/z=554.

Step 4—Synthesis of 4-(2-(3,3-difluoropyrrolidin-1-yl)-6-(4-(trifluoromethyl)pyridin-2-ylamino)pyrimidin-4-yl)piperidine-4-carbonitrile

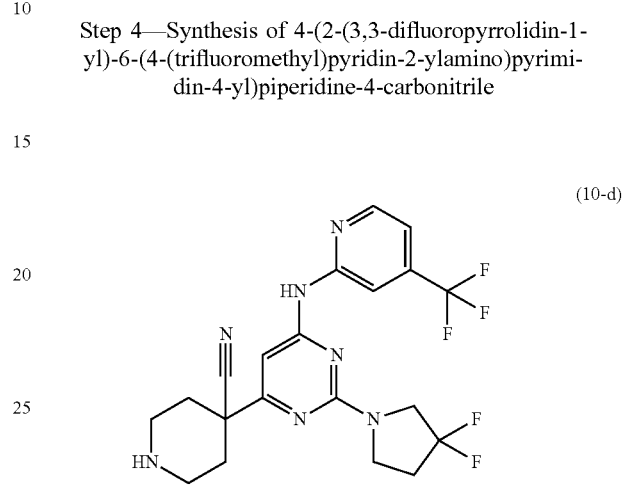

(10-d)

A suspension of tert-butyl 4-cyano-4-(2-(3,3-difluoropyrrolidin-1-yl)-6-(4-(trifluoromethyl)pyridin-2-ylamino)pyrimidin-4-yl)piperidine-1-carboxylat (50 mg, 0.09 mmol) and hydrogen chloride (4 mol/l) in dioxane (0.60 mL, 25 eq), was maintained at 25° C. for 2 h. After HPLC purification, 16.5 mg (40% yield) of the title compound was obtained as a white powder. $^1$H NMR (400 MHz, DMSO-d$_6$) δ 10.53 (s, 1H), 8.70 (s, 1H), 8.55 (d, J=5.2 Hz, 1H), 7.34 (d, J=5.1 Hz, 1H), 6.84 (s, 1H), 3.92 (t, J=13.1 Hz, 2H), 3.76 (t, J=7.3 Hz, 2H), 3.03 (d, J=12.9 Hz, 2H), 2.77 (t, J=11.3 Hz, 2H), 2.64-2.52 (m, 2H), 2.03-1.82 (m, 4H); MS (M+H$^+$) m/z=454.

Step 5—Synthesis of 1-acetyl-4-(2-(3,3-difluoropyrrolidin-1-yl)-6-(4-(trifluoromethyl)pyridin-2-ylamino)pyrimidin-4-yl)piperidine-4-carbonitrile (10-e)

To a solution of 4-[2-(3,3-difluoropyrrolidin-1-yl)-6-[[4-(trifluoromethyl)-2-pyridyl]amino]pyrimidin-4-yl]piperidine-4-carbonitrile (30 mg; 0.06617 mmol) and DMAP (1.0 mg, 0.007 mmol, 0.10 equiv.) in N-ethyldiisopropylamine (0.035 mL, 3.0 equiv.) and dichloromethane (1 mL) was added acetic anhydride (0.0095 mL, 0.09925 mmol, 1.5 equiv.), and the reaction was stirred at room temperature for 2 h. After HPLC purification, 23 mg (70% yield) of the title compound was obtained as a white powder. $^1$H NMR (400 MHz, CDCl$_3$) δ 8.60 (s, 1H), 8.44 (d, J=5.1 Hz, 1H), 7.46 (s, 1H), 7.17 (d, J=5.1 Hz, 1H), 6.55 (s, 1H), 4.81 (d, J=14.3 Hz, 1H), 3.95 (t, J=12.9 Hz, 3H), 3.85 (t, J=7.2 Hz, 2H), 3.53 (t, J=13.5 Hz, 1H), 2.99 (t, J=13.3 Hz, 1H), 2.57-2.41 (m, 2H), 2.29-1.95 (m, 7H); MS (M+H$^+$) m/z=496.

Additional compounds of the invention presented in Table 10 below were prepared by methods already described in the application.

TABLE 10

| No. | Structure | NMR | MS (M + H)+ |
|---|---|---|---|
| 10-e | 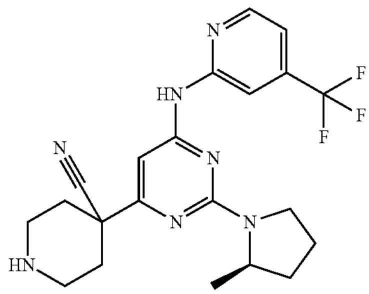 [SMILES: C[C@@H]1CCCN1c1nc(Nc2cc(C(F)(F)F)ccn2)cc(C2(C#N)CCNCC2)n1] | $^1$H NMR (400 MHz, CDCl$_3$) δ 8.84 (s, 1H), 8.40 (d, J = 5.2 Hz, 1H), 7.40 (s, 1H), 7.12 (d, J = 5.3 Hz, 1H), 6.28 (s, 1H), 4.40-4.25 (m, 1H), 3.75-3.48 (m, 2H), 3.13 (dt, J = 25.1, 12.4 Hz, 4H), 2.31-1.89 (m, 8H), 1.73 (m, 1H), 1.29 (d, J = 6.3 Hz, 3H). | 432 |
| 10-f | 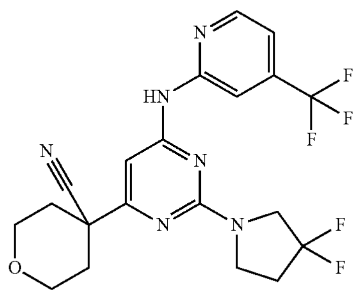 [SMILES: N#CC1(c2cc(Nc3cc(C(F)(F)F)ccn3)nc(N3CCC(F)(F)C3)n2)CCOCC1] | $^1$H NMR (400 MHz, CDCl$_3$) δ 8.63 (s, 1H), 8.44 (d, J = 5.2 Hz, 1H), 7.53 (s, 1H), 7.16 (d, J = 5.2 Hz, 1H), 6.52 (s, 1H), 4.07 (dd, J = 12.0, 3.9 Hz, 2H), 3.97 (t, J = 13.0 Hz, 2H), 3.85 (dt, J = 8.4, 4.6 Hz, 4H), 2.57-2.32 (m, 4H), 1.93 (d, J = 13.5 Hz, 2H). | 455 |
| 10-g | 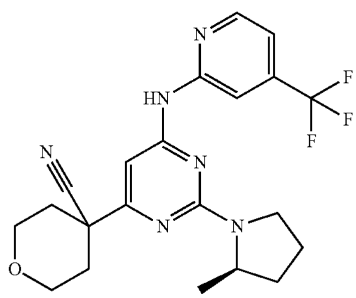 [SMILES: C[C@@H]1CCCN1c1nc(Nc2cc(C(F)(F)F)ccn2)cc(C2(C#N)CCOCC2)n1] | $^1$H NMR (400 MHz, CDCl$_3$) δ 8.83 (s, 1H), 8.40 (d, J = 5.2 Hz, 1H), 7.43 (s, 1H), 7.13 (d, J = 5.1 Hz, 1H), 6.29 (s, 1H), 4.37-4.26 (m, 1H), 4.07 (dd, J = 12.0, 3.8 Hz, 2H), 3.86 (t, J = 11.7 Hz, 2H), 3.76-3.46 (m, 2H), 2.50-2.30 (m, 2H), 2.18-1.84 (m, 5H), 1.80-1.70 (m, 1H), 1.29 (d, J = 6.3 Hz, 3H). | 433 |

Example 11

Synthesis of 2-isopropyl-6-(1-(methylsulfonyl)azetidin-3-yl)-N-(4-(trifluoromethyl)pyridin-2-yl)pyrimidin-4-amine

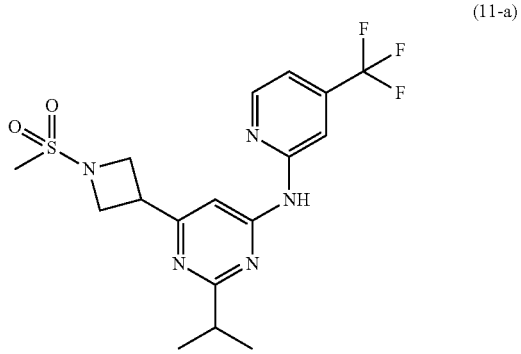 [SMILES: CC(C)c1nc(Nc2cc(C(F)(F)F)ccn2)cc(C2CN(S(C)(=O)=O)C2)n1]

(11-a)

To a solution of 6-(azetidin-3-yl)-2-isopropyl-N-(4-(trifluoromethyl)pyridin-3-yl)pyrimidin-4-amine (0.037 g, 0.1 mmols) in anhydrous dimethylformamide (1 mL), and triethylamine (0.042 ml, 0.3 mmols) was added methanesulfonyl chloride (0.015 ml, 0.2 mmols), and the mixture was stirred at ambient temperature for 16 h. After the completion of the reaction, the solvent was evaporated in vacuo. Purification of the residue by reverse phase HPLC chromatography (C18 10 μM, 30×100 mm, 0.01% ammonium hydroxide water/acetonitrile) afforded 2-isopropyl-6-(1-(methylsulfonyl)azetidin-3-yl)-N-(4-(trifluoromethyl)pyridin-3-yl)pyrimidin-4-amine (12.5 mg, 34%) as a white solid. $^1$H NMR (400 MHz, DMSO-d$_6$) δ 10.55 (d, J=14.9 Hz, 1H), 8.56 (d, J=5.2 Hz, 2H), 7.33 (d, J=5.8 Hz, 1H), 7.23 (s, 1H), 4.20-4.06 (m, 4H), 4.00-3.83 (m, 1H), 3.09 (d, J=11.1 Hz, 3H), 3.08-2.99 (m, 1H), 1.30 (t, J=7.4 Hz, 6H); MS (M+H$^+$) m/z=416.

Example 12

DLK TR-FRET assay: DLK kinase reactions (20 μL) containing 5 nM N-terminally GST-tagged DLK (catalytic domain amino acid 1-520) (Carna Bioscience), 40 nM N-terminally HIS-tagged MKK4 K131M substrate, and 30 μM ATP in kinase reaction buffer (50 mM HEPES, pH 7.5, 0.01% Triton X-100, 0.01% Bovine γ-Globulins, 2 mM DTT, 10 mM MgCl$_2$ and 1 mM EGTA), and testing compound 1:3 serial diluted starting at 20 uM were incubated at ambient temperature for 60 minutes in 384 well OptiPlate (Perkin Elmer). To quench kinase reactions and detect phosphorylated MKK4, 15 μL of TR-FRET antibody mixture containing 2 nM anti-phosphorylated MKK4 labeled with Europium cryptate (Cisbio) and 23 nM anti-HIS labeled with D2 (Cisbio) in detection buffer (25 mM Tris pH 7.5, 100 mM NaCl, 100 mM EDTA, 0.01% Tween-20, and 200 mM KF) was added to the reaction mixture. The detection mixture was incubated for 3 hours at ambient temperature and the TR-FRET was detected with an EnVision multilabel plate reader (Perkin-Elmer) using the LANCE/DELFIA Dual Enh label from Perkin-Elmer (excitation filter: UV2 (TRF) 320 and emission filters: APC 665 and Europium 615). Compounds of formula I as set forth in Table A inhibited the DLK kinase with the $K_i$s as provided in Table B below.

TABLE B

| No. | DLK HTRF (Ki) [uM] |
| --- | --- |
| 1 | 0.639 |
| 2 | |
| 3 | 0.691 |
| 4 | |
| 5 | 0.401 |
| 6 | 0.195 |
| 7 | 0.0207 |
| 8 | 0.795 |
| 9 | 0.0521 |
| 10 | |
| 11 | |
| 12 | |
| 13 | |
| 14 | |
| 15 | |
| 16 | |
| 17 | |
| 18 | |
| 19 | |
| 20 | |
| 21 | 0.0607 |
| 22 | 0.0436 |
| 23 | |
| 24 | 0.0205 |
| 25 | 0.05 |
| 26 | |
| 27 | |
| 28 | |
| 29 | |
| 30 | |
| 31 | |
| 32 | |
| 33 | |
| 34 | |
| 35 | |
| 36 | |
| 37 | |
| 38 | >2.1 |
| 39 | |
| 40 | 0.392 |
| 41 | |
| 42 | |
| 43 | |
| 44 | |
| 45 | |
| 46 | |
| 47 | 0.0126 |
| 48 | |
| 49 | 0.31 |
| 50 | |
| 51 | 0.166 |
| 52 | |
| 53 | |
| 54 | |
| 55 | |
| 56 | 0.293 |
| 57 | |
| 58 | |

TABLE B-continued

| No. | DLK HTRF (Ki) [uM] |
| --- | --- |
| 59 | |
| 60 | |
| 61 | |
| 62 | |
| 63 | |
| 64 | |
| 65 | 0.000735 |
| 66 | 0.0048 |
| 67 | |
| 68 | |
| 69 | |
| 70 | |
| 71 | |
| 72 | |
| 73 | |
| 74 | |
| 75 | |
| 76 | |
| 77 | |
| 78 | |
| 79 | |
| 80 | |
| 81 | |
| 82 | |
| 83 | |
| 84 | |
| 85 | |
| 86 | |
| 87 | 0.262 |
| 88 | |
| 89 | 0.059 |
| 90 | 0.104 |
| 91 | |
| 92 | 0.00243 |
| 93 | |
| 94 | |
| 95 | |
| 96 | 0.0031 |
| 97 | |
| 98 | |
| 99 | |
| 100 | |
| 101 | |
| 102 | |
| 103 | |
| 104 | |
| 105 | 0.0117 |
| 106 | 0.0307 |
| 107 | |
| 108 | |
| 109 | |
| 110 | |
| 111 | 0.00085 |
| 112 | 0.0158 |
| 113 | |
| 114 | |
| 115 | |
| 116 | |
| 117 | |
| 118 | |
| 119 | |
| 120 | 0.00855 |
| 121 | |
| 122 | |
| 123 | |
| 124 | |
| 125 | 0.0152 |
| 126 | |
| 127 | |
| 128 | |
| 129 | 0.1 |
| 130 | |
| 131 | |
| 132 | |
| 133 | |
| 134 | |
| 135 | |

TABLE B-continued

| No. | DLK HTRF (Ki) [uM] |
|---|---|
| 136 | |
| 137 | |
| 138 | |
| 139 | |
| 140 | |
| 141 | |
| 142 | |
| 143 | 0.0104 |
| 144 | |
| 145 | 0.141 |
| 146 | |
| 147 | |
| 148 | |
| 149 | |
| 150 | |
| 151 | |
| 152 | |
| 153 | |
| 154 | |
| 155 | |
| 156 | 0.0269 |
| 157 | |
| 158 | |
| 159 | |
| 160 | 0.00442 |
| 161 | 0.0153 |
| 162 | |
| 163 | |
| 164 | |
| 165 | |
| 166 | |
| 167 | |
| 168 | |
| 169 | 0.0004 |
| 170 | |
| 171 | |
| 172 | |
| 173 | 0.037 |
| 174 | |
| 175 | 0.0022 |
| 176 | |
| 177 | 0.00803 |
| 178 | 0.0268 |
| 179 | |
| 180 | 0.0462 |
| 181 | |
| 182 | |
| 183 | |
| 184 | 0.0415 |
| 185 | |
| 186 | |
| 187 | |
| 188 | |
| 189 | |
| 190 | |
| 191 | |
| 192 | |
| 193 | |
| 194 | |
| 195 | 0.143 |
| 196 | |
| 197 | |
| 198 | |
| 199 | |
| 200 | 0.00834 |
| 201 | 0.0032 |
| 202 | 0.00095 |
| 203 | |
| 204 | 0.00769 |
| 205 | |
| 206 | 0.0433 |
| 207 | |
| 208 | 0.322 |
| 209 | 0.0768 |
| 210 | |
| 211 | |
| 212 | |

TABLE B-continued

| No. | DLK HTRF (Ki) [uM] |
|---|---|
| 213 | |
| 214 | |
| 215 | |
| 216 | |
| 217 | |
| 218 | 0.288 |
| 219 | |
| 220 | |
| 221 | |
| 222 | |
| 223 | |
| 224 | |
| 225 | |
| 226 | |
| 227 | |
| 228 | |
| 229 | |
| 230 | |
| 231 | |
| 232 | |
| 233 | |
| 234 | |
| 235 | |
| 236 | |
| 237 | |
| 238 | |
| 239 | |
| 240 | |
| 241 | |
| 242 | |
| 243 | |
| 244 | |
| 245 | |
| 246 | |
| 247 | |
| 248 | |
| 249 | |
| 250 | 0.0267 |
| 251 | 0.183 |
| 252 | 0.0435 |
| 253 | 0.0877 |
| 254 | |
| 255 | |
| 256 | |
| 257 | |
| 258 | |
| 259 | |
| 260 | 0.347 |
| 261 | |
| 262 | |
| 263 | |
| 264 | |
| 265 | 0.159 |
| 266 | |
| 267 | |
| 268 | |
| 269 | |
| 270 | |
| 271 | |
| 272 | |
| 273 | |
| 274 | 0.0463 |
| 275 | |
| 276 | |
| 277 | |
| 278 | |
| 279 | |
| 280 | |
| 281 | |
| 282 | |
| 283 | |
| 284 | |
| 285 | |
| 286 | |
| 287 | |
| 288 | |
| 289 | |

TABLE B-continued

| No. | DLK HTRF (Ki) [uM] |
|---|---|
| 290 | |
| 291 | |
| 292 | |
| 293 | |
| 294 | 0.104 |
| 295 | 0.0827 |
| 296 | 0.174 |
| 297 | |
| 298 | |
| 299 | |
| 300 | |
| 301 | |
| 302 | |
| 303 | |
| 304 | |
| 305 | |
| 306 | |
| 307 | 0.0319 |
| 308 | |
| 309 | |
| 310 | |
| 311 | |
| 312 | |
| 313 | |
| 314 | |
| 315 | |
| 316 | |
| 317 | |
| 318 | |
| 319 | |
| 320 | |
| 321 | |
| 322 | |
| 323 | |
| 324 | |
| 325 | |
| 326 | |
| 327 | |
| 328 | 0.147 |
| 329 | 0.0701 |
| 330 | 0.0318 |
| 331 | 0.0184 |
| 332 | 0.00612 |
| 333 | |
| 334 | |
| 335 | |
| 336 | |
| 337 | |
| 338 | |
| 339 | |
| 340 | |
| 341 | |
| 342 | |
| 343 | |
| 344 | |
| 345 | |
| 346 | |
| 347 | |
| 348 | 0.0226 |
| 349 | |
| 350 | 0.0475 |
| 351 | |
| 352 | |
| 353 | |
| 354 | |
| 355 | |
| 356 | 0.101 |
| 357 | |
| 358 | |
| 359 | |
| 360 | |
| 361 | 0.0548 |
| 362 | |
| 363 | |
| 364 | |
| 365 | |
| 366 | |

TABLE B-continued

| No. | DLK HTRF (Ki) [uM] |
|---|---|
| 367 | |
| 368 | |
| 369 | |
| 370 | |
| 371 | 0.636 |
| 372 | |
| 373 | 0.173 |
| 374 | 0.0306 |
| 375 | 0.0111 |
| 376 | 0.00172 |
| 377 | |
| 378 | |
| 379 | |
| 380 | |
| 381 | |
| 382 | |
| 383 | |
| 384 | |
| 385 | 0.0368 |
| 386 | |
| 387 | |
| 388 | 0.00875 |
| 389 | |
| 390 | |
| 391 | 0.009 |
| 392 | 0.12 |
| 393 | |
| 394 | |
| 395 | |
| 396 | |
| 397 | |
| 398 | |
| 399 | 0.281 |
| 400 | |
| 401 | 0.122 |
| 402 | 0.00159 |
| 403 | |
| 404 | 0.00492 |
| 405 | |
| 406 | |
| 407 | 0.026 |
| 408 | 0.0978 |
| 409 | |
| 410 | |
| 411 | |
| 412 | 0.0475 |
| 413 | |
| 414 | |
| 415 | |
| 416 | |
| 417 | |
| 418 | |
| 419 | |
| 420 | |
| 421 | |
| 422 | |
| 423 | 0.00521 |
| 424 | 0.0124 |
| 425 | 0.00017 |
| 426 | 0.0005 |
| 427 | 0.016 |

Example 13 pJNK Cell based assay:HEK293 cells stably transfected with doxycycline-inducible N-terminally Flag-tagged full length DLK were plated at density of 7500 cells/well (40 μL)

in 384-well Greiner bio-one μclear plate coated with Poly-D-Lysine. The cells were incubated at 37° C. in DMEM (Dulbecco's Modified Eagle Medium) media containing 10% FBS and 2 mM L-Glutamine for 20-24 hours. 5 μL of 60 μM doxycycline was added to the cells to initiate DLK expression for 20 hours at 37° C. No doxycycline was added for the negative control wells. 5 μL of compounds of formula I in various concentrations in DMEM were added to the cells and the compound treated cell culture was incubated at 37° C. for 5.5 hours prior to fixation with addition of 50 μL 4% paraformaldehyde. The wells were washed with 40 μL PBS wash twice followed by permeabilization with 0.1% Triton X-100. The cells were washed with 40 μL PBS wash twice again prior to incubation in 20 μL SuperBlock (Thermo Scientific) for 1 hour at ambient temperature. The primary antibodies (1:3000 mouse anti-Flag and 1:1000 rabbit anti-pJNK in SuperBlock) were incubated with the fixed cells overnight at 4° C. The cells were washed with 40 μL PBS twice before the addition of secondary antibodies (Anti-mouse labeled with AlexaFluor555 and anti-rabbit labeled with AlexaFluor488 in 1:2000 dilution in SuperBlock). The secondary antibodies were incubated at ambient temperature for 2 hours and were protected from light. The cells were washed with 40 μL PBS before the addition of 20 μL Hoechst 33342 (1:5000 in PBS). The plate was sealed and stored at 4° C. in the dark until imaging analyses on Opera High Content Screening System (Evotec). Three data points were reported: pJNK (mean intensity inside the search stencil), DLK (mean intensity of the 1% brightest pixels inside the search stencil) and nuclear area.

Compounds of formula I inhibited the phosphorylation of JNK with the $K_i$s as provided in Table B below.

| Compound | p-JNK 293 IC50 (uM) |
|---|---|
| {3-[6-(4-Methyl-pyridin-2-ylamino)-2-pyrrolidin-1-yl-pyrimidin-4-yl]-piperidin-1-yl}-phenyl-methanone | 0.0779 |
| 2-{Methyl-[4-pyrrolidin-3-yl-6-(4-trifluoromethyl-pyridin-2-yl amino)-pyrimidin-2-yl]-amino}-ethanol | 0.193 |
| (2-Phenyl-6-piperidin-3-yl-pyrimidin-4-yl)-(4-trifluoromethyl-pyridin-2-yl)-amine | 1 |
| (4-Chloro-pyridin-2-yl)-[2-(3,3-difluoro-pyrrolidin-1-yl)-6-piperidin-4-yl-pyrimidin-4-yl]-amine | 0.113 |
| 1-Acetyl-4-[2-(3,3-difluoro-pyrrolidin-1-yl)-6-(4-trifluoromethyl-pyridin-2-ylamino)-pyrimidin-4-yl]-piperidine-4-carbonitrile | 0.605 |
| [2-(2-Oxa-5-aza-bicyclo[2.2.1]hept-5-yl)-6-piperidin-4-yl-pyrimidin-4-yl]-(4-trifluoromethyl-pyridin-2-yl)-amine | 0.389 |
| (4-Cyclobutyl-pyridin-2-yl)-[2-(3,3-difluoro-pyrrolidin-1-yl)-6-piperidin-4-yl-pyrimidin-4-yl]-amine | 0.2 |
| [2-(2-Oxa-5-aza-bicyclo[2.2.1]hept-5-yl)-6-(tetrahydro-pyran-4-yl)-pyrimidin-4-yl]-(4-trifluoromethyl-pyridin-2-yl)-amine | 0.268 |
| 1-{3-[2-(3,3-Difluoro-pyrrolidin-1-yl)-6-(4-trifluoromethyl-pyridin-2-ylamino)-pyrimidin-4-yl]-pyrrolidine-1-carbonyl}-cyclo propanecarbonitrile | 0.584 |
| [2-(3,4,6,7-Tetrahydro-imidazo[4,5-c]pyridin-5-yl)-6-(tetrahydro-pyran-4-yl)-pyrimidin-4-yl]-(4-trifluoromethyl-pyridin-2-yl)-amine | 0.24 |
| [2-[3-(2-Methyl-pyrimidin-4-yl)-pyrrolidin-1-yl]-6-(tetrahydro-pyran-4-yl)-pyrimidin-4-yl]-(4-trifluoromethyl-pyridin-2-yl)-amine | 0.227 |
| {2-(3,3-Difluoro-azetidin-1-yl)-6-[1-(4-methyl-1H-imidazol-2-ylmethyl)-pyrrolidin-3-yl]-pyrimidin-4-yl}-(4-trifluoromethyl-pyridin-2-yl)-amine | 0.418 |

We claim:
1. Compounds of formula (I)

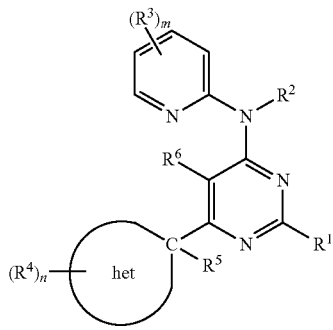

wherein $R^1$ is selected from the group consisting of $C_{1-6}$ haloalkyl, $C_{1-6}$ heteroalkyl, $C_{1-6}$ alkoxy, 3-10 membered cycloalkyl, 3-10 membered heterocycloalkyl, 6-10 membered aryl, 5-10 membered heteroaryl, —$OR^{1a}$, —$SR^{1a}$, —N(H)($R^{1a}$), and —N($R^{1a}$)($R^{1b}$) wherein $R^{1a}$ and $R^{1b}$ are each independently selected from the group consisting of $C_{1-6}$ alkyl, $C_{1-6}$ haloalkyl, $C_{1-6}$ heteroalkyl, 3-10 membered cycloalkyl and 3-10 membered heterocycloalkyl, and wherein the aliphatic and aromatic portions of $R^1$ are independently further substituted with 0 to 5 $R^{41}$ substituents selected from the group consisting of —F, —Cl, —Br, —I, —CN, —$NO_2$, —$SF_5$, —OH, —$NH_2$, —$CF_3$, =O, $C_{1-4}$ alkyl, $C_{1-4}$ haloalkyl, $C_{1-4}$ heteroalkyl, $C_{1-4}$ alkoxy, $C_{1-4}$ alkylthio, $C_{1-4}$ alkylamino, $C_{1-4}$ dialkylamino, $R^{1c}$—C(=O)—, $R^{1c}$—C(=O)N(H)—, $R^{1c}$—C(=O)N($R^{1d}$)—, $R^{1c}$—C(=O)O—, $R^{1c}$—S(O)$_{1-2}$—, $R^{1c}$—S(O)$_{1-2}$N($R^{1d}$)—, $R^{1c}$—S(O)$_{1-2}$N(H)—, 3-6 membered cycloalkyl, phenyl, 5-6 membered heteroaryl and 3-7 membered heterocycloalkyl, wherein $R^{1c}$ is selected from the group consisting of $C_{1-6}$ alkyl, $C_{1-6}$ haloalkyl, $C_{5-6}$ heteroaryl, 3-7 membered heterocycloalkyl, phenyl and 3-6 membered cycloalkyl, $R^{1d}$ is selected from the group consisting of hydrogen, $C_{1-3}$ alkyl and $C_{1-3}$ haloalkyl, and wherein said 5-6 membered heteroaryl, phenyl, 3-6 membered cycloalkyl and 3-7 membered heterocycloalkyl of a $R^{41}$ substituent are substituted with from 0-4 substituents selected from —F, —Cl, —Br, I, —CN, —$NO_2$, —$SF_5$, —OH, —$NH_2$, —$CF_3$, $C_{1-4}$ alkyl, $C_{1-4}$ haloalkyl, $C_{1-4}$ alkoxy, $C_{1-4}$ alkylthio, $C_{1-4}$ alkylamino and $C_{1-4}$ dialkylamino;

$R^2$ is selected from the group consisting of hydrogen, $C_{1-6}$ alkyl and $C_{1-6}$ haloalkyl;

$R^3$ is selected from the group consisting of —F, —Cl, —Br, —I, —$(X^3)_{0-1}$—CN, —$(X^3)_{0-1}$—$NO_2$, —$(X^3)_{0-1}$—$SF_5$, —$(X^3)_{0-1}$-OH, —$(X^3)_{0-1}$—$NH_2$, —$(X^3)_{0-1}$—N(H)($R^{3a}$), —$(X^3)_{0-1}$—N($R^{3b}$)($R^{3a}$), —$(X^3)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^3)_{0-1}$-3-7 membered cycloalkyl, —$(X^3)_{0-1}$-3-7 membered heterocycloalkyl, —$(X^3)_{0-1}$-5-6 membered heteroaryl, —$(X^3)_{0-1}$—$C_6$ aryl, —$(X^3)_{0-1}$—C(=$Y^3$)N(H)($R^{3a}$), —$(X^3)_{0-1}$—C(=$Y^3$)$NH_2$, —$(X^3)_{0-1}$—C(=$Y^3$)N($R^{3a}$)($R^{3b}$), —$(X^3)_{0-1}$—C(=$Y^3$)$OR^{3a}$, —$(X^3)_{0-1}$—C(=$Y^3$)OH, —$(X^3)_{0-1}$—N(H)C(=$Y^3$)($R^{3a}$), —$(X^3)_{0-1}$—N($R^{3b}$)C(=$Y^3$)($R^{3a}$), —$(X^3)_{0-1}$—N(H)C(=$Y^3$)$OR^{3a}$, —$(X^3)_{0-1}$—N($R^{3b}$)C(=$Y^3$)$OR^{3a}$, —$(X^3)_{0-1}$—S(O)$_{1-2}R^{3a}$, —$(X^3)_{0-1}$—N(H)S(O)$_{1-2}R^{3a}$, —$(X^3)_{0-1}$—N($R^{3b}$)S(O)$_{1-2}R^{3a}$, —$(X^3)_{0-1}$—S(O)$_{0-1}$N(H)($R^{3a}$), —$(X^3)_{0-1}$—S(O)$_{0-1}$N($R^{3b}$)($R^{3a}$), —$(X^3)_{0-1}$—S(O)$_{0-1}$—$NH_2$, —$(X^4)_{0-1}$—S(=O)(=$NR^{3b}$)$R^{3a}$, —$(X^3)_{0-1}$—C(=$Y^3$)$R^{3a}$, —$(X^3)_{0-1}$—C(=$Y^3$)H, —$(X^3)_{0-1}$—C(=NOH)$R^{3a}$, —$(X^3)_{0-1}$—C(=$NOR^{3b}$)$R^{3a}$, —$(X^3)_{0-1}$—NHC(=$Y^3$)N(H)($R^{3a}$), —$(X^3)_{0-1}$—NHC(=$Y^3$)$NH_2$, —$(X^3)_{0-1}$—NHC(=$Y^3$)N($R^{3b}$)($R^{3a}$), —$(X^3)_{0-1}$—N($R^{3a}$)C(=$Y^3$)N(H)($R^{3a}$), —$(X^3)_{0-1}$—N($R^{3a}$)C(=$Y^3$)$NH_2$, —$(X^3)_{0-1}$—OC(=$Y^3$)$R^{3a}$, —$(X^3)_{0-1}$—OC(=$Y^3$)H, —$(X^3)_{0-1}$—OC(=$Y^3$)$OR^{3a}$, —$(X^3)_{0-1}$—OP(=$Y^3$)($OR^{3a}$)($OR^{3b}$), —$(X^3)$—SC(=$Y^3$)$OR^{3a}$ and —$(X^3)$—SC(=$Y^3$)N($R^{3a}$)($R^{3b}$) wherein $X^3$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{3a}$ and $R^{3b}$ are each independently selected from the group consisting of $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl; $Y^3$ is O, $NR^{3d}$ or S wherein $R^{3d}$ is hydrogen or $C_{1-6}$ alkyl; wherein aliphatic or aromatic portion of $R^3$ is independently further substituted with from 0 to 4 $R^{43}$ substituents selected from the group consisting of —F, —Cl, —Br, —I, —CN, —$NO_2$, —$SF_5$, —OH, —$NH_2$, —$CF_3$, =O, $C_{1-6}$ alkyl, $C_{1-6}$ haloalkyl, $C_{1-6}$ heteroalkyl, $C_{1-6}$ alkoxy, $C_{1-6}$ alkylthio, 3-6 membered cycloalkyl, 3-6 membered heterocycloalkyl, —C(=O)N(H)($C_{1-6}$ alkyl), —C(=O)N($C_{1-6}$ alkyl)$_2$, —C(=O)$NH_2$, —C(=O)O$C_{1-6}$ alkyl, —C(=O)OH, —N(H)C(=O)($C_{1-6}$ alkyl), —N($C_{1-6}$ alkyl)C(=O)($C_{1-6}$ alkyl), —N(H)C(=O)O$C_{1-6}$ alkyl, —N($C_{1-6}$ alkyl)C(=O)O$C_{1-6}$ alkyl, —S(O)$_{1-2}C_{1-6}$ alkyl, —N(H)S(O)$_{1-2}C_{1-6}$ alkyl, —N($C_{1-6}$ alkyl)S(O)$_{1-2}$ $C_{1-6}$ alkyl, —S(O)$_{0-1}$N(H)($C_{1-6}$ alkyl), —S(O)$_{0-1}$N($C_{1-6}$ alkyl)$_2$, —S(O)$_{0-1}NH_2$, —C(=O)$C_{1-6}$ alkyl, —C(=NOH)$C_{1-6}$ alkyl, —C(=$NOC_{1-6}$ alkyl)$C_{1-6}$ alkyl, —NHC(=O)N(H)($C_{1-6}$ alkyl), —NHC(=O)N($C_{1-6}$ alkyl)$_2$, —NHC(=O)$NH_2$, —N($C_{1-6}$ alkyl)C(=O)N(H)($C_{1-6}$ alkyl), —N($C_{1-6}$ alkyl)C(=O)$NH_2$, —OC(=O)$C_{1-6}$ alkyl, —OC(=O)O$C_{1-6}$ alkyl, —OP(=O)(O$C_{1-6}$ alkyl)$_2$, —SC(=O)O$C_{1-6}$ alkyl and —SC(=O)N($C_{1-6}$ alkyl)$_2$; alternatively any two $R^3$ substituents located on adjacent atoms are optionally combined to form a 5-6 membered heteroaryl ring comprising 1-2 heteroatoms selected from N, O and S and further comprising 0 to 4 $R^{3a}$ substituents;

m is an integer from 0 to 4;

the ring represented by the structure

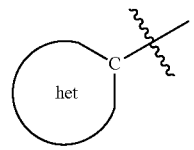 [SMILES: *C(C)C]

is a 4 to 10 membered heterocyclic ring comprising 1 to 2 heteroatoms selected from N, O and S, wherein said 4 to 7 membered heterocyclic ring is optionally substituted with 1 to 3 $R^4$ groups;

$R^4$ is selected from the group consisting of —F, —Cl, —Br, —I, —$(X^4)_{0-1}$—CN, —$(X^4)_{0-1}$—$NO_2$, —$(X^4)_{0-1}$ —SF$_5$, —(X$^4$)$_{0-1}$—OH, —(X$^4$)$_{0-1}$—NH$_2$, —(X$^4$)$_{0-1}$—N(H)(R$^{4a}$), (X$^4$)$_{0-1}$N(R$^{4b}$)(R$^{4a}$), —(X$^4$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^4$)$_{0-1}$-(3-10 membered heterocycloalkyl), —(X$^4$)$_{0-1}$-(5-10 membered heteroaryl), —(X$^4$)$_{0-1}$-(3-7 membered cycloalkyl), —(X$^4$)$_{0-1}$—C(=Y$^4$)N(H)(R$^{4a}$), —(X$^4$)$_{0-1}$—C(=Y$^4$)NH$_2$, —(X$^4$)$_{0-1}$—C(=Y$^4$)N(R$^{4a}$)(R$^{4b}$), —(X$^4$)$_{0-1}$—C(=Y$^4$)OR$^{4a}$, —(X$^4$)$_{0-1}$—C(=Y$^4$)OH, —(X$^4$)$_{0-1}$—N(H)C(=Y$^4$)(R$^{4a}$), —(X$^4$)$_{0-1}$—N(R$^{4b}$)C(=Y$^4$)(R$^{4a}$), —(X$^4$)$_{0-1}$—N(H)C(=Y$^4$)OR$^{4a}$, —(X$^4$)$_{0-1}$—N(R$^{4b}$)C(=Y$^4$)OR$^4$, —(X$^4$)$_{0-1}$—S(O)$_{1-2}$R$^{4a}$, —(X$^4$)$_{0-1}$—N(H)S(O)$_{1-2}$R$^{4a}$, —(X$^4$)$_{0-1}$—N(R$^{4b}$)S(O)$_{1-2}$R$^{4a}$, —(X$^4$)$_{0-1}$—S(O)$_{0-1}$N(H)(R$^{4a}$), —(X$^4$)$_{0-1}$—S(O)$_{0-1}$N(R$^{4b}$)(R$^{4a}$), —(X$^4$)$_{0-1}$—S(O)$_{0-1}$NH$_2$, —(X$^4$)$_{0-1}$—S(=O)(=NR$^{4b}$)R$^{4a}$, —(X$^4$)$_{0-1}$—C(=Y$^4$)R$^{4a}$, —(X$^4$)$_{0-1}$—C(=Y$^4$)H, —(X$^4$)$_{0-1}$—C(=NOH)R$^{4a}$, —(X$^4$)$_{0-1}$—C(=NOR$^{4b}$)R$^{4a}$, —(X$^4$)$_{0-1}$—NHC(=Y$^4$)N(H)(R$^{4a}$), —(X$^4$)$_{0-1}$—NHC(=Y$^4$)NH$_2$, —(X$^4$)$_{0-1}$—NHC(=Y$^4$)N(R$^{4b}$)(R$^{4a}$), —(X$^4$)$_{0-1}$—NR$^{4a}$C(=Y$^4$)N(H)(R$^{4a}$), —(X$^4$)$_{0-1}$—N(R$^{4a}$)C(=Y$^4$)NH$_2$, —(X$^4$)$_{0-1}$—OC(=Y$^4$)R$^{4a}$, —(X$^4$)$_{0-1}$—OC(=Y$^4$)H, —(X$^4$)$_{0-1}$—OC(=Y$^4$)OR$^{4a}$, —(X$^4$)$_{0-1}$—OP(=Y$^4$)(OR$^{4a}$)(OR$^{4b}$), —SC(=Y$^4$)OR$^{4a}$ and —SC(=Y$^4$)N(R$^{4a}$)(R$^{4b}$) wherein R$^{4a}$ and R$^{4b}$ at each occurrence are each independently selected from the group consisting of C$_{1-6}$ alkyl, C$_{1-6}$ haloalkyl, C$_{1-6}$ heteroalkyl, 6-10 membered aryl, 3-7 membered cycloalkyl, 5-10 membered heteroaryl, 3-7 membered heterocycloalkyl, 6-10 membered aryl-C$_{1-4}$ alkyl, 3-7 membered cycloalkyl-C$_{1-4}$ alkyl, 5-10 membered heteroaryl-C$_{1-4}$ alkyl and 3-7 membered heterocycloalkyl-C$_{1-4}$ alkyl, and X$^4$ is selected from the group consisting of C$_{1-4}$ alkylene, C$_{1-4}$ haloalkylene, C$_{1-4}$ heteroalkylene, C$_{2-4}$ alkenylene and C$_{2-4}$ alkynylene; Y$^4$ is O, NR$^{4c}$ or S wherein R$^{4c}$ is hydrogen or C$_{1-6}$ alkyl; wherein the aromatic and aliphatic portions of R$^4$ is independently further substituted with 0 to 4 R$^{44}$ substituents selected from the group consisting of —F, —Cl, —Br, I, —CN, —NO$_2$, —SF$_5$, —OH, —NH$_2$, —CF$_3$, =O, C$_{1-6}$ alkyl, C$_{1-6}$ haloalkyl, C$_{1-6}$ heteroalkyl, C$_{1-6}$ alkoxy, C$_{1-6}$ alkylthio, 3-6 membered cycloalkyl, 3-6 membered heterocycloalkyl, —C(=O)N(H)(C$_{1-6}$ alkyl), —C(=O)N(C$_{1-6}$ alkyl)$_2$, —C(=O)NH$_2$, —C(=O)OC$_{1-6}$ alkyl, —C(=O)OH, —N(H)C(=O)(C$_{1-6}$ alkyl), —N(C$_{1-6}$ alkyl)C(=O)(C$_{1-6}$ alkyl), —N(H)C(=O)OC$_{1-6}$ alkyl, —N(C$_{1-6}$ alkyl)C(=O)OC$_{1-6}$ alkyl, —S(O)$_{1-2}$C$_{1-6}$ alkyl, —N(H)S(O)$_{1-2}$C$_{1-6}$ alkyl, —N(C$_{1-6}$ alkyl)S(O)$_{1-2}$C$_{1-6}$ alkyl, —S(O)$_{0-1}$N(H)(C$_{1-6}$ alkyl), —S(O)$_{0-1}$N(C$_{1-6}$ alkyl)$_2$, —S(O)$_{0-1}$NH$_2$, —C(=O)C$_{1-6}$ alkyl, —C(=NOH)C$_{1-6}$ alkyl, —C(=NOC$_{1-6}$ alkyl)C$_{1-6}$ alkyl, —NHC(=O)N(H)(C$_{1-6}$ alkyl), —NHC(=O)N(C$_{1-6}$ alkyl)$_2$, —NHC(=O)NH$_2$, —N(C$_{1-6}$ alkyl)C(=O)N(H)(C$_{1-6}$ alkyl), —N(C$_{1-6}$ alkyl)C(=O)NH$_2$, —OC(=O)C$_{1-6}$ alkyl, —OC(=O)OC$_{1-6}$ alkyl, —OP(=O)(OC$_{1-6}$ alkyl)$_2$, —SC(=O)OC$_{1-6}$ alkyl and —SC(=O)N(C$_{1-6}$ alkyl)$_2$;

n is an integer from 0 to 5;

R$^5$ is absent or is selected from the group consisting of hydrogen, C$_{1-6}$ alkyl, C$_{1-6}$ haloalkyl, —OH, OR$^{5a}$, —CN and halogen, wherein R$^{5a}$ is selected from the group consisting of C$_{1-6}$ alkyl, C$_{1-6}$ haloalkyl and C$_{1-6}$ heteroalkyl; or optionally R$^4$ and R$^5$ are optionally combined to form a 5-7 membered cycloalkyl or heterocycloalkyl and is independently further substituted with 0-4 R$^{44}$ substituents;

R$^6$ is hydrogen, —F, —Cl, —Br, —I, C$_{1-3}$ alkyl or C$_{1-3}$ haloalkyl; and with the proviso that a compound of formula I is not:
1-(3-(2-methyl-6-((4-methylpyridin-2-yl)amino)pyrimidin-4-yl)piperidin-1-yl)-2-phenylethanone.

2. The compound of claim 1, wherein said 4 to 10 membered heterocyclic ring represented by the structure

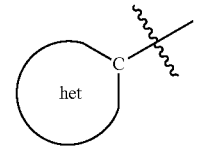 [SMILES: *C(C)C]

comprises an optionally substituted ring selected from the group consisting of morpholine, morpholinone, piperazine, piperazinone, thiomorpholine, thiomorpholinone, homopiperidine, homopiperidinone, piperidine, valerolactam, pyrrolidine, butyrolactam, azetidine, azetidinone, thiazepane-1,1-dioxide, thiazinane-1,1-dioxide, isothiazolidine-1,1-dioxide, pyridinone, tetrahydropyran, oxetane and tetrahydrofuran attached to the remainder of the compound represented by formula I.

3. The compound of claim 1, wherein said 4 to 10 membered heterocyclic ring represented by the structure

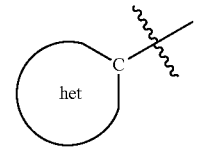

is selected from the group consisting of:

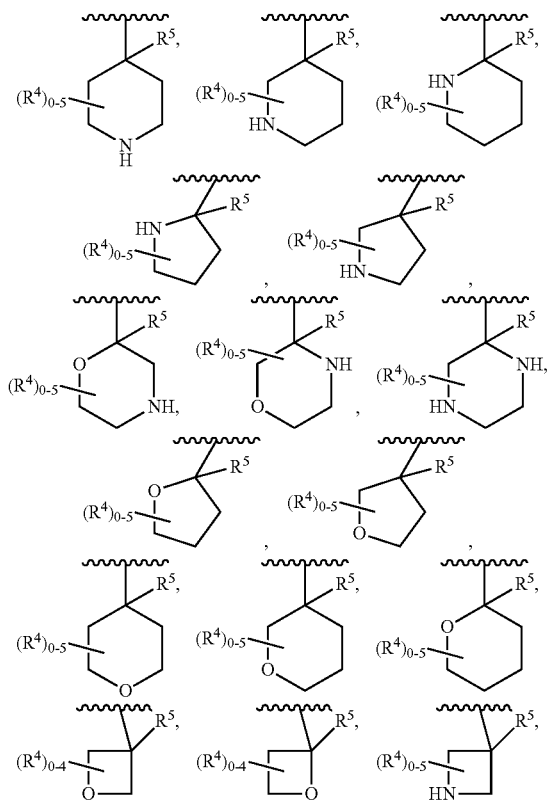

-continued
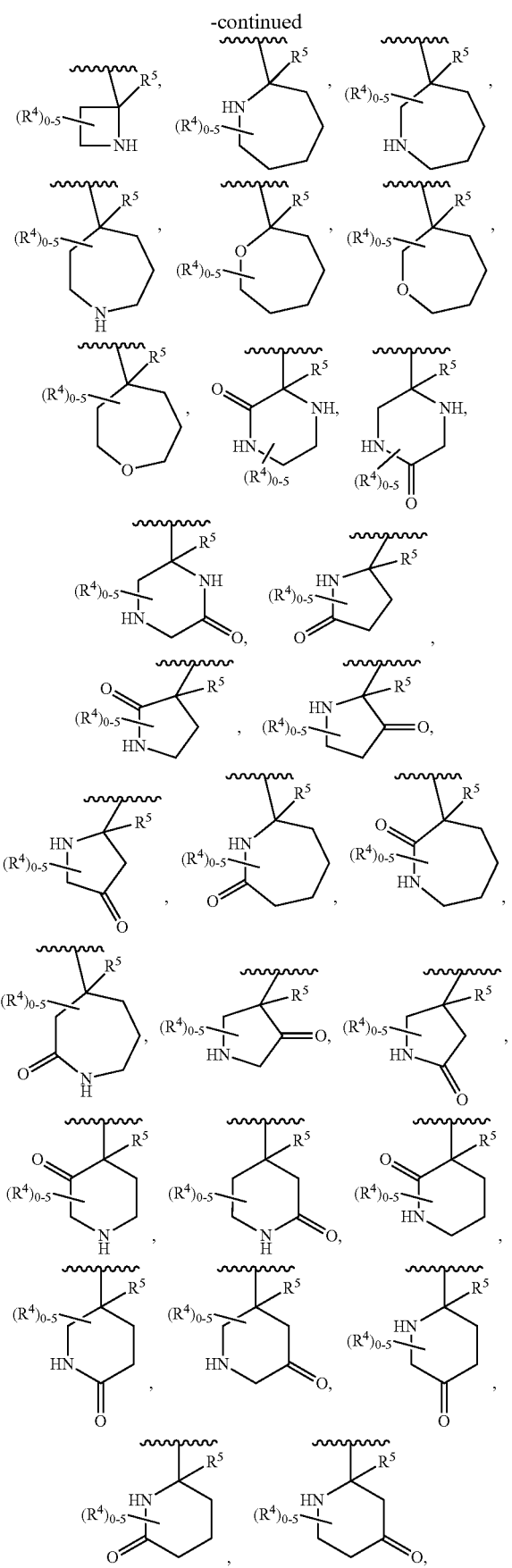
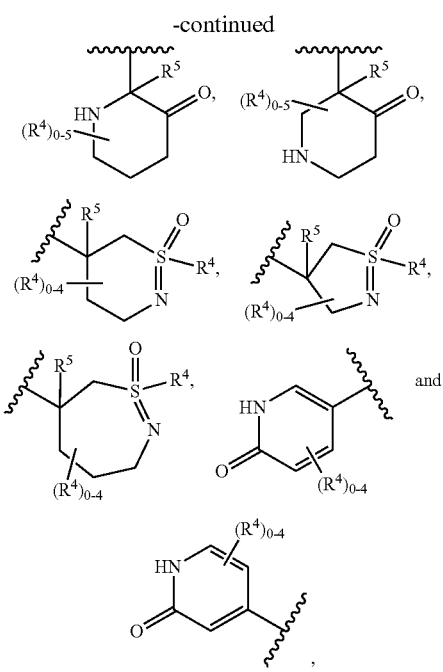
wherein the $R^4$ substituent, if present replaces a hydrogen atom that is attached to a carbon or a hydrogen atom attached to a nitrogen ring atom of said 4-10 membered heterocyclic ring.
4. The compound of claim 1, wherein said 4 to 10 membered heterocyclic ring represented by the structure
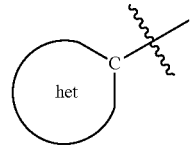 [SMILES: *C(C)C]
is selected from the group consisting of:
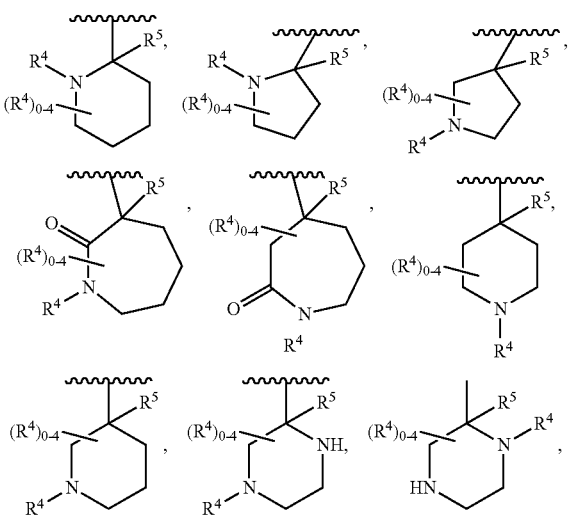

-continued

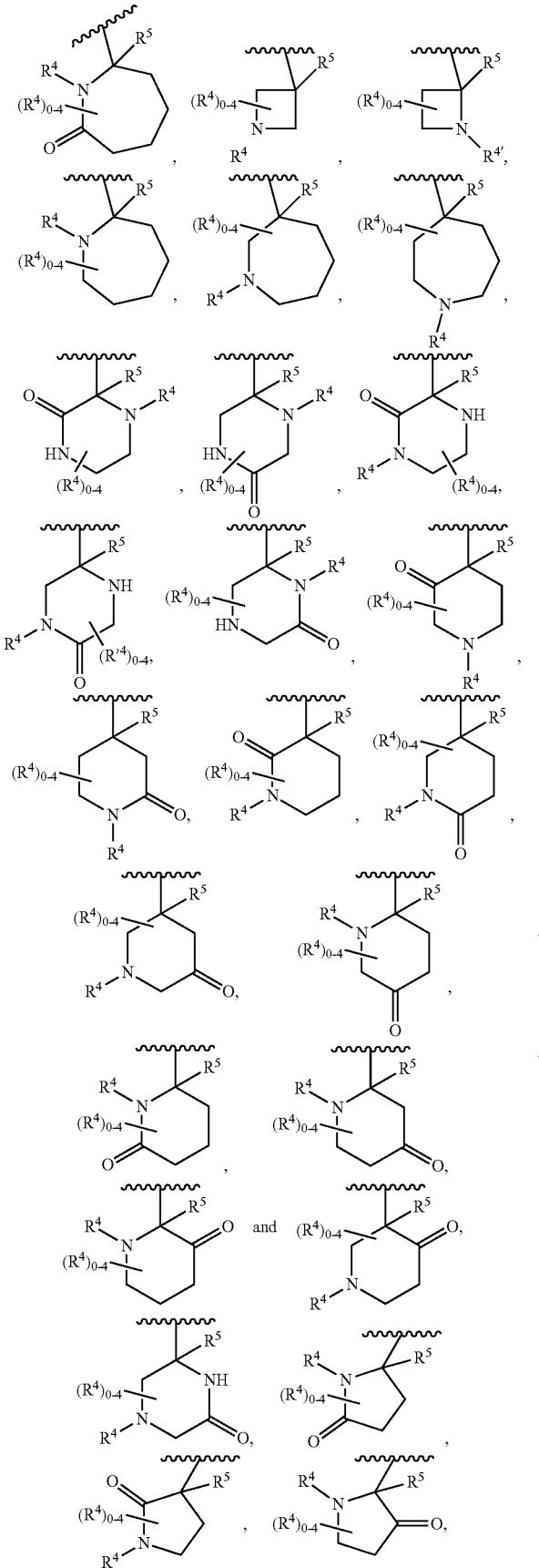

-continued

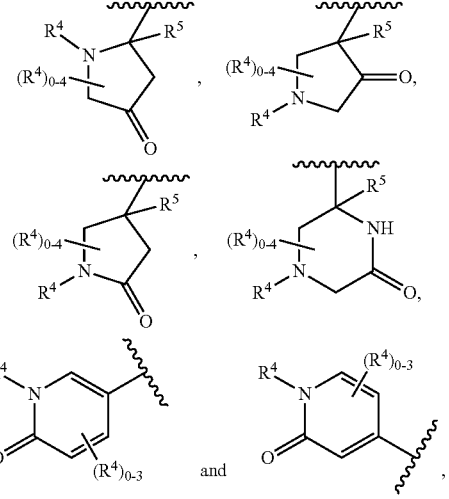

wherein R⁴ attached to the nitrogen atom of said 4 to 10 membered heterocyclic ring is selected from the group consisting of —$(X^4)_{0-1}$—CN, —$(X^4)_{0-1}$—NO$_2$, —$(X^4)_{0-1}$—SF$_5$, —$(X^4)_{0-1}$—OH, —$(X^4)_{0-1}$—NH$_2$, —$(X^4)_{0-1}$—N(H)(R$^{4a}$), —$(X^4)_{0-1}$—N(R$^{4b}$)(R$^{4a}$), —$(X^4)_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —$(X^4)_{0-1}$-(3-10 membered heterocycloalkyl), —$(X^4)_{0-1}$-(5-10 membered heteroaryl), —$(X^4)_{0-1}$-(3-7 membered cycloalkyl), —$(X^4)_{0-1}$—C(=Y$^4$)N(H)(R$^{4a}$), —$(X^4)_{0-1}$—C(=Y$^4$)NH$_2$, —$(X^4)_{0-1}$—C(=Y$^4$)N(R$^{4a}$)(R$^{4b}$), —$(X^4)_{0-1}$—C(=Y$^4$)OR$^{4a}$, —$(X^4)_{0-1}$—C(=Y$^4$)OH, —$(X^4)_{0-1}$—N(H)C(=Y$^4$)(R$^{4a}$), —$(X^4)_{0-1}$—N(R$^{4b}$)C(=Y$^4$)(R$^{4a}$), —$(X^4)_{0-1}$—N(H)C(=Y$^4$)OR$^{4a}$, —$(X^4)_{0-1}$—N(R$^{4b}$)C(=Y$^4$)OR$^4$, —$(X^4)_{0-1}$—S(O)$_{1-2}$R$^{4a}$, —$(X^4)_{0-1}$—N(H)S(O)$_{1-2}$R$^{4a}$, —$(X^4)_{0-1}$—N(R$^{4b}$)S(O)$_{1-2}$R$^{4a}$, —$(X^4)_{0-1}$—S(O)$_{0-1}$N(H)(R$^{4a}$), —$(X^4)_{0-1}$—S(O)$_{0-1}$N(R$^{4b}$)(R$^{4a}$), —$(X^4)_{0-1}$—S(O)$_{0-1}$NH$_2$, —$(X^4)_{0-1}$—S(=O)(=NR$^{4b}$)R$^{4a}$, —$(X^4)_{0-1}$—C(=Y$^4$)R$^{4a}$, —$(X^4)_{0-1}$—C(=Y$^4$)H, —$(X^4)_{0-1}$—C(=NOH)R$^{4a}$, —$(X^4)_{0-1}$—C(=NOR$^{4b}$)R$^{4a}$, —$(X^4)_{0-1}$—NHC(=Y$^4$)N(H)(R$^{4a}$), —$(X^4)_{0-1}$—NHC(=Y$^4$)NH$_2$, —$(X^4)_{0-1}$—NHC(=Y$^4$)N(R$^{4b}$)(R$^{4a}$), —$(X^4)_{0-1}$—NR$^{4a}$C(=Y$^4$)N(H)(R$^{4a}$), —$(X^4)_{0-1}$—N(R4a)C(=Y$^4$)NH$_2$, —$(X^4)_{0-1}$—C(=Y$^4$)R$^{4a}$, —$(X^4)_{0-1}$-OC(=Y$^4$)H, —$(X^4)_{0-1}$-OC(=Y$^4$)OR$^{4a}$, —$(X^4)_{0-1}$—OP(=Y$^4$)(OR$^{4a}$)(OR$^{4b}$), —SC(=Y$^4$)OR$^{4a}$ and —SC(=Y$^4$)N(R$^{4a}$)(R$^{4b}$) wherein R$^{4a}$ and R$^{4b}$ at each occurrence are each independently selected from the group consisting of C$_{1-6}$ alkyl, C$_{1-6}$ haloalkyl, C$_{1-6}$ heteroalkyl, 6-10 membered aryl, 3-7 membered cycloalkyl, 5-10 membered heteroaryl, 3-7 membered heterocycloalkyl, 6-10 membered aryl-C$_{1-4}$ alkyl, 3-7 membered cycloalkyl-C$_{1-4}$ alkyl, 5-10 membered heteroaryl-C$_{1-4}$ alkyl and 3-7 membered heterocycloalkyl-C$_{1-4}$ alkyl, and X$^4$ is selected from the group consisting of C$_{1-4}$ alkylene, C$_{1-4}$ haloalkylene, C$_{1-4}$ heteroalkylene, C$_{2-4}$ alkenylene and C$_{2-4}$ alkynylene; Y$^4$ is O, NR$^{4c}$ or S wherein R$^{4c}$ is hydrogen or C$_{1-6}$ alkyl; wherein the aromatic and aliphatic portions of R$^4$ is independently further substituted with 0 to 4 R$^{44}$ substituents selected from the group consisting of —F, —Cl, —Br, I, —CN, —NO$_2$, —SF$_5$, —OH, —NH$_2$, —CF$_3$, =O, C$_{1-6}$ alkyl, C$_{1-6}$ haloalkyl, C$_{1-6}$ heteroalkyl, C$_{1-6}$ alkoxy, C$_{1-6}$ alkylthio, 3-6 membered cycloalkyl, 3-6 membered heterocycloalkyl, —C(=O)N(H)(C$_{1-6}$ alkyl), —C(=O)N(C$_{1-6}$ alkyl)$_2$, —C(=O)NH$_2$, —C(=O)OC$_{1-6}$ alkyl, —C(=O)OH, —N(H)C(=O)(C$_{1-6}$ alkyl), —N(C$_{1-6}$ alkyl)C(=O)(C$_{1-6}$ alkyl), —N(H)C(=O)OC$_{1-6}$ alkyl, —N(C$_{1-6}$ alkyl)C(=O)OC$_{1-6}$ alkyl, —S(O)$_{1-2}$C$_{1-6}$ alkyl, —N(H)S(O)$_{1-2}$C$_{1-6}$ alkyl, —N(C$_{1-6}$ alkyl)S(O)$_{1-2}$C$_{1-6}$ alkyl, —S(O)$_{0-1}$N(H)(C$_{1-6}$ alkyl), —S(O)$_{0-1}$N(C$_{1-6}$ alkyl)$_2$, —S(O)$_{0-1}$NH$_2$, —C(=O)C$_{1-6}$ alkyl, —C(=NOH)C$_{1-6}$ alkyl, —C(=NOC$_{1-6}$ alkyl)C$_{1-6}$ alkyl, —NHC(=O)N(H)(C$_{1-6}$ alkyl), —NHC(=O)N(C$_{1-6}$ alkyl)$_2$, —NHC(=O)NH$_2$, —N(C$_1$-6 alkyl)C(=O)N(H)(C$_{1-6}$ alkyl), —N(C$_{1-6}$ alkyl)C(=O)NH$_2$, —OC(=O)C$_{1-6}$ alkyl, —OC(=O)OC$_{1-6}$ alkyl, —OP(=O)(OC$_{1-6}$ alkyl)$_2$, —SC(=O)OC$_{1-6}$ alkyl and —SC(=O)N(C$_{1-6}$ alkyl)$_2$; and the remainder R$^4$, if present on said 4-10 membered heterocyclic ring, is each independently selected from the group consisting of: —F, —Cl, —Br, I, —(X$^4$)$_{0-1}$—CN, —(X$^4$)$_{0-1}$—NO$_2$, —(X$^4$)$_{0-1}$—SF$_5$, —(X$^4$)$_{0-1}$—OH, —(X$^4$)$_{0-1}$—NH$_2$, —(X$^4$)$_{0-1}$—N(H)(R$^{4a}$), (X$^4$)$_{0-1}$—N(R$^{4b}$)(R$^{4a}$), —(X$^4$)$_{0-1}$—CF$_3$, C$_{1-6}$ alkyl, C$_{1-6}$ haloalkyl, C$_{1-6}$ heteroalkyl, C$_{1-6}$ alkoxy and C$_{1-6}$ alkylthio wherein X$^4$ is selected from the group consisting of C$_{1-4}$ alkylene, C$_{1-4}$ haloalkylene, C$_{1-4}$ heteroalkylene, C$_{2-4}$ alkenylene and C$_{2-4}$ alkynylene and R$^{4a}$ and R$^{4b}$ is each independently selected from the group consisting of: C$_{1-6}$ alkyl, C$_{1-6}$ haloalkyl and C$_{1-6}$ heteroalkyl.

5. The compound of claim 1, wherein R$^4$ is attached to a nitrogen atom (if present) in said 4-10 membered heterocyclic ring or is attached to a carbon atom of said 4-10 membered heterocyclic ring, wherein R$^4$ is selected from the group consisting of C$_{1-6}$ alkyl, C$_{1-6}$ haloalkyl, C$_{1-6}$ heteroalkyl, C$_{1-6}$ alkoxy, C$_{1-6}$ alkylthio, —(X$^4$)$_{0-1}$-(3-10 membered heterocycloalkyl), —(X$^4$)$_{0-1}$-(5-10 membered heteroaryl), —(X$^4$)$_{0-1}$-(3-7 membered cycloalkyl), —(X$^4$)$_{0-1}$—S(O)$_{1-2}$R$^{4a}$ and —(X$^4$)$_{0-1}$—C(=Y$^4$)R$^{4a}$, wherein Y$^4$ is O.

6. The compound of claim 1, wherein said 4 to 10 membered heterocyclic ring represented by the structure

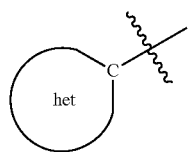

is selected from the group consisting of:

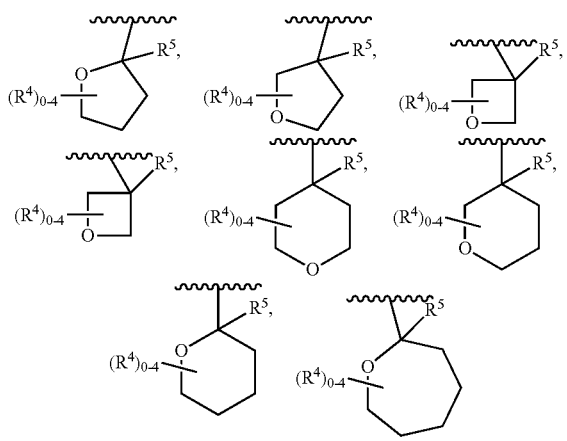

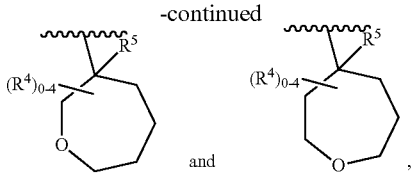

and wherein R$^4$ is selected from the group consisting of: —F, —Cl, —Br, —I, —(X$^4$)$_{0-1}$—CN, —(X$^4$)$_{0-1}$—NO$_2$, —(X$^4$)$_{0-1}$—SF$_5$, —(X$^4$)$_{0-1}$—OH, —(X$^4$)$_{0-1}$—NH$_2$, —(X$^4$)$_{0-1}$—N(H)(R$^{4a}$), —(X$^4$)$_{0-1}$N(R$^{4b}$)(R$^{4a}$), —(X$^4$)$_{0-1}$—CF$_3$, C$_{1-6}$ alkyl, C$_{1-6}$ haloalkyl, C$_{1-6}$ heteroalkyl, C$_{1-6}$ alkoxy and C$_{1-6}$ alkylthio wherein X$^4$ is selected from the group consisting of C$_{1-4}$ alkylene, C$_{1-4}$ haloalkylene, C$_{1-4}$ heteroalkylene, C$_{2-4}$ alkenylene and C$_{2-4}$ alkynylene and R$^{4a}$ and R$^{4b}$ is each independently selected from the group consisting of: C$_{1-6}$ alkyl, C$_{1-6}$ haloalkyl and C$_{1-6}$ heteroalkyl.

7. The compound of claim 1, wherein R$^5$ is selected from the group consisting of hydrogen, C$_{1-4}$ alkyl, C$_{1-4}$ haloalkyl, hydroxy, OR$^{5a}$, —CN, —F, —Cl, —Br and —I.

8. The compound of claim 1, wherein R$^1$ is selected from the group consisting of C$_{1-6}$ haloalkyl, C$_{1-6}$ heteroalkyl, —OR$^{1a}$, —SR$^{1a}$, —N(H)(R$^{1a}$), and —N(R$^{1a}$)(R$^{1b}$), methyl, ethyl, propyl, isopropyl, butyl, sec-butyl, tert-butyl, cyclopropane, cyclobutane, cyclopentane, cyclohexane, cycloheptane, morpholine, homomorpholine, piperidine, homopiperidine, piperazine, homopiperazine, azetidine, pyrrolidine, benzene, pyrrole, pyrazole, imidazole, triazole, tetrazole, pyridine, pyrimidine, pyrazine, pyridazine, oxetane, tetrahydrofuran, tetrahydropyran, -oxa-5-azabicyclo[2.2.1]heptane, 2-oxa-6-azaspiro[3.3]heptane, 8-oxa-3-azabicyclo[3.2.1]octane, 3-oxa-8-azabicyclo[3.2.1]octane, 7-oxabicyclo[2.2.1]heptane, 7-azabicyclo[2.2.1]heptane, nonbornane, bicyclo[2.2.2]octane, 2-azabicyclo[2.2.2]octane, 2-oxabicyclo[2.2.2]octane, 2-oxa-5-azabicyclo[2.2.2]octane and 2,5-diazabicyclo[2.2.2]octane, 5,6,7,8-tetrahydroimidazo[1,2-a]pyrazine, 4,5,6,7-tetrahydro-3H-imidazo[4,5-c]pyridine, wherein R$^{1a}$ and R$^{1b}$ are each independently selected from the group consisting of C$_{1-6}$ alkyl, C$_{1-6}$ haloalkyl, C$_{1-6}$ heteroalkyl, 3-10 membered cycloalkyl and 3-10 membered heterocycloalkyl, and wherein the aliphatic and aromatic portions of R$^1$ are independently further substituted with 0 to 5 R$^{41}$ substituents selected from the group consisting of —F, —Cl, —Br, I, —CN, —NO$_2$, —SF$_5$, —OH, —NH$_2$, —CF$_3$, =O, C$_{1-4}$ alkyl, C$_{1-4}$ haloalkyl, C$_{1-4}$ heteroalkyl, C$_{1-4}$ alkoxy, C$_{1-4}$ alkylthio, C$_{1-4}$ alkylamino, C$_{1-4}$ dialkylamino, R$^{1c}$—C(=O)—, —R$^{1c}$—C(=O)N(H)—, R$^{1c}$—C(=O)N(R$^{1d}$)—, R$^{1c}$—C(=O)O—, R$^{1c}$—C—S(O)$_{1-2}$—, R$^{1c}$—S(O)$_{1-2}$N(R$^{1d}$)—, R$^{1c}$—S(O)$_{1-2}$N(H)—, 3-6 membered cycloalkyl, phenyl, 5-6 membered heteroaryl and 3-7 membered heterocycloalkyl, wherein R$^{1c}$ is selected from the group consisting of C$_{1-6}$ alkyl, C$_{1-6}$ haloalkyl, C$_{5-6}$ heteraryl, 3-7 membered heterocycloalkyl, phenyl and 3-6 membered cycloalkyl, R$^{1d}$ is selected from the group consisting of hydrogen, C$_{1-3}$ alkyl and C$_{1-3}$ haloalkyl, and wherein said 5-6 membered heteraryl, phenyl, 3-6 membered heteroaryl, 3-6 membered cycloalkyl and 3-7 membered heterocycloalkyl of the R$^{41}$ substituent are substituted with from 0-4 substituents selected from —F, —Cl, —Br, I, —CN, —NO$_2$, —SF$_5$, —OH, —NH$_2$, —CF$_3$, C$_{1-4}$ alkyl, C$_{1-4}$ haloalkyl, C$_{1-4}$ alkoxy, C$_{1-4}$ alkylthio, C$_{1-4}$ alkylamino and C$_{1-4}$ dialkylamino.

9. The compound of claim 8, wherein R$^1$ is selected from the group consisting of pyrrolidin-1-yl, phenyl, piperidin-1- yl, pyrrol-1-yl, azetidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 2-oxa-6-azaspiro[3.3]hept-6-yl, -8-oxa-3-azabicyclo[3.2.1]octane, methyl, isopropyl, isobutyl, cyclopropyl, pyrazol-1-yl, 4,5,6,7-tetrahydro-1H-imidazo[4,5-c]pyridin-5-yl, 3,5,6,7,8,8a-hexahydroimidazo[1,2-a]pyrazin-7-yl, —N(H)R$^{1a}$, and —N(R$^{1a}$)(R$^{1b}$), wherein R$^{1a}$ and R$^{1b}$ are each independently selected from the group consisting of methyl, ethyl, propyl, butyl, methoxyethyl, ethoxyethyl, hydroxyethyl, methoxypropyl, ethyoxypropyl and hydroxypropyl, wherein the aliphatic and/or aromatic portions or R$^1$ is substituted with 0 to 4 substituents selected from the group consisting of methyl, ethyl, propyl, isopropyl, butyl, isobutyl, fluoro, chloro, bromo, iodo, cyano, methoxymethyl, methoxyethyl, methoxypropyl, trifluoromethyl, monofluoromethyl, difluromethyl, 2-methylpyrimidin-4-yl, 4-methyltriazol-3-yl, 1,2,4-triazol-3-yl, morpholinocarbonyl, morpholino, 2-methyl-pyrimidin-6-yl, 6-methyl-pyrimidin-2-yl, 4-methyl-1,2,4-triazol-3-yl, methyl aminomethylcarbonyl and hydroxy.

10. The compound of claim 1, wherein R$^3$ is selected from the group consisting of —F, —Cl, —Br, I, —(X$^3$)$_{0-1}$—CN, —(X$^3$)$_{0-1}$—NO$_2$, —(X$^3$)$_{0-1}$—SF$_5$, —(X$^3$)$_{0-1}$—OH, —(X$^3$)$_{0-1}$—NH$_2$, —(X$^3$)$_{0-1}$—N(H)(R$^{3a}$), (X$^3$)$_{0-1}$—N(R$^{3b}$)(R$^{3a}$), —(X$^3$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^3$)$_{0-1}$-3-7 membered cycloalkyl, —(X$^3$)$_{0-1}$-3-7 membered heterocycloalkyl, —(X$^3$)$_{0-1}$-5-6 membered heteroaryl, —(X$^3$)$_{0-1}$—C$_6$ aryl, —(X$^3$)$_{0-1}$—C(═Y$^3$)N(H)(R$^{3a}$), —(X$^3$)$_{0-1}$—C(═Y$^3$)NH$_2$, —(X$^3$)$_{0-1}$—C(═Y$^3$)N(R$^{3a}$)(R$^{3b}$), —(X$^3$)$_{0-1}$—C(═Y$^3$)OR$^{3a}$, —(X$^3$)$_{0-1}$—C(═Y$^3$)OH, —(X$^3$)$_{0-1}$—N(H)C(═Y$^3$)(R$^{3a}$), —(X$^3$)$_{0-1}$—N(R$^{3b}$)C(═Y$^3$)(R$^{3a}$), —(X$^3$)$_{0-1}$N(H)C(═Y$^3$)OR$^{3a}$, (X$^3$)$_{0-1}$N(R$^{3b}$)C(═Y$^3$)OR$^{3a}$, —(X$^3$)$_{0-1}$—S(O)$_{1-2}$R$^{3a}$, —(X$^3$)$_{0-1}$—N(H)S(O)$_{1-2}$ R$^{3a}$, —(X$^3$)$_{0-1}$—N(R$^{3b}$)S(O)$_{1-2}$R$^{3a}$, —(X$^3$)$_{0-1}$—S(O)$_{0-1}$ N(H)(R$^{3a}$), —(X$^3$)$_{0-1}$—S(O)$_{0-1}$N(R$^{3b}$)(R$^{3a}$), —(X$^3$)$_{0-1}$—S(O)$_{0-1}$NH$_2$, —(X$^3$)$_{0-1}$—C(═Y$^3$)R$^{3a}$, —(X$^3$)$_{0-1}$ —C(═Y$^3$)H, —(X$^3$)$_{0-1}$—NHC(═Y$^3$)N(H)(R$^{3a}$), —(X$^3$)$_{0-1}$ —NHC(═Y$^3$)NH$_2$, —(X$^3$)$_{0-1}$ —NHC(═Y$^3$)N(R$^{3b}$)(R$^{3a}$), —(X$^3$)$_{0-1}$N(R$^{3a}$)C(═Y$^3$)N(H)(R$^{3a}$), —(X$^3$)$_{0-1}$—N(R$^{3a}$)C(═Y$^3$)NH$_2$, wherein Y is O, or alternatively, any two R$^3$ substituents located on adjacent atoms are optionally combined to form a 5-6 membered heteroaryl ring comprising 1-2 heteroatoms selected from N, O and S and further comprising 0 to 4 R$^{3a}$ substituents, and m is an integer from 1 to 4.

11. The compound of claim 1, wherein R$^3$ is selected from the group consisting of —F, —Cl, —Br, I, C$_{1-6}$ alkyl, C$_{1-6}$ haloalkyl, C$_{1-6}$ heteroalkyl, C$_{1-6}$ alkoxy, —(X$^3$)$_{0-1}$—N(H)C(═Y$^3$)(R$^{3a}$), —(X$^3$)$_{0-1}$N(R$^{3b}$)C(═Y$^3$)(R$^{3a}$), —(X$^3$)$_{0-1}$—C(═Y$^3$)N(H)(R$^{3a}$), —(X$^3$)$_{0-1}$—C(═Y$^3$)NH$_2$, —(X$^3$)$_{0-1}$—C(═Y$^3$)N(R$^{3a}$)(R$^{3b}$), thiophene, wherein if R$^3$ is thiophene, or R$^{3a}$ and R$^{3b}$ is independently 3-7 membered cycloalkyl, 3-7 membered cycloalkyl-C$_{1-4}$ alkyl, 3-7 membered heterocycloalkyl, 3-7 membered heterocycloalkyl-C$_{1-4}$ alkyl, 5-6 membered heteroaryl, 5-6 membered heteroaryl-C$_{14}$ alkyl, C$_6$ aryl, C$_6$ aryl-C$_{1-4}$ alkyl or benzyl then said thiophene, 3-7 membered cycloalkyl, 3-7 membered cycloalkyl-C$_{1-4}$ alkyl, 3-7 membered heterocycloalkyl, 3-7 membered heterocycloalkyl-C$_{1-4}$ alkyl, 5-6 membered heteroaryl, 5-6 membered heteroaryl-C$_{1-4}$ alkyl, C$_6$ aryl, C$_6$ aryl-C$_{1-4}$ alkyl or benzyl is substituted from 0 to 4 R$^{43}$ substituents, or alternatively, any two R$^3$ substituents located on adjacent atoms are optionally combined to form a thiazole ring further comprising 0 to 4 R$^{3a}$ substituents, and m is an integer from 1 to 4.

12. The compound of claim 11, wherein R$^3$ is selected from the group consisting of trifluoromethyl, methyl, ethyl, propyl, butyl, isopropyl, sec-butyl, tert-butyl, methoxy, ethoxy, cyclopropyl, cyclobutyl, thienyl and —C(═O)NH$_2$.

13. The compound of claim 1, wherein said compound of formula I has the subformula selected from the group consisting of:

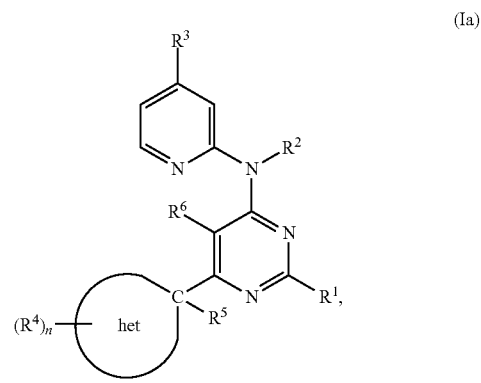

(Ia)

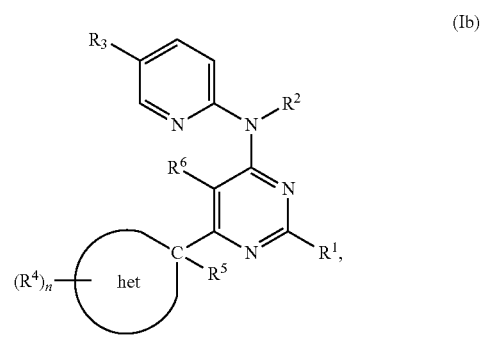

(Ib)

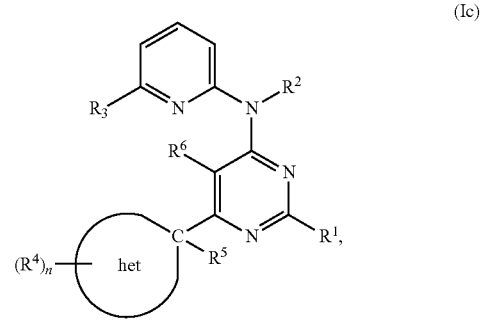

(Ic)

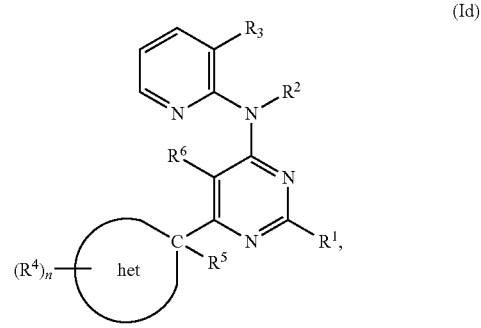

(Id)

507
-continued
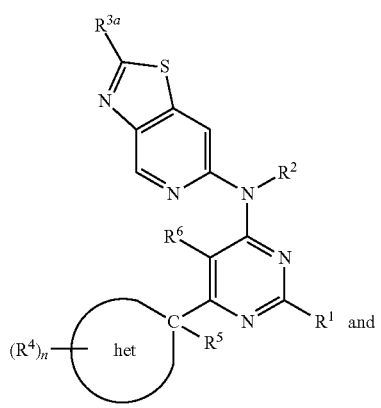
(Ie)
and
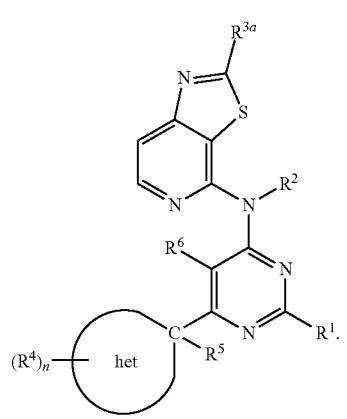
(If)
14. The compound of claim 1, wherein said compound of formula I has a subformula selected from the group consisting of:
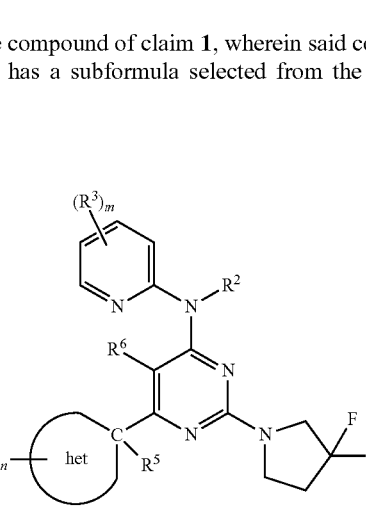
(IIa)
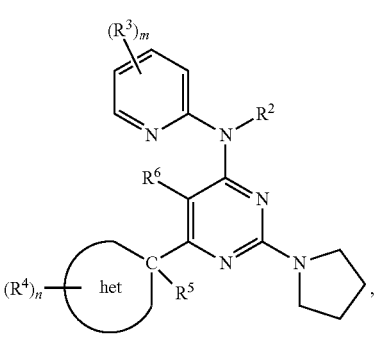
(IIb)
508
-continued
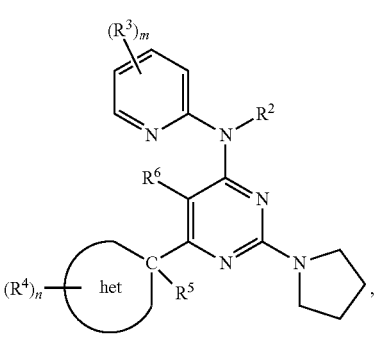
(IIc)
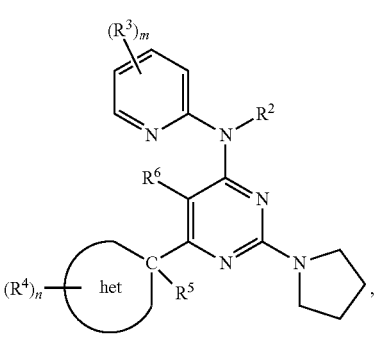
(IId)
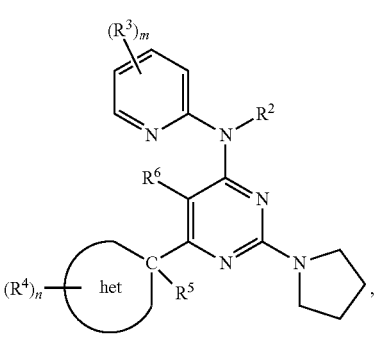
(IIe)
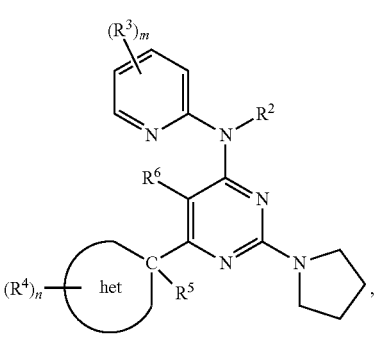
(IIf)

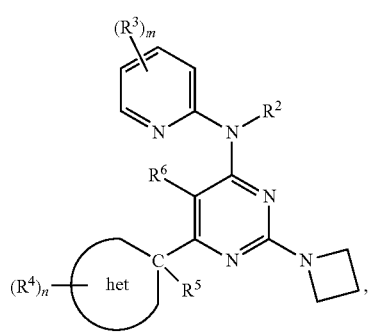
(IIg)
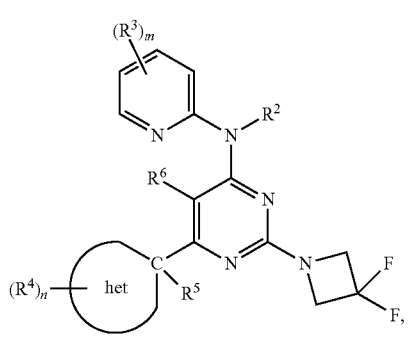
(IIh)
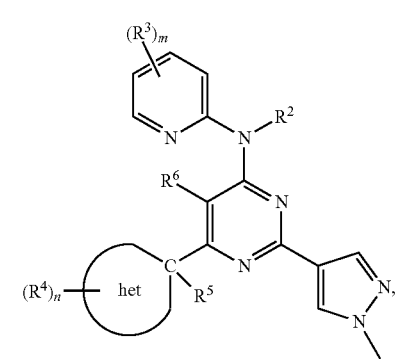
(IIi)
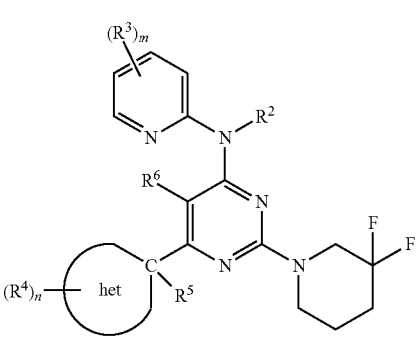
(IIj)
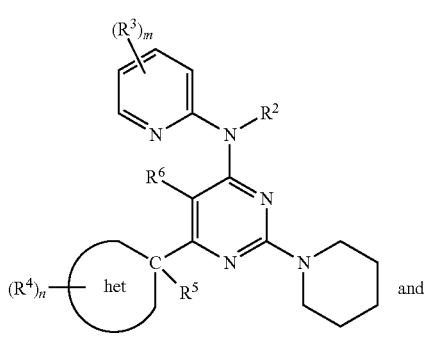
(IIk)
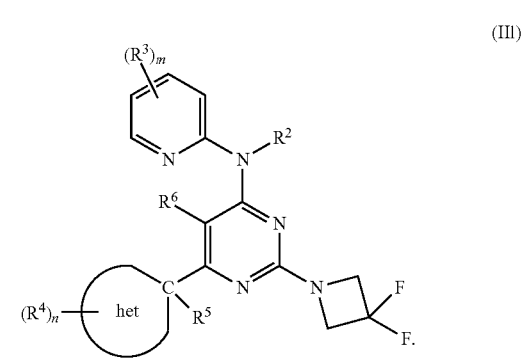
(IIl)
15. The compound of claim 1, wherein a compound of formula I has the subformula selected from the group consisting of:
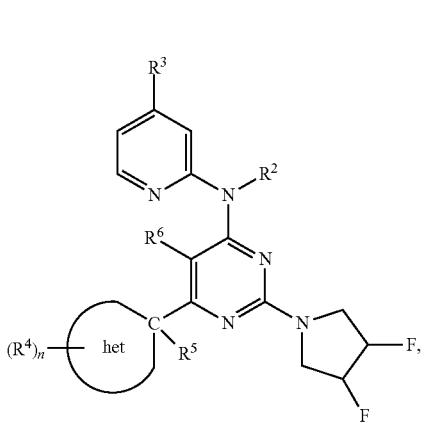
(IIIa)
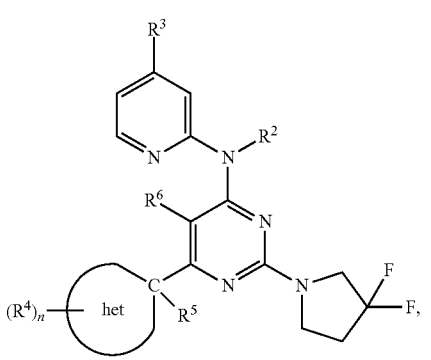
(IIIb)

(IIIc)
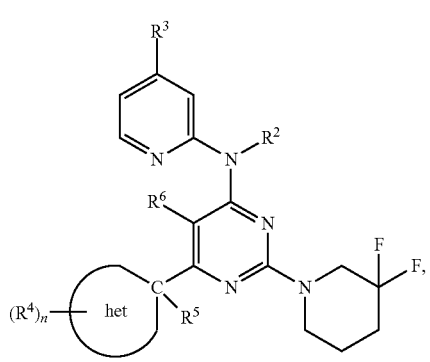
(IIId)
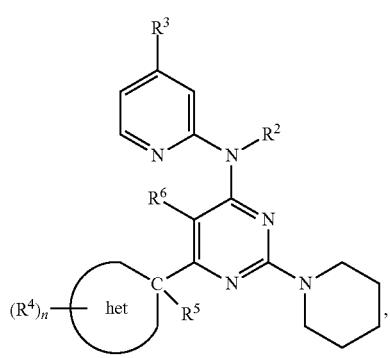
(IIIe)
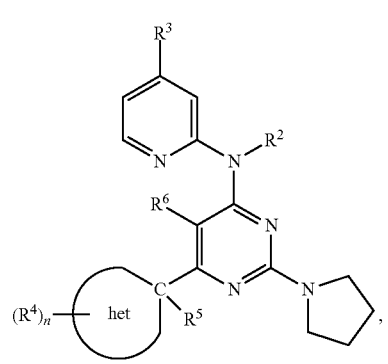
(IIIf)
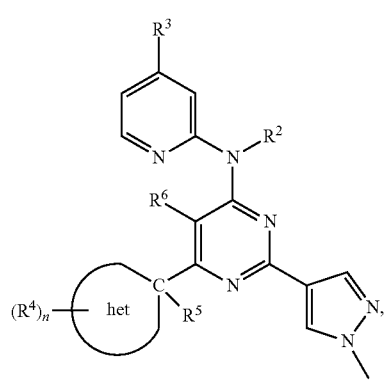
(IIIg)
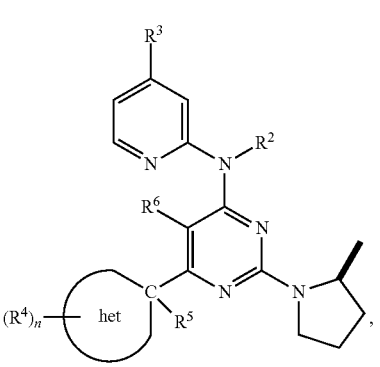
(IIIh)
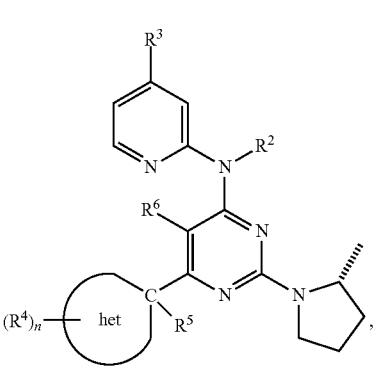
(IIIi)
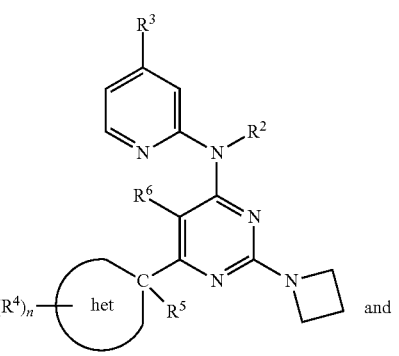
and
(IIIj)
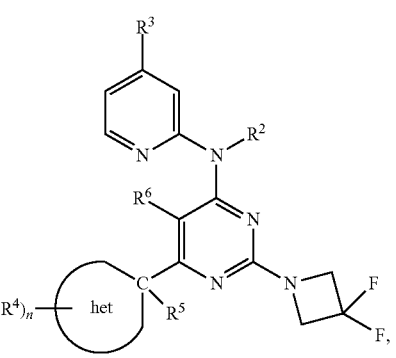
wherein $R^3$ is selected from the group consisting of methyl, monofluoromethyl, difluoromethyl, trifluoromethyl, isopropyl, cyclopropyl, cyclobutyl and methoxy.

16. A compound of claim 1 selected from the group consisting of:

| No | Name |
|---|---|
| 24 | (4-Methyl-pyridin-2-yl)-(6-piperidin-4-yl-2-pyrrolidin-1-yl-pyrimidin-4-yl)-amine; |
| 25 | {4-[6-(4-Methyl-pyridin-2-ylamino)-2-pyrrolidin-1-yl-pyrimidin-4-yl]-piperidin-1-yl}-phenyl-methanone; |
| 26 | (2-Piperidin-1-yl-6-piperidin-3-yl-pyrimidin-4-yl)-(4-trifluoromethyl-pyridin-2-yl)-amine; |
| 27 | (6-Piperidin-3-yl-2-pyrrolidin-1-yl-pyrimidin-4-yl)-(4-trifluoromethyl-pyridin-2-yl)-amine; |
| 28 | [6-Piperidin-3-yl-2-(3-trifluoromethyl-pyrrolidin-1-yl)-pyrimidin-4-yl]-(4-trifluoromethyl-pyridin-2-yl)-amine; |
| 29 | [2-(3,3-Difluoro-piperidin-1-yl)-6-piperidin-3-yl-pyrimidin-4-yl]-(4-trifluoromethyl-pyridin-2-yl)-amine; |
| 30 | [2-(3,3-Difluoro-pyrrolidin-1-yl)-6-piperidin-3-yl-pyrimidin-4-yl]-(4-trifluoromethyl-pyridin-2-yl)-amine; |
| 31 | [2-(2-Methyl-pyrrolidin-1-yl)-6-piperidin-3-yl-pyrimidin-4-yl]-(4-trifluoromethyl-pyridin-2-yl)-amine; |
| 41 | (2-Azetidin-1-yl-6-piperidin-4-yl-pyrimidin-4-yl)-(4-methyl-pyridin-2-yl)-amine; |
| 42 | (4-Methyl-pyridin-2-yl)-(2-piperidin-1-yl-6-piperidin-3-yl-pyrimidin-4-yl)-amine; |
| 43 | (4-Methyl-pyridin-2-yl)-(2-piperidin-1-yl-6-piperidin-4-yl-pyrimidin-4-yl)-amine; |
| 44 | {3-[6-(4-Methyl-pyridin-2-ylamino)-2-pyrrolidin-1-yl-pyrimidin-4-yl]-piperidin-1-yl}-phenyl-methanone; |
| 45 | 1-{3-[6-(4-Methyl-pyridin-2-ylamino)-2-pyrrolidin-1-yl-pyrimidin-4-yl]-piperidin-1-yl}-ethanone; |
| 46 | 2-{Methyl-[4-piperidin-3-yl-6-(4-trifluoromethyl-pyridin-2-ylamino)-pyrimidin-2-yl]-amino}-ethanol; |
| 47 | 2-{Methyl-[4-pyrrolidin-3-yl-6-(4-trifluoromethyl-pyridin-2-ylamino)-pyrimidin-2-yl]-amino}-ethanol; |
| 63 | [2-(3,3-Difluoro-azetidin-1-yl)-6-piperidin-4-yl-pyrimidin-4-yl]-(4-trifluoromethyl-pyridin-2-yl)-amine; |
| 64 | [2-(3,3-Difluoro-azetidin-1-yl)-6-piperidin-3-yl-pyrimidin-4-yl]-(4-trifluoromethyl-pyridin-2-yl)-amine; |
| 65 | [2-(2-Methyl-pyrrolidin-1-yl)-6-piperidin-4-yl-pyrimidin-4-yl]-(4-trifluoromethyl-pyridin-2-yl)-amine; |
| 66 | (2-Pyrrolidin-1-yl-6-pyrrolidin-3-yl-pyrimidin-4-yl)-(4-trifluoromethyl-pyridin-2-yl)-amine; |
| 67 | [6-Piperidin-4-yl-2-(3-trifluoromethyl-pyrrolidin-1-yl)-pyrimidin-4-yl]-(4-trifluoromethyl-pyridin-2-yl)-amine; |
| 68 | [2-(3,3-Difluoro-pyrrolidin-1-yl)-6-pyrrolidin-3-yl-pyrimidin-4-yl]-(4-trifluoromethyl-pyridin-2-yl)-amine; |
| 69 | [2-(3,3-Difluoro-piperidin-1-yl)-6-piperidin-4-yl-pyrimidin-4-yl]-(4-trifluoromethyl-pyridin-2-yl)-amine; |
| 70 | [2-(4,4-Difluoro-piperidin-1-yl)-6-piperidin-4-yl-pyrimidin-4-yl]-(4-trifluoromethyl-pyridin-2-yl)-amine; |
| 71 | [6-Pyrrolidin-3-yl-2-(3-trifluoromethyl-pyrrolidin-1-yl)-pyrimidin-4-yl]-(4-trifluoromethyl-pyridin-2-yl)-amine; |
| 72 | [2-(1-Methyl-1H-pyrazol-4-yl)-6-piperidin-3-yl-pyrimidin-4-yl]-(4-methyl-pyridin-2-yl)-amine; |
| 73 | (4-Methyl-pyridin-2-yl)-(2-piperidin-1-yl-6-pyrrolidin-3-yl-pyrimidin-4-yl)-amine; |
| 74 | {3-[2-Azetidin-1-yl-6-(4-methyl-pyridin-2-ylamino)-pyrimidin-4-yl]-piperidin-1-yl}-phenyl-methanone; |
| 75 | 1-{4-[2-Azetidin-1-yl-6-(4-methyl-pyridin-2-ylamino)-pyrimidin-4-yl]-piperidin-1-yl}-ethanone; |
| 76 | 1-{3-[6-(4-Methyl-pyridin-2-ylamino)-2-piperidin-1-yl-pyrimidin-4-yl]-piperidin-1-yl}-ethanone; |
| 77 | 2-{Methyl-[4-piperidin-4-yl-6-(4-trifluoromethyl-pyridin-2-ylamino)-pyrimidin-2-yl]-amino}-ethanol; |
| 80 | {3-[2-(1-Methyl-1H-pyrazol-4-yl)-6-(4-methyl-pyridin-2-ylamino)-pyrimidin-4-yl]-piperidin-1-yl}-phenyl-methanone; |
| 81 | (4-Methyl-pyridin-2-yl)-(6-piperidin-3-yl-2-pyrrolidin-1-yl-pyrimidin-4-yl)-amine; |
| 82 | (4-Methyl-pyridin-2-yl)-(2-pyrrolidin-1-yl-6-pyrrolidin-3-yl-pyrimidin-4-yl)-amine; |
| 83 | {3-[6-(4-Methyl-pyridin-2-ylamino)-2-pyrrolidin-1-yl-pyrimidin-4-yl]-pyrrolidin-1-yl}-phenyl-methanone; |
| 84 | {3-[6-(4-Methyl-pyridin-2-ylamino)-2-piperidin-1-yl-pyrimidin-4-yl]-piperidin-1-yl}-phenyl-methanone; |
| 85 | {3-[6-(4-Methyl-pyridin-2-ylamino)-2-piperidin-1-yl-pyrimidin-4-yl]-pyrrolidin-1-yl}-phenyl-methanone; |
| 86 | 1-{3-[2-(1-Methyl-1H-pyrazol-4-yl)-6-(4-methyl-pyridin-2-ylamino)-pyrimidin-4-yl]-piperidin-1-yl}-ethanone; |
| 87 | 1-{3-[2-Azetidin-1-yl-6-(4-methyl-pyridin-2-ylamino)-pyrimidin-4-yl]-piperidin-1-yl}-ethanone; |
| 88 | 1-{3-[2-Azetidin-1-yl-6-(4-methyl-pyridin-2-ylamino)-pyrimidin-4-yl]-pyrrolidin-1-yl}-ethanone; |
| 89 | 1-{3-[6-(4-Methyl-pyridin-2-ylamino)-2-pyrrolidin-1-yl-pyrimidin-4-yl]-pyrrolidin-1-yl}-ethanone; |
| 90 | 1-{3-[6-(4-Methyl-pyridin-2-ylamino)-2-piperidin-1-yl-pyrimidin-4-yl]-pyrrolidin-1-yl}-ethanone; |
| 91 | 1-{4-[6-4-Methyl-pyridin-2-ylamino)-2-piperidin-1-yl-pyrimidin-4-yl]-piperidin-1-yl}-ethanone; |
| 92 | [2-(3,3-Difluoro-pyrrolidin-1-yl)-6-piperidin-4-yl-pyrimidin-4-yl]-(4-trifluoromethyl-pyridin-2-yl)-amine; |
| 93 | (2-Piperidin-1-yl-6-piperidin-4-yl-pyrimidin-4-yl)-(4-trifluoromethyl-pyridin-2-yl)-amine; |
| 94 | [2-(2-Methyl-pyrrolidin-1-yl)-6-pyrrolidin-3-yl-pyrimidin-4-yl]-(4-trifluoromethyl-pyridin-2-yl)-amine; |
| 95 | (2-Piperidin-1-yl-6-pyrrolidin-3-yl-pyrimidin-4-yl)-(4-trifluoromethyl-pyridin-2-yl)-amine; |
| 96 | [2-(3,3-Difluoro-piperidin-1-yl)-6-pyrrolidin-3-yl-pyrimidin-4-yl]-(4-trifluoromethyl-pyridin-2-yl)-amine; |

| No | Name |
|---|---|
| 97 | [2-[3,3-Difluoro-azetidin-1-yl)-6-pyrrolidin-3-yl-pyrimidin-4-yl]-(4-trifluoromethyl-pyridin-2-yl)-amine; |
| 98 | (4-Methyl-pyridin-2-yl)-(2-phenyl-6-piperidin-3-yl-pyrimidin-4-yl)-amine; |
| 99 | (2-Phenyl-6-piperidin-3-yl-pyrimidin-4-yl)-(4-trifluoromethyl-pyridin-2-yl)-amine; |
| 100 | 1-{4-[2-(2-Methyl-pyrrolidin-1-yl)-6-(4-trifluoromethyl-pyridin-2-ylamino)-pyrimidin-4-yl]-piperidin-1-yl}-ethanone; |
| 101 | 1-{3-[2-(2-Methyl-pyrrolidin-1-yl)-6-(4-trifluoromethyl-pyridin-2-ylamino)-pyrimidin-4-yl]-piperidin-1-yl}-ethanone; |
| 102 | (2-Methyl-6-pyrrolidin-3-yl-pyrimidin-4-yl)-(5-trifluoromethyl-pyridin-2-yl)-amine; |
| 103 | (5-Methyl-pyridin-2-yl)-(2-methyl-6-pyrrolidin-3-yl-pyrimidin-4-yl)-amine; |
| 104 | [2-[1-Methyl-1H-pyrazol-4-yl)-6-pyrrolidin-3-yl-pyrimidin-4-yl]-(4-methyl-pyridin-2-yl)-amine; |
| 105 | 4-[2-(3,3-Difluoro-pyrrolidin-1-yl)-6-(4-trifluoromethyl-pyridin-2-ylamino)-pyrimidin-4-yl]-piperidine-4-carbonitrile; |
| 106 | 1-{3-[6-(4-Methyl-pyridin-2-ylamino)-2-phenyl-pyrimidin-4-yl]-piperidin-1-yl}-ethanone; |
| 107 | 1-{3-[2-Phenyl-6-(4-trifluoromethyl-pyridin-2-ylamino)-pyrimidin-4-yl]-piperidin-1-yl}-ethanone; |
| 108 | 1-{3-[2-Isopropyl-6-(4-methyl-pyridin-2-ylamino)-pyrimidin-4-yl]-piperidin-1-yl}-ethanone; |
| 109 | 1-{3-[2-Isopropyl-6-(4-trifluoromethyl-pyridin-2-ylamino)-pyrimidin-4-yl]-piperidin-1-yl}-ethanone; |
| 110 | (2-Morpholin-4-yl-6-piperidin-4-yl-pyrimidin-4-yl)-(4-trifluoromethyl-pyridin-2-yl)-amine; |
| 111 | [2-((R)-2-Methyl-pyrrolidin-1-yl)-6-piperidin-4-yl-pyrimidin-4-yl]-(4-trifluoromethyl-pyridin-2-yl)-amine; |
| 112 | [2-((S)-2-Methyl-pyrrolidin-1-yl)-6-piperidin-4-yl-pyrimidin-4-yl]-(4-trifluoromethyl-pyridin-2-yl)-amine; |
| 113 | [2-(1-Methyl-1H-pyrazol-4-yl)-6-piperidin-4-yl-pyrimidin-4-yl]-(4-methyl-pyridin-2-yl)-amine; |
| 114 | {3-[2-(1-Methyl-1H-pyrazol-4-yl)-6-(4-methyl-pyridin-2-ylamino)-pyrimidin-4-yl]-pyrrolidin-1-yl}-phenyl-methanone; |
| 115 | (2-Azetidin-1-yl-6-piperidin-3-yl-pyrimidin-4-yl)-(4-methyl-pyridin-2-yl)-amine; |
| 116 | {3-[2-Azetidin-1-yl-6-(4-methyl-pyridin-2-ylamino)-pyrimidin-4-yl]-pyrrolidin-1-yl}-phenyl-methanone; |
| 117 | 3-{4-[6-(4-Methyl-pyridin-2-ylamino)-2-piperidin-1-yl-pyrimidin-4-yl]-piperidin-1-yl{-3-oxo-propionitrile; |
| 118 | 1-{3-[2-(1-Methyl-1H-pyrazol-4-yl)-6-(4-methyl-pyridin-2-ylamino)-pyrimidin-4-yl]-pyrrolidin-1-yl}-ethanone; |
| 119 | 1-{4-[6-(4-Methyl-pyridin-2-ylamino)-2-pyrrolidin-1-yl-pyrimidin-4-yl]-piperidin-1-yl{-ethanone; |
| 120 | (4-Chloro-pyridin-2-yl)-[2-(3,3-difluoro-pyrrolidin-1-yl)-6-piperidin-4-yl-pyrimidin-4-yl]-amine; |
| 121 | [2-{3,3-Difluoro-pyrrolidin-1-yl)-6-(1-methyl-pyrrolidin-3-yl)-pyrimidin-4-yl]-(4-trifluoromethyl-pyridin-2-yl)-amine; |
| 122 | (4-Methyl-pyridin-2-yl)-[2-(2-methyl-pyrrolidin-1-yl)-6-piperidin-4-yl-pyrimidin-4-yl]-amine; |
| 123 | 3-{3-[2-(1-Methyl-1H-pyrazol-4-yl)-6-(4-methyl-pyridin-2-ylamino)-pyrimidin-4-yl]-piperidin-1-yl}-3-oxo-propionitrile; |
| 124 | 3-{4-[6-(4-Methyl-pyridin-2-ylamino)-2-pyrrolidin-1-yl-pyrimidin-4-yl]-piperidin-1-yl{-3-oxo-propionitrile; |
| 125 | (4-Methoxy-pyridin-2-yl)-[2-(2-methyl-pyrrolidin-1-yl)-6-piperidin-4-yl-pyrimidin-4-yl]-amine; |
| 126 | (4-Methoxy-pyridin-2-yl)-[2-(2-methyl-pyrrolidin-1-yl)-6-pyrrolidin-3-yl-pyrimidin-4-yl]-amine; |
| 127 | (4-Methoxy-pyridin-2-yl)-[2-(2-methyl-pyrrolidin-1-yl)-6-piperidin-3-yl-pyrimidin-4-yl]-amine; |
| 128 | 1-{4-[6-(4-Methoxy-pyridin-2-ylamino)-2-(2-methyl-pyrrolidin-1-yl)-pyrimidin-4-yl]-piperidin-1-yl}-ethanone; |
| 129 | 1-{3-[6-(4-Methoxy-pyridin-2-ylamino)-2-(2-methyl-pyrrolidin-1-yl)-pyrimidin-4-yl]-pyrrolidin-1-yl}-ethanone; |
| 130 | (2-Morpholin-4-yl-6-piperidin-3-yl-pyrimidin-4-yl)-(4-trifluoromethyl-pyridin-2-yl)-amine; |
| 131 | (2-Morpholin-4-yl-6-pyrrolidin-3-yl-pyrimidin-4-yl)-(4-trifluoromethyl-pyridin-2-yl)-amine; |
| 132 | 1-{3-[2-Morpholin-4-yl-6-(4-trifluoromethyl-pyridin-2-ylamino)-pyrimidin-4-yl]-piperidin-1-yl}-ethanone; |
| 133 | 1-{4-[2-Morpholin-4-yl-6-(4-trifluoromethyl-pyridin-2-ylamino)-pyrimidin-4-yl]-piperidin-1-yl}-ethanone; |
| 134 | 1-{3-[2-Morpholin-4-yl-6-(4-trifluoromethyl-pyridin-2-ylamino)-pyrimidin-4-yl]-pyrrolidin-1-yl}-ethanone; |
| 135 | (4-Methyl-pyridin-2-yl)-(2-morpholin-4-yl-6-piperidin-3-yl-pyrimidin-4-yl)-amine; |
| 136 | (4-Methyl-pyridin-2-yl)-(2-morpholin-4-yl-6-piperidin-4-yl-pyrimidin-4-yl)-amine; |
| 137 | (4-Methyl-pyridin-2-yl)-(2-morpholin-4-yl-6-pyrrolidin-3-yl-pyrimidin-4-yl)-amine; |
| 138 | 1-{3-[6-(4-Methyl-pyridin-2-ylamino)-2-morpholin-4-yl-pyrimidin-4-yl]-piperidin-1-yl{-ethanone; |
| 139 | 1-{4-[6-(4-Methyl-pyridin-2-ylamino)-2-morpholin-4-yl-pyrimidin-4-yl]-piperidin-1-yl{-ethanone; |
| 140 | 1-{3-[6-(4-Methyl-pyridin-2-ylamino)-2-morpholin-4-yl-pyrimidin-4-yl]-pyrrolidin-1-yl{-ethanone; |
| 141 | 1-{4-{2-(3,3-Difluoro-pyrrolidin-1-yl)-6-(4-trifluoromethyl-pyridin-2-ylamino)-pyrimidin-4-yl]-piperidin-1-yl{-ethanone; |
| 142 | (4-Cyclopropyl-pyridin-2-yl)[2-(3,3-difluoro-pyrrolidin-1-yl)-6-piperidin-4-yl-pyrimidin-4-yl]-amine; |
| 143 | [2-((2R,5R)-2,5-Dimethyl-pyrrolidin-1-yl)-6-piperidin-4-yl-pyrimidin-4-yl]-(4-trifluoromethyl-pyridin-2-yl)-amine; |
| 148 | [6-(1-Methyl-piperidin-3-yl)-2-phenyl-pyrimidin-4-yl]-(4-trifluoromethyl-pyridin-2-yl)-amine; |
| 149 | [6-(1-Methyl-piperidin-3-yl)-2-phenyl-pyrimidin-4-yl]-(4-methyl-pyridin-2-yl)-amine; |
| 151 | [2-(3,3-Difluoro-pyrrolidin-1-yl)-6-(1-methyl-piperidin-3-yl)-pyrimidin-4-yl]-(4-methyl-pyridin-2-yl)-amine; |
| 152 | 1-{3-[6-(4-Methoxy-pyridin-2-ylamino)-2-(2-methyl-pyrrolidin-1-yl)-pyrimidin-4-yl]-piperidin-1-yl}-ethanone; |

| No | Name |
|---|---|
| 153 | [6-(1-Methyl-piperidin-4-yl)-2-[2-methyl-pyrrolidin-1-yl)-pyrimidin-4-yl]-(4-methyl-pyridin-2-yl)-amine; |
| 156 | 1-Acetyl-4-[2-(3,3-difluoro-pyrrolidin-1-yl)-6-(4-trifluoromethyl-pyridin-2-ylamino)-pyrimidin-4-yl]-piperidine-4-carbonitrile; |
| 157 | [2-(2-Methyl-pyrrolidin-1-yl)-6-(1-methyl-pyrrolidin-3-yl)-pyrimidin-4-yl]-(4-trifluoromethyl-pyridin-2-yl)-amine; |
| 158 | 1-{3-[2-(2-Methyl-pyrrolidin-1-yl)-6-(4-trifluoromethyl-pyridin-2-ylamino)-pyrimidin-4-yl]-pyrrolidin-1-yl}-ethanone; |
| 159 | 3-{3-[2-(2-Methyl-pyrrolidin-1-yl)-6-(4-trifluoromethyl-pyridin-2-ylamino)-pyrimidin-4-yl]-pyrrolidin-1-yl}-3-oxo-propionitrile; |
| 160 | [2-(3,3-Difluoro-pyrrolidin-1-yl)-6-(1-methyl-piperidin-4-yl)-pyrimidin-4-yl]-(4-trifluoromethyl-pyridin-2-yl)-amine; |
| 161 | 3-Oxo-3-{4-[2-pyrrolidin-1-yl-6-(4-trifluoromethyl-pyridin-2-ylamino)-pyrimidin-4-yl]-piperidin-1-yl}-propionitrile; |
| 162 | [2-(2-Oxa-5-aza-bicyclo[2.2.1]hept-5-yl)-6-piperidin-4-yl-pyrimidin-4-yl]-(4-trifluoromethyl-pyridin-2-yl)-amine; |
| 163 | 1-{4-[2-(2-Oxa-5-aza-bicyclo[2.2.1]hept-5-yl)-6-(4-trifluoromethyl-pyridin-2-ylamino)-pyrimidin-4-yl]-piperidin-1-yl}-ethanone; |
| 164 | [6-(1-Methyl-piperidin-4-yl)-2-(2-oxa-5-aza-bicyclo[-2.2.l]hept-5-yl)-pyrimidin-4-yl]-(4-trifluoromethyl-pyridin-2-yl)-amine; |
| 165 | [2-(2-Methyl-pyrrolidin-1-yl)-6-pyrrolidin-3-yl-pyrimidin-4-yl]-(4-trifluoromethyl-pyridin-2-yl)-amine; |
| 168 | 3-{4-[2-(2-Oxa-5-aza-bicyclo[2.2.1]hept-5-yl)-6-(4-trifluoromethyl-pyridin-2-ylamino)-pyrimidin-4-yl]-piperidin-1-yl}-3-oxo-propionitrile; |
| 169 | [6-(1-Methyl-piperidin-4-yl)-24(R)-2-methyl-pyrrolidin-1-yl)-pyrimidin-4-yl]-(4-trifluoromethyl-pyridin-2-yl)-amine; |
| 170 | 243,3-Difluoro-pyrrolidin-1-yl)-6-piperidin-4-yl-pyrimidin-4-yl]-(4-isopropyl-pyridin-2-yl)-amine; |
| 172 | (4-Cyclobutyl-pyridin-2-yl){243,3-difluoro-pyrrolidin-1-yl)-6-piperidin-4-yl-pyrimidin-4-yl]-amine; |
| 173 | 3-{3-[2-Cyclopropyl-6-(4-trifluoromethyl-pyridin-2-ylamino)-pyrimidin-4-yl]-piperidin-1-yl}-3-oxo-propionitrile; |
| 174 | (2-Cyclopropyl-6-piperidin-3-yl-pyrimidin-4-yl)-(4-trifluoromethyl-pyridin-2-yl)-amine; |
| 175 | 1-{4-[2-((R)-2-Methyl-pyrrolidin-1-yl)-6-(4-trifluoromethyl-pyridin-2-ylamino)-pyrimidin-4-yl]-piperidin-1-yl}-ethanone; |
| 176 | 1-{4-[2-((S)-2-Methyl-pyrrolidin-1-yl)-6-(4-trifluoromethyl-pyridin-2-ylamino)-pyrimidin-4-yl]-piperidin-1-yl}-ethanone; |
| 177 | 1-{4-[2--Methyl-pyrrolidin-1-yl)-6-(4-trifluoromethyl-pyridin-2-ylamino)-pyrimidin-4-yl]-piperidin-1-yl}-3-oxo-propionitrile; |
| 178 | 1-{3-[2-(3,3-Difluoro-pyrrolidin-1-yl)-6-(4-trifluoromethyl-pyridin-2-ylamino)-pyrimidin-4-yl]-piperidin-1-yl}-2,2-difluoro-ethanone; |
| 179 | 1-{4-[2-(3,3-Difluoro-pyrrolidin-1-yl)-6-(4-trifluoromethyl-pyridin-2-ylamino)-pyrimidin-4-yl]-piperidin-1-yl}-2,2-difluoro-ethanone; |
| 180 | {3-[2-(3,3-Difluoro-pyrrolidin-1-yl)-6-(4-trifluoromethyl-pyridin-2-ylamino)-pyrimidin-4-yl]-pyrrolidin-1-yl}[2-methyl-cyclopropyl)-methanone; |
| 181 | 1-{3-[2-(3,3-Difluoro-pyrrolidin-1-yl)-6-(4-trifluoromethyl-pyridin-2-ylamino)-pyrimidin-4-yl]-piperidin-1-yl}-ethanone; |
| 182 | 3-{3-[2-(3,3-Difluoro-pyrrolidin-1-yl)-6-(4-trifluoromethyl-pyridin-2-ylamino)-pyrimidin-4-yl]-piperidin-1-yl}-3-oxo-propionitrile; |
| 183 | 1-{4-[2-(3,3-Difluoro-pyrrolidin-1-yl)-6-(4-trifluoromethyl-pyridin-2-ylamino)-pyrimidin-4-yl]-piperidin-1-yl}-propan-1-one; |
| 184 | Cyclopropyl-{3-[2-(3,3-difluoro-pyrrolidin-1-yl)-6-(4-trifluoromethyl-pyridin-2-ylamino)-pyrimidin-4-yl]-pyrrolidin-1-yl}-methanone; |
| 185 | Cyclopropyl-{3-[2-(3,3-difluoro-pyrrolidin-1-yl)-6-(4-trifluoromethyl-pyridin-2-ylamino)-pyrimidin-4-yl]-piperidin-1-yl}-methanone; |
| 186 | Cyclopropyl-{4-[2-(3,3-difluoro-pyrrolidin-1-yl)-6-(4-trifluoromethyl-pyridin-2-ylamino)-pyrimidin-4-yl]-piperidin-1-yl}-methanone; |
| 187 | 1-{3-[2-Cyclopropyl-6-(4-trifluoromethyl-pyridin-2-ylamino)-pyrimidin-4-yl]-piperidin-1-yl}-3-methoxy-propan-1-one; |
| 189 | 1-{3-[2-Cyclopropyl-6-(4-trifluoromethyl-pyridin-2-ylamino)-pyrimidin-4-yl}-piperidin-1-yl]-ethanone; |
| 191 | 1-{3-P-(3,3-Difluoro-pyrrolidin-1-yl)-6-(4-trifluoromethyl-pyridin-2-ylamino)-pyrimidin-4-yl]-pyrrolidin-1-yl}-propan-1-one; |
| 192 | 1-{3-[2-(3,3-Difluoro-pyrrolidin-1-yl)-6-(4-trifluoromethyl-pyridin-2-ylamino)-pyrimidin-4-yl]-pyrrolidin-1-yl}-butan-1-one; |
| 193 | Cyclobutyl-{3-[2-(3,3-difluoro-pyrrolidin-1-yl)-6-(4-trifluoromethyl-pyridin-2-ylamino)-pyrimidin-4-yl]-pyrrolidin-1-yl}-methanone; |
| 194 | 2-Cyclopropyl-1-{3-[2-(3,3-difluoro-pyrrolidin-1-yl)-6-(4-trifluoromethyl-pyridin-2-ylamino)-pyrimidin-4-yl]-pyrrolidin-1-yl}-ethanone; |
| 196 | 1-{3-[2-Cyclopropyl-6-(4-trifluoromethyl-pyridin-2-ylamino)-pyrimidin-4-yl]-piperidin-1-yl}-2,2-difluoro-ethanone; |
| 197 | 4-[2-((R)-2-Methyl-pyrrolidin-1-yl)-6-(4-trifluoromethyl-pyridin-2-ylamino)-pyrimidin-4-yl]-piperidine-4-carbonitrile; |
| 199 | P-Cyclopropyl-6-(1-methyl-piperidin-3-yl)-pyrimidin-4-yl]-(4-trifluoromethyl-pyridin-2-yl)-amine; |
| 200 | (4-tert-Butyl-pyridin-2-yl)[2-(3,3-difluoro-pyrrolidin-1-yl)-6-piperidin-4-yl-pyrimidin-4-yl]-amine; |
| 201 | [2-(3,3-Difluoro-pyrrolidin-1-yl)-6-piperidin-4-yl-pyrimidin-4-yl]-(4-thiophen-2-yl-pyridin-2-yl)-amine; |

| No | Name |
|---|---|
| 202 | (4-Cyclopropyl-pyridin-2-yl)-[2-((R)-2-methyl-pyrrolidin-1-yl)-6-piperidin-4-yl-pyrimidin-4-yl]-amine; |
| 203 | (1-Methyl-1H-imidazol-4-yl)-{3-[2-(2-methyl-pyrrolidin-1-yl)-6-(4-trifluoromethyl-pyridin-2-ylamino)-pyrimidin-4-yl]-pyrrolidin-1-yl}-methanone; |
| 204 | 2-Imidazol-1-yl-1-{3-[2-(2-methyl-pyrrolidin-1-yl)-6-(4-trifluoromethyl-pyridin-2-ylamino)-pyrimidin-4-yl]-pyrrolidin-1-yl}-ethanone; |
| 205 | 1-{3-[6-(4-Trifluoromethyl-pyridin-2-ylamino)-2-(3-trifluoromethyl-pyrrolidin-1-yl)-pyrimidin-4-yl]-pyrrolidin-1-yl}-propan-1-one; |
| 206 | 1-{4-[6-(4-Trifluoromethyl-pyridin-2-ylamino)-2-(3-trifluoromethyl-pyrrolidin-1-yl)-pyrimidin-4-yl]-piperidin-1-yl}-ethanone; |
| 207 | 1-{4-[6-(4-Cyclopropyl-pyridin-2-ylamino)-2-(3,3-difluoro-pyrrolidin-1-yl)-pyrimidin-4-yl]-piperidin-1-yl}-ethanone; |
| 208 | 4-[2,6-Bis-(4-trifluoromethyl-pyridin-2-ylamino)-pyrimidin-4-yl]-tetrahydro-pyran-4-carbonitrile; |
| 209 | 4-[2-((R)-2-Methyl-pyrrolidin-1-yl)-6-(4-trifluoromethyl-pyridin-2-ylamino)-pyrimidin-4-yl]-tetrahydro-pyran-4-carbonitrile; |
| 210 | 4-[2-(3,3-Difluoro-pyrrolidin-1-yl)-6-(4-trifluoromethyl-pyridin-2-ylamino)-pyrimidin-4-yl]-tetrahydro-pyran-4-carbonitrile; |
| 211 | [2-(2-Methoxymethyl-pyrrolidin-1-yl)-6-piperidin-4-yl-pyrimidin-4-yl]-(4-trifluoromethyl-pyridin-2-yl)-amine; |
| 215 | [2-(2,2-Dimethyl-morpholin-4-yl)-6-(tetrahydro-pyran-4-yl)-pyrimidin-4-yl]-(4-trifluoromethyl-pyridin-2-yl)-amine; |
| 216 | 2-(3-Morpholin-4-yl-azetidin-1-yl)-6-(tetrahydro-pyran-4-yl)-pyrimidin-4-yl]-(4-trifluoromethyl-pyridin-2-yl)-amine; |
| 217 | 1-[4-(Tetrahydro-pyran-4-yl)-6-(4-trifluoromethyl-pyridin-2-ylamino)-pyrimidin-2-yl]-azetidine-3-carbonitrile, |
| 218 | [2(2-Oxa-6-aza-spiro[3.3]hept-6-yl)-6-(tetrahydro-pyran-4-yl)-pyrimidin-4-yl]-(4-trifluoromethyl-pyridin-2-yl)-amine; |
| 219 | [2-(3,3-Difluoro-pyrrolidin-1-yl)-6-(tetrahydro-pyran-4-yl)-pyrimidin-4-yl]-(4-trifluoromethyl-pyridin-2-yl)-amine; |
| 220 | [2-((S)-2-Methyl-pyrrolidin-1-yl)-6-(tetrahydro-pyran-4-yl)-pyrimidin-4-yl]-(4-trifluoromethyl-pyridin-2-yl)-amine; |
| 221 | [2-((R)-2-Methyl-pyrrolidin-1-yl)-6-(tetrahydro-pyran-4-yl)-pyrimidin-4-yl]-(4-trifluoromethyl-pyridin-2-yl)-amine; |
| 222 | [2-Morpholin-4-yl-6-(tetrahydro-pyran-4-yl)-pyrimidin-4-yl]-(4-trifluoromethyl-pyridin-2-yl)-amine; |
| 223 | [2(2-Oxa-5-aza-bicyclo[2.2.1]hept-5-yl)-6-(tetrahydro-pyran-4-yl)-pyrimidin-4-yl]-(4-trifluoromethyl-pyridin-2-yl)-amine; |
| 224 | [2-(3,3-Difluoro-azetidin-1-yl)-6-(tetrahydro-pyran-4-yl)-pyrimidin-4-yl]-(4-trifluoromethyl-pyridin-2-yl)-amine; |
| 225 | {2-(3,3-Difluoro-pyrrolidin-1-yl)-6-(1-(1H-imidazol-2-ylmethyl)-pyrrolidin-3-yl]-pyrimidin-4-yl}-(4-trifluoromethyl-pyridin-2-yl)-amine; |
| 226 | 1-{3-[2-(3,3-Difluoro-pyrrolidin-1-yl)-6-(4-trifluoromethyl-pyridin-2-ylamino)-pyrimidin-4-yl]-pyrrolidin-1-yl}-2,2-difluoro-ethanone; |
| 227 | 1-{3-[2-(3,3-Difluoro-pyrrolidin-1-yl)-6-(4-trifluoromethyl-pyridin-2-ylamino)-pyrimidin-4-yl]-pyrrolidine-1-carbonyl1-cyclopropanecarbonitrile; |
| 228 | 1-{3-[2-(3,3-Difluoro-pyrrolidin-1-yl)-6-(4-trifluoromethyl-pyridin-2-ylamino)-pyrimidin-4-yl]-pyrrolidin-1-yl}-3-methoxy-propan-1-one, |
| 229 | {3-[2-(3,3-Difluoro-pyrrolidin-1-yl)-6-(4-trifluoromethyl-pyridin-2-ylamino)-pyrimidin-4-yl]-pyrrolidin-1-yl}-(1-methyl-cyclopropyl)-methanone; |
| 230 | 2,2-Difluoro-1-{3-[2-(2-methyl-pyrrolidin-1-yl)-6-(4-trifluoromethyl-pyridin-2-ylamino)-pyrimidin-4-yl]-pyrrolidin-1-yl}-ethanone; |
| 231 | 1-{3-[6-(4-Trifluoromethyl-pyridin-2-ylamino)-2-(3-trifluoromethyl-pyrrolidin-1-yl)-pyrimidin-4-yl]-pyrrolidin-1-yl}-ethanone; |
| 232 | 1-{3-[6-(4-Trifluoromethyl-pyridin-2-ylamino)-2-(3-trifluoromethyl-pyrrolidin-1-yl)-pyrimidin-4-yl]-piperidin-1-yl}-ethanone; |
| 233 | 1-{3-[2-(3,3-Difluoro-azetidin-1-yl)-6-(4-trifluoromethyl-pyridin-2-ylamino)-pyrimidin-4-yl]-pyrrolidin-1-yl}-2,2-difluoro-ethanone; |
| 234 | 3-{3-[2-(3,3-Difluoro-azetidin-1-yl)-6-(4-trifluoromethyl-pyridin-2-ylamino)-pyrimidin-4-yl]-pyrrolidin-1-yl}-3-oxo-propionitrile; |
| 235 | 1-{4-[2-(3,3-Difluoro-azetidin-1-yl)-6-(4-trifluoromethyl-pyridin-2-ylamino)-pyrimidin-4-yl]-piperidin-1-yl}-3-methoxy-propan-1-one; |
| 236 | 1-{3-[2-(3,3-Difluoro-azetidin-1-yl)-6-(4-trifluoromethyl-pyridin-2-ylamino)-pyrimidin-4-yl]-pyrrolidin-1-yl}-ethanone; |
| 237 | 1-{4-[2-(3,3-Difluoro-azetidin-1-yl)-6-(4-trifluoromethyl-pyridin-2-ylamino)-pyrimidin-4-yl]-piperidin-1-yl}-ethanone; |
| 238 | 1-{3-[2-(3,3-Difluoro-azetidin-1-yl)-6-(4-trifluoromethyl-pyridin-2-ylamino)-pyrimidin-4-yl]-pyrrolidin-1-yl}-propan-1-one, |
| 239 | 1-{4-[2-(3,3-Difluoro-azetidin-1-yl)-6-(4-trifluoromethyl-pyridin-2-ylamino)-pyrimidin-4-yl]-piperidin-1-yl}-propan-1-one; |
| 240 | {4-[2-(3,3-Difluoro-azetidin-1-yl)-6-(4-trifluoromethyl-pyridin-2-ylamino)-pyrimidin-4-yl]-piperidin-1-yl}-(1-methyl-cyclopropyl)-methanone; |
| 241 | Cyclopropyl-{4-[2-(3,3-difluoro-azetidin-1-yl)-6-(4-trifluoromethyl-pyridin-2-ylamino)-pyrimidin-4-yl]-piperidin-1-yl}-methanone; |
| 242 | 2-Cyclopropyl-1-{4-[2-(3,3-difluoro-azetidin-1-yl)-6-(4-trifluoromethyl-pyridin-2-ylamino)-pyrimidin-4-yl]-piperidin-1-yl}-ethanone; |

| No | Name |
|---|---|
| 243 | 1-{3-[2-(2-Oxa-5-aza-bicyclo[2.2.1]hept-5-yl)-6-(4-trifluoromethyl-pyridin-2-ylamino)-pyrimidin-4-yl]-pyrrolidin-1-yl}-ethanone; |
| 244 | 2-Difluoro-1-{3-[2-(2-oxa-5-aza-bicyclo[2.2.1]hept-5-yl)-6-(4-trifluoromethyl-pyridin-2-ylamino)-pyrimidin-4-yl]-pyrrolidin-1-yl}-ethanone; |
| 245 | [6-(1-Methyl-piperidin-3-yl)-2-(2-oxa-5-aza-bicyclo[2.2.l]hept-5-yl)-pyrimidin-4-yl]-(4-trifluoromethyl-pyridin-2-yl)-amine; |
| 246 | 1-{3-[2-(2-Oxa-5-aza-bicyclo[2.2.1]hept-5-yl)-6-(4-trifluoromethyl-pyridin-2-ylamino)-pyrimidin-4-yl]-piperidin-1-yl}-ethanone; |
| 247 | 2,2-Difluoro-1-{3-[2-(2-oxa-5-aza-bicyclo[2.2.1]hept-5-yl)-6-(4-trifluoromethyl-pyridin-2-ylamino)-pyrimidin-4-yl]-piperidin-1-yl}-ethanone; |
| 248 | 1-{4-[6-(4-Cyclopropyl-pyridin-2-ylamino)-2-((R)-2-methyl-pyrrolidin-1-yl)-pyrimidin-4-yl]-piperidin-1-yl}-ethanone; |
| 249 | 2-Difluoro-1-{4-[2-(2-methoxymethyl-pyrrolidin-1-yl)-6-(4-trifluoromethyl-pyridin-2-ylamino)-pyrimidin-4-yl]-piperidin-1-yl}-ethanone; |
| 250 | 1-{4-[2-(3,4-Difluoro-pyrrolidin-1-yl)-6-(4-trifluoromethyl-pyridin-2-ylamino)-pyrimidin-4-yl]-piperidin-1-yl}-ethanone; |
| 251 | 2-(3-Oxa-8-aza-bicyclo[3.2.1]oct-8-yl)-6-(tetrahydro-pyran-4-yl)-pyrimidin-4-yl]-(4-trifluoromethyl-pyridin-2-yl)-amine; |
| 252 | [2,-(3,4,6,7-Tetrahydro-imidazo[4,5-clpyridin-5-yl)-6-(tetrahydro-pyran-4-yl)-pyrimidin-4-yl]-(4-trifluoromethyl-pyridin-2-yl)-amine; |
| 253 | 2-(5,6-Dihydro-8H-imidazo[1,2-a]pyrazin-7-yl)-6-(tetrahydro-pyran-4-yl)-pyrimidin-4-yl]-(4-trifluoromethyl-pyridin-2-yl)-amine; |
| 254 | 2-(4-Morpholin-4-yl-piperidin-1-yl)-6-(tetrahydro-pyran-4-yl)-pyrimidin-4-yl]-(4-trifluoromethyl-pyridin-2-yl)-amine; |
| 255 | [2-(4-(2-Methyl-pyrimidin-4-yl)-piperidin-1-yl]-6-(tetrahydro-pyran-4-yl)-pyrimidin-4-yl]-(4-trifluoromethyl-pyridin-2-yl)-amine; |
| 256 | 2-{3-(4-Methyl-pyrimidin-2-yl)-azetidin-1-yl]-6-(tetrahydro-pyran-4-yl)-pyrimidin-4-yl]-(4-trifluoromethyl-pyridin-2-yl)-amine; |
| 257 | [2-[2-(4-Methyl-4H-[1,2,4]triazol-3-yl)-pyrrolidin-1-yl]-6-(tetrahydro-pyran-4-yl)-pyrimidin-4-yl]-(4-trifluoromethyl-pyridin-2-yl)-amine; |
| 258 | [2-(4-(4-Methyl-4H-[1,2,4]triazol-3-yl)-piperidin-1-yl]-6-(tetrahydro-pyran-4-yl)-pyrimidin-4-yl]-(4-trifluoromethyl-pyridin-2-yl)-amine; |
| 259 | [2-(3-(4-Methyl-4H-[1,2,4]triazol-3-yl)-piperidin-1-yl]-6-(tetrahydro-pyran-4-yl)-pyrimidin-4-yl]-(4-trifluoromethyl-pyridin-2-yl)-amine; |
| 260 | Morpholin-4-yl-{1-[4-(tetrahydro-pyran-4-yl)-6-(4-trifluoromethyl-pyridin-2-ylamino)-pyrimidin-2-yl]-azetidin-3-yl}-methanone; |
| 261 | 2-[3-(2-Methyl-pyrimidin-4-yl)-pyrrolidin-1-yl]-6-(tetrahydro-pyran-4-yl)-pyrimidin-4-yl]-(4-trifluoromethyl-pyridin-2-yl)-amine; |
| 262 | [2-(3,3-Difluoro-azetidin-1-yl)-6-(1-ethyl-piperidin-4-yl)-pyrimidin-4-yl]-(4-trifluoromethyl-pyridin-2-yl)-amine; |
| 263 | {3-[2-(3,3-Difluoro-azetidin-1-yl)-6-(4-trifluoromethyl-pyridin-2-ylamino)-pyrimidin-4-yl]-pyrrolidin-1-yl}-(tetrahydro-furan-3-yl)-methanone; |
| 264 | 1-{4-[-2-(3,3-Difluoro-azetidin-1-yl)-6-(4-trifluoromethyl-pyridin-2-ylamino)-pyrimidin-4-yl]-piperidin-1-yl}-2,2-difluoro-ethanone; |
| 265 | {3-{2-(3,3-Difluoro-azetidin-1-yl)-6-(4-trifluoromethyl-pyridin-2-ylamino)-pyrimidin-4-yl]-pyrrolidin-1-yl}-(tetrahydro-furan-2-yl)-methanone; |
| 266 | 1-{3-[2-(3,3-Difluoro-azetidin-1-yl)-6-(4-trifluoromethyl-pyridin-2-ylamino)-pynmidin-4-yl]-pyrrolidin-1-yl}-3-methoxy-propan-1-one; |
| 267 | 1-{3-[2-(3,3-Difluoro-azetidin-1-yl)-6-(4-trifluoromethyl-pyridin-2-ylamino)-pyrimidin-4-yl]-pyrrolidin-1-yl}-3-dimethylamino-propan-1-one; |
| 268 | {3-[2-(3,3-Difluoro-azetidin-1-yl)-6-(4-trifluoromethyl-pyridin-2-ylamino)-pyrimidin-4-yl]-pyrrolidin-1-yl}-(2-methyl-cyclopropyl)-methanone; |
| 269 | 1-{3-[2-(3,3-Difluoro-azetidin-1-yl)-6-(4-trifluoromethyl-pyridin-2-ylamino)-pyrimidin-4-yl]-pyrrolidin-1-yl}-butan-1-one; |
| 270 | {3-[2-(3,3-Difluoro-azetidin-1-yl)-6-(4-trifluoromethyl-pyridin-2-ylamino)-pyrimidin-4-yl]-pyrrolidin-1-yl}-(1-methyl-cyclopropyl)-methanone; |
| 271 | Cyclopropyl-{3-[2-(3,3-difluoro-azetidin-1-yl)-6-(4-trifluoromethyl-pyridin-2-ylamino)-pyrimidin-4-yl]-pyrrolidin-1-yl}-methanone; |
| 272 | Cyclobutyl-{3-[2-(3,3-difluoro-azetidin-1-yl)-6-(4-trifluoromethyl-pyridin-2-ylamino)-pyrimidin-4-yl]-pyrrolidin-1-yl}-methanone; |
| 273 | 2-Cyclopropyl-1-{3-[2-(3,3-difluoro-azetidin-1-yl)-6-(4-trifluoromethyl-pyridin-2-ylamino)-pyrimidin-4-yl]-pyrrolidin-1-yl}-ethanone; |
| 274 | [6-(1-Methyl-pyrrolidin-3-yl)-2-(2-oxa-5-aza-bicyclo[2.2.1]hept-5-yl)-pyrimidin-4-yl]-(4-trifluoromethyl-pyridin-2-yl)-amine; |
| 275 | 1-{4-1-2,-(2,2-Dimethyl-morpholin-4-yl)-6-(4-trifluoromethyl-pyridin-2-ylamino)-pyrimidin-4-yl]-piperidin-1-yl}-ethanone |
| 276 | 1-{3-[2,-(2,2-Dimethyl-morpholin-4-yl)-6-(4-trifluoromethyl-pyridin-2-ylamino)-pyrimidin-4-yl]-piperidin-1-yl}-ethanone; |
| 277 | 1-{4-[2-(2,6-Dimethyl-morpholin-4-yl)-6-(4-trifluoromethyl-pyridin-2-ylamino)-pyrimidin-4-yl]-piperidin-1-yl}-ethanone; |
| 278 | 1-{3-[2,-(2,6-Dimethyl-morpholin-4-yl)-6-(4-trifluoromethyl-pyridin-2-ylamino)-pyrimidin-4-yl]-piperidin-1-yl}-ethanone; |
| 279 | 1-{3-[2-(2,6-Dimethyl-morpholin-4-yl)-6-(4-trifluoromethyl-pyridin-2-ylamino)-pyrimidin-4-yl]-pyrrolidin-1-yl}-ethanone; |
| 280 | 1-{3-[2,-(2,6-Dimethyl-morpholin-4-yl)-6-(4-trifluoromethyl-pyridin-2-ylamino)-pyrimidin-4-yl]-pyrrolidin-1-yl}-2,2-difluoro-ethanone; |

| No | Name |
|---|---|
| 281 | 1-[4-[1-(2,2-Difluoro-acetyl)-piperidin-4-yl]-6-(4-trifluoromethyl-pyridin-2-ylamino)-pyrimidin-2-yl]-azetidine-3-carbonitrile; |
| 282 | 1-[4-[1-(2,2-Difluoro-acetyl)-piperidin-3-yl]-6-(4-trifluoromethyl-pyridin-2-ylamino)-pyrimidin-2-yl]-azetidine-3-carbonitrile; |
| 283 | 1-[4-(1-Acetyl-piperidin-4-yl)-6-(4-trifluoromethyl-pyridin-2-ylamino)-pyrimidin-2-yl]-azetidine-3-carbonitrile; |
| 284 | 1-[4-(1-Acetyl-piperidin-3-yl)-6-(4-trifluoromethyl-pyridin-2-ylamino)-pyrimidin-2-yl]-azetidine-3-carbonitrile; |
| 285 | 1-{4-[2-(2-Ethyl-morpholin-4-yl)-6-(4-trifluoromethyl-pyridin-2-ylamino)-pyrimidin-4-yl]-piperidin-1-yl}-ethanone; |
| 286 | 1-{3-[2-(2-Ethyl-morpholin-4-yl)-6-(4-trifluoromethyl-pyridin-2-ylamino)-pyrimidin-4-yl]-piperidin-1-yl}-ethanone; |
| 287 | [6-(1-Methyl-piperidin-4-yl)-2-(3-morpholin-4-yl-azetidin-1-yl)-pyrimidin-4-yl]-(4-trifluoromethyl-pyridin-2-yl)-amine; |
| 288 | 1-{3-[2-(2-Ethyl-morpholin-4-yl)-6-(4-trifluoromethyl-pyridin-2-ylamino)-pyrimidin-4-yl]-pyrrolidin-1-yl}-ethanone; |
| 289 | 1-[4-(1-Methyl-piperidin-4-yl)-6-(4-trifluoromethyl-pyridin-2-ylamino)-pyrimidin-2-yl]-azetidine-3-carbonitrile; |
| 290 | 1-{3-[2-(8-Oxa-3-aza-bicyclo[3.2.1]oct-3-yl)-6-(4-trifluoromethyl-pyridin-2-ylamino)-pyrimidin-4-yl]-piperidin-1-yl}-ethanone; |
| 291 | 2,2-Difluoro-1-{3-[2-(8-oxa-3-aza-bicyclo[3.2.1]oct-3-yl)-6-(4-trifluoromethyl-pyridin-2-ylamino)-pyrimidin-4-yl]-piperidin-1-yl}-ethanone; |
| 292 | [6-(1-Methyl-piperidin-4-yl)-2-(8-oxa-3-aza-bicyclo[3.2.1]oct-3-yl)-pyrimidin-4-yl]-(4-trifluoromethyl-pyridin-2-yl)-amine; |
| 293 | 1-{4-[2-(8-Oxa-3-aza-bicyclo[3.2.1]oct-3-yl)-6-(4-trifluoromethyl-pyridin-2-ylamino)-pyrimidin-4-yl]-piperidin-1-yl}-ethanone; |
| 294 | 2,2-Difluoro-1-{4-[2-(8-oxa-3-aza-bicyclo[3.2.1]oct-3-yl)-6-(4-trifluoromethyl-pyridin-2-ylamino)-pyrimidin-4-yl]-piperidin-1-yl}-ethanone; |
| 295 | [2-[1,4]Oxazepan-4-yl-6-(tetrahydro-pyran-4-yl)-pyrimidin-4-yl]-(4-trifluoromethyl-pyridin-2-yl)-amine; |
| 296 | [2-(8-Oxa-3-aza-bicyclo[3.2.1]oct-3-yl)-6-(tetrahydro-pyran-4-yl)-pynmidin-4-yl]-(4-trifluoromethyl-pyridin-2-yl)-amine; |
| 297 | [2-(2-Methoxymethyl-pyrrolidin-1-yl)-6-(tetrahydro-pyran-4-yl)-pyrimidin-4-yl]-(4-trifluoromethyl-pyridine-2-yl)-amine; |
| 298 | {2-(3,3-Difluoro-azetidin-1-yl)-6-(1-(5-methyl-isoxazol-3-ylmethyl)-pyrrolidin-3-yl]-pyrimidin-4-yl}-(4-trifluoromethyl-pyridin-2-yl)-amine; |
| 299 | {2-(3,3-Difluoro-azetidin-1-yl)-6-(1-(5-methyl-3H-imidazol-4-ylmethyl)-pyrrolidin-3-yl]-pyrimidin-4-yl}-(4-trifluoromethyl-pyridin-2-yl)-amine |
| 300 | [2-(3,3-Difluoro-azetidin-1-yl)-6-(1-oxazol-2-ylmethyl-pyrrolidin-3-yl)-pyrimidin-4-yl]-(4-trifluoromethyl-pyridin-2-yl)-amine; |
| 301 | {2-(3,3-Difluoro-azetidin-1-yl)-6-(1-(2-methyl-1H-imidazol-4-ylmethyl)-pyrrolidin-3-yl]-pyrimidin-4-yl}-(4-trifluoromethyl-pyridin-2-yl)-amine; |
| 302 | [2-(3,3-Difluoro-azetidin-1-yl)-6-(1-oxazol-4-ylmethyl-piperidin-4-yl)-pyrimidin-4-yl]-(4-trifluoromethyl-pyridin-2-yl)-amine; |
| 303 | [2-(3,3-Difluoro-azetidin-1-yl)-6-(1-oxazol-2-ylmethyl-piperidin-4-yl)-pyrimidin-4-yl]-(4-trifluoromethyl-pyridin-2-yl)-amine; |
| 304 | {2-(3,3-Difluoro-azetidin-1-yl)-6-(1-(4-methyl-1H-imidazol-2-ylmethyl)-pyrrolidin-3-yl]-pyrimidin-4-yl}-(4-trifluoromethyl-pyridin-2-yl)-amine; |
| 305 | {2-(3,3-Difluoro-azetidin-1-yl)-6-(1-(1H-imidazol-2-ylmethyl)-pyrrolidin-3-yl]-pyrimidin-4-yl}-(4-trifluoromethyl-pyridin-2-yl)-amine; |
| 306 | {2-(3,3-Difluoro-azetidin-1-yl)-6-(1-(3-methyl-3H-imidazol-4-ylmethyl)-pyrrolidin-3-yl]-pyrimidin-4-yl}-(4-trifluoromethyl-pyridin-2-yl)-amine; |
| 307 | {2-(3,3-Difluoro-azetidin-1-yl)-6-(1-(tetrahydro-pyran-4-ylmethyl)-pyrrolidin-3-yl]-pyrimidin-4-yl}-(4-trifluoromethyl-pyridin-2-yl)-amine; |
| 308 | {2-(3,3-Difluoro-azetidin-1-yl)-6-(1-(tetrahydro-furan-3-ylmethyl)-piperidin-4-yl]-pyrimidin-4-yl}-(4-trifluoromethyl-pyridin-2-yl)-amine; |
| 309 | {2-(3,3-Difluoro-azetidin-1-yl)-6-(1-(1H-imidazol-2-ylmethyl)-piperidin-4-yl]-pyrimidin-4-yl}-(4-trifluoromethyl-pyridin-2-yl)-amine; |
| 310 | {2-(3,3-Difluoro-azetidin-1-yl)-6-(1-(tetrahydro-pyran-3-ylmethyl)-pyrrolidin-3-yl]-pyrimidin-4-yl}-(4-trifluoromethyl-pyridin-2-yl)-amine; |
| 311 | {2-(3,3-Difluoro-azetidin-1-yl)-6-(1-(1H-imidazol-4-ylmethyl)-piperidin-4-yl]-pyrimidin-4-yl}-(4-trifluoromethyl-pyridin-2-yl)-amine; |
| 312 | {2-(3,3-Difluoro-azetidin-1-yl)-6-(1-(2H-pyrazol-3-ylmethyl)-piperidin-4-yl]-pyrimidin-4-yl}-(4-trifluoromethyl-pyridin-2-yl)-amine; |
| 313 | {2-(3,3-Difluoro-azetidin-1-yl)-6-(1-(1-methyl-1H-pyrazol-4-ylmethyl)-pyrrolidin-3-yl]-pyrimidin-4-yl}-(4-trifluoromethyl-pyridin-2-yl)-amine; |
| 314 | [2-(3,3-Difluoro-azetidin-1-yl)-6-(1-pyridin-3-ylmethyl-pyrrolidin-3-yl)-pyrimidin-4-yl]-(4-trifluoromethyl-pyridin-2-yl)-amine; |
| 315 | {2-(3,3-Difluoro-azetidin-1-yl)-6-(1-(1H-pyrazol-4-ylmethyl)-piperidin-4-yl]-pynmidin-4-yl}-(4-trifluoromethyl-pyridin-2-yl)-amine; |
| 316 | [2-(3,3-Difluoro-azetidin-1-yl)-6-(1-pyridin-4-ylmethyl-pyrrolidin-3-yl)-pyrimidin-4-yl]-(4-trifluoromethyl-pyridin-2-yl)-amine; |
| 317 | {2-(3,3-Difluoro-azetidin-1-yl)-6-(1-(1-methyl-1H-imidazol-2-ylmethyl)-pyrrolidin-3-yl]-pyrimidin-4-yl}-(4-trifluoromethyl-pyridin-2-yl)-amine; |
| 318 | 1-{3-[2-(3,3-Difluoro-azetidin-1-yl)-6-(4-trifluoromethyl-pyridin-2-ylamino)-pyrimidin-4-yl]-pyrrolidine-1-carbonyl1-cyclopropanecarbonitrile; |

| No | Name |
|---|---|
| 319 | 2,2-Difluoro-1-{4-[2-(2-oxa-5-aza-bicyclo[2.2.1]hept-5-yl)-6-(4-trifluoromethyl-pyridin-2-ylamino)-pyrimidin-4-yl]-piperidin-1-yl}-ethanone; |
| 320 | 1-{3-[2-(2,2-Dimethyl-morpholin-4-yl)-6-(4-trifluoromethyl-pyridin-2-ylamino)-pyrimidin-4-yl]-pyrrolidin-1-yl}-ethanone; |
| 321 | 1-{3-[2-(2,2-Dimethyl-morpholin-4-yl)-6-(4-trifluoromethyl-pyridin-2-ylamino)-pyrimidin-4-yl]-pyrrolidin-1-yl}-2,2-difluoro-ethanone; |
| 322 | 1-{3-12-(2-Ethyl-morpholin-4-yl)-6-(4-trifluoromethyl-pyridin-2-ylamino)-pyrimidin-4-yl]-pyrrolidin-1-yl}-2,2-difluoro-ethanone; |
| 323 | 1-[4-[1-(2,2-Difluoro-acetyl)-pyrrolidin-3-yl]-6-(4-trifluoromethyl-pyridin-2-ylamino)-pyrimidin-2-yl]-azetidine-3-carbonitrile; |
| 324 | [6-(1-Methyl-pyrrolidin-3-yl)-2-(3-morpholin-4-yl-azetidin-1-yl)-pyrimidin-4-yl]-(4-trifluoromethyl-pyridin-2-yl)-amine; |
| 325 | 1-[4-(1-Acetyl-pyrrolidin-3-yl)-6-(4-trifluoromethyl-pyridin-2-ylamino)-pyrimidin-2-yl]-azetidine-3-carbonitrile; |
| 326 | 2-(2,2-Dimethyl-morpholin-4-yl)-6-(1-methyl-pyrrolidin-3-yl)-pyrimidin-4-yl]-(4-trifluoromethyl-pyridin-2-yl)-amine; |
| 327 | [2-(2,6-Dimethyl-morpholin-4-yl)-6-(1-methyl-pyrrolidin-3-yl)-pyrimidin-4-yl]-(4-trifluoromethyl-pyridin-2-yl)-amine; |
| 328 | 1-[4-(1-Methyl-pyrrolidin-3-yl)-6-(4-trifluoromethyl-pyridin-2-ylamino)-pyrimidin-2-yl]-azetidine-3-carbonitrile; |
| 329 | [6-(1-Methyl-piperidin-3-yl)-2-(8-oxa-3-aza-bicyclo[3.2.1]oct-3-yl)-pyrimidin-4-yl]-(4-trifluoromethyl-pyridin-2-yl)-amine; |
| 330 | [6-(1-Methanesulfonyl-piperidin-4-yl)-2-((R)-2-methyl-pyrrolidin-1-yl)-pyrimidin-4-yl]-(4-trifluoromethyl-pyridin-2-yl)-amine; |
| 331 | 1-Methyl-5-[2-((R)-2-methyl-pyrrolidin-1-yl)-6-(4-trifluoromethyl-pyridin-2-ylamino)-pyrimidin-4-yl]-1H-pyridin-2-one; |
| 332 | 1-Methyl-4-[2-(2-methyl-pyrrolidin-1-yl)-6-(4-trifluoromethyl-pyridin-2-ylamino)-pyrimidin-4-yl]-piperidin-2-one; |
| 333 | 5-[6-(4-Cyclopropyl-pyridin-2-ylamino)-2-((R)-2-methyl-pyrrolidin-1-yl)-pyrimidin-4-yl]-1-methyl-1H-pyridin-2-one; |
| 334 | (4-Cyclopropyl-pyridin-2-yl)[2-((R)-2-methyl-pyrrolidin-1-yl)-6-(tetrahydro-pyran-4-yl)-pyrimidin-4-yl]-amine; |
| 335 | {2-(3,3-Difluoro-pyrrolidin-1-yl)-6-(1-(1H-imidazol-4-ylmethyl)-pyrrolidin-3-yl]-pyrimidin-4-yl}-(4-trifluoromethyl-pyridin-2-yl)-amine; |
| 336 | 3-{3-[2-(3,3-Difluoro-pyrrolidin-1-yl)-6-(4-trifluoromethyl-pyridin-2-ylamino)-pyrimidin-4-yl]-pyrrolidin-1-yl}-3-oxo-propionitrile; |
| 337 | (3-Methyl-3H-imidazol-4-yl)-{3-[2-(2-methyl-pyrrolidin-1-yl)-6-(4-trifluoromethyl-pyridin-2-ylamino)-pyrimidin-4-yl]-pyrrolidin-1-yl}-methanone; |
| 338 | {2-(3,3-Difluoro-azetidin-1-yl)-6-(1-(tetrahydro-furan-3-ylmethyl)-pyrrolidin-3-yl]-pyrimidin-4-yl}-(4-trifluoromethyl-pyridin-2-yl)-amine; |
| 339 | [2-(3,3-Difluoro-azetidin-1-yl)-6-(1-pyrimidin-5-ylmethyl-pyrrolidin-3-yl)-pyrimidin-4-yl]-(4-trifluoromethyl-pyridin-2-yl)-amine; |
| 340 | {2-(3,3-Difluoro-azetidin-1-yl)-6-{1-(1H-imidazol-4-ylmethyl)-pyrrolidin-3-yl]-pyrimidin-4-yl}-(4-trifluoromethyl-pyridin-2-yl)-amine; |
| 341 | {2-(3,3-Difluoro-azetidin-1-yl)-6-{1-(2H-pyrazol-3-ylmethyl)-pyrrolidin-3-yl]-pyrimidin-4-yl}-(4-trifluoromethyl-pyridin-2-yl)-amine; |
| 342 | [2-(3,3-Difluoro-azetidin-1-yl)-6-(1-ethyl-pyrrolidin-3-yl)-pyrimidin-4-yl]-(4-trifluoromethyl-pyridin-2-yl)-amine; |
| 343 | {2-(3,3-Difluoro-azetidin-1-yl)-6-{1-(1H-pyrazol-4-ylmethyl)-pyrrolidin-3-yl]-pyrimidin-4-yl}-(4-trifluoromethyl-pyridin-2-yl)-amine; |
| 344 | {2-(3,3-Difluoro-azetidin-1-yl)-6-[1-(1-methyl-1H-pyrazol-3-ylmethyl)-pyrrolidin-3-yl]-pyrimidin-4-yl}-(4-trifluoromethyl-pyridin-2-yl)-amine; |
| 345 | [2-(3,3-Difluoro-azetidin-1-yl)-6-(1-propyl-pyrrolidin-3-yl)-pyrimidin-4-yl]-(4-trifluoromethyl-pyridin-2-yl)-amine; |
| 346 | {2-(3,3-Difluoro-azetidin-1-yl)-6-[1-(2-methyl-2H-pyrazol-3-ylmethyl)-pyrrolidin-3-yl]-pyrimidin-4-yl-(4-trifluoromethyl-pyridin-2-yl)-amine; |
| 347 | [2-(3,3-Difluoro-azetidin-1-yl)-6-(1-pyridin-2-ylmethyl-pyrrolidin-3-yl)-pyrimidin-4-yl]-(4-trifluoromethyl-pyridin-2-yl)-amine; |
| 348 | [2-(2-Ethyl-morpholin-4-yl)-6-(1-methyl-pyrrolidin-3-yl)-pyrimidin-4-yl]-(4-trifluoromethyl-pyridin-2-yl)-amine; |
| 349 | 1-Methyl-4-[2-((R)-2-methyl-pyrrolidin-1-yl)-6-(4-trifluoromethyl-pyridin-2-ylamino)-pyrimidin-4-yl]-1H-pyridin-2-one; |
| 350 | [2-Isopropoxy-6-(tetrahydro-pyran-4-yl)-pyrimidin-4-yl]-(4-trifluoromethyl-pyridin-2-yl)-amine; |
| 351 | [2-((R)-2-Methoxymethyl-pyrrolidin-1-yl)-6-(tetrahydro-pyran-4-yl)-pyrimidin-4-yl]-(4-trifluoromethyl-pyridin-2-yl)-amine; |
| 352 | [2-(3-(2-Methyl-pyrimidin-4-yl)-pyrrolidin-1-yl]-6-(tetrahydro-pyran-4-yl)-pyrimidin-4-yl]-(4-trifluoromethyl-pyridin-2-yl)-amine; |
| 353 | [2-[3-(2-Methyl-pyrimidin-4-yl)-pyrrolidin-1-yl]-6-(tetrahydro-pyran-4-yl)-pyrimidin-4-yl]-(4-trifluoromethyl-pyridin-2-yl)-amine; |
| 354 | [2-(3-(4-Methyl-4H41,2,4]triazol-3-yl)-piperidin-1-yl)-6-(tetrahydro-pyran-4-yl)-pyrimidin-4-yl]-(4-trifluoromethyl-pyridin-2-yl)-amine; |
| 355 | [2-[3-(4-Methyl-4H41,2,4]triazol-3-yl)-piperidin-1-yl]-6-(tetrahydro-pyran-4-yl)-pyrimidin-4-yl]-(4-trifluoromethyl-pyridin-2-yl)-amine; |
| 356 | 1-{3-[2-Cyclopropyl-6-(4-trifluoromethyl-pyridin-2-ylamino)-pyrimidin-4-yl]-azetidin-1-yl}-ethanone; |
| 357 | [2-Cyclopropyl-6-(1-methanesulfonyl-azetidin-3-yl)-pyrimidin-4-yl]-(4-trifluoromethyl-pyridin-2-yl)-amine; |

| No | Name |
|---|---|
| 360 | 1-{4-[5-Fluoro-2-((R)-2-methyl-pyrrolidin-1-yl)-6-(4-trifluoromethyl-pyridin-2-ylamino)-pyrimidin-4-yl]-piperidin-1-yl}-ethanone; |
| 361 | 1-{4-[2-((R)-2-Methoxymethyl-pyrrolidin-1-yl)-6-(4-trifluoromethyl-pyridin-2-ylamino)-pyrimidin-4-yl]-piperidin-1-yl}-ethanone; |
| 362 | 1-{4-[2-Isopropoxy-6-(4-trifluoromethyl-pyridin-2-ylamino)-pyrimidin-4-yl]-piperidin-1-yl}-ethanone; |
| 363 | {2-(3,3-Difluoro-azetidin-1-yl)-6-[1-(2,2,2-trifluoro-ethyl)-pyrrolidin-3-yl]-pyrimidin-4-yl}-(4-trifluoromethyl-pyridin-2-yl)-amine; |
| 364 | {2-(3,3-Difluoro-azetidin-1-yl)-6-{1-(1H-imidazol-4-ylmethyl)-piperidin-3-yl]-pyrimidin-4-yl}-(4-trifluoromethyl-pyridin-2-yl)-amine; |
| 365 | 1-{3-[2-(3,3-Difluoro-azetidin-1-yl)-6-(4-trifluoromethyl-pyridin-2-ylamino)-pyrimidin-4-yl]-piperidin-1-yl}-ethanone; |
| 366 | 3-{4-[2-(3,3-Difluoro-azetidin-1-yl)-6-(4-trifluoromethyl-pyridin-2-ylamino)-pyrimidin-4-yl]-piperidin-1-yl}-3-oxo-propionitrile; |
| 367 | 1-{3-[2-(3,3-Difluoro-azetidin-1-yl)-6-(4-trifluoromethyl-pyridin-2-ylamino)-pyrimidin-4-yl]-piperidin-1-yl}-propan-1-one; |
| 368 | {3-[2-(3,3-Difluoro-azetidin-1-yl)-6-(4-trifluoromethyl-pyridin-2-ylamino)-pyrimidin-4-yl]-piperidin-1-yl}-(1-methyl-cyclopropyl)-methanone; |
| 369 | Cyclopropyl-{3-[2-(3,3-difluoro-azetidin-1-yl)-6-(4-trifluoromethyl-pyridin-2-ylamino)-pyrimidin-4-yl]-piperidin-1-yl}-methanone; |
| 370 | 2-Cyclopropyl-1-{3-[2-(3,3-difluoro-azetidin-1-yl)-6-(4-trifluoromethyl-pyridin-2-ylamino)-pyrimidin-4-yl]-piperidin-1-yl}-ethanone; |
| 371 | [6-(1-Methyl-piperidin-3-yl)-2-(3-morpholin-4-yl-azetidin-1-yl)-pyrimidin-4-yl]-(4-trifluoromethyl-pyridin-2-yl)-amine; |
| 372 | 1-{3-[2-(8-Oxa-3-aza-bicyclo[3.2.1]oct-3-yl)-6-(4-trifluoromethyl-pyridin-2-ylamino)-pynmidin-4-yl]-pyrrolidin-1-yl}-ethanone; |
| 373 | 2,2-Difluoro-1-{3-[2-(8-oxa-3-aza-bicyclo[3.2.1]oct-3-yl)-6-(4-trifluoromethyl-pyridin-2-ylamino)-pyrimidin-4-yl]-pyrrolidin-1-yl}-ethanone; |
| 374 | [6-(1-Methanesulfonyl-azetidin-3-yl)-2-((R)-2-methyl-pyrrolidin-1-yl)-pyrimidin-4-yl]-(4-trifluoromethyl-pyridin-2-yl)-amine; |
| 375 | 1-{3-[2-((R)-2-Methyl-pyrrolidin-1-yl)-6-(4-trifluoromethyl-pyridin-2-ylamino)-pyrimidin-4-yl]-azetidin-1-yl}-ethanone; |
| 376 | (1-Methyl-1H-imidazol-4-yl)-{3-[2-(2-methyl-pyrrolidin-1-yl)-6-(4-trifluoromethyl-pyridin-2-ylamino)-pyrimidin-4-yl]-pyrrolidin-1-yl}-methanone; |
| 377 | 1-{3-[2-(2-Methyl-pyrrolidin-1-yl)-6-(4-trifluoromethyl-pyridin-2-ylamino)-pyrimidin-4-yl]-pyrrolidin-1-yl}-ethanone; |
| 378 | [6-(1-Methanesulfonyl-pyrrolidin-3-yl)-2-(2-methyl-pyrrolidin-1-yl)-pyrimidin-4-yl]-(4-trifluoromethyl-pyridin-2-yl)-amine; |
| 379 | [2-(3,3-Difluoro-azetidin-1-yl)-6-(1-methanesulfonyl-pyrrolidin-3-yl)-pyrimidin-4-yl]-(4-trifluoromethyl-pyridin-2-yl)-amine; |
| 380 | 1-{3-[2-(Tetrahydro-furan-3-yl)-6-(4-trifluoromethyl-pyridin-2-ylamino)-pyrimidin-4-yl]-piperidin-1-yl-ethanone; |
| 381 | 1-{3-[6-(4-Methyl-pyridin-2-ylamino)-2-(tetrahydro-furan-3-yl)-pyrimidin-4-yl]-piperidin-1-yl}-ethanone; |
| 382 | 1-{4-[2-(Tetrahydro-furan-3-yl)-6-(4-trifluoromethyl-pyridin-2-ylamino)-pyrimidin-4-yl]-piperidin-1-yl}-ethanone; |
| 383 | 1-{4-[6-(4-Methyl-pyridin-2-ylamino)-2-(tetrahydro-furan-3-yl)-pyrimidin-4-yl]-piperidin-1-yl}-ethanone; |
| 384 | 1-{3-[2-(3-Morpholin-4-yl-azetidin-1-yl)-6-(4-trifluoromethyl-pyridin-2-ylamino)-pyrimidin-4-yl]-pyrrolidin-1-yl}-ethanone; |
| 385 | [2-Cyclopentyl-6-(1-methanesulfonyl-piperidin-3-yl)-pyrimidin-4-yl]-(4-trifluoromethyl-pyridin-2-yl)-amine; |
| 386 | [2-Cyclobutyl-6-(1-methanesulfonyl-piperidin-3-yl)-pyrimidin-4-yl]-(4-trifluoromethyl-pyridin-2-yl)-amine; |
| 387 | [2-(3,3-Difluoro-azetidin-1-yl)-6-(1-methanesulfonyl-azetidin-3-yl)-pyrimidin-4-yl]-(4-trifluoromethyl-pyridin-2-yl)-amine; |
| 388 | {2-(2-Methyl-2H-pyrazol-3-yl)-6-(1-(tetrahydro-pyran-4-ylmethyl)-pyrrolidin-3-yl)-pyrimidin-4-yl}-(4-trifluoromethyl-pyridin-2-yl)-amine; |
| 389 | 1-{3-[2-(2-Methyl-2H-pyrazol-3-yl)-6-(4-trifluoromethyl-pyridin-2-ylamino)-pyrimidin-4-yl]-piperidin-1-yl}-ethanone; |
| 390 | {2-(3,3-Difluoro-pyrrolidin-1-yl)-6-(1-(2H-pyrazol-3-ylmethyl)-pyrrolidin-3-yl)-pyrimidin-4-yl}-(4-trifluoromethyl-pyridin-2-yl)-amine; |
| 391 | [2-Cyclopentyl-6-(1-oxetan-3-yl-piperidin-3-yl)-pynmidin-4-yl]-(4-trifluoromethyl-pyridin-2-yl)-amine; |
| 392 | 4-[2-(Tetrahydro-furan-3-yl)-6-(4-trifluoromethyl-pyridin-2-ylamino)-pyrimidin-4-yl]-piperidin-2-one; |
| 393 | [6-(1-Methanesulfonyl-piperidin-4-yl)-2-(tetrahydro-furan-3-yl)-pyrimidin-4-yl]-(4-trifluoromethyl-pyridin-2-yl)-amine; |
| 394 | 1-{3-[2-Cyclopentyl-6-(4-trifluoromethyl-pyridin-2-ylamino)-pyrimidin-4-yl]-piperidin-1-yl}-ethanone; |
| 395 | 4-[2-(2-Methoxymethyl-pyrrolidin-1-yl)-6-(4-trifluoromethyl-pyridin-2-ylamino)-pyrimidin-4-yl]-piperidin-2-one; |
| 396 | [6-(1-Cyclopropylmethyl-pyrrolidin-3-yl)-2-(3,3-difluoro-azetidin-1-yl)-pyrimidin-4-yl]-(4-trifluoromethyl-pyridin-2-yl)-amine; |
| 397 | 1-{3-[2-(2,5-Dimethyl-2H-pyrazol-3-yl)-6-(4-trifluoromethyl-pyridin-2-ylamino)-pyrimidin-4-yl]-piperidin-1-yl}-ethanone; |

| No | Name |
|---|---|
| 398 | [6-(1-Oxetan-3-yl-piperidin-4-yl)-2-(tetrahydro-furan-3-yl)-pyrimidin-4-yl]-(4-trifluoromethyl-pyridin-2-yl)-amine; |
| 399 | [2-Isopropyl-6-(1-oxetan-3-yl-azetidin-3-yl)-pyrimidin-4-yl]-(4-trifluoromethyl-pyridin-2-yl)-amine; |
| 400 | [2-(3,3-Difluoro-azetidin-1-yl)-6-(1-oxazol-5-ylmethyl-piperidin-3-yl)-pyrimidin-4-yl]-(4-trifluoromethyl-pyridin-2-yl)-amine; |
| 401 | [6-(1-Methanesulfonyl-piperidin-3-yl)-2-(tetrahydro-furan-3-yl)-pyrimidin-4-yl]-(4-trifluoromethyl-pyridin-2-yl)-amine; |
| 402 | 2-Imidazol-1-yl-1-{3-[2-(2-methyl-pyrrolidin-1-yl)-6-(4-trifluoromethyl-pyridin-2-ylamino)-pyrimidin-4-yl]-pyrrolidin-1-yl}-ethanone; |
| 403 | 1-{3-[2-(2-Methyl-2H-pyrazol-3-yl)-6-(4-trifluoromethyl-pyridin-2-ylamino)-pyrimidin-4-yl]-pyrrolidin-1-yl}-ethanone; |
| 404 | {2-(3,3-Difluoro-pyrrolidin-1-yl)-6-[1-(1H-pyrazol-4-ylmethyl)-pyrrolidin-3-yl]-pyrimidin-4-yl}-(4-trifluoromethyl-pyridin-2-yl)-amine; |
| 405 | 1-{3-[2-Cyclobutyl-6-(4-trifluoromethyl-pyridin-2-ylamino)-pyrimidin-4-yl]-piperidin-1-yl]-ethanone; |
| 406 | 1-{3-[2-(3,3-Difluoro-azetidin-1-yl)-6-(4-trifluoromethyl-pyridin-2-ylamino)-pyrimidin-4-yl]-piperidin-1-yl}-3-methoxy-propan-1-one; |
| 407 | [2-Cyclobutyl-6-(1-oxetan-3-yl-piperidin-3-yl)-pyrimidin-4-yl]-(4-trifluoromethyl-pyridin-2-yl)-amine; |
| 409 | 1-{3-[6-(4-Cyclopropyl-pyridin-2-ylamino)-2-(3,3-difluoro-azetidin-1-yl)-pyrimidin-4-yl]-azetidin-1-yl}-ethanone; |
| 410 | [2-Cyclopropyl-6-(1-oxetan-3-yl-azetidin-3-yl)-pyrimidin-4-yl]-(4-trifluoromethyl-pyridin-2-yl)-amine; |
| 411 | [2-(3,3-Difluoro-pyrrolidin-1-yl)-6-(1-oxazol-5-ylmethyl-pyrrolidin-3-yl)-pyrimidin-4-yl]-(4-trifluoromethyl-pyridin-2-yl)-amine; |
| 412 | 4-[2-(2-Methyl-pyrrolidin-1-yl)-6-(4-trifluoromethyl-pyridin-2-ylamino)-pyrimidin-4-yl]-piperidin-2-one; |
| 413 | 2-{4-[6-(4-Cyclobutyl-pyridin-2-ylamino)-2-(2-oxa-5-aza-bicyclo[2.2.1]hept-5-yl)-pyrimidin-4-yl]-piperidin-1-yl}-ethanol; |
| 414 | 1-{3-[2-(1-Methyl-1H-pyrazol-4-yl)-6-(4-trifluoromethyl-pyridin-2-ylamino)-pyrimidin-4-yl]-pyrrolidin-1-yl}-ethanone; |
| 415 | [6-(1-Oxetan-3-yl-piperidin-3-yl)-2-(tetrahydro-furan-3-yl)-pyrimidin-4-yl]-(4-trifluoromethyl-pyridin-2-yl)-amine; |
| 416 | 1-{3-[2-(3,3-Difluoro-azetidin-1-yl)-6-(4-trifluoromethyl-pyridin-2-ylamino)-pyrimidin-4-yl]-azetidin-1-yl}-ethanone; |
| 417 | 1-[4-(1-Methyl-piperidin-3-yl)-6-(4-trifluoromethyl-pyridin-2-ylamino)-pyrimidin-2-yl]-azetidine-3-carbonitrile; |
| 418 | {2-(3,3-Difluoro-azetidin-1-yl)-6-(1-(1H-pyrazol-4-ylmethyl)-piperidin-3-yl]-pyrimidin-4-yl}-(4-trifluoromethyl-pyridin-2-yl)-amine; |
| 419 | 1-{3-[2-(1-Methyl-1H-pyrazol-4-yl)-6-(4-trifluoromethyl-pyridin-2-ylamino)-pyrimidin-4-yl]-piperidin-1-yl}-ethanone; |
| 420 | {2-(3,3-Difluoro-azetidin-1-yl)-6-((R)-1-(2-methyl-1H-imidazol-4-ylmethyl)-pyrrolidin-3-yl]-pyrimidin-4-yl}-(4-trifluoromethyl-pyridin-2-yl)-amine; |
| 421 | [2-(2-Methyl-pyrrolidin-1-yl)-6-(1-oxazol-5-ylmethyl-pyrrolidin-3-yl)-pyrimidin-4-yl]-(4-trifluoromethyl-pyridin-2-yl)-amine; |
| 423 | {2-(1-Methyl-1H-pyrazol-4-yl)-6-(1-(tetrahydro-pyran-4-ylmethyl)-pyrrolidin-3-yl]-pyrimidin-4-yl}-(4-trifluoromethyl-pyridin-2-yl)-amine; |
| 424 | 1-{4-[2-(1-Methyl-1H-pyrazol-4-yl)-6-(4-trifluoromethyl-pyridin-2-ylamino)-pyrimidin-4-yl]-piperidin-1-yl}-ethanone; |
| 425 | (2-Methoxy-4-methyl-phenyl)-{3-[6-(4-methyl-pyridin-2-ylamino)-2-(2-methyl-pyrrolidin-1-yl)-pyrimidin-4-yl]-piperidin-1-yl}-methanone;. |
| 426 | {3-[2-(3,3-Difluoro-pyrrolidin-1-yl)-6-(4-methyl-pyridin-2-ylamino)-pyrimidin-4-yl]-piperidin-1-yl}-(2-methoxy-4-methyl-phenyl)-methanone; and |
| 427 | N-(4-chloropyridin-2-yl)-2-(3,3-difluoropyrrolidin-1-yl)-6-(1-(oxetan-3-yl)piperidin-4-yl)pyrimidin-4-amine. |

17. A pharmaceutical composition comprising a compound of formula I-I and a pharmaceutically acceptable carrier, diluent or excipient, wherein in said compound of formula I-I

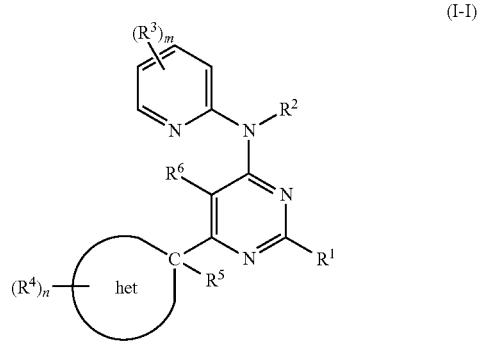

(I-I)

wherein $R^1$ is selected from the group consisting of $C_{1-6}$ haloalkyl, $C_{1-6}$ heteroalkyl, $C_{1-6}$ alkoxy, 3-10 membered cycloalkyl, 3-10 membered heterocycloalkyl, 6-10 membered aryl, 5-10 membered heteroaryl, $-OR^{1a}$, $-SR^{1a}$, $-N(H)(R^{1a})$, and $-N(R^{1a})(R^{1b})$ wherein $R^{1a}$ and $R^{1b}$ are each independently selected from the group consisting of $C_{1-6}$ alkyl, $C_{1-6}$ haloalkyl, $C_{1-6}$ heteroalkyl, 3-10 membered cycloalkyl and 3-10 membered heterocycloalkyl, and wherein the aliphatic and aromatic portions of $R^1$ are independently further substituted with 0 to 5 $R^{41}$ substituents selected from the group consisting of $-F$, $-Cl$, $-Br$, $-I$, $-CN$, $-NO_2$, $-SF_5$, $-OH$, $-NH_2$, $-CF_3$, $=O$, $C_{1-4}$ alkyl, $C_{1-4}$ haloalkyl, $C_{1-4}$ heteroalkyl, $C_{1-4}$ alkoxy, $C_{1-4}$ alkylthio, $C_{1-4}$ alkylamino, $C_{1-4}$ dialkylamino, $R^{1c}-C(=O)-$, $R^{1c}-C(=O)N(H)-$, $R^{1c}-C(=O)N(R^{1d})-$, $R^{1c}-C(=O)O-$, $R^{1c}-S(O)_{1-2}-$, $R^{1c}-S(O)_{1-2}N(R^{1d})-$, $R^{1c}-S(O)_{1-2}N(H)-$, 3-6 membered cycloalkyl, phenyl, 5-6 membered heteroaryl and 3-7 membered heterocycloalkyl, wherein $R^{1c}$ is selected from the group consisting of $C_{1-6}$ alkyl, $C_{1-6}$ haloalkyl, $C_{5-6}$ heteroaryl, 3-7 membered heterocycloalkyl, phenyl and 3-6 membered cycloalkyl, $R^{1d}$ is selected from the group consisting of hydrogen, $C_{1-3}$ alkyl and $C_{1-3}$ haloalkyl, and wherein said 5-6 membered heteroaryl, phenyl, 3-6 membered cycloalkyl and 3-7 membered heterocycloalkyl of a $R^{41}$ substituent are substituted with from 0-4 substituents selected from $-F$, $-Cl$, $-Br$, $I$, $-CN$, $-NO_2$, $-SF_5$, $-OH$, $-NH_2$, $-CF_3$, $C_{1-4}$ alkyl, $C_{1-4}$ haloalkyl, $C_{1-4}$ alkoxy, $C_{1-4}$ alkylthio, $C_{1-4}$ alkylamino and $C_{1-4}$ dialkylamino;

$R^2$ is selected from the group consisting of hydrogen, $C_{1-6}$ alkyl and $C_{1-6}$ haloalkyl;

$R^3$ is selected from the group consisting of $-F$, $-Cl$, $-Br$, $-I$, $-(X^3)_{0-1}-CN$, $-(X^3)_{0-1}-NO_2$, $-(X^3)_{0-1}-SF_5$, $-(X^3)_{0-1}-OH$, $-(X^3)_{0-1}-NH_2$, $-(X^3)_{0-1}-N(H)(R^{3a})$, $-(X^3)_{0-1}-N(R^{3b})(R^{3a})$, $-(X^3)_{0-1}-CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^3)_{0-1}$-3-7 membered cycloalkyl, $-(X^3)_{0-1}$-3-7 membered heterocycloalkyl, $-(X^3)_{0-1}$-5-6 membered heteroaryl, $-(X^3)_{0-1}-C_6$ aryl, $-(X^3)_{0-1}-C(=Y^3)N(H)(R^{3a})$, $-(X^3)_{0-1}-C(=Y^3)NH_2$, $-(X^3)_{0-1}-C(=Y^3)N(R^{3a})(R^{3b})$, $-(X^3)_{0-1}-C(=Y^3)OR^{3a}$, $-(X^3)_{0-1}-C(=Y^3)OH$, $-(X^3)_{0-1}-N(H)C(=Y^3)(R^{3a})$, $-(X^3)_{0-1}-N(R^{3b})C(=Y^3)(R^{3a})$, $-(X^3)_{0-1}-N(H)C(=Y^3)OR^{3a}$, $-(X^3)_{0-1}-N(R^{3b})C(=Y^3)OR^{3a}$, $(X^3)_{0-1}-S(O)_{1-2}R^{3a}$, $-(X^3)_{0-1}-N(H)S(O)_{1-2}R^{3a}$, $-(X^3)_{0-1}-N(R^{3b})S(O)_{1-2}R^{3a}$, $-(X^3)_{0-1}-S(O)_{0-1}N(H)(R^{3a})$, $-(X^3)_{0-1}-S(O)_{0-1}N(R^{3b})(R^{3a})$, $-(X^3)_{0-1}-S(O)_{0-1}NH_2$, $-(X^4)_{0-1}-S(=O)(=NR^{3b})R^{3a}$, $-(X^3)_{0-1}-C(=Y^3)R^{3a}$, $-(X^3)_{0-1}-C(=Y^3)H$, $-(X^3)_{0-1}-C(=NOH)R^{3a}$, $-(X^3)_{0-1}-C(=NOR^{3b})R^{3a}$, $-(X^3)_{0-1}-NHC(=Y^3)N(H)(R^{3a})$, $-(X^3)_{0-1}-NHC(=Y^3)NH_2$, $-(X^3)_{0-1}-NHC(=Y^3)N(R^{3b})(R^{3a})$, $-(X^3)_{0-1}-N(R^{3a})C(=Y^3)N(H)(R^{3a})$, $-(X^3)_{0-1}-N(R^{3a})C(=Y^3)NH_2$, $-(X^3)_{0-1}-OC(=Y^3)R^{3a}$, $-(X^3)_{0-1}-OC(=Y^3)H$, $-(X^3)_{0-1}-OC(=Y^3)OR^{3a}$, $-(X^3)_{0-1}-OP(=Y^3)(OR^{3a})(OR^{3b})$, $-(X^3)-SC(=Y^3)OR^{3a}$ and $-(X^3)-SC(=Y^3)N(R^{3a})(R^{3b})$ wherein $X^3$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{3a}$ and $R^{3b}$ are each independently selected from the group consisting of $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl; $Y^3$ is O, $NR^{3d}$ or S wherein $R^{3d}$ is hydrogen or $C_{1-6}$ alkyl; wherein aliphatic or aromatic portion of $R^3$ is independently further substituted with from 0 to 4 $R^{43}$ substituents selected from the group consisting of $-F$, $-Cl$, $-Br$, $-I$, $-CN$, $-NO_2$, $-SF_5$, $-OH$, $-NH_2$, $-CF_3$, $=O$, $C_{1-6}$ alkyl, $C_{1-6}$ haloalkyl, $C_{1-6}$ heteroalkyl, $C_{1-6}$ alkoxy, $C_{1-6}$ alkylthio, 3-6 membered cycloalkyl, 3-6 membered heterocycloalkyl, $-C(=O)N(H)(C_{1-6}$ alkyl), $-C(=O)N(C_{1-6}$ alkyl)$_2$, $-C(=O)NH_2$, $-C(=O)OC_{1-6}$ alkyl, $-C(=O)OH$, $-N(H)C(=O)(C_{1-6}$ alkyl), $-N(C_{1-6}$ alkyl)$C(=O)(C_{1-6}$ alkyl), $-N(H)C(=O)OC_{1-6}$ alkyl, $-N(C_{1-6}$ alkyl)$C(=O)OC_{1-6}$ alkyl, $-S(O)_{1-2}C_{1-6}$ alkyl, $-N(H)S(O)_{1-2}C_{1-6}$ alkyl, $-N(C_{1-6}$ alkyl)$S(O)_{1-2}$ $C_{1-6}$ alkyl, $-S(O)_{0-1}N(H)(C_{1-6}$ alkyl), $-S(O)_{0-1}N(C_{1-6}$ alkyl)$_2$, $-S(O)_{0-1}NH_2$, $-C(=O)C_{1-6}$ alkyl, $-C(=NOH)C_{1-6}$ alkyl, $-C(=NOC_{1-6}$ alkyl)$C_{1-6}$ alkyl, $-NHC(=O)N(H)(C_{1-6}$ alkyl), $-NHC(=O)N(C_{1-6}$ alkyl)$_2$, $-NHC(=O)NH_2$, $-N(C_{1-6}$ alkyl)$C(=O)N(H)(C_{1-6}$ alkyl), $-N(C_{1-6}$ alkyl)$C(=O)NH_2$, $-OC(=O)C_{1-6}$ alkyl, $-OC(=O)OC_{1-6}$ alkyl, $-OP(=O)(OC_{1-6}$ alkyl)$_2$, $-SC(=O)OC_{1-6}$ alkyl and $-SC(=O)N(C_{1-6}$ alkyl)$_2$; alternatively any two $R^3$ substituents located on adjacent atoms are optionally combined to form a 5-6 membered heteroaryl ring comprising 1-2 heteroatoms selected from N, O and S and further comprising 0 to 4 $R^{3a}$ substituents;

m is an integer from 0 to 4;

the ring represented by the structure

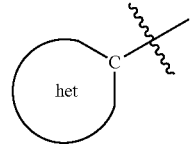 [SMILES: *C(C)C]

is a 4 to 10 membered heterocyclic ring comprising 1 to 2 heteroatoms selected from N, O and S, wherein said 4 to 7 membered heterocyclic ring is optionally substituted with 1 to 3 $R^4$ groups;

$R^4$ is selected from the group consisting of —F, —Cl, —Br, —I, —$(X^4)_{0-1}$—CN, —$(X^4)_{0-1}$—NO$_2$, —$(X^4)_{0-1}$—SF$_5$, —$(X^4)_{0-1}$-OH, —$(X^4)_{0-1}$—NH$_2$, —$(X^4)_{0-1}$—N(H)(R$^{4a}$), —$(X^4)_{0-1}$—N(R$^{4b}$)(R$^{4a}$), —$(X^4)_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —$(X^4)_{0-1}$-(3-10 membered heterocycloalkyl), —$(X^4)_{0-1}$-(5-10 membered heteroaryl), —$(X^4)_{0-1}$-(3-7 membered cycloalkyl), —$(X^4)_{0-1}$—C(=Y$^4$)N(H)(R$^{4a}$), —$(X^4)_{0-1}$—C(=Y$^4$)NH$_2$, —$(X^4)_{0-1}$—C(=Y$^4$)N(R$^{4a}$)(R$^{4b}$), —$(X^4)_{0-1}$—C(=Y$^4$)OR$^{4a}$, —$(X^4)_{0-1}$—C(=Y$^4$)OH, —$(X^4)_{0-1}$—N(H)C(=Y$^4$)(R$^{4a}$), —$(X^4)_{0-1}$—N(R$^{4b}$)C(=Y$^4$)(R$^{4a}$), —$(X^4)_{0-1}$—N(H)C(=Y$^4$)OR$^{4a}$, —$(X^4)_{0-1}$—N(R$^{4b}$)(=Y$^4$)OR$^4$, —$(X^4)_{0-1}$—S(O)$_{1-2}$R$^{4a}$, —$(X^4)_{0-1}$—N(H)S(O)$_{1-2}$R$^{4a}$, —$(X^4)_{0-1}$—N(R$^{4b}$)S(O)$_{1-2}$R$^{4a}$, —$(X^4)_{0-1}$—S(O)$_{0-1}$N(H)(R$^{4a}$), —$(X^4)_{0-1}$—S(O)$_{0-1}$N(R$^{4b}$)(R$^{4a}$), —$(X^4)_{0-1}$—S(O)$_{0-1}$NH$_2$, —$(X^4)_{0-1}$—S(=O)(=NR$^{4b}$)R$^{4a}$, —$(X^4)_{0-1}$—C(=Y$^4$)R$^{4a}$, —$(X^4)_{0-1}$—C(=Y$^4$)H, —$(X^4)_{0-1}$—C(=NOH)R$^{4a}$, —$(X^4)_{0-1}$—C(=NOR$^{4b}$)R$^{4a}$, —$(X^4)_{0-1}$—NHC(=Y$^4$)N(H)(R$^{4a}$), —$(X^4)_{0-1}$—NHC(=Y$^3$)NH$_2$, —$(X^4)_{0-1}$—NHC(=Y$^4$)N(R$^{4b}$)(R$^{4a}$), —$(X^4)_{0-1}$—NR$^{4a}$C(=Y$^4$)N(H)(R$^{4a}$), —$(X^4)_{0-1}$—N(R$^{4a}$)C(=Y$^4$)NH$_2$, —$(X^4)_{0-1}$—OC(=Y$^4$)R$^{4a}$, —$(X^4)_{0-1}$—OC(=Y$^4$)H, —$(X^4)_{0-1}$—OC(=Y$^4$)OR$^{4a}$, —$(X^4)_{0-1}$—P(=Y$^4$)(OR)(OR$^{4a}$)(OR$^{4b}$), —SC(=Y$^4$)OR$^{4a}$ and —SC(=Y$^4$)N(R$^{4a}$)(R$^{4b}$) wherein R$^{4a}$ and R$^{4b}$ at each occurrence are each independently selected from the group consisting of C$_{1-6}$ alkyl, C$_{1-6}$ haloalkyl, C$_{1-6}$ heteroalkyl, 6-10 membered aryl, 3-7 membered cycloalkyl, 5-10 membered heteroaryl, 3-7 membered heterocycloalkyl, 6-10 membered aryl-C$_{1-4}$ alkyl, 3-7 membered cycloalkyl-C$_{1-4}$ alkyl, 5-10 membered heteroaryl-C$_{1-4}$ alkyl and 3-7 membered heterocycloalkyl-C$_{1-4}$ alkyl, and X$^4$ is selected from the group consisting of C$_{1-4}$ alkylene, C$_{1-4}$ haloalkylene, C$_{1-4}$ heteroalkylene, C$_{2-4}$ alkenylene and C$_{2-4}$ alkynylene; Y$^4$ is O, NR$^{4c}$ or S wherein R$^{4c}$ is hydrogen or C$_{1-6}$ alkyl; wherein the aromatic and aliphatic portions of R$^4$ is independently further substituted with 0 to 4 R$^{44}$ substituents selected from the group consisting of —F, —Cl, —Br, I, —CN, —NO$_2$, —SF$_5$, —OH, —NH$_2$, —CF$_3$, =O, C$_{1-6}$ alkyl, C$_{1-6}$ haloalkyl, C$_{1-6}$ heteroalkyl, C$_{1-6}$ alkoxy, C$_{1-6}$ alkylthio, 3-6 membered cycloalkyl, 3-6 membered heterocycloalkyl, —C(=O)N(H)(C$_{1-6}$ alkyl), —C(=O)N(C$_{1-6}$ alkyl)$_2$, —C(=O)NH$_2$, —C(=O)OC$_{1-6}$ alkyl, —C(=O)OH, —N(H)C(=O)(C$_{1-6}$ alkyl), —N(H)C(=O)(C$_{1-6}$ alkyl), —N(H)C(=O)OC$_{1-6}$ alkyl, —N(C$_{1-6}$ alkyl)C(=O)OC$_{1-6}$ alkyl, —S(O)$_{1-2}$C$_{1-6}$ alkyl, —N(H)S(O)$_{1-2}$C$_{1-6}$ alkyl, —N(C$_{1-6}$ alkyl)S(O)$_{1-2}$C$_{1-6}$ alkyl, —S(O)$_{0-1}$N(H)(C$_{1-6}$ alkyl), —S(O)$_{0-1}$N(C$_{1-6}$ alkyl)$_2$, —S(O)$_{0-1}$NH$_2$, —C(=O)C$_{1-6}$ alkyl, —C(=NOH)C$_{1-6}$ alkyl, —C(=NOC$_{1-6}$ alkyl)C$_{1-6}$ alkyl, —NHC(=O)N(H)(C$_{1-6}$ alkyl), —NHC(=O)N(C$_{1-6}$ alkyl)$_2$, —NHC(=O)NH$_2$, —N(C$_{1-6}$ alkyl)C(=O)N(H)(C$_{1-6}$ alkyl), —N(C$_{1-6}$ alkyl)C(=O)NH$_2$, —OC(=O)C$_{1-6}$ alkyl, —OC(=O)OC$_{1-6}$ alkyl, —OP(=O)(OC$_{1-6}$ alkyl)$_2$, —SC(=O)OC$_{1-6}$ alkyl and —SC(=O)N(C$_{1-6}$ alkyl)$_2$;

n is an integer from 0 to 5;

$R^5$ is absent or is selected from the group consisting of hydrogen, C$_{1-6}$ alkyl, C$_{1-6}$ haloalkyl, —OH, OR$^{5a}$, —CN and halogen, wherein R$^{5a}$ is selected from the group consisting of C$_{1-6}$ alkyl, C$_{1-6}$ haloalkyl and C$_{1-6}$ heteroalkyl; or optionally R$^4$ and R$^5$ are optionally combined to form a 5-7 membered cycloalkyl or heterocycloalkyl and is independently further substituted with 0-4 R$^{44}$ substituents; and $R^6$ is hydrogen, —F, —Cl, —Br, —I, C$_{1-3}$ alkyl or C$_{1-3}$ haloalkyl.

18. A method for inhibiting or preventing degeneration of a central nervous system (CNS) neuron in a patient having or at risk of developing a neurodegenerative disease or condition selected from the group consisting of Alzheimer's disease, Huntington's disease, Parkinson's disease, and amyotrophic lateral sclerosis (ALS), comprising administering to said patient a therapeutically effective amount of a compound of formula I-I of claim 17, or a pharmaceutically acceptable salt thereof.

19. The method of claim 18, wherein the compound of formula I-I is administered in combination with one or more additional pharmaceutical agents.

20. A compound of claim 1 selected from the group consisting of:
- {3-[6-(4-Methyl-pyridin-2-ylamino)-2-pyrrolidin-1-yl-pyrimidin-4-yl]-piperidin-1-yl}-phenyl-methanone;
- 2-{Methyl-[4-pyrrolidin-3-yl-6-(4-trifluoromethyl-pyridin-2-ylamino)-pyrimidin-2-yl]-amino}-ethanol;
- (2-Phenyl-6-piperidin-3-yl-pyrimidin-4-yl)-(4-trifluoromethyl-pyridin-2-yl)-amine,
- (4-Chloro-pyridin-2-yl)-[2-(3,3-difluoro-pyrrolidin-1-yl)-6-piperidin-4-yl-pyrimidin-4-yl]-amine;
- 1-Acetyl-4-[2-(3,3-difluoro-pyrrolidin-1-yl)-6-(4-trifluoromethyl-pyridin-2-ylamino)-pyrimidin-4-yl]-piperidine-4-carbonitrile;
- [2-(2-Oxa-5-aza-bicyclo[2.2.1]hept-5-yl)-6-piperidin-4-yl-pyrimidin-4-yl]-(4-trnfluoromethyl-pyridin-2-yl)-amine;
- (4-Cyclobutyl-pyridin-2-yl)-[2-(3,3-difluoro-pyrrolidin-1-yl)-6-piperidin-4-yl-pyrimidin-4-yl]-amine;
- [2-(2-Oxa-5-aza-bicyclo[2.2.1]hept-5-yl)-6-(tetrahydro-pyran-4-yl)-pyrimidin-4-yl]-(4-trifluoromethyl-pyridin-2-yl)-amine;
- 1-{3-[2-(3,3-Difluoro-pyrrolidin-1-yl)-6-(4-trifluoromethyl-pyridin-2-ylamino)-pyrimidin-4-yl]-pyrrolidine-1-carbonyl}-cyclopropanecarbonitrile;
- [2-(3,4,6,7-Tetrahydro-imidazo[4,5-c]pyridin-5-yl)-6-tetrahydro-pyran-4-yl)-pyrimidin-4-yl]-(4-trifluoromethyl-pyridin-2-yl)-amine;
- [2-[3-(2-Methyl-pyrimidin-4-yl)-pyrrolidin-1-yl]-6-(tetrahydro-pyran-4-yl)-pyrimidin-4-yl]-(4-trifluoromethyl-pyridin-2-yl)-amine; and
- {2-(3,3-Difluoro-azetidin-1-yl)-6-[1-(4-methyl-1H-imidazol-2-ylmethyl)-pyrrolidin-3-yl]-pyrimidin-4-yl}-(4-trifluoromethyl-pyridin-2-yl)-amine.

* * * * *